(12) United States Patent
Wu et al.

(10) Patent No.: US 9,085,638 B2
(45) Date of Patent: Jul. 21, 2015

(54) DNA VACCINE ENHANCEMENT WITH MHC CLASS II ACTIVATORS

(75) Inventors: Tzyy-Choou Wu, Stevenson, MD (US); Chien-Fu Hung, Timonium, MD (US)

(73) Assignee: The Johns Hopkins University, Baltimore, MD (US)

( * ) Notice: Subject to any disclaimer, the term of this patent is extended or adjusted under 35 U.S.C. 154(b) by 1010 days.

(21) Appl. No.: 12/043,656

(22) Filed: Mar. 6, 2008

(65) Prior Publication Data

US 2009/0093050 A1   Apr. 9, 2009

Related U.S. Application Data

(60) Provisional application No. 60/905,476, filed on Mar. 7, 2007.

(51) Int. Cl.
*A61K 39/00* (2006.01)
*A61K 39/395* (2006.01)
*C07H 21/00* (2006.01)
*C07K 14/47* (2006.01)
*A61K 39/39* (2006.01)

(52) U.S. Cl.
CPC ......... *C07K 14/4705* (2013.01); *A61K 39/0011* (2013.01); *A61K 39/39* (2013.01); *A61K 2039/53* (2013.01); *A61K 2039/57* (2013.01)

(58) Field of Classification Search
CPC ............ A61K 39/0011; A61K 39/385; A61K 2039/605; A61K 39/12; A61K 2039/53; A61K 2039/5256; A61K 2217/05; A61K 39/39; A61K 2039/57; C07K 14/005; C07K 14/70539; C07K 2319/00; C07K 14/4705; C12N 2770/24222
USPC .................. 536/23.1, 23.4; 424/184.1, 173.1; 530/350
See application file for complete search history.

(56) References Cited

U.S. PATENT DOCUMENTS

| | | |
|---|---|---|
| 4,898,730 A | 2/1990 | Levy et al. |
| 5,217,879 A | 6/1993 | Huang et al. |
| 5,348,945 A | 9/1994 | Berberian et al. |
| 5,426,097 A | 6/1995 | Stern et al. |
| 5,547,846 A | 8/1996 | Bartsch et al. |
| 5,582,831 A | 12/1996 | Shinitzky |
| 5,591,716 A | 1/1997 | Siebert et al. |
| 5,618,536 A | 4/1997 | Lowy et al. |
| 5,629,161 A | 5/1997 | Muller et al. |
| 5,674,486 A | 10/1997 | Sobol et al. |
| 5,744,133 A | 4/1998 | Lathe et al. |
| 5,750,119 A | 5/1998 | Srivastava |
| 5,821,088 A | 10/1998 | Darzins et al. |
| 5,830,464 A | 11/1998 | Srivastava |
| 5,834,309 A | 11/1998 | Thompson et al. |
| 5,837,251 A | 11/1998 | Srivastava |
| 5,844,089 A | 12/1998 | Hoffman et al. |
| 5,854,202 A | 12/1998 | Dedhar |
| 5,855,891 A | 1/1999 | Lowy et al. |
| 5,935,576 A | 8/1999 | Srivastava |
| 5,948,646 A | 9/1999 | Srivastava |
| 5,951,975 A | 9/1999 | Falo, Jr. et al. |
| 5,962,318 A | 10/1999 | Rooney et al. |
| 5,997,869 A | 12/1999 | Goletz et al. |
| 6,007,821 A | 12/1999 | Srivastava et al. |
| 6,013,262 A | 1/2000 | Frazer et al. |
| 6,017,544 A | 1/2000 | Srivastava |
| 6,017,735 A | 1/2000 | O'Hare et al. |
| 6,020,309 A | 2/2000 | Campo et al. |
| 6,030,618 A | 2/2000 | Srivastava |
| 6,046,158 A | 4/2000 | Ariizumi et al. |
| 6,066,716 A | 5/2000 | Wallen et al. |
| 6,235,523 B1 | 5/2001 | Gajewczyk et al. |
| 6,331,388 B1 | 12/2001 | Malkovsky et al. |
| 6,399,070 B1 | 6/2002 | Srivastava et al. |
| 6,403,080 B1 | 6/2002 | Segal |
| 6,410,027 B1 | 6/2002 | Srivastava |
| 6,410,028 B1 | 6/2002 | Srivastava |
| 6,541,010 B1 | 4/2003 | Johnston et al. |
| 6,734,173 B1 | 5/2004 | Wu et al. |
| 7,001,995 B1 | 2/2006 | Neeper et al. |
| 7,318,928 B2 | 1/2008 | Wu et al. |
| 7,342,002 B2 | 3/2008 | Wu et al. |
| 2001/0034042 A1 | 10/2001 | Srivastava |
| 2002/0064771 A1* | 5/2002 | Zhong et al. ...... 435/5 |
| 2002/0091246 A1 | 7/2002 | Pardoll et al. |
| 2002/0182586 A1* | 12/2002 | Morris et al. ...... 435/4 |
| 2004/0028693 A1 | 2/2004 | Wu et al. |
| 2004/0086845 A1 | 5/2004 | Wu et al. |
| 2004/0106128 A1 | 6/2004 | Majumdar et al. |
| 2004/0259247 A1 | 12/2004 | Tuschl et al. |

(Continued)

FOREIGN PATENT DOCUMENTS

| CA | 2413543 | 1/2002 |
|---|---|---|
| EP | 0 763 740 | 3/1997 |

(Continued)

OTHER PUBLICATIONS

Tienhoven et al Vaccine. Jan. 8, 2001; 19(11-12):1515-9.*
van Tienhoven et al Cancer Res. Nov. 15, 2000; 60(22):6427-33.*
Cheng et al Journal of Clinical Investigation, 2001, 108, 5, 669-679.*
Bae et al Clinical cancer research, 2007, 13(1), 341-349.*
Alexander, Immunity, 1994,1, 751-761.*
Koch et al Immunology Today, 200, 21(11), 546-550.*
Kim et al Human Gene Therap 16:26-34 (Jan. 2005.*
Bennett et al (J Expt. Medicine vol. 186, No. 1, Jul. 7, 1997 65-70.*
Xiang, J,. J Immunol 2005, 174: 7497-7505.*

(Continued)

*Primary Examiner* — Anoop Singh
(74) *Attorney, Agent, or Firm* — Foley Hoag LLP

(57) ABSTRACT

Methods for treating or preventing hyperproliferating diseases, e.g., cancer, are described. A method may comprise administering to a subject in need thereof a therapeutically effective amount of a nucleic acid encoding an MHC class I and/or II activator and optionally a nucleic acid encoding an antigen.

9 Claims, 43 Drawing Sheets

(56) References Cited

U.S. PATENT DOCUMENTS

| | | | |
|---|---|---|---|
| 2005/0048467 | A1 | 3/2005 | Sastry et al. |
| 2005/0054820 | A1 | 3/2005 | Wu et al. |
| 2005/0277605 | A1 | 12/2005 | Wu et al. |
| 2007/0026076 | A1 | 2/2007 | Wu et al. |

FOREIGN PATENT DOCUMENTS

| | | | |
|---|---|---|---|
| WO | WO-89/12455 | | 12/1989 |
| WO | WO-92/05248 | | 4/1992 |
| WO | WO-93/20844 | | 10/1993 |
| WO | WO-94/04696 | | 3/1994 |
| WO | WO-94/29459 | | 12/1994 |
| WO | WO-95/17212 | | 6/1995 |
| WO | WO-96/36643 | | 11/1996 |
| WO | WO-97/03703 | | 2/1997 |
| WO | WO-97/06685 | | 2/1997 |
| WO | WO-97/41440 | | 11/1997 |
| WO | WO-98/20135 | | 5/1998 |
| WO | WO-98/23735 | | 6/1998 |
| WO | WO-98/32866 | | 7/1998 |
| WO | WO-98/48003 | | 10/1998 |
| WO | WO-99/07860 | | 2/1999 |
| WO | WO-99/07869 | | 2/1999 |
| WO | WO-99/42121 | | 8/1999 |
| WO | WO-99/42472 | | 8/1999 |
| WO | WO-99/58658 | | 11/1999 |
| WO | WO-99/65940 | | 12/1999 |
| WO | WO-01/29233 | | 4/2001 |
| WO | WO-02/09645 | | 2/2002 |
| WO | WO-02/12281 | | 2/2002 |
| WO | WO-02/061113 | A2 | 8/2002 |
| WO | WO-02/074920 | | 9/2002 |
| WO | WO-03/008543 | | 1/2003 |
| WO | WO-03/080111 | | 10/2003 |
| WO | WO-03/083052 | | 10/2003 |
| WO | WO-03/085085 | A2 | 10/2003 |
| WO | WO-2004/030636 | | 4/2004 |
| WO | WO/2004/060304 | * | 7/2004 |
| WO | WO-2004/098526 | | 11/2004 |
| WO | WO-2005/047501 | | 5/2005 |
| WO | WO-2005/081716 | | 9/2005 |
| WO | WO-2006/073970 | | 7/2006 |
| WO | WO-2006/081323 | | 8/2006 |
| WO | WO-2006/120474 | | 11/2006 |
| WO | WO-2007/027751 | | 3/2007 |
| WO | WO-2007/071997 | | 6/2007 |
| WO | WO-2009/007336 | | 1/2009 |

OTHER PUBLICATIONS

Whisstock, Quarterly review of Biophysics, 2003, 307-340.*
Oltersdorf et al., "Identification of Human Papillomavirus Type 16 E7 Protein by Monoclonal Antibodies," J. Gen. Virol., 68:2933-2938 (1987).
Aguiar et al., "Enhancement of the immune response in rabbits to a malaria DNA vaccine by immunization with a needle-free jet device," Vaccine, 20:275-280 (2001).
Anonymous: "E7 vaccine (NSC 723254)," Timeless Success Story, Online, XP002394109 (2002).
Anthony et al., "Priming of CD8 CTL Effector Cells in Mice by Immunizationwith a Stress-Protein-Influenza Virus Nucleoprotein Fusion Molecule," Vaccine, 17(4):373-383 (1999).
Asea et al., "Novel Signal Transduction Pathway Utilized by Extracellular HSP70," Journal of Biological Chemistry, 277(7):15028-15034 (2002).
Ausbel, et al., Current Protocols in Molecular Biology, John Wiley & Sons (1989).
Babiuk et al., " Immunization of animals: from DNA to the dinner plate," Veterinary Immunology and Immunopathology, 72:189-202 (1999).
Bancherau, J., "Dendritic Cells: Therapeutic Potentials," Transfus Sci., 18(2):313-326 (1997).
Banu et al., "Modulation of Haematopoietic Progenitor Development by FLT-3 Ligand," Cytokine, 11(9):679-688 (1999).

Barrios et al., "Mycobacterial heat-shock proteins as carrier molecules. II: The use of the 70-kDa mycobacterial heat-shock protein as carrier for conjugated vaccines can circumvent the need for adjuvants and *Bacillus* Calmette Guerin priming," Eur. J. Immunol., 22:1365-1372 (1992).
Basu et al., "Calreticulin, A Peptide-Binding Chaperone of the Endoplasmic Reticulum, Elicits Tumor- and Peptide-Specific Immunity," Journal of Experimental Medicine, 189(5):797-802 (1999).
Becker et al., "CD40, an extracellular receptor for binding and uptake of Hsp70-peptide complexes," Journal of Cell Biology, 158(7):1277-1285 (2002).
Beissbarth et al., "Increased efficiency of folding and peptide loading of mutant MHC class I molecules," Eur. J. Immunol., 30:1203-1213 (2000).
Bennett et al., "Calnexin Association Is Not Sufficient to Protect T Cell Receptor α Proteins from Rapid Degradation in CD4+CD8+ Thymocytes," The Journal of Biological Chemistry 273(37):23674-23680 (1998).
Benton et al., "DNA Vaccine Strategies for the Treatment of Cancer," Curr Top Microbiol Immunol., 226:1-20 (1998).
Bhoola et al., "Diagnosis and management of epithelial ovarian cancer," Obstet. Gynecol., 107(6):1399-1410 (2006).
Biragyn et al., "Genetic fusion of chemokines to a self tumor antigen induces protective, T-Cell dependent antitumor immunity," Nature Biotechnology, 17:253-258 (1993) Abstract.
Blachere et al., "Heat shock Protein-peptide complexes, Reconstituted in vitro, Elicit Peptide-specific cytotoxic T Lymphocyte Response and Tumor Immunity," J. Exp. Med., 186(8):1315-1322 (1997).
Blachere et al. "Heat shock proteins against cancer," J. of Immunotherapy Emphasis Tumor Immunol., 14:352-356 (1993).
Bohm et al., "Routes of plasmid DNA vaccination that prime murine humoral and cellular immune responses," Vaccine, 16:949-954 (1998).
Boyle et al. "Enhanced responses to a DNA vaccine encoding a fusion antigen that is directed to sites of immune induction," Nature, 392:408-411 (1998).
Bredenbeek et al., "Sindbis Virus Expression Vectors: Packaging of RNA Replicons by Using Defective Helper RNAs," Journal of Virology, 67(11):6439-6446 (1993).
Breitburd et al., "Human papillomavirus vaccines," Cancer Biology, 9:431-445 (1999).
Brossart et al., "Identification of HLA-A2-Restricted T-Cell Epitopes Derived From the MUC1 Tumor Antigen for Broadly Applicable Vaccine Therapies," Blood, 93(12):4309-4317 (1999).
Buck et al., "Efficient Intracellular Assembly of Papillomaviral Vectors," Journal of Virology, 78(2):751-757 (2004).
Bueler et al., "Induction of Antigen-Specific Tumor Immunity by Genetic and Cellular Vaccines against MACE: Enhanced Tumor Protection by Coexpression of Granulocyte-Macrophage Colony-Stimulating Factor and B7-1," Molecular Medicine, 2(5):545-555 (1996).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 111:2129-2138 (1990).
Carbonetti et al., "Intracellular Delivery of a Cytolytic T-Lymphocyte Epitope Peptide by Pertussis Toxin to Major Histocompatibioity Complex Class I without Involvement of the Cytosolic Class I Antigen Processing Pathway," Infection and Immunity 67(2):602-607 (1999).
Cavill et al., "Generation of a Monoclonal Antibody Against Human Calreticulin by Immunization with a Recombinant Calreticulin Fusion Protein: Application in Paraffin-Embedded Sections," Appl. Immunohistochemistry & Molecular Morphology 7(2):150-155 (1999).
Celluzzi et al., "Peptide-pulsed Dendritic Cells Induce Antigen-specific, CTL-mediated Protective Tumor Immunity," J. Exp. Med. 183:283-287 (1996).
Chang et al., "Cancer Immunotherapy Using Irradiated Tumor Cells Secreting Heat Shock Protein 70," Cancer Res., 67(20):10047-10057 (2007).

(56) References Cited

OTHER PUBLICATIONS

Chang, C-L. et al., "Control of human mesothelin-expressing tumors by DNA vaccines." Gene Therapy 1-10 (2007).
Chavin, K. et al., "Obesity Induces Expression of Uncoupling Protein-2 in Hepatocytes and Promotes Liver ATP Depletion." J. Biol. Chem. 274(9):5692-5700 (1999).
Chen, C-H. et al., "Antigen-specific immunotherapy for human papillomavirus 16 E7-expressing tumors grown in the liver." Journal of Hepatology 33:91-98 (2000).
Chen, C.-H. et al., "Boosting with recombinant vaccinia increases HPV-16 E7-specific T cell precursor frequencies of HPV-16 E7-expressing DNA vaccines," Vaccine, 18:2015-2022 (2000).
Chen et al., Design of a genetic immunotoxin to eliminate toxin immunogenicity, Gene Therapy, 2:116-123 (1992).
Chen, C-H et al., "Enhancement of DNA Vaccine Potency by Linkage of Antigen Gene to an HSP70 Gene," Cancer Research, 60(4):1035-1042 (2000).
Chen, C.-H. et al., "Gene gun-mediated DNA vaccination induces antitumor immunity against human papillomavirus type 16 E7-expressing murine tumor metastases in the liver and lungs." Gene Therapy, 6:1972-1981 (1999).
Chen et al., "Human pappillomavirus type 16 nucleoprotein E7 is a tumor rejection antigen," PNAS, 88:110-114 (1991).
Chen et al., "Induction of Cytotoxic T Lymphocytes Specific for a Syngeneic Tumor Expressing the E6 Oncoprotein of Human Papillomavirus Type 16," Journal of Immunology, 148:2617-2621 (1992).
Chen, W. et al., "Modulatory Effects of the Human Heat Shock Protein 70 on DNA Vaccination," J. Biomed. Sci., 7(5):412-419 (2000).
Chen et al., "Mycobacterial heat shock protein 65 enhances antigen cross-presentation in dendritic cells independent of Toll-like receptor 4 signaling," Journal of Leukocyte Biology, 75:260-266 (2004).
Chen, C-H. et al. "Recombinant DNA vaccines protect against tumors that are resistant to recombinant vaccinia vaccines containing the same gene." Gene Therapy, 8:128-138 (2001).
Cheng et al., "Bax-independent inhibition of apoptosis by Bcl-$x_L$," Nature, 379(8):554-556 (1996).
Cheng, W-F. et al., "CD8+ T cells, NK cells and IFN-γ are important for control of tumor with downregulated MHC class I expression by DNA vaccination." Gene Therapy 10:1311-1320, (2003).
Cheng, W-F. et al., "Cancer Immunotherapy Using Sindbis Virus Replicon Particles Encoding a VP22-Antigen Fusion." Human Gene Therapy. 13:553-568 (2002).
Cheng, W.-F., et al.; "Characterization of DNA Vaccines Encoding the Domains of Calreticulin for Their Ability to Elicit Tumor-Specific Immunity and Antiangiogenesis," Vaccine, 23(29):3864-3874 (2005).
Cheng, W-F. et al. "Enhancement of Sindbis Virus Self-Replicating RNA Vaccine Potency by Linkage of Herpes Simplex Virus Type 1 VP22 Protein to Antigen." Journal of Virology, 75(5): 2368-2376 (2001).
Cheng, W-F. et al. "Enhancement of Sindbis Virus Self-Replicating RNA Vaccine Potency by Linkage of *Mycobacterium tuberculosis* Heat Shock Protein 70 Gene to an Antigen Gene." Journal of Immunology, 166:6218-6226 (2001).
Cheng, W-F. et al., "Enhancement of Sindbis Virus Self-Replicating RNA Vaccine Potency by Targeting Antigen to Endosomal/Lysosomal Compartments." Human Gene Therapy 12:235-252 (2001).
Cheng, W-F. et al., "Repeated DNA Vaccinations Elicited Qualitatively Different Cytotoxic T Lymphocytes and Improved Protective Antitumor Effects." J Biomed Sci 9:675-687 (2002).
Cheng et al. (Report on Results of Monographic Study # NSC91-2314-B-002-377, National Taiwan University, National Scientific Committee, available to public Oct. 31, 2003).
Cho et al., "Enhanced cellular immunity to hepatitis C virus nonstructural proteins by codelivery of granulocyte macrophage-colony stimulating factor gene in intramuscular DNA immunization," Vaccine, 17:1136-1144 (1999).

Chow et al., "Development of Thi1 and Th2 Populations and the Nature of Immune Responses to Hepatitis B Virus DNA Vaccines Can Be Modulated by Codelivery of Various Cytokine Genes," The Journal of Immunology, 160(3):1320-1329 (1998).
Chu et al., "Cancer Immunotherapy Using Adjuvant-Free, Fusion Protein Encoding M. Golvis BCG HSP65 and HPV16 E7," FASEB Journal 12(5), Mar. 20, 1998 Abstract XP000960840.
Chu et al., Immunotherapy of a human papillomavirus (HPV) type 16 E7-expressing tumour by administration of fusion protein comprising *Mycobacterium bovis* bacille Calmette-Guerin (BGG) hsp65 and HPV 16 E7, Clin. Exp. Immunol., 121(2):216-225 (2000).
Ciupitu et al., "Immunization with a Lymphocytec Choriomeningitis Virus Peptide Mixed Heat Sbcok Protein 70 Results in Protective Antiviral Immunity and Specific Cytotoxic T Lymphocytes," J. Exp. Med., 187(5):685-691 (1998).
Corr et al., "Costimulation Provided by DNA Immunization Enhances Antitumor Immunity," The Journal of Immunology, 159(10):4999-5004 (1997).
Coukos et al., "Immunotherapy for gynaecological malignancies," Expert Opin. Biol. Ther., 5(9):1193-1210 (2005).
Crum et al., "Vaccines for Cervical Cancer," Cancer Journal from Scientific American, 9(5):368-376 (2003).
Davidoff et al., "Immune Response to P53 is Dependent upon P53/HSP70 Complexes in Breast Cancers," Proceedings of the National Academy of Sciences of USA, 89(8):3442 (1992).
Debinsky et al., "A Wide Range of Human Cancers Express Interleukin 4 (IL-4) Receptors That Can Be Targeted with Chimeric Toxin Composed of Il-4 and *Pseudomonas* Exotoxin," The Journal of Biological Chemistry, 268(19):14065-14070 (1993).
de Jong et al., "Enhancement of human papillomavirus (HPV) type 16 E6 and E7-specific T-cell immunity in healthy volunteers through vaccination with TA-CIN, an HPV16 L2E7E6 fusion protein vaccine," Vaccine, 20:3456-3464 (2002).
Devaraj, K. et al., "Development of HPV Vaccines for HPV-Associated Head and Neck Squamous Cell Carcinoma," Crit. Rev. Oral Biol. Med. 14(5):345-362, (2003).
Dialynas et al., "Characterization of the Murine T Cell Surface Molecule Designated L3T4, Identified by Monocolonal Antibody GK1.5: Similarity of L3T4 to the Human Leu-3/T4 Molecule," J. Immunol., 131(5):2445-2451 (1983).
Donnelly et al., "DNA Vaccines," Annual Review of Immunology, 15:617-48 (1997).
Donnelly et al., "DNA Vaccines: Progress and Challenges," J. Immunol., 175:633-639 (2005).
Donnelly et al., "Targeted delivery of peptide epitopes to class I major histocompatibility molecules by a modified *Pseudomonas* exotoxin," Proc. Natl. Acad. Sci. USA 90:3530-3534 (1993).
Drake et al., "Assessing tumor growth and distribution in a model of prostate cancer metastasis using bioluminescence imaging," Clin. Exp. Metastasis, 22:674-684 (2005).
Eggleton, P. and Llewellyn, D.H., "Pathophysiological Roles of Calreticulin in Autoimmune Disease," Scand. J. Immunol. 49:466-473 (1999).
Eiben et al., "Establishment of an HLA-a*0201 Human Papillovavrus Type 16 Tumor Model to Determine the Efficacy of Vaccination Strategies in HLA-A*0201 Transgenic Mice," Cancer Research, 62:5792-5799 (2002).
Eisenbraun et al., "Examination of parameters affecting the elicitation of humoral immune responses by particle bombardment-mediated genetic immunization," DNA Cell Biol., 12(9):791-797 (1993).
Elliott et al., "Intercellular trafficking and protein delivery by a herpesvirus structural protein," Cell, 88(2):223-233 (1997).
Elsaghier et al., "Localisation of Linear Epitopes at the Carboxy-Terminal End of the Mycobacterial 71 KDA Heat Shock Protein," Molecular Immunology 29(9):1153-1156 (1992).
Feltkamp et al., "Vaccination with cytotoxic T lymphocyte epitope-containing peptide protects against a tumor induced by human papillomavirus type 16-transformed cells," Eur. J. Immunol., 23(9):2242-2249 (1993).
Fernando et al., "Expression, purification and immunological characterization of the transforming protein E7, from cervical cancer-associated human papilloma virus type 16," Clin. Exp. Immunol., 115:397-403 (1999).

(56) References Cited

OTHER PUBLICATIONS

Flohe et al., "Human Heat Shock Protein 60 Induces Maturation of Dendritic Cells Versus a Th1-Promoting Phenotype," The Journal of Immunology, 170:2340-2348 (2003).
Fominaya et al., "Target Cell-specific DNA Transfer Mediated by a Chimeric Multidomain Protein," The Journal of Biological Chemistry, 271(18):10560-10568 (1996).
Fomsgaard et al., "Improved Humoral and Cellular Immune Responses Against the gp120 V3 Loop of HIV-1 Following Genetic Immunization with a Chimeric DNA Vaccine Encoding the V3 Inserted into the Hepatitis B Surface Antigen," Scand J. Immunol., 47(4):289-95 (1998).
Forni et al., "Cytokine gene-engineered vaccines," Curr. Opin. Mol. Ther. Feb;1(1):34-38 (Abstract) (1999).
Frydman et al., "Folding of nascent polypeptide chains in a high molecular mass assembly with molecular chaperones," Nature, 370:111-117 (1994).
Galloway, D.A., "Papillomavirus vaccines in clinical trials," Lancet Infect. Dis., 3(8):469-475 (2003).
Gao et al., "Immune response to human papillomavirus type 16 E6 gene in a live vaccinia vector," Journal of General Virology, 75:157-164 (1994).
Gavarasana et al., "Prevention of Carcinoma of Cervix with Human Papillomavirus Vaccine," Indian Journal of Cancer, 37:57-66 (2000).
Geissler et al., "Enhancement of Cellular and Humoral Immune Responses to Hepatitis C Virus Protein Using DNA Based Vaccines Augmented with Cytokine-Expressing Plasmids," The Journal of Immunology, 158(3):1231-1237 (1997).
Georgopoulos et al., "Role of the Major Heat Shock Proteins as Molecular Chaperones," Annu. Rev. Cell. Bio., 9:601-634 (1993).
Goletz et al., "Delivery of Antigens to the MHC Class I Pathway Using Bacterial Toxins," Human Immunology, 54:129-136 (1997).
Grandis et al., "Head and Neck Cancer: Meeting Summary and Research Opportunities," Cancer Research, 64:8126-8129 (2004).
Graner et al., "Immunoprotective Activities of Multiple Chaperone Proteins Isolated from Murine B-Cell Leukemia/Lymphoma," Clinical Cancer Research, 6:909-915 (2000).
Haas et al., "cDNA cloning of the immunoglobulin heavy chain binding protein," Proc. Natl. Acad. Sci. USA, 85:2250-2254 (1988).
Hannum et al., "Ligand for FLT3/FLK2 Receptor Tyrosine Kinase Regulates Growth of Haematopoietic Stem Cells and is Encoded by Variant RNAs," Nature 368:643-8 (1994).
Hansen et al., "Structural features of MHC class I molecules that might facilitate alternative pathways of presentation," Immunology Today, 21(2):83-88 (2000).
Harris et al., "Calreticulin and Calnexin Interact with Different Protein and Glycan Determinants During the Assembly of MHC Class I," The Journal of Immunology 160:5404-5409 (1998).
Hartl, F., "Molecular chaperones in cellular protein folding," Nature, 381:571-579 (1996).
Hasan et al., "Nucleic acid immunization: concepts and techniques associated with third generation vaccines," Journal of Immunological Methods, 229:1-22 (1999).
Hauser et al., "Secretory heat-shock protein as a dendritic cell-targeting molecule: a new strategy to enchance the potency of genetic vaccines,"Gene Therapy, 11:924-932 (2004).
He et al., "Viral Recombinant Vaccines to the E6 and E7 Antigens of HPV-16," Virology, 270:146-161 (2000).
Heikema et al., "Generation of heat shock protein-based vaccines by intracellular loading of gp96 with antigen peptides," Immunology Letters, 57(1-3):69-74 (1997).
Heller, J. et al., "Tetra-O-methyl Nordihydroguaiaretic Acid Induces G2 Arrest in Mammalian Cells and Exhibits Tumoricidal Activity in Vivo," Cancer Research 61:5499-5504, (2001).
Hendrick et al., "Molecular chaperone functions of heat-shock proteins," Annu. Rev. Biochem., 62:349-384 (1993).
Higgins et al., "Fast and Sensitive Multiple Sequence Alignments on a Microcomputer," Comput. Appl. Biosci. 5(2):151-153 (1989).
Hokey et al., "DNA vaccines for HIV: challenges and opportunities," Springer Semin. Immunopathol., 28(3):267-279 (2006).

Hope et al., "Flt-3 Ligand, in Combination with Bovine Granulocyte-Macrophage Colony-Stimulating Factor and Interleukin-4, Promotes the Growth of Bovine Bone Marrow Derived Dendritic Cells," Scand. J. Immunol., 51:60-66 (2000).
Hsieh, C.-J. et al., "Enhancement of vaccinia vaccine potency by linkage of tumor antigen gene to gene encoding calreticulin," Vaccine, 22:3993-4001 (2004).
Hsu, K.-F. et al., "Enhancement of suicidal DNA vaccine potency by linking *Mycobacterium tuberculosis* heat shock protein 70 to an antigen." Gene Therapy 8, 376-383 (2001).
Huang, C-H. et al. "Cancer Immunotherapy using a DNA vaccine encoding a single-chain trimer of MHC class I linked to an HPV-16 E6 immunodominant CTL epitope." Gene Therapy. 12:1180-1186 (2005).
Huang, C-C. et al., "Generation of Type-Specific Probes for the Detection of Single-Copy Human Papillomavirus by a Novel In Situ Hybridization Method," Mod. Pathol. 11(10):971-977 (1998).
Huang, C-C. et al., "HPV In Situ Hybridization with Catalyzed Signal Amplification and Polymerase Chain Reaction in Establishing Cerebellar Metastasis of a Cervical Carcinoma." Human Pathology, 30(5):587-591 (1999).
Huang, Q. et al., "In Vivo Cytotoxic T Lymphocyte Elicitation by Mycobacterial Heat Shock Protein 70 Fusion Proteins Maps to a Discrete Domain and Is CD4+ T Cell Independent," J. Exp. Med., 191(2):403-408 (2000).
Hung, C-F. et al. "A DNA vaccine encoding a single-chain trimer HLA-A2 linked to human mesothelin peptide generates anti-tumor effects against human mesothelin-expressing tumors." Vaccine 25:127-135 (2007).
Hung, C-F. et al., "Cancer Immunotherapy Using a DNA Vaccine Encoding the Translocation Domain of a Bacterial Toxin Linked to a Tumor Antigen." Cancer Research 61: 3698-3703 (2001).
Hung, C-F. et al., "Control of mesothelin-expressing ovarian cancer using adoptive transfer of mesothelin peptide-specific CD8+ T cells." Gene Therapy, pp. 1-9 (2007).
Hung et al., "Control of mesothelin-expressing ovarian cancer using adoptive transfer of mesothelin peptide-specific CD8+ T cells," Gene Therapy, 14(12):921-929 (2007).
Hung, C-F. et al., "DNA Vaccines Encoding Ii-PADRE Generates Potent PADRE-specific CD4+ T-Cell Immune Responses and Enhances Vaccine Potency." Mol. Ther. 15(6):1211-1219 (2007).
Hung, C-F. et al., "Enhancement of DNA Vaccine Potency by Linkage of Antigen Gene to a Gene Encoding the Extracellular Domain of Fms-like Tyrosine Kinase 3-Ligand." Cancer Research 61:1080-1088, (2001).
Hung, C-F. et al., "Enhancing Major Histocompatibility Complex Class I Antigen Presentation by Targeting Antigen to Centrosomes," Cancer Research, 63:2393-2398 (2003).
Hung, C-F., et al., "Improving DNA Vaccine Potency by Linking Marek's Disease Virus Type 1 VP22 to an Antigen," Journal of Virology, 76(6):2676-2682 (2002).
Hung, C-F. et al., "Improving DNA vaccine potency via modification of professional antigen presenting cells." Current Opinion in Molecular Therapeutics, 5(1):20-24 (2003).
Hung et al., "Improving vaccine potency through intercellular spreading and enhanced MHC class I presentation of antigen," J. Immunology, 166(9):5733-5740 (2001).
Hung, C-F. et al., "Modifying professional antigen-presenting cells to enhance DNA vaccine potency," Methods in Molecular Medicine, 127:199-220 (2006).
Hung, C-F. et al., "Vaccinia virus preferentially infects and controls human and murine ovarian tumors in mice." Gene Therapy. 14:20-29 (2007).
Hunt et al., "Characterization and sequence of a mouse hsp70 gene and its expression in mouse cell lines," Gene, 87(2):199-204 (1990).
Hunt et al., "Conserved features of eurkaryotic hsp70 genes revealed by comparison with the nucleotide sequence of human hsp70," Proc. Natl. Acad. Sci. USA, 82:6455-6459 (1985).
Indraccolo et al., "Generation of expression plasmids for angiostatin, endostatin and TIMP-2 for cancer gene therapy," Int. J. Biological Markers, 14(4):251-256 (1999) (Abstract).

(56) References Cited

OTHER PUBLICATIONS

Iwasaki et al., "Enhanced CTL Responses Mediated by Plasmid DNA Immunogens Encoding Costimulatory Molecules and Cytokines," The Journal of Immunology, 158(10):4591-4601 (1997).

Jaffee et al., "Novel allogeneic granulocyte-macrophage colony-stimulating factor-secreting tumor vaccine for pancreatic cancer: a phase I trial of safety and immune activation," J. Clin. Oncol., 19(1):145-156 (2001).

Jager et al., "Simultaneous Humoral and Cellular Immune Response against Cancer-Testis Antigen NY-ESO-1: Definition of Human Histocompatibility Leukocyte Antigen (HLA)-A2-binding Peptide Epitopes," J. Exp. Med., 187:265-270 (1998).

Janetzki et al., "Generation of Tumor-Specific Cytotoxic T Lymphocytes and Memory T Cells by Immunization with Tumor-Derived Heat Shock Protein gp96," Journal of Immunotherapy, 21(4):269-276 (1998).

Jenkins et al., "Bioluminescent Imaging (BLI) to Improve and Refine Traditional Murine Models of Tumor Growth and Metastasis," Clin. Exp. Metastatis, 20(8):733-744 (2003).

Ji, H et al., "Antigen-Specific Immunotherapy for Murine lung Metastatic Tumors Expressing Human Papillomavirus Type 16 E7 Oncoprotein." Int. J. Cancer: 78, 41-45 (1998).

Ji, H et al., "Targeting Human Papillomavirus Type 16 E7 to the Endosomal/Lysosomal Compartment Enhances the Antitumor Immunity of DNA Vaccines against Murine Human Papillomavirus Type 16 E7-Expressing Tumors," Human Gene Therapy 10:2727-2740 (1999).

Jinno et al., "Domain II Mutants of Pseudomonas Exotoxin Deficient in Translocation," J. Biol. Chem., 264(7):15953-15959 (1989).

Kadkol, S. et al., Chapter 5: "In Situ Hybridization in Cancer and Normal Tissue," Methods in Molecular Biology, Tumor Suppressor Genes, vol. II, Edited by W. El-Deiry, Humana Press Inc., Totowa, NJ., 223:51-72 (2003).

Kang, T. et al., "Enhancing dendritic cell vaccine potency by combining a BAK/BAX siRNA-mediated antiapoptotic strategy to prolong dendritic cell life with an intracellular strategy to target antigen to lysosomal compartments." Int. J. Cancer, 120:1696-1703 (2007).

Kerbel, Robert S., "Tumor angiogenesis: past, present and the near future," Carcinogenesis 21(3):505-515 (2000).

Kim et al., "Co-transfection with cDNA encoding the Bcl family of anti-apoptotic proteins improves the efficiency of transfection in primary fetal neural stem cells," J. Neuroscience Methods, 117(2):153-158 (2002).

Kim et al., "Cytokine Molecular Adjuvants Modulate Immune Responses Induced by DNA Vaccine Constructs for HIV-1 and SIV," Journal of Interferon and Cytokine Research, 19(1):77-84 (1999).

Kim, J. et al., "Comparison of HPV DNA vaccines employing intracellular targeting strategies." Gene Therapy, 11:1011-1018 (2004).

Kim, T. et al., "A DNA Vaccine Co-Expressing Antigen and an Anti-Apoptotic Molecule Further Enhances the Antigen-Specific CD8+ T-Cell Immune Response." J. Biomed. Sci. 11:493-499 (2004).

Kim, T. et al., "DNA Vaccines Employing Intracellular Targeting Strategies and a Strategy to Prolong Dendritic Cell Life Generate a Higher Number of CD8+Memory T Cells and Better Long-Term Antitumor Effects Compared with a DNA Prime-Vaccinia Boost Regimin." Human Gene Therapy 16:26-34 (2005).

Kim, T. et al., "Enhancement of suicidal DNA vaccine potency by delaying suicidal DNA-induced cell death." Gene Therapy. 11:336-342. (2004).

Kim, T. et al., "Enhancement of DNA Vaccine Potency by Coadministration of a Tumor Antigen Gene and DNA Encoding Serine Protease Inhibitor-6." Cancer Research. 64:400-405 (2004).

Kim, T. et al., Enhancing DNA vaccine potency by coadministration of DNA encoding antiapoptotic proteins. J. Clin. Invest. 112:109-117 (2003).

Kim, T. et al., "Enhancing DNA Vaccine Potency by Combining a Strategy to Prolong Dendritic Cell Life with Intracellular Targeting Strategies." The Journal of Immunology, 171:2970-2976, (2003).

Kim, T. et al., "Generation and Characterization of DNA Vaccines Targeting the Nucleocapsid Protein of Severe Acute Respiratory Syndrome Caronavirus." Journal of Virology, 78(9):4638-4645. (2004).

Kim, T. et al. "Modification of Professional Antigen-Presenting Cells with Small Interfering RNA in vivo to Enhance Cancer Vaccine Potency." Cancer Res. 65(1):309-316 (2005).

Kim, D. et al., "Monitoring the Trafficking of Adoptively Transferred Antigen-Specific CD8-Positive T Cells in Vivo, Using Noninvasive Luminescence Imaging." Human Gene Therapy. 18: 1-14 (2007).

Kim, T. et al., "Vaccination with a DNA Vaccine Encoding Herpes Simplex Type 1 VP22 Linked to Antigen Generates Long-Term Antigen-Specific CD8-Positive memory T Cells and Protective Immunity." Human Gene Therapy. 15:167-177. (2004).

King et al., "DNA vaccines with single-chain Fv fused to fragment C of tetanus toxin induce protective immunity against lymphoma and myeloma," Nature Medicine, 4(11):1281-1286 (1998).

Kita et al., "Frequent Gene Expression of Granulocyte Colony-Stimulating Factor (G-CSF) Receptor in CD7+ Surface CD3—Acute Lymphoblastic Leukaemia," Leukemia, 7(8):1184-1190 (1993).

Klinman et al., "Contribution of CpG Motifs to the Immunogenicity of DNA vaccines," The Journal of Immunology, 158(8):3635-3639 (1997).

Konen-Waisman et al., "Self and Foreign 60-Kilodalton Heat Shock Protein T Cell Epitope Peptides Serve As Immunogenic Carriers for a T Cell-Independent Sugar Antigen," J. Immunology, 154:5977-5985 (1995).

Konishi et al., "Japanese encephalitis DNA vaccine candidates expressing premembrane and envelope genes induce virus-specific memory B cells and long-lasting antibodies in swine," Virology, 268(1):49-55 (2000).

Koo et al., "The Nk-1.1(−) Mouse: A Model to Study Differentiation of Murine NK Cells," J. Immunol. 125:2665-2672 (1986).

Lafond-Walker, A. et al., "Inducible Nitric Oxide Synthase Expression in Coronary Arteries of Transplanted Human Hearts with Accelerated Graft Arteriosclerosis." American Journal of Pathology, 151(4): 919-925 (1997).

Larregina et al., "Pattern of cytokine receptors expressed by human dendritic cells migrated from dermal explants," Immunology, 91:303-313 (1997).

Lazar et al., "Transforming Growth Factor α: Mutation of Aspartic Acid 47 and Leucine 48 Results in Different Biological Activities," Mol. Cell Biol., 8(3):1247-1252 (1988).

Lee et al., "DNA inoculations with HIV-1 recombinant genomes that express cytokine genes enhance HIV-1 specific immune responses," Vaccine, 17:473-479 (1999).

Lee et al., "Optimal Induction of Hepatitis C Virus Envelope-Specific Immunity by BiCistronic Plasmid DNA Inoculation with the Granulocyte-Macrophage Colony-Stimulating Factor Gene," Journal of Virology, 72(10):8430-8436 (1998).

Leitner et al., "DNA and RNA-Based Vaccines: Principles, Progress and Prospects," Vaccine 18(9-10):765-777 (1999).

Lemon et al., "Subcutaneous administration of inactivated hepatitis B vaccine by automatic jet injection," J. Med. Virol., 12(2):129-136 (1983).

Li et al., "Roles of heat-shock proteins in antigen presentation and cross-presentation," Curr. Opin. Immunol., 14(1):45-51 (2002).

Liaw, K. et al., "Human papillomavirus and cervical neoplasia: a case-control study in Taiwan." Int. J. Cancer. 62(5):565-71 (1995).

Lim et al., "Vaccination with an ovalbumin/interleukin-4 fusion DNA efficiently induces Th2 cell-mediated immune responses in an ovalbumin-specific manner," Arch. Pharm. Res., 21(5):537-542 (Abstract) (1998).

Lin, C-T. et al., "Boosting with Recombinant Vaccinia Increases HPV-16 E7-Specific T Cell Precursor Frequencies and Antitumor Effects of HPV-16 E7-Expressing Sindbis Virus Replicon Particles." Molecular Therapy. 8(4):559-566 (2003).

Lin, K.Y. et al., "Coinfection of HPV-11 and HPV-16 in a case of Laryngeal Squamous Papillomas With severe Dysplasia." Laryngoscope. 107(7):942-947 (1997).

Lin, K-Y. et al., "Ectopic Expression of Vascular Cell Adhesion Molecule-1 as a New Mechanism for Tumor Immune Evasion." Cancer. Res. 67(4):1832-1841 (2007).

(56) References Cited

OTHER PUBLICATIONS

Lin, K-Y. et al., "Treatment of Established Tumors with a Novel Vaccine That Enhances Major Histocompatibility Class II Presentation of Tumor Antigen." Cancer Research 56:21-26 (1996).
Lin, Y-Y. et al., "Vaccines against human papillomavirus." Frontiers in Bioscience. 12:246-264 (2007).
Ling, M. et al., "Preventive and Therapeutic Vaccines for Human Papillomavirus-Associated Cervical Cancers." J Biomed Sci 7:341-356 (2000).
Liu et al., "The emerging role of IL-15 in NK-cell development," Immunology Today, 21(3):113-116 (2000).
Liu et al., "Recombinant Adeno-Associated Virus Expressing Human Papillomavirus Type 16 E7 Peptide DNA Fused with Heat Shock Protein DNA as a Potential Vaccine for Cervical Cancer," Journal of Virology, 2888-2894 (2000).
Luke et al., "An OspA-based DNA vaccine protects mice against infection with *Borrelia burgdorferi*," J. Infect. Dis., 175(1):91-97 (1997).
Lyras and Rood, "Genetic Organization and Distribution of Tetracycline Resistance Determinants in *Clostridium perfringens*," Antimicrobial Agents and Chemotherapy 40:2500-2504 (1996).
Maecker et al., "DNA vaccination with cytokine fusion constructs biases the immune response to ovalbumin," Vaccine, 15(15):1687-1696 (Abstract) (1997).
Maki et al., "Human homologue of murine tumor rejection antigen pg96: 5'-Regulatory and coding regions and relationship to stress-induced proteins," Proc. Natl. Acad. Sci. USA, 87:5658-5662 (1990).
Mao, C-P. et al., "Immunological research using RNA interference technology." Immunology, 121:295-307 (2007).
Mao, C-P. et al. "Immunotherapeutic strategies employing RNA interference technology for the control of cancers." Journal of Biomedical Science 14:15-29 (2007).
Maraskovsky et al., "Dramatic Increase in the Numbers of Funtionally Mature Dendritic Cells in Flt-3 Ligand-treated Mice: Multiple Dendritie Cell Subpopulations Identified," J. Exp. Med., 184:1953-1962 (1996).
Massa et al., "Enhanced Efficacy of Tumor Cell Vaccines Transfected with Secretable hsp70," Cancer Research, 64:1502-1508 (2004).
McCluskie, et al., "Route and Method of Delivery of DNA Vaccine Influence Immune Responses in Mice and Non-Human Primates," Mol. Med. 5:287-300 (1999).
McKenzie et al., "Sequence and Immunogenicity of the 70-kDa Heat Shock Protein of *Mycobacterium leprae*," J. Immunol., 147(1):312-319 (1991).
Meinkoth et al., "Hybridization of nucleic acids immobilized on solid supports," Anal. Biochem., 138(2):267-284 (1984).
Meneguzzi et al., "Immunization against Human Papillomavirus Type 16 Tumor Cells with Recombinant Vaccinia Viruses Expressing E6 and E7," Virology, 181:62-69 (1991).
MHC Class-I Binding Peptide Prediction Results for the Maltose Binding Protein of Vector pMAL used in D8, using ProPred-I (http://www.imtech.res.in/raghava/propred1/) (2007).
Michel, N., et al., "Enhanced Immunogenicity of HPV 16 E7 Fusion Proteins in DNA Vaccination," Virology, 294:47-59 (2002) XP002201708.
Michel, N. et al., "Improved Immunogenicity of Human Papillomavirus Type 16 E7 DNA After Fusion to the Herpes Simplex Virus 1 VP22 Gene"; Barcelona, Spain, 23-28, Jul. 2000, Abstract, 458, XP002201712.
Mikayama et al., "Molecular cloning and functional expression of a cDNA encoding glycosylation-inhibiting factor," PNAS, 90:10056-10060 (1993).
Mold, D. et al., "Four Classes of HERV-K Long Terminal Repeats and Their Relative Promoter Strengths for Transcription." J Biomed Sci 4:78-82 (1997).
Molinari and Helenius, "Chaperone Selection During Glycoprotein Translocation into the Endoplasmic Reticulum," Science, 288(5464):331 (2000).
Moniz, M. et al., "HPV DNA Vaccines," Frontiers in Bioscience 8, d55-68, (2003).

More et al., "Activation of cytotoxic T cells in vitro by recombinant gp96 fusion proteins irrespective of the 'fused' antigenic peptide sequence," Immunol. Lett., 69(2):275-282 (1999).
Mrsny et al., "Mucosal administration of a chimera composed of *Pseudomonas exotoxin* and the gp120 loop sequence of HIV-1 induces both salivary and serum antibody responses," Vaccine, 17:1425-1433 (1999).
Nair et al., "Calreticulin Displays in Vivo Peptide-Binding Activity and Can Elicit CTL Responses Against Bound Peptides," Journal of Immunology 162(11):6426-5432 (1999).
Nakano et al., "Immunization with Plasmid DNA Encoding Hepatitis C Virus Envelope E2 Antigenic Domains Induces Antibodies Whose Immune Reactivity Is Linked to the Injection Mode," Journal of Virology 71:7101-7109 (1997).
Nawrocki, S. and Mackiewicz, A., "Genetically modified tumour vaccines—where we are today," Cancer Treatment Reviews 25:29-46 (1999).
Nguyen et al., "A Mutant of Human Papillomavirus Type 16 E6 Deficient in Bindong α-Helix Partners Displays Reduced Oncogenic Potential in Vivo," Journal of Virology, 76(24):13039-13048 (2002).
Nicchitta, C.V. and Reed, R.C., "The immunological properties of endoplasmic reticulum chaperones: a conflict of interest?," Essays in Biochemistry 36:15-25 (2000).
Noessner et al., "Tumor-Derived Heat Shock Protein 70 Peptide Complexes Are Cross-Presented by Human Dendritic Cells," The Journal of Immunology, 169:5424-5432 (2002).
Ockert et al., "Advances in Cancer Immunotherapy Symposium, Dresden, Germany," Immunology Today 20(2):63-65 (1999). Abstract.
Ohtsuka, K., "Cloning of a cDNA for heat-shock protein hsp40, a human homologue of bacterial DnaJ," Biochem. Biophys. Res. Commun., 197(1):235-240 (1993).
Okada et al., "Intranasal Immunization of a DNA Vaccine with IL-12- and Granulocyte-Macrophage Colony-Stimulating Factor (GM-CSF)-Expressing Plasmids in Lipsomes Induces Strong Mucosal and Cell Mediated Immune Responses Against HIV-1 Antigens," The Journal of Immunology, 159(7):3638-3647 (1997).
Operschall et al., "Enhanced protection against viral infection by co-administration of plasmid DNA coding for viral antigen and cytokines in mice," Journal of Clinical Virology, 13:17-27 (1999).
Ozols, RF., "Systemic therapy for ovarian cancer: current status and new treatments," Semin. Oncol., 33:53-11 (2006).
Pai, S I et al., "Prospects of RNA interference therapy for cancer." Gene Therapy. 13:464-477 (2006).
Pan et al., "A recombinant Listeria Monocytogenes Vaccine Expressing a Model Tumour Antigen Protects Mice Against Lethal Tumour Cell Challenge and Causes Regression of Established Tumours," Nature Medicine, 1(5):471-7 (1995).
Pan et al., "Regression of Established Tumors in Mice Mediated by the Oral Administration of a Recombinant Listeria monocytogenes Vaccine," Cancer Research, 55(21):4776-4779 (1995).
Pardoll et al., "Exposing the Immunology of Naked DNA Vaccines," Immunity, 3:165-169 (1995).
Pejawar-Gaddy et al., "Cancer vaccines: accomplishments and challenges," Crit. Rev. Oncol. Hematol., 67(2):93-102 (2008).
Peng et al., "A combination of DNA vaccines targeting human papillomavirus type 16 E6 and E7 generates potent antitumor effects." Gene Therapy. 13:257-265 (2006).
Peng, S. et al., "Characterization of HLA-A2-restricted HPV-16 E7-specific CD8+ T-cell immune responses induced by DNA vaccines in HLA-A2 transgenic mice." Gene Therapy. 13:67-77 (2006).
Peng, S., et al.; "Characterization of HPV16-E6 DNA vaccines employing intracellular targeting and intercellular spreading strategies;" Journal of Biomedical Science, 12:689-700 (2005).
Peng, S. et al., "Development of a DNA Vaccine targeting Human Papillomavirus Type 16 Oncoprotein E6." Journal of Virology. 78(16):8468-8476. (2004).
Peng et al., "Efficient delivery of DNA vaccines using human papillomavirus pseudovirions," Gene Therapy, 17(12):1453-1464 (2010).
Peng, S. et al., "HLA-DQB1*02—restricted HPV-16 E7 Peptide-Specific CD4+ T-Cell Immune Responses Correlate with Regression of HPV-16-Associated High-Grade Squamous Intraepithelial Lesions." Clin. Cancer Res. 13(8):2479-2487 (2007).

(56) References Cited

OTHER PUBLICATIONS

Peng, S. et al., "Vaccination with Dendritic Cells Transgected with BAK and BAX siRNA Enhances Antigen-Specific Immune Responses by Prolonging Dendritic Cell Life." Human Gene Therapy 16:584-593 (2005).

Peoples et al., "Vaccine Implications of Folate Binding Protein, a Novel Cytotoxic T Lymphocyte-recognized Antigen System in Epithelial Cancers," Clinical Cancer Research, 5:4214-4223 (1999).

Pfisterer et al., "Management of platinum-sensitive recurrent ovarian cancer," Semin. Oncol., 33:512-516 (2006).

Przepiorka et al., "Heat shock protein peptide complexes as Immunotherapy for human cancer," Molecular Medicine Today (Reviews), 4(11):478-484 (1998).

Ramos-Soriano, A. et al., "Enteric pathogens associated with gastrointestinal dysfunction in children with HIV infection." Molecular and Cellular Probes 10: 67-73 (1996).

Rashid, A. et al., "Mitochondria Proteins That Regulate Apoptosis and Necrosis Are Induced in Mouse Fatty Liver." Hepatology 29:1131-1138 (1999).

Ray et al., "Apoptosis Induction in Prostate Cancer Cells and Xenografts by Combined Treatment with APO2 Ligand/Tumor Necrosis Factor-related apoptosis-inducing Ligand and CPT-11," Cancer Research, 63:4713-4723 (2003).

Robinson et al., "DNA Vaccines," Seminars in Immunology, 9(5):271-283 (1997).

Roby et al., "Development of a syngeneic mouse model for events related to ovarian cancer," Carcinogenesis, 21(4):585-591 (2000).

Roden, R. et al. "The impact of preventative HPV Vaccination," Discovery Medicine, 6(35):175-181 (2006).

Roden, R. et al., "Vaccination to Prevent and Treat Cervical Cancer." Human Pathology. 35(8): 971-982. (2004).

Roden and Wu, "How will HPV vaccines affect cervical cancer?" Nature Reviews, 6:753-763 (2006).

Rodriguez et al., "DNA Immunization with Minigenes: Low Frequency of Memory Cytotoxic T Lymphocytes and Inefficient Antiviral Protection Are Rectified by Ubiquitination," Journal of Virology, 72(6):5174-5181 (1998).

Rogers et al., "Multistage Multiantigen Heterologous Prime Boost Vaccine for *Plasmodium knowlesi* Malaria Provides Partial Protection in Rhesus Macaques," Infection and Immunity, 69(9):5565-5572 (2001).

Rouse et al., "Induction in Vitro of Primary Cytotoxic T-Lymphocyte Responses with DNA Encoding Herpes Simplex Virus Proteins," Journal of Virology, 68(9):5685-5689 (1994).

Sanchez-Perez et al., "Killing of Normal Melanocytes, Combined with Heat Shock Protein 70 and CD4OL Expression, Cures Large Established Melanomas," The Journal of Immunology, 177:4168-4177 (2006).

Sarmiento et al., "IgCx or IgM Monoclonal Antibodies Reactive with Different Determinants of the Molecular Complex Bearing LYT 2 Antigen Block T Cell Mediated Cytolysis in the Absence of Complement," J. Immunol., 125(6):2665-2672 (1980).

Sasaki et al., "Adjuvant formulations and delivery systems for DNA vaccines," Methods, 31(3):243-254 (2003).

Schultes et al., "Monitoring of immune responses to CA125 with IFN-gamma ELISPOT assay," J. Immunol. Methods, 279:1-15 (2003).

Schutze-Redelmeier et al., "Introduction of Exogenous Antigens into the MHC Class I Processing and Presentation Pathway by *Drosophila* Antennapedia Homeodomain Primes Cytotoxic T Cells in Vivo," Journal of Immunology 157:650-655 (1996).

Serody et al., "T Cell Activity After Dendritic Cell Vaccination Is Dependent on Both the Type of Antigen and the Mode of Delivery," J. Immunology, 164(9):4961-4967 (2000).

Shalinsky et al., "Marked Antiangiogenic and Antitumor Efficacy of AG3340 in Chemoresistant Human Non-Small Cell Lung Cancer Tumors: Single Agent and Combination Chemotherapy Studies," Clincal Cancer Research 5:1905-1917 (1999).

Sheikh et al., "Guns, genes, and spleen: a coming of age for rational vaccine design," Methods, 31(3):183-192 (2003).

Sin et al., "Enhancement of protective humoral (Th2) and cell mediated (Th1) immune responses against herpes simplex virus-2 co-delivery of granulocyte-macrophage colony-stimulating factor expression cassettes," Eur. J. Immunol., 28:3530-3540 (1998).

Sin, J.I., "Human papillomavirus vaccines for the treatment of cervical cancer," Expert Review Vaccines, 5(6):783-792 (2006).

Smahel et al., "DNA vaccine against oncogenic hamster cells transformed by HPV16 E6/E7 oncogenes and the activated *ras* oncogene," Oncology Reports, 6:211-215 (1999).

Smahel et al., "Immunisation with modified HPV16 E7 genes against mouse oncogenic TC-1 cell sublines with downregulated expression of MHC class I molecules," Vaccine, 21:1125-1136 (2003).

Srivastava et al., "Evidence for Peptide-Chaperoning by the Endoplasmic Reticular Heat Shock Protein GP96: Implications for Vaccination Against Cancer and Infectious Diseases," J. Cell. Biochem. Suppl. 17D:94 (Abstract NZ 014) (1993).

Srivastava et al., "Heat Shock Proteins Come of Age: Primitive Functions Acquire New Roles in an Adaptive World," Immunity, 8:657-665 (1998).

Srivastava, P., "Interaction of heat shock proteins with peptides and antigen presenting cells: chaperoning of the innate and adaptive immune responses," Annu. Rev. Immunol., 20:395-425 (2002).

Srivastava et al., "5'-Structural analysis of genes encoding polymorphic antigens of chemically induced tumors," Proc. Natl. Acad. Sci. USA, 84:3807-3811 (1987).

Srivastava et al., "The Serologically Unique Cell Surface Antigen of Zajdela Ascitic Heptoma is also its Tumor-Associated Transplantation Antigen," Int. J. Cancer, 33:417-422 (1984).

Srivastava et al., "Tumor rejection antigens of chemically induced sarcomas of inbred mice," Proc. Natl.-Acad. Sci. USA, 83:3407-3411 (1986).

Steinman et al., "The Sensitization Phase of T-Cell-mediated Immunity," Annals of the New York Academy of Sciences, 546:80-90 (1988).

Stevenson et al., "Idiotypic DNA Vaccines Against B-cell Lymphoma," Immunological Reviews, 145:211-228 (1995).

Suto et al., "A Mechanism for the Specific Immunagenicity of Heat Shcck Protein-Chaperoned Peptides," Science, 269:1585-1588 (1995).

Suzue et al., "Adjuvant-Free HSP70 Fusion Protein System Elicits Humoral and Cellular Immune Responses to HIV-1," Journal of Immunology 156:873-879 (1996).

Suzue et al., "Heat shock fusion proteins as vehicles for antigen delivery into the major histocompatibility complex class I presentation pathway," Proc. Natl. Acad. Sci. USA 94:13146-13151 (1997).

Syrengelas et al., "DNA immunization induces protective immunity against B-cell lymphoma," Nature Medicine, 2(9):1038-1041 (1996).

Szymczak et al., "Correction of multi-gene deficiency in vivo using a single 'self-cleaving' 2A peptide-based retroviral vector," Nat. Biotechnol., 22(5):589-594 (2004).

Tamura et al., "Immunotherapy of Tumors with Autologous Tumor-Derived Heat Shock Protein Preparations," Science, 278:117-120 (1997).

Theriault et al., "Extracellular HSP70 binding to surface receptors present on antigen presenting cells and endothelial/epithelial cells," FEBS Lett., 579(9):1951-1960 (2005).

Thomas et al., "Mesothelin-specific CD8+ T Cell Responses Provide Evidence of In Vivo Cross-Priming by Antigen-Presenting Cells in Vaccinated Pancreatic Cancer Patients," J. Exp. Med., 200(3):297-306 (2004).

Thornburg et al., "Induction of Cytotoxic T Lymphocytes With Dendritic Cells Transfected With Human Papillomavirus E6 and E7 RNA: Implications for Cervical Cancer Immunotherapy," Journal of Immunotherapy, 23(4):412-418 (2000).

Ting et al., "Human gene encoding the 78,000-dalton glucose-regulated protein and its pseudogene: structure, conservation, and regulation," DNA, 7(4):275-286 (1988).

Tobery et al., "Targeting of HIV-1 antigen for rapid intracellular degradation enhances cytotoxic T lymphocyte (CTL) recognition and the induction of De Novo CTL responses in Vivo after immunization," J. Exp. Med., 185(5):909-920 (1997).

(56) References Cited

OTHER PUBLICATIONS

Tomson, T. et al. "Human papillomavirus vaccines for the prevention and treatment of cervical cancer." Current Opinion in Investigational Drugs, 5(12):1247-1261. (2004).
Torres et al., "Differential Dependence on Target Site Tissue for Gene Gun and Intramuscular DNA Immunizations," The Journal of Immunology 158:4529-4532 (1997).
Trimble, C. et al., "Comparison of the CD8+ T cell responses and antitumor effects generated by DNA vaccine administered through gen gun, biojector and syringe," Vaccine. 21:4036-4042 (2003).
Trimble C, et al., "Spontaneous Regression of High-Grade Cervical Dysplasia: Effects of Human Papillomavirus Type and HLA Phenotype." Clin. Cancer Res. 11(13):4717-4723 (2005).
Trompeter, Hans-Ingo et al., "Variable Nuclear Cytoplasmic Distribution of the 11.5-kDa Zinc-binding Protein (Parathymosin-α) and Identification of a Bipartite Nuclear Localization Signal," The Journal of Biological Chemistry 271(2):1187-1193 (1996).
Trujillo, J. et al., "Characterization of human papillomavirus type 57b: transforming activity and comparative sequence analysis as probes for biological determinants associated with high-risk oncogenic viruses." Virus genes. 12(2):165-78 (1996).
Tsen, S-W. et al., "Enhancing DNA Vaccine Potency by Modifying the Properties of Antigen-Presenting Cells," Expert Review of Vaccines, 6(2):227-239 (2007).
Tseng et al., "Systemic tumor targeting and killing by Sindbis viral vectors," Nature Biotechnology, 22(1):70-77 (2004).
Tseng et al., "Using Sindbis Viral Vectors for Specific Detection and Suppression of Advanced Ovarian Cancer in Animal Models," Cancer Research, 64:6684-6692 (2004).
Tuting et al., "Autologous Human Monocyte-Derived Dendritic Cells Genetically Modified to Express Melanoma Antigens Elicit Primary Cytotoxic T Cell Responses In Vitro: Enhancement by Cotransfection of Genes Encoding the Th1-Biasing Cytokines IL-12 and IFN-$α^1$," Journal of Immunology 160:1139-1147 (1998).
Udono et al., "Cellular requirements for tumor-specific immunity elicited by hear shock proteins: Tumor rejection antigen gp96 primes CD8+ T cells in vivo," Proc. Natl. Acad. Sci. USA, 91:3077-3081 (1994).
Udono et al., "Comparison of Tumor specific immunogenicities of stress-induced proteins gp96, hsp90, and hsp70'," The Journal of Immunology, 152(11):5398-5403 (1994).
Udono et al., "Heat Shock Protein 70-associated Peptides Elicit Specific Cancer Immunity," J. Exp. Med., 178:1391-1396 (1993).
Ulmer et al., "Presentation of an exogenous antigen by major histocompatibility complex class I molecules," Eur. J. Immunol., 24:1590-1596 (1994).
van der Burg et al., "Pre-clinical safety and efficacy of TA-CIN, a recombinant HPV16 L2E6E7 fusion protein vaccine, in homologous and heterologous prime-boost regimens," Vaccine, 19:3652-3660 (2001).
Vu, K. et al., "Cellular Proliferation, Estrogen Receptor, Progesterone Receptor, and bcl-2 Expression in GnRH Agonist-Treated Uterine Leiomyomas." Human Pathology 29:359-363 (1998).
Wang et al., "CD40 Is a Cellular Receptor Mediating Mycobacterial Heat Shock Protein 70 Stimulation of CC-Chemokines," Immunity, 15:971-983 (2001).
Wang et al., "A Single Amino Acid Determines Lysophospholipid Specificity of the $S1P_1$ (EDG1) and $LPA_1$ (EDG2) Phospholipid Growth Factor Receptors," The Journal of Biological Chemistry, 276(52):49213-49220 (2001).
Wang, T-L. et al., "Intramuscular administration of E7-transfected dendritic cells generates the most potent E7-specific anti-tumor immunity." Gene Therapy 7:726-733 (2000).
Weiss et al., "A plasmid encoding murine granulocyte-macrophage colony-stimulating factor increases protection conferred by a malaria DNA vaccine," The Journal of Immunology, 161(5):2325-2332 (1998).
Whisstock et al., "Prediction of protein function from protein sequence and structure," Quarterly Reviews of Biophysics, 3:307-340 (2003).
Whittall et al., "Interaction between the CCR5 chemokine receptors and microbial HSP70," Eur. J. Immunol., 36(9):2304-2314 (2006).
Wu, T-C. et al., "A Reassessment of the Role of B7-1 Expression in Tumor Rejection." J. Exp. Med. 182:1415-1421 (1995).
Wu, T-C. et al., "Demonstration of human papillomavirus (HPV) genomic amplification and viral-like particles from CaSki cell line in SCID mice." Journal of Virological Methods 65:287-298 (1997).
Wu, T-C. et al., "Detection of the Human Cytomegalovirus 2.0-kb Immediate Early Gene I Transcripts in Permissive and Nonpermissive Infections by RNA in situ Hybridization." J Biomed Sci 4:19-27 (1997).
Wu, T-C, et al., "Engineering an intracellular pathway for major histocompatibility complex class II presentation of antigens." Proc. Natl. Acad. Sci. 92:11671-11675 (1995).
Wu, T-C. "Therapeutic human papillomavirus DNA vaccination strategies to control cervical cancer." European Journal of immunology. 37:310-314 (2007).
Yen, M. et al., "Diffuse Mesothelin Expression Correlates with Prolonged Patient Survival in Ovarian Serous Carcinoma." Clin. Cancer. Res. 12(3):827-831 (2006).
Yokokawa et al., "Identification of Novel Human CTL Epitopes and Their Agonist Epitopes of Mesotheliin," Clin. Cancer Res., 11(17):6342-6351 (2005).
International Search Report dated Oct. 15, 2001 from PCT/US2000/41422.
International Search Report dated Nov. 13, 2007 from PCT/US2003/10235.
International Search Report dated Dec. 3, 2002 from PCT/US2001/24134.
International Search Report dated Sep. 20, 2002 from PCT/US2002/02598.
International Search Report dated Jun. 28, 2002 from PCT/US2001/23966.
International Search Report dated Mar. 25, 2005 from PCT/US2004/05292.
International Search Report dated Apr. 1, 2005 from PCT/US2004/13756.
International Search Report dated Jul. 7, 2008 from PCT/US2005/47200.
International Search Report dated Mar. 22, 2007 from PCT/US2006/02707.
International Search Report dated Aug. 13, 2008 from PCT/US2007/76525.
Supplementary EP Search Report dated Mar. 6, 2006 from EP 02 70 7618.
Supplementary EP Search Report dated Sep. 28, 2006 from EP 04 75 1244.
Supplementary EP Search Report dated May 30, 2008 from EP 06 73 3904.
International Search Report dated Jan. 3, 2011 from PCT/US2010/032779.
Chuang et al., "Combination of Viral Oncolysis and Tumor-Specific Immunity to Control Established Tumors," Clinical Cancer Research, 15(14):4581-4588 (2009).
Edmonds et al., "A Point Mutational Analysis of Human Papillomavirus Type 16 E7 Protein," Journal of Virology, 63(6):2650-2656 (1989).
Ye et al., "Cytokine Transgene Expression and Promoter Usage in Primary CD34+ Cells Using Particle-Mediated Gene Delivery," Human Gene Therapy, 9:2197-2205 (1998).
Ballard et al., "Anthrax toxin-mediated delivery of a cytotoxic T-cell epitope in vivo," Proc. Natl. Acad. Sci., 93:12531-12534 (1996).
Cassetti et al., "Antitumor efficacy of Venezuelan equine encephalitis virus replicon particles encoding mutated HPV16 *E6* and *E7* genes," Vaccine, 22:520-527 (2004).
Demierre et al., "Chemoprevention of Melanoma," Current Oncology Reports, 6:406-413 (2004).
Diaz, Rosa Maria, et al. "Oncolytic Immunovirotherapy for Melanoma Using Vesicular Stomatitis Virus," Cancer Research, 67(6):2840-2848 (2007).

(56) References Cited

OTHER PUBLICATIONS

Extended European Search Report dated Apr. 15, 2013, from EP 10772568.1.

Fayolle et al., "In Vivo Induction of CTL Responses by Recombinant Adenylate Cyclase of *Bordetella pertussis* Carrying Viral CD8+ T Cell Epitopes[1]," J. Immunol., 156:4697-4706 (1996).

Galbraith et al., "Effects of 5,6-Dimethylxanthenone-4-Acetic Acid on Human Tumor Microcirculation Assessed by Dynamic Contrast-Enhanced Magnetic Resonance Imaging," Journal of Clinical Oncology, 20(18):3826-3840 (2002).

Gambhira et al., "Vaccination of Healthy Volunteers with Human Papillomavirus Type 16 L2E7E6 Fusion Protein Induces Serum Antibody that Neutralizes across Papillomavirus Species," Cancer Reseach, 66:11120-11124 (2006).

Mandavi et al., "Vaccines Against Human Papillomavirus and Cervical Cancer: Promises and Challenges," The Oncologist, 10:528-538 (2005).

Pike et al., "Calreticulin and Calreticulin Fragments Are Endothelial Cell Inhibitors That Suppress Tumor Growth," Blood, 94:2461-2468 (1999).

Roitt et al., Immunology (textbook), 5th Edition, p. 128 (1998).

Tagawa et al., "Phase I Study of Intranodal Delivery of a Plasmid DNA Vaccine for Patients with Stage IV Melanoma," Cancer, 98:144-154 (2003).

\* cited by examiner

```
taacaaaaat ttaagcgaa tcaattta ggaatgtgt tcagttaggg tgtggaaagt cccaggtc cccaggcagg cagaagtatg
caaagaatgc atctcaatta gtcagcaacc agtgtggaa agtcccagg ctcccagca ggcagaagta tgcaaagcat ggatctcaat
tagtcagcaa ccatagtccc gccctaact ccgccatcc agccctaac tccgccagt tccgccatt ctccgccca tgctgacta
atttttta tttatgcaga ggccgaggc gcctgcct ctgagctatt ccagaagtag tgaggaggct tttggagg cctaggcttt
tgcaaaaagc tccgggagc tgtatatcc atttcggat ctgatcaaga gacaggatga ggatcgtttc gcatgattga acaagatga
ttgcacgcag gttctccggc cgttggggtg gagggctat tccggctatga ctggcacaa ctggcgtgcc cagacaatcg gctgctga tgcggcgtg
ttccggctgt cagcgcagg gcgcgcagg gggcgttcct tgcgcagctg tgcactgacg tgtcactgaa tgcaggaaca tgcaggacga tgcaggcgg ctatcgtgc
ctatgctgga tggccacgac gggcgttcct tgcgagctg tgcgacgact tgtcactgaa gcggaaggg actgctgct attggcgca gtgccgggc
tggccacgao gggcgttcct tgctgagctg tgctcgacgt tgtcactgaa gcggaaggg actgctgct attggcgca gtgccgggc
aggatctct gtcatctcac cttgctcctg ccgaaagt atccatcatg gctgatgcaa tgggcggct gcatacgctt gatcgcta
cctgccatt cgaccaccaa gcgaaacatc gcatcgagcg agcacgtact cggatggaag ccggctggt ccggtcttgt gatctaggat gatctgacg
aagagcatca gggctcgcg ccagccgaac tgttcgccag gctcaaggcg cgcatgccg atcgactgtg acggagga tctgtgtg accatggcg
atgcctgctt gccgaatatc atggccgcag atgccgctt tctgattcc atcgactgtg accgactgg tgtggcgac cgctatcagg
acatagcgt ggctacccgt gatattgctg aagagcttgg cgcgaatgg gctgaccgct tcctcgtgct ttacggtatc gccgctccg
attcgcagcg catcgccttc tatcgccttc tgacgagtt cttctgagcg ggactctgg gttcgaaatg accgaccaag cgacgcccaa
ctgccatca cgagatttcg atccaccge gccttctat gaaaggttgg gcttcggaat cgtttccgg gacgccggct ggatgatcct
ccagcgcgg gatctcatgc tggagttctt cgcccaccc aacttgtta ttgcagctta caatgttac tatcatgtct gtataccgtc
aaatttcaca aataaagcat tttttcact gcattctagt tgtggtttgt ccaaactcat caatgtatct tatcatgtct gtataccgtc
gacctctagc tagagcttgg cgtaatcatg gtcatagctg tttcctgtgt gaaattgtta tccgctcaca attccacaca acatacgagc
cggaagcata aagtgtaaag cctggggtgc ctaatgagtg agctaactca cattaattgc gttgcgctca ctgcccgctt tccagtcggg
aaacctgtcg tgccagctgc attaatgaat cggccaacgc gcggggagag gcggtttgcg tattgggcgc tcttccgctt cctcgctcac
tgactcgctg cgctcgtcg ttcggctgcg gcgagcggta tcagctcact caaaggcggt aatacggtta tccacagaat cagggggataa
cgcagaaag acatgtgag caaaaggcca gcaaaaggcc aggaaccgta aaaaggccgc gttgctggcg tttttccata ggctccgccc
aagtcagagg tggcgaaacc cgacaggact ataaagatac caggcgttc cccctggaag ctccctcgtg cgctctcctg ttccgaccct
gccgcttacc ggatacctgt ccgcctttct cccttcggga agcgtggcgc tttctcaatg ctcacgctgt aggtatctca gttcggtga
ggtcgttcgc tccaagctgg gctgtgtgca cgaaccccc gttcagcccg accgctgcgc cttatccggt aactatcgtc ttgagtccaa
ccggtaaga cacgacttat cgccactggc agcagccact ggtaacagga ttagcagagc gaggtatgta ggcgtgcta cagagttctt
gaagtgtgg cctaactacg gctacactag aaggacagta tttggtatct gcgtctgct gaagccagtt accttcggaa aaagaggtgg
tagctcttga tccggcaaac aaaccaccgc tggtagcggt ggtttttttg tttgcaagca gcagattacg cgcagaaaaa aaggatctca
agaagatcct ttgatctttt ctacggggtc tgacgctcag tggaacgaaa actcacgtta agggattttg gtcatgagat tatcaaaag
gatcttcacc tagatccttt taaattaaaa atgaagttt atcttcatca gttaccaatg cttaatcagt gaggcaccta tctcagcgat
cttaatcagt gaggcaccta tctcagcgat ctgtctattt cgttcatcca tagttgcctg actccccgtc gtgtagataa ctacgatacg
ggagggctta ccatctggcc ccagtgctgc aatgataccg cgagacccac gctcaccggc tccagattta tcagcaataa accagccagc
cggaaggcc gagcgcagaa gtggtcctgc aactttatcc gcctccatcc agtctattaa ttgttgccgg gaagctagag taagtagttc
gccagttaat agtttgcgca acgttgttgc cattgctaca ggcatcgtgg tgtcacgctc gtcgtttggt atggcttcat tcagctccgg
ttcccaacga tcaaggcgag ttacatgatc cccatgttgt gcaaaaaaag cggttagctc cttcggtcct ccgatcgttg tcagaagtaa
gttggccgca gtgttatcac tcatggttat ggcagcactg cataattctc ttactgtcat gccatccgta agatgctttt ctgtgactgg
tgagtactca accaagtcat tctgagaata gtgtatgcgg cgaccgagtt gctcttgccc ggcgtcaata cgggataata ccgcgccaca
tagcagaact ttaaaagtgc tcatcattgg aaaacgttct tcggggcgaa aactctcaag gatcttaccg ctgttgagat ccagttcgat
gtaacccact cgtgcaccca actgatcttc agcatctttt acttcattcc acttcatcca gtttcaata atattgaagc acggaaaatgccgc aaaatgccg
aaaaaggga ataagggcga cacggaaatg ttgaatactc atactcttcc tttttcaata ttattgaagc atttatcagg gttattgtct
catgagcgga tacatatttg aatgtattta gaaaaataaa caaataggg ttccgcgcac atttcccga aaagtgccac ctgacgtc 7518
          10        20        30        40        50        60        70        80        90
```

```
1/1                              31/11
ATG ACC TCT CGC CGC TCC GTG AAG TCG GGT CCG CGG GAG GTT CCG CGC GAT GAG TAC GAG
Met thr ser arg arg ser val lys ser gly pro arg glu val pro arg asp glu tyr glu
61/21                            91/31
GAT CTG TAC TAC ACC CCG TCT TCA GGT ATG GCG AGT CCC GAT AGT CCG CCT GAC ACC TCC
asp leu tyr tyr thr pro ser ser gly met ala ser pro asp ser pro pro asp thr ser
121/41                           151/51
CGC CGT GGC GCC CTA CAG ACA CGC TCG CGC CAG AGG GGC GAG GTC CGT TTC GTC CAG TAC
arg arg gly ala leu gln thr arg ser arg gln arg gly glu val arg phe val gln tyr
181/61                           211/71
GAC GAG TCG GAT TAT GCC CTC TAC GGG GGC TCG TCT TCC GAA GAC GAC GAA CAC CCG GAG
asp glu ser asp tyr ala leu tyr gly gly ser ser ser glu asp asp glu his pro glu
241/81                           271/91
GTC CCC CGG ACG CGG CGT CCC GTT TCC GGG GCG GTT TTG TCC GGC CCG GGG CCT GCG CGG
val pro arg thr arg arg pro val ser gly ala val leu ser gly pro gly pro ala arg
301/101                          331/111
GCG GCT CCG CCA CCC GCT GGG TCC GGA GGC GGA CGC ACA CCC ACC ACC GCC CCC CGG
ala pro pro pro ala gly ser gly gly ala gly arg thr pro thr thr ala pro arg
361/121                          391/131
GCC CCC CGA ACC CAG CGG GTG GCG TCT AAG GCC CCC GCG GCC CCG GCG GCG GAG ACC ACC
ala pro arg thr gln arg val ala ser lys ala pro ala ala pro ala ala glu thr thr
421/141                          451/151
CGC GGC AGG AAA TCG GCC CAG CCA GAA TCC GCC GCA CTC CCA GAC GCC CCC GCG TCG ACG
arg gly arg lys ser ala gln pro glu ser ala ala leu pro asp ala pro ala ser thr
481/161                          511/171
GCG CCA ACC CGA TCC AAG ACA CCC GCG CAG GGG CTG GCC AGA AAG CTG CAC TTT ACC ACC
ala pro thr arg ser lys thr pro ala gln gly leu ala arg lys leu his phe ser thr
541/181                          571/191
GCC CCC CCA AAC CCC GAC GCG CCA TGG ACC CGC CGG GTG GCC GGC TTT AAC AAG CGC GTC
ala pro pro asn pro asp ala pro trp thr pro arg val ala gly phe asn lys arg val
601/201                          631/211
TTC TGC GCC GCG GTC GGG CGC CTG GCG GCC ATG CAT GCC CGG ATG GCG GCT GTC CAG CTC
phe cys ala ala val gly arg leu ala ala met his ala arg met ala ala val gln leu
661/221                          691/231
TGG GAC ATG TCG CGT CCG CGC ACA GAC GAA GAC CTC AAC GAA CTC CTT GGC ATC ACC ACC
trp asp met ser arg pro arg thr asp glu asp leu asn glu leu leu gly ile thr thr
721/241                          751/251
ATC CGC GTG ACG GTC TGC GAG GGC AAA AAC CTG CTT CAG CGC GCC AAC GAG TTG GTG AAT
ile arg val thr val cys glu gly lys asn leu leu gln arg ala asn glu leu val asn
781/261                          811/271
CCA GAC GTG GTG CAG GAC GTC GAC GCG GCC ACG CCG ACT CGA GGG CGT TCT GCG GCG TCG
pro asp val val gln asp val asp ala ala thr ala thr arg gly arg ser ala ala ser
841/281                          871/291
CGC CCC ACC GAG CGA CCT CGA GCC CCA GCC CGC TCC GCT TCT CGC CCC AGA CGG CCC GTC
arg pro thr glu arg pro arg ala pro ala arg ser ala ser arg pro arg arg pro val
901/301                          931/311
GAG GGT ACC GAG CTC GGA TCC atg cat gga gat aca cct aca ttg cat gaa tat atg tta
glu gly thr glu leu gly ser met his gly asp thr pro thr leu his glu tyr met leu
961/321                          991/331
gat ttg caa cca gag aca act gat ctc tac tgt tat gag caa tta aat gac agc tca gag
asp leu gln pro glu thr thr asp leu tyr cys tyr glu gln leu asn asp ser ser glu
1021/341                         1051/351
gag gag gat gaa ata gat ggt cca gct gga caa gca gaa ccg gac aga gcc cat tac aat
glu glu asp glu ile asp gly pro ala gly gln ala glu pro asp arg ala his tyr asn
1081/361                         1111/371
act gta acc ttt tgt tgc aag tgt gac tct acg ctt cgg ttg tgc gta caa agc aca cac
ile val thr phe cys cys lys cys asp ser thr leu arg leu cys val gln ser thr his
1141/381                         1171/391
gta gac att cgt act ttg gaa gac ctg tta atg ggc aca cta gga att gtg tgc ccc atc
val asp ile arg thr leu glu asp leu leu met gly thr leu gly ile val cys pro ile
1201/401                         1231/411
tgt tct cag gat aag ctt aag ttt aaa ccg ctg atc agc ctc gac tgt gcc ttc tag
cys ser gln asp lys leu lys phe lys pro leu ile ser leu asp cys ala phe ***
```

SEQ ID NO: 6

SEQ ID NO: 39

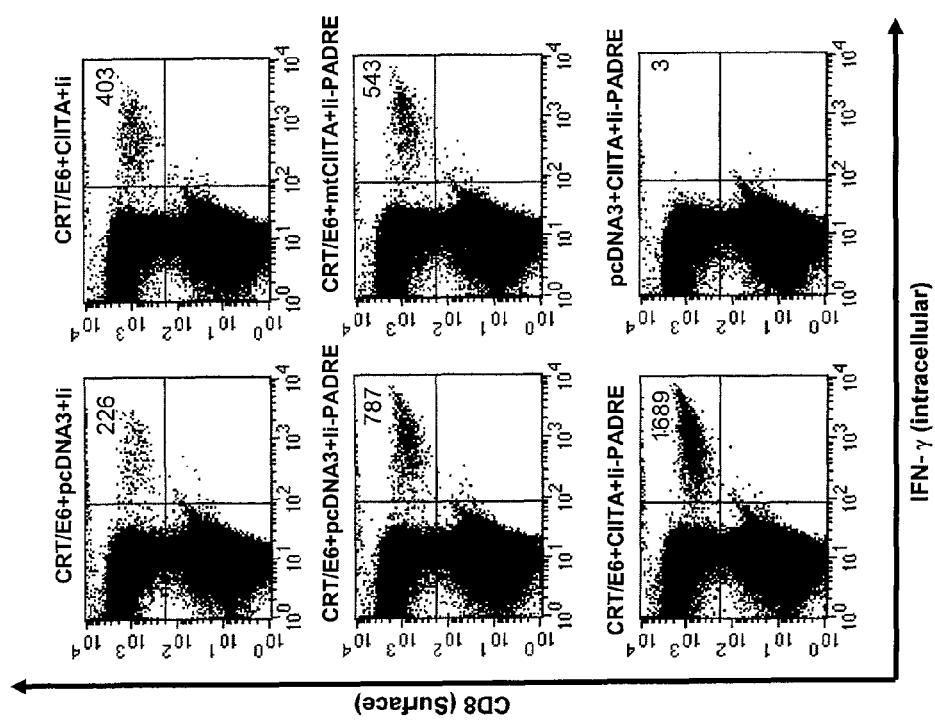
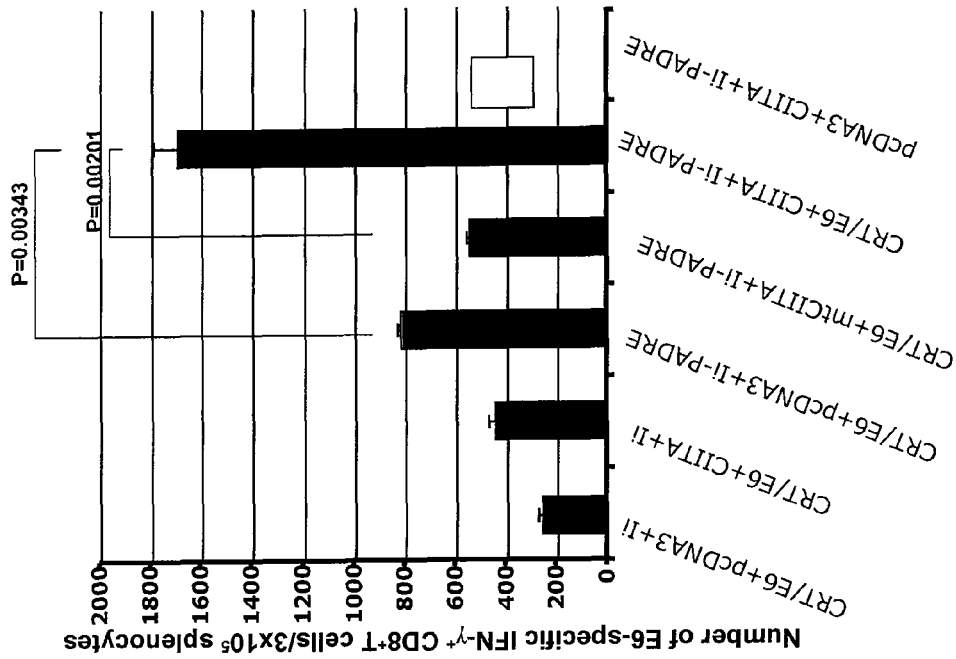
Figure 28

Figure 35

Human Ii (ACCESSION NM_001025159)-PADRE(underlined)

```
        |   10       |   20       |   30       |   40       |   50       |   60       |   70       |   80
  1 atggatgacc agcgcgacct tatctccaac aatgagcaac tgcccatgct gggccggcgc cctggggccc cggagagcaa  80
 81 gtgcagccgc ggagccctgt acacaggctt ttccatcctg gtgactctgc tcctcgctgg ccaggccacc accgcctact 160
161 tcctgtacca gcagcagggc cggctggaca aactgacagt cacctcccag aacctgcagc tggagaacct gcgcatgaag 240
241 cttGCCAAGT TCGTGGCTGC CTGGACCCTG AAGGCTGCCG CTgccctgcc ccagggggccc atgcagaatg ccaccaagta 320
321 tggcaacatg acagaggacc atgtgatgca cctgctccag aatgctgacc ccctgaaggt gtacccgcca ctgaagggga 400
401 gcttcccgga gaacctgaga caccttaaga acaccatgga gaccatagac tggaaggtct tgagagctg gatgcaccat 480
481 tggctcctgt ttgaaatgag caggcactcc ttggagcaaa agcccactga cgctccaccg aaagtactga ccaagtgcca 560
561 ggaagaggtc agccacatcc ctgctgtcca cccgggttca ttcaggccca gtgcgacga gaacggcaac tatctgccac 640
641 tccagtgcta tgggagcatc ggctactgct ggtgtgtctt ccccaacggc acggaggtcc ccaacaccag aagccgcggg 720
721 caccataact gcagtgagtc actggaactg gaggacccgt cttctgggct gggtgtgacc aagcaggatc tgggcccagt 800
801 ccccatgtga                                                                                810
        |   10       |   20       |   30       |   40       |   50       |   60       |   70       |   80
```

```
        |   10       |   20       |   30       |   40       |   50       |   60       |   70       |   80
  1 mddqrdlisn neqlpmlgrr pgapeskcsr galytgfsil vtlllaggat tayflyqqqg rldkltvtsq nlqlenlrmk  80
 81 lAKFVAAWTL KAAAalpqgp mqnatkygnm tedhvmhllq nadplkvypp lkgsfpenlr hlkntmetid wkvfeswmhh 160
161 wllfemsrhs leqkptdapp kvltkcqeev shipavhpgs frpkcdengn ylplqcygsi gycwcvfpng tevpntrsrg 240
241 hhncseslel edpssglgvt kqdlgpvpm                                                          269
        |   10       |   20       |   30       |   40       |   50       |   60       |   70       |   80
```

Figure 36

Human CIITA accession P33076

```
        |   10       |   20       |   30       |   40       |   50       |   60       |   70       |   80
   1 atgcgttgcc tggctccacg ccctgctggg tcctacctgt cagagcccca aggcagctca cagtgtgcca ccatggagtt   80
  81 ggggccccta gaaggtggct acctggagct tcttaacagc gatgctgacc ccctgtgcct ctaccacttc tatgaccaga  160
 161 tggacctggc tggagaagaa gagattgagc tctactcaga acccgacaca gacaccatca actgcgacca gttcagcagg  240
 241 ctgttgtgtg acatggaagg tgatgaagag accaggagag cttatgccaa tatcgcggaa ctggaccagt atgtcttcca  320
 321 ggactcccag ctggagggcc tgagcaagga cattttcaag cacataggac cagatgaagt gatcggtgag agtatggaga  400
 401 tgccagcaga agttgggcag aaaagtcaga aagacccctt cccagaggag cttccggcag acctgaagca ctggaagcca  480
 481 gctgagcccc ccactgtggt gactggcagt ctcctagtgg gaccagtgag cgactgctcc accctgcccc gcctgccact  560
 561 gcctgcgctg ttcaaccagg agccagcctc cggccagatg cgcctggaga aaaccgacca gattcccatg ctttctcca  640
 641 gttcctcgtt gagctgcctg aatctccctg agggacccat ccagtttgtc cccaccatct ccactctgcc ccatgggctc  720
 721 tggcaaatct ctgaggctgg aacagggggtc tccagtatat tcatctacca tggtgaggtg ccccaggcca gcaagtacc  800
 801 ccctcccagt ggattcactg tccacggcct ccaacatct ccagaccggc caggctccac cagcccctc gctccatcag  880
 881 ccactgacct gccagcatg cctgaacctg ccctgacctc ccgagccaaac atgacagagc acaagacgtc cccacccaa  960
 961 tgcccggcag ctggagaggt ctccaacaag cttccaaat ggcctgagcc ggtggagcag ttctaccgct cactgcagga 1040
1041 cacgtatggt gccgagccga caggcccgga tggcatccta gtggaggtgg atctggtgca ggccaggctg agaggagca 1120
1121 gcagcaagag cctggacggg aactggcca ccccggactg ggcagaacgg cagctggccc aaggaggcct ggctgaggtg 1200
1201 ctgttggctg ccaaggacca ccggccgcca cgtgacacac gagtgattgc tgtgctggaa aagctggtc agggcaagag 1280
1281 ctattgggct gggcagtga gccgggcctg ggcttgtggc cggcttcccc agtacgactt tgtcttctct gtccctgcc 1360
1361 attgcttgaa ccgtccgggg gatgccatg gcctgcagga tctgctcttc tccctgggcc acagccact cgtggcggcc 1440
1441 gatgaggttt tcagccacat cttgaagaga cctgaccgcg ttctgctcat cctagacggc ttcgaggagc tggaagcga 1520
1521 agatgcttc ctgcacagca cgtgcggacc cggacccgg gagccctgct ccctccgggg gctgctggcc gctttcc 1600
1601 agaagaagct gctccgaggt tgcaccctcc tcctcacagc ccggcccgg ggccgctgg tccagagcct gagcaaggcc 1680
1681 gacgccctat ttgagctgtc cggcttctct atggagcagg cccaggcata cgtgatgcgc tactttgaga gtcaggat 1760
1761 gacagagcac caagacagag ccctgacgct cctccgggac cggccacttc ttctcagtca cagccacagc ctactttgt 1840
1841 gccgggcagt gtgccagctc tcagaggccc tcagaggacac tggggaggac gccaagctgc cctccacgct cacggggactc 1920
1921 tatgtcggcc tgctgggccg tgcagccctc gacagccccc ccgggcct ggcagagctg gccaagctgg cctgggagct 2000
2001 gggccgcaga catcaaagta ccctacagga ggaccagttc ccatccgcag acgtgaggac ctgggcgatg gccaaggct 2080
2081 tagtccaaca cccaccgcgg gccgcagagt ccgagctggc cttcccagc ttcctcctgc aatgcttcct gggggccctg 2160
2161 tggctggctc tgagtggcga aatcaaggac aaggagctcc cgcagtacct agcattgacc ccaaggaaga agaggccta 2240
2241 tgacaactgg ctggagggcg tgccacgctt tctggctggg ctgatcttcc agcctcccac ccgctgcctg ggagcccta 2320
2321 tcgggccatc ggcggctgcc tcggtggaca cgaagcagaa ggtgcttgcg aggtacctga gcgcgcta gccggggaca 2400
2401 ctgcgggcgc ggcagctgct ggagctgctg cactcgccc acgaggccga ggaggctgga atttggcagc acgtggtaca 2480
2481 ggagctccc ggccgcctc cttttctggg agaagttct cggaagacac agctggggag tccctgctg ttccggcaag 2560
2561 cggcgggcca agacttctcc ctggacctcc gcagcactgg catttgcccc tctggattgg ggagcctcgt gggactcagc 2640
2641 tgtgtcaccc ctttcagggc tgccttgagc gacacggtgg cgctgtggga gtccctgcag cagcatgggg agaccaagct 2720
2721 acttcaggca gcagaggaga agttcaccat cgagcctttc aaagccaagt ccctgaagga tgtggaagac ctgggaaagc 2800
2801 ttgtgcagac tcagaggacg agaagttcct cggaagacac agctggggag ctccctgctg ttccggcaag aaagaaactg 2880
2881 gagtttcgc tgggccctgt ctcaggcccc caggcttcc ccaaactggt gcggatcctc acgcctttt cctcctgca 2960
2961 gcatctggac ctggatgcgc tgagtgagaa caagatcggg gacgagggtg tctcgcagct ctcagccacc ttcccccagc 3040
3041 tgaagtcctt ggaaaccctc aatctgtccc agaacaacat cactgacctg ggtgcctaca actgccga ggccctgct 3120
3121 tcgctcgctg catcctgct caggctagac ttgtacaata actgcatctg cgacgtggga gccgagact tggctcgtgt 3200
3201 gcttccggac atggtgtccc tccggtgat ggacgtccag tacaacaagt tcacggctgc cggggccag cagctcgctg 3280
3281 ccagccttcg gaggtgtcct catgtggaga cgctggcgat gtggacgccc accatccat tcagtgtcca ggaacacctg 3360
3361 caacaacagg attcacggat cagcctgaga tga                                                      3393
        |   10       |   20       |   30       |   40       |   50       |   60       |   70       |   80
```

```
        |   10       |   20       |   30       |   40       |   50       |   60       |   70       |   80
   1 MRCLAPRPAG SYLSEPQGSS QCATMELGPL EGGYLELLNS DADPLCLYHF YDQMDLAGEE EIELYSEPDT DTINCDQFSR   80
  81 LLCDMEGDEE TREAYANIAE LDQYVFQDSQ LEGLSKDIFK HIGPDEVIGE SMEMPAEVGQ KSQKRPFPEE LPADLKHWKP  160
 161 AEPPTVVTGS LLVGPVSDCS TLPCLPLPAL FNQEPASGQM RLEKTDQIPM PFSSSSLSCL NLPEGPIQFV PTISTLPHGL  240
 241 WQISEAGTGV SSIFIYHGEV PQASQVPPPS GFTVHGLPTS PDRPGSTSPF APSATDLPSM PEPALTSRAN MTEHKTSPTQ  320
 321 CPAAGEVSNK LPKWPEPVEQ FYRSLQDTYG AEPAGPDGIL VEVDLVQARL ERSSSKSLER ELATPDWAER QLAQGGLAEV  400
 401 LLAAKEHRRP RETRVIAVLG KAGQGKSYWA GAVSRAWACG RLPQYDFVFS VPCHCLNRPG DAYGLQDLLF SLGPQGPLVAA  480
 481 DEVFSHILKR PDRVLLILDG FEELEAQDGF LHSTCGPAPA EPCSLRGLLA GLFQKKLLRG CTLLLTARPR GRLVQSLSKA  560
 561 DALFELSGFS MEQAQAYVMR YFESSGMTEH QDRALTLLRD RPLLLSHSHS PTLCRAVCQL SEALLELGED AKLPFSTLTGL  640
 641 YVGLLGRAAL DSPPGALAEL AKLAWELGRR HQSTLQEDQF PSADVRTWAM AKGLVQHPPR AAESELAFPS FLLQCFLGAL  720
 721 WLALSGEIKD KELPQYLALT PRKKRPYDNW LEGVPRFLAG LIFQPPARCL GALLGPSAAA SVDRKQVKLA RYLKRLQPGT  800
 801 LRARQLLELL HCAHEABEAG IWQHVVQELP GRLSFLGTRL TPPDAHVLGK ALEAAGQDFS LDLRSTGICP SGLGSLVGLS  880
 881 CVTRFRAALS DTVALWESLQ QHGETKLLQA AEEKFTIEPF KAKSLKDVED LGKLVQTQRT RSSSEDTAGE LPAVRDLKKL  960
 961 EFALGPVSGP QAFPKLVRIL TAFSSLQHLD LDALSENKIG DEGVSQLSAT FPQLKSLETL NLSQNNITDL GAYKLAEALP 1040
1041 SLAASLLRLS LYNNCICDVG AESLARVLPD MVSLRVMDVQ YNKFTAAGAQ QLAASLRRCP HVETLAMWTP TIPFSVQEHL 1120
1121 QQQDSRISLR Z                                                                             1131
        |   10       |   20       |   30       |   40       |   50       |   60       |   70       |   80
```

DNA VACCINE ENHANCEMENT WITH MHC CLASS II ACTIVATORS

CROSS-REFERENCE TO RELATED APPLICATIONS

This application claims the benefit of U.S. Provisional Application No. 60/905,476, filed on Mar. 7, 2007, the content of which is specifically incorporated by reference herein in its entirety.

GOVERNMENTAL SUPPORT

This invention was made with government support under grant numbers P50 CA098252 and RO1 CA114425, awarded by the U.S. National Institutes of Health. The government has certain rights in this invention.

BACKGROUND

Although chemotherapeutic regimens have been useful in treating cancer, their success is limited by the often severe systemic toxicity frequently associated with their use. Similarly, cancer immunotherapeutics have shown promise for the treatment of a number of tumors and hyperproliferative diseases, but their utility is limited in situations where the tumor is relatively large or rapidly growing.

The present inventors have developed a number of DNA vaccine systems for HPV-associated cervical neoplasia as well as HPV-associated head and neck cancers. Cervical cancer can serve as a model of how a viral infection can progress through a multistep process from initial infection to premalignant dysplasia, called cervical intraepithelial neoplasia (CIN), to invasive cancer. Human papilloma virus (HPV), particularly HPV-16, is associated with a majority of cervical cancers and a subset of head and neck cancers. HPV-16 E7, one of its oncoproteins, is essential for the induction and maintenance of cellular transformation. Thus, HPV-16 E7 is an ideal target for developing vaccine and immunotherapeutic strategies for the control of HPV infections and HPV-associated lesions. However, the antigen-specific immune responses and antitumor effects generated by DNA vaccines encoding wild type E7 is weak and not enough to be effective in controlling tumor growth. To overcome the weak antigenicity of E7, the present inventors have previously created a DNA vaccine encoding HPV-16 E7 linked to the sorting signal of the lysosome-associated membrane protein 1 (LAMP-1). The encoded chimeric protein (Sig/E7/LAMP-1) also includes the signal peptide derived from LAMP-1 protein. Vaccination with Sig/E7/LAMP-1 DNA led to a significantly enhanced E7-specific CD4+ and CD8+ T cell-mediated immune responses, resulting in potent antitumor effects against E7-expressing tumors in vaccinated mice.

In addition to the Sig/E7/LAMP-1 construct described above, the present inventors and their colleagues have also previously developed several additional intracellular targeting and intercellular spreading strategies to enhance DNA vaccine potency using various immunogenicity-potentiating polypeptides (IPPs), described in further detail below. See for example, publications of the present inventors and their colleagues: Hung, C F et al., *J Virol* 76:2676-82, 2002; Cheng, W F et al., *J Clin Invest* 108:669-78, 2001; Hung, C F et al., *J Immunol* 166:5733-40, 2001; Chen, C H et al., *Gene Ther* 6:1972-81, 1999; Ji, H et al., *Hum Gene Ther* 10:2727-40, 1999; Chen, C H et al., *Cancer Res* 60:1035-42, 2000; U.S. Pat. No. 6,734,173, WO 01/29233; WO03/085085; WO 02/012281; WO 02/061113.

Among these strategies was the linkage of antigen to the intracellular targeting moiety calreticulin (CRT). The present inventors and their colleagues were the first to provide naked DNA and self-replicating RNA vaccines that incorporated CRT (or other IPPs). The present inventors and their colleagues also demonstrated that linking antigen to *Mycobacterium tuberculosis* heat shock protein 70 (HSP70) or its C-terminal domain, domain II of *Pseudomonas aeruginosa* exotoxin A (ETA(dII)) enhanced DNA vaccine potency compared to compositions comprising only DNA encoding the antigen of interest. As discussed above, to enhance MHC class II antigen processing, the present inventors' colleagues (Lin, K Y et al., *Cancer Res* 56: 21-6, 1996) linked the sorting signals of the lysosome-associated membrane protein (LAMP-1) to the cytoplasmic/nuclear human papilloma virus (HPV-16) E7 antigen, creating a chimera (Sig/E7/LAMP-1). These findings point to the importance of adding an additional "element" to an antigenic composition at the DNA level to enhance in vivo potency of a recombinant DNA vaccine.

Intradermal administration of DNA vaccines via gene gun in vivo has proven to be an effective means to deliver such vaccines into professional antigen-presenting cells (APCs), primarily dendritic cells (DCs), which function in the uptake, processing, and presentation of antigen to T cells. The interaction between APCs and T cells is crucial for developing a potent specific immune response.

Even if current cancer therapies are effective, there remains a need for anticancer therapies that are yet more effective.

SUMMARY OF THE INVENTION

Provided herein are nucleic acids encoding a protein that comprises an amino acid sequence that is at least about 90% identical to the amino acid sequence of a fusion protein comprising an Ii protein, wherein the class II-associated Ii peptide (CLIP) region is replaced with a promiscuous CD4+ T cell epitope, e.g., the Pan HLA-DR reactive epitope (PADRE), wherein the protein stimulates an immune response. The nucleic acid may encode a fusion protein comprising a human Ii protein, wherein the class II-associated Ii peptide (CLIP) region is replaced with the Pan HLA-DR reactive epitope (PADRE), e.g., a fusion protein comprising the amino acid sequence set forth in SEQ ID NO: 91. A nucleic acid may be present in a composition which also comprises a nucleic acid encoding an antigen. The antigen may be linked to an immunogenicity potentiating peptide (IPP), e.g., a protein selected from the group consisting of a cytoplasmic chaperone protein, an endoplasmic reticulumn chaperone protein, a viral intercellular spreading protein, a cytoplasmic translocation polypeptide domain of a pathogenic toxin, and a polypeptide that targets the centrosome compartment of a cell, a protein involved in sorting of the lysosome-associated membrane protein type 1, or a functional homolog of any of these. The IPP may be calreticulin (CRT), N-CRT, P-CRT, C-CRT, *Mycobacterium tuberculosis* HSP70, a protein consisting of amino acids 517-625 of *M. tuberculosis* HSP70, a protein consisting of amino acids 161-370 and 517-625 of *M. tuberculosis* HSP70, γ-tubulin, Sig/LAMP-1, VP22 or a functional homolog of any of these.

Also provided herein are compositions comprising (i) a nucleic acid encoding a protein that comprises an amino acid sequence that is at least about 90% identical to the amino acid sequence of a fusion protein comprising an Ii protein, wherein the class II-associated Ii peptide (CLIP) region is replaced with a promiscuous CD4+ T cell epitope, e.g., the Pan HLA-DR reactive epitope (PADRE), wherein the protein stimulates an immune response, and (ii) a nucleic acid encoding a second protein comprising an amino acid sequence that is at least about 90% identical to the amino acid sequence of CIITA, which is set forth in SEQ ID NO: 95, wherein the second protein enhances an immune response. The composition may further comprise a nucleic acid encoding an antigen.

Also provided are compositions comprising (i) a nucleic acid encoding a protein comprising an amino acid sequence that is at least about 90% identical to the amino acid sequence of CIITA, which is set forth in SEQ ID NO: 95, wherein the protein enhances an immune response; and (ii) a nucleic acid encoding an antigen.

Compositions may further comprise a nucleic acid that inhibits the expression of a pro-apoptotic protein and/or a nucleic acid that encoding an anti-apoptotic protein.

Also provided herein are compositions, e.g., as described in this Summary section, further comprising a chemotherapeutic drug, e.g., an apoptosis inducing chemotherapeutic drug. Exemplary drugs that may be used in combination with the nucleic acids include epigallocatechin-3-gallate (EGCG), 5,6 di-methylxanthenone-4-acetic acid (DMXAA), cisplatin, apigenin, doxorubicin, an anti-death receptor 5 antibody, a proteasome inhibitor, an inhibitor of DNA methylation, genistein, celecoxib and biologically active analogs thereof.

Also provided are proteins that are encoded by the nucleic acids described herein, e.g., those described in this Summary section, as well as cells including these nucleic acids.

Further provided herein are methods for treating or preventing cancer in a subject and/or for enhancing an immune response in a subject, e.g., an antigen specific immune response. A method may comprise administering to a subject in need thereof a nucleic acid encoding a protein that comprises an amino acid sequence that is at least about 90% identical to the amino acid sequence of a fusion protein comprising an Ii protein, wherein the class II-associated Ii peptide (CLIP) region is replaced with a promiscuous CD4+ T cell epitope, e.g., the Pan HLA-DR reactive epitope (PADRE), wherein the protein stimulates an immune response. The cancer may be a head and neck cancer or cervical cancer. Other methods comprise administering to a subject in need thereof two or more of the following agents: (i) 90% identical to the amino acid sequence of a fusion protein comprising an Ii protein, wherein the class II-associated Ii peptide (CLIP) region is replaced with a promiscuous CD4+ T cell epitope, e.g., the Pan HLA-DR reactive epitope (PADRE), wherein the protein stimulates an immune response; (ii) a nucleic acid encoding a protein comprising an amino acid sequence that is at least about 90% identical to the amino acid sequence of CIITA, which is set forth in SEQ ID NO: 95, wherein the protein enhances an immune response; (iii) a nucleic acid encoding an antigen; and (iv) a chemotherapeutic drug. Methods may further comprise administering a nucleic acid that inhibits the expression of a pro-apoptotic protein and/or a nucleic acid that encoding an anti-apoptotic protein.

Also provided herein are kits, e.g., a kit for therapeutic purposes. A kit may comprise two or more of the following agents: (i) 90% identical to the amino acid sequence of a fusion protein comprising an Ii protein, wherein the class II-associated Ii peptide (CLIP) region is replaced with a promiscuous CD4+ T cell epitope, e.g., the Pan HLA-DR reactive epitope (PADRE), wherein the protein stimulates an immune response; (ii) a nucleic acid encoding a protein comprising an amino acid sequence that is at least about 90% identical to the amino acid sequence of CIITA, which is set forth in SEQ ID NO: 95, wherein the protein enhances an immune response; (iii) a nucleic acid encoding an antigen; and (iv) a chemotherapeutic drug. Kits may further comprise a nucleic acid that inhibits the expression of a pro-apoptotic protein and/or a nucleic acid that encoding an anti-apoptotic protein.

BRIEF DESCRIPTION OF THE DRAWINGS

Figure 19:
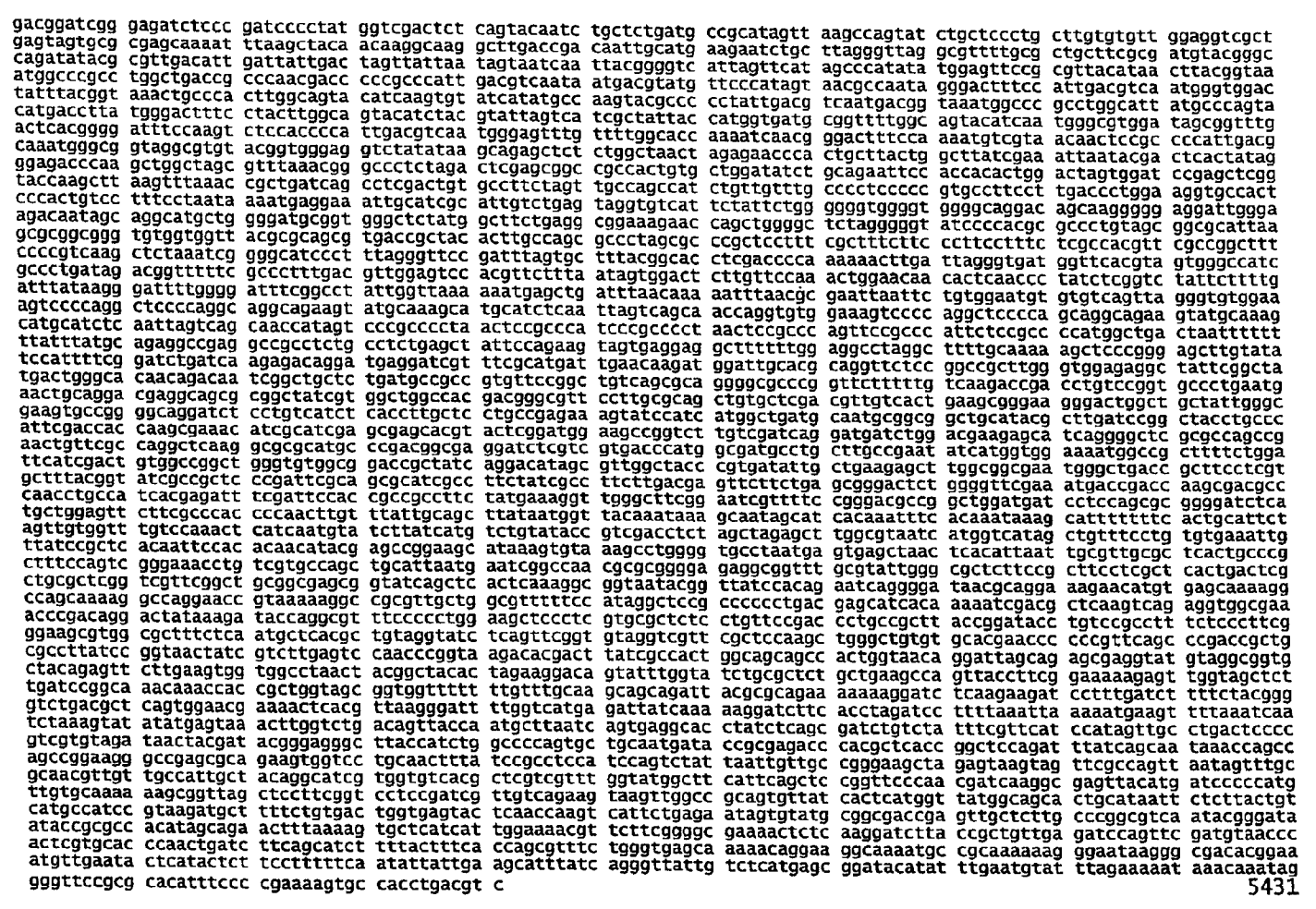

FIG. 19. Sequence of the pcDNA3 plasmid vector (SEQ ID NO: 1).

Figure 20:
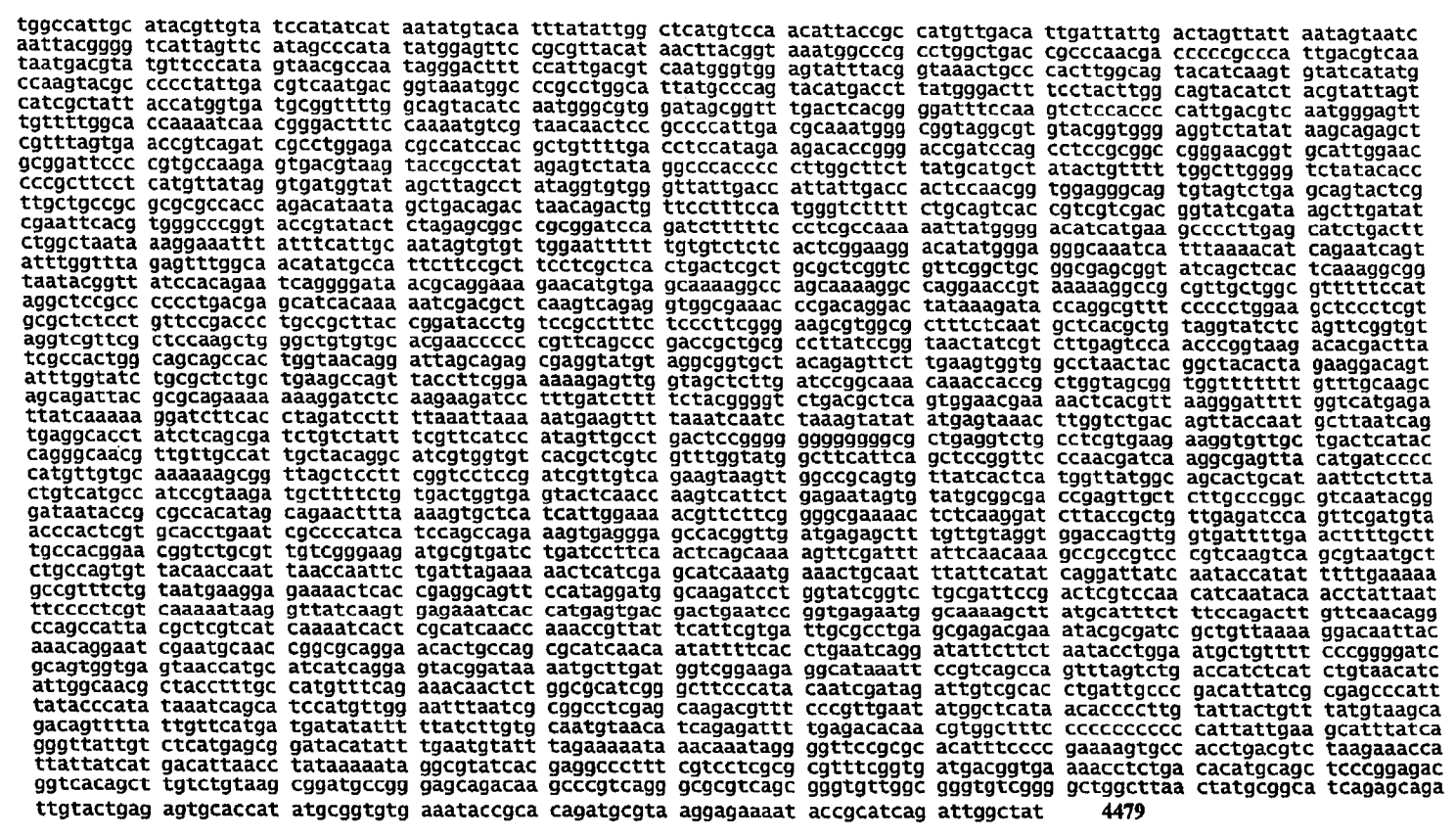

FIG. 20. Sequence of the pNGVL4a plasmid vector (SEQ ID NO: 2).

Figure 21:
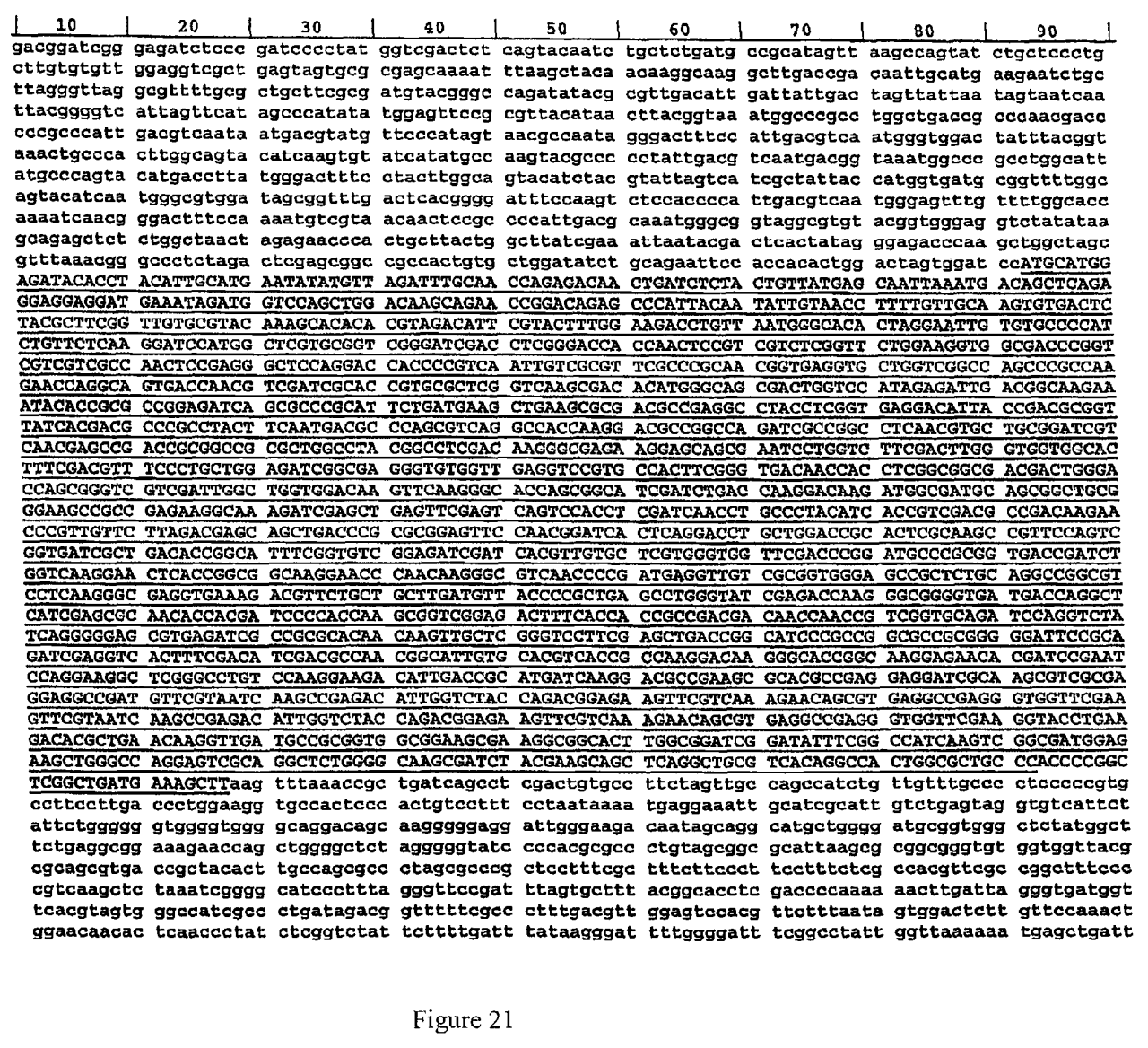

FIG. 21. Sequence of the pcDNA3-E7-Hsp70 plasmid (SEQ ID NO: 3).

FIG. 22. Sequence of the pcDNA3-ETA(dII)/E7 plasmid (SEQ ID NO: 4).

FIG. 23. Sequence of the pNGVL4a-CRT/E7(detox) plasmid (SEQ ID NO: 5).

FIG. 24. Nucleotide sequence of VP22/E7 DNA as it appears in the pCDNA3 vector (SEQ ID NO: 6 (encoding SEQ ID NO: 39)) which is 1254 nucleotides (+stop codon). SEQ ID NO: 7 includes nucleotides 1-903 encoding VP22 (SEQ ID NO: 38). Nucleotides 904-921 and the corresponding amino acids 302-307 are a "linker" sequence. Nucleotides 922-1209 (lower case) encode 96 of the 98 amino acids of wild-type E7 protein (SEQ ID NO: 41). Also shown is a stretch of vector sequence (underscored) from nucleotides 1210-1257 (including stop codon).

FIG. 28: Characterization of the E6-specific CD8+ T cells in mice vaccinated with CRT/E6, CIITA DNA and Ii-PADRE DNA vaccines. C57BL/6 mice (5 per group) were immunized with 2 µg/mouse twice with a 1-wk interval of the DNA combinations listed in Table 1. Splenocytes from vaccinated mice were harvested 1 week after the last vaccination and characterized for E6-specific CD8+ T cells using intracellular IFN-γ staining followed by flow cytometry analysis. A. Representative flow cytometry data. The numbers in the upper right-hand corner represent the number of E6-specific IFN-γ-secreting CD8+ T cells per $5 \times 10^6$ pooled splenocytes. B. Bar graphs depicting the numbers of E6-specific IFN-γ-secreting CD8+ T cells per $5 \times 10^6$ pooled splenocytes (means±s.d.). The data presented in this figure are from one representative experiment of two performed.

FIG. 35 shows the nucleotide (SEQ ID NO: 90) and amino acid (SEQ ID NO: 91) sequences of a human Ia-PADRE.

FIG. 36 shows the nucleotide (SEQ ID NO: 94) and amino acid (SEQ ID NO: 95) sequences of human CIITA.

DETAILED DESCRIPTION

Partial List of Abbreviations

Figure 1:
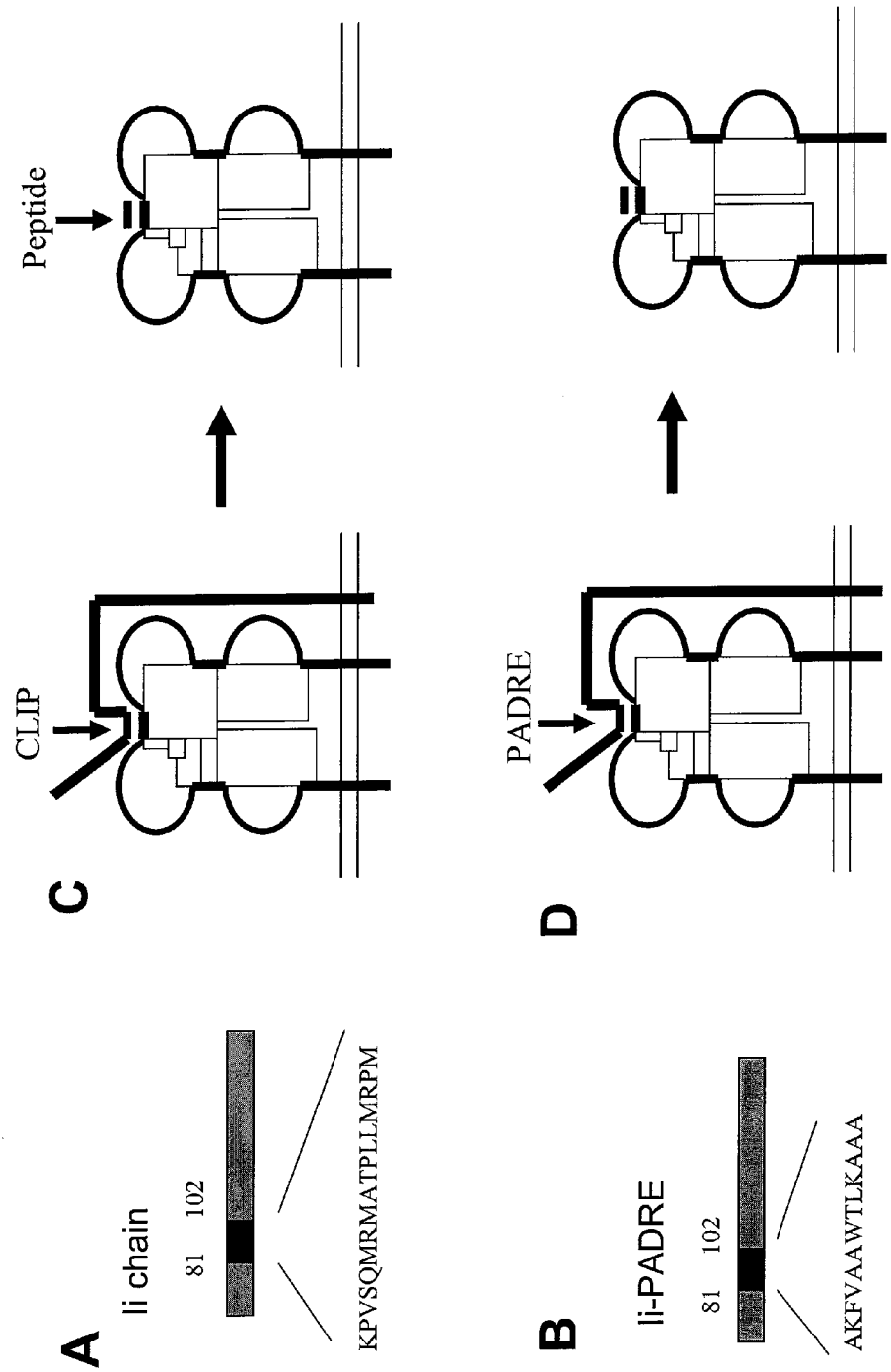
FIG. 1. Schematic diagrams of the Ii chain and the chimeric Ii-PADRE. (A) Diagram of the Invariant (Ii) chain. The blue region indicates the location of the CLIP (aa81-102) (SEQ ID NO: 92). (B) Diagram of the Ii-PADRE chimeric protein. The red region indicates the location of the PADRE (SEQ ID NO: 93), which replaces the CLIP region of the Ii chain. (C) Diagram of a typical MHC class II molecule associated with the Ii chain. The CLIP region of the Ii chain occupies the peptide binding site and is eventually replaced by an antigenic peptide in the endosomal/lysosomal compartments (D) Diagram of a MHC class II molecule associated with the Ii-PADRE chimeric protein. The PADRE peptide remains attached to the peptide binding site of the MHC class II molecule.

APC, antigen presenting cell; CRT, calreticulin; CTL, cytotoxic T lymphocyte; DC, dendritic cell; ECD, extracellular domain; EGCG, epigallocatechin-3-gallate; E6, HPV oncoprotein E6; E7, HPV oncoproteinE7; ELISA, enzyme-linked immunosorbent assay; HPV, human papillomavirus;

HSP, heat shock protein; Hsp70, mycobacterial heat shock protein 70; IFN γ, interferon-γ; i.m., intramuscular(ly); i.v., intravenous(ly); MHC, major histocompatibility complex; PBS, phosphate-buffered saline; PCR, polymerase chain reaction; β-gal, β-galactosidase.

General

Provided herein are methods and compositions for increasing or stimulating an immune response, e.g., for treating a hyperproliferating disease, e.g., cancer. In one embodiment, a method comprises administering to a subject in need thereof a nucleic acid, e.g., a DNA vaccine, encoding an MHC class I and/or II ("class I/II") activator. Such vaccines may be therapeutic vaccines or preventative vaccines. A method may also comprise administering to a subject in need thereof a nucleic acid encoding an MHC class I/II activator and one or more nucleic acid vaccines, e.g., a nucleic acid encoding an antigen or a biologically active homolog thereof. Other nucleic acid vaccines that may be administered include nucleic acids encoding a protein that enhances the immune system, but do not comprise an antigen, e.g., those that prolong the life of antigen presenting cells, as further described herein. Methods for stimulating an immune response may also comprise administering to a subject in need thereof a nucleic acid encoding an MHC class I/II activator; a nucleic vaccine encoding an antigen; and a nucleic acid vaccine that does not encode an antigen. Other methods may comprise administering a nucleic acid encoding an MHC class I/II activator and an agent or drug, e.g., a drug that is not a nucleic acid vaccine, such as a drug that induces apoptosis of cancer cells, e.g., a chemotherapeutic agent. Yet other methods may comprise administering a nucleic acid encoding an MHC class I/II activator; a nucleic acid vaccine encoding an antigen; and a chemotherapeutic agent. Yet other methods may comprise administering a nucleic acid encoding an MHC class I/II activator; a nucleic acid vaccine encoding an antigen; a nucleic acid vaccine that does not encode an antigen; and a chemotherapeutic agent. Any other combinations of one or more of a nucleic acid encoding an MHC class I/II activator; one or more nucleic vaccines encoding an antigen; one or more nucleic vaccines that do not encode an antigen; and one or more drugs, e.g., chemotherapeutic drugs, may also be used for stimulating an immune response in a subject. These methods may be used for treating a subject in need thereof, e.g., a subject having or likely to develop a hyperproliferative disease, e.g., cancer, e.g., an HPV-associated malignancy.

At least some of the methods may also be used to enhance the efficacy of another treatment, e.g., a treatment that comprises administering a nucleic acid vaccine.

Administration of an MHC class I/II activator may be done at the same time, before or after administration of one or more other agents, such as nucleic acid vaccines or drugs.

MHC Class I/II Activators

"MHC class I/II activators" refers to molecules or complexes thereof that increase immune responses by increasing MHC class I or II ("I/II") antigen presentation, such as by increasing MHC class I, class II or class I and class II activity or gene expression. In one embodiment, an MHC class I/II activator is a nucleic acid encoding a protein that enhances MHC class I/II antigen presentation. Exemplary MHC class I/II activators include nucleic acids encoding an MHC class II associated invariant chain (Ii), in which the CLIP region is replaced with a T cell epitope, e.g., a promiscuous T cell epitope, such as the Pan HLA-DR reactive epitope (PADRE), or a variant thereof. Other MHC class I/II activators are nucleic acids encoding the MHC class II transactivator CIITA or a variant thereof.

In one embodiment, an MHC class I/II activator is a nucleic acid, e.g., an isolated nucleic acid, encoding a protein comprising, consisting or consisting essentially of an invariant (Ii) chain, wherein the CLIP region is replaced with a promiscuous CD4+ T cell epitope. A "promiscuous CD4+ T cell epitope" is used interchangeably with "universal CD4+ T cell epitope" and refers to peptides that bind to numerous histocompatibility alleles, e.g., human MHC class II molecules. In one embodiment, the promiscuous CD4+ T cell epitope is a Pan HLA-DR reactive epitope (PADRE), thereby forming an Ii-PADRE protein that is encoded by an Ii-PADRE nucleic acid. In one embodiment, a nucleic acid encodes an Ii chain, wherein amino acids 81-102 (KPVSQMRMATPLLMRPM (SEQ ID NO: 92) are replaced with the PADRE sequence AKFVAAWTLKAAA (SEQ ID NO: 93). An exemplary human Ii-PADRE amino acid sequence is set forth as SEQ ID NO: 91, and is encoded by nucleotide sequence SEQ ID NO: 90 (see FIG. 35).

Also provided herein are variants of a protein consisting of SEQ ID NO: 91. A protein may comprise, consist essentially of, or consist of an amino acid sequence that is at least about 80%, 85%, 90%, 95%, 96%, 97%, 98% or 99% identical to SEQ ID NO: 91. A protein may comprise a PADRE that is identical to the PADRE of SEQ ID NO: 91, i.e., consisting of SEQ ID NO: 93. A protein may comprise a PADRE sequence that is at least about 80%, 85%, 90%, 95%, 96%, 97%, 98% or 99% identical to SEQ ID NO: 93; and/or an Ii sequence that is at least about 80%, 85%, 90%, 95%, 96%, 97%, 98% or 99% identical to the Ii sequence of SEQ ID NO: 91.

An amino acid sequence may differ from that of SEQ ID NO: 91 or the Ii or PADRE sequences thereof by the addition, deletion or substitution of at least about 1, 2, 3, 4, 5, 6, 7, 8, 9, 10, 11, 12, 13, 14, 15, 16, 17, 18, 19, 20, 25, 30 or more amino acids. In certain embodiments, a protein lacks one or more, e.g., 2, 3, 4, 5, 6, 7, 8, 9, 10 or more amino acids at the C- and/or N-terminus and/or internal relative to that of SEQ ID NO: 91 or the Ii or PADRE region thereof. In certain embodiments, an amino acid sequence differs from that of SEQ ID NO: 93 or from that of the Ii sequence by the addition, deletion or substitution of at least about 1, 2, 3, 4, or 5 amino acids.

Variants of SEQ ID NOs: 91 or the PADRE or Ii regions thereof preferably have a biological activity. Such variants are referred to as "functional homologs" or "functional variants." Functional homologs include variants of SEQ ID NOs: 91 that increase an immune response, e.g., an antigen specific immune response, in a subject to whom it is administered, or has any of the biological activities set forth in the Examples pertaining to Ii-PADRE. Variants of the PADRE sequence or the Ii sequence may have a biological activity that is associated with that of the wildtype PADRE or Ii sequences, respectively. Biological activities can be determined as know in the art or as set forth in the Examples. In addition, comparison (or alignment) of the Ii and PADRE sequences from different species is expected to be helpful in determining which amino acids may be varied and which ones should preferably not be varied.

Other proteins provided herein comprise a PADRE amino acid sequence that replaces a larger portion of Ii, e.g., wherein Ii is lacking about amino acids 81-103, 81-104, 81-105, 81-106, 81-107, 81-108, 81-109, 81-110 or more; is lacking about amino acids 70-102, 71-102, 72-102, 73-102, 74-102, 75-102, 76-102, 77-102, 78-102, 79-102, 80-102 or more.

Other promiscuous CD4+ T cell epitopes that may be used instead of PADRE are listed in Table 2.

TABLE 2

Exemplary promiscuous CD4+ T cell epitopes
(SEQ ID NOS 96-120, respectively in order of appearance)

| Promiscuous CD4+ T cell epitopes | Reference |
|---|---|
| EBV-latent membrane protein 1(LMP1$_{159-175}$) YLQQNWWTLLVDLLWLL | (1) |
| MAGF-A6$_{172-187}$; IGHVYIFATCLGLSYD | (2) |
| Mycoplasma penetrans HF-2$_{219-226}$; IYIFAACL | |
| six-transmembrane epithelial antigen of prostate (STEAP) | (3) |
| STEAP$_{102-116}$ HQQYFYKIPILVINK | |
| STEAP$_{192-206}$ LLNWAYQQVQQNKED | |
| Taxol-resistance-associated gene-3 (TRAG3)$_{35-48}$ | (4) |
| EFHACW PAFTVLGE | |
| Survivin$_{10-24}$ WQPFLKDHRISTFKN | (5) |
| HPV 18-E6$_{52-66}$; LFVVYRDSIPHAACH | (6) |
| HPV 18-E6$_{97-111}$; GLYNLLIRCLRCQKP | |
| Carcinoembryonic antigen$_{177-189}$; LWWVNNQSLPVSP | (7) |
| mycobacterial antigen MPB70 | (8) |
| MPB70$_{106-130}$; FSKLPASTIDELKTNSSLLTSILTY | |
| MPB70$_{166-193}$; GNADVVCGGVSTANATVYMIDSVLMPPA | |
| HER-2$_{776-788}$ GSPYVSRLLGICL | (9) |
| HER-2$_{833-849}$ KVPIKWMALESILRRRF | (10) |
| NY-ESO-1$_{119-143}$ PGVLLKEFTVSGNILTIRLTAADHR | (11) |
| Tetanus toxin$_{1084-1099}$ VSIDKFRIFCKANPK | (12) |
| Tetanus toxin$_{1174-1189}$ LKFIIKRYTPNNEIDS | |
| Tetanus toxin$_{1064-1079}$ IREDNNITLKLDRCN | |
| Tetanus toxin$_{947-967}$ FNNFTVSFWLRVPKVSASHLE | |
| Tetanus toxin$_{830-843}$ QYIKANSKFIGITE | |
| HBV nuclear capside$_{50-69}$ PHHTALRQAILCWGELMTLA | |
| Influenza haemagglutinin$_{307-319}$ PKYVKQNTLKLAT | |
| HBV surface antigen$_{19-33}$-FFLLTRILTIPQSLD | |
| Influenza marix$_{17-31}$ YSGPLKAEIAQRLEDV | |
| P. falciparum CSP$_{380-398}$ EKKIAKMEKASSVFNVVN | |

(1). Kobayashi, H., T. Nagato, M. Takahara, K. Sato, S. Kimura, N. Aoki, M. Azumi, M. Tateno, Y. Harabuchi, and E. Celis. 2008. Induction of EBV-latent membrane protein 1-specific MHC class II-restricted T-cell responses against natural killer lymphoma cells. *Cancer Res* 68: 901-908.
(2). Vujanovic, L., M. Mandic, W. C. Olson, J. M. Kirkwood, and W. J. Storkus. 2007. A mycoplasma peptide elicits heteroclitic CD4+ T cell responses against tumor antigen MAGE-A6. *Clin Cancer Res* 13: 6796-6806.
(3). Kobayashi, H., T. Nagato, K. Sato, N. Aoki, S. Kimura, M. Murakami, H. Iizuka, M. Azumi, H. Kakizaki, M. Tateno, and E. Celis. 2007. Recognition of prostate and melanoma tumor cells by six-transmembrane epithelial antigen of prostate-specific helper T lymphocytes in a human leukocyte antigen class II-restricted manner. *Cancer Res* 67: 54985504
(4). Janjic, B., P. Andrade, X. F. Wang, J. Fourcade, C. Almunia, P. Kudela, A. Brufsky, S. Jacobs, D. Friedland, R. Stoller, D. Gillet, R. B. Herberman, J. M. Kirkwood, B. Maillere, and H. M. Zarour. 2006. Spontaneous CD4+ T cell responses against TRAG-3 in patients with melanoma and breast cancers. *J Immunol* 177: 2717-2727.
(5). Piesche, M., Y. Hildebrandt, F. Zettl, B. Chapuy, M. Schmitz, G. Wulf, L. Trumper, and R. Schroers. 2007. Identification of a promiscuous HLA DR-restricted T-cell epitope derived from the inhibitor of apoptosis protein survivin. *Hum Immunol* 68: 572-576.
(6). Facchinetti, V., S. Seresini, R. Longhi, C. Garavaglia, G. Casorati, and M. P. Protti. 2005. CD4+ T cell immunity against the human papillomavirus-18 E6 transforming protein in healthy donors: identification of promiscuous naturally processed epitopes. *Eur J Immunol* 35: 806-815.
(7). Campi, G., M. Crosti, G. Consogno, V. Facchinetti, B. M. Conti-Fine, R. Longhi, G. Casorati, P. Dellabona, and M. P. Protti. 2003. CD4(+) T cells from healthy subjects and colon cancer patients recognize a carcinoembryonic antigen-specific immunodominant epitope. *Cancer Res* 63: 8481-8486.
(8). Al-Attiyah, R., F. A. Shaban, H. G. Wiker, F. Oftung, and A. S. Mustafa. 2003. Synthetic peptides identify promiscuous human Th1 cell epitopes of the secreted mycobacterial antigen MPB70. *Infect Immun* 71: 1953-1960.
(9). Sotiriadou, R., S. A. Perez, A. D. Gritzapis, P. A. Sotiropoulou, H. Echner, S. Heinzel, A. Mamalaki, G. Pawelec, W. Voelter, C. N. Baxevanis, and M. Papamichail. 2001. Peptide HER2(776-788) represents a naturally processed broad MHC class II-restricted T cell epitope. *Br J Cancer* 85: 1527-1534.
(10). Kobayashi, H., M. Wood, Y. Song, E. Appella, and E. Celis. 2000. Defining promiscuous MHC class II helper T-cell epitopes for the HER2/neu tumor antigen. *Cancer Res* 60: 5228-5236
(11). Zarour, H. M., B. Maillere, V. Brusic, K. Coval, E. Williams, S. Pouvelle-Moratille, F. Castelli, S. Land, J. Bennouna, T. Logan, and J. M. Kirkwood. 2002. NY-ESO-1 119-143 is a promiscuous major histocompatibility complex class II T-helper epitope recognized by Th1-and Th2-type tumor-reactive CD4+ T cells. *Cancer Res* 62: 213-218.
(12). Falugi, F., R. Petracca, M. Mariani, F. Luzzi, S. Mancianti, V. Carinci, M. L. Melli, O. Finco, A. Wack, A. Di Tommaso, M. T. De Magistris, P. Costantino, G. Del Giudice, S. Abrignani, R. Rappuoli, and G. Grandi. 2001. Rationally designed strings of promiscuous CD4(+) T cell epitopes provide help to Haemophilus influenzae type b oligosaccharide: a model for new conjugate vaccines. *Eur J Immunol* 31: 3816-3824.

The CLIP region in an Ii molecule, e.g., having the amino acid sequence of the Ii portion set forth in SEQ ID NO: 91, may be replaced with any of the peptides in Table 2 or other promiscuous epitopes set forth in the references of Table 2, or functional variants thereof. Preferred epitopes include those from tetanus toxin and influenza. Any other promiscuous CD4+ T cell epitopes may be used, e.g., those described in the following references:

1. Campi, G., M. Crosti, G. Consogno, V. Facchinetti, B. M. Conti-Fine, R. Longhi, G. Casorati, P. Dellabona, and M. P. Protti. 2003. CD4(+) T cells from healthy subjects and colon cancer patients recognize a carcinoembryonic antigen-specific immunodominant epitope. *Cancer Res* 63:8481-8486.
2. Castelli, F. A., M. Leleu, S. Pouvelle-Moratille, S. Farci, H. M. Zarour, M. Andrieu, C. Auriault, A. Menez, B. Georges, and B. Maillere. 2007. Differential capacity of T cell priming in naive donors of promiscuous CD4+ T cell epitopes of HCV NS3 and Core proteins. *Eur J Immunol* 37:1513-1523.
3. Consogno, G., S. Manici, V. Facchinetti, A. Bachi, J. Hammer, B. M. Conti-Fine, C. Rugarli, C. Traversari, and M. P. Protti. 2003. Identification of immunodominant regions among promiscuous HLA-DR-restricted CD4+ T-cell epitopes on the tumor antigen MAGE-3. *Blood* 101:1038-1044.
4. Depil, S., O. Morales, F. A. Castelli, N. Delhem, V. Francois, B. Georges, F. Dufosse, F. Morschhauser, J. Hammer, B. Maillere, C. Auriault, and V. Pancre. 2007. Determination of a HLA II promiscuous peptide cocktail as potential vaccine against EBV latency II malignancies. *J Immunother* (1997) 30:215-226.
5. Facchinetti, V., S. Seresini, R. Longhi, C. Garavaglia, G. Casorati, and M. P. Protti. 2005. CD4+ T cell immunity against the human papillomavirus-18 E6 transforming protein in healthy donors: identification of promiscuous naturally processed epitopes. *Eur J Immunol* 35:806-815.
6. Kobayashi, H., T. Nagato, K. Sato, N. Aoki, S. Kimura, M. Murakami, H. Iizuka, M. Azumi, H. Kakizaki, M. Tateno, and E. Celis. 2007. Recognition of prostate and melanoma tumor cells by six-transmembrane epithelial antigen of prostate-specific helper T lymphocytes in a human leukocyte antigen class II-restricted manner. *Cancer Res* 67:5498-5504.
7. Kobayashi, H., M. Wood, Y. Song, E. Appella, and E. Celis. 2000. Defining promiscuous MHC class II helper T-cell epitopes for the HER2/neu tumor antigen. *Cancer Res* 60:5228-5236.
8. Mandic, M., C. Almunia, S. Vicel, D. Gillet, B. Janjic, K. Coval, B. Maillere, J. M. Kirkwood, and H. M. Zarour. 2003. The alternative open reading frame of LAGE-1 gives rise to multiple promiscuous HLA-DR-restricted epitopes recognized by T-helper 1-type tumor-reactive CD4+ T cells. *Cancer Res* 63:6506-6515.
9. Neumann, F., C. Wagner, S. Stevanovic, B. Kubuschok, C. Schormann, A. Mischo, K. Ertan, W. Schmidt, and M. Pfreundschuh. 2004. Identification of an HLA-DR-restricted peptide epitope with a promiscuous binding pattern derived from the cancer testis antigen HOM-MEL-40/SSX2. *Int J Cancer* 112:661-668.
10. Ohkuri, T., M. Sato, H. Abe, K. Tsuji, Y. Yamagishi, H. Ikeda, N. Matsubara, H. Kitamura, and T. Nishimura. 2007. Identification of a novel NY-ESO-1 promiscuous helper epitope presented by multiple MHC class II molecules found frequently in the Japanese population. *Cancer Sci* 98:1092-1098.
11. Piesche, M., Y. Hildebrandt, F. Zettl, B. Chapuy, M. Schmitz, G. Wulf, L. Trumper, and R. Schroers. 2007. Identification of a promiscuous HLA DR-restricted T-cell epitope derived from the inhibitor of apoptosis protein survivin. *Hum Immunol* 68:572-576.
12. Sotiriadou, R., S. A. Perez, A. D. Gritzapis, P. A. Sotiropoulou, H. Echner, S. Heinzel, A. Mamalaki, G. Pawelec, W. Voelter, C. N. Baxevanis, and M. Papamichail. 2001. Peptide HER2(776-788) represents a naturally processed broad MHC class II-restricted T cell epitope. *Br J Cancer* 85:1527-1534.
13. Texier, C., S. Pouvelle-Moratille, C. Buhot, F. A. Castelli, C. Pecquet, A. Menez, F. Leynadier, and B. Maillere. 2002. Emerging principles for the design of promiscuous HLA-DR-restricted peptides: an example from the major bee venom allergen. *Eur J Immunol* 32:3699-3707.
14. Vujanovic, L., M. Mandic, W. C. Olson, J. M. Kirkwood, and W. J. Storkus. 2007. A mycoplasma peptide elicits heteroclitic CD4+ T cell responses against tumor antigen MAGE-A6. *Clin Cancer Res* 13:6796-6806.
15. Zarour, H. M., B. Maillere, V. Brusic, K. Coval, E. Williams, S. Pouvelle-Moratille, F. Castelli, S. Land, J. Bennouna, T. Logan, and J. M. Kirkwood. 2002. NY-ESO-1 119-143 is a promiscuous major histocompatibility complex class II T-helper epitope recognized by Th1- and Th2-type tumor-reactive CD4+ T cells. *Cancer Res* 62:213-218.
16. Gao, M., H. P. Wang, Y. N. Wang, Y. Zhou, and Q. L. Wang. 2006. HCV-NS3 Th1 minigene vaccine based on invariant chain CLIP genetic substitution enhances CD4 (+) Th1 cell responses in vivo. *Vaccine* 24:5491-5497.
17. Nagata, T., T. Aoshi, M. Suzuki, M. Uchijima, Y. H. Kim, Z. Yang, and Y. Koide. 2002. Induction of protective immunity to *Listeria monocytogenes* by immunization with plasmid DNA expressing a helper T-cell epitope that replaces the class II-associated invariant chain peptide of the invariant chain. *Infect Immun* 70:2676-2680.
18. Nagata, T., T. Higashi, T. Aoshi, M. Suzuki, M. Uchijima, and Y. Koide. 2001. Immunization with plasmid DNA encoding MHC class II binding peptide/CLIP-replaced invariant chain (Ii) induces specific helper T cells in vivo: the assessment of Ii p31 and p41 isoforms as vehicles for immunization. *Vaccine* 20:105-114.
19. Toda, M., M. Kasai, H. Hosokawa, N. Nakano, Y. Taniguchi, S. Inouye, S. Kaminogawa, T. Takemori, and M. Sakaguchi. 2002. DNA vaccine using invariant chain gene for delivery of CD4+ T cell epitope peptide derived from Japanese cedar pollen allergen inhibits allergen-specific IgE response. *Eur J Immunol* 32:1631-1639.
20. van Bergen, J., M. Camps, R. Offringa, C. J. Melief, F. Ossendorp, and F. Koning. 2000. Superior tumor protection induced by a cellular vaccine carrying a tumor-specific T helper epitope by genetic exchange of the class II-associated invariant chain peptide. *Cancer Res* 60:6427-6433.
21. van Tienhoven, E. A., C. T. ten Brink, J. van Bergen, F. Koning, W. van Eden, and C. P. Broeren. 2001. Induction of antigen specific CD4+ T cell responses by invariant chain based DNA vaccines. *Vaccine* 19:1515-1519.

In certain embodiments, the CLIP region of Ii is replaced with a T cell epitope, e.g., a CD4+ T cell epitope, such as a promiscuous CD4+ T cell epitope, with the proviso that the resulting construct is not one that has been publicly disclosed previously, e.g., one year prior to the filing of the priority application of the instant application. For example, in certain embodiments, the epitope that replaces the CLIP region is not a promiscuous CD4+ T cell epitope from an HCV antigen, *Listeria* LLO antigen, ovalbumin antigen, Japanese cedar pollen allergen, MuLV env/gp70-derived helper epitope, and Heat Shock Protein 60 (described in references 16-21 above), or epitopes replacing CLIP regions that are described in publications that are referenced to in the Examples.

In certain embodiments, a nucleic acid comprises, consists essentially of, or consists of the nucleotide sequence set forth in SEQ ID NO: 90, or comprises a nucleotide sequence sequence encoding the PADRE or Ii portion thereof. A nucleic acid may also comprise a nucleotide sequence that is at least about 80%, 85%, 90%, 95%, 96%, 97%, 98% or 99% identical to SEQ ID NO: 90 and/or to the PADRE and/or to the Ii portion thereof. Nucleic acids may differ by the addition, deletion or substitution of one or more, e.g., 1, 3, 5, 10, 15, 20, 25, 30 or more nucleotides, which may be located at the 5' end, 3' end, and/or internally to the sequence.

In certain embodiments, a nucleic acid encodes a protein that is a functional homolog of an Ii-PADRE protein, with the proviso that the Ii sequence and/or PADRE sequence is (or are) not the wild-type or a naturally-occurring sequence, e.g., the wild-type or naturally-occurring human sequence.

In another embodiment, an MHC class I/II activator is a protein that enhances MHC class II expression, e.g., an MHC class II transactivator (CIITA). The nucleotide and amino acid sequences of human CIITA are set forth as GenBank Accession Nos. P33076, NM_000246.3 and NP_000237.2 and set forth as SEQ ID NOs: 94 and 95, respectively (GeneID: 4261)). The nucleotide and amino acid sequences are set forth in FIG. 36.

Variants of the protein may also be used. Exemplary variants comprise, consist essentially of, or consist of an amino acid sequence that is at least about 80%, 85%, 90%, 95%, 96%, 97%, 98% or 99% identical to SEQ ID NO: 95. An amino acid sequence may differ from that of SEQ ID NO: 95 by the addition, deletion or substitution of at least about 1, 2, 3, 4, 5, 6, 7, 8, 9, 10, 11, 12, 13, 14, 15, 16, 17, 18, 19, 20, 25, 30 or more amino acids. In certain embodiments, a protein lacks one or more, e.g., 2, 3, 4, 5, 6, 7, 8, 9, 10 or more amino acids at the C- and/or N-terminus and/or internally relative to that of SEQ ID NO: 95. The locations at which amino acid changes (i.e., deletions, additions or substitutions) may be made may be determined by comparing, i.e., aligning, the amino acid sequences of CIITA homologues, e.g., those from various animal species.

Exemplary amino acids that may be changed include S286, S288 and S293. Indeed, as described in Greer et al., mutation of these amino acids results in a stronger transactivation function relative to the wild-type protein. Changes are preferably not made in the guanine-nucleotide binding motifs within residues 420-561, as these appear to be necessary for CIITA activity (see Chin et al. (1997) PNAS 94:2501). Amino acids 59-94 have also been shown to be necessary for CIITA activity, as further described herein. Additional structure/function data are provided, e.g., in Chin et al., supra.

In certain embodiments, a nucleic acid comprises, consists essentially of, or consists of the nucleotide sequence set forth in SEQ ID NO: 94. A nucleic acid may also comprise a nucleotide sequence that is at least about 80%, 85%, 90%, 95%, 96%, 97%, 98% or 99% identical to SEQ ID NO: 94. Nucleic acids may differ by the addition, deletion or substitution of one or more, e.g., 1, 3, 5, 10, 15, 20, 25, 30 or more nucleotides, which may be located at the 5' end, 3' end, and/or internally to the sequence.

In certain embodiments, a nucleic acid encodes a protein that is a functional homolog of a CIITA protein, with the proviso that the sequence is not the wild-type or a naturally-occurring sequence, e.g., the wild-type or naturally-occurring human sequence.

Other nucleic acids encoding MHC class I/II activators that may be used include those that hybridize, e.g., under stringent hybridization conditions to a nucleic acid encoding an MHC class I/II activator described herein, e.g., consisting of SEQ ID NO: 90 or 94 or portions thereof. Hybridization conditions are further described herein.

Nucleic acids encoding an MHC class I/II activator may be included in plasmids or expression vectors, such as those further described herein in the context of DNA vaccines.

In one embodiment, a nucleic acid encoding an Ii-PADRE protein or functional homolog thereof is administered to a subject who is also receiving a nucleic acid encoding a CIITA protein or functional homolog thereof. The nucleic acids may be administered simultaneously or consecutively. The nucleic acids may also be linked, i.e., forming one nucleic acid molecule. For example, one or more nucleotide sequences encoding an Ii-PADRE protein or a functional variant thereof; one or more nucleotide sequences encoding an antigen or a fusion protein comprising an antigen; one or more nucleotide sequences encoding a CIITA protein of a functional variant thereof may be linked to each other, i.e., present on one nucleic acid molecule.

Nucleic Acid Vaccines

Vaccines that may be administered to a subject who is receiving an MHC class I/II activator include any vaccine, e.g., a nucleic acid vaccine (e.g., a DNA vaccine). A nucleic acid vaccine may encode an antigen, e.g., an antigen against which an immune response is desired. Other nucleic acids that may be used are those that increase or enhance an immune reaction, but which do not encode an antigen against which an immune reaction is desired. These vaccines are further described below.

Exemplary antigens include proteins or fragments thereof from a pathogenic organism, e.g., a bacterium or virus or other microorganism, as well as proteins or fragments thereof from a cell, e.g., a cancer cell. In one embodiment, the antigen is from a virus, such as human papilloma virus (HPV), e.g., E7 or E6. These proteins are also oncogenic proteins, which are important in the induction and maintenance of cellular transformation and co-expressed in most HPV-containing cervical cancers and their precursor lesions. Therefore, cancer vaccines, such as the compositions of the invention, that target E7 or E6 can be used to control of HPV-associated neoplasms (Wu, T-C, *Curr Opin Immunol.* 6:746-54, 1994).

However, as noted, the present invention is not limited to the exemplified antigen(s). Rather, one of skill in the art will appreciate that the same results are expected for any antigen (and epitopes thereof) for which a T cell-mediated response is desired. The response so generated will be effective in providing protective or therapeutic immunity, or both, directed to an organism or disease in which the epitope or antigenic determinant is involved—for example as a cell surface antigen of a pathogenic cell or an envelope or other antigen of a pathogenic virus, or a bacterial antigen, or an antigen expressed as or as part of a pathogenic molecule.

Exemplary antigens and their sequences are set forth below.

E7 Protein from HPV-16

The E7 nucleic acid sequence (SEQ ID NO: 8) and amino acid sequence (SEQ ID NO: 9) from HPV-16 are shown below (see GenBank Accession No. NC_001526)

```
atg cat gga gat aca cct aca ttg cat gaa tat atg tta gat ttg caa cca gag aca act    60
Met His Gly Asp Thr Pro Thr Leu His Glu Tyr Met Leu Asp Leu Gln Pro Glu Thr Thr     20 gat ctc tac tgt tat gag caa tta aat gac agc tca gag gag gag gat gaa ata gat ggt   120
Asp Leu Tyr Cys Tyr Glu Gln Leu Asn Asp Ser Ser Glu Glu Glu Asp Glu Ile Asp Gly    40 cca gct gga caa gca gaa ccg gac aga gcc cat tac aat att gta acc ttt tgt tgc aag   180
Pro Ala Gly Gln Ala Glu Pro Asp Arg Ala His Tyr Asn Ile Val Thr Phe Cys Cys Lys    60 tgt gac tct acg ctt cgg ttg tgc gta caa agc aca cac gta gac att cgt act ttg gaa   240
Cys Asp Ser Thr Leu Arg Leu Cys Val Gln Ser Thr His Val Asp Ile Arg Thr Leu Glu    80 gac ctg tta atg ggc aca cta gga att gtg tgc ccc atc tgt tct cag gat aag ctt       297
Asp Leu Leu Met Gly Thr Leu Gly Ile Val Cys Pro Ile Cys Ser Gln Asp Lys Leu        99
```

In single letter code, the wild type E7 amino acid sequence is:

(SEQ ID NO: 9 above)
```
MHGDTPTLHE YMLDLQPETT DLYCYEQLND SSEEEDEIDG     99
PAGQAEPDRA HYNIVTFCCK CDSTLRLCVQ STHVDIRTLE
DLLMGTLGIV CPICSQDKL
```

In another embodiment (See GenBank Accession No. AF125673, nucleotides 562-858 and the E7 amino acid sequence), the C-terminal four amino acids QDKL (SEQ ID NO: 121) (and their codons) above are replaced with the three amino acids QKP (and the codons cag aaa cca), yielding a protein of 98 residues.

When an oncoprotein or an epitope thereof is the immunizing moiety, it is preferable to reduce the tumorigenic risk of the vaccine itself. Because of the potential oncogenicity of the HPV E7 protein, the E7 protein is preferably used in a "detoxified" form.

To reduce oncogenic potential of E7 in a construct of this invention, one or more of the following positions of E7 is mutated:

| Original residue | Preferred Mutant residue | nt codon mutation | nt Position (in SEQ ID NO: 8) | Amino acid Position (in SEQ ID NO: 9) |
|---|---|---|---|---|
| Cys | Gly (or Ala) | TGT→GGT | 70 | 24 |
| Glu | Gly (or Ala) | GAG→GGG (or GCG) | 77 | 26 |
| Cys | Gly (or Ala) | TGC→GGC | 271 | 91 |

The preferred E7 (detox) mutant sequence has the following two mutations:

a TGT→GGT mutation resulting in a Cys→Gly substitution at position 24 of SEQ ID NO: 9 and GAG→GGG mutation resulting in a Glu→Gly substitution at position 26 of SEQ ID NO: 9. This mutated amino acid sequence is shown below with the replacement residues underscored:

(SEQ ID NO: 10)
```
MHGDTPTLHE YMLDLQPETT DLYGYEGLND SSEEEDEIDG     97
PAGQAEPDRA HYNIVTFCCK CDSTLRLCVQ STHVDIRTLE
DLLMGTLGIV CPICSQKP
```

These substitutions completely eliminate the capacity of the E7 to bind to Rb, and thereby nullify its transforming activity. Any nucleotide sequence that encodes the above E7 or E7(detox) polypeptide, or an antigenic fragment or epitope thereof, can be used in the present compositions and methods, though the preferred E7 and E7(detox) sequences are shown above.

E6 Protein from HPV-16

The wild type E6 nucleotide (SEQ ID NO: 11) and amino acid (SEQ ID NO: 12) sequences are shown below (see GenBank accession Nos. K02718 and NC_001526)):

```
atg cac caa aag aga act gca atg ttt cag gac cca cag gag cga ccc aga aag tta cca    60
Met His Gln Lys Arg Thr Ala Met Phe Gln Asp Pro Gln Glu Arg Pro Arg Lys Leu Pro    20 cag tta tgc aca gag ctg caa aca act ata cat gat ata ata tta gaa tgt gtg tac tgc   120
Gln Leu Cys Thr Glu Leu Gln Thr Thr Ile His Asp Ile Ile Leu Glu Cys Val Tyr Cys    40 aag caa cag tta ctg cga cgt gag gta tat gac ttt gct ttt cgg gat tta tgc ata gta   180
Lys Gln Gln Leu Leu Arg Arg Glu Val Tyr Asp Phe Ala Phe Arg Asp Leu Cys Ile Val    60 tat aga gat ggg aat cca tat gct gta tgt gat aaa tgt tta aag ttt tat tct aaa att   240
Tyr Arg Asp Gly Asn Pro Tyr Ala Val Cys Asp Lys Cys Leu Lys Phe Tyr Ser Lys Ile    80 agt gag tat aga cat tat tgt tat agt ttg tat gga aca aca tta gaa cag caa tac aac   300
Ser Glu Tyr Arg His Tyr Cys Tyr Ser Leu Tyr Gly Thr Thr Leu Glu Gln Gln Tyr Asn   100 aaa ccg ttg tgt gat ttg tta att agg tgt att aac tgt caa aag cca ctg tgt cct gaa   360
Lys Pro Leu Cys Asp Leu Leu Ile Arg Cys Ile Asn Cys Gln Lys Pro Leu Cys Pro Glu   120 gaa aag caa aga cat ctg gac aaa aag caa aga ttc cat aat ata agg ggt cgg tgg acc   420
Glu Lys Gln Arg His Leu Asp Lys Lys Gln Arg Phe His Asn Ile Arg Gly Arg Trp Thr   140 ggt cga tgt atg tct tgt tgc aga tca tca aga aca cgt aga gaa acc cag ctg taa       474
Gly Arg Cys Met Ser Cys Cys Arg Ser Ser Arg Thr Arg Arg Glu Thr Gln Leu stop      158
```

This polypeptide has 158 amino acids and is shown below in single letter code:

```
MHQKRTAMFQ DPQERPRKLP QLCTELQTTI HDIILECVYC    158
KQQLLRREVY DFAFRDLCIV YRDGNPYAVC DKCLKFYSKI
SEYRHYCYSL YGTTLEQQYN KPLCDLLIRC INCQKPLCPE
EKQRHLDKKQ RFHNIRGRWT GRCMSCCRSS RTRRETQL
[SEQ ID NO: 12, above]
```

E6 proteins from cervical cancer-associated HPV types such as HPV-16 induce proteolysis of the p53 tumor suppressor protein through interaction with E6-AP. Human mammary epithelial cells (MECs) immortalized by E6 display low levels of p53. HPV-16 E6, as well as other cancer-related papillomavirus E6 proteins, also binds the cellular protein E6BP (ERC-55). As with E7, described below, it is preferred to use a non-oncogenic mutated form of E6, referred to as "E6(detox)." Several different E6 mutations and publications describing them are discussed below.

The preferred amino acid residues to be mutated are underscored in the E6 amino acid sequence above. Some studies of E6 mutants are based upon a shorter E6 protein of 151 nucleic acids, wherein the N-terminal residue was considered to be the Met at position 8 in SEQ ID NO: 12 above. That shorter version of E6 is shown below as SEQ ID NO: 13.

```
MFQDPQERPR KLPQLCTELQ TTIHDIILEC VYCKQQLLRR

EVYDFAFRDL CIVYRDGNPY AVCDKCLKFY SKISEYRHYC

YSLYGTTLEQ QYNKPLCDLL IRCINCQKPL CPEEKQRHLD

KKQRFHNIRG RWTGRCMSCC RSSRTRRETQ L
```

To reduce oncogenic potential of E6 in a construct of this invention, one or more of the following positions of E6 is mutated:

| Original residue | Mutant residue | aa position in SEQ ID NO: 12 | aa position in SEQ ID NO: 13 |
| --- | --- | --- | --- |
| Cys | Gly (or Ala) | 70 | 63 |
| Cys | Gly (or Ala) | 113 | 106 |
| Ile | Thr | 135 | 128 |

Nguyen et al., *J Virol.* 6:13039-48, 2002, described a mutant of HPV-16 E6 deficient in binding α-helix partners which displays reduced oncogenic potential in vivo. This mutant, which includes a replacement of Ile with Thr as position 128 (of SEQ ID NO: 13), may be used in accordance with the present invention to make an E6 DNA vaccine that has a lower risk of being oncogenic. This E6($I^{128}T$) mutant is defective in its ability to bind at least a subset of α-helix partners, including E6AP, the ubiquitin ligase that mediates E6-dependent degradation of the p53 protein.

Cassetti M C et al., *Vaccine* 22:520-52, 2004, examined the effects of mutations four or five amino acid positions in E6 and E7 to inactivate their oncogenic potential. The following mutations were examined: E6-$C^{63}G$ and E6 $C^{106}G$ (positions based on SEQ ID NO: 13); E7-$C^{24}G$, E7-$E^{26}G$, and E7 $C^{91}G$ (positions based on SEQ ID NO: 9). Venezuelan equine encephalitis virus replicon particle (VRP) vaccines encoding mutant or wild type E6 and E7 proteins elicited comparable CTL responses and generated comparable antitumor responses in several HPV16 E6(+)E7(+) tumor challenge models: protection from either C3 or TC-1 tumor challenge was observed in 100% of vaccinated mice. Eradication of C3 tumors was observed in approximately 90% of the mice. The predicted inactivation of E6 and E7 oncogenic potential was confirmed by demonstrating normal levels of both p53 and Rb proteins in human mammary epithelial cells infected with VRPs expressing mutant E6 and E7 genes.

The HPV16 E6 protein contains two zinc fingers important for structure and function; one cysteine (C) amino acid position in each pair of C-X-X-C (where X is any amino acid) zinc finger motifs are preferably was mutated at E6 positions 63 and 106 (based on SEQ ID NO: 13). Mutants are created, for example, using the Quick Change Site-Directed Mutagenesis Kit (Stratagene, La Jolla, Calif.). HPV16 E6 containing a single point mutation in the codon for $Cys^{106}$ in SEQ ID NO: 13 (=Cys 113 in SEQ ID NO: 12). $Cys^{106}$ neither binds nor facilitates degradation of p53 and is incapable of immortalizing human mammary epithelial cells (MEC), a phenotype dependent upon p53 degradation. A single amino acid substitution at position $Cys^{63}$ of SEQ ID NO: 13 (=$Cys^{70}$ in SEQ ID NO: 12) destroys several HPV16 E6 functions: p53 degradation, E6TP-1 degradation, activation of telomerase, and, consequently, immortalization of primary epithelial cells.

Any nucleotide sequence that encodes these E6 polypeptides, or preferably, one of the mutants thereof, or an antigenic fragment or epitope thereof, can be used in the present invention. Other mutations can be tested and used in accordance with the methods described herein including those described in Cassetti et al., supra. These mutations can be produced from any appropriate starting sequences by mutation of the coding DNA.

The present invention also includes the use of a tandem E6-E7 vaccine, using one or more of the mutations described herein to render the oncoproteins inactive with respect to their oncogenic potential in vivo. VRP vaccines (described in Cassetti et al., supra) comprised fused E6 and E7 genes in one open reading frame which were mutated at four or five amino acid positions (see below). Thus, the present constructs may include one or more epitopes of E6 and E7, which may be arranged in their native order or shuffled in any way that permits the expressed protein to bear the E6 and E7 antigenic epitopes in an immunogenic form. DNA encoding amino acid spacers between E6 and E7 or between individual epitopes of these proteins may be introduced into the vector, provided again, that the spacers permit the expression or presentation of the epitopes in an immunogenic manner after they have been expressed by transduced host cells.

Influenza Hemagglutinin (HA)

A nucleic acid sequence encoding HA [SEQ ID NO: 14] is shown below.

```
atgaaggcaaacctactggtcctgttaagtgcacttgcagctgcagatgc agacacaatatgtataggctaccatgcgaacaattcaaccgacactgttg acacagtactcgagaagaatgtgacagtgacacactctgttaacctgctc gaagacagccacaacggaaaactatgtagattaaaaggaatagccccact acaattggggaaatgtaacatcgccggatggctcttgggaaacccagaat gcgacccactgcttccagtgagatcatggtcctacattgtagaaacacca aactctgagaatggaatatgttatccaggagatttcatcgactatgagga gctgagggagcaattgagctcagtgtcatcattcgaaagattcgaaatat ttcccaaagaaagctcatggcccaaccacaacacaaacggagtaacggca gcatgctcccatgaggggaaaagcagttttacagaaatttgctatggct gacggagaaggagggctcatacccaaagctgaaaaattcttatgtgaaca aaaaagggaaagaagtccttgtactgtggggtattcatcacccgcctaac agtaaggaacaacagaatatctatcagaatgaaaatgcttatgtctctgt agtgacttcaaattataacaggagatttaccccggaaatagcagaaagac ccaaagtaagagatcaagctgggaggatgaactattactggaccttgcta aaacccggagacacaataatatttgaggcaaatggaaatctaatagcacc aatgtatgctttcgcactgagtagaggctttgggtccggcatcatcacct caaacgcatcaatgcatgagtgtaacacgaagtgtcaaacacccctggga gctataaacagcagtctcccttaccagaatatacacccagtcacaatagg agagtgcccaaaatacgtcaggagtgccaaattgaggatggttacaggac taaggaacactccgtccattcaatccagaggtctatttggagccattgcc ggttttattgaaggggatggactggaatgatagatggatggtatggtta tcatcatcagaatgaacagggatcaggctatgcagcggatcaaaaaagca
```

```
cacaaaatgccattaacgggattacaaacaaggtgaacactgttatcgag aaaatgaacattcaattcacagctgtgggtaaagaattcaacaaattaga aaaaaggatggaaaatttaaataaaaaagttgatgatggatttctggaca tttggacatataatgcagaattgttagttctactggaaaatgaaaggact ctggatttccatgactcaaatgtgaagaatctgtatgagaaagtaaaaag ccaattaaagaataatgccaaagaaatcggaaatggatgttttgagttct accacaagtgtgacaatgaatgcatggaaagtgtaagaaatgggacttat gattatcccaaatattcagaagagtcaaagttgaacagggaaaaggtaga tggagtgaaattggaatcaatggggatctatcagattctggcgatctact caactgtcgccagttcactggtgcttttggtctccctggggggcaatcagt ttctggatgtgttctaatggatctttgcagtgcagaatatgcatctga
```

The amino acid sequence of HA [SEQ ID NO: 15; immunodominant epitope underscored, is:

```
MKANLLVLLS ALAAADADTI CIGYHANNST DTVDTVLEKN

VTVTHSVNLL EDSHNGKLCR LKGIAPLQLG KCNIAGWLLG

NPECDPLLPV RSWSYIVETP NSENGICYPG DFIDYEELRE

QLSSVSSFER FEIFPKESSW PNHNTNGVTA ACSHEGKSSF

YRNLLWLTEK EGSYPKLKNS YVNKKGKEVL VLWGIHHPPN

SKEQQNIYQN ENAYVSVVTS NYNRRFTPEI AERPKVRDQA

GRMNYYWTLL KPGDTIIFEA NGNLIAPMYA FALSRGFGSG

IITSNASMHE CNTKCQTPLG AINSSLPYQN IHPVTIGECP

KYVRSAKLRM VTGLRNTPSI QSRGLFGAIA GFIEGGWTGM

IDGWYGYHHQ NEQGSGYAAD QKSTQNAING ITNKVNTVIE

KMNIQFTAVG KEFNKLEKRM ENLNKKVDDG FLDIWTYNAE

LLVLLENERT LDFHDSNVKN LYEKVKSQLK NNAKEIGNGC

FEFYHKCDNE CMESVRNGTY DYPKYSEESK LNREKVDGVK

LESMGIYQIL AIYSTVASSL VLLVSLGAIS FWMCSNGSLQ

CRICI
```

Other Exemplary Antigens

Exemplary antigens are epitopes of pathogenic microorganisms against which the host is defended by effector T cells responses, including CTL and delayed type hypersensitivity. These typically include viruses, intracellular parasites such as malaria, and bacteria that grow intracellularly such as *Mycobacterium* and *Listeria* species. Thus, the types of antigens included in the vaccine compositions of this invention may be any of those associated with such pathogens as well as tumor-specific antigens. It is noteworthy that some viral antigens are also tumor antigens in the case where the virus is a causative factor in the tumor.

In fact, the two most common cancers worldwide, hepatoma and cervical cancer, are associated with viral infection. Hepatitis B virus (HBV) (Beasley, R. P. et al., *Lancet* 2:1129-1133 (1981)) has been implicated as etiologic agent of hepatomas. About 80-90% of cervical cancers express the E6 and E7 antigens (discussed above and exemplified herein) from one of four "high risk" human papillomavirus types: HPV-16, HPV-18, HPV-31 and HPV-45 (Gissmann, L. et al., *Ciba Found Symp.* 120:190-207, 1986; Beaudenon, S., et al. *Nature* 321:246-9, 1986). The HPV E6 and E7 antigens are the most promising targets for virus associated cancers in immunocompetent individuals because of their ubiquitous expression in cervical cancer. In addition to their importance as targets for therapeutic cancer vaccines, virus-associated tumor antigens are also ideal candidates for prophylactic vaccines. Indeed, introduction of prophylactic HBV vaccines in Asia have decreased the incidence of hepatoma (Chang, M H et al. *New Engl. J. Med.* 336, 1855-1859 (1997), representing a great impact on cancer prevention.

Among the most important viruses in chronic human viral infections are HPV, HBV, hepatitis C Virus (HCV), retroviruses such as human immunodeficiency virus (HIV-1 and HIV-2), herpesviruses such as Epstein Barr Virus (EBV), cytomegalovirus (CMV), HSV-1 and HSV-2, and influenza virus. Useful antigens include HBV surface antigen or HBV core antigen; ppUL83 or pp89 of CMV; antigens of gp120, gp41 or p24 proteins of HIV-1; ICP27, gD2, gB of HSV; or influenza hemagglutinin or nucleoprotein (Anthony, L S et al., *Vaccine* 1999; 17:373-83). Other antigens associated with pathogens that can be utilized as described herein are antigens of various parasites, includes malaria, preferably malaria peptide based on repeats of NANP.

In alternative embodiments, the antigen is from a pathogen that is a bacterium, such as *Bordetella pertussis; Ehrlichia chaffeensis; Staphylococcus aureus; Toxoplasma gondii; Legionella pneumophila; Brucella suis; Salmonella enterica; Mycobacterium avium; Mycobacterium tuberculosis; Listeria monocytogenes; Chlamydia trachomatis; Chlamydia pneumoniae; Rickettsia rickettsii;* or, a fungus, such as, e.g., *Paracoccidioides brasiliensis;* or other pathogen, e.g., *Plasmodium falciparum.*

In addition to its applicability to human cancer and infectious diseases, the present invention is also intended for use in treating animal diseases in the veterinary medicine context. Thus, the approaches described herein may be readily applied by one skilled in the art to treatment of veterinary herpesvirus infections including equine herpesviruses, bovine viruses such as bovine viral diarrhea virus (for example, the E2 antigen), bovine herpesviruses, Marek's disease virus in chickens and other fowl; animal retroviral and lentiviral diseases (e.g., feline leukemia, feline immunodeficiency, simian immunodeficiency viruses, etc.); pseudorabies and rabies; and the like.

As for tumor antigens, any tumor-associated or tumor-specific antigen (or tumor cell derived epitope) that can be recognized by T cells, preferably by CTL, can be used. These include, without limitation, mutant p53, HER2/neu or a peptide thereof, or any of a number of melanoma-associated antigens such as MAGE-1, MAGE-3, MART-1/Melan-A, tyrosinase, gp75, gp100, BAGE, GAGE-1, GAGE-2, GnT-V, and p15 (see, for example, U.S. Pat. No. 6,187,306).

It is not necessary to include a full length antigen in a nucleic acid vaccine; it suffices to include a fragment that will be presented by MHC class I and/or II. A nucleic acid may include 1, 2, 3, 4, 5 or more antigens, which may be the same or different ones.

Approaches for Mutagenesis of E6, E7, and Other Antigens

Mutants of the antigens described here may be created, for example, using the Quick Change Site-Directed Mutagenesis Kit (Stratagene, La Jolla, Calif.). Generally, antigens that may be used herein may be proteins or peptides that differ from the naturally-occurring proteins or peptides but yet retain the necessary epitopes for functional activity. An antigen may comprise, consist essentially of, or consist of an amino acid sequence that is at least about 50%, 55%, 60%, 65%, 70%, 75%, 80%, 85%, 90%, 95%, 96%, 97%, 98%, or 99% identical to that of the naturally-occurring antigen or a fragment thereof. An antigen may also comprise, consist essentially of, or consist of an amino acid sequence that is encoded by a nucleotide sequence that is at least about 50%, 55%, 60%, 65%, 70%, 75%, 80%, 85%, 90%, 95%, 96%, 97%, 98%, or 99% identical to a nucleotide sequence encoding the naturally-occurring antigen or a fragment thereof. An antigen may also comprise, consist essentially of, or consist of an amino acid sequence that is encoded by a nucleic acid that hybridizes under high stringency conditions to a nucleic acid encoding the naturally-occurring antigen or a fragment thereof. Hybridization conditions are further described herein.

An exemplary protein may comprise, consist essentially of, or consist of, an amino acid sequence that is at least about 50%, 55%, 60%, 65%, 70%, 75%, 80%, 85%, 90%, 95%, 96%, 97%, 98%, or 99% identical to that of a viral protein, such as E6 or E7, such as an E6 or E7 sequence provided herein. Where the E6 or E7 protein is a detox E6 or E7 protein, the amino acid sequence of the protein may comprise, consist essentially of, or consist of an amino acid sequence that is at least about 50%, 55%, 60%, 65%, 70%, 75%, 80%, 85%, 90%, 95%, 96%, 97%, 98%, or 99% identical to that of an E6 or E7 protein, wherein the amino acids that render the protein a "detox" protein are present.

Exemplary DNA Vaccines Encoding an Immunogenicity-Potentiating Polypeptide (IPP) and an Antigen In one embodiment, a nucleic vaccine encodes a fusion protein comprising an antigen and a second protein, e.g., an IPP. An IPP may act in potentiating an immune response by promoting: processing of the linked antigenic polypeptide via the MHC class I pathway or targeting of a cellular compartment that increases the processing. This basic strategy may be combined with an additional strategy pioneered by the present inventors and colleagues, that involve linking DNA encoding another protein, generically termed a "targeting polypeptide," to the antigen-encoding DNA. Again, for the sake of simplicity, the DNA encoding such a targeting polypeptide will be referred to herein as a "targeting DNA." That strategy has been shown to be effective in enhancing the potency of the vectors carrying only antigen-encoding DNA. See for example, the following PCT publications by Wu et al: WO 01/29233; WO 02/009645; WO 02/061113; WO 02/074920; and WO 02/12281, all of which are incorporated by reference in their entirety. The other strategies include the use of DNA encoding polypeptides that promote or enhance:

(a) development, accumulation or activity of antigen presenting cells or targeting of antigen to compartments of the antigen presenting cells leading to enhanced antigen presentation;
(b) intercellular transport and spreading of the antigen; or
(c) any combination of (a) and (b).
(d) sorting of the lysosome-associated membrane protein type 1 (Sig/LAMP-1).

The strategy includes use of:
(e) a viral intercellular spreading protein selected from the group of herpes simplex virus-1 VP22 protein, Marek's disease virus UL49 (see WO 02/09645 and U.S. Pat. No. 7,318,928), protein or a functional homologue or derivative thereof;
(f) calreticulin (CRT) and other endoplasmic reticulum chaperone polypeptides selected from the group of CRT-like molecules ER60, GRP94, gp96, or a functional homologue or derivative thereof (see WO 02/12281 and U.S. Pat. No. 7,3442,002);
(g) a cytoplasmic translocation polypeptide domains of a pathogen toxin selected from the group of domain II of *Pseudomonas* exotoxin ETA or a functional homologue or derivative thereof (see published US application 20040086845);
(h) a polypeptide that targets the centrosome compartment of a cell selected from γ-tubulin or a functional homologue or derivative thereof; or
(i) a polypeptide that stimulates dendritic cell precursors or activates dendritic cell activity selected from the group of GM-CSF, Flt3-ligand extracellular domain, or a functional homologue or derivative thereof; or.
(j) a costimulatory signal, such as a B7 family protein, including B7-DC (see U.S. Ser. No. 09/794,210), B7.1, B7.2, soluble CD40, etc.).
(k) an anti-apoptotic polypeptide preferably selected from the group consisting of (1) BCL-xL, (2) BCL2, (3) XIAP, (4) FLICEc-s, (5) dominant-negative caspase-8, (6) dominant negative caspase-9, (7) SPI-6, and (8) a functional homologue or derivative of any of (1)-(7). (See WO 2005/047501).

The following publications, all of which are incorporated by reference in their entirety, describe IPPs: Kim T W et al., *J Clin Invest* 112: 109-117, 2003; Cheng W F et al., *J Clin Invest* 108: 669-678, 2001; Hung C F et al., *Cancer Res* 61:3698-3703, 2001; Chen C H et al., 2000, supra; U.S. Pat. No. 6,734,173; published patent applications WO05/081716, WO05/047501, WO03/085085, WO02/12281, WO02/074920, WO02/061113, WO02/09645, and WO01/29233. Comparative studies of these IPPs using HPV E6 as the antigen are described in Peng, S. et al., *J Biomed Sci.* 12:689-700 2005.

An antigen may be linked N-terminally or C-terminally to an IPP. Exemplary IPPs and fusion constructs encoding such are described below.

Lysosomal Associated Membrane Protein 1 (LAMP-1)

The DNA sequence encoding the E7 protein fused to the translocation signal sequence and LAMP-1 domain (Sig-E7-LAMP-1) [SEQ ID NO: 16] is:

ATGGCGGCCCCCGGCGCCCGGCGGCCGCTGCTCCTGCTGCTGCTGGCAGG

CCTTGCACATGGCGCCTCAGCACTCTTTGAGGATCTAATCATGCATGGAG

ATACACCTACATTGCATGAATATATGTTAGATTTGCAACCAGAGACAACT

GATCTCTACTGTTATGAGCAATTAAATGACAGCTCAGAGGAGGAGGATGA

AATAGATGGTCCAGCTGGACAAGCAGAACCGGACAGAGCCCATTACAATA

TTGTTACCTTTTGTTGCAAGTGTGACTCTACGCTTCGGTTGTGCGTACAA

AGCACACACGTAGACATTCGTACTTTGGAAGACCTGTTAATGGGCACACT

AGGAATTGTGTGCCCCATCTGTTCTCAGGATCTTAACAACATGTTGATCC

CCATTGCTGTGGGCGGTGCCCTGGCAGGGCTGGTCCTCATCGTCCTCATT

GCCTACCTCATTGGCAGGAAGAGGAGTCACGCCGGCTATCAGACCATCTA

G

The amino acid sequence of Sig/E7/LAMP-1 [SEQ ID NO: 17] is:

```
MAAPGARRPL LLLLLAGLAH GASALFEDLI MHGDTPTLHE

YMLDLQPETT DLYCYEQLND SSEEEDEIDG PAGQAEPDRA

HYNIVTFCCK CDSTLRLCVQ STHVDIRTLE DLLMGTLGIV
```

CPICSQDLNN MLIPIAVGGA LAGLVLIVLI AYLIGRKRSH

AGYQTI

The nucleotide sequence of the immunogenic vector pcDNA3-Sig/E7/LAMP-1 [SEQ ID NO: 18] is shown below with the SigE7-LAMP-1 coding sequence in lower case and underscored:

GACGGATCGGGAGATCTCCCGATCCCTATGGTCGACTCTCAGTACAATC

TGCTCTGATGCCGCATAGTTAAGCCAGTATCTGCTCCCTGCTTGTGTGTT

GGAGGTCGCTGAGTAGTGCGCGAGCAAAATTTAAGCTACAACAAGGCAAG

GCTTGACCGACAATTGCATGAAGAATCTGCTTAGGGTTAGGCGTTTTGCG

CTGCTTCGCGATGTACGGGCCAGATATACGCGTTGACATTGATTATTGAC

TAGTTATTAATAGTAATCAATTACGGGGTCATTAGTTCATAGCCCATATA

TGGAGTTCCGCGTTACATAACTTACGGTAAATGGCCCGCCTGGCTGACCG

CCCAACGACCCCCGCCCATTGACGTCAATAATGACGTATGTTCCCATAGT

AACGCCAATAGGGACTTTCCATTGACGTCAATGGGTGGACTATTTACGGT

AAACTGCCCACTTGGCAGTACATCAAGTGTATCATATGCCAAGTACGCCC

CCTATTGACGTCAATGACGGTAAATGGCCCGCCTGGCATTATGCCCAGTA

CATGACCTTATGGGACTTTCCTACTTGGCAGTACATCTACGTATTAGTCA

TCGCTATTACCATGGTGATGCGGTTTTGGCAGTACATCAATGGGCGTGGA

TAGCGGTTTGACTCACGGGGATTTCCAAGTCTCCACCCCATTGACGTCAA

TGGGAGTTTGTTTTGGCACCAAAATCAACGGGACTTTCCAAAATGTCGTA

ACAACTCCGCCCCATTGACGCAAATGGGCGGTAGGCGTGTACGGTGGGAG

GTCTATATAAGCAGAGCTCTCTGGCTAACTAGAGAACCCACTGCTTACTG

GCTTATCGAAATTAATACGACTCACTATAGGGAGACCCAAGCTGGCTAGC

GTTTAAACGGGCCCTCTAGACTCGAGCGGCCGCCACTGTGCTGGATATCT

GCAGAATTC<u>atggcggccccggcgccggcggccgctgctcctgctgct</u>

<u>gctggcaggccttgcacatggcgcctcagcactctttgaggatctaatca</u>

<u>tgcatggagatacacctacattgcatgaatatatgttagatttgcaacca</u>

<u>gagacaactgatctctactgttatgagcaattaaatgacagctcagagga</u>

<u>ggaggatgaaatagatggtccagctggacaagcagaaccggacagagccc</u>

<u>attacaatattgttacctttgttgcaagtgtgactctacgcttcggttg</u>

<u>tgcgtacaaagcacacacgtagacattcgtactttggaagacctgttaat</u>

<u>gggcacactaggaattgtgtgccccatctgttctcaggatcttaacaaca</u>

<u>tgttgatcccattgctgtgggcggtgccctggcagggctggtcctcatc</u>

<u>gtcctcattgcctacctcattggcaggaagaggagtcacgccggctatca</u>

<u>gaccatctag</u>GGATCCGAGCTCGGTACCAAGCTTAAGTTTAAACCGCTGA

TCAGCCTCGACTGTGCCTTCTAGTTGCCAGCCATCTGTTGTTTGCCCCTC

CCCCGTGCCTTCCTTGACCCTGGAAGGTGCCACTCCCACTGTCCTTTCCT

AATAAAATGAGGAAATTGCATCGCATTGTCTGAGTAGGTGTCATTCTATT

CTGGGGGGTGGGGTGGGGCAGGACAGCAAGGGGGAGGATTGGGAAGACAA

TAGCAGGCATGCTGGGGATGCGGTGGGCTCTATGGCTTCTGAGGCGGAAA

GAACCAGCTGGGGCTCTAGGGGGTATCCCCACGCGCCCTGTAGCGGCGCA

TTAAGCGCGGCGGGTGTGGTGGTTACGCGCAGCGTGACCGCTACACTTGC

CAGCGCCCTAGCGCCCGCTCCTTTCGCTTTCTTCCCTTCCTTTCTCGCCA

CGTTCGCCGGCTTTCCCCGTCAAGCTCTAAATCGGGGCATCCCTTTAGGG

TTCCGATTTAGTGCTTTACGGCACCTCGACCCCAAAAAACTTGATTAGGG

TGATGGTTCACGTAGTGGGCCATCGCCCTGATAGACGGTTTTTCGCCCTT

TGACGTTGGAGTCCACGTTCTTTAATAGTGGACTCTTGTTCCAAACTGGA

ACAACACTCAACCCTATCTCGGTCTATTCTTTTGATTTATAAGGGATTTT

GGGGATTTCGGCCTATTGGTTAAAAAATGAGCTGATTTAACAAAAATTTA

ACGCGAATTAATTCTGTGGAATGTGTGTCAGTTAGGGTGTGGAAAGTCCC

CAGGCTCCCCAGGCAGGCAGAAGTATGCAAAGCATGCATCTCAATTAGTC

AGCAACCAGGTGTGGAAAGTCCCCAGGCTCCCCAGCAGGCAGAAGTATGC

AAAGCATGCATCTCAATTAGTCAGCAACCATAGTCCCGCCCCTAACTCCG

CCCATCCCGCCCCTAACTCCGCCCAGTTCCGCCCATTCTCCGCCCCATGG

CTGACTAATTTTTTTTATTTATGCAGAGGCCGAGGCCGCCTCTGCCTCTG

AGCTATTCCAGAAGTAGTGAGGAGGCTTTTTTGGAGGCCTAGGCTTTTGC

AAAAAGCTCCCGGGAGCTTGTATATCCATTTTCGGATCTGATCAAGAGAC

AGGATGAGGATCGTTTCGCATGATTGAACAAGATGGATTGCACGCAGGTT

CTCCGGCCGCTTGGGTGGAGAGGCTATTCGGCTATGACTGGGCACAACAG

ACAATCGGCTGCTCTGATGCCGCCGTGTTCCGGCTGTCAGCGCAGGGGCG

CCCGGTTCTTTTTGTCAAGACCGACCTGTCCGGTGCCCTGAATGAACTGC

AGGACGAGGCAGCGCGGCTATCGTGGCTGGCCACGACGGGCGTTCCTTGC

GCAGCTGTGCTCGACGTTGTCACTGAAGCGGGAAGGGACTGGCTGCTATT

GGGCGAAGTGCCGGGGCAGGATCTCCTGTCATCTCACCTTGCTCCTGCCG

AGAAAGTATCCATCATGGCTGATGCAATGCGGCGGCTGCATACGCTTGAT

CCGGCTACCTGCCCATTCGACCACCAAGCGAAACATCGCATCGAGCGAGC

ACGTACTCGGATGGAAGCCGGTCTTGTCGATCAGGATGATCTGGACGAAG

AGCATCAGGGGCTCGCGCCAGCCGAACTGTTCGCCAGGCTCAAGGCGCGC

ATGCCCGACGGCGAGGATCTCGTCGTGACCCATGGCGATGCCTGCTTGCC

GAATATCATGGTGGAAAATGGCCGCTTTTCTGGATTCATCGACTGTGGCC

GGCTGGGTGTGGCGGACCGCTATCAGGACATAGCGTTGGCTACCCGTGAT

ATTGCTGAAGAGCTTGGCGGCGAATGGGCTGACCGCTTCCTCGTGCTTTA

CGGTATCGCCGCTCCCGATTCGCAGCGCATCGCCTTCTATCGCCTTCTTG

ACGAGTTCTTCTGAGCGGGACTCTGGGGTTCGAAATGACCGACCAAGCGA

CGCCCAACCTGCCATCACGAGATTTCGATTCCACCGCCGCCTTCTATGAA

AGGTTGGGCTTCGGAATCGTTTTCCGGGACGCCGGCTGGATGATCCTCCA

GCGCGGGGATCTCATGCTGGAGTTCTTCGCCCACCCCAACTTGTTTATTG

CAGCTTATAATGGTTACAAATAAAGCAATAGCATCACAAATTTCACAAAT

AAAGCATTTTTTCACTGCATTCTAGTTGTGGTTTGTCCAAACTCATCAA

TGTATCTTATCATGTCTGTATACCGTCGACCTCTAGCTAGAGCTTGGCGT

-continued

AATCATGGTCATAGCTGTTTCCTGTGTGAAATTGTTATCCGCTCACAATT

CCACACAACATACGAGCCGGAAGCATAAAGTGTAAAGCCTGGGGTGCCTA

ATGAGTGAGCTAACTCACATTAATTGCGTTGCGCTCACTGCCCGCTTTCC

AGTCGGGAAACCTGTCGTGCCAGCTGCATTAATGAATCGGCCAACGCGCG

GGGAGAGGCGGTTTGCGTATTGGGCGCTCTTCCGCTTCCTCGCTCACTGA

CTCGCTGCGCTCGGTCGTTCGGCTGCGGCGAGCGGTATCAGCTCACTCAA

AGGCGGTAATACGGTTATCCACAGAATCAGGGGATAACGCAGGAAAGAAC

ATGTGAGCAAAAGGCCAGCAAAAGGCCAGGAACCGTAAAAAGGCCGCGTT

GCTGGCGTTTTTCCATAGGCTCCGCCCCCCTGACGAGCATCACAAAAATC

GACGCTCAAGTCAGAGGTGGCGAAACCCGACAGGACTATAAAGATACCAG

GCGTTTCCCCCTGGAAGCTCCCTCGTGCGCTCTCCTGTTCCGACCCTGCC

GCTTACCGGATACCTGTCCGCCTTTCTCCCTTCGGGAAGCGTGGCGCTTT

CTCAATGCTCACGCTGTAGGTATCTCAGTTCGGTGTAGGTCGTTCGCTCC

AAGCTGGGCTGTGTGCACGAACCCCCCGTTCAGCCCGACCGCTGCGCCTT

ATCCGGTAACTATCGTCTTGAGTCCAACCCGGTAAGACACGACTTATCGC

CACTGGCAGCAGCCACTGGTAACAGGATTAGCAGAGCGAGGTATGTAGGC

GGTGCTACAGAGTTCTTGAAGTGGTGGCCTAACTACGGCTACACTAGAAG

GACAGTATTTGGTATCTGCGCTCTGCTGAAGCCAGTTACCTTCGGAAAAA

GAGTTGGTAGCTCTTGATCCGGCAAACAAACCACCGCTGGTAGCGGTGGT

TTTTTTGTTTGCAAGCAGCAGATTACGCGCAGAAAAAAAGGATCTCAAGA

AGATCCTTTGATCTTTTCTACGGGGTCTGACGCTCAGTGGAACGAAAACT

CACGTTAAGGGATTTTGGTCATGAGATTATCAAAAAGGATCTTCACCTAG

ATCCTTTTAAATTAAAAATGAAGTTTTAAATCAATCTAAAGTATATATGA

GTAAACTTGGTCTGACAGTTACCAATGCTTAATCAGTGAGGCACCTATCT

CAGCGATCTGTCTATTTCGTTCATCCATAGTTGCCTGACTCCCCGTCGTG

TAGATAACTACGATACGGGAGGGCTTACCATCTGGCCCCAGTGCTGCAAT

GATACCGCGAGACCCACGCTCACCGGCTCCAGATTTATCAGCAATAAACC

AGCCAGCCGGAAGGGCCGAGCGCAGAAGTGGTCCTGCAACTTTATCCGCC

TCCATCCAGTCTATTAATTGTTGCCGGGAAGCTAGAGTAAGTAGTTCGCC

AGTTAATAGTTTGCGCAACGTTGTTGCCATTGCTACAGGCATCGTGGTGT

CACGCTCGTCGTTTGGTATGGCTTCATTCAGCTCCGGTTCCCAACGATCA

AGGCGAGTTACATGATCCCCCATGTTGTGCAAAAAAGCGGTTAGCTCCTT

CGGTCCTCCGATCGTTGTCAGAAGTAAGTTGGCCGCAGTGTTATCACTCA

TGGTTATGGCAGCACTGCATAATTCTCTTACTGTCATGCCATCCGTAAGA

TGCTTTTCTGTGACTGGTGAGTACTCAACCAAGTCATTCTGAGAATAGTG

TATGCGGCGACCGAGTTGCTCTTGCCCGGCGTCAATACGGGATAATACCG

CGCCACATAGCAGAACTTTAAAAGTGCTCATCATTGGAAAACGTTCTTCG

GGGCGAAAACTCTCAAGGATCTTACCGCTGTTGAGATCCAGTTCGATGTA

ACCCACTCGTGCACCCAACTGATCTTCAGCATCTTTTACTTTCACCAGCG

TTTCTGGGTGAGCAAAAACAGGAAGGCAAAATGCCGCAAAAAAGGGAATA

-continued

AGGGCGACACGGAAATGTTGAATACTCATACTCTTCCTTTTTCAATATTA

TTGAAGCATTTATCAGGGTTATTGTCTCATGAGCGGATACATATTTGAAT

GTATTTAGAAAAATAAACAAATAGGGGTTCCGCGCACATTTCCCCGAAAA

GTGCCACCTGACGTC

HSP70 from *M. tuberculosis*

The nucleotide sequence encoding HSP70 (SEQ ID NO: 19) is (nucleotides 10633-12510 of the *M. tuberculosis* genome in GenBank NC_000962):

```
atggctcg tgcggtcggg atcgacctcg ggaccaccaa
ctccgtcgtc tcggttctgg aaggtggcga cccggtcgtc
gtcgccaact ccgagggctc caggaccacc ccgtcaattg
tcgcgttcgc ccgcaacggt gaggtgctgg tcggccagcc
cgccaagaac caggcagtga ccaacgtcga tcgcaccgtg
cgctcggtca agcgacacat gggcagcgac tggtccatag
agattgacgg caagaaatac accgcgccgg agatcagcgc
ccgcattctg atgaagctga agcgcgacgc cgaggcctac
ctcggtgagg acattaccga cgcggttatc acgacgcccg
cctacttcaa tgacgcccag cgtcaggcca ccaaggacgc
cggccagatc gccggcctca acgtgctgcg gatcgtcaac
gagccgaccg cggccgcgct ggcctacggc ctcgacaagg
gcgagaagga gcagcgaatc ctggtcttcg acttgggtgg
tggcactttc gacgtttccc tgctggagat cggcgagggt
gtggttgagg tccgtgccac ttcgggtgac aaccacctcg
gcggcgacga ctgggaccag cgggtcgtcg attggctggt
ggacaagttc aagggcacca gcggcatcga tctgaccaag
gacaagatgg cgatgcagcg gctgcgggaa gccgccgaga
aggcaaagat cgagctgagt tcgagtcagt ccacctcgat
caacctgccc tacatcaccg tcgacgccga caagaacccg
ttgttcttag acgagcagct gacccgcgcg gagttccaac
ggatcactca ggacctgctg gaccgcactc gcaagccgtt
ccagtcggtg atcgctgaca ccggcatttc ggtgtcggag
atcgatcacg ttgtgctcgt gggtggttcg acccggatgc
ccgcggtgac cgatctggtc aaggaactca ccggcggcaa
ggaacccaac aagggcgtca accccgatga ggttgtcgcg
gtgggagccg ctctgcaggc cggcgtcctc aagggcgagg
tgaaagacgt tctgctgctt gatgttaccc cgctgagcct
gggtatcgag accaagggcg gggtgatgac caggctcatc
gagcgcaaca ccacgatccc caccaagcgg tcggagactt
tcaccaccgc cgacgacaac caaccgtcgg tgcagatcca
ggtctatcag gggggagcgtg agatcgccgc gcacaacaag
ttgctcgggt ccttcgagct gaccggcatc ccgccggcgc
```

```
cgcggggat tccgcagatc gaggtcactt tcgacatcga
cgccaacggc attgtgcacg tcaccgccaa ggacaagggc
accggcaagg agaacacgat ccgaatccag gaaggctcgg
gcctgtccaa ggaagacatt gaccgcatga tcaaggacgc
cgaagcgcac gccgaggagg atcgcaagcg tcgcgaggag
gccgatgttc gtaatcaagc cgagacattg gtctaccaga
cggagaagtt cgtcaaagaa cagcgtgagg ccgagggtgg
ttcgaaggta cctgaagaca cgctgaacaa ggttgatgcc
gcggtggcgg aagcgaaggc ggcacttggc ggatcggata
tttcggccat caagtcggcg atggagaagc tgggccagga
gtcgcaggct ctggggcaag cgatctacga agcagctcag
gctgcgtcac aggccactgg cgctgcccac cccggcggcg
agccgggcgg tgcccacccc ggctcggctg atgacgttgt
ggacgcggag gtggtcgacg acggccggga ggccaagtga
```

The amino acid sequence of HSP70 [SEQ ID NO: 20] is:

```
MARAVGIDLG TTNSVVSVLE GGDPVVVANS EGSRTTPSIV
AFARNGEVLV GQPAKNQAVT NVDRTVRSVK RHMGSDWSIE
IDGKKYTAPE ISARILMKLK RDAEAYLGED ITDAVITTPA
YFNDAQRQAT KDAGQIAGLN VLRIVNEPTA AALAYGLDKG
EKEQRILVFD LGGGTFDVSL LEIGEGVVEV RATSGDNHLG
GDDWDQRVVD WLVDKFKGTS GIDLTKDKMA MQRLREAAEK
AKIELSSSQS TSINLPYITV DADKNPLFLD EQLTFAEFQR
ITQDLLDRTR KPFQSVIADT GISVSEIDHV VLVGGSTRMP
AVTDLVKELT GGKEPNKGVN PDEVVAVGAA LQAGVLKGEV
KDVLLLDVTP LSLGIETKGG VMTRLIERNT TIPTKRSETF
TTADDNQPSV QIQVYQGERE IAAHNKLLGS FELTGIPPAP
RGIPQIEVTF DIDANGIVHV TAKDKGTGKE NTIRIQEGSG
LSKEDIDRMI KDAEAHAEED RKRREEADVR NQAETLVYQT
EKFVKEQREA EGGSKVPEDT LNKVDAAVAE AKAALGGSDI
SAIKSAMEKL GQESQALGQA IYEAAQAASQ ATGAAHPGGE
PGGAHPGSAD DVVDAEVVDD GREAK
```

The E7-Hsp70 chimera/fusion polypeptide sequences (Nucleotide sequence SEQ ID NO: 21 and amino acid sequence SEQ ID NO: 22) are provided below. The E7 coding sequence is shown in upper case and underscored.

```
1/1                                  31/11
ATG CAT GGA GAT ACA CCT ACA TTG CAT GAA TAT ATG TTA GAT TTG CAA CCA GAG ACA ACT
Met His Gly Asp Thr Pro Thr Leu His Glu Tyr Met Leu Asp Leu Gln Pro Glu Thr Thr

61/21                                91/31
GAT CTC TAC TGT TAT GAG CAA TTA AAT GAC AGC TCA GAG GAG GAG GAT GAA ATA GAT GGT
Asp Leu Tyr Cys Tyr Glu Gln Leu Asn Asp Ser Ser Glu Glu Glu Asp Glu Ile Asp Gly

121/41                               151/51
CCA GCT GGA CAA GCA GAA CCG GAC AGA GCC CAT TAC AAT ATT GTA ACC TTT TGT TGC AAG
Pro Ala Gly Gln Ala Glu Pro Asp Arg Ala His Tyr Asn Ile Val Thr Phe Cys Cys Lys

181/61                               211/71
TGT GAC TCT ACG CTT CGG TTG TGC GTA CAA AGC ACA CAC GTA GAC ATT CGT ACT TTG GAA
Cys Asp Ser Thr Leu Arg Leu Cys Val Gln Ser Thr His Val Asp Ile Arg Thr Leu Glu

241/81                               271/91
GAC CTG TTA ATG GGC ACA CTA GGA ATT GTG TGC CCC ATC TGT TCT CAA GGA TCC atg gct
Asp Leu Leu Met Gly Thr Leu Gly Ile Val Cys Pro Ile Cys Ser Gln Gly Ser Met Ala 301/101                              331/111
cgt gcg gtc ggg atc gac ctc ggg acc acc aac tcc gtc gtc tcg gtt ctg gaa ggt ggc
Arg Ala Val Gly Ile Asp Leu Gly Thr Thr Asn Ser Val Val Ser Val Leu Glu Gly Gly 361/121                              391/131
gac ccg gtc gtc gtc gcc aac tcc gag ggc tcc agg acc acc ccg tca att gtc gcg ttc
Asp Pro Val Val Val Ala Asn Ser Glu Gly Ser Arg Thr Thr Pro Ser Ile Val Ala Phe 421/141                              451/151
gcc cgc aac ggt gag gtg ctg gtc ggc cag ccc gcc aag aac cag gca gtg acc aac gtc
Ala Arg Asn Gly Glu Val Leu Val Gly Gln Pro Ala Lys Asn Gln Ala Val Thr Asn Val 481/161                              511/171
gat cgc acc gtg cgc tcg gtc aag cga cac atg ggc agc gac tgg tcc ata gag att gac
Asp Arg Thr Val Arg Ser Val Lys Arg His Met Gly Ser Asp Trp Ser Ile Glu Ile Asp 541/181                              571/191
ggc aag aaa tac acc gcg ccg gag atc agc gcc cgc att ctg atg aag ctg aag cgc gac
Gly Lys Lys Tyr Thr Ala Pro Glu Ile Ser Ala Arg Ile Leu Met Lys Leu Lys Arg Asp 601/201                              631/211
gcc gag gcc tac ctc ggt gag gac att acc gac gcg gtt atc acg acg ccc gcc tac ttc
Ala Glu Ala Tyr Leu Gly Glu Asp Ile Thr Asp Ala Val Ile Thr Thr Pro Ala Tyr Phe
```

-continued

```
661/221                              691/231
aat gac gcc cag cgt cag gcc acc aag gac gcc ggc cag atc gcc ggc ctc aac gtg ctg
Asn Asp Ala Gln Arg Gln Ala Thr Lys Asp Ala Gly Gln Ile Ala Gly Leu Asn Val Leu 721/241                              751/251
cgg atc gtc aac gag ccg acc gcg gcc gcg ctg gcc tac ggc ctc gac aag ggc gag aag
Arg Ile Val Asn Glu Pro Thr Ala Ala Ala Leu Ala Tyr Gly Leu Asp Lys Gly Glu Lys 781/261                              811/271
gag cag cga atc ctg gtc ttc gac ttg ggt ggt ggc act ttc gac gtt tcc ctg ctg gag
Glu Gln Arg Ile Leu Val Phe Asp Leu Gly Gly Gly Thr Phe Asp Val Ser Leu Leu Glu 841/281                              871/291
atc ggc gag ggt gtg gtt gag gtc cgt gcc act tcg ggt gac aac cac ctc ggc ggc gac
Ile Gly Glu Gly Val Val Glu Val Arg Ala Thr Ser Gly Asp Asn His Leu Gly Gly Asp 901/301                              931/311
gac tgg gac cag cgg gtc gtc gat tgg ctg gtg gac aag ttc aag ggc acc agc ggc atc
Asp Trp Asp Gln Arg Val Val Asp Trp Leu Val Asp Lys Phe Lys Gly Thr Ser Gly Ile 961/321                              991/331
gat ctg acc aag gac aag atg gcg atg cag cgg ctg cgg gaa gcc gcc gag aag gca aag
Asp Leu Thr Lys Asp Lys Met Ala Met Gln Arg Leu Arg Glu Ala Ala Glu Lys Ala Lys 1021/341                             1051/351
atc gag ctg agt tcg agt cag tcc acc tcg atc aac ctg ccc tac atc acc gtc gac gcc
Ile Glu Leu Ser Ser Ser Gln Ser Thr Ser Ile Asn Leu Pro Tyr Ile Thr Val Asp Ala 1081/361                             1111/371
gac aag aac ccg ttg ttc tta gac gag cag ctg acc cgc gcg gag ttc caa cgg atc act
Asp Lys Asn Pro Leu Phe Leu Asp Glu Gln Leu Thr Arg Ala Glu Phe Gln Arg Ile Thr 1141/381                             1171/391
cag gac ctg ctg gac cgc act cgc aag ccg ttc cag tcg gtg atc gct gac acc ggc att
Gln Asp Leu Leu Asp Arg Thr Arg Lys Pro Phe Gln Ser Val Ile Ala Asp Thr
Gly Ile
1201/401                             1231/411
tcg gtg tcg gag atc gat cac gtt gtg ctc gtg ggt ggt tcg acc cgg atg ccc gcg gtg
Ser Val Ser Glu Ile Asp His Val Val Leu Val Gly Gly Ser Thr Arg Met Pro Ala Val 1261/421                             1291/431
acc gat ctg gtc aag gaa ctc acc ggc ggc aag gag ccc aac aag ggc gtc aac ccc gat
Thr Asp Leu Val Lys Glu Leu Thr Gly Gly Lys Glu Pro Asn Lys Gly Val Asn Pro Asp 1321/441                             1351/451
gag gtt gtc gcg gtg gga gcc gct ctg cag gcc ggc gtc ctc aag ggc gag gtg aaa gac
Glu Val Val Ala Val Gly Ala Ala Leu Gln Ala Gly Val Leu Lys Gly Glu Val Lys Asp 1381/461                             1411/471
gtt ctg ctg ctt gat gtt acc ccg ctg agc ctg ggt atc gag acc aag ggc ggg gtg atg
Val Leu Leu Leu Asp Val Thr Pro Leu Ser Leu Gly Ile Glu Thr Lys Gly Gly Val Met 1441/481                             1471/491
acc agg ctc atc gag cgc aac acc acg atc ccc acc aag cgg tcg gag act ttc acc acc
Thr Arg Leu Ile Glu Arg Asn Thr Thr Ile Pro Thr Lys Arg Ser Glu Thr Phe Thr Thr 1501/501                             1531/ 511
gcc gac gac aac caa ccg tcg gtg cag atc cag gtc tat cag ggg gag cgt gag atc gcc
Ala Asp Asp Asn Gln Pro Ser Val Gln Ile Gln Val Tyr Gln Gly Glu Arg Glu Ile Ala 1561/521                             1591/531
gcg cac aac aag ttg ctc ggg tcc ttc gag ctg acc ggc atc ccg ccg gcg ccg cgg ggg
Ala His Asn Lys Leu Leu Gly Ser Phe Glu Leu Thr Gly Ile Pro Pro Ala Pro Arg Gly 1621/541                             1651/551
att ccg cag atc gag gtc act ttc gac atc gac gcc aac ggc att gtg cac gtc acc gcc
Ile Pro Gln Ile Glu Val Thr Phe Asp Ile Asp Ala Asn Gly Ile Val His Val Thr Ala 1681/561                             1711/571
aag gac aag ggc acc ggc aag gag aac acg atc cga atc cag gaa ggc tcg ggc ctg tcc
Lys Asp Lys Gly Thr Gly Lys Glu Asn Thr Ile Arg Ile Gln Glu Gly Ser Gly Leu Ser 1741/581                             1771/591
aag gaa gac att gac cgc atg atc aag gac gcc gaa gcg cac gcc gag gag gat cgc aag
Lys Glu Asp Ile Asp Arg Met Ile Lys Asp Ala Glu Ala His Ala Glu Glu Asp Arg Lys 1801/601                             1831/611
cgt cgc gag gag gcc gat gtt cgt aat caa gcc gag aca ttg gtc tac cag acg gag aag
Arg Arg Glu Glu Ala Asp Val Arg Asn Gln Ala Glu Thr Leu Val Tyr Gln Thr Glu Lys
```

-continued

```
1861/621                          1891/631
ttc gtc aaa gaa cag cgt gag gcc gag ggt ggt tcg aag gta ect gaa gac acg ctg aac
Phe Val Lys Glu Gln Arg Glu Ala Glu Gly Gly Ser Lys Val Pro Glu Asp Thr Leu Asn 1921/641                          1951/651
aag gtt gat gcc gcg gtg gcg gaa gcg aag gcg gca ctt ggc gga tcg gat att tcg gcc
Lys Val Asp Ala Ala Val Ala Glu Ala Lys Ala Ala Leu Gly Gly Ser Asp Ile Ser Ala 1981/661                          2011/671
atc aag tcg gcg atg gag aag ctg ggc cag gag tcg cag gct ctg ggg caa gcg atc tac
Ile Lys Ser Ala Met Glu Lys Leu Gly Gln Glu Ser Gln Ala Leu Gly Gln Ala Ile Tyr 2041/681                          2071/691
gaa gca gct cag gct gcg tca cag gcc act ggc gct gcc cac ccc ggc tcg gct gat gaA
GLU ALA ALA GLN ALA ALA SER GLN ALA THR GLY ALA ALA HIS PRO GLY SER ALA ASP GLU 2101/701
AGC a
Ser
```

ETA(dII) from *Pseudomonas aeruginosa*

The complete coding sequence for *Pseudomonas aeruginosa* exotoxin type A (ETA)—SEQ ID NO: 23—GenBank Accession No. K01397, is shown below:

```
ctgcagctgg tcaggccgtt ccgcaacgc ttgaagtcct    2760
ggccgatata ccggcagggc cagccatcgt tcgacgaata
aagccacctc agccatgatg ccctttccat ccccagcgga
accccgacat ggacgccaaa gccctgctcc tcggcagcct
ctgcctggcc gccccattcg ccgacgcgg gacgctcgac
aatgctctct ccgcctgcct cgccgccgg ctcggtgcac
cgcacacggc ggagggccag ttgcacctgc cactcaccct
tgaggcccgg cgctccaccg gcgaatgcg ctgtacctcg
gcgctggtgc gatatcggct gctggccagg ggcgccagcg
ccgacagcct cgtgcttcaa gagggctgct cgatagtcgc
caggacacgc cgcgcacgct gaccctggcg gcggacgccg
gcttggcgag cggccgcgaa ctggtcgtca ccctgggttg
tcaggcgcct gactgacagg ccgggctgcc accaccaggc
cgagatggac gccctgcatg tatcctccga tcggcaagcc
tcccgttcgc acattcacca ctctgcaatc cagttcataa
atcccataaa agccctcttc cgctccccgc cagcctcccc
gcatcccgca ccctagacgc cccgccgctc tccgccggct
cgcccgacaa gaaaaaccaa ccgctcgatc agcctcatcc
ttcacccatc acaggagcca tcgcgatgca cctgatacccc
cattggatcc ccctggtcgc cagcctcggc ctgctcgccg
gcggctcgtc cgcgtccgcc gccgaggaag ccttcgacct
ctggaacgaa tgcgccaaag cctgcgtgct cgacctcaag
gacggcgtgc gttccagccg catgagcgtc gacccggcca
tcgccgacac caacggccag ggcgtgctgc actactccat
ggtcctggag ggcggcaacg acgcgctcaa gctggccatc
gacaacgccc tcagcatcac cagcgacggc ctgaccatcc
```

-continued

```
gcctcgaagg cggcgtcgag ccgaacaagc cggtgcgcta
cagctacacg cgccaggcgc gcggcagttg gtcgctgaac
tggctggtac cgatcggcca cgagaagccc tcgaacatca
aggtgttcat ccacgaactg aacgccggca accagctcag
ccacatgtcg ccgatctaca ccatcgagat gggcgacgag
ttgctggcga agctggcgcg cgatgccacc ttcttcgtca
gggcgcacga gagcaacgag atgcagccga cgctcgccat
cagccatgcc ggggtcagcg tggtcatggc ccagacccag
ccgcgccggg aaaagcgctg gagcgaatgg ccagcggca
aggtgttgtg cctgctcgac ccgctggacg gggtctacaa
ctacctcgcc cagcaacgct gcaacctcga cgatacctgg
gaaggcaaga tctaccgggt gctcgccggc aacccggcga
agcatgacct ggacatcaaa cccacggtca tcagtcatcg
cctgcacttt cccgagggcg gcagcctggc cgcgctgacc
gcgcaccagg cttgccacct gccgctggag actttcaccc
gtcatcgcca gccgcgcggc tgggaacaac tggagcagtg
cggctatccg gtgcagcggc tggtcgccct ctacctggcg
gcgcggctgt cgtggaacca ggtcgaccag gtgatccgca
acgccctggc cagccccggc agcggcggcc acctgggcga
agcgatccgc gagcagccgg agcaggcccg tctggccctg
accctggccg ccgccgagag cgagcgcttc gtccggcagg
gcaccggcaa cgacgaggcc ggcgcggcca cgccgacgt
ggtgagcctg acctgcccgg tcgccgccgt gaatgcgcg
ggcccggcgg acagcggcga cgccctgctg gagcgcaact
atcccactgg cgcggagttc ctcggcgacg gcggcgacgt
cagcttcagc acccgcgca cgcagaactg gacggtggag
cggctgctcc aggcgcaccg ccaactggag gagcgcggct
atgtgttcgt cggctaccac ggcaccttcc tcgaagcggc
gcaaagcatc gtcttcggcg gggtgcgcgc gcgcagccag
```

-continued
```
gacctcgacg cgatctggcg cggttctat atcgccggcg
atccggcgct ggcctacggc tacgcccagg accaggaacc
cgacgcacgc ggccggatcc gcaacggtgc cctgctgcgg
gtctatgtgc cgcgctcgag cctgccgggc ttctaccgca
ccagcctgac cctggccgcg ccggaggcgg cgggcgaggt
cgaacggctg atcggccatc cgctgccgct gcgcctggac
gccatcaccg gccccgagga ggaaggcggg cgcctggaga
ccattctcgg ctggccgctg gccgagcgca ccgtggtgat
tccctcggcg atccccaccg acccgcgcaa cgtcggcggc
gacctcgacc cgtccagcat ccccgacaag aacaggcga
tcagcgccct gccggactac gccagccagc ccggcaaacc
gccgcgcgag gacctgaagt aactgccgcg accggccggc
tcccttcgca ggagccggcc ttctcggggc ctggccatac
atcaggtttt cctgatgcca gcccaatcga atatgaattc
```

The amino acid sequence of ETA (SEQ ID NO: 24), GenBank Accession No. K01397, is:

*MHLIPHWIPL VASLGLLAGG SSASA*AEEAF DLWNECAKAC 638

```
VLDLKDGVRS SRMSVDPAIA DTNGQGVLHY SMVLEGGNDA
LKLAIDNALS ITSDGLTIRL EGGVEPNKPV RYSYTRQARG
SWSLNWLVPI GHEKPSNIKV FIHELNAGNQ LSHMSPIYTI
EMGDELLAKL ARDATFFVRA HESNEMQPTL AISHAGVSVV
MAQTQPRREK RWSEWASGKV LCLLDPLDGV YNYLAQQRCN
LDDTWEGKIY RVLAGNPAKH DLDIKPTVIS HRLHFPEGGS
LAALTAHQAC HLPLETFTRH RQPRGWEQLE QCGYPVQRLV
```

-continued

```
ALYLAARLSW NQVDQVIRNA LASPGSGGDL GEAIREQPEQ
ARLALTLAAA ESERFVRQGT GNDEAGAANA DVVSLTCPVA
AGECAGPADS GDALLERNYP TGAEFLGDGG DVSFSTRGTQ
NWTVERLLQA HRQLEERGYV FVGYHGTFLE AAQSIVFGGV
RARSQDLDAI WRGFYIAGDP ALAYGYAQDQ EPDARGRIRN
GALLRVYVPR SSLPGFYRTS LTLAAPEAAG EVERLIGHPL
PLRLDAITGP EEEGGRLETI LGWPLAERTV VIPSAIPTDP
RNVGGDLDPS SIPDKEQAIS ALPDYASQPG KPPREDLK
```

Residues 1-25 (italicized) above represent the signal peptide. The first residue of the mature polypeptide, Ala, is bolded/underscored. The mature polypeptide is residues 26-638 of SEQ ID NO: 24.

Domain II (ETA(II)), translocation domain (underscored above) spans residues 247-417 of the mature polypeptide (corresponding to residues 272-442 of SEQ ID NO: 24) and is presented below separately as SEQ ID NO: 25.

```
RLHFPEGGSL AALTAHQACH LPLETFTRHR QPRGWEQLEQ     171
CGYPVQRLVA LYLAARLSWN QVDQVIRNAL ASPGSGGDLG
EAIREQPEQA RLALTLAAAE SERFVRQGTG NDEAGAANAD
VVSLTCPVAA GECAGPADSG DALLERNYPT GAEFLGDGGD
VSFSTRGTQN W
```

The construct in which ETA(dII) is fused to HPV-16 E7 is shown below (nucleotides; SEQ ID NO: 26 and amino acids; SEQ ID NO: 27). The ETA(dII) sequence appears in plain font, extra codons from plasmid pcDNA3 are italicized. Nucleotides between ETA(dII) and E7 are also bolded (and result in the interposition of two amino acids between ETA (dII) and E7). The E7 amino acid sequence is underscored (ends with Gln at position 269).

```
1/1                                     31/11
atg cgc ctg cac ttt ccc gag ggc ggc agc ctg gcc gcg ctg acc gcg cac cag gct tgc
Met arg leu his phe pro glu gly gly ser leu ala ala leu thr ala his gln ala cys 61/21                                   91/31
cac ctg ccg ctg gag act ttc acc cgt cat cgc cag ccg cgc ggc tgg gaa caa ctg gag
His Leu Pro Leu Glu Thr Phe Thr Arg His Arg Gln Pro Arg Gly Trp Glu Gln Leu Glu 121/41                                  151/51
cag tgc ggc tat ccg gtg cag cgg ctg gtc gcc ctc tac ctg gcg gcg cgg ctg tcg tgg
Gln Cys Gly Tyr Pro Val Gln Arg Leu Val Ala Leu Tyr Leu Ala Ala Arg Leu Ser Trp 181/61                                  211/71
aac cag gtc gac cag gtg atc cgc aac gcc ctg gcc agc ccc ggc agc ggc ggc gac ctg
Asn Gln Val Asp Gln Val Ile Arg Asn Ala Leu Ala Ser Pro Gly Ser Gly Gly Asp Leu 241/81                                  271/91
ggc gaa gcg atc cgc gag cag ccg gag cag gcc cgt ctg gcc ctg acc ctg gcc gcc gcc
Gly Glu Ala Ile Arg Glu Gln Pro Glu Gln Ala Arg Leu Ala Leu Thr Leu Ala Ala Ala 301/101                                 331/111
gag agc gag cgc ttc gtc cgg cag ggc acc ggc aac gac gag gcc ggc gcg gcc aac gcc
Glu Ser Glu Arg Phe Val Arg Gln Gly Thr Gly Asn Asp Glu Ala Gly Ala Ala Asn Ala 361/121                                 391/131
gac gtg gtg agc ctg acc tgc ccg gtc gcc gcc ggt gaa tgc gcg ggc ccg gcg gac agc
Asp Val Val Ser Leu Thr Cys Pro Val Ala Ala Gly Glu Cys Ala Gly Pro Ala Asp Ser
```

```
421/141                              451/151
ggc gac gcc ctg ctg gag cgc aac tat ccc act ggc gcg gag ttc ctc ggc gac ggc ggc
Gly Asp Ala Leu Leu Glu Arg Asn Tyr Pro Thr Gly Ala Glu Phe Leu Gly Asp Gly Gly 481/161                              511/171
gac gtc agc ttc agc acc cgc ggc acg cag aac gaa ttc atg cat gga gat aca cct aca
Asp Val Ser Phe Ser Thr Arg Gly Thr Gln Asn Glu Phe Met His Gly Asp Thr Pro Thr 541/181                              571/191
ttg cat gaa tat atg tta gat ttg caa cca gag aca act gat ctc tac tgt tat gag caa
Leu His Glu Tyr Met Leu Asp Leu Gln Pro Glu Thr Thr Asp Leu Tyr Cys Tyr Glu Gln 601/201                              631/211
tta aat gac agc tca gag gag gag gat gaa ata gat ggt cca gct gga caa gca gaa ccg
Leu Asn Asp Ser Ser Glu Glu Glu Asp Glu Ile Asp Gly Pro Ala Gly Gln Ala Glu Pro 661/221                              691/231
gac aga gcc cat tac aat att gta acc ttt tgt tgc aag tgt gac tct acg ctt cgg ttg
Asp Arg Ala His Tyr Asn Ile Val Thr Phe Cys Cys Lys Cys Asp Ser Thr Leu Arg Leu 721/241                              751/251
tgc gta caa agc aca cac gta gac att cgt act ttg gaa gac ctg tta atg ggc aca cta
Cys Val Gln Ser Thr His Val Asp Ile Arg Thr Leu Glu Asp Leu Leu Met Gly Thr Leu 781/261                              811/271
gga att gtg tgc ccc atc tgt tct caa gga tcc gag ctc ggt acc aag ctt aag ttt aaa
Gly Ile Val Cys Pro Ile Cys Ser Gln Gly Ser Glu Leu Gly Thr Lys Leu Lys Phe Lys 841/281
ccg ctg atc agc ctc gac tgt gcc ttc tag
Pro Leu Ile Ser Leu Asp Cys Ala Phe AMB
```

The nucleotide sequence of the pcDNA3 vector encoding E7 and HSP70 (pcDNA3-E7-Hsp70) (SEQ ID NO: 3) is shown in FIG. 24. The E7-Hsp70 fusion sequence is shown in upper case, underscored. Plasmid sequences are in lower case.

Figure 25:
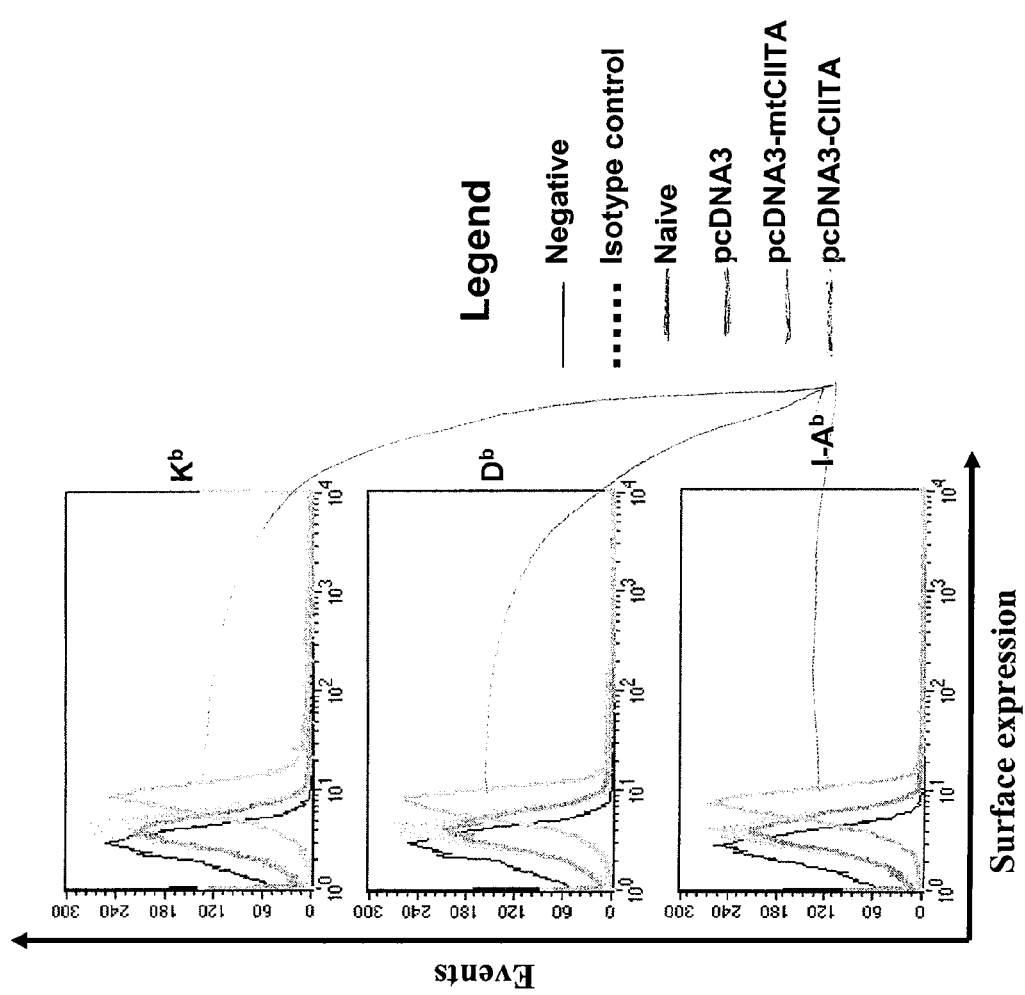
FIG. 25: Flow cytometry analysis to demonstrate the expression of murine MHC molecules in CIITA-transfected DC-1 cells. Flow cytometry data demonstrating the levels of H-2 K$^b$, H-2 D$^b$, and I-A$^b$ expression in CIITA-transfected cells and controls. The legend shows the vector plasmids with which the DCs were transfected. An immortalized dendritic cell line (DC-1) was transfected with CIITA or mutant CIITA (mtCIITA). Untransfected cells and cells transfected with the pcDNA3 vector backbone were used as a control. The expression of MHC I and II molecules was characterized using antibodies to MHC I H-2 K$^b$, H-2 D$^b$, and MHC II I-A$^b$ by flow cytometry analysis.

The nucleic acid sequence of plasmid construct pcDNA3-ETA(dII)/E7 (SEQ ID NO: 4) is shown in FIG. 25. ETA(dII)/E7 is ligated into the EcoRI/BamHI sites of pcDNA3 vector. The nucleotides encoding ETA(dII)/E7 are shown in upper case and underscored. Plasmid sequence is lower case.

Calreticulin (CRT)

Calreticulin (CRT), a well-characterized ~46 kDa protein was described briefly above, as were a number of its biological and biochemical activities. As used herein, "calreticulin" or "CRT" refers to polypeptides and nucleic acids molecules having substantial identity (defined herein) to the exemplary human CRT sequences as described herein or homologues thereof, such as rabbit and rat CRT—well-known in the art. A CRT polypeptide is a polypeptides comprising a sequence identical to or substantially identical (defined herein) to the amino acid sequence of CRT. An exemplary nucleotide and amino acid sequence for a CRT used in the present compositions and methods are presented below. The terms "calreticulin" or "CRT" encompass native proteins as well as recombinantly produced modified proteins that, when fused with an antigen (at the DNA or protein level) promote the induction of induce immune responses and, promote angiogenesis, including a CTL response. Thus, the terms "calreticulin" or "CRT" encompass homologues and allelic variants of human CRT, including variants of native proteins constructed by in vitro techniques, and proteins isolated from natural sources. The CRT polypeptides of the invention, and sequences encoding them, also include fusion proteins comprising non-CRT sequences, particularly MHC class I-binding peptides; and also further comprising other domains, e.g., epitope tags, enzyme cleavage recognition sequences, signal sequences, secretion signals and the like.

A human CRT coding sequence is shown below (SEQ ID NO: 28):

```
  1 atgctgctat ccgtgccgct gctgctcggc ctcctcggcc tggccgtcgc cgagcccgcc 61 gtctacttca aggagcagtt tctggacgga gacgggtgga cttcccgctg gatcgaatcc 121 aaacacaagt cagattttgg caaattcgtt ctcagttccg gcaagttcta cggtgacgag 181 gagaaagata aagtttgca gacaagccag gatgcacgct tttatgctct gtcggccagt 241 ttcgagcctt tcagcaacaa aggccagacg ctggtggtgc agttcacggt gaaacatgag 301 cagaacatcg actgtggggg cggctatgtg aagctgtttc ctaatagttt ggaccagaca 361 gacatgcacg gagactcaga atacaacatc atgtttggtc ccgacatctg tggccctggc 421 accaagaagg ttcatgtcat cttcaactac aagggcaaga acgtgctgat caacaaggac 481 atccgttgca aggatgatga gtttacacac ctgtacacac tgattgtgcg gccagacaac 541 acctatgagg tgaagattga caacagccag gtggagtccg gctccttgga agacgattgg
```

```
601 gacttcctgc cacccaagaa gataaaggat cctgatgctt caaaaccgga agactgggat 661 gagcgggcca agatcgatga tcccacagac tccaagcctg aggactggga caagcccgag 721 catatccctg accctgatgc taagaagccc gaggactggg atgaaagagat ggacggagag 781 tgggaacccc cagtgattca gaaccctgag tacaaggtg agtggaagcc ccggcagatc 841 gacaacccag attacaaggg cacttggatc cacccagaaa ttgacaaccc cgagtattct 901 cccgatccca gtatctatgc ctatgataac tttggcgtgc tgggcctgga cctctggcag 961 gtcaagtctg gcaccatctt tgacaacttc ctcatcacca acgatgaggc atacgctgag 1021 gagtttggca acgagacgtg gggcgtaaca aaggcagcag agaaacaaat agaggacaaa 1081 caggacgagg agcagaggct taaggaggag gaagaagaca agaaacgcaa agaggaggag 1141 gaggcagagg acaaggagga tgatgaggac aaagatgagg atgaggagga tgaggaggac 1201 aaggaggaag atgaggagga agatgtcccc ggccaggcca aggacgagct g_tag_
1251
```

The amino acid sequence of the human CRT protein encoded by SEQ ID NO: 28 is set forth below (SEQ ID NO: 29). This amino acid sequence is highly homologous to GenBank Accession No. NM 004343.

```
  1 MLLSVPLLLG LLGLAVAEPA VYFKEQFLDG DGWTSRWIES KHKSDFGKFV LSSGKFYGDE

61 EKDKGLQTSQ DARFYALSAS FEPFSNKGQT LVVQFTVKHE QNIDCGGGYV KLFPNSLDQT

121 DMHGDSEYNI MFGPDICGPG TKKVHVIFNY KGKNVLINKD IRCKDDEFTH LYTLIVRPDN

181 TYEVKIDNSQ VESGSLEDDW DFLPPKKIKD PDASKPEDWD ERAKIDDPTD SKPEDWDKPE

241 HIPDPDAKKP EDWDEEMDGE WEPPVIQNPE YKGEWKPRQI DNPDYKGTWI HPEIDNPEYS

301 PDPSIYAYDN FGVLGLDLWQ VKSGTIFDNF LITNDEAYAE EFGNETWGVT KAAEKQMKDK

361 QDEEQRLKEE EEDKKRKEEE EAEDKEDDED KDEDEEDEED KEEDEEEDVP GQAKDEL
417
```

The amino acid sequence of the rabbit and rat CRT proteins are set forth in GenBank Accession Nos. P15253 and NM 022399, respectively). An alignment of human, rabbit and rat CRT shows that these proteins are highly conserved, and most of the amino acid differences between species are conservative in nature. Most of the variation is found in the alignment of the approximately 36 C-terminal residues. Thus, for the present invention, although human CRT is preferred, DNA encoding any homologue of CRT from any species that has the requisite biological activity (as an IPP) or any active domain or fragment thereof, may be used in place of human CRT or a domain thereof.

The present inventors and colleagues (Cheng et al., supra; incorporated by reference in its entirety) that DNA vaccines encoding each of the N, P, and C domains of CRT chimerically linked to HPV-16 E7 elicited potent antigen-specific CD8+ T cell responses and antitumor immunity in mice vaccinated i.d., by gene gun administration. N-CRT/E7, P-CRT/E7 or C-CRT/E7 DNA each exhibited significantly increased numbers of E7-specific CD8+ T cell precursors and impressive antitumor effects against E7-expressing tumors when compared with mice vaccinated with E7 DNA (antigen only). N-CRT DNA administration also resulted in anti-angiogenic antitumor effects. Thus, cancer therapy using DNA encoding N-CRT linked to a tumor antigen may be used for treating tumors through a combination of antigen-specific immunotherapy and inhibition of angiogenesis.

The constructs comprising CRT or one of its domains linked to E7 is illustrated schematically below.

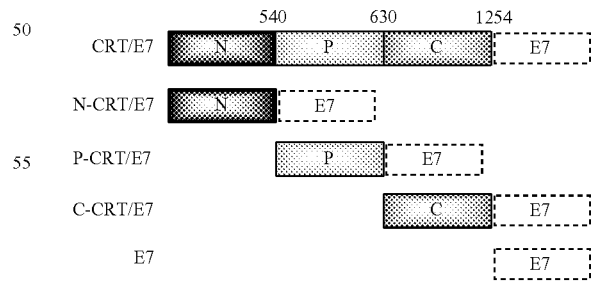

The amino acid sequences of the 3 human CRT domains are shown as annotations of the full length protein (SEQ ID NO: 29). The N domain comprises residues 1-170 (normal text); the P domain comprises residues 171-269 (underscored); and the C domain comprises residues 270-417 (bold/italic)

```
  1 MLLSVPLLLG LLGLAVAEPA VYFKEQFLDG DGWTSRWIES KHKSDFGKFV LSSGKFYGDE

61 EKDKGLQTSQ DARFYALSAS FEPFSNKGQT LVVQFTVKHE QNIDCGGGYV KLFPNSLDQT

121 DMHGDSEYNI MFGPDICGPG TKKVHVIFNY KGKNVLINKD IRCKDDEFTH LYTLIVRPDN

181 TYEVKIDNSQ VESGSLEDDW DFLPPKKIKD PDASKPEDWD ERAKIDDPTD SKPEDWDKPE

241 HIPDPDAKKP EDWDEEMDGE WEPPVIQNPE YKGEWKPRQI DNPDYKGTWI HPEIDNPEYS

301 PDPSIYAYDN  FGVLGLDLWQ VKSGTIFDNF LITNDEAYAE EFGNETWGVT KAAEKQMKDK

361 QDEEQRLKEE EEDKKRKEEE EAEDKEDDED KDEDEEDEED  KEEDEEEDVP GQAKDEL

417
```

The sequences of the three domains are shown as separate polypeptides below:

Human N-CRT (SEQ ID NO: 30)

```
  1 MLLSVPLLLG LLGLAVAEPA VYFKEQFLDG DGWTSRWTES KHKSDFGKFV LSSGKFYGDE

61 EKDKGLQTSQ DARFYALSAS FEPFSNKGQT LVVQFTVKHE QNIDCGGGYV KLFPNSLDQT

121 DMHGDSEYNI MFGPDICGPG TKKVHVIFNY KGKNVLINKD IRCKDDEFTH

170
```

Human P-CRT (SEQ ID NO: 31)

```
  1 LYTLIVRPDN TYEVKIDNSQ VESGSLEDDW DFLPPKKIKD PDASKPEDWD ERAKIDDPTD

61 SKPEDWDKPE HIPDPDAKKP EDWDEEMDGE WEPPVIQNPE YKGEWKPRQ

109
```

Human C-CRT (SEQ ID NO: 32)

```
  1 IDNPDYKGTW IHPEIDNPEY SPDPSIYAYD NFGVLGLDLW QVKSGTIFDN FLITNDEAYA

61 EEFGNETWGV TKAAEKQMKD KQDEEQRLKE EEEDKKRKEE EEAEDKEDDE DKDEDEEDEE

121 DKEEDEEEDV PGQAKDEL

138
```

The present vectors may comprises DNA encoding one or more of these domain sequences, which are shown by annotation of SEQ ID NO: 28, below, wherein the N-domain sequence is upper case, the P-domain sequence is lower case/italic/underscored, and the C domain sequence is lower case. The stop codon is also shown but not counted.

```
  1 ATGCTGCTAT CCGTGCCGCT GCTGCTCGGC CTCCTCGGCC TGGCCGTCGC CGAGCCCGCC

61 GTCTACTTCA AGGAGCAGTT TCTGGACGGA GACGGGTGGA CTTCCCGCTG GATCGAATCC

121 AAACACAAGT CAGATTTTGG CAAATTCGTT CTCAGTTCCG GCAAGTTCTA CGGTGACGAG

181 GAGAAAGATA AGGTTTGCA GACAAGCCAG GATGCACGCT TTTATGCTCT GTCGGCCAGT

241 TTCGAGCCTT TCAGCAACAA AGGCCAGACG CTGGTGGTGC AGTTCACGGT GAAACATGAG

301 CAGAACATCG ACTGTGGGGG CGGCTATGTG AAGCTGTTTC CTAATAGTTT GGACCAGACA

361 GACATGCACG GAGACTCAGA ATACAACATC ATGTTTGGTC CCGACATCTG TGGCCCTGGC

421 ACCAAGAAGG TTCATGTCAT CTTCAACTAC AAGGGCAAGA ACGTGCTGAT CAACAAGGAC

481 ATCCGTTGCA AGGATGATGA GTTTACACAC CTGTACACAC TGATTGTGCG GCCAGACAAC
```

```
541 acctatgagg tgaagattga caacagccag gtggagtccg gctccttgga agacgattgg 601 gacttcctgc cacccaagaa gataaaggat cctgatgctt caaaaccgga agactgggat 661 gagcgggcca agatcgatga tcccacagac tccaagcctg aggactggga caagcccgag 721 catatccctg accctgatgc taagaagccc gaggactggg atgaagagat ggacggagag 781 tgggaacccc cagtgattca gaaccctgag tacaagggtg agtggaagcc ccggcagatc 841 gacaacccag attacaaggg cacttggatc cacccagaaa ttgacaaccc cgagtattct 901 cccgatccca gtatctatgc ctatgataac tttggcgtgc tgggcctgga cctctggcag 961 gtcaagtctg gcaccatctt tgacaacttc ctcatcacca acgatgaggc atacgctgag 1021 gagtttggca acgagacgtg gggcgtaaca aaggcagcag agaaacaaat gaaggacaaa 1081 caggacgagg agcagaggct taaggaggag gaagaagaca agaaacgcaa agaggaggag 1141 gaggcagagg acaaggagga tgatgaggac aaagatgagg atgaggagga tgaggaggac 1201 aaggaggaag atgaggagga agatgtcccc ggccaggcca aggacgagct gtag

1251
```

The coding sequence for each separate domain is provided below:

Human N-CRT DNA (SEQ ID NO: 33)

```
  1 ATGCTGCTAT CCGTGCCGCT GCTGCTCGGC CTCCTCGGCC TGGCCGTCGC CGAGCCCGCC

61 GTCTACTTCA AGGAGCAGTT TCTGGAC<u>GGA</u> GACGGGTGGA CTTCCCGCTG GATCGAATCC

121 AAACACAAGT CAGATTTTGG CAAATTCGTT CTCAGTTCCG GCAAGTTCTA CGGTGACGAG

181 GAGAAAGATA AAGGTTTGCA GACAAGCCAG GATGCACGCT TTTATGCTCT GTCGGCCAGT

241 TTCGAGCCTT TCAGCAACAA AGGCCAGACG CTGGTGGTGC AGTTCACGGT GAAACATGAG

301 CAGAACATCG ACTGTGGGGG CGGCTATGTG AAGCTGTTTC CTAATAGTTT GGACCAGACA

361 GACATGCACG GAGACTCAGA ATACAACATC ATGTTTGGTC CCGACATCTG TGGCCCTGGC

421 ACCAAGAAGG TTCATGTCAT CTTCAACTAC AAGGGCAAGA ACGTGCTGAT CAACAAGGAC

481 ATCCGTTGCA AGGATGATGA GTTTACACAC CTGTACACAC TGATTGTGCG GCCAGACAAC
```

Human P-CRT DNA (SEQ ID NO: 34)

```
  1 acctatgagg tgaagattga caacagccag gtggagtccg gctccttgga agacgattgg 61 gacttcctgc cacccaagaa gataaaggat cctgatgctt caaaaccgga agactgggat 121 gagcgggcca agatcgatga tcccacagac tccaagcctg aggactggga caagcccgag 181 catatccctg accctgatgc taagaagccc gaggactggg atgaagagat ggacggagag 241 tgggaacccc cagtgattca gaaccct

267
```

Human C-CRT DNA (SEQ ID NO: 35)

```
  1 gagtacaagg gtgagtggaa gccccggcag atcgacaacc cagattacaa gggcacttgg 61 atccacccag aaattgacaa ccccgagtat tctcccgatc ccagtatcta tgcctatgat 121 aactttggcg tgctgggcct ggacctctgg caggtcaagt ctggcaccat ctttgacaac 181 ttcctcatca ccaacgatga ggcatacgct gaggagtttg gcaacgagac gtggggcgta 241 acaaaggcag cagagaaaca aatgaaggac aaacaggacg aggagcagag gcttaaggag
```

```
301 gaggaagaag acaagaaacg caaagaggag gaggaggcag aggacaagga ggatgatgag 361 gacaaagatg aggatgagga ggatgaggag gacaaggagg aagatgagga ggaagatgtc 421 cccggccagg ccaaggacga gctg

444
```

Alternatively, any nucleotide sequences that encodes these domains may be used in the present constructs. Thus, for use in humans, the sequences may be further codon-optimized.

The present construct may employ combinations of one or more CRT domains, in any of a number of orientations. Using the designations $N^{CRT}$, $P^{CRT}$ and $C^{CRT}$ to designate the domains, the following are but a few examples of the combinations that may be used in the DNA vaccine vectors of the present invention (where it is understood that Ag can be any antigen, preferably E7(detox) or E6 (detox).

| | | | |
|---|---|---|---|
| $N^{CRT}\text{-}P^{CRT}\text{-}$Ag; | $N^{CRT}\text{-}P^{CRT}\text{-}$Ag; | $N^{CRT}\text{-}C^{CRT}\text{-}$Ag; | $N^{CRT}\text{-}N^{CRT}\text{-}$Ag; |
| $N^{CRT}\text{-}N^{CRT}\text{-}N^{CRT}\text{-}$Ag; | $P^{CRT}\text{-}P^{CRT}\text{-}$Ag; | $P^{CRT}\text{-}C^{CRT}\text{-}$Ag; | $P^{CRT}\text{-}N^{CRT}\text{-}$Ag; |
| $C^{CRT}\text{-}P^{CRT}\text{-}$Ag; | $N^{CRT}\text{-}P^{CRT}\text{-}$Ag; | etc. | |

The present invention may employ shorter polypeptide fragments of CRT or CRT domains provided such fragments can enhance the immune response to an antigen with which they are paired. Shorter peptides from the CRT or domain sequences shown above that have the ability to promote protein processing via the MHC-1 class I pathway are also included, and may be defined by routine experimentation.

The present invention may also employ shorter nucleic acid fragments that encode CRT or CRT domains provided such fragments are functional, e.g., encode polypeptides that can enhance the immune response to an antigen with which they are paired (e.g., linked). Nucleic acids that encode shorter peptides from the CRT or domain sequences shown above and are functional, e.g., have the ability to promote protein processing via the MHC-1 class I pathway, are also included, and may be defined by routine experimentation.

A polypeptide fragment of CRT may include at least or about 50, 100, 200, 300, or 400 amino acids. A polypeptide fragment of CRT may also include at least or about 25, 50, 75, 100, 25-50, 50-100, or 75-125 amino acids from a CRT domain selected from the group consisting of the N-CRT, P-CRT, and C-CRT. A polypeptide fragment of CRT may include residues 1-50, 50-75, 75-100, 100-125, 125-150, 150-170 of the N-domain (e.g., of SEQ ID NO: 30). A polypeptide fragment of CRT may include residues 1-50, 50-75, 75-100, 100-109 of the P-domain (e.g., of SEQ ID NO: 31). A polypeptide fragment of CRT may include residues 1-50, 50-75, 75-100, 100-125, 125-138 of the C-domain (e.g., of SEQ ID NO: 32).

A nucleic acid fragment of CRT may encode at least or about 50, 100, 200, 300, or 400 amino acids. A nucleic acid fragment of CRT may also encode at least or about 25, 50, 75, 100, 25-50, 50-100, or 75-125 amino acids from a CRT domain selected from the group consisting of the N-CRT, P-CRT, and C-CRT. A nucleic acid fragment of CRT may encode residues 1-50, 50-75, 75-100, 100-125, 125-150, 150-170 of the N-domain (e.g., of SEQ ID NO: 30). A nucleic acid fragment of CRT may encode residues 1-50, 50-75, 75-100, 100-109 of the P-domain (e.g., of SEQ ID NO: 31). A nucleic acid fragment of CRT may encode residues 1-50, 50-75, 75-100, 100-125, 125-138 of the C-domain (e.g., of SEQ ID NO: 32).

Polypeptide "fragments" of CRT, as provided herein, do not include full-length CRT. Likewise, nucleic acid "fragments" of CRT, as provided herein, do not include a full-length CRT nucleic acid sequence and do not encode a full-length CRT polypeptide.

A most preferred vector construct of a complete chimeric nucleic acid of the invention, is shown below (SEQ ID NO: 36). The sequence is annotated to show plasmid-derived nucleotides (lower case letters), CRT-derived nucleotides (upper case bold letters), and HPV-E7-derived nucleotides (upper case, italicized/underlined letters). Note that 5 plasmid nucleotides are found between the CRT and E7 coding sequences and that the stop codon for the E7 sequence is double underscored. This plasmid is also referred to as pNGVL4a-CRT/E7(detox).

```
  1 gctccgcccc cctgacgagc atcacaaaaa tcgacgctca agtcagaggt ggcgaaaccc 61 gacaggacta taaagatacc aggcgtttcc ccctggaagc tccctcgtgc gctctcctgt 121 tccgaccctg ccgcttaccg gatacctgtc cgcctttctc ccttcgggaa gcgtggcgct 181 ttctcatagc tcacgctgta ggtatctcag ttcggtgtag gtcgttcgct ccaagctggg 241 ctgtgtgcac gaaccccccg ttcagcccga ccgctgcgcc ttatccggta actatcgtct 301 tgagtccaac ccgtaagac acgacttatc gccactggca gcagccactg gtaacaggat 361 tagcagagcg aggtatgtag gcggtgctac agagttcttg aagtggtggc ctaactacgg 421 ctacactaga agaacagtat ttggtatctg cgctctgctg aagccagtta ccttcggaaa 481 aagagttggt agctcttgat ccggcaaaca aaccaccgct ggtagcggtg ttttttttgt 541 ttgcaagcag cagattacgc gcagaaaaaa aggatctcaa gaagatcctt tgatctttc 601 tacggggtct gacgctcagt ggaacgaaaa ctcacgttaa gggattttgg tcatgagatt
```

-continued

```
 661 atcaaaaagg atcttcacct agatccttt aaattaaaaa tgaagtttta aatcaatcta
 721 aagtatatat gagtaaactt ggtctgacag ttaccaatgc ttaatcagtg aggcacctat
 781 ctcagcgatc tgtctatttc gttcatccat agttgcctga ctcggggggg ggggcgctg
 841 aggtctgcct cgtgaagaag gtgttgctga ctcataccag ggcaacgttg ttgccattgc
 901 tacaggcatc gtggtgtcac gctcgtcgtt tggtatggct tcattcagct ccggttccca
 961 acgatcaagg cgagttacat gatcccccat gttgtgcaaa aaagcggtta gctccttcgg
1021 tcctccgatc gttgtcagaa gtaagttggc cgcagtgtta tcactcatgg ttatggcagc
1081 actgcataat tctcttactg tcatgccatc cgtaagatgc tttctgtga ctggtgagta
1141 ctcaaccaag tcattctgag aatagtgtat gcggcgaccg agttgctctt gcccggcgtc
1201 aatacgggat aataccgcgc cacatagcag aactttaaaa gtgctcatca ttggaaaacg
1261 ttcttcgggg cgaaaactct caaggatctt accgctgttg agatccagtt cgatgtaacc
1321 cactcgtgca cctgaatcgc cccatcatcc agccagaaag tgagggagcc acggttgatg
1381 agagctttgt tgtaggtgga ccagttggtg attttgaact tttgctttgc cacggaacgg
1441 tctgcgttgt cgggaagatg cgtgatctga tccttcaact cagcaaaagt tcgatttatt
1501 caacaaagcc gccgtcccgt caagtcagcg taatgctctg ccagtgttac aaccaattaa
1561 ccaattctga ttagaaaaac tcatcgagca tcaaatgaaa ctgcaattta ttcatatcag
1621 gattatcaat accatatttt tgaaaagcc gtttctgtaa tgaaggagaa actcaccga
1681 ggcagttcca taggatggca agatcctggt atcggtctgc gattccgact cgtccaacat
1741 caatacaacc tattaatttc ccctcgtcaa aaataaggtt atcaagtgag aaatcaccat
1801 gagtgacgac tgaatccggt gagaatggca aaagcttatg catttctttc cagacttgtt
1861 caacaggcca gccattacgc tcgtcatcaa aatcactcgc atcaaccaaa ccgttattca
1921 ttcgtgattg cgcctgagcg agacgaaata cgcgatcgct gttaaaagga caattacaaa
1981 caggaatcga atgcaaccgg cgcaggaaca ctgccagcgc atcaacaata ttttcacctg
2041 aatcaggata ttcttctaat acctggaatg ctgttttccc ggggatcgca gtggtgagta
2101 accatgcatc atcaggagta cggataaaat gcttgatggt cggaagaggc ataaattccg
2161 tcagccagtt tagtctgacc atctcatctg taacatcatt ggcaacgcta cctttgccat
2221 gtttcagaaa caactctggc gcatcgggct tcccatacaa tcgatagatt gtcgcacctg
2281 attgcccgac attatcgcga gcccatttat acccatataa atcagcatcc atgttggaat
2341 ttaatcgcgg cctcgagcaa gacgtttccc gttgaatatg gctcataaca ccccttgtat
2401 tactgtttat gtaagcagac agtttttattg ttcatgatga tatattttta tcttgtgcaa
2461 tgtaacatca gagattttga gacacaacgt ggctttcccc ccccccccat tattgaagca
2521 tttatcaggg ttattgtctc atgagcggat acatatttga atgtatttag aaaaataaac
2581 aaataggggt tccgcgcaca tttccccgaa aagtgccacc tgacgtctaa gaaaccatta
2641 ttatcatgac attaacctat aaaaataggc gtatcacgag gcccttcgt ctcgcgcgtt
2701 tcggtgatga cggtgaaaac ctctgacaca tgcagctccc ggagacggtc acagcttgtc
2761 tgtaagcgga tgccgggagc agacaagccc gtcagggcgc gtcagcgggt gttggcgggt
2821 gtcggggctg gcttaactat gcggcatcag agcagattgt actgagagtg caccatatgc
2881 ggtgtgaaat accgcacaga tgcgtaagga gaaataccg catcagattg ctattggcc
2941 attgcatacg ttgtatccat atcataatat gtacatttat attggctcat gtccaacatt
3001 accgccatgt tgacattgat tattgactag ttattaatag taatcaatta cggggtcatt
3061 agttcatagc ccatatatgg agttccgcgt tacataactt acggtaaatg gcccgcctgg
```

-continued

```
3121 ctgaccgccc aacgaccccc gcccattgac gtcaataatg acgtatgttc ccatagtaac
3181 gccaataggg actttccatt gacgtcaatg ggtggagtat ttacggtaaa ctgcccactt
3241 ggcagtacat caagtgtatc atatgccaag tacgccccct attgacgtca atgacggtaa
3301 atggcccgcc tggcattatg cccagtacat gaccttatgg gactttccta cttggcagta
3361 catctacgta ttagtcatcg ctattaccat ggtgatgcgg ttttggcagt acatcaatgg
3421 gcgtggatag cggtttgact cacggggatt tccaagtctc cacccccattg acgtcaatgg
3481 gagtttgttt tggcaccaaa atcaacggga ctttccaaaa tgtcgtaaca actccgcccc
3541 attgacgcaa atgggcggta ggcgtgtacg gtgggaggtc tatataagca gagctcgttt
3601 agtgaaccgt cagatcgcct ggagacgcca tccacgctgt tttgacctcc atagaagaca
3661 ccgggaccga tccagcctcc gcggccggga acggtgcatt ggaacgcgga ttccccgtgc
3721 caagagtgac gtaagtaccg cctatagact ctataggcac ccccttttgg ctcttatgca
3781 tgctatactg ttttttggctt ggggcctata caccccccgct tccttatgct ataggtgatg
3841 gtatagctta gcctataggt gtgggttatt gaccattatt gaccactcca acggtggagg
3901 gcagtgtagt ctgagcagta ctcgttgctg ccgcgcgcgc caccagacat aatagctgac
3961 agactaacag actgttcctt tccatgggtc ttttctgcag tcaccgtcgt cgacATGCTG
4021 CTATCCGTGC CGCTGCTGCT CGGCCTCCTC GGCCTGGCCG TCGCCGAGCC TGCCGTCTAC
4081 TTCAAGGAGC AGTTTCTGGA CGGGGACGGG TGGACTTCCC GCTGGATCGA ATCCAAACAC
4141 AAGTCAGATT TTGGCAAATT CGTTCTCAGT TCCGGCAAGT TCTACGGTGA CGAGGAGAAA
4201 GATAAAGGTT TGCAGACAAG CCAGGATGCA CGCTTTTATG CTCTGTCGGC CAGTTTCGAG
4261 CCTTTCAGCA ACAAAGGCCA GACGCTGGTG GTGCAGTTCA CGGTGAAACA TGAGCAGAAC
4321 ATCGACTGTG GGGGCGGCTA TGTGAAGCTG TTTCCTAATA GTTTGGACCA GACAGACATG
4381 CACGGAGACT CAGAATACAA CATCATGTTT GGTCCCGACA TCTGTGGCCC TGGCACCAAG
4441 AAGGTTCATG TCATCTTCAA CTACAAGGGC AAGAACGTGC TGATCAACAA GGACATCCGT
4501 TGCAAGGATG ATGAGTTTAC ACACCTGTAC ACACTGATTG TGCGGCCAGA CAACACCTAT
4561 GAGGTGAAGA TTGACAACAG CCAGGTGGAG TCCGGCTCCT TGGAAGACGA TTGGGACTTC
4621 CTGCCACCCA AGAAGATAAA GGATCCTGAT GCTTCAAAAC CGGAAGACTG GGATGAGCGG
4681 GCCAAGATCG ATGATCCCAC AGACTCCAAG CCTGAGGACT GGGACAAGCC CGAGCATATC
4741 CCTGACCCTG ATGCTAAGAA GCCCGAGGAC TGGGATGAAG AGATGGACGG AGAGTGGGAA
4801 CCCCCAGTGA TTCAGAACCC TGAGTACAAG GGTGAGTGGA AGCCCCGGCA GATCGACAAC
4861 CCAGATTACA AGGGCACTTG GATCCACCCA GAAATTGACA ACCCCGAGTA TTCTCCCGAT
4921 CCCAGTATCT ATGCCTATGA TAACTTTGGC GTGCTGGGCC TGGACCTCTG GCAGGTCAAG
4981 TCTGGCACCA TCTTTGACAA CTTCCTCATC ACCAACGATG AGGCATACGC TGAGGAGTTT
5041 GGCAACGAGA CGTGGGGCGT AACAAAGGCA GCAGAGAAAC AAATGAAGGA CAAACAGGAC
5101 GAGGAGCAGA GGCTTAAGGA GGAGGAAGAA GACAAGAAAC GCAAAGAGGA GGAGGAGGCA
5161 GAGGACAAGG AGGATGATGA GGACAAAGAT GAGGATGAGG AGGATGAGGA GGACAAGGAG
5221 GAAGATGAGG AGGAAGATGT CCCCGGCCAG GCCAAGGACG AGCTGgaatt <u>CATGCATGGA</u>
5281 <u>GATACACCTA CATTGCATGA ATATATGTTA GATTTGCAAC CAGAGACAAC TGATCTCTAC</u>
5341 <u>GGTTATGGGC AATTAAATGA CAGCTCAGAG GAGGAGGATG AAATAGATGG TCCAGCTGGA</u>
5401 <u>CAAGCAGAAC CGGACAGAGC CCATTACAAT ATTGTAACCT TTTGTTGCAA GTGTGACTCT</u>
5461 <u>ACGCTTCGGT TGTGCGTACA AAGCACACAC GTAGACATTC GTACTTTGGA AGACCTGTTA</u>
```

```
5521 ATGGGCACAC TAGGAATTGT GTGCCCCATC TGTTCTCAGA AACCA TAAgg atccagatct 5581 ttttccctct gccaaaaatt atggggacat catgaagccc cttgagcatc tgacttctgg 5641 ctaataaagg aaatttattt tcattgcaat agtgtgttgg aatttttgt gtctctcact 5701 cggaaggaca tatgggaggg caaatcattt aaaacatcag aatgagtatt tggtttagag 5761 tttggcaaca tatgcccatt cttccgcttc ctcgctcact gactcgctgc gctcggtcgt 5821 tcggctgcgg cgagcggtat cagctcactc aaaggcggta atacggttat ccacagaatc 5881 aggggataac gcaggaaaga acatgtgagc aaaaggccag caaaaggcca ggaaccgtaa 5941 aaaggccgcg ttgctggcgt ttttccatag

5970
```

Table 3 below describes the structure of the above plasmid.

TABLE 3

| Plasmid Position | Genetic Construct | Source of Construct |
|---|---|---|
| 5970-0823 | E. coli ORI (ColE1) | pBR/E. coli-derived |
| 0837-0881 | portion of transposase (tpnA) | Common plasmid sequence Tn5/Tn903 |
| 0882-1332 | β-Lactamase (Amp$^R$) | pBRpUC derived plasmid |
| 1331-2496 | AphA (Kan$^R$) | Tn903 |
| 2509-2691 | P3 Promoter DNA binding site | Tn3/pBR322 |
| 2692-2926 | pUC backbone | Common plasmid sequence pBR322-derived |
| 2931-4009 | NF1 binding and promoter | HHV-5(HCMV UL-10 IE1 gene) |
| 4010-4014 | Poly-cloning site | Common plasmid sequence |
| 4015-5265 | Calreticulin (CRT) | Human Calreticulin |
| 5266-5271 | GAATTC plasmid sequence | Remain after cloning |
| 5272-5568 | dE7 gene (detoxified partial) | HPV-16 (E7 gene) incl. stop codon |
| 5569-5580 | Poly-cloning site | Common plasmid sequence |
| 551-5970 | Poly-Adenylation site | Mammalian signal, pHCMV-derived |

In some embodiments, an alternative to CRT is one the other ER chaperone polypeptide exemplified by ER60, GRP94 or gp96, well-characterized ER chaperone polypeptide that representatives of the HSP90 family of stress-induced proteins (see WO 02/012281). The term "endoplasmic reticulum chaperone polypeptide" as used herein means any polypeptide having substantially the same ER chaperone function as the exemplary chaperone proteins CRT, tapasin, ER60 or calnexin. Thus, the term includes all functional fragments or variants or mimics thereof. A polypeptide or peptide can be routinely screened for its activity as an ER chaperone using assays known in the art. While the invention is not limited by any particular mechanism of action, in vivo chaperones promote the correct folding and oligomerization of many glycoproteins in the ER, including the assembly of the MHC class I heterotrimeric molecule (heavy (H) chain, β2m, and peptide). They also retain incompletely assembled MHC class I heterotrimeric complexes in the ER (Hauri FEBS Lett. 476:32-37, 2000).

Intercellular Spreading Proteins

The potency of naked DNA vaccines may be enhanced by their ability to amplify and spread in vivo. VP22, a herpes simplex virus type 1 (HSV-1) protein and its "homologues" in other herpes viruses, such as the avian Marek's Disease Virus (MDV) have the property of intercellular transport that provide an approach for enhancing vaccine potency. The present inventors have previously created novel fusions of VP22 with a model antigen, human papillomavirus type 16 (HPV-16) E7, in a DNA vaccine which generated enhanced spreading and MHC class I presentation of antigen. These properties led to a dramatic increase in the number of E7-specific CD8+ T cell precursors in vaccinated mice (at least 50-fold) and converted a less effective DNA vaccine into one with significant potency against E7-expressing tumors. In comparison, a non-spreading mutant, VP22(1-267), failed to enhance vaccine potency. Results presented in U.S. Patent Application publication No. 20040028693 (U.S. Pat. No. 7,318,928), hereby incorporated by reference in its entirety, show that the potency of DNA vaccines is dramatically improved through enhanced intercellular spreading and MHC class I presentation of the antigen.

A similar study linking MDV-1 UL49 to E7 also led to a dramatic increase in the number of E7-specific CD8+ T cell precursors and potency response against E7-expressing tumors in vaccinated mice. Mice vaccinated with a MDV-1 UL49 DNA vaccine stimulated E7-specific CD8+ T cell precursor at a level comparable to that induced by HSV-1 VP22/E7. Thus, fusion of MDV-1UL49 DNA to DNA encoding a target antigen gene significantly enhances the DNA vaccine potency.

The spreading protein is preferably a viral spreading protein, most preferably a herpesvirus VP22 protein. Exemplified herein are fusion constructs that comprise herpes simplex virus-1 (HSV-1) VP22 (abbreviated HVP22) and its homologue from Marek's disease virus (MDV) termed MDV-VP22 or MVP-22). Also included in the invention are homologues of VP22 from other members of the herpesviridae or polypeptides from nonviral sources that are considered to be homologous and share the functional characteristic of promoting intercellular spreading of a polypeptide or peptide that is fused or chemically conjugated thereto.

DNA encoding HVP22 has the sequence SEQ ID NO: 7 which is shown in FIG. 24 as nucleotides 1-903 of the longer sequence SEQ ID NO: 6 (which is the full length nucleotide sequence of a vector that comprises HVP22). DNA encoding MDV-VP22 is SEQ ID NO: 37 shown below:

```
 1 atg ggg gat tct gaa agg cgg aaa tcg gaa cgg cgt cgt tcc ctt gga 48 tat ccc tct gca tat gat gac gtc tcg att cct gct cgc aga cca tca
```

-continued

```
 96 aca cgt act cag cga aat tta aac cag gat gat ttg tca aaa cat gga 144 cca ttt acc gac cat cca aca caa aaa cat aaa tcg gcg aaa gcc gta 192 tcg gaa gac gtt tcg tct acc acc cgg ggt ggc ttt aca aac aaa ccc 240 cgt acc aag ccc ggg gtc aga gct gta caa agt aat aaa ttc gct ttc 288 agt acg gct cct tca tca gca tct agc act tgg aga tca aat aca gtg 336 gca ttt aat cag cgt atg ttt tgc gga gcg gtt gca act gtg gct caa 384 tat cac gca tac caa ggc gcg ctc gcc ctt tgg cgt caa gat cct ccg 432 cga aca aat gaa gaa tta gat gca ttt ctt tcc aga gct gtc att aaa 480 att acc att caa gag ggt cca aat ttg atg ggg gaa gcc gaa acc tgt 528 gcc cgc aaa cta ttg gaa gag tct gga tta tcc cag ggg aac gag aac 576 gta aag tcc aaa tct gaa cgt aca acc aaa tct gaa cgt aca aga cgc 624 ggc ggt gaa att gaa atc aaa tcg cca gat ccg gga tct cat cgt aca 672 cat aac cct cgc act ccc gca act tcg cgt cgc cat cat tca tcc gcc 720 cgc gga tat cgt agc agt gat agc gaa taa

747
```

The amino acid sequence of HVP22 polypeptide is SEQ ID NO: 38 which is shown in FIG. 24 as amino acid residues 1-301 of SEQ ID NO: 39 (the full length amino acid encoded by the vector).

The amino acid sequence of the MDV-VP22, SEQ ID NO: 40, is below:

```
  2 Met Gly Asp Ser Glu Arg Arg Lys Ser Glu Arg Arg Ser Leu Gly

16 Tyr Pro Ser Ala Tyr Asp Asp Val Ser Ile Pro Ala Arg Arg Pro Ser

32 Thr Arg Thr Gln Arg Asn Leu Asn Gln Asp Asp Leu Ser Lys His Gly

48 Pro Phe Thr Asp His Pro Thr Gln Lys His Lys Ser Ala Lys Ala Val

64 Ser Glu Asp Val Ser Ser Thr Thr Arg Gly Gly Phe Thr Asn Lys Pro

80 Arg Thr Lys Pro Gly Val Arg Ala Val Gln Ser Asn Lys Phe Ala Phe

96 Ser Thr Ala Pro Ser Ser Ala Ser Ser Thr Trp Arg Ser Asn Thr Val

112 Ala Phe Asn Gln Arg Met Phe Cys Gly Ala Val Ala Thr Val Ala Gln

128 Tyr His Ala Tyr Gln Gly Ala Leu Ala Leu Trp Arg Gln Asp Pro Pro

144 Arg Thr Asn Glu Glu Leu Asp Ala Phe Leu Ser Arg Ala Val Ile Lys

160 Ile Thr Ile Gln Glu Gly Pro Asn Leu Met Gly Glu Ala Glu Thr Cys

176 Ala Arg Lys Leu Leu Glu Glu Ser Gly Leu Ser Gln Gly Asn Glu Asn

192 Val Lys Ser Lys Ser Glu Arg Thr Thr Lys Ser Glu Arg Thr Arg Arg

208 Gly Gly Glu Ile Glu Ile Lys Ser Pro Asp Pro Gly Ser His Arg Thr

224 His Asn Pro Arg Thr Pro Ala Thr Ser Arg Arg His His Ser Ser Ala

240 Arg Gly Tyr Arg Ser Ser Asp Ser Glu

249
```

A DNA clone pcDNA3 VP22/E7, that includes the coding sequence for HVP22 and the HPV-16 protein, E7 (plus some additional vector sequence) is SEQ ID NO: 6.

The amino acid sequence of E7 (SEQ ID NO: 41) is residues 308-403 of SEQ ID NO: 39. This particular clone has only 96 of the 98 residues present in E7. The C-terminal residues of wild-type E7, Lys and Pro, are absent from this construct. This is an example of a deletion variant as the term is described below. Such deletion variants (e.g., terminal truncation of two or a small number of amino acids) of other antigenic polypeptides are examples of the embodiments intended within the scope of the fusion polypeptides of this invention.

Homologues of IPPs

Homologues or variants of IPPs described herein, may also be used, provided that they have the requisite biological activity. These include various substitutions, deletions, or additions of the amino acid or nucleic acid sequences. Due to code degeneracy, for example, there may be considerable variation in nucleotide sequences encoding the same amino acid sequence.

A functional derivative of an IPP retains measurable IPP-like activity, preferably that of promoting immunogenicity of one or more antigenic epitopes fused thereto by promoting presentation by class I pathways. "Functional derivatives" encompass "variants" and "fragments" regardless of whether the terms are used in the conjunctive or the alternative herein.

The term "chimeric" or "fusion" polypeptide or protein refers to a composition comprising at least one polypeptide or peptide sequence or domain that is chemically bound in a linear fashion with a second polypeptide or peptide domain. One embodiment of this invention is an isolated or recombinant nucleic acid molecule encoding a fusion protein comprising at least two domains, wherein the first domain comprises an IPP and the second domain comprises an antigenic epitope, e.g., an MHC class I-binding peptide epitope. The "fusion" can be an association generated by a peptide bond, a chemical linking, a charge interaction (e.g., electrostatic attractions, such as salt bridges, H-bonding, etc.) or the like. If the polypeptides are recombinant, the "fusion protein" can be translated from a common mRNA. Alternatively, the compositions of the domains can be linked by any chemical or electrostatic means. The chimeric molecules of the invention (e.g., targeting polypeptide fusion proteins) can also include additional sequences, e.g., linkers, epitope tags, enzyme cleavage recognition sequences, signal sequences, secretion signals, and the like. Alternatively, a peptide can be linked to a carrier simply to facilitate manipulation or identification/location of the peptide.

Also included is a "functional derivative" of an IPP, which refers to an amino acid substitution variant, a "fragment," etc., of the protein, which terms are defined below. A functional derivative of an IPP retains measurable activity, preferably that is manifest as promoting immunogenicity of one or more antigenic epitopes fused thereto or co-administered therewith. "Functional derivatives" encompass "variants" and "fragments" regardless of whether the terms are used in the conjunctive or the alternative herein.

A functional homologue must possess the above biochemical and biological activity. In view of this functional characterization, use of homologous proteins including proteins not yet discovered, fall within the scope of the invention if these proteins have sequence similarity and the recited biochemical and biological activity.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred method of alignment, Cys residues are aligned.

In a preferred embodiment, the length of a sequence being compared is at least 30%, preferably at least 40%, more preferably at least 50%, even more preferably at least 60%, and even more preferably at least 70%, 80%, 90%, 95%, 96%, 97%, 98%, or 99% of the length of the IPP reference sequence. The amino acid residues (or nucleotides) at corresponding amino acid (or nucleotide) positions are then compared. When a position in the first sequence is occupied by the same amino acid residue (or nucleotide) as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to IPP nucleic acid molecules. BLAST protein searches can be performed with the XBLAST program, score=50, wordlength=3 to obtain amino acid sequences homologous to IPP protein molecules. To obtain gapped alignments for comparison purposes, Gapped BLAST can be utilized as described in Altschul et al. (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

Thus, a homologue of an IPP or of an IPP domain described above is characterized as having (a) functional activity of native IPP or domain thereof and (b) amino acid sequence similarity to a native IPP protein or domain thereof when determined as above, of at least about 50%, 55%, 60%, 65%, 70%, 75%, 80%, 85%, 90%, 95%, 96%, 97%, 98%, or 99%.

It is within the skill in the art to obtain and express such a protein using DNA probes based on the disclosed sequences of an IPP. Then, the fusion protein's biochemical and biological activity can be tested readily using art-recognized methods such as those described herein, for example, a T cell proliferation, cytokine secretion or a cytolytic assay, or an in vivo assay of tumor protection or tumor therapy. A biological assay of the stimulation of antigen-specific T cell reactivity will indicate whether the homologue has the requisite activity to qualify as a "functional" homologue.

A "variant" refers to a molecule substantially identical to either the full protein or to a fragment thereof in which one or more amino acid residues have been replaced (substitution variant) or which has one or several residues deleted (deletion variant) or added (addition variant). A "fragment" of an IPP refers to any subset of the molecule, that is, a shorter polypeptide of the full-length protein.

A number of processes can be used to generate fragments, mutants and variants of the isolated DNA sequence. Small subregions or fragments of the nucleic acid encoding the spreading protein, for example 1-30 bases in length, can be prepared by standard, chemical synthesis. Antisense oligonucleotides and primers for use in the generation of larger synthetic fragment.

A preferred group of variants are those in which at least one amino acid residue and preferably, only one, has been substituted by different residue. For a detailed description of protein chemistry and structure, see Schulz, G E et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:

| | | |
|---|---|---|
| 1. | Small aliphatic, nonpolar or slightly polar residues | Ala, Ser, Thr (Pro, Gly); |
| 2. | Polar, negatively charged residues and their amides | Asp, Asn, Glu, Gln; |
| 3. | Polar, positively charged residues | His, Arg, Lys; |
| 4. | Large aliphatic, nonpolar residues | Met, Leu, Ile, Val (Cys) |
| 5. | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

More substantial changes in biochemical, functional (or immunological) properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g., Leu, Ile, Phe, Val or Ala; (iii) substitution of a Cys residue for (or by) any other residue; (iv) substitution of a residue having an electropositive side chain, e.g., Lys, Arg or His, for (or by) a residue having an electronegative charge, e.g., Glu or Asp; or (v) substitution of a residue having a bulky side chain, e.g., Phe, for (or by) a residue not having such a side chain, e.g., Gly.

Most acceptable deletions, insertions and substitutions according to the present invention are those that do not produce radical changes in the characteristics of the wild-type or native protein in terms of its relevant biological activity, e.g., its ability to stimulate antigen specific T cell reactivity to an antigenic epitope or epitopes that are fused to the protein. However, when it is difficult to predict the exact effect of the substitution, deletion or insertion in advance of doing so, one skilled in the art will appreciate that the effect can be evaluated by routine screening assays such as those described here, without requiring undue experimentation.

Exemplary fusion proteins provided herein comprise an IPP protein or homolog thereof and an antigen. For example, a fusion protein may comprise, consists essentially of, or consists of an IPP or a an IPP fragment, e.g., N-CRT, P-CRT and/or C-CRT, or an amino acid sequence that is at least about 50%, 55%, 60%, 65%, 70%, 75%, 80%, 85%, 90%, 95%, 96%, 97%, 98%, or 99% identical to the amino acid sequence of the IPP or IPP fragment, wherein the IPP fragment is functionally active as further described herein, linked to an antigen. A fusion protein may also comprise an IPP or an IPP fragment and at least 1, 2, 3, 4, 5, 6, 7, 8, 9, 10 or more amino acids, or about 1-5, 1-10, 1-15, 1-20, 1-25, 1-30, 1-50 amino acids, at the N- and/or C-terminus of the IPP fragment. These additional amino acids may have an amino acid sequence that is unrelated to the amino acid sequence at the corresponding position in the IPP protein.

Homologs of an IPP or an IPP fragments may also comprise, consist essentially of, or consist of an amino acid sequence that differs from that of an IPP or IPP fragment by the addition, deletion, or substitution, e.g., conservative substitution, of at least about 1, 2, 3, 4, 5, 6, 7, 8, 9 or 10 amino acids, or from about 1-5, 1-10, 1-15 or 1-20 amino acids. Homologs of an IPP or IPP fragments may be encoded by nucleotide sequences that are at least about 50%, 55%, 60%, 65%, 70%, 75%, 80%, 85%, 90%, 95%, 96%, 97%, 98%, or 99% identical to the nucleotide sequence encoding an IPP or IPP fragment, such as those described herein.

Yet other homologs of an IPP or IPP fragments are encoded by nucleic acids that hybridize under stringent hybridization conditions to a nucleic acid that encodes an IPP or IPP fragment. For example, homologs may be encoded by nucleic acids that hybridize under high stringency conditions of 0.2 to 1×SSC at 65° C. followed by a wash at 0.2×SSC at 65° C. to a nucleic acid consisting of a sequence described herein. Nucleic acids that hybridize under low stringency conditions of 6×SSC at room temperature followed by a wash at 2×SSC at room temperature to nucleic acid consisting of a sequence described herein or a portion thereof can be used. Other hybridization conditions include 3×SSC at 40 or 50° C., followed by a wash in 1 or 2×SSC at 20, 30, 40, 50, 60, or 65° C. Hybridizations can be conducted in the presence of formaldehyde, e.g., 10%, 20%, 30% 40% or 50%, which further increases the stringency of hybridization. Theory and practice of nucleic acid hybridization is described, e.g., in S. Agrawal (ed.) Methods in Molecular Biology, volume 20; and Tijssen (1993) Laboratory Techniques in biochemistry and molecular biology-hybridization with nucleic acid probes, e.g., part I chapter 2 "Overview of principles of hybridization and the strategy of nucleic acid probe assays," Elsevier, N.Y. provide a basic guide to nucleic acid hybridization.

A fragment of a nucleic acid sequence is defined as a nucleotide sequence having fewer nucleotides than the nucleotide sequence encoding the full length CRT polypeptide, antigenic polypeptide, or the fusion thereof. This invention includes such nucleic acid fragments that encode polypeptides which retain (1) the ability of the fusion polypeptide to induce increases in frequency or reactivity of T cells, preferably CD8+ T cells, that are specific for the antigen part of the fusion polypeptide.

Nucleic acid sequences of this invention may also include linker sequences, natural or modified restriction endonuclease sites and other sequences that are useful for manipulations related to cloning, expression or purification of encoded protein or fragments. For example, a fusion protein may comprise a linker between the antigen and the IPP protein.

Other nucleic acid vaccines that may be used include single chain trimers (SCT), as further described in the Examples and in references cited therein, all of which are specifically incorporated by reference herein.

Backbone of Nucleic Acid Vaccine

A nucleic acid, e.g., DNA vaccine may comprise an "expression vector" or "expression cassette," i.e., a nucleotide sequence which is capable of affecting expression of a protein coding sequence in a host compatible with such sequences. Expression cassettes include at least a promoter operably linked with the polypeptide coding sequence; and, optionally, with other sequences, e.g., transcription termination signals. Additional factors necessary or helpful in effecting expression may also be included, e.g., enhancers.

"Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, *Gene Expression Technology. Methods in Enzymology*, vol. 185, Academic Press, San Diego, Calif. (1990)).

A promoter region of a DNA or RNA molecule binds RNA polymerase and promotes the transcription of an "operably linked" nucleic acid sequence. As used herein, a "promoter sequence" is the nucleotide sequence of the promoter which is found on that strand of the DNA or RNA which is transcribed by the RNA polymerase. Two sequences of a nucleic acid molecule, such as a promoter and a coding sequence, are "operably linked" when they are linked to each other in a manner which permits both sequences to be transcribed onto the same RNA transcript or permits an RNA transcript begun in one sequence to be extended into the second sequence. Thus, two sequences, such as a promoter sequence and a coding sequence of DNA or RNA are operably linked if transcription commencing in the promoter sequence will produce an RNA transcript of the operably linked coding sequence. In order to be "operably linked" it is not necessary that two sequences be immediately adjacent to one another in the linear sequence.

The preferred promoter sequences of the present invention must be operable in mammalian cells and may be either eukaryotic or viral promoters. Although preferred promoters are described in the Examples, other useful promoters and regulatory elements are discussed below. Suitable promoters may be inducible, repressible or constitutive. A "constitutive" promoter is one which is active under most conditions encountered in the cell's environmental and throughout development. An "inducible" promoter is one which is under environmental or developmental regulation. A "tissue specific" promoter is active in certain tissue types of an organism. An example of a constitutive promoter is the viral promoter MSV-LTR, which is efficient and active in a variety of cell types, and, in contrast to most other promoters, has the same enhancing activity in arrested and growing cells. Other preferred viral promoters include that present in the CMV-LTR (from cytomegalovirus) (Bashart, M. et al., *Cell* 41:521, 1985) or in the RSV-LTR (from Rous sarcoma virus) (Gorman, C. M., *Proc. Natl. Acad. Sci. USA* 79:6777, 1982). Also useful are the promoter of the mouse metallothionein I gene (Hamer, D, et al., *J. Mol. Appl. Gen.* 1:273-88, 1982; the TK promoter of Herpes virus (McKnight, S, *Cell* 31:355-65, 1982); the SV40 early promoter (Benoist, C., et al., *Nature* 290:304-10, 1981); and the yeast gal4 gene promoter (Johnston, S A et al., *Proc. Natl. Acad. Sci. USA* 79:6971-5, 1982); Silver, P A, et al., *Proc. Natl. Acad. Sci. (USA)* 81:5951-5, 1984)). Other illustrative descriptions of transcriptional factor association with promoter regions and the separate activation and DNA binding of transcription factors include: Keegan et al., *Nature* 231:699, 1986; Fields et al., *Nature* 340:245, 1989; Jones, *Cell* 61:9, 1990; Lewin, *Cell* 61:1161, 1990; Ptashne et al., *Nature* 346:329, 1990; Adams et al., *Cell* 72:306, 1993.

The promoter region may further include an octamer region which may also function as a tissue specific enhancer, by interacting with certain proteins found in the specific tissue. The enhancer domain of the DNA construct of the present invention is one which is specific for the target cells to be transfected, or is highly activated by cellular factors of such target cells. Examples of vectors (plasmid or retrovirus) are disclosed, e.g., in Roy-Burman et al., U.S. Pat. No. 5,112,767. For a general discussion of enhancers and their actions in transcription, see, Lewin, B M, *Genes IV*, Oxford University Press pp. 552-576, 1990 (or later edition). Particularly useful are retroviral enhancers (e.g., viral LTR) that is preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency.

Thus, expression cassettes include plasmids, recombinant viruses, any form of a recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include replicons (e.g., RNA replicons), bacteriophages) to which fragments of DNA may be attached and become replicated. Vectors thus include, but are not limited to RNA, autonomous self-replicating circular or linear DNA or RNA, e.g., plasmids, viruses, and the like (U.S. Pat. No. 5,217,879), and includes both the expression and nonexpression plasmids. Where a recombinant cell or culture is described as hosting an "expression vector" this includes both extrachromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

Exemplary virus vectors that may be used include recombinant adenoviruses (Horowitz, M S, In: *Virology*, Fields, B N et al., eds, Raven Press, NY, 1990, p. 1679; Berkner, K L,

*Biotechniques* 6:616-29, 1988; Strauss, S E, In: *The Adenoviruses*, Ginsberg, H S, ed., Plenum Press, NY, 1984, chapter 11) and herpes simplex virus (HSV). Advantages of adenovirus vectors for human gene delivery include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human therapy (Samulski, R J et al., *EMBO J.* 10:3941, 1991) according to the present invention.

Another vector which can express the DNA molecule of the present invention, and is useful in the present therapeutic setting is vaccinia virus, which can be rendered non-replicating (U.S. Pat. Nos. 5,225,336; 5,204,243; 5,155,020; 4,769,330; Fuerst, T R et al., *Proc. Natl. Acad. Sci. USA* 86:2549-53, 1992; Chakrabarti, S et al., *Mol Cell Biol* 5:3403-9, 1985). Descriptions of recombinant vaccinia viruses and other viruses containing heterologous DNA and their uses in immunization and DNA therapy are reviewed in: Moss, B, *Curr Opin Genet Dev* 3:86-90, 1993; Moss, B, *Biotechnol.* 20:345-62, 1992).

Other viral vectors that may be used include viral or non-viral vectors, including adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus).

A DNA vaccine may also use a replicon, e.g., an RNA replicon, a self-replicating RNA vector. A preferred replicon is one based on a Sindbis virus RNA replicon, e.g., SINrep5. The present inventors tested E7 in the context of such a vaccine and showed (see Wu et al, U.S. patent application Ser. No. 10/343,719) that a Sindbis virus RNA vaccine encoding HSV-1 VP22 linked to E7 significantly increased activation of E7-specific CD8 T cells, resulting in potent antitumor immunity against E7-expressing tumors. The Sindbis virus RNA replicon vector used in these studies, SINrep5, has been described (Bredenbeek, P J et al., 1993, J. Virol. 67:6439-6446).

Generally, RNA replicon vaccines may be derived from alphavirus vectors, such as Sindbis virus (Hariharan, M J et al., 1998. J Virol 72:950-8.), Semliki Forest virus (Berglund, P M et al., 1997. AIDS Res Hum Retroviruses 13:1487-95; Ying, H T et al., 1999. Nat Med 5:823-7) or Venezuelan equine encephalitis virus (Pushko, P M et al., 1997. Virology 239:389-401). These self-replicating and self-limiting vaccines may be administered as either (1) RNA or (2) DNA which is then transcribed into RNA replicons in cells transfected in vitro or in vivo (Berglund, P C et al., 1998. Nat Biotechnol 16:562-5; Leitner, W W et al., 2000. Cancer Res 60:51-5). An exemplary Semliki Forest virus is pSCA1 (Di-Ciommo, D P et al., J Biol Chem 1998; 273:18060-6).

Figure 22:
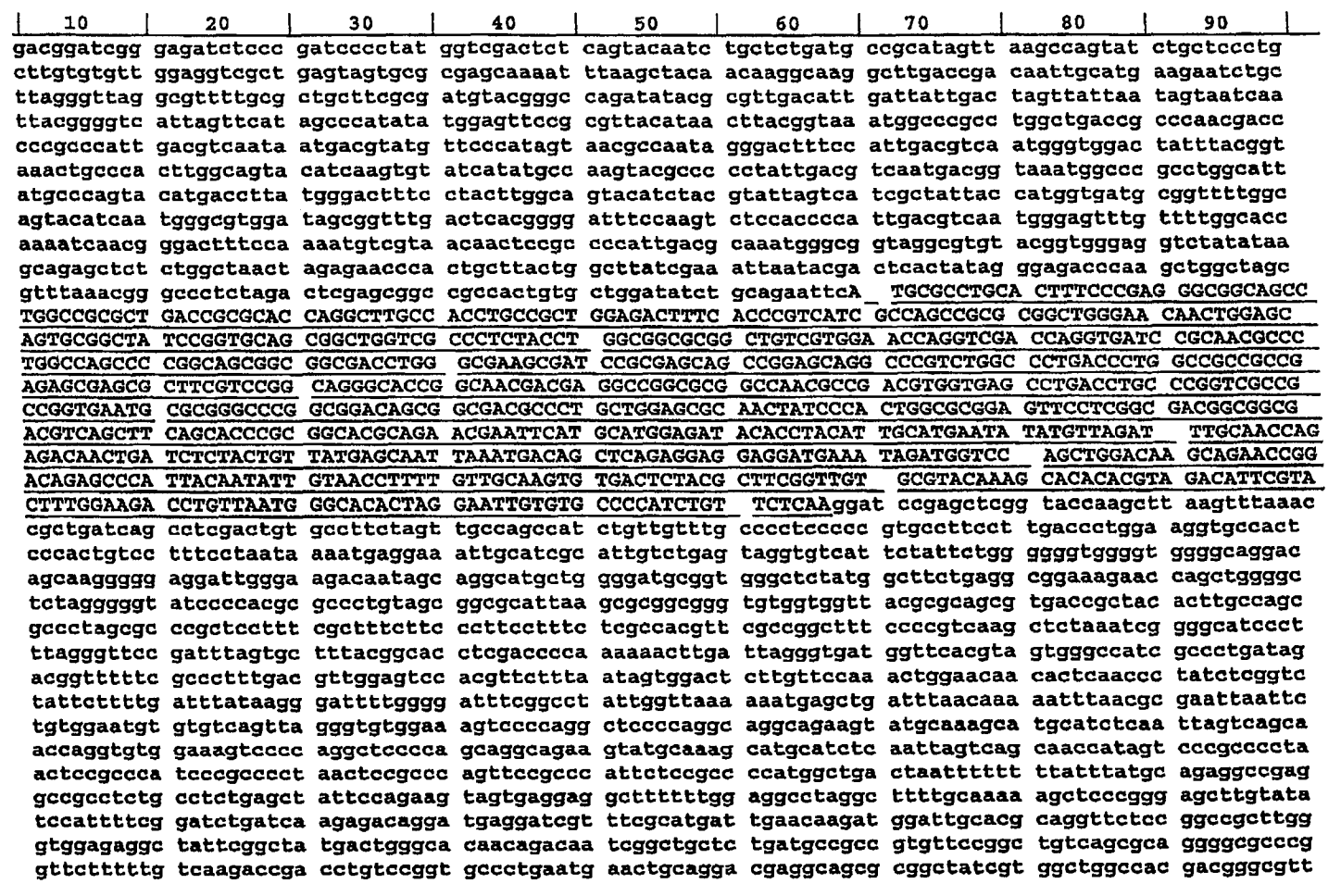
Figure 22:
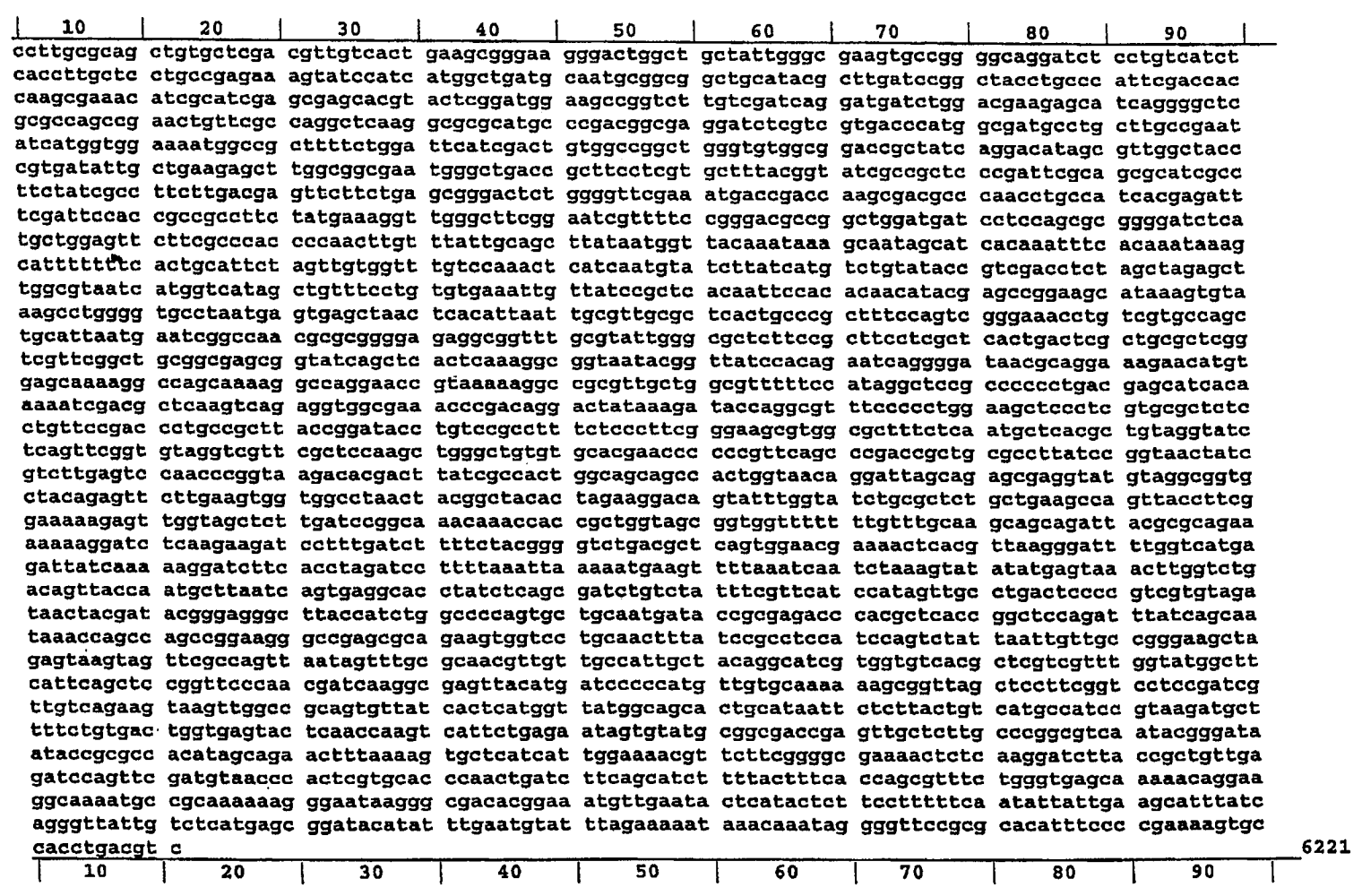
Figure 23:
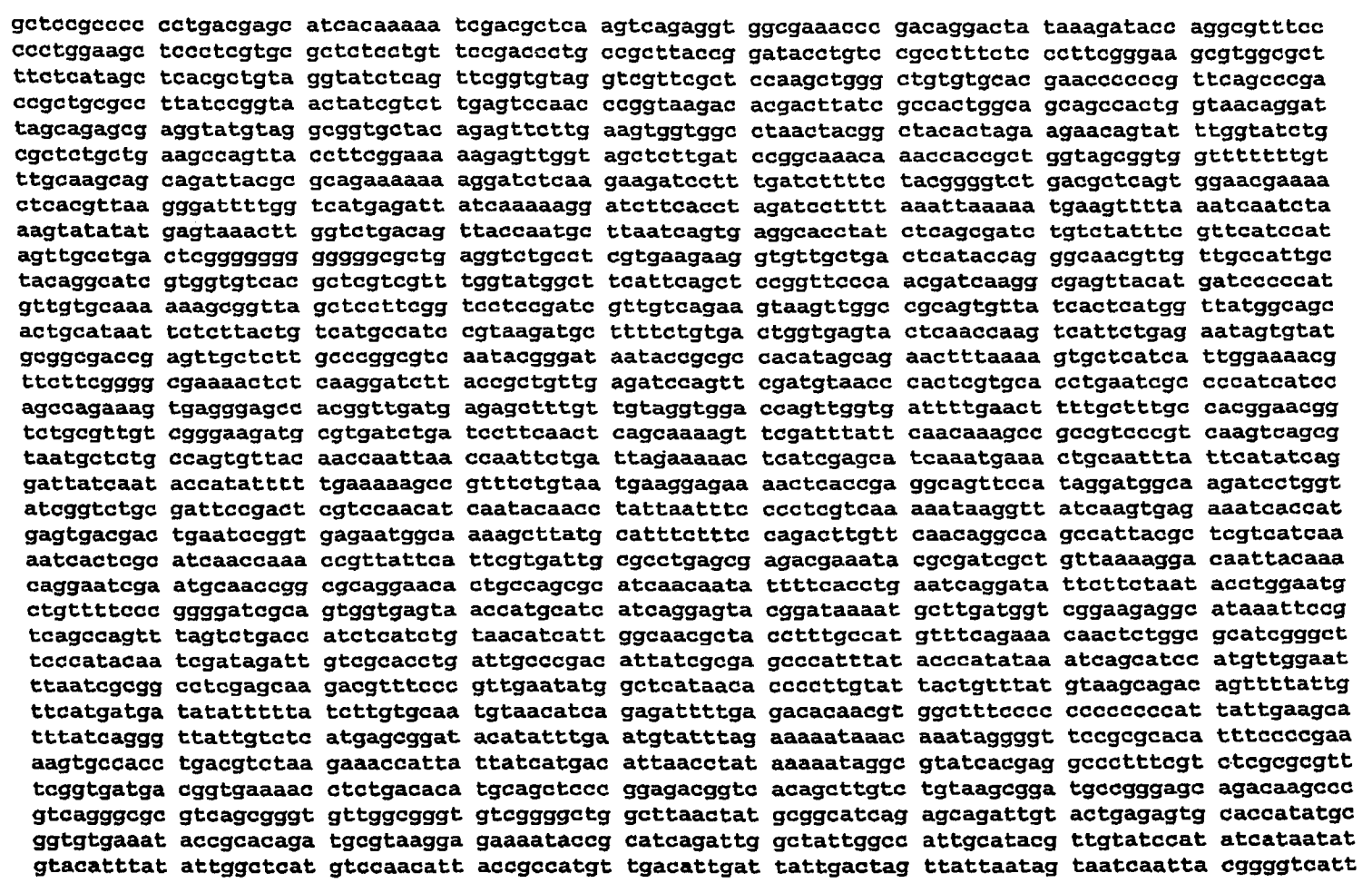
Figure 23:
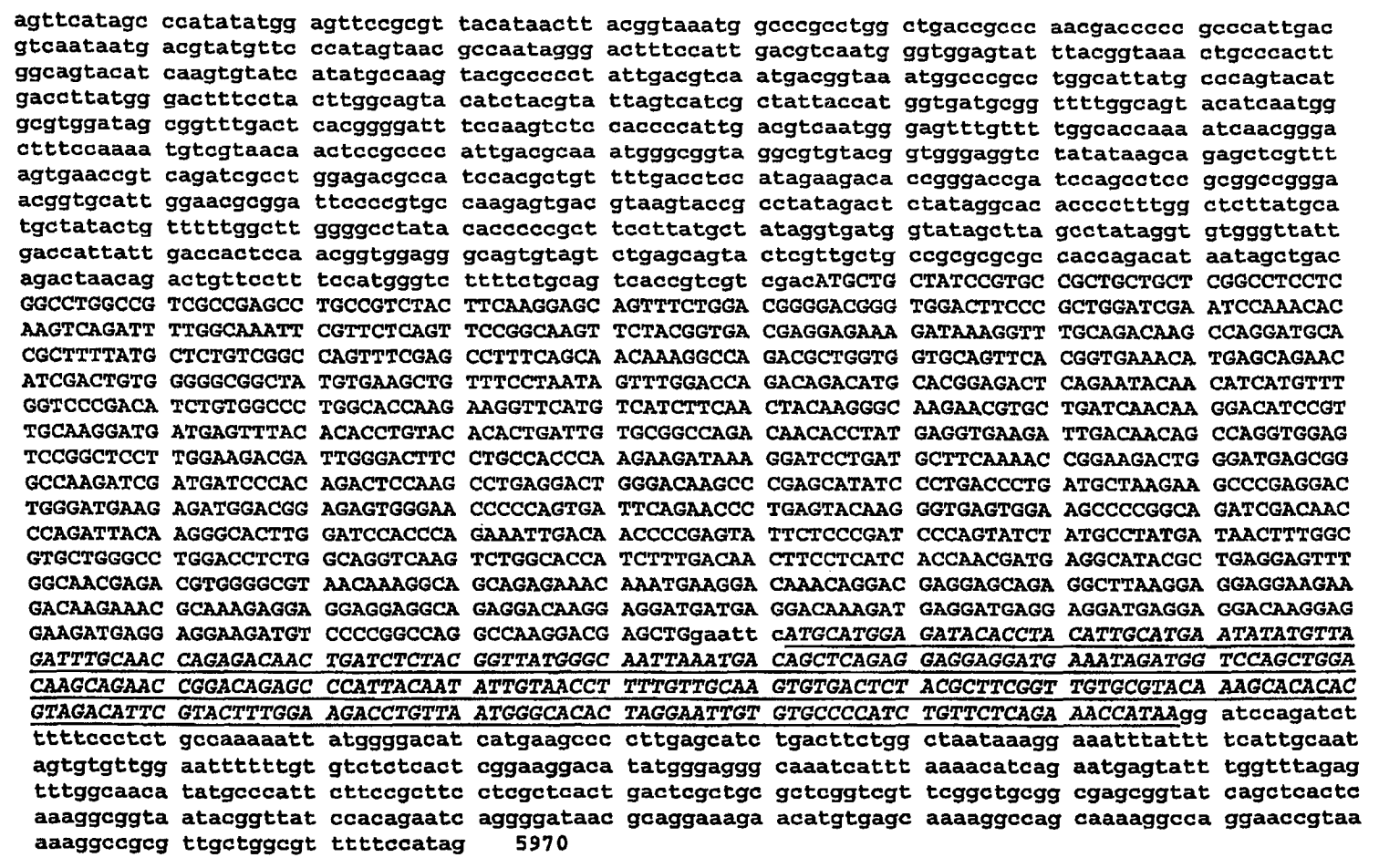

The plasmid vector pcDNA3 or a functional homolog thereof, which is shown in FIG. 22 (SEQ ID NO: 1) may be used in a DNA vaccine. In other embodiments, pNGVL4a, shown in FIG. 23 (SEQ ID NO: 2) is used.

pNGVL4a, one preferred plasmid backbone for the present invention was originally derived from the pNGVL3 vector, which has been approved for human vaccine trials. The pNGVL4a vector includes two immunostimulatory sequences (tandem repeats of CpG dinucleotides) in the non-coding region. Whereas any other plasmid DNA that can transform either APCs, preferably DC's or other cells which, via cross-priming, transfer the antigenic moiety to DCs, is useful in the present invention, pNGFVLA4a is preferred because of the fact that it has already been approved for human therapeutic use.

The following references set forth principles and current information in the field of basic, medical and veterinary virology and are incorporated by reference: *Fields Virology*, Fields, B N et al., eds., Lippincott Williams & Wilkins, NY, 1996; *Principles of Virology: Molecular Biology, Pathogenesis, and Control*, Flint, S. J. et al., eds., Amer Soc Microbiol, Washington D.C., 1999; *Principles and Practice of Clinical Virology*, 4th Edition, Zuckerman. A. J. et al., eds, John Wiley & Sons, NY, 1999; *The Hepatitis C Viruses*, by Hagedorn, C H et al., eds., Springer Verlag, 1999; *Hepatitis B Virus: Molecular Mechanisms in Disease and Novel Strategies for Therapy*, Koshy, R. et al., eds, World Scientific Pub Co, 1998; *Veterinary Virology*, Murphy, F. A. et al., eds., Academic Press, NY, 1999; *Avian Viruses: Function and Control*, Ritchie, B. W., Iowa State University Press, Ames, 2000; *Virus Taxonomy: Classification and Nomenclature of Viruses: Seventh Report of the International Committee on Taxonomy of Viruses*, by M. H. V. Van Regenmortel, M H V et al., eds., Academic Press; NY, 2000.

In addition to naked DNA or viral vectors, engineered bacteria may be used as vectors. A number of bacterial strains including *Salmonella*, BCG and *Listeria monocytogenes* (LM) (Hoiseth et al., *Nature* 291:238-9, 1981; Poirier, T P et al., *J Exp Med* 168:25-32, 1988); Sadoff, J C et al., *Science* 240:336-8, 1988; Stover, C K et al., *Nature* 351:456-60, 1991; Aldovini, A et al., *Nature* 351:479-82, 1991). These organisms display two promising characteristics for use as vaccine vectors: (1) enteric routes of infection, providing the possibility of oral vaccine delivery; and (2) infection of monocytes/macrophages thereby targeting antigens to professional APCs.

In addition to virus-mediated gene transfer in vivo, physical means well-known in the art can be used for direct transfer of DNA, including administration of plasmid DNA (Wolff et al., 1990, supra) and particle-bombardment mediated gene transfer (Yang, N-S, et al., *Proc Natl Acad Sci USA* 87:9568, 1990; Williams, R S et al., *Proc Natl Acad Sci USA* 88:2726, 1991; Zelenin, A V et al., *FEBS Lett* 280:94, 1991; Zelenin, A V et al., *FEBS Lett* 244:65, 1989); Johnston, S A et al., *In Vitro Cell Dev Biol* 27:11, 1991). Furthermore, electroporation, a well-known means to transfer genes into cell in vitro, can be used to transfer DNA molecules according to the present invention to tissues in vivo (Titomirov, A V et al., *Biochim Biophys Acta* 1088:131, 1991).

"Carrier mediated gene transfer" has also been described (Wu, C H et al., *J Biol Chem* 264:16985, 1989; Wu, G Y et al., *J Biol Chem* 263:14621, 1988; Soriano, P et al., *Proc Nat. Acad Sci USA* 80:7128, 1983; Wang, C-Y et al., *Pro. Natl Acad Sci USA* 84:7851, 1982; Wilson, J M et al., *J Biol Chem* 267:963, 1992). Preferred carriers are targeted liposomes (Nicolau, C et al., *Proc Natl Acad Sci USA* 80:1068, 1983; Soriano et al., supra) such as immunoliposomes, which can incorporate acylated mAbs into the lipid bilayer (Wang et al., supra). Polycations such as asialoglycoprotein/polylysine (Wu et al., 1989, supra) may be used, where the conjugate includes a target tissue-recognizing molecule (e.g., asialoorosomucoid for liver) and a DNA binding compound to bind to the DNA to be transfected without causing damage, such as polylysine. This conjugate is then complexed with plasmid DNA of the present invention.

Plasmid DNA used for transfection or microinjection may be prepared using methods well-known in the art, for example using the Quiagen procedure (Quiagen), followed by DNA purification using known methods, such as the methods exemplified herein.

Such expression vectors may be used to transfect host cells (in vitro, ex vivo or in vivo) for expression of the DNA and production of the encoded proteins which include fusion proteins or peptides. In one embodiment, a DNA vaccine is administered to or contacted with a cell, e.g., a cell obtained from a subject (e.g., an antigen presenting cell), and administered to a subject, wherein the subject is treated before, after or at the same time as the cells are administered to the subject.

The term "isolated" as used herein, when referring to a molecule or composition, such as a translocation polypeptide or a nucleic acid coding therefor, means that the molecule or composition is separated from at least one other compound (protein, other nucleic acid, etc.) or from other contaminants with which it is natively associated or becomes associated during processing. An isolated composition can also be substantially pure. An isolated composition can be in a homogeneous state and can be dry or in aqueous solution. Purity and homogeneity can be determined, for example, using analytical chemical techniques such as polyacrylamide gel electrophoresis (PAGE) or high performance liquid chromatography (HPLC). Even where a protein has been isolated so as to appear as a homogenous or dominant band in a gel pattern, there are trace contaminants which co-purify with it.

Host cells transformed or transfected to express the fusion polypeptide or a homologue or functional derivative thereof are within the scope of the invention. For example, the fusion polypeptide may be expressed in yeast, or mammalian cells such as Chinese hamster ovary cells (CHO) or, preferably human cells. Preferred cells for expression according to the present invention are APCs most preferably, DCs. Other suitable host cells are known to those skilled in the art.

Other Nucleic Acids for Potentiating Immune Responses

Methods of administrating a chemotherapeutic drug and a vaccine may further comprise administration of one or more other constructs, e.g., to prolong the life of antigen presenting cells. Exemplary constructs are described in the following two sections. Such constructs may be administered simultaneously or at the same time as a DNA vaccine. Alternatively, they may be administered before or after administration of the DNA vaccine or chemotherapeutic drug.

Potentiation of Immune Responses Using siRNA Directed at Apoptotic Pathways

Administration to a subject of a DNA vaccine and a chemotherapeutic drug may accompanied by administration of one or more other agents, e.g., constructs. In one embodiment, a method comprises further administering to a subject an siRNA directed at an apoptotic pathway, such as described in WO 2006/073970, which is incorporated herein in its entirety.

The present inventors have previously designed siRNA sequences that hybridize to, and block expression of the activation of Bak and Bax proteins that are central players in the apoptosis signalling pathway. The present invention is also directed to the methods of treating tumors or hyperproliferative disease involving the administration of siRNA molecules (sequences), vectors containing or encoding the siRNA, expression vectors with a promoter operably linked to the siRNA coding sequence that drives transcription of siRNA sequences that are "specific" for sequences Bak and Bax nucleic acid. siRNAs may include single stranded "hairpin" sequences because of their stability and binding to the target mRNA.

Since Bak and Bax are involved, among other death proteins, in apoptosis of APCs, particularly DCs, the present siRNA sequences may be used in conjunction with a broad range of DNA vaccine constructs encoding antigens to enhance the immune response induced by such DNA vaccine constructs, particularly CD8+ T cell mediated immune responses typified by CTL activation and action. This is believed to occur as a result of the effect of the siRNA in prolonging the life of antigen-presenting DCs which may otherwise be killed in the course of a developing immune response by the very same CTLs that the DCs are responsible for inducing.

In addition to Bak and Bax, additional targets for siRNAs designed in an analogous manner include caspase 8, caspase 9 and caspase 3. The present invention includes compositions and methods in which siRNAs targeting any two or more of Bak, Bax, caspase 8, caspase 9 and caspase 3 are used in combination, optionally simultaneously (along with a DNA immunogen that encodes an antigen), to administer to a subject. Such combinations of siRNAs may also be used to transfect DCs (along with antigen loading) to improve the immunogenicity of the DCs as cellular vaccines by rendering them resistant to apoptosis.

siRNAs suppress gene expression through a highly regulated enzyme-mediated process called RNA interference (RNAi) (Sharp, P. A., *Genes Dev.* 15:485-90, 2001; Bernstein, E et al., *Nature* 409:363-66, 2001; Nykanen, A et al., *Cell* 107:309-21, 2001; Elbashir et al., *Genes Dev.* 15:188-200, 2001). RNA interference is the sequence-specific degradation of homologues in an mRNA of a targeting sequence in an siNA. As used herein, the term siNA (small, or short, interfering nucleic acid) is meant to be equivalent to other terms used to describe nucleic acid molecules that are capable of mediating sequence specific RNAi (RNA interference), for example short (or small) interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), translational silencing, and others. RNAi involves multiple RNA-protein interactions characterized by four major steps: assembly of siRNA with the RNA-induced silencing complex (RISC), activation of the RISC, target recognition and target cleavage. These interactions may bias strand selection during siRNA-RISC assembly and activation, and contribute to the overall efficiency of RNAi (Khvorova, A et al., *Cell* 115:209-216 (2003); Schwarz, D S et al. 115:199-208 (2003)))

Considerations to be taken into account when designing an RNAi molecule include, among others, the sequence to be targeted, secondary structure of the RNA target and binding of RNA binding proteins. Methods of optimizing siRNA sequences will be evident to the skilled worker. Typical algorithms and methods are described in Vickers et al (2003) *J Biol Chem* 278:7108-7118; Yang et al. (2003) *Proc Natl Acad Sci USA* 99:9942-9947; Far et al. (2003) *Nuc. Acids Res.* 31:4417-4424; and Reynolds et al. (2004) *Nature Biotechnology* 22:326-330, all of which are incorporated by reference in their entirety.

The methods described in Far et al., supra, and Reynolds et al., supra, may be used by those of ordinary skill in the art to select targeted sequences and design siRNA sequences that are effective at silencing the transcription of the relevant mRNA. Far et al. suggests options for assessing target accessibility for siRNA and supports the design of active siRNA constructs. This approach can be automated, adapted to high throughput and is open to include additional parameters relevant to the biological activity of siRNA. To identify siRNA-specific features likely to contribute to efficient processing at each of the steps of RNAi noted above. Reynolds et al., supra, present a systematic analysis of 180 siRNAs targeting the mRNA of two genes. Eight characteristics associated with siRNA functionality were identified: low G/C content, a bias towards low internal stability at the sense strand 3'-terminus, lack of inverted repeats, and sense strand base preferences (positions 3, 10, 13 and 19). Application of an algorithm incorporating all eight criteria significantly improves potent siRNA selection. This highlights the utility of rational design for selecting potent siRNAs that facilitate functional gene knockdown.

Candidate siRNA sequences against mouse and human Bax and Bak are selected using a process that involves running a BLAST search against the sequence of Bax or Bak (or any other target) and selecting sequences that "survive" to ensure that these sequences will not be cross matched with any other genes.

siRNA sequences selected according to such a process and algorithm may be cloned into an expression plasmid and tested for their activity in abrogating Bak/Bax function cells of the appropriate animal species. Those sequences that show RNAi activity may be used by direct administration bound to particles, or recloned into a viral vector such as a replication-defective human adenovirus serotype 5 (Ad5).

One advantage of this viral vector is the high titer obtainable (in the range of $10^{10}$) and therefore the high multiplicities-of infection that can be attained. For example, infection with 100 infectious units/cell ensures all cells are infected. Another advantage of this virus is the high susceptibility and infectivity and the host range (with respect to cell types). Even if expression is transient, cells would survive, possibly replicate, and continue to function before Bak/Bax activity would recover and lead to cell death. Preferred constructs include the following:
For Bak:

```
                                                    (SEQ ID NO: 42)
5'P-UGCCUACGAACUCUUCACCdTdT-3'  (sense)

(SEQ ID NO: 43)
5'P-GGUGAAGAGUUCGUAGGCAdTdT-3'  (antisense),
```

The nucleotide sequence encoding the Bak protein (including the stop codon) (GenBank accession No. NM_007523 is shown below (SEQ ID NO: 44) with the targeted sequence in upper case, underscored.

```
atggcatctggacaaggaccaggtcccccgaaggtgggctgcgatgagtc cccgtcccttctgaacagcaggttgcccaggacacagaggaggtctttc gaagctacgttttttacctccaccagcaggaacaggagacccaggggcgg ccgcctgccaacccgagatggacaacttgccctggaacccaacagcat cttgggtcaggtgggtcggcagcttgctctcatcggagatgatattaacc
``` ggcgctacgacacagagttccagaatttactagaacagcttcagcccaca gccgggaaTGCCTACGAACTCTTCACCaagatcgcctccagcctatttaa gagtggcatcagctggggccgcgtggtggctctcctgggctttggctacc gtctggccctgtacgtctaccagcgtggtttgaccggcttcctgggccag gtgacctgcttttttggctgatatcatactgcatcattacatcgccagatg gatcgcacagagaggcggttgggtggcagccctgaatttgcgtagagacc ccatcctgaccgtaatggtgattttttggtgtggttctgttgggccaattc gtggtacacagattcttcagatcatga 637

The targeted sequence of Bak, TGCCTACGAACTCT-TCACC is SEQ ID NO: 45
For Bax:

```
                                                    (SEQ ID NO: 46)
5'P-UAUGGAGCUGCAGAGGAUGdTdT-3'  (sense)

(SEQ ID NO: 47)
5'P-CAUCCUCUGCAGCUCCAUAdTdT-3'  (antisense)
```

The nucleotide sequence encoding Bax (including the stop codon) (GenBank accession No. L22472 is shown below (SEQ ID NO: 48) with the targeted sequence shown in upper case and underscored

```
atggacgggtccggggagcagcttgggagcggcgggcccaccagctctga acagatcatgaagacaggggccttttttgctacagggtttcatccaggatc gagcagggaggatggctggggagacacctgagctgaccttggagcagccg ccccaggatgcgtccaccaagaagctgagcgagtgtctccggcgaattgg agatgaactggatagcaaTATGGAGCTGCAGAGGATGattgctgacgtgg acacggactcccccgagaggtcttcttccgggtggcagctgacatgttt gctgatggcaacttcaactggggccgcgtggttgccctcttctactttgc tagcaaactggtgctcaaggccctgtgcactaaagtgcccgagctgatca gaaccatcatgggctggacactggacttcctccgtgagcggctgcttgtc tggatccaagaccagggtggctgggaaggcctcctctcctacttcgggac ccccacatggcagacagtgaccatctttgtggctggagtcctcaccgcct cgctcaccatctggaagaagatgggctga 589
```

The targeted sequence of Bax, TATGGAGCTGCAGAG-GATG is SEQ ID NO: 49

In a preferred embodiment, the inhibitory molecule is a double stranded nucleic acid (preferably an RNA), used in a method of RNA interference. The following show the "paired" 19 nucleotide structures of the siRNA sequences shown above, where the symbol ↕:

```
Bak: 5' P-    UGCCUACGAACUCUUCACCdTdT-3'  (sense)    (SEQ ID NO: 42)
              ↕↕↕↕↕↕↕↕↕↕↕↕↕↕↕↕↕↕↕
         3' P-dTdtACGGAUGCUUGAGAAGUGG    -5'  (antisense)(SEQ ID NO: 43)

Bak: 5' P-    UAUGGAGCUGCAGAGGAUGdTdT-3'  (sense)    (SEQ ID NO: 46)
              ↕↕↕↕↕↕↕↕↕↕↕↕↕↕↕↕↕↕↕
         3' P-dTdTAUACCUCGACGUCUCCUAC    -5'  (antisense)(SEQ ID NO: 47)
```

Other Pro-Apoptotic Proteins to be Targeted

1. Caspase 8: The nucleotide sequence of human caspase-8 is shown below (SEQ ID NO: 50). GenBank Access. # NM_001228. One target sequence for RNAi is underscored. Others may be identified using methods such as those described herein (and in reference cited herein, primarily Far et al., supra and Reynolds et al., supra).

```
atg gac ttc agc aga aat ctt tat gat att ggg gaa
caa ctg gac agt gaa gat ctg gcc tcc ctc aag ttc
ctg agc ctg gac tac att ccg caa agg aag caa gaa
ccc atc aag gat gcc ttg atg tta ttc cag aga ctc
cag gaa aag aga atg ttg gag gaa agc aat ctg tcc
ttc ctg aag gag ctg ctc ttc cga att aat aga ctg
gat ttg ctg att acc tac cta aac act aga aag gag
gag atg gaa agg gaa ctt cag aca cca ggc agg gct
caa att tct gcc tac agg ttc cac ttc tgc cgc atg
agc tgg gct gaa gca aac agc cag tgc aga aca cag
tct gta cct ttc tgg cgg agg gtc gat cat cta tta
ata agg gtc atg ctc tat cag att tca gaa gaa gtg
agc aga tca gaa ttg agg tct ttt aag ttt ctt tgg
caa gag gaa atc tcc aaa tgc aaa ctg gat gat gac
atg aac ctg ctg gat att ttc ata gag atg gag aag
agg gtc atc ctg gga gaa gga aag ttg gac atc ctg
aaa aga gtc tgt gcc caa atc aac aag agc ctg ctg
aag ata atc aac gac tat gaa gaa ttc agc aaa ggg
gag gag ttg tgt ggg gta atg aca atc tcg gac tct
cca aga gaa cag gat agt gaa tca cag act ttg gac
aaa gtt tac caa atg aaa agc aaa cct cgg gga tac
tgt ctg atc atc aac aat cac aat ttt gca aaa gca
cgg gag aaa gtg ccc aaa ctt cac agc att agg gac
agg aat gga aca cac ttg gat gca ggg gct ttg acc
acg acc ttt gaa gag ctt cat ttt gag atc aag ccc
cac gat gac tgc aca gta gag caa atc tat gag att
ttg aaa atc tac caa ctc atg gac cac agt aac atg
gac tgc ttc atc tgc tgt atc ctc tcc cat gga gac
aag ggc atc atc tat ggc act gat gga cag gag gcc
ccc atc tat gag ctg aca tct cag ttc act ggt ttg
aag tgc cct tcc ctt gct gga aaa ccc aaa gtg ttt
ttt att cag gct tgt cag ggg gat aac tac cag aaa
ggt ata cct gtt gag act gat tca gag gag caa ccc
tat tta gaa atg gat tta tca tca cct caa acg aga
tat atc ccg gat gag gct gac ttt ctg ctg ggg atg
gcc act gtg aat aac tgt gtt tcc tac cga aac cct
gca gag gga acc tgg tac atc cag tca ctt tgc cag
agc ctg aga gag cga tgt cct cga ggc gat gat att
ctc acc atc ctg act gaa gtg aac tat gaa gta agc
aac aag gat gac aag aaa aac atg ggg aaa cag atg
cct cag cct act ttc aca cta aga aaa aaa ctt gtc
ttc cct tct gat tga 1491
```

The sequences of sense and antisense siRNA strands for targeting this sequence (including dTdT 3' overhangs, are:

```
                                        (SEQ ID NO: 51)
    5'-AACCUCGGGGAUACUGUCUGAdTdT-3' (sense)

(SEQ ID NO: 52)
    5'-UCAGACAGUAUCCCCGAGGUUdTdT-3' (antisense)
```

2. Caspase 9: The nucleotide sequence of human caspase-9 is shown below (SEQ ID NO: 53). See GenBank Access. # NM_001229. The sequence below is of "variant α" which is longer than a second alternatively spliced variant β, which lacks the underscored part of the sequence shown below (and which is anti-apoptotic). Target sequences for RNAi, expected to fall in the underscored segment, are identified using known methods such as those described herein and in Far et al., supra and Reynolds et al., supra). and siNAs, such as siRNAs, are designed accordingly.

```
atg gac gaa gcg gat cgg cgg ctc ctg cgg cgg tgc
cgg ctg cgg ctg gtg gaa gag ctg cag gtg gac cag
ctc tgg gac gcc ctg ctg agc cgc gag ctg ttc agg
ccc cat atg atc gag gac atc cag cgg gca ggc tct
gga tct cgg cgg gat cag gcc agg cag ctg atc ata
gat ctg gag act cga ggg agt cag gct ctt cct ttg
ttc atc tcc tgc tta gag gac aca ggc agg gac atg
ctg gct tcg ttt ctg cga act aac agg caa gca gca
aag ttg tcg aag cca acc cta gaa aac ctt acc cca
gtg gtg ctc aga cca gag att cgc aaa cca gag gtt
ctc aga ccg gaa aca ccc aga cca gtg gac att ggt
tct gga gga ttt ggt gat gtc ggt gct ctt gag agt
ttg agg gga aat gca gat ttg gct tac atc ctg agc
atg gag ccc tgt ggc cac tgc ctc att atc aac aat
gtg aac ttc tgc cgt gag tcc ggg ctc cgc acc cgc
act ggc tcc aac atc gac tgt gag aag ttg cgg cgt
cgc ttc tcc tcg ctg cat ttc atg gtg gag gtg aag
ggc gac ctg act gcc aag aaa atg gtg ctg gct ttg
ctg gag ctg gcg cag cag gac cac ggt gct ctg gac
tgc tgc gtg gtg gtc att ctc tct cac ggc tgt cag
gcc agc cac ctg cag ttc cca ggg gct gtc tac ggc
```

```
aca gat gga tgc cct gtg tcg gtc gag aag att gtg aac atc ttc aat ggg acc agc tgc ccc agc ctg gga ggg aag ccc aag ctc ttt ttc atc cag gcc tgt ggt ggg gag cag aaa gac cat ggg ttt gag gtg gcc tcc act tcc cct gaa gac gag tcc cct ggc agt aac ccc gag cca gat gcc acc ccg ttc cag gaa ggt ttg agg acc ttc gac cag ctg gac gcc ata tct agt ttg ccc aca ccc agt gac atc ttt gtg tcc tac tct act ttc cca ggt ttt gtt tcc tgg agg gac ccc aag agt ggc tcc tgg tac gtt gag acc ctg gac gac atc ttt gag cag tgg gct cac tct gaa gac ctg cag tcc ctc ctg ctt agg gtc gct aat gct gtt tcg gtg aaa ggg att tat aaa cag atg cct ggt tgc ttt aat ttc ctc cgg aaa aaa ctt ttc ttt aaa aca tca taa 1191
```

3. Caspase 3: The nucleotide sequence of human caspase-3 is shown below (SEQ ID NO: 54). See GenBank Access. # NM_004346. The sequence below is of "variant α" which is the longer of two alternatively spliced variants, all of which encode the full protein. Target sequences for RNAi are identified using known methods such as those described herein and in Far et al., supra and Reynolds et al., supra) and siNAs, such as siRNAs, are designed accordingly.

```
atg gag aac act gaa aac tca gtg gat tca aaa tcc att aaa aat ttg gaa cca aag atc ata cat gga agc gaa tca atg gac tct gga ata tcc ctg gac aac agt tat aaa atg gat tat cct gag atg ggt tta tgt ata ata att aat aat aag aat ttt cat aaa agc act gga atg aca tct cgg tct ggt aca gat gtc gat gca gca aac ctc agg gaa aca ttc aga aac ttg aaa tat gaa gtc agg aat aaa aat gat ctt aca cgt gaa gaa att gtg gaa ttg atg cgt gat gtt tct aaa gaa gat cac agc aaa agg agc agt ttt gtt tgt gtg ctt ctg agc cat ggt gaa gaa gga ata att ttt gga aca aat gga cct gtt gac ctg aaa aaa ata aca aac ttt ttc aga ggg gat cgt tgt aga agt cta act gga aaa ccc aaa ctt ttc att att cag gcc tgc cgt ggt aca gaa ctg gac tgt ggc att gag aca gac agt ggt gtt gat gat gac atg gcg tgt cat aaa ata cca gtg gag gcc gac ttc ttg tat gca tac tcc aca gca cct ggt tat tat tct tgg cga aat tca aag gat ggc tcc tgg ttc atc cag tcg ctt tgt gcc atg ctg aaa cag tat gcc gac aag ctt gaa ttt atg cac att ctt acc cgg gtt aac
```

```
cga aag gtg gca aca gaa ttt gag tcc ttt tcc ttt gac gct act ttt cat gca aag aaa cag att cca tgt att gtt tcc atg ctc aca aaa gaa ctc tat ttt tat cac taa 834
```

Long double stranded interfering RNAs, such a miRNAs, appear to tolerate mismatches more readily than do short double stranded RNAs. In addition, as used herein, the term RNAi is meant to be equivalent to other terms used to describe sequence specific RNA interference, such as post transcriptional gene silencing, or an epigenetic phenomenon. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure and thereby alter gene expression (see, for example, Allshire *Science* 297:1818-19, 2002; Volpe et al., *Science* 297:1833-37, 2002; Jenuwein, *Science* 297:2215-18, 2002; and Hall et al., *Science* 297, 2232-2237, 2002.)

An siNA can be designed to target any region of the coding or non-coding sequence of an mRNA. An siNA is a double-stranded polynucleotide molecule comprising self-complementary sense and antisense regions, wherein the antisense region comprises nucleotide sequence that is complementary to nucleotide sequence in a target nucleic acid molecule or a portion thereof and the sense region has a nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary. The siNA can be assembled from a single oligonucleotide, where the self-complementary sense and antisense regions of the siNA are linked by means of a nucleic acid based or non-nucleic acid-based linker(s). The siNA can be a polynucleotide with a hairpin secondary structure, having self-complementary sense and antisense regions. The siNA can be a circular single-stranded polynucleotide having two or more loop structures and a stem comprising self-complementary sense and antisense regions, wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (or can be an siNA molecule that does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al. (2002) *Cell* 110, 563-574 and Schwarz et al. (2002) *Molecular Cell* 10, 537-568), or 5',3'-diphosphate.

In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, Van der Waal's interactions, hydrophobic interactions, and/or stacking interactions. Some preferred siRNAs are discussed above and in the Examples.

As used herein, siNA molecules need not be limited to those molecules containing only ribonucleotides but may also further encompass deoxyribonucleotides (as in the preferred siRNAs which each include a dTdT dinucleotide) chemically-modified nucleotides, and non-nucleotides. In certain embodiments, the siNA molecules of the invention lack 2'-hydroxy (2'-OH) containing nucleotides. In certain embodiments, siNAs do not require the presence of nucleotides having a 2'-hydroxy group for mediating RNAi and as such, siNAs of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. If modified, the siNAs of the invention can also be referred to as "short interfering modified oligonucleotides" or "siMON." Other chemical modifications, e.g., as described in Int'l Patent Publications WO 03/070918 and WO 03/074654, can be applied to any siNA sequence of the invention.

Preferably a molecule mediating RNAi has a 2 nucleotide 3' overhang (dTdT in the preferred sequences disclosed herein). If the RNAi molecule is expressed in a cell from a construct, for example from a hairpin molecule or from an inverted repeat of the desired sequence, then the endogenous cellular machinery will create the overhangs.

Methods of making siRNAs are conventional. In vitro methods include processing the polyribonucleotide sequence in a cell-free system (e.g., digesting long dsRNAs with RNAse III or Dicer), transcribing recombinant double stranded DNA in vitro, and, preferably, chemical synthesis of nucleotide sequences homologous to Bak or Bax sequences. See, e.g., Tuschl et al., *Genes & Dev.* 13:3191-3197, 1999. In vivo methods include (1) transfecting DNA vectors into a cell such that a substrate is converted into siRNA in vivo. See, for example, Kawasaki et al., *Nucleic Acids Res* 31:700-07, 2003; Miyagishi et al., *Nature Biotechnol* 20:497-500, 2003; Lee et al., *Nature Biotechnol* 20:500-05, 2002; Brummelkamp et al., *Science* 296:550-53, 2002; McManus et al., *RNA* 8:842-50, 2002; Paddison et al, *Genes Dev* 16:948-58, 2002; Paddison et al., *Proc Natl Acad Sci USA* 99:1443-48, 2002; Paul et al., *Nature Biotechnol* 20:505-08, 2002; Sui et al., *Proc Natl Acad Sci USA* 99:5515-20, 2002; Yu et al., *Proc Natl Acad Sci USA* 99:6047-52, 2002)

(2) expressing short hairpin RNAs from plasmid systems using RNA polymerase III (pol III) promoters. See, for example, Kawasaki et al., supra; Miyagishi et al., supra; Lee et al., supra; Brummelkamp et al., supra; McManus et al., supra), Paddison et al., supra (both); Paul et al., supra, Sui et al., supra; and Yu et al., supra; and/or (3) expressing short RNA from tandem promoters. See, for example, Miyagishi et al., supra; Lee et al., supra).

When synthesized in vitro, a typical micromolar scale RNA synthesis provides about 1 mg of siRNA, which is sufficient for about 1000 transfection experiments using a 24-well tissue culture plate format. In general, to inhibit Bak or Bax expression in cells in culture, one or more siRNAs can be added to cells in culture media, typically at about 1 ng/ml to about 10 µg siRNA/ml.

For reviews and more general description of inhibitory RNAs, see Lau et al., *Sci Amer* August 2003: 34-41; McManus et al., *Nature Rev Genetics* 3, 737-47, 2002; and Dykxhoorn et al., *Nature Rev Mol Cell Bio* 4:457-467, 2003.

For further guidance regarding methods of designing and preparing siRNAs, testing them for efficacy, and using them in methods of RNA interference (both in vitro and in vivo), see, e.g., Allshire, *Science* 297:1818-19, 2002; Volpe et al., *Science* 297:1833-37, 2002; Jenuwein, *Science* 297:2215-18, 2002; Hall et al., *Science* 2972232-37, 2002; Hutvagner et al., *Science* 297:2056-60, 2002; McManus et al. *RNA* 8:842-850, 2002; Reinhart et al., *Genes Dev.* 16:1616-26, 2002; Reinhart et al., *Science* 297:1831, 2002; Fire et al. (1998) *Nature* 391:806-11, 2002; Moss, *Curr Biol* 11:R772-5, 2002: Brummelkamp et al., supra; Bass, *Nature* 411 428-9, 2001; Elbashir et al., *Nature* 411:494-8; U.S. Pat. No. 6,506,559; Published US Pat App. 20030206887; and PCT applications WO99/07409, WO99/32619, WO 00/01846, WO 00/44914, WO00/44895, WO01/29058, WO01/36646, WO01/75164, WO01/92513, WO 01/29058, WO01/89304, WO01/90401, WO02/16620, and WO02/29858.

Ribozymes and siNAs can take any of the forms, including modified versions, described for antisense nucleic acid molecules; and they can be introduced into cells as oligonucleotides (single or double stranded), or in the form of an expression vector.

In a preferred embodiment, an antisense nucleic acid, siNA (e.g., siRNA) or ribozyme comprises a single stranded polynucleotide comprising a sequence that is at least about 90% (e.g., at least about 93%, 95%, 97%, 98% or 99%) identical to a target segment (such as those indicted for Bak and Bax above) or a complement thereof. As used herein, a DNA and an RNA encoded by it are said to contain the same "sequence," taking into account that the thymine bases in DNA are replaced by uracil bases in RNA.

Active variants (e.g., length variants, including fragments; and sequence variants) of the nucleic acid-based inhibitors discussed herein are also within the scope of the invention. An "active" variant is one that retains an activity of the inhibitor from which it is derived (preferably the ability to inhibit expression). It is routine to test a variant to determine for its activity using conventional procedures.

As for length variants, an antisense nucleic acid or siRNA may be of any length that is effective for inhibition of a gene of interest. Typically, an antisense nucleic acid is between about 6 and about 50 nucleotides (e.g., at least about 12, 15, 20, 25, 30, 35, 40, 45 or 50 nt), and may be as long as about 100 to about 200 nucleotides or more. Antisense nucleic acids having about the same length as the gene or coding sequence to be inhibited may be used. When referring to length, the terms bases and base pairs (bp) are used interchangeably, and will be understood to correspond to single stranded (ss) and double stranded (ds) nucleic acids. The length of an effective siNA is generally between about 15 bp and about 29 bp in length, preferably between about 19 and about 29 bp (e.g., about 15, 17, 19, 21, 23, 25, 27 or 29 bp), with shorter and longer sequences being acceptable. Generally, siNAs are shorter than about 30 bases to prevent eliciting interferon effects. For example, an active variant of an siRNA having, for one of its strands, the 19 nucleotide sequence of any of SEQ ID NOs: 42, 43, 46, and 47 herein can lack base pairs from either, or both, of ends of the dsRNA; or can comprise additional base pairs at either, or both, ends of the ds RNA, provided that the total of length of the siRNA is between about 19 and about 29 bp, inclusive. One embodiment of the invention is an siRNA that "consists essentially of" sequences represented by SEQ ID NOs: 42, 43, 46, and 47 or complements of these sequence. The term "consists essentially of" is an intermediate transitional phrase, and in this case excludes, for example, sequences that are long enough to induce a significant interferon response. An siRNA of the invention may consist essentially of between about 19 and about 29 bp in length.

As for sequence variants, it is generally preferred that an inhibitory nucleic acid, whether an antisense molecule, a ribozyme (the recognition sequences), or an siNA, comprise a strand that is complementary (100% identical in sequence) to a sequence of a gene that it is designed to inhibit. However, 100% sequence identity is not required to practice the present invention. Thus, the invention has the advantage of being able to tolerate naturally occurring sequence variations, for example, in human c-met, that might be expected due to genetic mutation, polymorphism, or evolutionary divergence. Alternatively, the variant sequences may be artificially generated. Nucleic acid sequences with small insertions, deletions, or single point mutations relative to the target sequence can be effective inhibitors.

The degree of sequence identity may be optimized by sequence comparison and alignment algorithms well-known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). At least about 90% sequence identity is preferred (e.g., at least about 92%, 95%, 98% or 99%), or even 100% sequence identity, between the inhibitory nucleic acid and the targeted sequence of targeted gene.

Alternatively, an active variant of an inhibitory nucleic acid of the invention is one that hybridizes to the sequence it is intended to inhibit under conditions of high stringency. For example, the duplex region of an siRNA may be defined functionally as a nucleotide sequence that is capable of hybridizing with a portion of the target gene transcript under high stringency conditions (e.g., 400 mM NaCl, 40 mM PIPES pH 6.4, 1 mM EDTA, 50° C. or 70° C., hybridization for 12-16 hours), followed generally by washing.

DC-1 cells or BM-DCs presenting a given antigen X, when not treated with the siRNAs of the invention, respond to sufficient numbers X-specific CD8+ CTL by apoptotic cell death. In contrast, the same cells transfected with the siRNA or infected with a viral vector encoding the present siRNA sequences survive better despite the delivery of killing signals.

Delivery and expression of the siRNA compositions of the present invention inhibit the death of DCs in vivo in the process of a developing T cell response, and thereby promote and stimulate the generation of an immune response induced by immunization with an antigen-encoding DNA vaccine vector. These capabilities have been exemplified by showing that:

(1) co-administration of DNA vaccines encoding HPV-16 E7 with siRNA targeted to Bak and Bax prolongs the lives of antigen-presenting DCs in the draining lymph nodes, thereby enhancing antigen-specific $CD8^+$ T cell responses, and eliciting potent antitumor effects against an E7-expressing tumor in vaccinated subjects.

(2) DCs transfected with siRNA targeting Bak and Bax resist killing by T cells in vivo. E7-loaded DCs transfected with Bak/Bax siRNA so that Bak and Bax protein expression is downregulated resist apoptotic death induced by T cells in vivo. When administered to subjects, these DCs generate stronger antigen-specific immune responses and manifest therapeutic effects (compared to DCs transfected with control siRNA).

Thus, siRNA constructs are useful as a part of the nucleic acid vaccination and chemotherapy regimen described in this application.

Potentiation of Immune Responses Using Anti-Apoptotic Proteins

Administration to a subject of a DNA vaccine and a chemotherapeutic drug may also be accompanied by administration of a nucleic acid encoding an anti-apoptotic protein, as described in WO2005/047501 and in U.S. Patent Application Publication No. 20070026076.

The present inventors have previously designed and disclosed an immunotherapeutic strategy that combines antigen-encoding DNA vaccine compositions with additional DNA vectors comprising anti-apoptotic genes including bcl-2, bc-1xL, XIAP, dominant negative mutants of caspase-8 and caspase-9, the products of which are known to inhibit apoptosis (Wu, et al. U.S. Patent Application Publication No. 20070026076). Serine protease inhibitor 6 (SPI-6) which inhibits granzyme B, may also be employed in compositions and methods to delay apoptotic cell death of DCs. The present inventors have shown that the harnessing of an additional biological mechanism, that of inhibiting apoptosis, significantly enhances T cell responses to DNA vaccines comprising antigen-coding sequences, as well as linked sequences encoding such IPPs.

Intradermal vaccination by gene gun efficiently delivers a DNA vaccine into DCs of the skin, resulting in the activation and priming of antigen-specific T cells in vivo. DCs, however, have a limited life span, hindering their long-term ability to prime antigen-specific T cells. According to the present invention, a strategy that combines combination therapy with methods to prolong the survival of DNA-transduced DCs enhances priming of antigen-specific T cells and thereby, increase DNA vaccine potency. Co-delivery of DNA encoding inhibitors of apoptosis (BCL-xL, BCL-2, XIAP, dominant negative caspase-9, or dominant negative caspase-8) with DNA encoding an antigen (exemplified as HPV-16 E7 protein) prolongs the survival of transduced DCs. More importantly, vaccinated subjects exhibited significant enhancement in antigen-specific CD8+ T cell immune responses, resulting in a potent antitumor effect against antigen-expressing tumors. Among these anti-apoptotic factors, BCL-XL demonstrated the greatest enhancement of both antigen-specific immune responses and antitumor effects. Thus, co-administration of a combination therapy including a DNA vaccine with one or more DNA constructs encoding anti-apoptotic proteins provides a way to enhance DNA vaccine potency.

Serine protease inhibitor 6 (SPI-6), also called Serpinb9, inhibits granzyme B, and may thereby delay apoptotic cell death in DCs. Intradermal co-administration of DNA encoding SPI-6 with DNA constructs encoding E7 linked to various IPPs significantly increased E7-specific CD8+ T cell and CD4+ Th1 cell responses and enhanced anti-tumor effects when compared to vaccination without SPI-6. Thus it is preferred to combine methods that enhance MHC class I and II antigen processing with delivery of SPI-6 to potentiate immunity A similar approach employs DNA-based alphaviral RNA replicon vectors, also called suicidal DNA vectors. To enhance the immune response to an antigen, e.g., HPV E7, a DNA-based Semliki Forest virus vector, pSCA1, the antigen DNA is fused with DNA encoding an anti-apoptotic polypeptide such BCL-xL, a member of the BCL-2 family. pSCA1 encoding a fusion protein of an antigen polypeptide and/BCL-xL delays cell death in transfected DCs and generates significantly higher antigen-specific CD8+ T-cell-mediated immunity. The antiapoptotic function of BCL-xL is important for the enhancement of antigen-specific CD8+ T-cell responses. Thus, in one embodiment, delaying cell death induced by an otherwise desirable suicidal DNA vaccine enhances its potency.

Thus, the present invention is also directed to combination therapies including administering a chemotherapeutic drug with a nucleic acid composition useful as an immunogen, comprising a combination of: (a) first nucleic acid vector comprising a first sequence encoding an antigenic polypeptide or peptide, which first vector optionally comprises a second sequence linked to the first sequence, which second sequence encodes an immunogenicity-potentiating polypeptide (IPP); b) a second nucleic acid vector encoding an anti-apoptotic polypeptide, wherein, when the second vector is administered with the first vector to a subject, a T cell-mediated immune response to the antigenic polypeptide or peptide is induced that is greater in magnitude and/or duration than an immune response induced by administration of the first vector alone. The first vector above may comprises a promoter operatively linked the first and/or the second sequence.

In the above compositions the anti-apoptotic polypeptide is preferably selected from the group consisting of (a) BCL-xL, (b) BCL2, (c) XIAP, (d) FLICEc-s, (e) dominant-negative caspase-8, (f) dominant negative caspase-9, (g) SPI-6, and (h) a functional homologue or derivative of any of (a)-(g). The anti-apoptotic DNA may be physically linked to the antigen-encoding DNA. Examples of this are provided in U.S. Patent Application publication No. 20070026076, primarily in the form of suicidal DNA vaccine vectors. Alternatively, the anti-apoptotic DNA may be administered separately from, but in combination with the antigen-endcoding DNA molecule. Even more examples of the co-administration of these two types of vectors are provided in U.S. patent application Ser. No. 10/546,810.

Exemplary nucleotide and amino acid sequences of anti-apoptotic and other proteins are provided in the sequence listing. Biologically active homologs of these proteins and constructs may also be used. Biologically active homologs is to be understood as described herein in the context of other proteins, e.g., IPPs.

The coding sequence for BCL-xL as present in the pcDNA3 vector of the present invention is SEQ ID NO:55; the amino acid sequence of BCL-xL is SEQ ID NO:56; the sequence pcDNA3-BCL-xL is SEQ ID NO:57 (the BCL-xL coding sequence corresponds to nucleotides 983 to 1732); a pcDNA3 vector combining E7 and BCL-xL, designated pcDNA3-E7/BCL-xL is SEQ ID NO:58 (the E7 and BCL-xL sequences correspond to nucleotides 960 to 2009); the amino acid sequence of the E7-BCL-xL chimeric or fusion polypeptide is SEQ ID NO: 59; a mutant BCL-xL ("mtBCL-xL") DNA sequence is SEQ ID NO:60; the amino acid sequence of mtBCL-xL is SEQ ID NO:61; the amino acid sequence of the E7-mtBCL-xL chimeric or fusion polypeptide is SEQ ID NO:62; in the pcDNA-mtBCL-xL [SEQ ID NO:63] vector, this mutant sequence is inserted in the same position that BCL-xL is inserted in SEQ ID NO:57 and in the pcDNA-E7/mtBCL-XL [SEQ ID NO:64], this sequence is inserted in the same position as the BCL-xL sequence is in SEQ ID NO:58; the sequence of the suicidal DNA vector pSCA1-BCL-xL is SEQ ID NO:65 (the BCL-xL sequence corresponds to nucleotides 7484 to 8233); the sequence of the "combined" vector, pSCA1-E7/BCL-xL is SEQ ID NO:66 (the sequence of E7 and BCL-xL corresponds to nucleotides 7461 to 8510); the sequence of pSCA1-mtBCL-xL [SEQ ID NO:67] is the same as that for the wild type BCL-xL except that the mtBCL-xL sequence is inserted in the same position as the wild type sequence in the pSCA1-mtBCL-xL vector; the sequence pSCA1-E7/mtBCL-xL [SEQ ID NO:68] is the same as that for the wild type pSCA1-E7/BCL-xL above, except that the mtBCL-xL sequence is inserted in the same position as the wild type sequence; the sequence of the vector pSG5-BCL-xL is SEQ ID NO:69 (the BCL-xL coding sequence corresponds to nucleotides 1061 to 1810); the sequenced of the vector pSG5-mtBCL-xL is SEQ ID NO:70 with the mutant BCL-xL sequence has the mtBCL-xL, shown above, inserted in the same location as for the wild type vector immediately above; the nucleotide sequence of the DNA encoding the XIAP anti-apoptotic protein is SEQ ID NO:71; the amino acid of the vector comprising the XIAP anti-apoptotic protein coding sequence is SEQ ID NO:72; the nucleotide sequence of the vector comprising the XIAP anti-apoptotic protein coding sequence, designated PSG5-XIAP is shown in SEQ ID NO:73 (with the XIAP corresponding to nucleotides 1055 to 2553); the sequence of DNA encoding the anti-apoptotic protein FLICEc-s is SEQ ID NO:74; the amino acid sequence of the anti-apoptotic protein FLICEc-s is SEQ ID NO:75; the PSG5 vector encoding the anti-apoptotic protein FLICEc-s, designated PSG5-FLICEc-s, has the sequence SEQ ID NO:76 (with the FLICEc-s sequence corresponding to nucleotides 1049 to 2443); the sequence of DNA encoding the anti-apoptotic protein Bcl2 is SEQ ID NO:77; the amino acid sequence of Bcl2 is SEQ ID NO:78; the PSG5 vector encoding Bcl2, designated PSG5-BCL2, has the sequence SEQ ID NO:79 (with the Bcl2 sequence corresponding to nucleotides 1061 to 1678); the pSG5-dn-caspase-8 vector is SEQ ID NO:80 (encoding the dominant-negative caspase-8 corresponding to nucleotides 1055 to 2449); the amino acid sequence of dn-caspase-8 is SEQ ID NO:81; the pSG5-dn-caspase-9 vector is SEQ ID NO:82 (encoding the dominant-negative caspase-9 as nucleotides 1055 to 2305); the amino acid sequence of dn-caspase-9 is SEQ ID NO:83); the nucleotide sequence of murine serine protease inhibitor 6 (SPI-6, deposited in GENEBANK as NM 009256) is SEQ ID NO:84; the amino acid sequence of the SPI-6 protein is SEQ ID NO:85; the nucleic acid sequence of the mutant SPI-6 (mtSPI6) is SEQ ID NO:86; the amino acid sequence of the mutant SPI-6 protein (mtSPI-6) is SEQ ID NO:87; the sequence of the pcDNA3-Spi6 vector is SEQ ID NO:88 (the SPI-6 sequence corresponds to nucleotides 960 to 2081); and the sequence of the mutant vector pcDNA3-mtSpi6 vector [SEQ ID NO:89] is the same as that above, except that the mtSPI-6 sequence is inserted in the same location in place of the wild type SPI-6.

Biologically active homologs of these nucleic acids and proteins may be used. Biologically active homologs are to be understood as described in the context of other proteins, e.g., IPPs, herein. For example, a vector may encode an anti-apoptotic protein that is at least about 90%, 95%, 98% or 99% identical to that of a sequence set forth herein.

Chemotherapeutic Drugs

Drugs may also be administered to a subject to whom an MHC class I/II activator with or without a nucleic acid encoding an antigen is administered. Generally, any drug that reduces the growth of cells without significantly affecting the immune system may be used, or at least not suppressing the immune system to the extent of eliminating the positive effects of a DNA vaccine that is administered to the subject. Preferred drugs are chemotherapeutic drugs.

A wide variety of chemotherapeutic drugs may be used, provided that the drug stimulates the effect of a vaccine, e.g., DNA vaccine. In certain embodiments, a chemotherapeutic drug may be a drug that (a) induces apoptosis of cells, in particular, cancer cells, when contacted therewith; (b)

reduces tumor burden; and/or (c) enhances CD8+ T cell-mediated antitumor immunity. In certain embodiments, the drug must also be on that does not inhibit the immune system, or at least not at certain concentrations.

In one embodiment, the chemotherapeutic drug is epigallocatechin-3-gallate (EGCG) or a chemical derivative or pharmaceutically acceptable salt thereof. Epigallocatechin gallate (EGCG) is the major polyphenol component found in green tea (for reviews, see (12-17)). EGCG has demonstrated antitumor effects in various human and animal models, including cancers of the breast, prostate, stomach, esophagus, colon, pancreas, skin, lung, and other sites (for reviews, see (18, 19, 12)). EGCG has been shown to act on different pathways to regulate cancer cell growth, survival, angiogenesis and metastasis (for review see (12, 13, 20)). For example, some studies suggest that EGCG protects against cancer by causing cell cycle arrest and inducing apoptosis (21). It is also reported that telomerase inhibition might be one of the major mechanisms underlying the anticancer effects of EGCG (22, 23). In comparison with commonly-used antitumor agents, including retinoids and doxorubicin, EGCG has a relatively low toxicity and is convenient to administer due to its oral bioavailability (24, 25). Thus, EGCG has been used in clinical trials (26) and appears to be a potentially ideal antitumor agent (27, 28).

Exemplary analogs or derivatives of EGCG include (−)-EGCG, (+)-EGCG, (−)-EGCG-amide, (−)-GCG, (+)-GCG, (+)-EGCG-amide, (−)-ECG, (−)-CG, genistein, GTP-1, GTP-2, GTP-3, GTP-4, GTP-5, Bn-(+)-epigallocatechin gallate (US 2004/0186167), and dideoxy-epigallocatechin gallate (Furuta, et al., Bioorg. Med. Chem. Letters, 2007, 11: 3095-3098), For additional examples, see US 2004/0186167 (incorporated by reference in its entirety); Waleh, et al., Anticancer Res., 2005, 25: 397-402; Wai, et al., Bioorg. Med. Chem., 2004, 12: 5587-5593; Smith, et al., Proteins: Struc. Func. & Bioinform., 2003, 54: 58-70; U.S. Pat. No. 7,109,236 (incorporated by reference in its entirety); Landis-Piwowar, et al., Int. J. Mol. Med., 2005, 15: 735-742; Landis-Piwowar, et al., J. Cell. Phys., 2007, 213: 252-260; Daniel, et al., Int. J. Mol. Med., 2006, 18: 625-632; Tanaka, et al., Ang. Chemie Int., 2007, 46: 5934-5937.

Another chemotherapeutic drug that may be used is (a) 5,6 di-methylxanthenone-4-acetic acid (DMXAA), or a chemical derivative or analog thereof or a pharmaceutically acceptable salt thereof. Exemplary analogs or derivatives include xanthenone-4-acetic acid, flavone-8-acetic acid, xanthen-9-one-4-acetic acid, methyl (2,2-dimethyl-6-oxo-1,2-dihydro-6H-3,1-dioxacyclopenta[α]anthracen-10-yl)acetate, methyl (2-methyl-6-oxo-1,2-dihydro-6H-3,11-dioxacyclopenta[α]anthracen-10-yl)acetate, methyl (3,3-dimethyl-7-oxo-3H, 7H-4,12-dioxabenzo[α]anthracen-10-yl)acetate, methyl-6-alkyloxyxanthen-9-one-4-acetates (Gobbi, et al., 2002, J. Med. Chem., 45: 4931) or a. For additional examples, see WO 2007/023302 A1, WO 2007/023307 A1, US 2006/9505, WO 2004/39363 A1, WO 2003/80044 A1, AU 2003/217035 A1, and AU 2003/282215 A1, each incorporated by reference in their entirety.

A chemotherapeutic drug may also be cisplatin, or a chemical derivative or analog thereof or a pharmaceutically acceptable salt thereof. Exemplary analogs or derivatives include dichloro[4,4'-bis(4,4,4-trifluorobutyl)-2,2'-bipyridine]platinum (Kyler et al., Bioorganic & Medicinal Chemistry, 2006, 14: 8692-8700), cis-[Rh2(—O2CCH3)2(CH3CN)6]2+ (Lutterman et al., J. Am. Chem. Soc., 2006, 128: 738-739), (+)-cis-(1,1-Cyclobutanedicarboxylato)((2R)-2-methyl-1,4-butanediamine-N,N')platinum (O'Brien et al., Cancer Res., 1992, 52: 4130-4134), cis-bisneodecanoato-trans-R,R-1,2-diaminocyclohexane platinum(II) (Lu et al., J. of Clin. Oncol., 2005, 23: 3495-3501), carboplatin (Woloschuk, Drug Intell. Clin. Pharm., 1988, 22: 843-849), sebriplatin (Kanazawa et al., Head & Neck, 2006, 14: 38-43), satraplatin (Amorino et al., Cancer Chemother. and Pharmacol., 2000, 46: 423-426), azane (dichloroplatinum) (CID: 11961987), azanide (CID: 6712951), platinol (CID: 5702198), lopac-P-4394 (CID: 5460033), MOLI001226 (CID: 450696), trichloroplatinum (CID: 420479), platinate(1-), amminetrichloro-, ammonium (CID: 160995), triammineplatinum (CID: 119232), biocisplatinum (CID: 84691), platiblastin (CID: 2767) and pharmaceutically acceptable salts thereof. For additional examples, see U.S. Pat. No. 5,922,689, U.S. Pat. No. 4,996,337, U.S. Pat. No. 4,937,358, U.S. Pat. No. 4,808, 730, U.S. Pat. No. 6,130,245, U.S. Pat. No. 7,232,919, and U.S. Pat. No. 7,038,071, each incorporated by reference in their entirety.

Another chemotherapeutic drug that may be used is apigenin, or a chemical derivative or analog thereof or a pharmaceutically acceptable salt thereof. Exemplary analogs or derivatives include acacetin, chrysin, kampherol, luteolin, myricetin, naringenin, quercetin (Wang et al., Nutrition and Cancer, 2004, 48: 106-114), puerarin (US 2006/0276458, incorporated by reference in its entirety) and pharmaceutically acceptable salts thereof. For additional examples, see US 2006/189680 A1, incorporated by reference in its entirety).

Another chemotherapeutic drug that may be used is doxorubicin, or a chemical derivative or analog thereof or a pharmaceutically acceptable salt thereof. Exemplary analogs or derivatives include anthracyclines, 3'-deamino-3'-(3-cyano-4-morpholinyl)doxorubicin, WP744 (Faderl, et al., Cancer Res., 2001, 21: 3777-3784), annamycin (Zou, et al., Cancer Chemother. Pharmacol., 1993, 32:190-196), 5-imino-daunorubicin, 2-pyrrolinodoxorubicin, DA-125 (Lim, et al., Cancer Chemother. Pharmacol., 1997, 40: 23-30), 4-demethoxy-4'-O-methyldoxorubicin, PNU 152243 and pharmaceutically acceptable salts thereof (Yuan, et al., Anti-Cancer Drugs, 2004, 15: 641-646). For additional examples, see EP 1242438 B1, U.S. Pat. No. 6,630,579, AU 2001/29066 B2, U.S. Pat. No. 4,826,964, U.S. Pat. No. 4,672,057, U.S. Pat. No. 4,314, 054, AU 2002/358298 A1, and U.S. Pat. No. 4,301,277, each incorporated by reference in their entirety);

Other chemotherapeutic drugs that may be used are anti-death receptor 5 antibodies and binding proteins, and their derivatives, including antibody fragments, single-chain antibodies (scFvs), Avimers, chimeric antibodies, humanized antibodies, human antibodies and peptides binding death receptor 5. For examples, see US 2007/31414 and US 2006/269554, each incorporated by reference in their entirety.

Another chemotherapeutic drug that may be used is bortezomib, or a chemical derivative or analog thereof or a pharmaceutically acceptable salt thereof. Exemplary analogs or derivatives include MLN-273 and pharmaceutically acceptable salts thereof (Witola, et al., Eukaryotic Cell, 2007, doi: 10.128/EC.00229-07). For additional possibilities, see Groll, et al., Structure, 14:451.

Another chemotherapeutic drug that may be used is 5-aza-2-deoxycytidine, or a chemical derivative or analog thereof or a pharmaceutically acceptable salt thereof. Exemplary analogs or derivatives include other deoxycytidine derivatives and other nucleotide derivatives, such as deoxyadenine derivatives, deoxyguanine derivatives, deoxythymidine derivatives and pharmaceutically acceptable salts thereof.

Another chemotherapeutic drug that may be used is genistein, or a chemical derivative or analog thereof or a pharmaceutically acceptable salt thereof. Exemplary analogs or derivatives include 7-O-modified genistein derivatives (Zhang, et al., Chem. & Biodiv., 2007, 4: 248-255), 4',5,7-tri[3-(2-hydroxyethylthio)propoxy]isoflavone, genistein glycosides (Polkowski, Cancer Letters, 2004, 203: 59-69), other genistein derivatives (Li, et al., Chem & Biodiv., 2006, 4: 463-472; Sarkar, et al., Mini. Rev. Med. Chem., 2006, 6: 401-407) or pharmaceutically acceptable salts thereof. For additional examples, see U.S. Pat. No. 6,541,613, U.S. Pat. No. 6,958,156, and WO/2002/081491, each incorporated by reference in their entirety.

Another chemotherapeutic drug that may be used is celecoxib, or a chemical derivative or analog thereof or a pharmaceutically acceptable salt thereof. Exemplary analogs or derivatives include N-(2-aminoethyl)-4-[5-(4-tolyl)-3-(trifluoromethyl)-1H-pyrazol-1-yl]benzenesulfonamide, 4-[5-(4-aminophenyl)-3-(trifluoromethyl)-1H-pyrazol-1-yl]benzenesulfonamide, OSU03012 (Johnson, et al., Blood, 2005, 105: 2504-2509), OSU03013 (Tong, et. al, Lung Cancer, 2006, 52: 117-124), dimethyl celecoxib (Backhus, et al., J. Thorac. and Cardiovasc. Surg., 2005, 130: 1406-1412), and other derivatives or pharmaceutically acceptable salts thereof (Ding, et al., Int. J. Cancer, 2005, 113: 803-810; Zhu, et al., Cancer Res., 2004, 64: 4309-4318; Song, et al., J. Natl. Cancer Inst., 2002, 94: 585-591). For additional examples, see U.S. Pat. No. 7,026,346, incorporated by reference in its entirety.

One of skill in the art will readily recognize that other chemotherapeutics can be used with the methods and kits disclosed in the present invention, including proteasome inhibitors (in addition to bortezomib) and inhibitors of DNA methylation. Other drugs that may be used include Paclitaxel; selenium compounds; SN38, etoposide, 5-Fluorouracil; VP-16, cox-2 inhibitors, Vioxx, cyclooxygenase-2 inhibitors, curcumin, MPC-6827, tamoxifen or flutamide, etoposide, PG490, 2-methoxyestradiol, AEE-788, aglycon protopanaxadiol, aplidine, ARQ-501, arsenic trioxide, BMS-387032, canertinib dihydrochloride, canfosfamide hydrochloride, combretastatin A-4 prodrug, idronoxil, indisulam, INGN-201, mapatumumab, motexafin gadolinium, oblimersen sodium, OGX-011, patupilone, PXD-101, rubitecan, tipifarnib, trabectedin PXD-101, methotrexate, Zerumbone, camptothecin, MG-98, VX-680, Ceflatonin, Oblimersen sodium, motexafin gadolinium, 1D09C3, PCK-3145, ME-2 and apoptosis-inducing-ligand (TRAIL/Apo-2 ligand). Others are provided in a report entitled "competitive outlook on apoptosis in oncology, December 2006, published by Bioseeker, and available, e.g., at http://bizwiz.bioseeker.com/bw/Archives/Files/TOC_BSG0612193.pdf.

Generally, any drug that affects an apoptosis target may also be used. Apoptosis targets include the tumour-necrosis factor (TNF)-related apoptosis-inducing ligand (TRAIL) receptors, the BCL2 family of anti-apoptotic proteins (such as Bcl-2), inhibitor of apoptosis (IAP) proteins, MDM2, p53, TRAIL and caspases. Exemplary targets include B-cell CLL/lymphoma 2, Caspase 3, CD4 molecule, Cytosolic ovarian carcinoma antigen 1, Eukaryotic translation elongation factor 2, Farnesyltransferase, CAAX box, alpha; Fc fragment of IgE; Histone deacetylase 1; Histone deacetylase 2; Interleukin 13 receptor, alpha 1; Phosphodiesterase 2A, cGMP-stimulated Phosphodiesterase 5A, cGMP-specific; Protein kinase C, beta 1; Steroid 5-alpha-reductase, alpha polypeptide 1; 8.1.15 Topoisomerase (DNA) I; Topoisomerase (DNA) II alpha; Tubulin, beta polypeptide; and p53 protein.

In certain embodiments, the compounds described herein, e.g., EGCG, are naturally-occurring and may, e.g., be isolated from nature. Accordingly, in certain embodiments, a compound is used in an isolated or purified form, i.e., it is not in a form in which it is naturally occurring. For example, an isolated compound may contain less than about 50%, 30%, 10%, 1%, 0.1% or 0.01% of a molecule that is associated with the compound in nature. A purified preparation of a compound may comprise at least about 50%, 70%, 80%, 90%, 95%, 97%, 98% or 99% of the compound, by molecule number or by weight. Compositions may comprise, consist essentially of consist of one or more compounds described herein. Some compounds that are naturally occurring may also be synthesized in a laboratory and may be referred to as "synthetic." Yet other compounds described herein are non-naturally occurring.

In certain embodiments, the chemotherapeutic drug is in a preparation from a natural source, e.g., a preparation from green tea.

Pharmaceutical compositions comprising 1, 2, 3, 4, 5 or more chemotherapeutic drugs or pharmaceutically acceptable salts thereof are also provided herein. A pharmaceutical composition may comprise a pharmaceutically acceptable carrier. A composition, e.g., a pharmaceutical composition, may also comprise a vaccine, e.g., a DNA vaccine, and optionally 1, 2, 3, 4, 5 or more vectors, e.g., other DNA vaccines or other constructs, e.g., described herein.

Compounds may be provided with a pharmaceutically acceptable salt. The term "pharmaceutically acceptable salts" is art-recognized, and includes relatively non-toxic, inorganic and organic acid addition salts of compositions, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.*, 66:1-19 (1977).

Also provided herein are compositions and kits comprising one or more DNA vaccines and one or more chemotherapeutic drugs, and optionally one or more other constructs described herein.

Therapeutic Compositions and their Administration

A vaccine composition comprising a nucleic acid, a particle comprising the nucleic acid or a cell expressing this nucleic acid, may be administered to a mammalian subject. The vaccine composition may be administered in a pharmaceutically acceptable carrier in a biologically-effective and/or a therapeutically-effective amount.

Certain preferred conditions are disclosed in the Examples. The composition may be given alone or in combination with another protein or peptide such as an immunostimulatory molecule. Treatment may include administration of an adjuvant, used in its broadest sense to include any nonspecific immune stimulating compound such as an interferon. Adjuvants contemplated herein include resorcinols, non-ionic surfactants such as polyoxyethylene oleyl ether and n-hexadecyl polyethylene ether.

A therapeutically effective amount is a dosage that, when given for an effective period of time, achieves the desired immunological or clinical effect.

A therapeutically active amount of a nucleic acid encoding the fusion polypeptide may vary according to factors such as the disease state, age, sex, and weight of the individual, and the ability of the peptide to elicit a desired response in the individual. Dosage regimes may be adjusted to provide the optimum therapeutic response. For example, several divided doses may be administered daily or the dose may be proportionally reduced as indicated by the exigencies of the therapeutic situation. A therapeutically effective amounts of the protein, in cell associated form may be stated in terms of the protein or cell equivalents.

Thus an effective amount of the vaccine may be between about 1 nanogram and about 1 gram per kilogram of body weight of the recipient, more preferably between about 0.1 µg/kg and about 10 mg/kg, more preferably between about 1 µg/kg and about 1 mg/kg. Dosage forms suitable for internal administration preferably contain (for the latter dose range) from about 0.1 µg to 100 µg of active ingredient per unit. The active ingredient may vary from 0.5 to 95% by weight based on the total weight of the composition. Alternatively, an effective dose of cells transfected with the DNA vaccine constructs of the present invention is between about $10^4$ and $10^8$ cells. Those skilled in the art of immunotherapy will be able to adjust these doses without undue experimentation.

Preferred routes of administration of the DNA include (a) intradermal "gene gun" delivery wherein DNA-coated gold particles in an effective amount are delivered using a helium-driven gene gun (BioRad, Hercules, Calif.) with a discharge pressure set at a known level, e.g., of 400 p.s.i.; (b) intramuscularly (i.m.) injection using a conventional syringe needle; and (c) use of a needle-free biojector such as the Biojector 2000 (Bioject Inc., Portland, Oreg.) which is an injection device consisting of an injector and a disposable syringe. The orifice size controls the depth of penetration. For example, 50 µg of DNA may be delivered using the Biojector with no. 2 syringe nozzle.

Other routes of administration include the following. The term "systemic administration" refers to administration of a composition or agent such as a DNA vaccine as described herein, in a manner that results in the introduction of the composition into the subject's circulatory system or otherwise permits its spread throughout the body. "Regional" administration refers to administration into a specific, and somewhat more limited, anatomical space, such as intraperitoneal, intrathecal, subdural, or to a specific organ. "Local administration" refers to administration of a composition or drug into a limited, or circumscribed, anatomic space, such as intratumoral injection into a tumor mass, subcutaneous injections, intradermal or intramuscular injections. Those of skill in the art will understand that local administration or regional administration may also result in entry of a composition into the circulatory system—i.e., rendering it systemic to one degree or another. Other routes of administration include oral, intranasal or rectal or any other route known in the art.

For accomplishing the objectives of the present invention, nucleic acid therapy may be accomplished by direct transfer of a functionally active DNA into mammalian somatic tissue or organ in vivo. DNA transfer can be achieved using a number of approaches described below. These systems can be tested for successful expression in vitro by use of a selectable marker (e.g., G418 resistance) to select transfected clones expressing the DNA, followed by detection of the presence of the antigen-containing expression product (after treatment with the inducer in the case of an inducible system) using an antibody to the product in an appropriate immunoassay.

The DNA molecules, e.g., encoding a fusion polypeptides, may also be packaged into retrovirus vectors using packaging cell lines that produce replication-defective retroviruses, as is well-known in the art (e.g., Cone, R. D. et al., *Proc Natl Acad Sci USA* 81:6349-53, 1984; Mann, R F et al., *Cell* 33:153-9, 1983; Miller, A D et al., *Molec Cell Biol* 5:431-7, 1985; Sorge, J, et al., *Molec Cell Biol* 4:1730-7, 1984; Hock, R A et al., *Nature* 320:257, 1986; Miller, A D et al., *Molec Cell Biol* 6:2895-2902 (1986). Newer packaging cell lines which are efficient an safe for gene transfer have also been described (Bank et al., U.S. Pat. No. 5,278,056).

The above approach can be utilized in a site specific manner to deliver the retroviral vector to the tissue or organ of choice. Thus, for example, a catheter delivery system can be used (Nabel, E G et al., *Science* 244:1342 (1989)). Such methods, using either a retroviral vector or a liposome vector, are particularly useful to deliver the nucleic acid to be expressed to a blood vessel wall, or into the blood circulation of a tumor.

Depending on the route of administration, the composition may be coated in a material to protect the compound from the action of enzymes, acids and other natural conditions which may inactivate the compound. Thus it may be necessary to coat the composition with, or co-administer the composition with, a material to prevent its inactivation. For example, an enzyme inhibitors of nucleases or proteases (e.g., pancreatic trypsin inhibitor, diisopropylfluorophosphate and trasylol). or in an appropriate carrier such as liposomes (including water-in-oil-in-water emulsions as well as conventional liposomes (Strejan et al., *J. Neuroimmunol* 7:27, 1984).

Other pharmaceutically acceptable carriers for the nucleic acid vaccine compositions according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Those skilled in the art will appreciate other suitable embodiments of the present liposomal formulations.

A chemotherapeutic drug may be administered in doses that are similar to the doses that the chemotherapeutic drug is used to be administered for cancer therapy. Alternatively, it may be possible to use lower doses, e.g., doses that are lower by 10%, 30%, 50%, or 2, 5, or 10 fold lower. Generally, the dose of chemotherapeutic agent is a dose that is effective to increase the effectiveness of a DNA vaccine, but less than a dose that results in significant immunosuppression or immunosuppression that essentially cancels out the effect of the DNA vaccine.

The route of administration of chemotherapeutic drugs may depend on the drug. For use in the methods described herein, a chemotherapeutic drug may be used as it is commonly used in known methods. Generally, the drugs will be administered orally or they may be injected. The regimen of administration of the drugs may be the same as it is commonly used in known methods. For example, certain drugs are administered one time, other drugs are administered every third day for a set period of time, yet other drugs are administered every other day or every third, fourth, fifth, sixth day or weekly. The Examples provide exemplary regimens for administrating the drugs, as well as DNA vaccines.

One or more of a nucleic acid encoding an MHC class I/II activator, a nucleic acid vaccine, a drug, such as a chemotherapeutic drug, and any other agents of interest, may be administered simultaneously or subsequently. When administered simultaneously, the different components may be administered as one composition. Accordingly, also provided herein are compositions, e.g., pharmaceutical compositions comprising one or more agents, e.g., one or more MHC class I/II activator, one or more nucleic acid vaccines, and one or more drugs.

In one embodiment, a subject first receives one or more doses of chemotherapeutic drug and then one or more doses of DNA vaccine. In the case of DMXAA, it may be preferable to administer to the subject a dose of DNA vaccine first and then a dose of chemotherapeutic drug. One may administer 1, 2, 3, 4, 5 or more doses of DNA vaccine and 1, 2, 3, 4, 5 or more doses of chemotherapeutic agent.

A method may further comprise subjecting a subject to another cancer treatment, e.g., radiotherapy, an anti-angiogenesis agent and/or a hydrogel-based system.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

Preferred pharmaceutically acceptable diluents include saline and aqueous buffer solutions. Pharmaceutical compositions suitable for injection include sterile aqueous solutions (where water soluble) or dispersions and sterile powders for the extemporaneous preparation of sterile injectable solutions or dispersion. Isotonic agents, for example, sugars, polyalcohols such as mannitol, sorbitol, sodium chloride may be included in the pharmaceutical composition. In all cases, the composition should be sterile and should be fluid. It should be stable under the conditions of manufacture and storage and must include preservatives that prevent contamination with microorganisms such as bacteria and fungi. Dispersions can also be prepared in glycerol, liquid polyethylene glycols, and mixtures thereof and in oils. Under ordinary conditions of storage and use, these preparations may contain a preservative to prevent the growth of microorganisms.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms in the pharmaceutical composition can be achieved by various antibacterial and antifungal agents, for example, parabens, chlorobutanol, phenol, ascorbic acid, thimerosal, and the like.

Compositions are preferably formulated in dosage unit form for ease of administration and uniformity of dosage. Dosage unit form refers to physically discrete units suited as unitary dosages for a mammalian subject; each unit contains a predetermined quantity of active material (e.g., the nucleic acid vaccine) calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects For lung instillation, aerosolized solutions are used. In a sprayable aerosol preparations, the active protein may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

Diseases that may be treated as described herein include hyperproliferative diseases, e.g., cancer, whether localized or having metastasized. Exemplary cancers include head and neck cancers and cervical cancer. Any cancer can be treated provided that there is a tumor associated antigen that is associated with the particular cancer. Other cancers include skin cancer, lung cancer, colon cancer, kidney cancer, breast cancer, prostate cancer, pancreatic cancer, bone cancer, brain cancer, as well as blood cancers, e.g., myeloma, leukemia and lymphoma. Generally, any cell growth can be treated provided that there is an antigen associated with the cell growth, which antigen or homolog thereof can be encoded by a DNA vaccine.

Treating a subject includes curing a subject or improving at least one symptom of the disease or preventing or reducing the likelihood of the disease to return. For example, treating a subject having cancer could be reducing the tumor mass of a subject, e.g., by about 10%, 30%, 50%, 75%, 90% or more, eliminating the tumor, preventing or reducing the likelihood of the tumor to return, or partial or complete remission.

The present description is further illustrated by the following examples, which should not be construed as limiting in any way.

EXAMPLES

Example 1

Co-Administration of DNA Vaccines with DNA Encoding Ii-PADRE Generates Potent PADRE-Specific CD4+ T Cell Immune Responses and Enhances Vaccine Potency This Example is published as Hung et al. (June 2007) *Mol. Therapy.* 15:1211, which is specifically incorporated by reference herein.

Abstract

It is now clear that CD4$^+$ T cells play a crucial role in the generation of CD8$^+$ T effector and memory T cell immune responses. In the current study, we enhanced the CD4$^+$ T cell immune responses in mice by constructing a DNA vaccine encoding an Ii chain in which the CLIP region is replaced with a CD4$^+$ T helper epitope, PADRE (Ii-PADRE). C57BL/6 mice vaccinated with DNA encoding Ii-PADRE showed significantly greater PADRE-specific CD4$^+$ T cell immune responses compared to mice vaccinated with DNA encoding Ii chain alone (Ii DNA). More importantly, co-administration of DNA encoding HPV E6 or E7 antigen and DNA encoding Ii-PADRE led to significantly stronger E6- or E7-specific CD8$^+$ T cell immune responses and more potent protective and therapeutic antitumor effects against an E6/E7-expressing tumor model in mice compared to co-administration of E6 or E7 DNA and Ii DNA. Taken together, our data indicate that co-administration of DNA vaccines with Ii-PADRE DNA represents an effective approach for enhancing the generation of CD4$^+$ T cells and eliciting stronger antigen-specific CD8$^+$ T cell immune responses. Therefore, it is expected that this strategy may have significant potential for clinical translation.

Introduction

DNA vaccines have emerged as a potentially important form of antigen-specific immunotherapy because of their safety, ease of production, and stability. Intradermal administration of DNA vaccines using a gene gun represents an efficient means of directly delivering DNA into dendritic cells, the most potent professional antigen-presenting cells. The DNA-expressing dendritic cells mature and migrate to the draining lymph nodes, where they prime helper and killer T cells in vivo [1, 2]. We have previously used this system to modify the properties of dendritic cells for enhancing DNA vaccine potency (for a review, see reference [3]).

It is now clear that CD4$^+$ T cells play a crucial role in the generation of CD8$^+$ T effector and memory T cell populations [4]. CD4$^+$ T cells at tumor sites can also interact with natural killer cells and macrophages to enhance tumor destruction [5, 6]. Thus, it is desirable to design an immunization regimen that is capable of generating antigen-specific CD4$^+$ T cells, and for this task it is important to understand the mechanisms of antigen presentation to the CD4$^+$ T cells through the MHC class II pathway.

CD4$^+$ T cells recognize antigens in the context of MHC class II molecules. In general, exogenous antigens are taken up by APCs through phagocytosis or endocytosis and are degraded into antigenic peptides by acid proteases in low pH endosomal or lysosome-like compartments [7-10]. The antigenic peptides later associate with the MHC class II molecules on the surface of the APCs for recognition by the CD4$^+$ T cells. An essential component of this MHC class II-mediated antigen presentation is the Invariant (Ii) chain molecule. In the endoplasmic reticulum, MHC class II molecules assemble and then bind with the Ii chain. The class II-associated Ii peptide (CLIP) region of the Ii chain occupies the MHC class II peptide-binding grove. The Ii chain is then degraded until only the CLIP region remains; this region prevents premature binding of the antigenic peptide into the MHC class II peptide-binding groove. In the lysosomes, CLIP is later replaced by one of the antigenic peptides.

Previous studies have demonstrated that transfection of MHC class II-positive cells with DNA encoding an Ii chain in which CLIP is replaced with a CD4$^+$ T helper epitope of an antigen of interest can lead to the presentation CD4$^+$ T cell epitope through the MHC class II pathway [11-18]. We reasoned that the replacement of the CLIP region of the Ii chain with a high-affinity and "promiscuous" CD4$^+$ T cell epitope such as the Pan HLA-DR reactive epitope (PADRE) [19] may lead to the stable presentation of the PADRE epitope through MHC class II molecules. We also hypothesized that immunization with DNA vaccines encoding an Ii chain in which the CLIP region is replaced with PADRE (Ii-PADRE DNA) may lead to the generation of PADRE-specific CD4$^+$ T cell immune responses in mice.

In the current study, we created a DNA vaccine encoding an Ii chain in which the CLIP region is replaced with PADRE (Ii-PADRE DNA). Vaccination of mice with Ii-PADRE DNA increased the number of PADRE-specific CD4$^+$ T cells in the immunized C57BL/6 mice. In addition, co-administration of Ii-PADRE DNA and DNA vaccines containing either the E6 or E7 protein of Human Papillomavirus Type 16 (HPV-16) led to enhanced HPV antigen-specific CD8$^+$ T cell immune responses and potent protective and therapeutic anti-tumor effects against an E6/E7-expressing tumor model, TC-1, in mice. These findings have clinical implications for enhancing the potency of DNA vaccines and for improving antigen-specific immune responses in many antigenic systems.

Results

Vaccination with Ii-PADRE DNA Generated the Highest PADRE-Specific CD4$^+$ T Cell Immune Responses in Mice Among all the DNA Vaccines Tested We constructed a DNA vaccine encoding an Ii chain in which the CLIP sequence (aa81-102, KPVSQMRMATPLL-MRPM) (SEQ ID NO: 92) was replaced with the PADRE sequence (AKFVAAWTLKAAA) (SEQ ID NO: 93) to form Ii-PADRE DNA. FIGS. 1A and 1B show the schematic diagrams of the Ii-chain protein and Ii-PADRE chimeric protein. FIG. 1C shows schematic diagram of a typical MHC class II molecule associated with the Ii chain. The CLIP region of the Ii chain occupies the peptide binding site and is eventually replaced by an antigenic peptide in the endosomal/lysosomal compartments. FIG. 1D shows schematic diagram of a MHC class II molecule associated with the Ii-PADRE chimeric protein. The PADRE peptide remains attached to the peptide binding site of the MHC class II molecule.

To demonstrate whether Ii-PADRE DNA can generate PADRE-specific CD4$^+$ T cells in vaccinated mice, we immunized C57BL/6 mice with Ii DNA or Ii-PADRE DNA intradermally via gene gun. Splenocytes from vaccinated mice were harvested, stimulated with PADRE peptide and characterized for the presence of PADRE-specific CD4$^+$ T cells by intracellular cytokine staining for IFN-γ and staining for CD4$^+$ followed by flow cytometry analysis (see FIG. 9). Mice vaccinated with Ii-PADRE DNA generated a significantly higher number of PADRE-specific CD4$^+$ T cells compared to mice vaccinated with wild-type Ii DNA. Thus, these data suggested that the replacement of the CLIP region with the PADRE peptide sequence in the Ii chain DNA vaccine could lead to the presentation of PADRE through the MHC class II pathway to activate PADRE-specific CD4$^+$ T cells in vaccinated mice.

Figure 2:
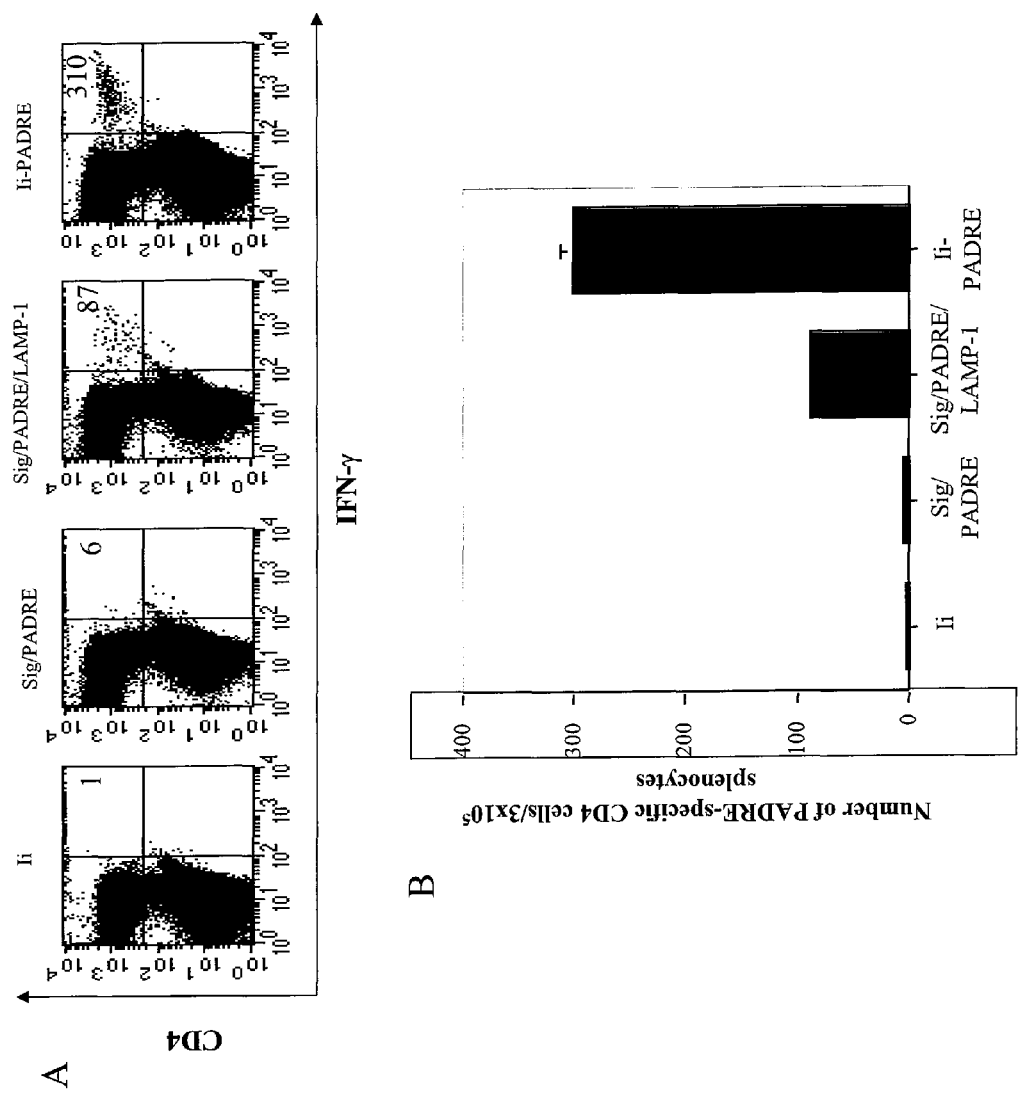
FIG. 2. Flow cytometry analysis of IFN-γ-secreting CD4+ T cells in vaccinated mice. C57BL/6 mice (five per group) were immunized twice with 2 μg/mouse of at one-week interval. Splenocytes from vaccinated mice were harvested 1 week after the last vaccination and stimulated overnight with the PADRE peptide. (A) Representative figure of the flow cytometry data. The numbers on the right upper corner represent the number of IFN-γ-secreting CD4+ T cells per $3 \times 10^5$ splenocytes acquired. (B) Bar graph depicting the number of PADRE-specific CD4+ T cells per $3 \times 10^5$ splenocytes (means±s.e.). The data presented in this figure are from one representative experiment of two performed.
Figure 3:
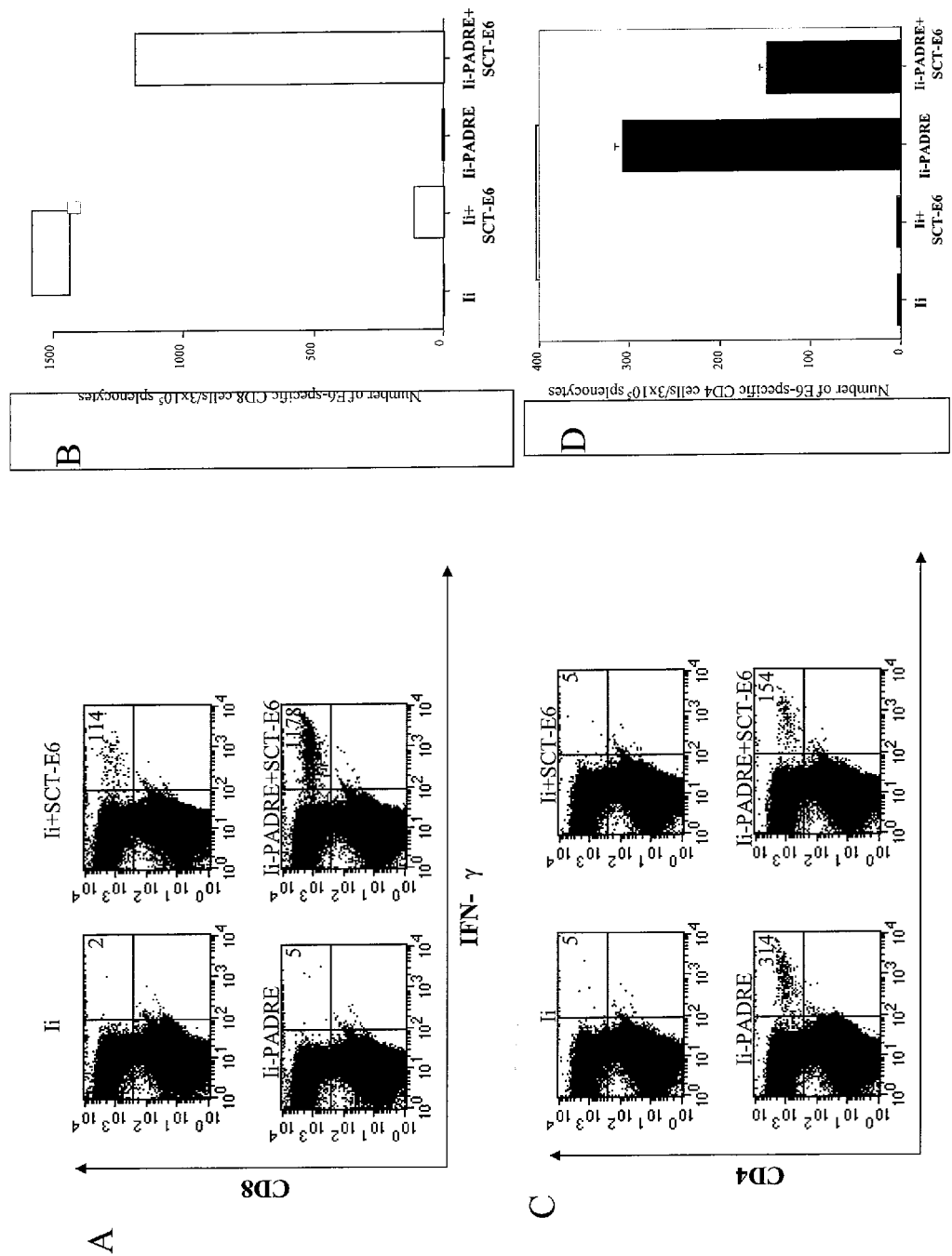
FIG. 3. Intracellular cytokine staining followed by flow cytometry analysis to determine the number of E6-specific CD8+ T cells and PADRE-specific CD4+ T cells in vaccinated mice. C57BL/6 mice (5 per group) were immunized twice intradermally via gene gun with 2 μg/mouse of Ii DNA, Ii DNA+SCT-E6 DNA, Ii-PADRE DNA or Ii-PADRE DNA+SCT-E6 DNA at one-week interval. Splenocytes from vaccinated mice were harvested 1 week after the last vaccination and stimulated with E6 or PADRE peptide. Splenocytes without peptide stimulation were used as a negative control. The splenocytes were stained for CD8 or CD4 and intracellular IFN-γ. (A) & (C) Representative figures of the flow cytometry data. The numbers on the right upper corner represent the number of E6-specific CD8+ T cells (A) or PADRE-specific CD4+ T cells (C) per $3 \times 10^5$ splenocytes acquired. (B) & (D). Bar graph depicting the numbers of E6-specific CD8+ T-cells (B) or PADRE-specific CD4+ T cells (D) per $3 \times 10^5$ splenocytes (mean±s.e.). The data presented in this figure are from one representative experiment of two performed.

We next compared the various PADRE-containing DNA vaccines for their ability to generate PADRE-specific CD4$^+$ T cells in vaccinated mice. These DNA vaccines included Sig/PADRE, Sig/PADRE/LAMP-1 and Ii-PADRE. We have previously shown that linkage of an antigen to the sorting signal of the lysosome-associated membrane protein type I (LAMP-1) can enhance presentation of the linked antigen to the MHC class II-restricted antigen-specific CD4$^+$ T cells [20]. In the current study, we created a DNA vaccine encoding a chimeric protein linking the signal peptide, PADRE antigen and LAMP-1 (Sig/PADRE/LAMP-1). In addition, we created a DNA vaccine encoding a signal peptide linked to PADRE (Sig/PADRE) for comparison. Furthermore, Ii DNA was used as a negative control. As shown in FIG. 2, vaccination with Ii-PADRE DNA generated the most potent PADRE-specific CD4$^+$ T cell immune responses in mice among all the DNA vaccines tested. Our data indicated that vaccination with Ii-PADRE DNA represents an effective approach to enhance PADRE-specific CD4$^+$ T cell immune responses in mice.

Co-Administration of Ii-PADRE DNA and SCT-E6 DNA Intradermally Via Gene Gun Generated Both E6-Specific CD8$^+$ T Cells and PADRE-Specific CD4$^+$ T Cells in Vaccinated Mice We have previously constructed a DNA vaccine encoding an SCT of β2-microglobulin, MHC class I heavy chain and immunodominant CTL epitope of HPV-16 E6 antigen (SCT-E6 DNA). C57BL/6 mice vaccinated with SCT-E6 DNA exhibited significantly increased E6 peptide-specific CD8$^+$ T cell immune responses and more potent anti-tumor effects against E6-expressing tumors compared to mice vaccinated with DNA encoding wild-type E6 [21]. Although vaccination with the SCT-E6 DNA could enhance E6-specific CD8$^+$ T cell immune responses, it could not generate antigen-specific CD4$^+$ T cell immune responses. It is now clear that CD4$^+$ T cells are important for facilitating the activation of antigen-specific CD8$^+$ T cells and generation of long-term memory T cells. Since we have shown that vaccination with the Ii-PADRE DNA could generate a significantly increased number of PADRE-specific CD4$^+$ T cells (see FIG. 9), we next explored whether co-administration of the Ii-PADRE DNA and the SCT-E6 DNA can further enhance E6-specific CD8$^+$ T cell immune responses in vaccinated mice. We immunized mice with Ii-PADRE DNA+SCT-E6 DNA or Ii DNA+SCT-E6 DNA. In addition, we vaccinated mice with Ii-PADRE DNA or Ii DNA alone as controls. Splenocytes from vaccinated mice were harvested, stimulated with either E6 or PADRE peptide and characterized for the presence of E6-specific CD8$^+$ T cells or PADRE-specific CD4$^+$ T cells by intracellular IFN-γ staining followed by flow cytometry analysis. As shown in FIGS. 3A and 3B, co-administration of Ii-PADRE DNA and SCT-E6 DNA intradermally via gene gun significantly enhanced E6-specific CD8$^+$ T cell immune responses compared to vaccination with Ii DNA+SCT-E6. Vaccination with Ii DNA or Ii-PADRE DNA alone failed to generate E6-specific CD8$^+$ T cells in immunized mice. In addition, vaccination with Ii-PADRE DNA alone or together with SCT-E6 DNA was able to generate PADRE-specific CD4$^+$ T cells in immunized mice while immunization with Ii DNA alone or in conjunction with SCT-E6 DNA failed to generate appreciable number of PADRE-specific CD4$^+$ T cells (FIGS. 3C and 3D). Thus, these data indicated that co-administration of the Ii-PADRE DNA and the SCT-E6 DNA were capable of further enhancing the generation of E6-specific CD8$^+$ T cells by SCT-E6 DNA vaccines.

Figure 4:
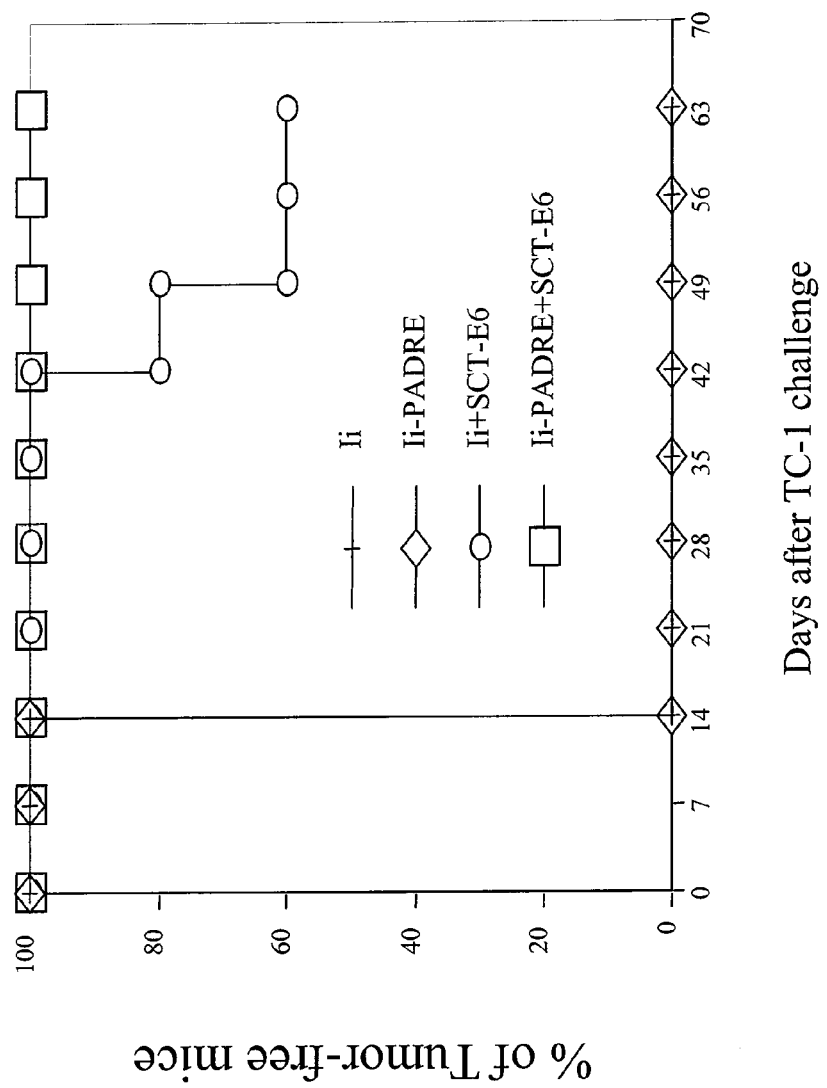
FIG. 4. In vivo tumor protection experiments. C57BL/6 mice (five per group) were immunized twice via gene gun with 2 μg/mouse of Ii DNA, Ii-PADRE DNA, Ii DNA+SCT-E6 DNA or Ii-PADRE DNA+SCT-E6 DNA at one-week interval. One week after the last vaccination, the vaccinated mice were challenged subcutaneously with $5 \times 10^4$ TC-1 cells/mouse. The mice were monitored for evidence of tumor growth by inspection and palpation twice a week. The data shown here are from one representative experiment of two performed.
Figure 5:
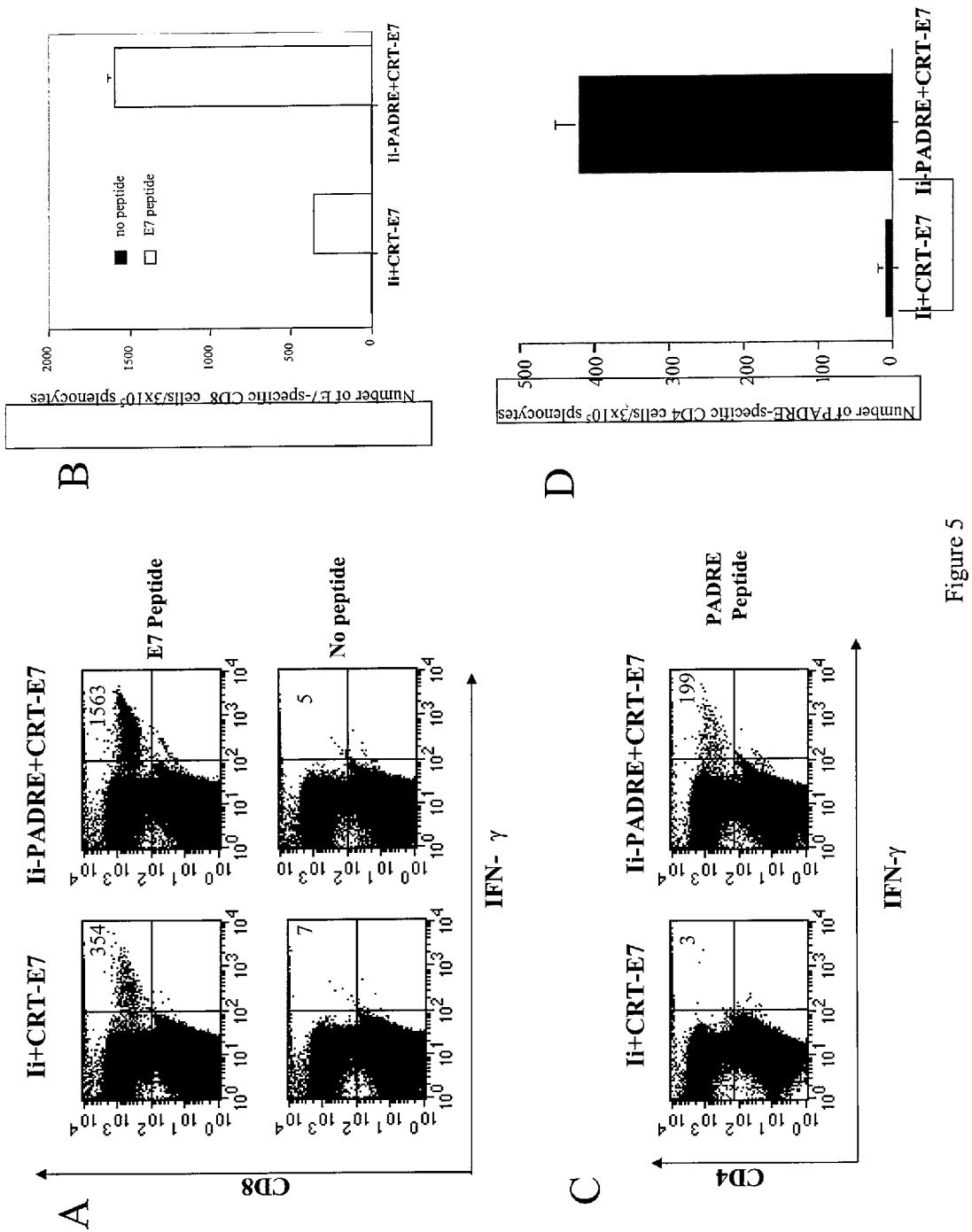
FIG. 5. Characterization of E7-specific IFN-γ-secreting CD8+ T cells and PADRE-specific CD4+ T cells by flow cytometry analysis in vaccinated mice. C57BL/6 mice (five per group) were immunized twice intradermally via gene gun with 2 μg/mouse of Ii DNA+CRT-E7 DNA or Ii-PADRE DNA+CRT-E7 DNA at one-week interval. Splenocytes from vaccinated mice were harvested 1 week after the last vaccination and stimulated with E7 peptide or PADRE peptide. Splenocytes without peptide stimulation were used as a negative control. The splenocytes were stained for both CD8 and intracellular IFN-γ. (A) & (C). Representative figures of the flow cytometry data. The numbers on the right upper corner represent the number of E7-specific IFN-γ-secreting CD8+ T cells (A) or PADRE-specific CD4+ T cells (C) per $3\times10^5$ splenocytes acquired. (B) & (D) Bar graphs depicting the number of E7-specific T-cells (B) or PADRE-specific CD4+ T cells (D) per $3\times10^5$ splenocytes (means±s.e.). The data presented in this figure are from one representative experiment of two performed.

Intradermal Vaccination with Ii-PADRE DNA in Conjunction with SCT-E6 DNA Generated the Most Potent Antitumor Effects Against an E6-Expressing TC-1 Tumor To determine whether the observed increase in the number of E6-specific CD8$^+$ T cell generated by vaccination with Ii-PADRE DNA+SCT-E6 DNA can be translated into better antitumor effects, we performed an in vivo protection experiment using a previously characterized E6-expressing tumor model, TC-1 [7]. As shown in FIG. 4, 100% of mice vaccinated with Ii-PADRE DNA+SCT-E6 DNA remained tumor-free 63 days after subcutaneous challenge with TC-1 tumor cells. In contrast, only 60% of mice vaccinated with Ii DNA+SCT-E6 DNA remained tumor-free 63 days after TC-1 tumor challenge, and all of the mice immunized with Ii DNA or Ii-PADRE DNA developed tumors within 14 days after TC-1 tumor challenge.

Figure 10:
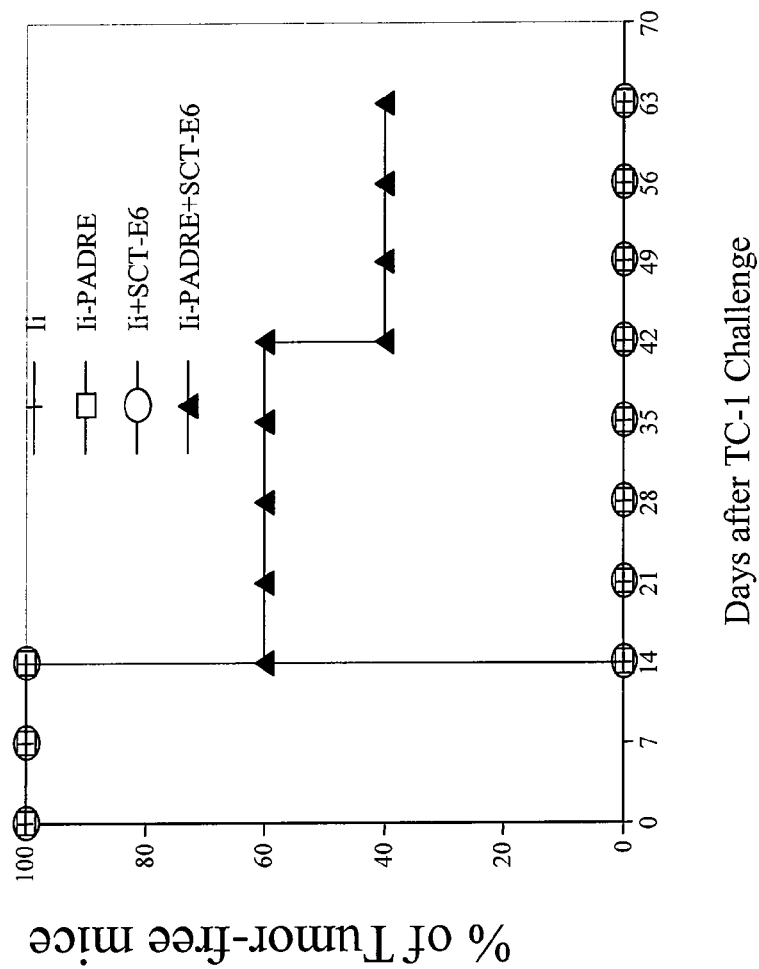
FIG. 10. In vivo tumor treatment experiments to compare the anti-tumor effects of various DNA vaccines in mice. C57BL/6 mice (5 per group) were subcutaneously challenged with $1\times10^4$ TC-1 tumor cells/mouse. Three days later, the mice were immunized twice with 2 μg/mouse of Ii DNA, Ii-PADRE DNA, Ii DNA+SCT-E6 DNA or Ii-PADRE DNA+SCT-E6 DNA at one-week interval. Data are expressed at means±s.e. The data presented in this figure are from one representative of two performed.

We further assessed the therapeutic potential of each vaccine by performing an in vivo tumor treatment experiment using a subcutaneous TC-1 tumor challenge model. Mice were challenged with TC-1 tumor cells and then treated with the various DNA vaccines three days later. While 60% of the mice treated with Ii-PADRE DNA+SCT-E6 DNA remained tumor-free 42 days after TC-1 tumor challenge, all of the mice treated with Ii DNA, Ii-PADRE DNA or Ii DNA+SCT-E6 DNA exhibited tumor growth 14 days after the tumor challenge (see FIG. 10). Taken together, these data indicated that co-administration of Ii-PADRE DNA and SCT-E6 DNA could elicit potent antitumor effects against challenge with an E6-expressing tumor cell line.

Figure 11:
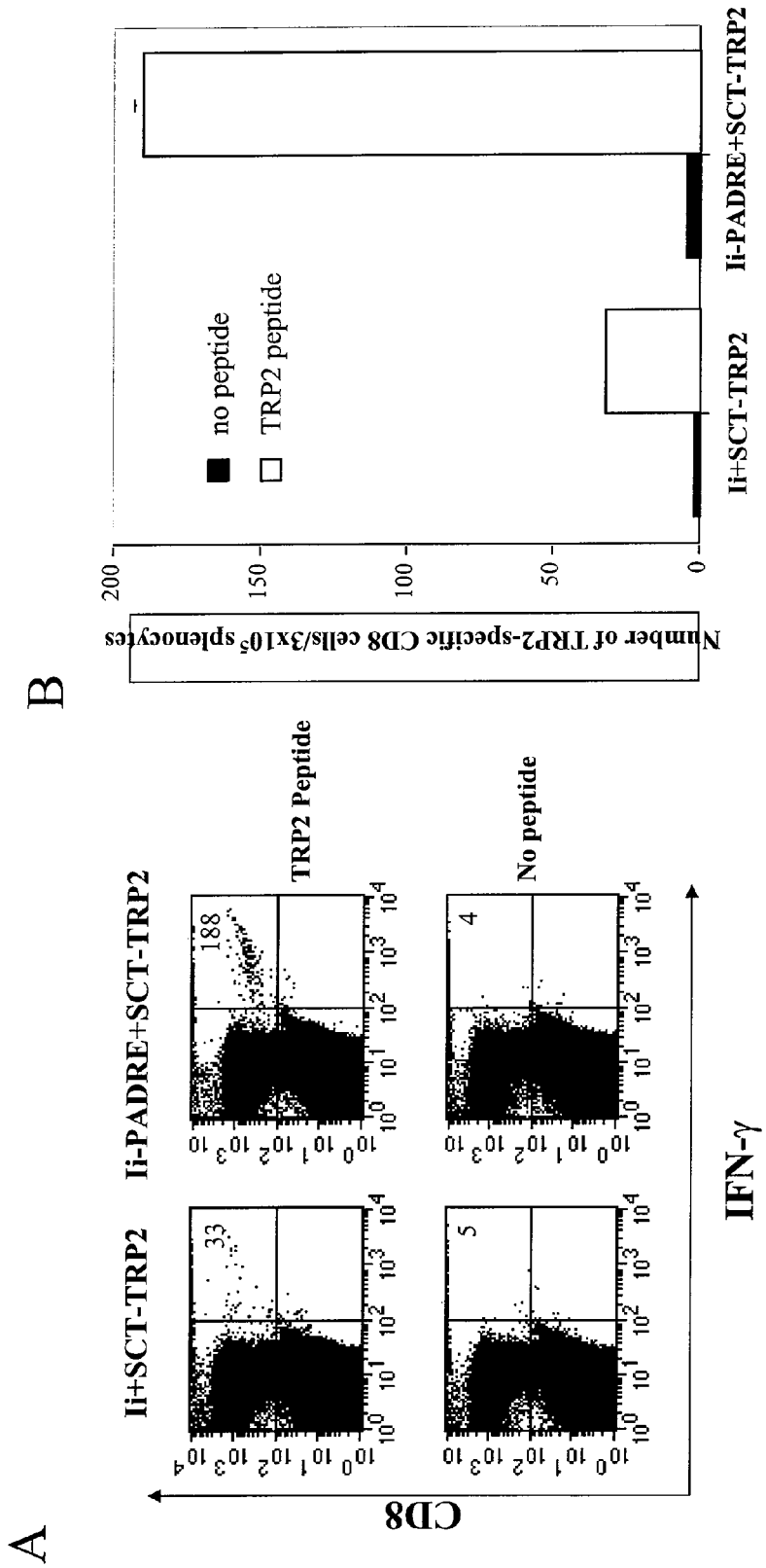
FIG. 11. Flow cytometry analysis to characterize TRP2-specific CD8+ T-cell responses in vaccinated mice. C57BL/6 mice (five per group) were immunized twice intradermally via gene gun with 2 μg/mouse of Ii DNA+SCT-TRP2 DNA or Ii-PADRE DNA+SCT-TRP2 DNA at one-week interval. Splenocytes from vaccinated mice were harvested 1 week after the last vaccination and were stimulated with TRP2 peptide. Splenocytes without peptide stimulation were used as a negative control. The splenocytes were stained for CD8 and intracellular IFN-γ. (A) Representative figure of the flow cytometry data. The numbers on the upper right corner represent the number of TRP2-specific CD8+ T cells per $3\times10^5$ splenocytes acquired. (B) Bar graph depicting the number of TRP2-specific T cells per $3\times10^5$ splenocytes (means±s.e.). The data presented in this figure are from one representative experiment of two performed.

Vaccination with Ii-PADRE DNA in Conjunction with SCT-TRP2 DNA Significantly Enhanced TRP2-Specific CD8$^+$ T Cell-Mediated Immune Responses We further explored if the Ii-PADRE DNA vaccine could enhance the generation of antigen-specific CD8$^+$ T cell immune responses in mice vaccinated with DNA vaccine employing an SCT technology targeting other tumor antigenic peptides. Tyrosine-related protein 2 (TRP2) has been shown to be a tumor-associated antigen that is highly expressed in murine melanomas such as B-16. Furthermore, the immunodominant epitope has been identified to be located at the aa181-188, VYDFFVWL (SEQ ID NO: 122). We therefore created a DNA vaccine encoding an SCT linking β2-microglobulin, MHC class I heavy chain and immunodominant CTL epitope of TRP2 antigen (SCT-TRP2). To determine if the co-administration of the Ii-PADRE DNA and SCT-TRP2 intradermally via gene gun could further enhance TRP2-specific CD8$^+$ T cell-mediated immune responses, C57BL/6 mice were vaccinated with either Ii DNA+SCT-TRP2 DNA or Ii-PADRE DNA+SCT-TRP2 DNA. We then characterized the presence of TRP2-specific CD8$^+$ T cell precursors using splenocytes from vaccinated mice by flow cytometry analysis. Co-administration of Ii-PADRE DNA and SCT-TRP2 DNA generated a significantly higher frequency of TRP2-specific CD8$^+$ T cell precursors compared to the co-administration of Ii DNA and SCT-TRP2 DNA (see FIG. 11, $P<0.01$). These data indicated that co-administration of the Ii-PADRE DNA and the SCT DNA could also enhance antigen-specific CD8$^+$ T cell immune responses in other antigenic systems.

Co-Administration of the Ii-PADRE DNA and the CRT-E7 DNA Via Gene Gun Significantly Enhanced E7-Specific CD8$^+$ T Cell-Mediated Immune Responses We have previously shown that vaccination with DNA encoding Calreticulin (CRT) linked to E7 antigen (CRT-E7) intradermally via gene gun could significantly enhance E7-specific CD8$^+$ T cells in mice compared to vaccination with wild-type E7 DNA [22]. To determine if co-administration of Ii-PADRE DNA with CRT-E7 DNA could further enhance E7-specific CD8$^+$ T cells, we vaccinated mice with Ii-PADRE DNA+CRT-E7 DNA or Ii DNA+CRT-E7 DNA. As shown in FIGS. 5A and 5B, gene gun administration of Ii-PADRE DNA+CRT-E7 DNA generated a higher number of E7-specific CD8$^+$ T cells in mice compared to vaccination with Ii DNA+CRT-E7 DNA ($P<0.01$). Vaccination with Ii-PADRE DNA+CRT-E7 DNA also generated a significantly increased number of PADRE-specific CD4$^+$ T cells in mice (FIGS. 5C and 5D). Our data indicated that antigen-specific CD8$^+$ T cells generated by DNA vaccines employing an intracellular targeting strategy could further be enhanced by co-administration with the Ii-PADRE DNA.

Figure 6:
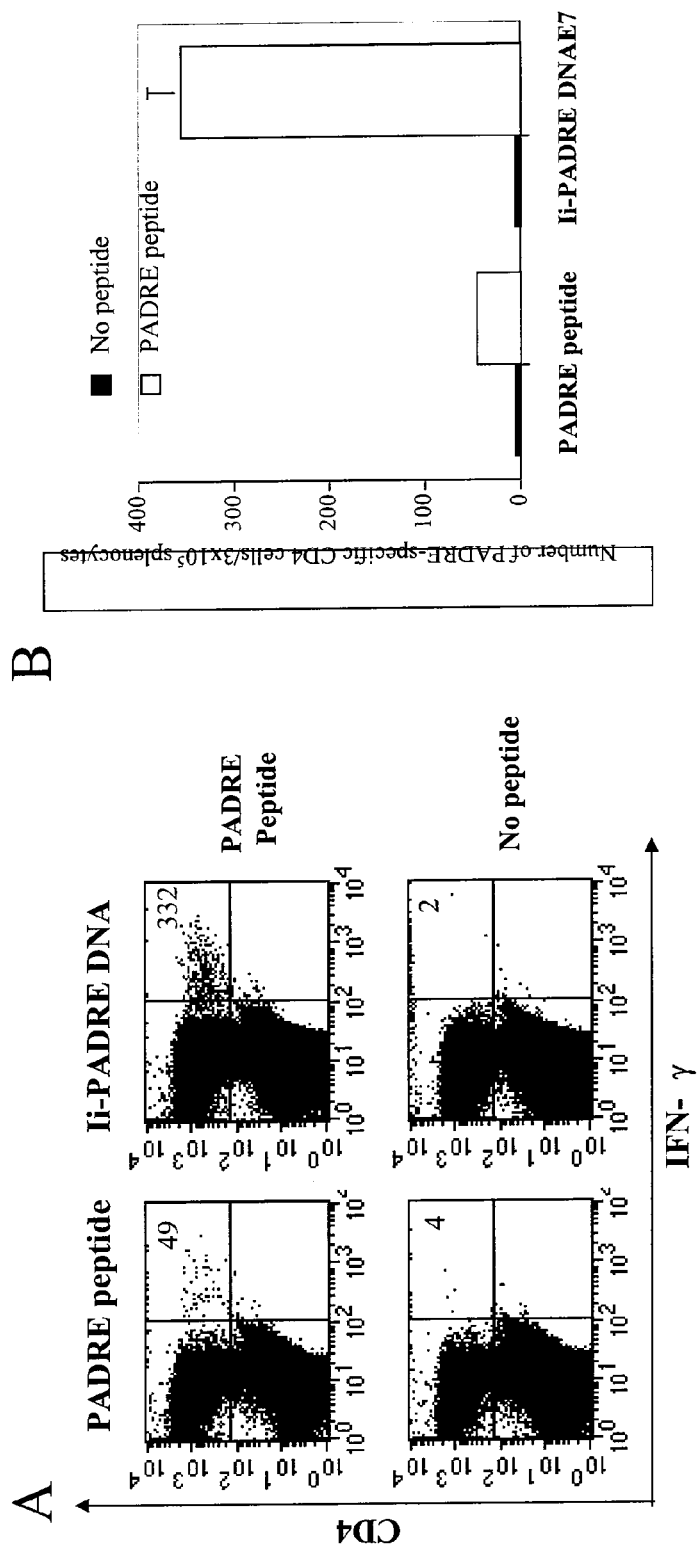
FIG. 6. Flow cytometry analysis to characterize PADRE-specific CD4+ T cells in mice vaccinated with PADRE peptide or Ii-PADRE DNA. C57BL/6 mice (five per group) were immunized twice with 100 μg/mouse of PADRE peptide subcutaneously or 2 μg/mouse of Ii-PADRE DNA intradermally at one-week interval. Splenocytes from vaccinated mice were harvested 1 week after the last vaccination and stimulated with PADRE peptide. Splenocytes without peptide stimulation were used as a negative control. The splenocytes were stained for both CD4 and intracellular IFN-γ. (A) Representative figure of the flow cytometry data. The numbers on the right upper corner represent the number of PADRE-specific CD4+ T cells per $3\times10^5$ splenocytes acquired. (B) Bar graph depicting the number of PADRE-specific CD4+ T cells per $3\times10^5$ splenocytes (means±s.e.). The data presented in this figure are from one representative experiment of two performed.
Figure 7:
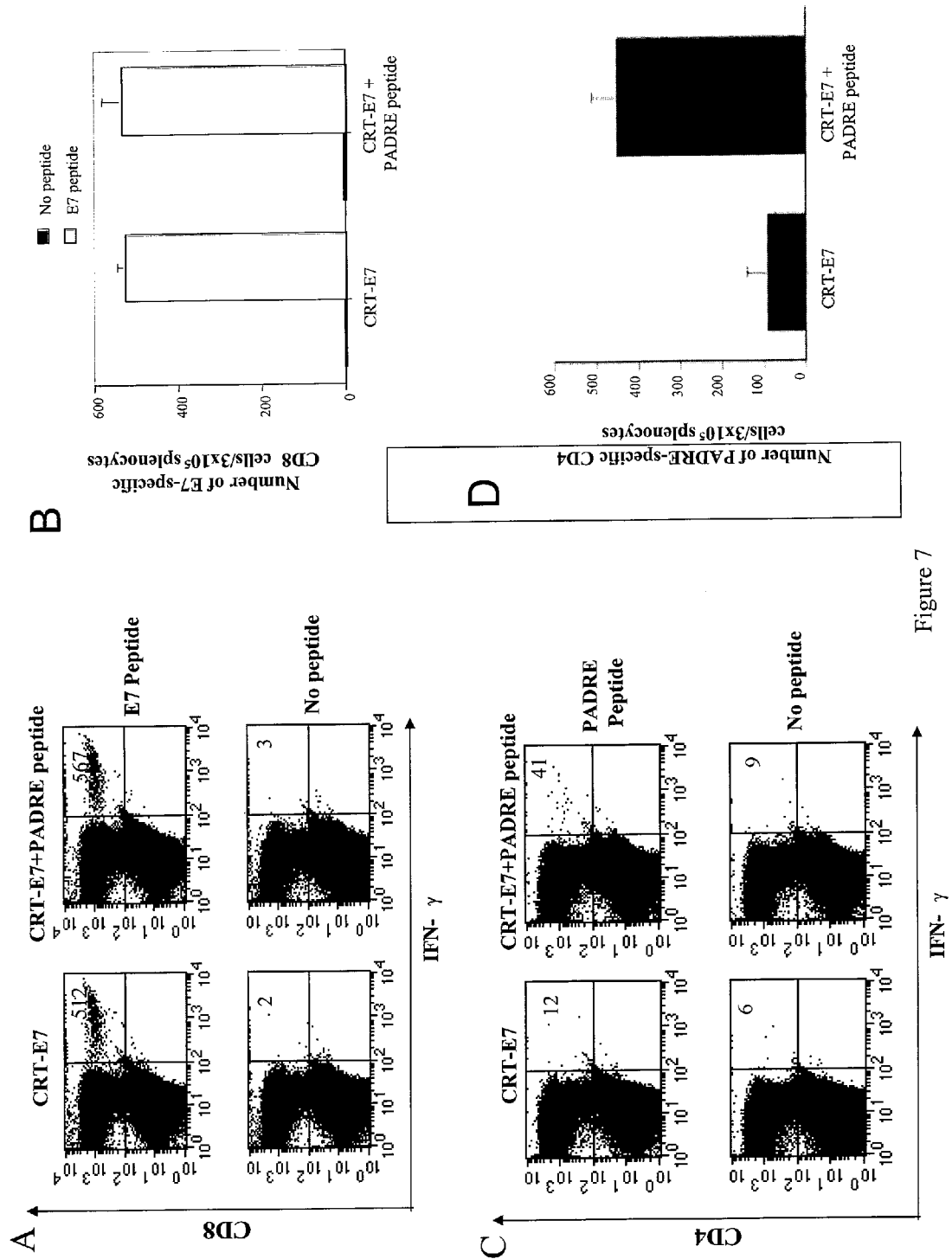
FIG. 7. Characterization of E7-specific IFN-γ-secreting CD8+ T cells and PADRE-specific CD4+ T cells in mice vaccinated with PADRE peptide and CRT-E7. C57BL/6 mice (five per group) were immunized twice with 2 μg of CRT-E7 DNA intradermally via gene gun and 100 g of PADRE in 200 μL incomplete Freund's adjuvant by subcutaneous tail base injection at one-week interval. Mice vaccinated with 2 μg CRT-E7 DNA by gene gun and 200 μL incomplete Freund's adjuvant by subcutaneous tail base injection were used as a negative control. Splenocytes were harvested 1 week after the last vaccination and stimulated with E7 peptide or PADRE peptide. Splenocytes without peptide stimulation were used as a negative control. The splenocytes were stained for both CD8 and intracellular IFN-γ. (A) & (C) Representative figures of the flow cytometry data. The numbers on the upper right corner represent the numbers of E7-specific IFN-γ-secreting CD8+ T cells (A) or PADRE-specific CD4+ T cells (C) per $3\times10^5$ splenocytes acquired. (B) & (D) Bar graphs depicting the numbers of E7-specific CD8+ T cells (B) or PADRE-specific CD4+ T cells (D) per $3\times10^5$ splenocytes (means±s.e.).

Vaccination with Ii-PADRE DNA Generates More PADRE-Specific CD4$^+$ T Cells than Vaccination with PADRE Peptide To determine if vaccination with Ii-PADRE DNA could elicit better PADRE-specific CD4$^+$ T cell immune responses in vaccinated mice than vaccination with PADRE peptide, we vaccinated C57BL/6 mice with Ii-PADRE DNA intradermally via gene gun or with PADRE peptide mixed with incomplete Freund's adjuvant subcutaneously. Splenocytes from vaccinated mice were isolated and characterized for the presence of PADRE-specific CD4$^+$ T cell precursors by intracellular cytokine staining with flow cytometry analysis. As shown in FIG. 6, vaccination with Ii-PADRE DNA generated a significantly higher number of PADRE-specific CD4$^+$ T cells than immunization with a PADRE peptide.

Co-Administration of PADRE Peptide and CRT-E7 DNA Failed to Enhance E7-Specific CD8+ T Cell Immune Responses We also assessed if the E7-specific CD8+ T cells generated by vaccination with CRT-E7 DNA intradermally can be enhanced by PADRE peptide mixed with incomplete Freund's adjuvant administered subcutaneously. As shown in FIGS. 7A and 7B, mice vaccinated with CRT-E7 DNA in conjunction with PADRE peptide (mixed with incomplete Freund's adjuvant) failed to generate a significantly higher number of E7-specific CD8+ T cells compared to mice vaccinated with CRT-E7 DNA in conjunction with incomplete Freund's adjuvant. However, the combination of CRT-E7 DNA and PADRE peptide led to an increase of PADRE-specific CD4+ T cells compared to vaccination with CRT-E7 DNA with incomplete Freund's adjuvant (FIGS. 7C and 7D).

Figure 8:
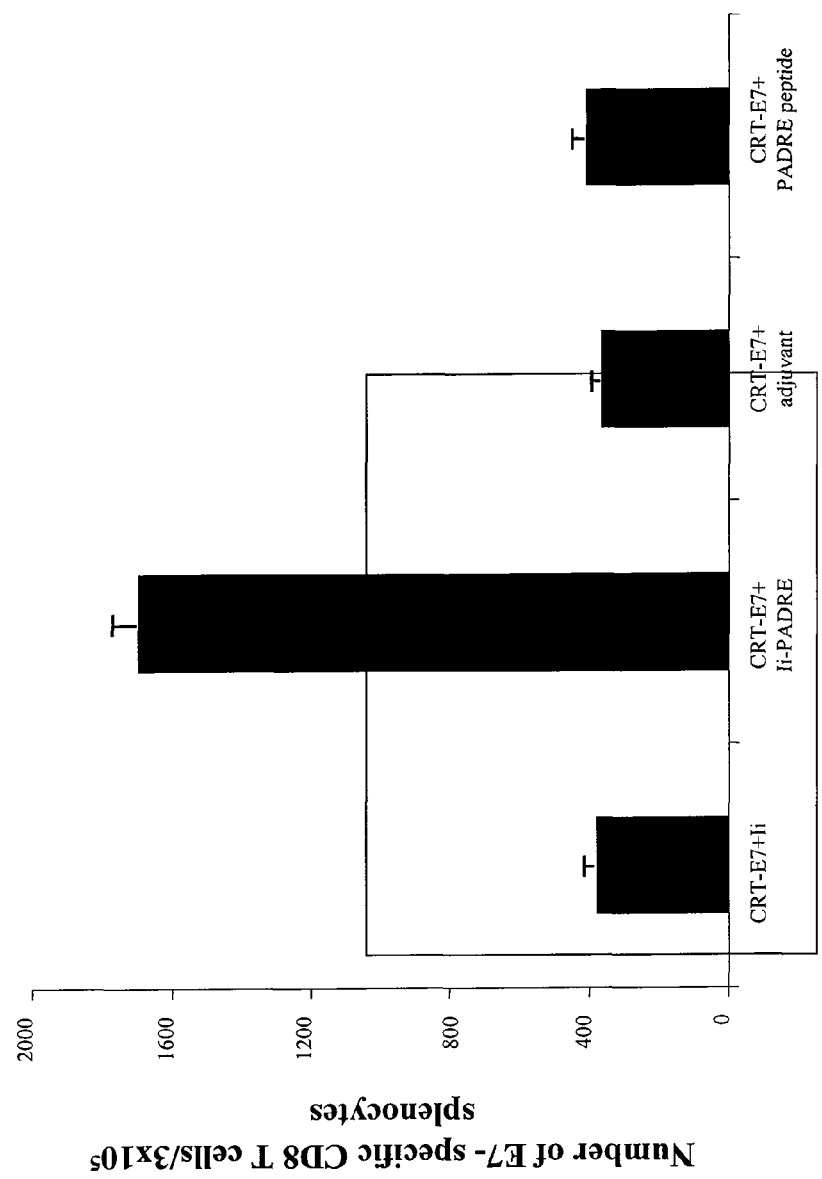
FIG. 8. Flow cytometry analysis to characterize E7-specific CD8+ T cells in vaccinated mice. C57BL/6 mice (five per group) were immunized twice with CRT-E7 DNA (i.d.)+Ii DNA (i.d.), CRT-E7 DNA (i.d.)+Ii-PADRE DNA (i.d.), CRT-E7 DNA (i.d.)+adjuvant (s.c.) or CRT-E7 DNA (i.d.)+PADRE peptide (s.c.) at one-week interval. Splenocytes were harvested 1 week after the last vaccination and stimulated with E7 peptide. The splenocytes were stained for both CD8 and intracellular IFN-γ. Bar graph depicting the number of E7-specific CD8+ T cells/$3\times10^5$ splenocytes (means±s.e.).
Figure 9:
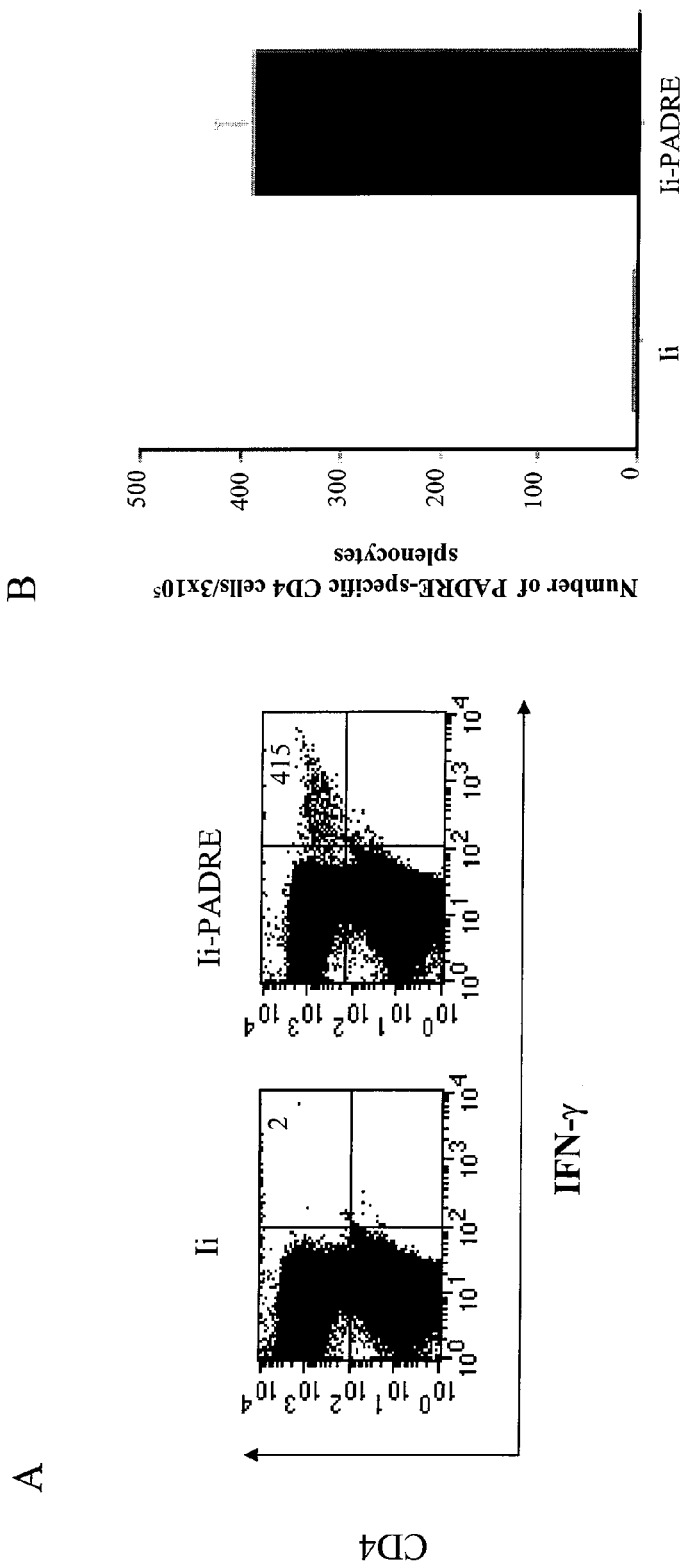
FIG. 9. Intracellular cytokine staining with flow cytometry analysis to determine the number of PADRE-specific CD4+ T cells in mice vaccinated with various DNA constructs. C57BL/6 mice (five per group) were immunized intradermally via gene gun with 2 μg/mouse of Ii DNA, Sig/PADRE DNA, Sig/PADRE/LAMP-1 DNA or Ii-PADRE DNA at one-week intervals. The vaccinated mice received a booster with the same dose and regimen one week later. Splenocytes from vaccinated mice were harvested 1 week after the last vaccination and stimulated with PADRE peptide. Splenocytes without peptide stimulation were used as a negative control. The splenocytes were stained for both CD4 and intracellular IFN-γ. (A) Representative figure of the flow cytometry data. The numbers on the upper right corner represent the number of PADRE-specific IFN-γ-secreting CD4+ T cells per $3\times10^5$ splenocytes acquired. (B) Bar graph demonstrating the number of PADRE-specific CD4+ T cells per $3\times10^5$ splenocytes (means±s.e.). The data presented in this figure are from one representative experiment of two performed.

Co-Administration of Ii-PADRE DNA with DNA Vaccines is More Effective in Enhancing Antigen-Specific CD8+ T Cells Compared to Co-Administration of PADRE Peptide We next determined whether C57BL/6 mice vaccinated with CRT-E7 DNA+Ii-PADRE DNA could generate better E7-specific CD8+ T cell immune responses than mice immunized with CRT-E7 DNA+PADRE peptide. The mice were immunized twice with CRT-E7 DNA (i.d.)+Ii DNA (i.d.), CRT-E7 DNA (i.d.)+Ii-PADRE DNA (i.d.), CRT-E7 DNA (i.d.)+adjuvant (s.c.) or CRT-E7 DNA (i.d.)+PADRE peptide (s.c.) at one-week interval. Splenocytes from immunized mice were harvested 1 week after the last vaccination and stimulated with E7 peptide. The splenocytes were characterized for the presence of E7-specific CD8+ T cells using intracellular staining for IFN-γ and staining for CD8 followed by flow cytometry analysis. As shown in FIG. 8, mice vaccinated with CRT-E7 DNA+Ii-PADRE DNA generated a significantly higher number of E7-specific CD8+ T cells than mice immunized with CRT-E7 DNA+PADRE peptide. CRT-E7 DNA co-administered with PADRE peptide generated similar levels of E7-specific CD8+ T cells compared to co-administration with adjuvant alone or DNA encoding Ii chain. These data indicated that DNA vaccines in conjunction with Ii-PADRE DNA is more effective in enhancing antigen-specific CD8+ T cells compared to combination with PADRE peptide.

Discussion

Our study demonstrated that vaccination with the Ii-PADRE DNA could increase the number of PADRE-specific CD4+ T cells in immunized mice. In addition, DNA vaccines co-administered with Ii-PADRE DNA led to an increase in the number of antigen-specific CD8+ T cells, resulting in potent protective and therapeutic anti-tumor effects. Furthermore, we showed that this strategy to enhance CD4+ T cell immune responses by Ii-PADRE DNA not only applied to other antigenic systems, but could also be used to enhance DNA vaccine potency when employed in conjunction with other DNA vaccination strategies such as intracellular targeting strategy.

In the current study, we observed that DNA vaccines co-administered with Ii-PADRE DNA led to the generation of PADRE-specific CD4+ T cells, resulting in the enhancement of antigen-specific CD8+ T cell immune responses. Several models have been proposed to illustrate the roles of CD4+ T cells in facilitating the generation of antigen-specific CD8+ T cell immune responses. In the "Three Cell Interaction" model, APCs deliver costimulatory signals to the CD4+ Th cells, which in turn generate IL-2. This IL-2 production is necessary for CTL activation [23-25]. On the other hand, the "Sequential Two-Cell Interactions" model proposes that the engagement of CD4+ T cells to APCs lead to the maturation of APCs, which subsequently activate CD8+ T cells [25-27]. A recently proposed model suggests that APCs can directly transfer MHC class I-Ag complexes and costimulatory molecules to expanding populations of IL-2-producing T helper cells, which then function as APCs to directly stimulate CTL activation [25]. More recently, dendritic cell-CD4 T cell interaction has been shown to lead to the production of CCL3 and CCL4 chemokines (also known as MIP-1alpha and MIP-1beta). These chemokines may be important for attracting antigen-specific CD8+ T cells to the antigen-expressing dendritic cells [28]. All these models suggest that CD4+ T helper cells are important for the activation and proliferation of CD8+ T cells.

One concern was raised that the PADRE epitope might activate CD4+ CD25+ T regulatory cells. In a study done by Phan, et al., it was found that in patients with metastatic melanoma that were immunized with an MHC class II-restricted peptide in addition to MHC class I-restricted peptides, the immunologic response of circulating PBMC to a class I-restricted peptide was diminished [29]. Their results raised the possibility that class II-restricted peptides may activate CD4+ CD25+ T regulatory cells. To rule out that possibility, we examined the PADRE-specific CD4+ T cells generated by intradermal vaccination with DNA encoding Ii-PADRE for their expression of FoxP3, a marker for CD4+ CD25+ T regulatory cells. We found that the PADRE-specific CD4+ T cells did not express FoxP3 (data not shown). Furthermore, we have observed that co-administration of Ii-PADRE DNA with the DNA vaccine led to significant enhancement rather than suppression of the antigen-specific CD8+ T cells. The discrepancy of the observed results compared to previous reports may be due to the form of the PADRE-related vaccine or the antigen used in the study. Thus, these results indicate that the PADRE epitope in the context of the Ii-PADRE DNA vaccine does not activate CD4+ CD25+ T regulatory cells.

The success of Ii-PADRE DNA in enhancing antigen-specific CD8+ T cell immune responses warrants further exploration of innovative strategies that are capable of generating CD4+ T cell immune responses to enhance CD8+ T cell immune responses. One potential strategy is to generate a single chain MHC class II molecule linking a CD4+ T helper epitope. For instance, Thayer et al described the design of a single chain I-$A^b$:antigenic peptide complex, with a linker that connects α chain, β chain and, peptide. The chimeric molecule was used to stabilize antigenic peptide in the peptide binding groove of MHC class II molecule [18]. Cells transfected with DNA encoding such chimeric molecule have been shown to stimulate an IL-2 response from an antigen-specific T cell hybridoma [18]. Thus, it will be of interest to generate a DNA construct encoding a similar chimeric molecule that targets PADRE and to explore if such DNA vaccine can lead to the activation of PADRE-specific CD4+ T cells in immunized mice.

Materials and Methods

Mice: C57BL/6 mice (6 to 8 weeks old) were purchased from the National Cancer Institute (Frederick, Md.). All animals were maintained under specific pathogen-free conditions at the Johns Hopkins Hospital (Baltimore, Md.). All procedures were performed according to approved protocols and in accordance with recommendations for the proper care of laboratory animals.

Cells: Briefly, TC-1 cells were obtained by co-transformation of primary C57BL/6 mouse lung epithelial cells with HPV-16 E6 and E7 and an activated ras oncogene as described previously [7]. The expression of E6 in TC-1 cells has also been characterized previously by He et al [30].

DNA Constructs

A DNA vaccine encoding an SCT composed of an immunodominant CTL epitope of HPV-16 E6, β2-microglobulin, and H-2K$^b$ heavy chain (SCT-E6) was previously described [21]. A DNA vaccine encoding an SCT composed of an CTL epitope aa 181-188 (VYDFFVWL (SEQ ID NO: 122)) of TRP2, β2-microglobulin, and H-2K$^b$ heavy chain (SCT-TRP2) [31] was constructed. Briefly, an insert containing the immunodominant TRP2 aa 181-188 epitope and flanking AgeI/NheI restriction enzyme sites was made by annealing two single-stranded oligo-nucleotides (5'-CCGGTTTGTAT-GCTGTGTATGACTTTTTTGTGTGGCTCG-GAGGAGGTG-3' (SEQ ID NO: 123) and 5'-CTAGCAC-CTCCTCCGAGCCACACAAAAAAGTCATACACAGCA TACAAA-3' (SEQ ID NO: 124)). It was then cloned into pIRES-OVA-K$^b$ [21] using AgeI/NheI sites to replace the OVA epitope, generating pIRES-E6-β2m-K$^b$.

A DNA vaccine encoding an Ii-chain was constructed by RT-PCR amplification using RNA isolated from dendritic cells and primers (5'aaagaattcatggatgaccaacgcgacctc3' (SEQ ID NO: 125) and 5'aaaggatcctcacagggtgacttgacccag3' (SEQ ID NO: 126)). The RT-PCR product was cloned into the EcoRI/BamHI sites of pcDNA3.1(−) to generate pcDNA3-Ii. For the generation of pcDNA3-Ii-PADRE (Ii-PADRE DNA), we first generated Ii-PADRE DNA fragment in which the CLIP epitope in the Ii chain was replaced by PADRE epitope. Briefly, the DNA fragments encoding Ii chain 1-80 amino acids and PADRE epitope were amplified by PCR with a set of primers (5'aaagaattcatggatgaccaacgcgacctc3' (SEQ ID NO: 125) and 5' tccaggcagccacgaacttggcaagct-tcatgcgaaggctct3' (SEQ ID NO: 127)). The DNA fragment encoding the PADRE epitope and Ii chain 103-279 amino acids were amplified by PCR with a set of primers (5'aaag-gatcctcacagggtgacttgacccag3' (SEQ ID NO: 126), 5'ctggac-cctgaaggctgccgctatggataacatgctccttgg3' (SEQ ID NO: 128), and 5'gccaagttcgtggctgcctggaccctgaaggctgccgct3' (SEQ ID NO: 129)). The overlapping PCR fragments were then used as template to create Ii-PADRE using PCR with a set of primers (5'aaagaattcatggatgaccaacgcgacctc3' (SEQ ID NO: 125) and 5'aaaggatcctcacagggtgacttgacccag3' (SEQ ID NO: 126)). The DNA fragment encoding Ii-PADRE was further cloned into EcoRI/BamHI of pcDNA3.1(−) vector to generate pcDNS3-Ii-PADRE. To generate pcDNA3-sig, a signal peptide of LAMP-1 was PCR amplified by using template pcDNA3-sigE7L1 and a set of primers (5'AAATCTAGAATGGCGGC-CCCCGGCGCCCG3' (SEQ ID NO: 130) AND 5'GGG-GAATTCTAGATCCTCAAAGAGTGCTG3' (SEQ ID NO: 131)) and cloned into the XbaI/EcoRI sites of pcDNA3.1(−). To generate pcDNA3-sigPADRE, a set of oligos encoding PADRE (5'AATTCGCCAAGTTCGTGGCTGCCTGGAC-CCTGAAGGCTGCCGCTTGAA3' (SEQ ID NO: 132) and 5'AGCTTTCAAGCGGCAGCCTTCAGGGTC-CAGGCAGCCACGAACTTGGCG3' (SEQ ID NO: 133)) was cloned into EcoRI/HindIII sites of pcDNA3-sig. To generate pcDNA3/sig/PADRE/LAMP-1, PADRE-LAMP-1 fragment was amplified by using pcDNA3/sigE7L1 as a template and a set of primers (5'AAAGAATTCGCCAAGT-TCGTGGCTGCCTGGACCCTGAAGGCTGC-CGCTCTTAACAACAT GTTGATCCCC3' (SEQ ID NO: 134) and 5' TTTGGATCCCTAGATGGTCTGATAGC-CGG3' (SEQ ID NO: 135)) and cloned into EcoRI/BamHI sites of pcDNA3/sig.

DNA Vaccination by Gene Gun

DNA-coated gold particles were prepared, and gene gun particle-mediated DNA vaccination was performed, according to a protocol described previously [32]. Gold particles coated with DNA vaccines were delivered to the shaved abdominal regions of mice by using a helium-driven gene gun (Bio-Rad Laboratories Inc., Hercules, Calif.) with a discharge pressure of 400 lb/in2. Mice were immunized with 2 µg of the DNA vaccine and received one boost with the same dose at 1-week interval. Splenocytes were harvested 1 week after the last vaccination.

Peptide Vaccination

Mice were immunized twice with 100 µg of the peptide emulsified in 200 µL incomplete Freund's adjuvant (IFA) by subcutaneous injection at the base of their tails at one-week intervals.

Intracellular Cytokine Staining and Flow Cytometry Analysis

Pooled splenocytes from the vaccinated mice were harvested 1 week after the last vaccination and incubated overnight with 1 µg/ml E6 peptide (aa50-57) or PADRE peptide (AKFVAAWTLKAAA) (SEQ ID NO: 93) in the presence of GolgiPlug (BD Pharmingen, San Diego, Calif., USA) (1 µl/ml). The stimulated splenocytes were then washed once with FACScan buffer and stained with phycoerythrin-conjugated monoclonal rat anti-mouse CD8a (clone 53.6.7). Cells were subjected to intracellular cytokine staining using the Cytofix/Cytoperm kit according to the manufacturer's instruction (BD Pharmingen, San Diego, Calif., USA). Intracellular IFN-γ was stained with FITC-conjugated rat anti-mouse IFN-γ. All antibodies were purchased from BD Pharmingen. Flow cytometry analysis was performed using FACSCalibur with CELLQuest software (BD Biosciences, Mountain View, Calif., USA).

In Vivo Tumor Protection Experiment

For in vivo tumor protection experiment, C57BL/6 mice (five per group) were immunized via gene gun with 1 µg pcDNA3+1 µg pcDNA3-Ii (Ii DNA), 1 µg of pcDNA3+1 µg of pcDNA3-Ii-PADRE (Ii-PADRE DNA), 1 µg pcDNA3-Ii+SCT-E6 (Ii DNA+SCT-E6 DNA), or 1 µg pcDNA3-Ii-PA-DRE+SCT-E6 (Ii-PADRE DNA+SCT-E6 DNA). Mice were boosted once using the dose and vaccination regimen. One week after the last vaccination, mice were challenged with 5×10$^4$ TC-1 tumor cells/mouse subcutaneously in the right leg and monitored twice a week by inspection and palpation.

In Vivo Tumor Treatment Experiment

For in vivo tumor treatment experiment, 1×10$^4$ TC-1 tumor cells were injected into 5-8 week-old C57BL/6 mice (five per group) subcutaneously in the right leg. After 3 days, the mice were immunized with the DNA vaccines as described above. After 1 week, these mice were boosted once with the same immunization regimen. Mice were monitored once a week by inspection and palpation.

Statistical Analysis

All data expressed as means±s.e. are representative of at least two different experiments. Data for intracellular cytokine staining with flow cytometry analysis were evaluated by ANOVA. Comparisons between individual data points were made using a Student's t-test. For statistical analysis of the tumor protection experiment, we used Kaplan-Meier analysis.

REFERENCES

1. Condon, C., Watkins, S. C., Celluzzi, C. M., Thompson, K., and Falo, L. D., Jr. (1996). DNA-based immunization by in vivo transfection of dendritic cells. *Nat. Med.* 2: 1122-1128.
2. Porgador, A., Irvine, K. R., Iwasaki, A., Barber, B. H., Restifo, N. P., and Germain, R. N. (1998). Predominant role for directly transfected dendritic cells in antigen presentation to CD8+ T cells after gene gun immunization. *J. Exp. Med.* 188: 1075-1082.

3. Hung, C. F., and Wu, T. C. (2003). Improving DNA vaccine potency via modification of professional antigen presenting cells. *Curr. Opin. Mol. Ther.* 5: 20-24.
4. Castellino, F., and Germain, R. N. (2006). Cooperation between CD4+ and CD8+ T cells: when, where, and how. *Ann. Rev. Immunol.* 24: 519-540.
5. Hung, K., Hayashi, R., Lafond-Walker, A., Lowenstein, C., Pardoll, D., and Levitsky, H. (1998). The central role of CD4(+) T cells in the antitumor immune response. *J. Exp. Med.* 188: 2357-2368.
6. Marzo, A. L., Kinnear, B. F., Lake, R. A., Frelinger, J. J., Collins, E. J., Robinson, B. W., et al. (2000). Tumor-specific CD4+ T cells have a major "post-licensing" role in CTL mediated anti-tumor immunity. *J. Immunol.* 165: 6047-6055.
7. Lin, K.-Y., Guarnieri, F. G., Staveley-O'Carroll, K. F., Levitsky, H. I., August, T., Pardoll, D. M., et al. (1996). Treatment of established tumors with a novel vaccine that enhances major histocompatibility class II presentation of tumor antigen. *Cancer Research* 56: 21-26.
8. Yewdell, J. W., and Bennink, J. R. (1990). The binary logic of antigen processing and presentation to T cells. [Review]. *Cell* 62: 203-206.
9. Neefjes, J. J., Stollorz, V., Peters, P. J., Geuze, H. J., and Ploegh, H. L. (1990). The biosynthetic pathway of MHC class II but not class 1 molecules intersects the endocytic route. *Cell* 61: 171-183.
10. Blum, J. S., and Cresswell, P. (1988). Role for intracellular proteases in the processing and transport of class II HLA antigens. *Proc. Natl. Acad. Sci. USA* 85: 3975-3979.
11. Fujii, S., Senju, S., Chen, Y. Z., Ando, M., Matsushita, S., and Nishimura, Y. (1998). The CLIP-substituted invariant chain efficiently targets an antigenic peptide to HLA class II pathway in L cells. *Hum. Immunol.* 59: 607-614.
12. Malcherek, G., Wirblich, C., Willcox, N., Rammensee, H. G., Trowsdale, J., and Melms, A. (1998). MHC class II-associated invariant chain peptide replacement by T cell epitopes: engineered invariant chain as a vehicle for directed and enhanced MHC class II antigen processing and presentation. *Eur. J. Immunol.* 28: 1524-1533.
13. van Bergen, J., Schoenberger, S. P., Verreck, F., Amons, R., Offringa, R., and Koning, F. (1997). Efficient loading of HLA-DR with a T helper epitope by genetic exchange of CLIP. *Proc Natl. Acad. Sci. USA* 94: 7499-7502.
14. van Tienhoven, E. A., ten Brink, C. T., van Bergen, J., Koning, F., van Eden, W., and Broeren, C. P. (2001). Induction of antigen specific CD4+ T cell responses by invariant chain based DNA vaccines. *Vaccine* 19: 1515-1519.
15. van Bergen, J., Camps, M., Offringa, R., Melief, C. J., Ossendorp, F., and Koning, F. (2000). Superior tumor protection induced by a cellular vaccine carrying a tumor-specific T helper epitope by genetic exchange of the class II-associated invariant chain peptide. *Cancer Res.* 60: 6427-6433.
16. Nagata, T., Higashi, T., Aoshi, T., Suzuki, M., Uchijima, M., and Koide, Y. (2001). Immunization with plasmid DNA encoding MHC class II binding peptide/CLIP-replaced invariant chain (Ii) induces specific helper T cells in vivo: the assessment of Ii p31 and p41 isoforms as vehicles for immunization. *Vaccine* 20: 105-114.
17. Nagata, T., Aoshi, T., Suzuki, M., Uchijima, M., Kim, Y.-H., Yang, Z., et al. (2002). Induction of Protective Immunity to *Listeria monocytogenes* by Immunization with Plasmid DNA Expressing a Helper T-cell Epitope That Replaces the Class II-Associated Invariant Chain Peptide of the Invariant Chain. *Infection and Immunity* 70: 2676-2680.
18. Thayer, W. P., Dao, C. T., Ignatowicz, L., and Jensen, P. E. (2003). A novel single chain I-A(b) molecule can stimulate and stain antigen-specific T cells. *Mol. Immunol.* 39: 861-870.
19. Alexander, J., Sidney, J., Southwood, S., Ruppert, J., Oseroff, C., Maewal, A., et al. (1994). Development of high potency universal DR-restricted helper epitopes by modification of high affinity DR-blocking peptides. *Immunity* 1: 751-761.
20. Wu, T.-C., Guarnieri, F. G., Staveley-O'Carroll, K. F., Viscidi, R. P., Levitsky, H. I., Hedrick, L., et al. (1995). Engineering an intracellular pathway for MHC class II presentation of HPV-16 E7. *Proc. Natl. Acad. Sci.* 92: 11671-11675.
21. Huang, C. H., Peng, S., He, L., Tsai, Y. C., Boyd, D. A., Hansen, T. H., et al. (2005). Cancer immunotherapy using a DNA vaccine encoding a single-chain trimer of MHC class I linked to an HPV-16 E6 immunodominant CTL epitope. *Gene Ther.* 12: 1180-1186.
22. Cheng, W. F., Hung, C. F., Chai, C. Y., Hsu, K. F., He, L., Ling, M., et al. (2001). Tumor-specific immunity and anti-angiogenesis generated by a DNA vaccine encoding calreticulin linked to a tumor antigen. *J. Clin. Invest.* 108: 669-678.
23. Mitchison, N. A., and O'Malley, C. (1987). Three-cell-type clusters of T cells with antigen-presenting cells best explain the epitope linkage and noncognate requirements of the in vivo cytolytic response. *Eur. J. Immunol.* 17: 1579-1583.
24. Bennett, S. R., Carbone, F. R., Karamalis, F., Miller, J. F., and Heath, W. R. (1997). Induction of a CD8+ cytotoxic T lymphocyte response by cross-priming requires cognate CD4+ T cell help. *J. Exp. Med.* 186: 65-70.
25. Xiang, J., Huang, H., and Liu, Y. (2005). A new dynamic model of CD8+ T effector cell responses via CD4+ T helper-antigen-presenting cells. *J. Immunol.* 174: 7497-7505.
26. Bousso, P., and Robey, E. (2003). Dynamics of CD8+ T cell priming by dendritic cells in intact lymph nodes. *Nat. Immunol.* 4: 579-585.
27. Bevan, M. J. (2004). Helping the CD8(+) T-cell response. *Nat. Rev. Immunol.* 4: 595-602.
28. Castellino, F., Huang, A. Y., Altan-Bonnet, G., Stoll, S., Scheinecker, C., and Germain, R. N. (2006). Chemokines enhance immunity by guiding naive CD8+ T cells to sites of CD4+ T cell-dendritic cell interaction. *Nature* 440: 890-895.
29. Phan, G. Q., Touloukian, C. E., Yang, J. C., Restifo, N. P., Sherry, R. M., Hwu, P., et al. (2003). Immunization of patients with metastatic melanoma using both class I- and class II-restricted peptides from melanoma-associated antigens. *J Immunother.* 26: 349-356.
30. He, Z., Wlazlo, A. P., Kowalczyk, D. W., Cheng, J., Xiang, Z. Q., Giles-Davis, W., et al. (2000). Viral recombinant vaccines to the E6 and E7 antigens of HPV-16. *Virology* 270: 146-161.
31. Bloom, M. B., Perry-Lalley, D., Robbins, P. F., Li, Y., el-Gamil, M., Rosenberg, S. A., et al. (1997). Identification of tyrosinase-related protein 2 as a tumor rejection antigen for the B16 melanoma. *J Exp Med* 185: 453-459.
32. Chen, C.-H., Wang, T.-L., Hung, C.-F., Yang, Y., Young, R. A., Pardoll, D. M., et al. (2000). Enhancement of DNA vaccine potency by linkage of antigen gene to an HSP70 gene. *Cancer Research* 60: 1035-1042.

Example 2

Role of IL-2 Secreted by PADRE-Specific CD4⁺ T Cells in Enhancing E7-Specific CD8⁺ T Cell Immune Responses Abstract:

CD4⁺ T helper cells are known to play an integral role in the generation of CD8⁺ T cell immune responses. We have previously shown that co-administration of DNA vaccines containing E6 or E7 protein of Human Papillomavirus 16 (HPV-16) combined with DNA encoding Invariant chain in which CLIP (class II-associated invariant peptide) region is replaced with the CD4⁺ T helper epitope, PADRE (Pan-DR-epitope) (Ii-PADRE DNA) enhanced HPV antigen-specific CD8⁺ T cell immune responses in vaccinated mice. In the current study, we investigated the enhancement of HPV E7-specific CD8⁺ T cell immune responses by PADRE-specific CD4⁺ T cells. We showed that intradermal administration of Ii-PADRE DNA at the same location as E7-expressing DNA is necessary to generate strong E7-specific CD8⁺ T cell immune responses. We also showed that PADRE-specific CD4⁺ T cells generated by Ii-PADRE DNA vaccination expressed Th1 cytokine profile. Furthermore, our in vitro study demonstrated that PADRE-specific CD4⁺ T cells stimulated with PADRE-loaded DCs secrete IL-2 that leads to the proliferation of E7-specific CD8⁺ T cells. Thus, our data suggest that activated PADRE-specific CD4⁺ T helper cells may be required at the vicinity of E7-specific CD8⁺ T cells where they secrete IL-2, which enhances the E7-specific CD8⁺ T cell immune responses generated by DNA vaccination.

Introduction:

DNA vaccines have become an attractive and potentially effective approach for antigen-specific immunotherapy. Naked DNA has numerous advantages including safety, stability, simplicity in production and the ability to generate sustain levels of antigen expression in cells (for a review, see [1,2]). Furthermore, multiple kinds of DNA vaccines can be repeatedly administered without the concerns associated with viral vectors. In addition, DNA can be efficiently delivered into DCs via intradermal administration using a gene gun. These DNA-expressing DCs mature and migrate to the draining lymph nodes, where they prime CD4⁺ and CD8⁺ T cells in vivo.[3,4] However, DNA vaccines suffer from the drawback of low immunogenicity. The potency of DNA vaccines may be enhanced by using strategies to modify the properties of DCs in order to boost vaccine-elicited immune responses (For review, see [5,6]).

CD4⁺ T helper cells have been shown to play an important role in the priming of CD8⁺ T effector and the generation of memory T cell populations (For review, see 7). Furthermore, CD4⁺ T cells can interact with macrophages and NK cells to enhance tumor destruction at tumor sites.[8,9] Thus, it is desirable to generate antigen-specific CD4⁺ T cells in addition to antigen-specific CD8⁺ T cells in vaccination strategies.

In our previous study, we successfully generated antigen-specific CD4⁺ T cell immune responses in mice by employing a DNA vaccine encoding the Invariant chain molecule, an essential component of the MHC class II-mediated antigen presentation process.[10] In the endoplasmic reticulum, MHC class II molecules assemble and bind with the Ii chain. The class II-associated Ii peptide (CLIP) region of the Ii chain occupies the MHC class II peptide-binding grove. The Ii chain is then degraded until only the CLIP region remains. This region prevents premature binding of the antigenic peptide into the MHC class II peptide-binding groove. CLIP is later replaced in the lysosome by one of the antigenic peptides. We have employed a DNA vaccine encoding the Ii chain in which the CLIP region is replaced with a CD4⁺ T helper epitope, PADRE (Pan-DR-epitope) (Ii-PADRE DNA). Vaccination of mice with the Ii-PADRE DNA increased the number of PADRE-specific CD4⁺ T cells in the immunized C57BL/6 mice. In addition, co-administration of Ii-PADRE DNA and DNA vaccines containing either the E6 or E7 protein of Human Papillomavirus Type 16 (HPV-16) led to enhanced HPV antigen-specific CD8⁺ T cell immune responses and potent protective and therapeutic anti-tumor effects against an E6/E7-expressing tumor model, TC-1, in mice.[10] These results indicate that co-administration of DNA vaccines with Ii-PADRE DNA represents an effective approach for enhancing the generation of PADRE-specific CD4⁺ T cells and eliciting stronger antigen-specific CD8⁺ T cell immune responses.

In the current study, we aim to gain insights into the enhancement of HPV E7-specific CD8⁺ T cell immune responses by PADRE-specific CD4⁺ T cells in vaccinated mice. We showed that intradermal administration of Ii-PADRE DNA are required to be at the same location as E7 expressing DNA in order to generate strong E7-specific CD8⁺ T cell immune responses. Furthermore, we showed that the PADRE-specific CD4⁺ T cells generated by vaccination with Ii-PADRE DNA expressed Th1 cytokine profile. Our in vitro study demonstrated that PADRE-specific CD4⁺ T cells stimulated with PADRE-loaded DCs secrete IL-2 that leads to the proliferation of E7-specific CD8⁺ T cells.

Results:

Intradermal Administration of CRT/E7 and Ii-PADRE DNA at the Same Location Generates Stronger E7-Specific CD8⁺ T Cell Immune Responses Compared to Administration of CRT/E7 and Ii-PADRE DNA Separately at Different Locations We have previously demonstrated that vaccination with CRT/E7 and Ii-PADRE DNA significantly enhanced the E7-specific CD8⁺ T cell immune responses.[10] However, it was not clear whether the Ii-PADRE DNA needed to be administered in the same location as CRT/E7 DNA to achieve the observed enhancement in E7-specific CD8⁺ T cells. In order to address this issue, we vaccinated C57BL/6 mice intradermally via gene gun with the DNA vaccine encoding CRT/E7 with Ii-PADRE either administered together at the same location (CRT/E7+Ii-PADRE (S)) or each of the DNA vaccines administered separately on different locations (opposite sides) of the mouse abdominal wall (CRT/E7+Ii-PADRE (D)). Splenocytes from vaccinated mice were harvested and characterized for the presence of E7-specific CD8⁺ T cells by intracellular IFN-γ staining and flow cytometry analysis. As shown in FIG. 12A, a significantly higher number of E7-specific CD8⁺ T cells was observed in mice vaccinated with DNA encoding CRT/E7+Ii-PADRE (S) compared to mice vaccinated with DNA encoding CRT/E7+Ii-PADRE (D). A graphical representation of the number of E7-specific CD8⁺ T cells is depicted in FIG. 12B. Thus, our data indicates that mice vaccinated with the DNA vaccine encoding CRT/E7 and Ii-PADRE administered together at the same location induce a stronger E7-specific CD8⁺ T cell immune response compared to administration of CRT/E7 and Ii-PADRE DNA separately.

We also determined the number of PADRE-specific CD4⁺ T cells using splenocytes from vaccinated mice stimulated with PADRE peptide using intracellular IFN-γ staining followed by flow cytometry analysis. A similar number of PADRE-specific CD4⁺ T cells was observed in mice vaccinated with DNA encoding CRT/E7+Ii-PADRE (S) compared to mice vaccinated with DNA encoding CRT/E7+Ii-PADRE (D). Thus, our data indicates that the location of administration of CRT/E7 DNA and Ii-PADRE DNA does not influence the generation of PADRE-specific CD4+ T cell immune response.

Taken together, our data suggest that vaccination with DNA encoding CRT/E7 and Ii-PADRE at the same location is required to induce a stronger E7-specific CD8+ T cell immune responses but does not influence the PADRE-specific CD4+ T cell immune responses in vaccinated mice.

Figure 13:
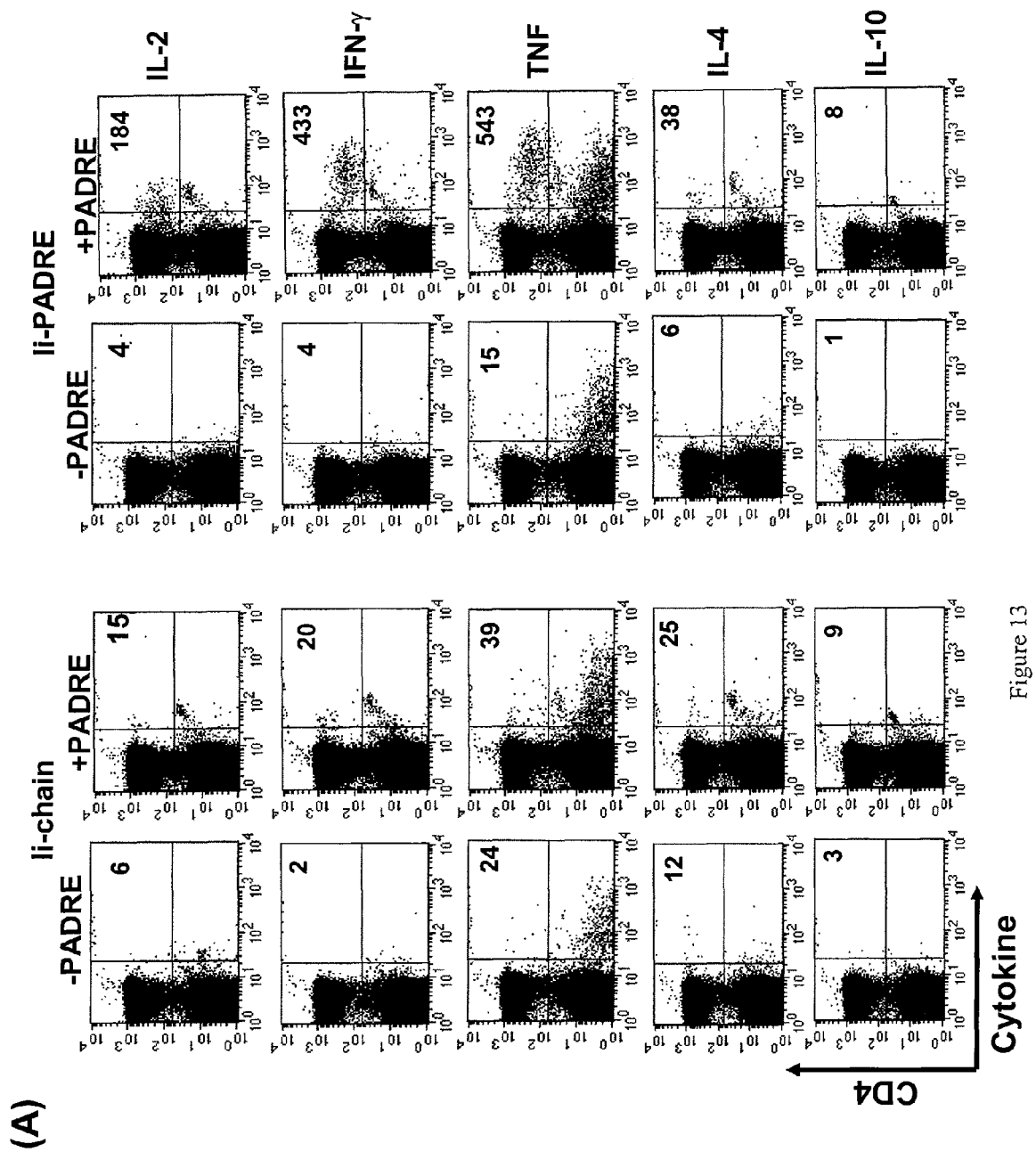
FIG. 13. Flow cytometry analysis of cytokine profile of PADRE-specific CD4+ T cells in mice vaccinated with DNA encoding Ii-PADRE. C57BL/6 mice (5 per group) were vaccinated intradermally via gene gun with DNA encoding Ii-PADRE or Ii chain twice with a one-week interval. The splenocytes were obtained from vaccinated mice one week after the last vaccination and cultured with PADRE peptide overnight. The cells were then analyzed for expression of CD4 and IL-2, IFN-γ, TNF-α, IL-4 and IL-10 by intracellular cytokine staining followed by flow cytometry analysis. A) Representative flow cytometry data showing the number of cytokine secreting CD4+ T cells/3×10⁵ splenocytes in the mice vaccinated with DNA encoding Ii-PADRE or Ii chain. B) Bar graph showing the number of cytokine secreting CD4+ T cells in mice vaccinated with DNA encoding Ii-PADRE (shaded bars) or Ii chain (empty bars) (p<0.01). The data was shown as mean±s.d.
Figure 13:
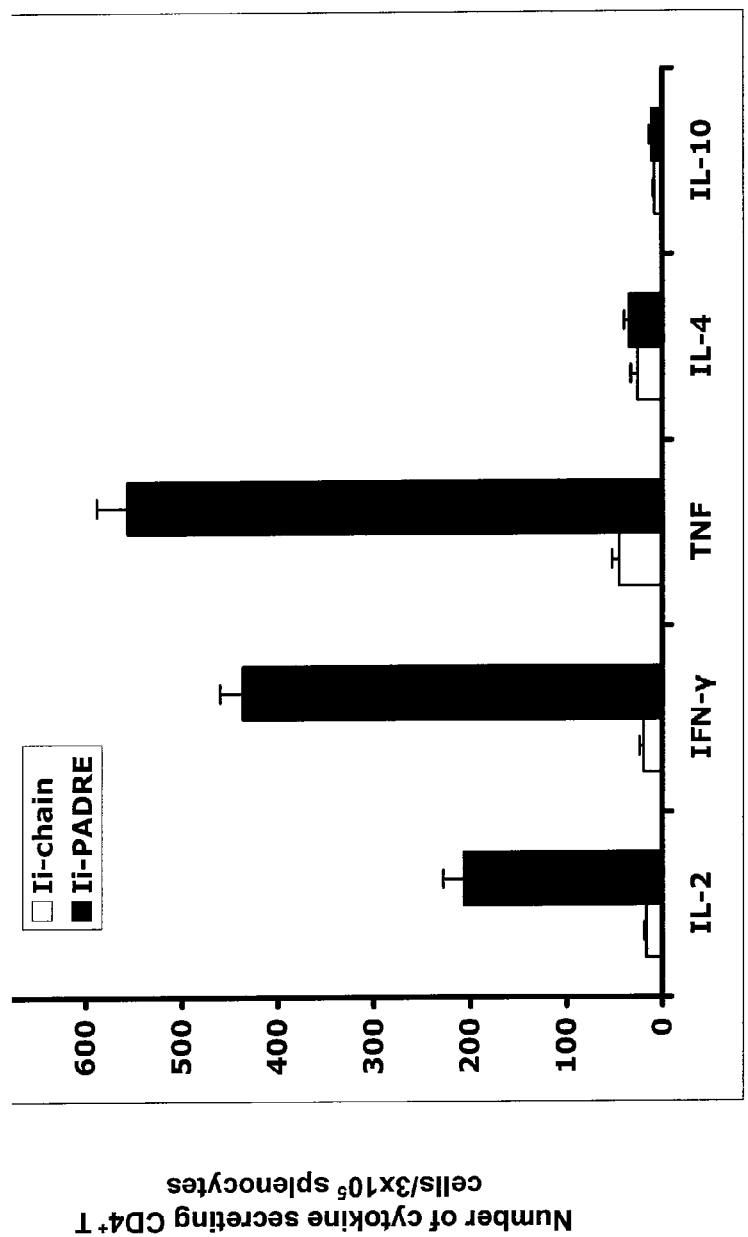

Vaccination with Ii-PADRE DNA Generate PADRE-Specific CD4+ T Cells Expressing Th1 Phenotype It is now clear that CD4+ T cells are important for the generation of antigen-specific CD8+ T cells. CD4+ T helper cells, particularly T helper type 1 cells (Th1) are important for the generation of cell-mediated immunity. In order to determine whether the cytokine profile expressed by the PADRE-specific CD4+ T cells in mice vaccinated with Ii-PADRE DNA represents the Th1 or Th2 phenotype, we performed intracellular cytokine staining for the Th1 cytokines; IL-2, IFN-γ, TNF-α and Th2 cytokines; IL-4 or IL-10 followed by flow cytometry analyses. C57BL/6 mice were vaccinated intradermally via gene gun with DNA encoding Ii-PADRE or Ii chain. Splenocytes from vaccinated mice were stimulated with PADRE peptide. As shown in FIG. 13A, mice vaccinated with DNA encoding Ii-PADRE showed significantly higher numbers of CD4+ T cells secreting IFN-γ, TNF-α and IL-2 compared to mice vaccinated with DNA encoding Ii chain. Furthermore, mice vaccinated Ii-PADRE DNA generate PADRE-specific CD4+ T cells mainly expressing Th1 cytokine profiles including IL-2, IFN-γ and TNF-α. A graphical representation of the percentage of cytokine secretion in the CD4+ T cells is depicted in FIG. 13B. Thus, our data indicate that vaccination with Ii-PADRE DNA is capable of generating PADRE-specific CD4+ T cells with Th1 cytokine profile.

DCs Loaded with E7 and PADRE Peptide Generate a Stronger E7-Specific CD8+ T Cell Immune Response Compared to DCs Loaded with E7 Alone in Vaccinated Mice.

Figure 12:
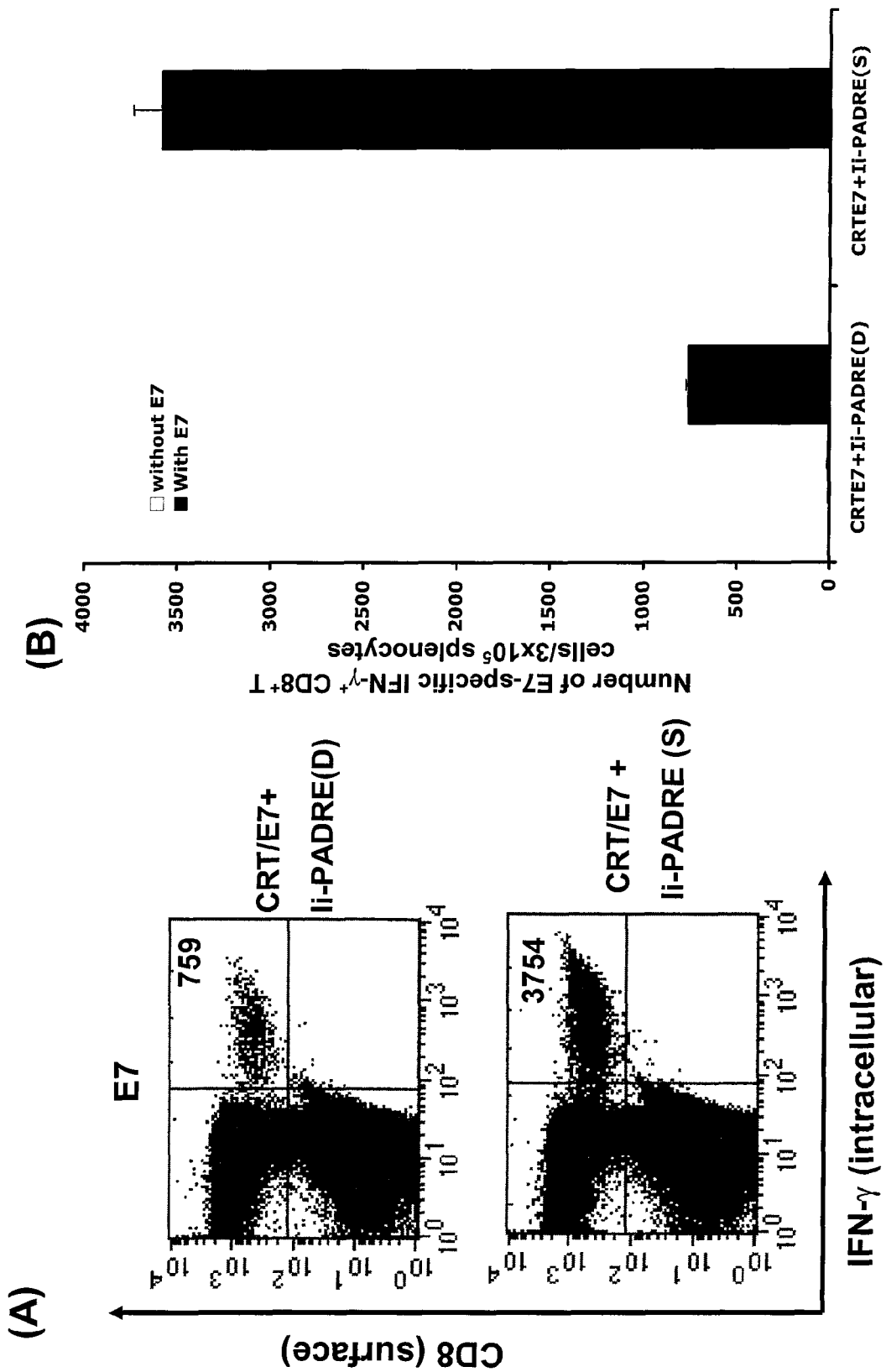
FIG. 12. Flow cytometry analysis of E7-specific CD8+ T cells in mice vaccinated with CRT/E7 and Ii-PADRE DNA. C57BL/6 mice (5 per group) were vaccinated intradermally via gene gun with the CRT/E7 DNA and Ii-PADRE DNA, either administered together at the same location (CRT/E7+ Ii-PADRE (S)) or each of the DNA vaccines administered separately at different locations (on opposites sides) of the mouse abdominal wall (CRT/E7+Ii-PADRE (D)). Mice received DNA vaccination with the same dose and regimen one week later. The splenocytes were obtained from vaccinated mice and cultured with E7 peptide (aa 49-57) overnight. The cells were then analyzed for CD8 and intracellular IFNγ staining by flow cytometry. A) Representative flow cytometry data showing the number of E7-specific IFNγ+ CD8+ T cells in the mice vaccinated with CRT/E7+Ii-PADRE (D) or CRT/E7+Ii-PADRE (S). B) Bar graph showing the number of E7-specific IFNγ+ CD8+ T cells from each group with (shaded bars) or without (empty bars) stimulation by the E7 peptide (p<0.01). The data was shown as means±s.d.

The observations from the DNA vaccination via gene gun in mice suggest that dendritic cells expressing both E7 and PADRE may be important for the enhancement in E7-specific CD8+ T cell responses (FIG. 12). In order to confirm this, we employed a dendritic cell line and loaded the DCs with E7 in conjunction with PADRE peptide for in vivo vaccination studies. Furthermore, in order to determine whether the enhancement of E7-specific CD8+ T cell immune responses are unique to PADRE, we included DCs pulsed with E7 and OVA peptides for comparison. C57BL/6 mice were vaccinated subcutaneously with DCs pulsed with both E7 and PADRE (DC-PADRE/E7) or DCs pulsed with both E7 and OVA (DC-OVA/E7). In addition, mice vaccinated with DCs pulsed with E7 (DC-E7) were included for comparison. As a negative control, one group of mice was vaccinated with DCs without peptide. Mice were vaccinated with the same dose and regimen one week later. Splenocytes from vaccinated mice were harvested one week after the last vaccination and characterized for the presence of E7-specific CD8+ T cells by intracellular IFN-γ staining and flow cytometry analysis. As shown in FIG. 14A, a significantly higher number of E7-specific CD8+ T cells was observed in mice vaccinated with DC-PADRE/E7 compared to mice vaccinated with DC-OVA/E7 or mice vaccinated with DC-E7(p<0.05). In contrast, only background levels of E7-specific CD8+ T cells were observed in mice vaccinated with DCs alone. A graphical representation of the number of E7-specific IFN-γ+ CD8+ T cells in each group is depicted in FIG. 14B. Thus, our data indicate that the vaccination with DCs pulsed with E7 and PADRE induces a stronger E7-specific CD8+ T cell immune response than DCs pulsed with E7 alone. In addition, the enhancement of E7-specific CD8+ T cell immune responses appears to be unique to PADRE peptide since vaccination with DCs pulsed with E7 and OVA does not increase the E7-specific CD8+ T cell immune responses.

Figure 15:
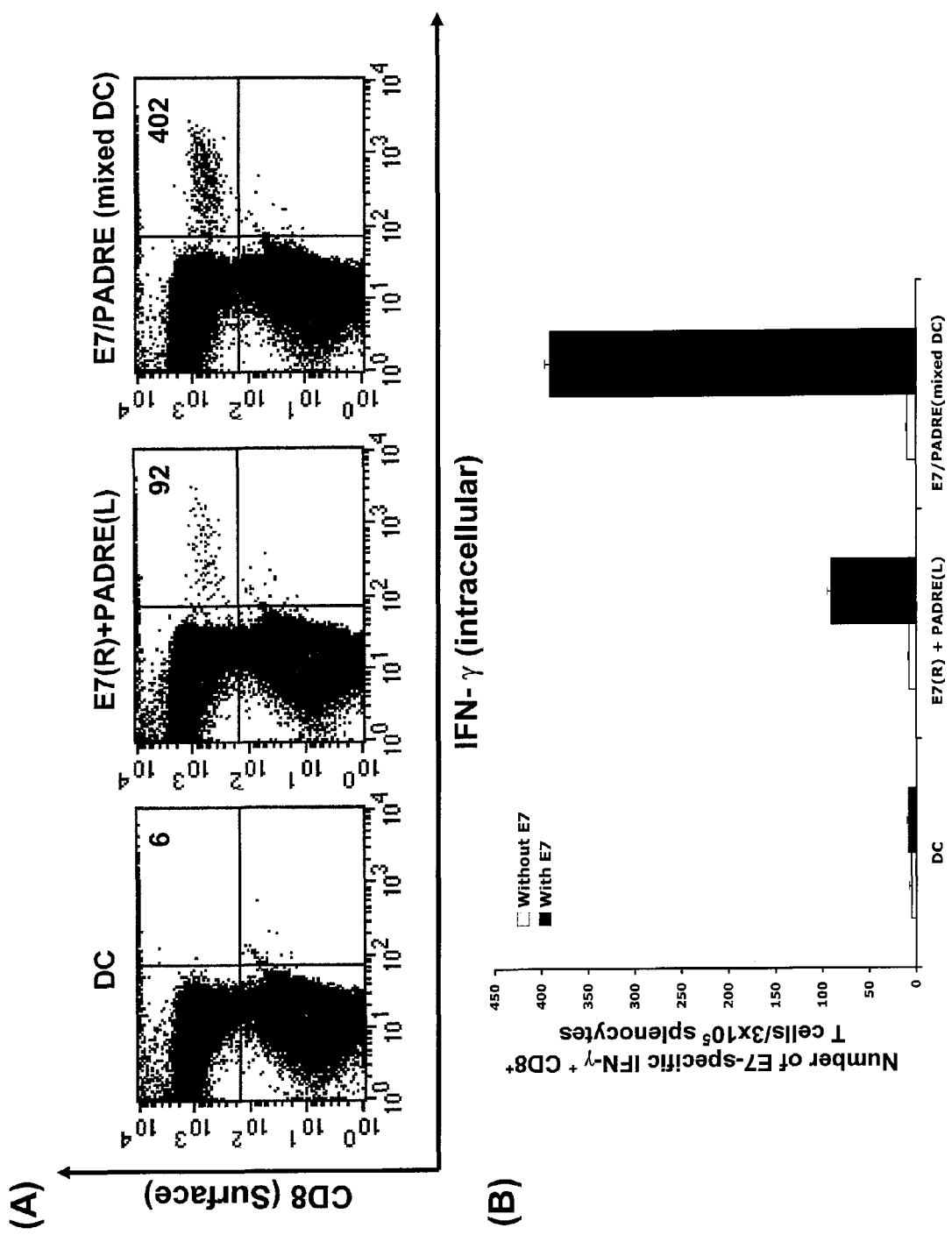
FIG. 15. Flow cytometry analysis of E7-specific CD8+ T cells in mice vaccinated with DCs loaded with E7 and DCs loaded with PADRE. C57BL/6 mice (5 per group) were vaccinated subcutaneously with DCs loaded with E7 on the right side of the abdominal wall and DCs loaded with PADRE on the left side of the abdominal wall (E7(R)+PADRE(L)). Another group of mice was vaccinated with the DC-based vaccine combining the E7-loaded DCs and the PADRE-loaded DCs administered on each side of the abdominal wall (E7/PADRE (mixed DC). Mice received vaccination with the same dose and regimen one week later. As a control, one group of mice was vaccinated with DCs without peptide. The splenocytes were obtained from vaccinated mice and cultured with E7 peptide (aa 49-57) overnight. The cells were then analyzed for CD8 and intracellular IFNγ staining by flow cytometry. A) Representative flow cytometry data showing the number of E7-specific IFNγ+ CD8+ T cells in the mice vaccinated with the different DC-based vaccines. B) Bar graph showing the number of IFNγ+ CD8+ T cells/3×10⁵ splenocytes from each group with (shaded bars) or without (empty bars) stimulation by the E7 peptide (p<0.05). The data was shown as mean±s.d.

Administration of DCs Loaded with E7 and DCs Loaded with PADRE Mixed Together at the Same Location Generates Stronger E7-Specific CD8+ T Cell Immune Responses Compared to DCs Loaded with E7 and DCs Loaded with PADRE Administered at Different Locations In our DNA vaccination studies, we observed that intradermal administration of CRT/E7 and Ii-PADRE DNA at the same location generated stronger E7-specific CD8+ T cell immune responses compared to administration of CRT/E7 and Ii-PADRE DNA separately (FIG. 12). These data suggest that DCs expressing PADRE are required to be in the vicinity of DCs expressing E7 in order to generate the observed enhancement of E7-specific CD8+ T cell responses. In order to test this, we employed DCs pulsed with either PADRE or E7 administered at the same location or at different locations and examined their ability to generate E7-specific CD8+ T cell responses. C57BL/6 mice were injected with DCs loaded with E7 on the right footpad and DCs loaded with PADRE on the left footpad (E7(R)+PADRE(L)). Another group of mice was vaccinated with the DC-based vaccine combining the E7-loaded DCs and the PADRE-loaded DCs administered on each footpad (E7/PADRE (mixed DC). As a negative control, one group of mice was vaccinated with DCs without peptide. Mice were vaccinated with the same dose and regimen one week later. Splenocytes from vaccinated mice were harvested one week after the last vaccination and characterized for the presence of E7-specific CD8+ T cells by intracellular IFN-γ staining and flow cytometry analysis. As shown in FIG. 15A, a significantly higher number of E7-specific CD8+ T cells was observed in mice vaccinated with E7/PADRE (mixed DC) compared to mice vaccinated with E7(R)+PADRE(L) (p<0.05). In contrast, only background levels of E7-specific CD8+ T cells were observed in mice vaccinated with the DCs alone. A graphical representation of the number of E7-specific IFN-γ+ CD8+ T cells is depicted in FIG. 15B. Thus, our data indicates that the vaccination with a DC-based vaccine combining the E7-loaded DCs and the PADRE-loaded DCs at the same location induces a stronger E7-specific CD8+ T cell immune response.

We also determined the number of PADRE-specific CD4+ T cells generated by vaccination with the various DC-based vaccines including E7(R)+PADRE(L), E7/PADRE (mixed DC) and DCs alone. Splenocytes from vaccinated mice were examined for PADRE-specific CD4+ T cells using intracellular IFN-γ staining followed by flow cytometry analysis. We observed a comparable number of PADRE-specific IFN-γ secreting CD4+ T cells was observed in mice vaccinated with E7/PADRE (mixed DC) compared to mice vaccinated with E7(R)+PADRE(L). In contrast, only background levels of PADRE-specific CD4+ T cells were observed in mice vaccinated with the DCs alone. Thus, our data indicates that the location of vaccination with DCs loaded with E7 and DCs loaded with PADRE does not influence the generation of PADRE-specific CD4+ T cell immune response.

Taken together, our data suggest that PADRE-loaded DCs are required to be in the vicinity of E7-loaded DCs in order to generate a stronger E7-specific CD8+ T cell immune response. In comparison, the generation of PADRE-specific CD4+ T cell responses is not influenced by the location of administration of PADRE-loaded DCs and E7-loaded DCs.

Figure 16:
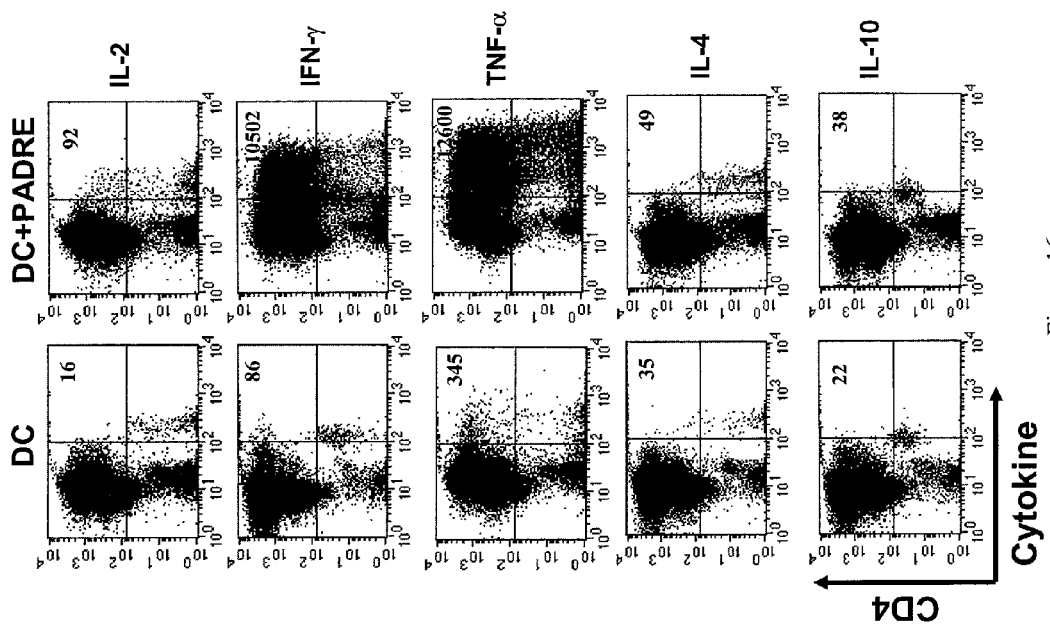
FIG. 16. Characterization of cytokine profile of the PADRE-specific CD4+ T cells following in vitro stimulation with PADRE pulsed DCs. Representative flow cytometry data showing the number of cytokine secreting cells/5×10⁴ CD4+ T cells stimulated in vitro with DCs pulsed with PADRE (DC+PADRE, right panel) or DCs without PADRE (DC, left panel). The PADRE-specific CD4+ T cell line was stimulated in vitro with DCs pulsed with or without PADRE peptide. The cells were then analyzed for expression of IL-2, IFN-γ, TNF-α, IL-4 and IL-10 by intracellular cytokine staining followed by flow cytometry.

In Vitro Stimulation of the PADRE-Specific CD4+ T Cell Line with DCs Pulsed with PADRE Resulted in Th1 Phenotype As mentioned above, CD4+ T helper cells, particularly T helper type 1 cells (Th1) are important for the generation of cell-mediated immunity. We generated a PADRE-specific CD4+ T cell line as described in the Materials and Methods. Thus, in order to determine whether the cytokine profile expressed by the PADRE-specific CD4+ T cell line stimulated in vitro with DCs loaded with PADRE peptide represents Th1 or Th2 phenotype, the PADRE-specific CD4+ T cell line was then stimulated in vitro with DCs loaded with PADRE peptide (DC+PADRE) or DCs alone and characterized for the cytokine profile including IL-2, IFN-γ, TNF-α, IL-4 or IL-10 using intracellular cytokine staining followed by flow cytometry analysis. As shown in FIG. 16, the PADRE-specific CD4+ T cells stimulated with PADRE-pulsed DCs showed significantly higher numbers of CD4+ T cells secreting IL-2, IFN-γ and TNF-α compared to those stimulated with DCs alone. Thus, our data indicates that in vitro stimulation of the PADRE-specific CD4+ T cell line with PADRE-pulsed DCs skews the cytokine profile of the CD4+ T cells to a Th1 phenotype.

Stimulation of PADRE-Specific CD4+ T Cells with PADRE-Loaded DCs Leads to the IL-2 Mediated Proliferation of E7-Specific CD8+ T Cells We observed that stimulation of PADRE-specific CD4+ T cells with PADRE-loaded DCs led to expression of Th1 cytokine profile, including IL-2 (FIG. 16). Thus, in order to determine the role of activated PADRE-specific CD4+ T cells in the proliferation of E7-specific CD8+ T cells, we employed an E7-specific CD8+ T cell line that expresses luciferase (E7T-LUC).[11] We have previously shown that the luminescence intensity correlates with the number of E7T-LUC cells.[11] We then performed a proliferation assay using E7T-LUC cells incubated with irradiated TC-1 cells into 24-well plates. PADRE-specific CD4+ T cells (PADRE-CD4) and DCs loaded with or without PADRE were added in wells as indicated in the Table of FIG. 17A. We also included the addition of IL-2 as a positive control. The proliferation of the E7-specific CD8+ T cells was characterized using bioluminescence imaging. As shown in FIG. 17A, there was significantly higher luciferase activity in the wells containing both PADRE-specific CD4+ T cells and PADRE-loaded DCs compared to the wells containing PADRE-specific CD4+ T cells and DCs alone (p<0.05). Furthermore, the wells containing PADRE-loaded DCs without PADRE-specific CD4+ T cells showed only background levels of luciferase activity (data not shown). A bar graph representing the bioluminescence activity of the E7-specific CD8+ T cells is depicted in FIG. 17B. As an alternative to assess the proliferation of E7-specific CD8+ T cells, these cells were pulsed with CFSE and incubated with PADRE-specific CD4+ T cells together with DCs pulsed with or without PADRE. E7-specific CD8+ T cells alone were included as a negative control and E7-specific CD8+ T cells incubated with IL-2 were included as a positive control. We then characterized the proliferation of the E7-specific CD8+ T cells by flow cytometry analysis in the presence of irradiated TC-1 cells. As shown in FIG. 17C, a high proliferation of E7-specific CD8+ T cells (E7-CD8) was observed when incubated with PADRE-specific CD4+ T cells (PADRE-CD4) and PADRE-loaded DCs (DC-PADRE) compared to those incubated with PADRE-specific CD4+ T cells and DCs alone as depicted by the CFSE staining pattern. Furthermore, the proliferation of E7-specific CD8+ T cells incubated with PADRE-specific CD4+ T cells and PADRE-loaded DCs was abolished when incubated with an IL-2 blocking antibody (FIG. 17D). Taken together, our data indicate that PADRE-specific CD4+ T cells activated by PADRE-loaded DCs secrete IL-2 that can lead to the proliferation of E7-specific CD8+ T cells in vitro.

Discussion

In the current study, we investigated the mechanisms by which PADRE-specific CD4+ T cells enhance the HPV E7-specific CD8+ T cell immune responses in vaccinated mice. We observed that intradermal administration of CRT/E7 and Ii-PADRE DNA at the same location generated stronger E7-specific CD8+ T cell immune responses compared to administration of CRT/E7 and Ii-PADRE DNA separately. Furthermore, we observed that vaccination with Ii-PADRE DNA generated PADRE-specific CD4+ T cells expressing Th1 phenotype. Our experiments using DC-based vaccines demonstrated that DCs loaded with E7 and PADRE peptide generated a stronger E7-specific CD8+ T cell immune response compared to DCs loaded with E7 alone in vaccinated mice. In addition, administration of DCs loaded with E7 and DCs loaded with PADRE mixed together at the same location generated stronger E7-specific CD8+ T cell immune responses compared to DCs loaded with E7 and DCs loaded with PADRE administered at different locations. In vitro stimulation of the PADRE-specific CD4+ T cell line with DCs pulsed with PADRE was shown to generate PADRE-specific CD4+ T cells expressing Th1 phenotype. Finally, we showed that PADRE-specific CD4+ T cells stimulated with PADRE-loaded DCs secreted IL-2 that led to the proliferation of E7-specific CD8+ T cells. Thus, our data suggest that activated PADRE-specific CD4+ T helper cells may be required at the vicinity of the antigen-specific CD8+ T cells where they secrete IL-2, which enhances the antigen-specific CD8+ T cell immune response.

Figure 17:
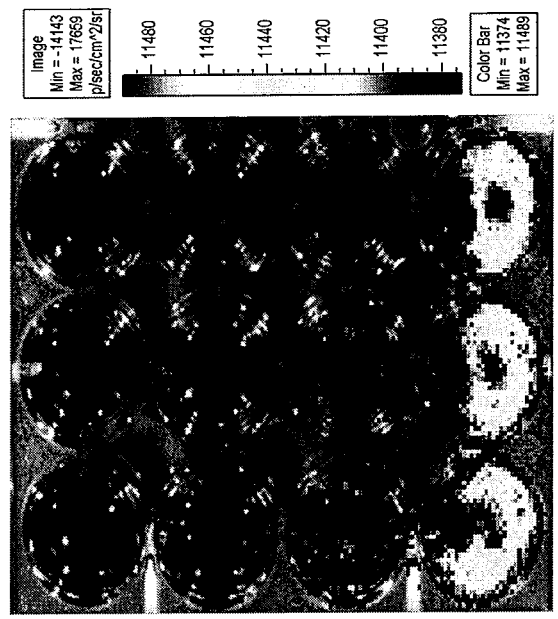
FIG. 17. Characterization of the proliferation of luciferase expressing E7-specific CD8+ T cells in the presence of PADRE-specific CD4+ T cells. A 24-well plate was loaded with 2×10⁴/well of irradiated TC-1 cells and 2×10⁵/well of E7-specific CD8+ T cells expressing luciferase (E7T-LUC). 1×10⁵/well of PADRE-specific CD4+ T cells and 1×10⁵/well of DCs pulsed with PADRE (DC-PADRE) or DCs without PADRE were added to the indicated wells. As a positive control, 10 U/ml IL-2 was added to the indicated wells. The wells without DCs or CD4+ T cells were used negative controls. The plates were incubated for 3 days and the degree of proliferation of E7-specific CD8+ T cells was characterized using bioluminescence imaging. A) Representative luminescence images of 24-well plates containing E7T-LUC cells at day 3 after in vitro simulation. B) Bar graph showing the bioluminescence of the E7T-LUC cells at day 0 (empty bars) and day 3 (shaded bars). As an alternative to assess the proliferation, E7-specific CD8+ T cells were pulsed with CFSE and incubated with the various cells as depicted. C) Flow cytometry analysis demonstrating CFSE expression in the CD8+ T cells in the different wells. The data was shown as mean±s.d. D) Flow cytometry analysis demonstrating IL-2 blocking using CFSE expression in the CD8+ T cells in the different wells.
Figure 17:
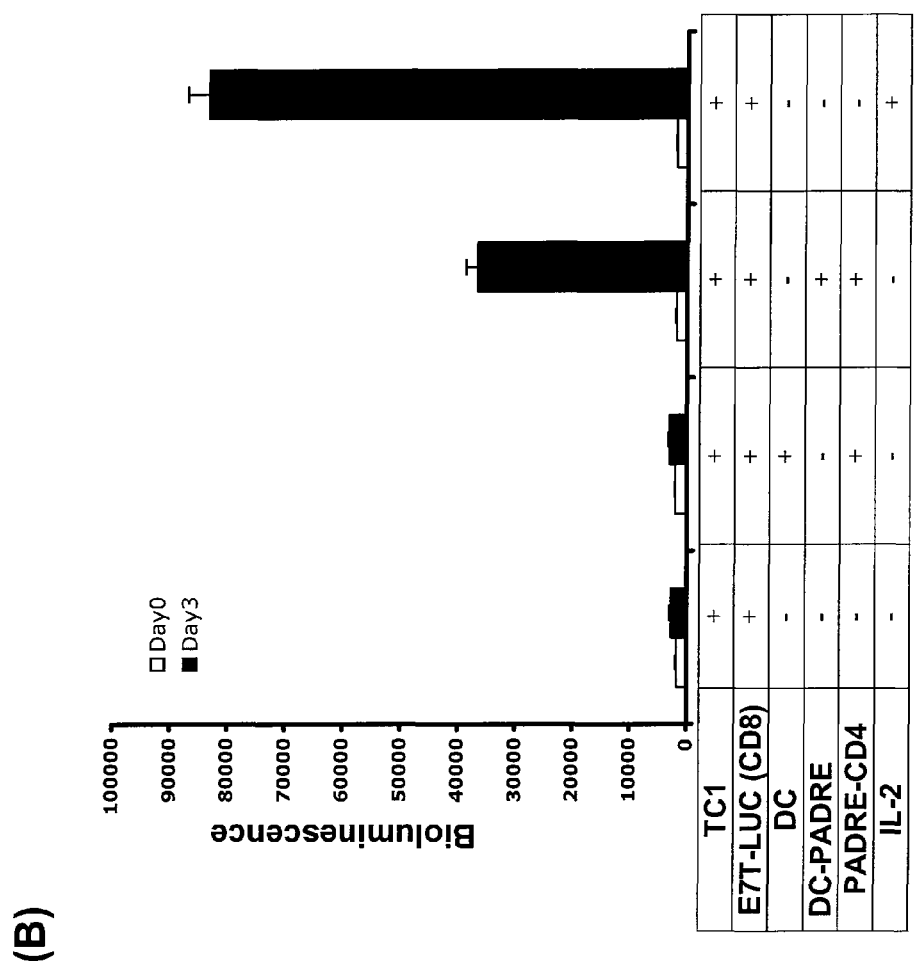
Figure 17:
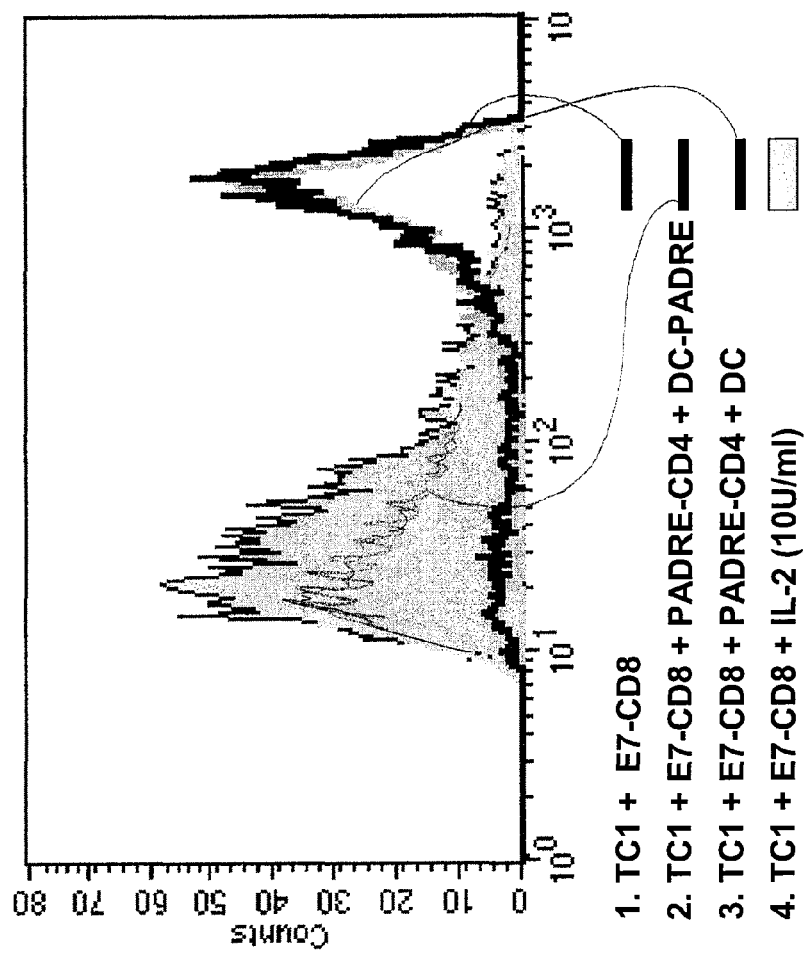
Figure 17:
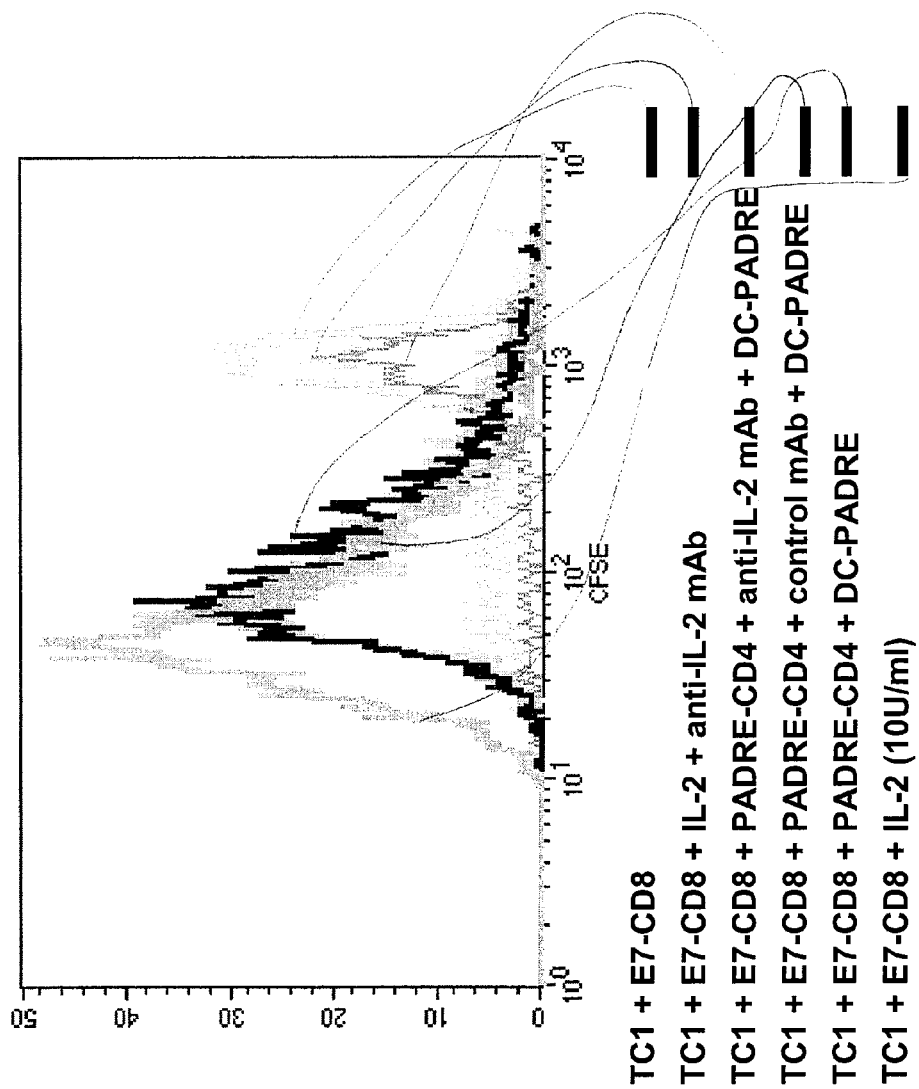

The current study serves to explore the role of PADRE-specific CD4+ T cells in the generation of increased number of antigen-specific CD8+ T cells via CD4+ T cell-mediated help mechanisms. Several models have been proposed to illustrate this role of CD4+ T cells in enhancing the antigen-specific CD8+ T cell immune responses.[12-16] Among these models, the 'Three Cell Interaction' model, which proposes that APCs deliver costimulatory signals to the CD4+ T helper cells, which in turn generate IL-2. This IL-2 production is thought to be necessary for CTL activation.[12,13,17,18] In our study, we show that the PADRE-specific CD4+ T cell line can be activated by PADRE-loaded DCs to release Th1 type of cytokines including IL-2 (FIG. 16). Furthermore, incubation of E7-specific CD8+ T cells with activated PADRE-specific CD4+ T cells stimulated by PADRE-loaded DCs led to proliferation of E7-specific CD8+ T cells and this proliferation was abolished by incubation with an IL-2 blocking antibody (FIG. 17). Thus, although we cannot exclude the possible contributions of the other models, our data is most consistent with the 'Three Cell Interaction' model illustrating the role of CD4+ T cells in enhancing antigen-specific CD8+ T cell immune responses.

Figure 14:
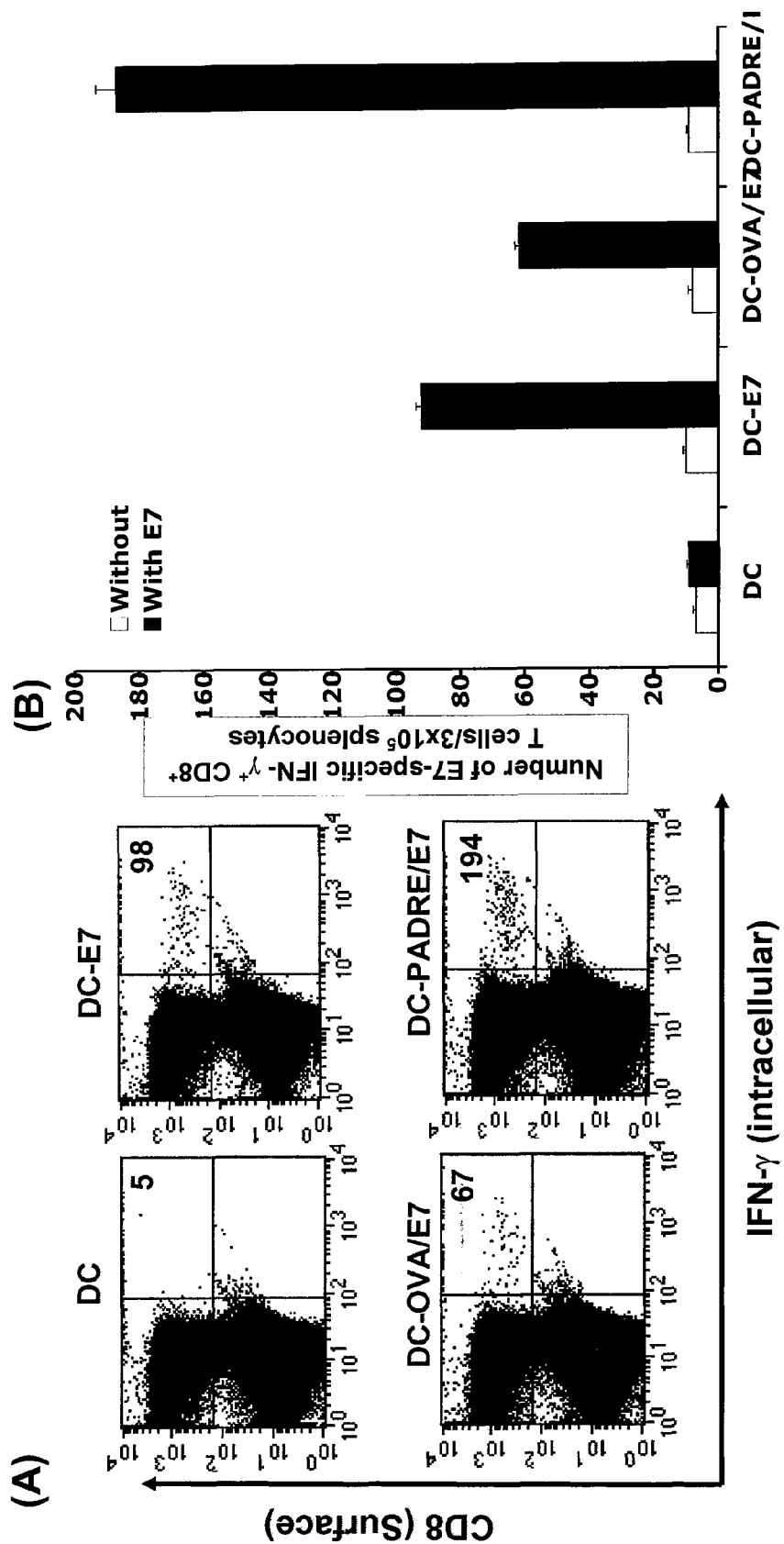
FIG. 14. Flow cytometry analysis of E7-specific CD8+ T cells in mice vaccinated with DCs loaded with PADRE or OVA in conjunction with E7 peptide. C57BL/6 mice (5 per group) were vaccinated subcutaneously with 2.5×10⁵/mouse of DCs pulsed with both E7 and PADRE (DC-PADRE/E7) or with 2.5×10⁵/mouse of DCs pulsed with both E7 and OVA (DC-OVA/E7). Mice received vaccination with the same dose and regimen one week later. As controls, C57BL/6 mice were vaccinated with 2.5×10⁵/mouse of DCs alone or DCs loaded with E7 (DC-E7). The splenocytes were obtained from vaccinated mice and cultured with E7 peptide (aa 49-57) overnight. The cells were then analyzed for CD8 and intracellular IFNγ staining by flow cytometry. A) Representative flow cytometry data showing the number of E7-specific IFNγ+ CD8+ T cells/3×10⁵ splenocytes in the mice vaccinated with the various DC-based vaccines. B) Bar graph showing the number of IFNγ+ CD8+ T cells from each group with (shaded bars) or without (empty bars) stimulation by the E7 peptide (p<0.05). The data was shown as mean±s.d.

The Ii-PADRE DNA vaccination strategy to enhance antigen-specific CD8+ T cell responses appears to be quite specific. We observed in our study that the enhancement of E7-specific CD8+ T cell immune responses by co-administration of Ii-PADRE DNA are unique to PADRE since vaccination with DNA encoding Ii-OVA (CLIP replaced by OVA MHC class II epitope in the invariant chain) or Ii-E7 (CLIP replaced by E7 MHC class II epitope in the invariant chain) does not increase the E7-specific CD8+ T cell immune responses (data not shown). Furthermore, in the current study, we showed that only DCs loaded with E7 and PADRE but not DCs loaded with E7 and OVA, were able to generate enhanced E7-specific CD8+ T cell responses (FIG. 14). Such discrepancy may be accounted for by the affinity of the PADRE peptide to MHC class II molecule. PADRE has been shown to be approximately 1000 times more powerful in its capacity to elicit CD4+ T helper cells compared to some natural T cell epitopes.[19]

The innovative strategy to enhance antigen-specific CD8+ T cell immune responses by co-administration of DNA vaccines with Ii-PADRE DNA may prove to be a highly useful approach that can be widely applied in different antigenic systems. It has been shown that PADRE can be presented by different kinds of MHC class II molecules including different species. Thus, the Ii-PADRE DNA can potentially be used in different individuals with different MHC haplotypes.[19] Furthermore, we have shown that Ii-PADRE DNA can be used in DNA vaccines targeting different antigenic systems such as HPV-16 E6.[10] Thus, Ii-PADRE DNA technology may represent a platform technology to enhance DNA vaccine potency in different individuals with different antigenic systems.

Strategies employing Ii-PADRE DNA can also be potentially be used in conjunction with other strategies that modify the properties of DCs to further enhance DNA vaccine potency (For reviews see [5,6]). These various strategies work by employing different mechanisms that are not mutually exclusive to each other. Thus, DNA vaccines combining these strategies generate a significant enhancement in DNA vaccine potency. For example, DNA vaccines employing intracellular targeting strategies can be further enhanced by co-administration with Ii-PADRE DNA (Kim et al., unpublished data). Thus, it is conceivable that such combination strategies may be employed for future clinical translation in order to generate most potent antigen-specific immune responses.

Materials and Methods

Mice

C57BL/6 mice (6-8 weeks old) were purchased from the National Cancer Institute Frederick, Md.). All animals were maintained under specific pathogen-free conditions at the Johns Hopkins Hospital (Baltimore, Md.). All procedures were performed according to approved protocols and in accordance with recommendations for the proper use and care of laboratory animals.

Cells, Antibodies, and Reagents

The HPV-16 E7-expressing murine tumor model, TC-1, has been described previously[20]. In brief, HPV-16 E6 and E7 and the ras oncogene were used to transform primary C57BL/6 mouse lung epithelial cells to generate TC-1. Dendritic cells were generated from the dendritic cell line[21] provided by Dr. Kenneth Rock (University of Massachusetts, Boston, Mass.). The production and maintenance of E7-specific CD8+ T cells has been described in a previous paper.[22] Firefly luciferase-expressing E7-specific CD8+ T cells (E7T-LUC) were generated using retrovirus containing luciferase.[11] The retrovirus was produced using a pLuci-thy1.1 construct expressing both luciferase and thy1.1. The pLuci-thy1.1 was transfected into Phoenix packaging cell line and the virion-containing supernatant was collected 48 h after transfection. The supernatant was immediately treated using a 0.45-mm cellulose acetate syringe filter (Nalgene, Rochester, N.Y.) and used to infect E7-specific CD8+ T cells in the presence of 8 mg/ml Polybrene (Sigma, St Louis, Mo.). E7T-LUC cells were isolated using preparative flow cytometry of stained cells with Thy1.1 antibody using methods similar to our previous study.[23] All cells were maintained in RPMI medium (Invitrogen, Carlsbad, Calif.) supplemented with 2 mM glutamine, 1 mM sodium pyruvate, 20 mM HEPES, 50 μM β-mercaptoethanol, 100 IU/ml penicillin, 100 μg/ml streptomycin, and 10% fetal bovine serum (Gemini Bio-Products, Woodland, Calif.). Anti-mouse CD8a mAb (clone 53.6.7), CD4 (clone GK1.5), IL-2, IL-4, IL-10, IFN-γ and TNF (BD Pharmingen, San Diego, Calif.) was used for intracellular cytokines analysis. PE-conjugated Thy1.1 mAb was used to sort the E7T-LUC. CFSE was purchased from Molecular Probes (Carlsbad, Calif.).

Plasmid DNA Constructs and DNA Preparation.

The generation of pcDNA3-CRT/E7 Ii-PADRE have been described previously.[10,24] The DNA construct encoding an Ii chain was constructed by real-time polymerase chain reaction (PCR) amplification using RNA isolated from dendritic cells and primers (5'aaagaattcatggatgaccaacgcgacctc3' (SEQ ID NO: 125)) and 5'aaaggatcctcacagggtgacttgacccag3' (SEQ ID NO: 126)). The RT-PCR product was cloned into the EcoRI/BamHI sites of pcDNA3.1(-) to generate pcDNA3-Ii. The DNA fragment encoding the PADRE epitope and Ii chain 103-279 amino acids were amplified by PCR with a set of primers (5'aaaggatcctcacagggtgacttgacccag3' (SEQ ID NO: 126), 5'ctggaccctgaaggctgccgctatggataacatgctccttgg3' (SEQ ID NO: 128), and 5'gccaagttcgtggctgcctggaccct-gaaggctgccgct3' (SEQ ID NO: 129)). The overlapping PCR fragments were then used as template to create Ii-PADRE using PCR with a set of primers (5'aaagaattcatggatgaccaacgc-gacctc3' (SEQ ID NO: 125)) and 5'aaaggatcctcacagggtgact-tgacccag3' (SEQ ID NO: 126)). The DNA fragment Ii-PADRE was further cloned into EcoRI/BamHI of pcDNA3.1(-) vector to generate pcDNA3-Ii-PADRE. The accuracy of these constructs was confirmed by DNA sequencing. DNA was amplified in *Escherichia coli* DH5α and purified as described previously.[25]

DNA Vaccination

DNA-coated gold particles were prepared according to a protocol described previously.[25] DNA-coated gold particles were delivered to the shaved abdominal region of mice using a helium-driven gene gun (Bio-Rad Laboratories Inc., Hercules, Calif.) with a discharge pressure of 400 psi. C57BL/6 mice were immunized with 2 μg of the plasmid encoding pcDNA3-CRT/E7 mixed with pcDNA3-Ii-PADRE for the vaccination strategy at the same location. The mice received a booster with the same dose and regimen 1 week later. For the vaccination strategy at different locations, mice were immunized intradermally via gene gun with pcDNA3-CRT/E7 (1 μg/mouse, right side of the abdomen) and pcDNA3-Ii-PADRE (1 μg/mouse, left side of the abdomen), and boosted with same regimen at same side 1 week later.

DC Immunization

DCs were co-pulsed with HPV-16 E7 (aa49-57) peptide (RAHYNIVTF (SEQ ID NO: 136), 10 ug/ml) and PADRE peptide (AKFVAAWTLKAAA (SEQ ID NO: 93), 10 ug/ml) or OVA (aa323-339) peptide (ISQAVHAAHAEINEAGR (SEQ ID NO: 137), 10 ug/ml) at 37° C. for 6 hours. DCs were then washed with RPMI-1640, supplemented with 10% FBS and HBSS, and re-suspended in HBSS at the final concentration of 5×10⁶/ml. 100 μl/mouse of DCs were injected into mice via footpad injection. One week later, the mice were boosted once with the same dose and immunization regimen. For comparing the effect of PADRE on the vaccination strategy at different locations v/s with mixed DCs, one group of DCs was pulsed with E7 aa49-57 peptide (RAHYNIVTF (SEQ ID NO: 136), 5 ug/ml), which was injected to the right footpad. The other group of DCs was pulsed with PADRE peptide (AKFVAAWTLKAAA (SEQ ID NO: 93), 5 ug/ml), which was injected to the left footpad. For the vaccination strategy using mixed DCs, each group of pulsed DCs was put together just after washing process before immunization, and then those cells were vaccinated with equal number and volume.

Intracellular Cytokine Staining and Flow Cytometry Analysis

Splenocytes were harvested from mice 1 week after the last vaccination. Prior to intracellular cytokine staining, $5 \times 10^6$ pooled splenocytes from each vaccination group were incubated for 16 hours with 1 μg/mL HPV-16 E7 H-2D$^b$ epitope (RAHYNIVTF (SEQ ID NO: 136)), and PADRE peptide (AKFVAAWTLKAAA (SEQ ID NO: 93)) or OVA peptide (ISQAVHAAHAEINEAGR (SEQ ID NO: 137)) in the presence of GolgiPlug (BD Pharmingen, San Diego, Calif.) (1 μl/ml). The stimulated splenocytes were then washed once with FACScan buffer and stained with phycoerythrin-conjugated monoclonal rat anti-mouse CD8a or CD4. Cells were subjected to intracellular cytokine staining using the Cytofix/Cytoperm kit according to the manufacturer's instructions (BD Pharmingen, San Diego, Calif.). Intracellular IFN-γ was stained with FITC-conjugated rat anti-mouse IFN-γ to identify the immune response and cytokines level. FITC-conjugated rat anti-mouse IL-2, IL-4, IL-10, and TNF were used to detect intracellular cytokine levels. Flow cytometry analysis was performed using FACSCalibur with CELLQuest software (BD Biosciences, Mountain View, Calif.).

Generation of a PADRE-Specific CD4$^+$ T Cell Line

Six-week-old female C57BL/6 mice were immunized with pcDNA3-Ii-PADRE by gene gun. After prime and booster vaccination at 1 week interval, splenocytes were harvested 1 week after the last vaccination. For initial in vitro stimulation, $5 \times 10^6$ splenocytes were pulsed with IL-2 (10 U/ml) and PADRE peptide (1 μg/ml) in RPMI media containing 10% FBS for 6 days. Propagation of the PADRE-specific CD4$^+$ T cell line was performed in 24-well plates by mixing $1 \times 10^6$ splenocytes containing PADRE-specific CD4$^+$ T cells with $1 \times 10^6$ irradiated DCs that were pulsed with PADRE peptide, and then cultured in RPMI media containing IL-2 (10 U/ml) for 6 days. This procedure was repeated weekly. Flow cytometry was performed to demonstrate the expression of the CD4 marker.

DCs and PADRE-Specific CD4 T Cells Co-Culture Assay

PADRE-specific CD4$^+$ T cells ($1 \times 10^6$/well) were cultured with irradiated DCs or PADRE pulsed DCs ($1 \times 10^5$/well) in 24-well plates for 16 hours. Cells were then stained for both surface CD4 and the indicated cytokines and analyzed by flow cytometry analysis as described above.

In Vitro Bioluminescence Imaging

For in vitro proliferation assay, we used the bioluminescence imaging system. Luciferase transfected E7-specific T cells (E7T-LUC) ($2 \times 10^5$/well) were mixed with irradiated TC-1 cells ($2 \times 10^4$/well) in 24-well plates with complete media. Irradiated DCs or PADRE peptide pulsed DCs ($1 \times 10^5$/well) and PADRE-specific CD4$^+$ T cells ($1 \times 10^5$/well) were added to each well according to the indicated conditions. The plates were incubated at 37° C. 5% $CO_2$ for 3 days. At day 3, D-luciferin (potassium salt; Xenogen Corp. Alameda, Calif.) at 150 ug/ml in media was added to each well 7-8 min before imaging. Imaging process was conducted on a cryogenically cooled IVIS system (Xenogen Corp., Alameda, Calif.) using Living Image acquisition and analysis software (Xenogen Corp. Alameda, Calif.). Imaging time was 1 min/plate.

CFSE Labeling of T Cells and IL-2 Blocking Experiment

E7-specific CD8$^+$ T cells were labeled at $1 \times 10^7$ cells/ml with 5 μM CFSE (Molecular Probes, Carlsbad, Calif.) in PBS for 5 min at room temperature followed by incubation with 5% FBS-PBS (5 mM EDTA) for 10 min at 37° C. After three washes with 5% FBS-PBS, $1 \times 10^6$/ml of the labeled cells in 200 μl of media were mixed at the indicated conditions in a 24-well plate. IL-2 blocking was achieved by anti-IL-2 mAb (10 μg/ml; close JES6-1A12, R&D Systems, Minneapolis, Minn.). Rat IgG2a mAb (10 μg/ml; close 54447, R&D Systems) was used as isotype control. All wells contained $2 \times 10^4$ irradiated TC-1 cells. After 4 days culture, flow cytometry acquisition was done as described above.

Statistical Analysis

All data expressed as means+/−standard deviation (s.d.) are representative of at least two different experiments. Data for intracellular cytokine staining with flow cytometry analysis and tumor treatment experiments were evaluated by analysis of variance. Comparisons between individual data points were made using Student's t test. All p values <0.05 were considered significant.

REFERENCES

1 Donnelly J J, Ulmer J B, Shiver J W, Liu M A. DNA vaccines. *Annu Rev Immunol* 1997; 15: 617-648.
2 Gurunathan S, Klinman D M, Seder R A. DNA vaccines: immunology, application, and optimization. *Annu Rev Immunol* 2000; 18: 927-974.
3 Condon C, Watkins S C, Celluzzi C M, Thompson K, Falo L D, Jr. DNA-based immunization by in vivo transfection of dendritic cells. *Nat Med* 1996; 2: 1122-1128.
4 Porgador A, Irvine K R, Iwasaki A, Barber B H, Restifo N P, Germain R N. Predominant role for directly transfected dendritic cells in antigen presentation to CD8+ T cells after gene gun immunization. *J Exp Med* 1998; 188: 1075-1082.
5 Hung C F, Wu T C. Improving DNA vaccine potency via modification of professional antigen presenting cells. *Curr Opin Mol Ther* 2003; 5: 20-24.
6 Tsen S W, Paik A H, Hung C F, Wu T C. Enhancing DNA vaccine potency by modifying the properties of antigen-presenting cells. *Expert Rev Vaccines* 2007; 6: 227-239.
7 Castellino F, Germain R N. Cooperation between CD4+ and CD8+ T cells: when, where, and how. *Ann Rev Immunol* 2006; 24: 519-540.
8 Hung K, Hayashi R, Lafond-Walker A, Lowenstein C, Pardoll D, Levitsky H. The central role of CD4(+) T cells in the antitumor immune response. *J Exp Med* 1998; 188: 2357-2368.
9 Marzo A L, Kinnear B F, Lake R A, Frelinger J J, Collins E J, Robinson B W et al. Tumor-specific CD4+ T cells have a major "post-licensing" role in CTL mediated anti-tumor immunity. *J Immunol* 2000; 165: 6047-6055.
10 Hung C F, Tsai Y C, He L, Wu T C. DNA Vaccines Encoding Ii-PADRE Generates Potent PADRE-specific CD4(+) T-Cell Immune Responses and Enhances Vaccine Potency. *Mol Ther* 2007.
11 Lin K Y, Lu D, Hung C F, Peng S, Huang L, Jie C et al. Ectopic expression of vascular cell adhesion molecule-1 as a new mechanism for tumor immune evasion. *Cancer Res* 2007; 67: 1832-1841.
12 Mitchison N A, O'Malley C. Three-cell-type clusters of T cells with antigen-presenting cells best explain the epitope linkage and noncognate requirements of the in vivo cytolytic response. *Eur J Immunol* 1987; 17: 1579-1583.
13 Bennett S R, Carbone F R, Karamalis F, Miller J F, Heath W R. Induction of a CD8+ cytotoxic T lymphocyte response by cross-priming requires cognate CD4+ T cell help. *J Exp Med* 1997; 186: 65-70.
14 Bousso P, Robey E. Dynamics of CD8+ T cell priming by dendritic cells in intact lymph nodes. *Nat Immunol* 2003; 4: 579-585.
15 Bevan M J. Helping the CD8(+) T-cell response. *Nat Rev Immunol* 2004; 4: 595-602.
16 Xiang J, Huang H, Liu Y. A new dynamic model of CD8+ T effector cell responses via CD4+ T helper-antigen-presenting cells. *J Immunol* 2005; 174: 7497-7505.

17 Keene J A, Forman J. Helper activity is required for the in vivo generation of cytotoxic T lymphocytes. *J Exp Med* 1982; 155: 768-782.

18 Cassell D, Forman J. Linked recognition of helper and cytotoxic antigenic determinants for the generation of cytotoxic T lymphocytes. *Ann NY Acad Sci* 1988; 532: 51-60.

19 Alexander J, Sidney J, Southwood S, Ruppert J, Oseroff C, Maewal A et al. Development of high potency universal DR-restricted helper epitopes by modification of high affinity DR-blocking peptides. *Immunity* 1994; 1: 751-761.

20 Lin K-Y, Guarnieri F G, Staveley-O'Carroll K F, Levitsky H I, August T, Pardoll D M et al. Treatment of established tumors with a novel vaccine that enhances major histocompatibility class II presentation of tumor antigen. *Cancer Res* 1996; 56: 21-26.

21 Shen Z, Reznikoff G, Dranoff G, Rock K L. Cloned dendritic cells can present exogenous antigens on both MHC class I and class II molecules. *J Immunol* 1997; 158: 2723-2730.

22 Ji H, Wang T-L, Chen C-H, Hung C-F, Pai S, Lin K-Y et al. Targeting HPV-16 E7 to the endosomal/lysosomal compartment enhances the antitumor immunity of DNA vaccines against murine HPV-16 E7-expressing tumors. *Hum Gene Ther* 1999; 10: 2727-2740.

23 Hung C F, Tsai Y C, He L, Coukos G, Fodor I, Qin L et al. Vaccinia virus preferentially infects and controls human and murine ovarian tumors in mice. *Gene Ther* 2007; 14: 20-29.

24 Cheng W F, Hung C F, Chai C Y, Hsu K F, He L, Ling M et al. Tumor-specific immunity and antiangiogenesis generated by a DNA vaccine encoding calreticulin linked to a tumor antigen. *J Clin Invest* 2001; 108: 669-678.

Chen C H, Wang T L, Hung C F, Yang Y, Young R A, Pardoll D M et al. Enhancement of DNA vaccine potency by linkage of antigen gene to an HSP70 gene. *Cancer Res* 2000; 60: 1035-1042.

Example 3

Treatment with CRT-E6, Ii-PADRE, and Doxorubicin

C57BL/6 mice (5 per group) were challenged subcutaneously with $5 \times 10^4$/mouse of TC-1 cells. Three days later, the mice were treated with doxorubicin (10 mg/kg body weight). Ten days after tumor challenge, mice were immunized via gene gun with 2 ug/mouse of the CRT/E6 DNA with Ii-PADRE or Ii DNA three times at 3-day intervals.

Figure 18:
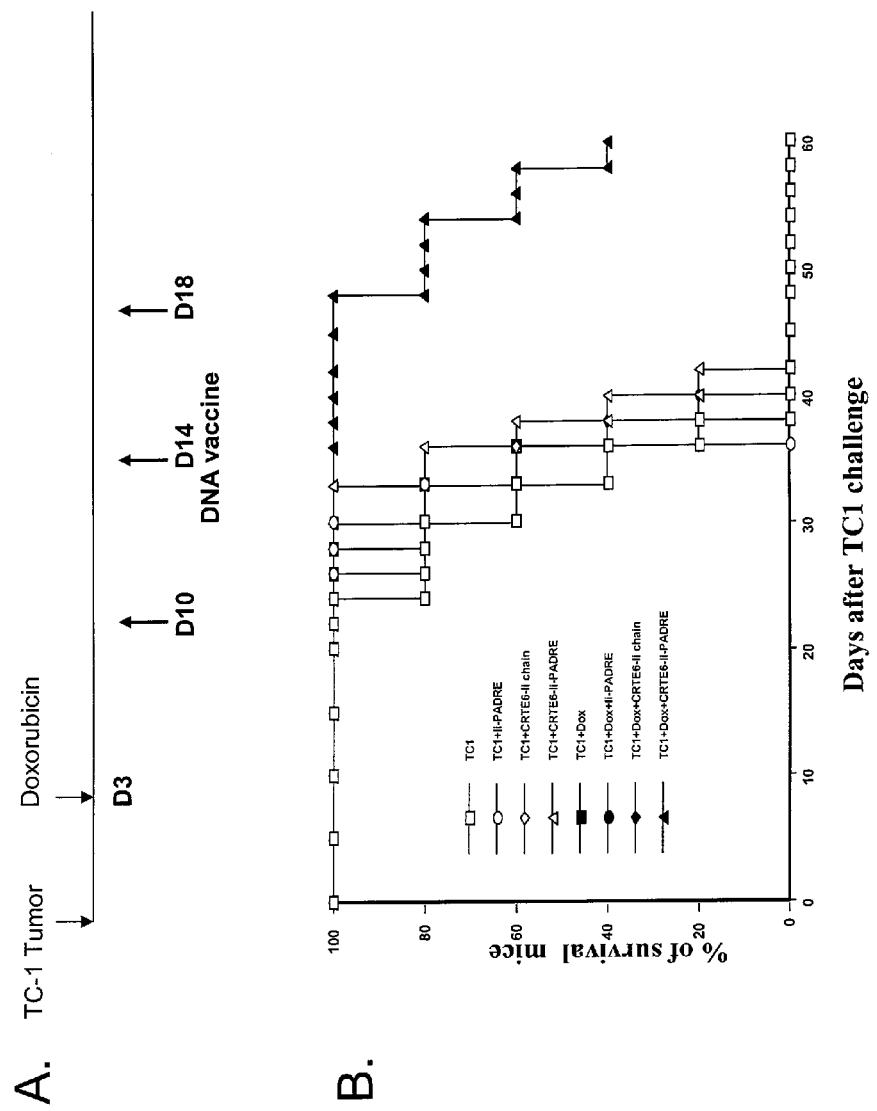
FIGS. 18 A and B. Anti-tumor effects generated by treatment with doxorubicin and/or CRT/E6 DNA vaccine in vaccinated mice.

The results are shown in FIG. 18. Panel A shows the Treatment regimen and panel B shows the Kaplan-Meier survival analysis of tumor-challenged mice treated with doxorubicin and/or the CRT/E6 DNA with Ii-PADRE or Ii DNA vaccine. The results indicate that the combination of Doxorubicin with CRT/E6 DNA and Ii-PADRE is efficient in enhancing the survival of the mice challenged with TC-1 cells.

Example 4

Enhancement of DNA Vaccine Potency Through Co-Administration of MHC Class II Transactivator (CIITA) DNA with DNA Vaccines Via Gene Gun Administration of DNA vaccines via gene gun has emerged as an important form of antigen-specific immunotherapy. The MHC class II transactivator (CIITA) is a master regulator of MHC II expression and also induces expression of class I molecules. We reasoned that the gene gun administration of CIITA DNA with DNA vaccines employing different strategies to improve MHC I and II processing could enhance DNA vaccine potency. We observed that DC-1 cells transfected with CIITA DNA lead to higher expression of MHC I and II molecules, leading to enhanced antigen presentation through the MHC class I/II pathways. Furthermore, our data suggested that co-administration of DNA encoding calreticulin (CRT) linked to HPV-16 E6 antigen (CRT/E6) with CIITA DNA leads to enhanced E6-specific CD8+ T cell immune responses in vaccinated mice. In addition, co-administration of the combination of CRT/E6 DNA with CIITA DNA and DNA encoding the invariant chain (Ii) linked to the pan HLA-DR reactive epitope (Ii-PADRE) further enhanced E6-specific CD8+ T cell immune responses in vaccinated mice. Treatment with the combination vaccine was also shown to enhance the antitumor effects and prolong survival in TC-1 tumor-bearing mice. Vaccination with the combination vaccine also led to enhanced E6-specific CD8+ memory T cells and led to long-term protection against TC-1 tumors and prolonged survival in vaccinated mice. Thus, our findings suggest that the combination of CIITA DNA with CRT/E6 and Ii-PADRE DNA vaccines represents a potentially effective means to combat tumors in the clinical setting.

Introduction

DNA vaccines have emerged as an interesting approach for antigen-specific immunotherapy because they are safe, stable and easy to produce. Gene gun administration of DNA vaccines represents an effective means of directly delivering antigenic DNA into dendritic cells (DCs), the most potent of the professional antigen-presenting cells. The antigen-expressing DCs mature and migrate to the draining lymph nodes, where they activate naive T lymphocytes in vivo to differentiate into activated, antigen-specific T cells (1, 2). Gene gun administration enables us to test the strategies that require direct delivery of the DNA vaccines into DCs to improve the potency of these DNA vaccines. We have previously used the gene gun delivery system for the development of several innovative strategies to enhance DNA vaccine potency (for review, see (3, 4)).

One of these strategies involves intracellular targeting of the encoded antigen to subcellular compartments to enhance MHC class I and class II antigen presentation in DCs. For example, DNA vaccines encoding antigen linked to calreticulin (CRT) are able to target the linked antigen to the endoplasmic reticulum, resulting in enhanced MHC class I presentation of the linked antigen (5). CRT is an abundant $Ca^{2+}$-binding protein that resides in the endoplasmic reticulum (for review see (6)) and has been shown to aid in antigen presentation by associating with peptides delivered to the ER by transporter associated with antigen processing (TAP) molecules (7) and with MHC class I molecules (8). We have demonstrated that DNA vaccines encoding CRT linked to model antigen HPV-16 E6 and E7 generated increased HPV antigen-specific CD8+ T cell responses and antitumor effects (5, 9). Therefore, DNA vaccines encoding CRT linked to a tumor-specific antigen present the opportunity to enhance vaccine potency via enhancing MHC class I processing and presentation.

Another strategy to enhance DNA vaccine potency involves the induction of CD4+ T cell help. The activation of CD8+ T cells can be significantly enhanced by CD4+ T helper cells (for review see (10)). Thus, strategies to induce CD4+ T helper cells at sites of CD8+ T cell priming can potentially enhance CTL immune responses. In previous studies, it has been shown that DNA vaccines encoding invariant (Ii) chain in which the CLIP region is replaced with a high-affinity and "promiscuous" CD4+ T-cell epitope such as the Pan HLA-DR reactive epitope (PADRE) (11) leads to the stable, accelerated presentation of PADRE through MHC class II molecules. More recently, we have shown that immunization with DNA vaccines encoding Ii-PADRE DNA leads to the generation of high numbers of PADRE-specific CD4+ T-cell immune responses in mice (12). Furthermore, co-administration of E7 DNA vaccines with Ii-PADRE DNA has led to enhanced E7-specific CD8+ T cell immune responses and antitumor effects in vaccinated mice (12, 13). Therefore, DNA vaccination encoding antigen of interest with Ii-PADRE DNA serves as a potentially useful means to improve DNA vaccine potency through the induction of CD4+ T cells.

We reasoned that a strategy that is capable of enhancing the MHC class I and II expression on DCs may further enhance DNA vaccine potency. The major histocompatability complex (MHC) class II transactivator (CIITA) is known as a master control factor for the genes required for MHC class II antigen-presentation (14, 15). It has also been shown that CIITA induces the surface expression of MHC 1 molecules (16, 17). Thus, we reasoned that co-administration of DNA vaccines with CIITA DNA would increase the levels of MHC class I/II molecules and lead to enhanced presentation of the antigen via the MHC class I and II processing pathways, resulting in enhanced DNA vaccine potency. Therefore, the employment of CIITA DNA in DNA vaccines represents a potential strategy to improve vaccine potency through enhancing antigen presentation via the MHC class I and II processing pathways.

In the current study, we employed a combination of DNA vaccines encoding CRT/E6, Ii-PADRE DNA and CIITA DNA to further improve DNA vaccine potency. We showed that DC-1 cells transfected with CIITA DNA exhibited increased MHC I/II expression resulting in enhanced antigen presentation through the MHC class I/II pathways. Furthermore, we found that co-administration of the combination of CRT/E6 DNA with CIITA DNA and Ii-PADRE further enhanced E6-specific CD8+ T cell immune responses and improved the antitumor effects against E7-expressing tumors. Thus, the combination of CIITA DNA with CRT/E6 and Ii-PADRE DNA vaccines represents a potentially effective means to enhance the potency of DNA vaccines. The clinical implications of the study are discussed.

Materials and Methods
Antibodies, Peptides, Cell Lines and Mice

The HPV-16 E6 (YDFAFRDL (SEQ ID NO: 138)) and PADRE (AKFVAAWTLKAAA (SEQ ID NO: 93)) peptides were synthesized by Macromolecular Resources (Denver, Colo.) at a purity of ≥70%. Antibodies against mouse CD4 (PE-conjugated, clone L3T4), IFN-γ (FITC-conjugated, clone XMG1.2), CD8a (PE-conjugated, clone Ly-1), I-A$^b$ (PE-conjugated, clone AF6-120.1), H-2K$^b$ (PE-conjugated, clone KH95), and H-2D$^b$ (PE-conjugated, clone AF6-88.5) were purchased from BD Pharmingen (San Jose, Calif.).

The immortalized DC line was kindly provided by Dr. Kenneth Rock (University of Massachusetts, Worcester, Mass.) (18). With continued passage, we have generated subclones of dendritic cells (DC-1) that are easily transfected using Lipofectamine 2000 (Invitrogen) (19). The production and maintenance of TC-1 have been described previously (20).

Six- to eight-week-old female C57BL/6 mice were purchased from the National Cancer Institute (Frederick, Md.) and housed in the oncology animal facility of the Johns Hopkins Hospital (Baltimore, Md.). All animal procedures were performed according to approved protocols and in accordance with recommendations for the proper use and care of laboratory animals.

Plasmid DNA Constructs and DNA Preparation

The generation of pcDNA-Ii and pcDNA-Ii-PADRE has been described previously (12). pcDNA3-CRT/E6 (9) was generated as described previously. The generation of the pcDNA3/F-CIITA and pcDNA3/F-CIITAΔ59-94 (pcDNA3-mtCIITA) expression vectors have been previously described (21). The DNA were amplified and purified as described previously (22).

Generation of PADRE-Specific CD4+ T Cell Line and E6-Specific CD8+ T Cell Line

Six-week-old female C57BL/6 mice were immunized with pcDNA3-Ii-PADRE by gene gun. After prime and booster vaccination at 1 week interval, splenocytes were harvested 1 week after the last vaccination. For initial in vitro stimulation, $5 \times 10^6$ splenocytes were pulsed with IL-2 (10 U/ml) and PADRE peptide (1 µg/ml) in RPMI media containing 10% FBS for 6 days. Propagation of the PADRE-specific CD4+ T cell line was performed in 24-well plates by mixing $1 \times 10^6$ splenocytes containing PADRE-specific CD4+ T cells with $1 \times 10^6$ irradiated DCs that were pulsed with PADRE peptide, and then cultured in RPMI media containing IL-2 (10 U/ml) for 6 days. This procedure was repeated weekly. Flow cytometry was performed to demonstrate the expression of the CD4 marker. The preparation of E6-specific CD8+ T cell line was performed similarly.

Transfection and Detection of MHC Class Molecules

DC-1 cells ($1.0 \times 10^6$) were transiently transfected with pcDNA3, pcDNA3-mtCIITA or pcDNA3-CIITA plasmid constructs using Lipfectamine 2000 according to the vendor's manual. Cells were grown at 37° C. and 5% $CO_2$. At 24 h after transfection, the effects of CIITA on the expression of MHC class I and II molecules were characterized by flow cytometry. Naïve DC-1 cells or DC-1 cells cotransfected with the same plasmid constructs (pcDNA3, pcDNA3-mtCIITA or pcDNA3-CIITA) and pcDNA-Ii or pcDNA-Ii-PADRE ($5 \times 10^4$/well) were mixed with PADRE-specific CD4+ T cells ($5 \times 10^5$/well) in 24 well plates.

Naïve DC-1 cells or DC-1 cells transiently cotransfected with the plasmid constructs pcDNA3, pcDNA3-mtCIITA or pcDNA3-CIITA and pcDNA3 or pcDNA3-CRT/E6 ($5 \times 10^4$/well) were mixed with E6-specific CD8+ T cells ($5 \times 10^5$/well) in 24 well plates. Cells were cultured at 37° C. and 5% $CO_2$ for 24 hrs. After mixed culture, the cells were subjected to intracellular cytokine staining with fluorescein-conjugated anti-mouse IFN-γ.

DNA Vaccination Using a Gene Gun

DNA-coated gold particles were prepared according to a previously described protocol (22). DNA-coated gold particles were delivered to the shaved abdominal region of mice, using a helium-driven gene gun (Bio-Rad, Hercules, Calif.) with a discharge pressure of 400 lb/in². C57BL/6 mice were immunized with various combinations of the DNA constructs illustrated in Table 1. Each cartridge contained 1 µg of plasmid DNA mixture and mice received 2 shots/mouse of the DNA mixtures by gene gun bombardment for a total of 2 µg/mouse. Each mouse received a booster of the same regimen 1 week later.

Intracellular Cytokine Staining and Flow Cytometry Analysis

Splenocytes were harvested from mice (5 per group) 1 week or 60 days after the last vaccination. Prior to intracellular cytokine staining, $5 \times 10^6$/mouse of pooled splenocytes from each vaccination group were incubated for 16 h with 1 µl/ml of E6 peptide (YDFAFRDL (SEQ ID NO: 138)) containing an MHC class I (H-2K$^b$ or D$^b$) epitope (aa 50-57) for detecting antigen-specific CD8+ T-cell precursors or MHC class II (I-A$^b$) PADRE peptide (AKFVAAWTLKAAA (SEQ ID NO: 93)) for detecting antigen-specific CD4+ T cell precursors in the presence of GolgiPlug (BD Pharmingen, San Diego, Calif.). Intracellular IFN-γ staining and flow cytometry analysis were performed as described previously (22). Analysis was performed on a Becton-Dickinson FACScan with CELLQuest software (Becton Dickinson Immunocytometry System, Mountain View, Calif., USA).

In Vivo Tumor Treatment Experiment

For the tumor treatment experiment, C57BL/6 mice (5 per group) were challenged with 5×10$^4$/mouse of TC-1 tumor cells by subcutaneous injection in the right leg. At 3 days after challenge with TC-1 tumor cells, mice were administered via gene gun 2 μg/mouse of each designated plasmid DNA mixture three times at 4-day intervals. Tumor growth was monitored by visual inspection and palpation twice weekly as described previously (20).

Long-Term In Vivo Tumor Protection Experiment

For long-term tumor protection experiment, mice (5 per group) were vaccinated via gene gun with 2 μg/mouse of each designated plasmid DNA mixture. After 1 week, mice were boosted with the same regimen as the first vaccination. At day 60 after the last vaccination, mice were subcutaneously challenged with 1×10$^5$/mouse of TC-1 tumor cells in the right leg. Tumor growth was monitored by visual inspection and palpation twice weekly as described previously (20).

Tumor Measurement and Conditional Survival

Three dimensional tumor sizes were measured two or three times per week with Vernier calipers. Tumor sizes were approximated by multiplying the measured lengths. From day 25 after challenging tumor cells, tumors were measured every other day, and mice with tumor sizes >19 mm in diameter or projected tumor volumes >10% body weight or >2700 mm$^3$ were considered moribund and sacrificed. Tumor volume was calculated using the following formula: V=(L×W×D), where V is tumor volume, L is length, W is width, and D is depth. All of the animal studies were approved by the Institutional Animal Care and use Committee at Johns Hopkins Hospital (Baltimore, Md.).

Statistical Analysis

All data expressed as mean±s.d. are representative of at least two different experiments. Comparisons between individual data points were made using a Student's t-test. Kaplan-Meier survival curves for tumor treatment and protection experiments were applied; for differences between curves, p-values were calculated using the log-rank test. The value of p<0.05 was considered significant.

Results

DC-1 Cells Transfected with CIITA DNA Lead to Higher Expression of MHC I and II Molecules.

We have previously developed a dendritic cell line, DC-1 that can be transfected with DNA with high efficiency (19). To characterize the expression of MHC class I and II molecules in DC-1 cells transfected with CIITA DNA, we performed flow cytometry analysis using antibodies specific for MHC I H-2 K$^b$, D$^b$ or MHC II I-A$^b$. DC-1 cells transfected with mutant CIITA, vector backbone DNA or untransfected were used as controls. The expression of MHC class I and II molecules on transfected DC-1 cells were characterized by flow cytometry, 24 hrs after transfection. As shown in FIG. 25, DC-1 cells transfected with CIITA DNA expressed higher levels of MHC I and II molecules compared to DC-1 cells transfected with the control constructs or nontransfected cells. Thus, our data indicate that transfection of DC-1 cells with CIITA DNA leads to increased expression of MHC class I and II molecules.

DCs Transfected with CIITA DNA Lead to Enhanced Antigen Presentation Through the MHC Class I and II Pathways.

Figure 26:
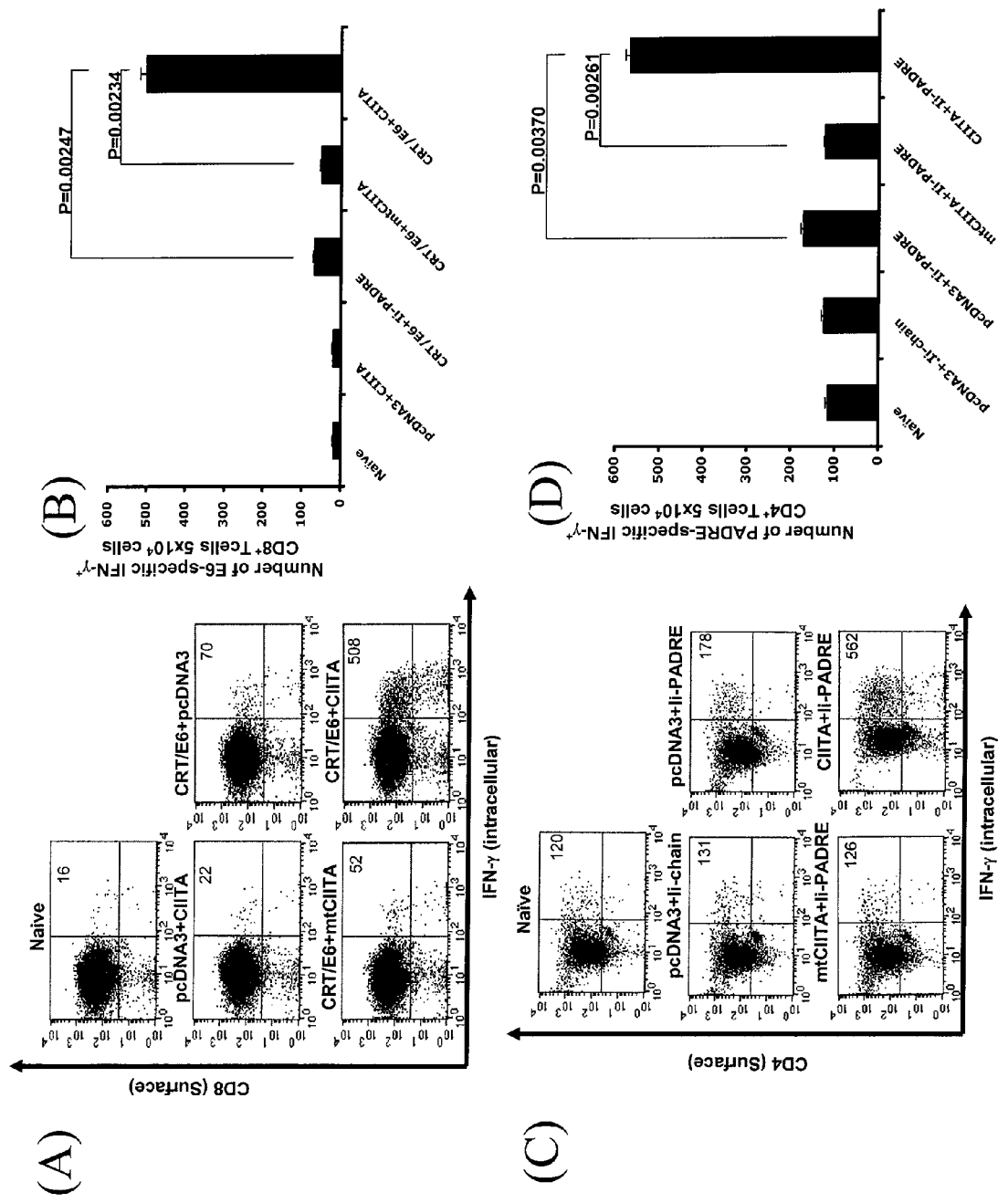
FIG. 26: Characterization of the MHC class I and II presentation of DCs transfected with CIITA DNA. DCs were cotransfected with CIITA DNA and CRT/E6 DNA (A & B) or Ii-PADRE DNA (C & D). The DCs were then incubated with E6-specific CD8+ T cells (A & B) or PADRE-specific CD4+ T cells (C & D) overnight. The activation of antigen-specific T cells was characterized by intracellular cytokine staining followed by flow cytometry analysis using IFN-γ and CD4 or CD8-specific antibodies. A and C. Representative flow cytometry data showing the numbers of activated E6-specific CD8+ T cells (A) and PADRE-specific CD4+ T cells (C) after incubation with the cotransfected DCs. B and D. Bar graphs depicting the numbers of E6-specific CD8+ T cells (B) and PADRE-specific CD4+ T cells (D) (means±s.d.). The data presented in this figure are from one representative experiment of two performed.

We then characterized the antigen presentation through MHC class I pathways in DCs cotransfected with CRT/E6 DNA and CIITA DNA. The transfected DCs were then incubated with E6-specific CD8+ T cells overnight. The degree of MHC class I presentation of E6 would correlate with the number of IFN-γ secreting activated E6-specific T cells. The activation of E6-specific CD8+ T cells was characterized by intracellular cytokine staining followed by flow cytometry analysis. As shown in FIG. 26A, DC-1 cells cotransfected with CRT/E6 DNA and CIITA DNA generated significantly higher numbers of activated E6-specific CD8+ T cells compared to DC-1 cells transfected with CRT/E6 DNA and mutant CIITA. A graphical representation of the number of activated E6-specific CD8+ T cells is depicted in FIG. 26B. Taken together, our data indicate that the increased MHC class I expression mediated by CIITA has led to enhanced MHC class I presentation of E6 in DC-1 cells transfected with CRT/E6 DNA.

We also characterized the antigen presentation through MHC class II pathway in DCs cotransfected with Ii-PADRE DNA and CIITA DNA. The transfected DCs were incubated with PADRE-specific CD4+ T cells overnight. The increased in MHC class II presentation of PADRE would lead to an increased number of IFN-γ secreting activated PADRE-specific T cells. We characterized the activation of PADRE-specific CD4+ T cells using intracellular cytokine staining followed by flow cytometry analysis. As shown in FIG. 26C, DC-1 cells cotransfected with CIITA DNA and Ii-PADRE DNA generated significantly higher numbers of activated PADRE-specific CD4+ T cells compared to DC-1 cells transfected with Ii-PADRE DNA and mutant CIITA. A graphical representation of the number of PADRE-specific CD4+ T cells is depicted in FIG. 26D. Thus, our data similarly suggest that the increased MHC class II expression mediated by CIITA led to enhanced MHC class II presentation of PADRE in DC-1 cells transfected with Ii-PADRE DNA.

Co-Administration of CRT/E6 DNA with CIITA DNA Leads to Enhanced E6-Specific CD8+ T Cell Immune Responses in Vaccinated Mice.

Figure 27:
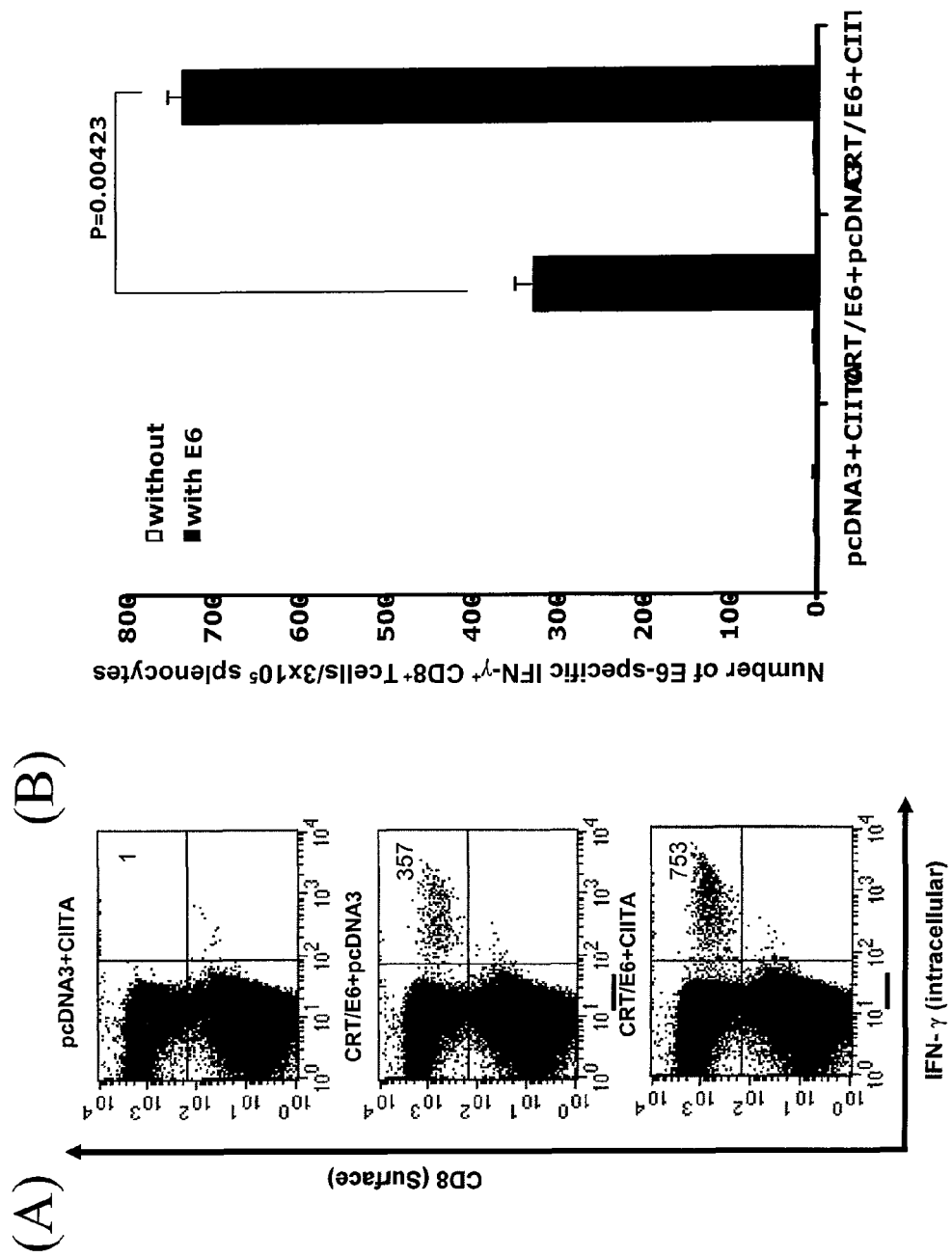
FIG. 27: Characterization of the E6-specific CD8+ T cell immune responses in mice vaccinated with CIITA DNA and CRT/E6 DNA. C57BL/6 mice (5 per group) were immunized with 2 µg/mouse of CIITA and/or CRT/E6 DNA twice with a 1-week interval. Splenocytes from vaccinated mice were harvested 1 week after the last vaccination and characterized for E6-specific CD8+ T cells using intracellular IFN-γ staining followed by flow cytometry analysis. A. Representative flow cytometry data for the E6-specific CD8+ T cell immune responses. The numbers in the upper right-hand corner represent the number of E6-specific IFN-γ-secreting CD8+ T cells per $5 \times 10^6$ pooled splenocytes. B. Bar graphs depicting the numbers of E6-specific IFN-γ-secreting CD8+ T cells per $5 \times 10^6$ pooled splenocytes (means±s.d.). The data presented in this figure are from one representative experiment of two performed.
Figure 32:
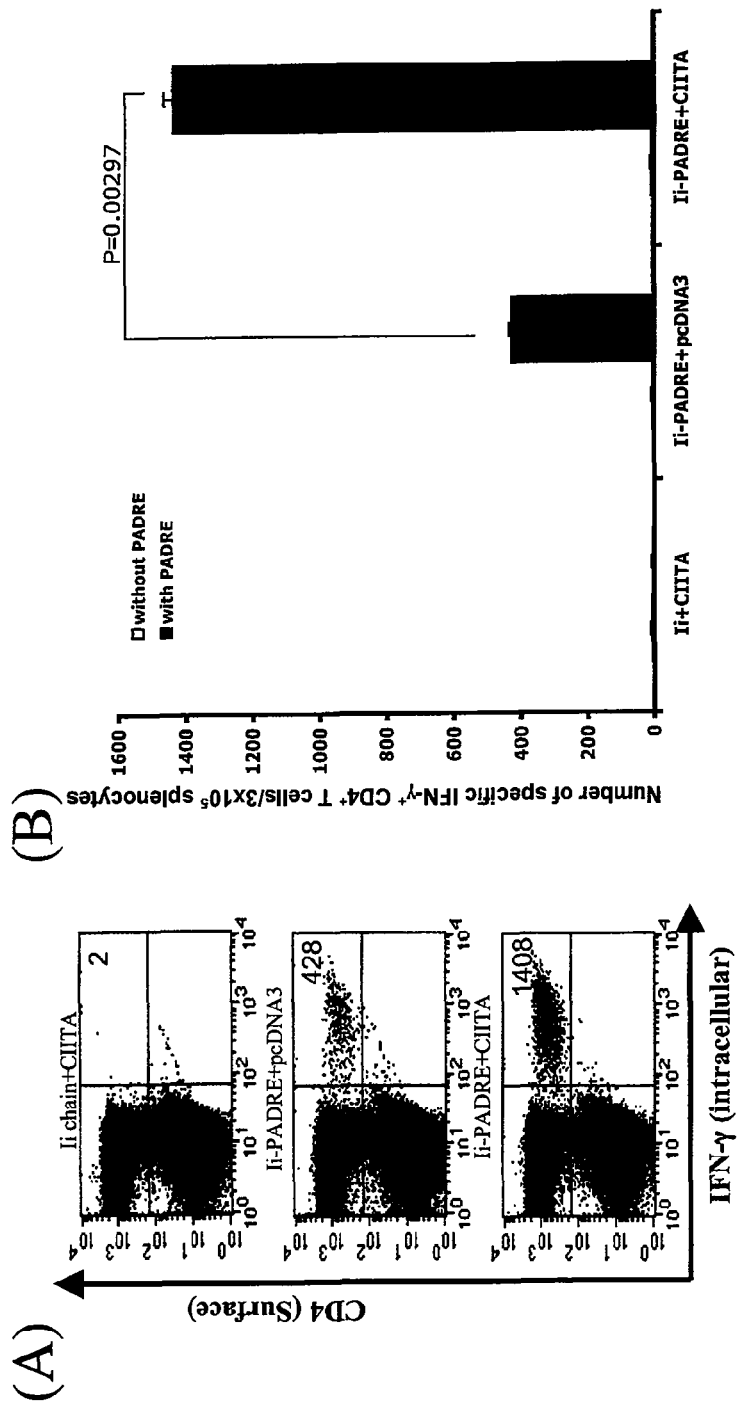
FIG. 32: Characterization of the PADRE-specific CD4+ T cell immune responses in mice vaccinated with CIITA and Ii-PADRE DNA vaccines. C57BL/6 mice (5 per group) were immunized with 2 µg/mouse of CIITA and/or Ii-PADRE DNA. Splenocytes from vaccinated mice were harvested 1 week after the last vaccination and were characterized for PADRE-specific CD4+ T cells using intracellular IFN-γ staining followed by flow cytometry analysis. A. Representative flow cytometry data for the PADRE-specific CD4+ T cell immune responses. The numbers in the upper right-hand corner represent the number of PADRE-specific IFN-γ-secreting CD4+ T cells per $5 \times 10^6$ pooled splenocytes. B. Bar graphs depicting the numbers of PADRE-specific IFN-γ-secreting CD4+ T cells per $5 \times 10^6$ pooled splenocytes (means+/−s.d.). The data presented in this figure are from one representative experiment of two performed.

We further characterized the antigen-specific CD8+ T cell immune responses in C57BL/6 mice vaccinated with CRT/E6 DNA in conjunction with CIITA DNA or pcDNA3. Mice vaccinated with pcDNA3 with CIITA DNA were used as a negative control. One week after the last vaccination, we measured the E6-specific CD8+ cell immune responses in vaccinated mice using intracellular IFN-γ staining followed by flow cytometry analysis. As shown in FIG. 27, mice vaccinated with both CRT/E6 DNA and CIITA DNA generated the highest numbers of E6-specific CD8+ T cells among the various groups. We also characterized the antigen-specific CD4+ T cell immune responses in mice vaccinated with Ii-PADRE DNA in conjunction with CIITA DNA or pcDNA3. Mice vaccinated with Ii-chain DNA with CIITA DNA were used as a negative control. We observed that mice vaccinated with Ii-PADRE DNA and CIITA DNA generated the highest numbers of PADRE-specific CD4+ T cells among all the vaccinated groups (FIG. 32). Thus, our data indicate that the increased MHC class I and II presentation by CIITA is capable of enhancing both the antigen-specific CD8+ and CD4+ T cell immune responses in vaccinated mice.

Coadministration of CRT/E6 DNA with CIITA DNA and Ii-PADRE Further Enhances E6-Specific CD8+ T Cell Immune Responses in Vaccinated Mice.

Figure 33:
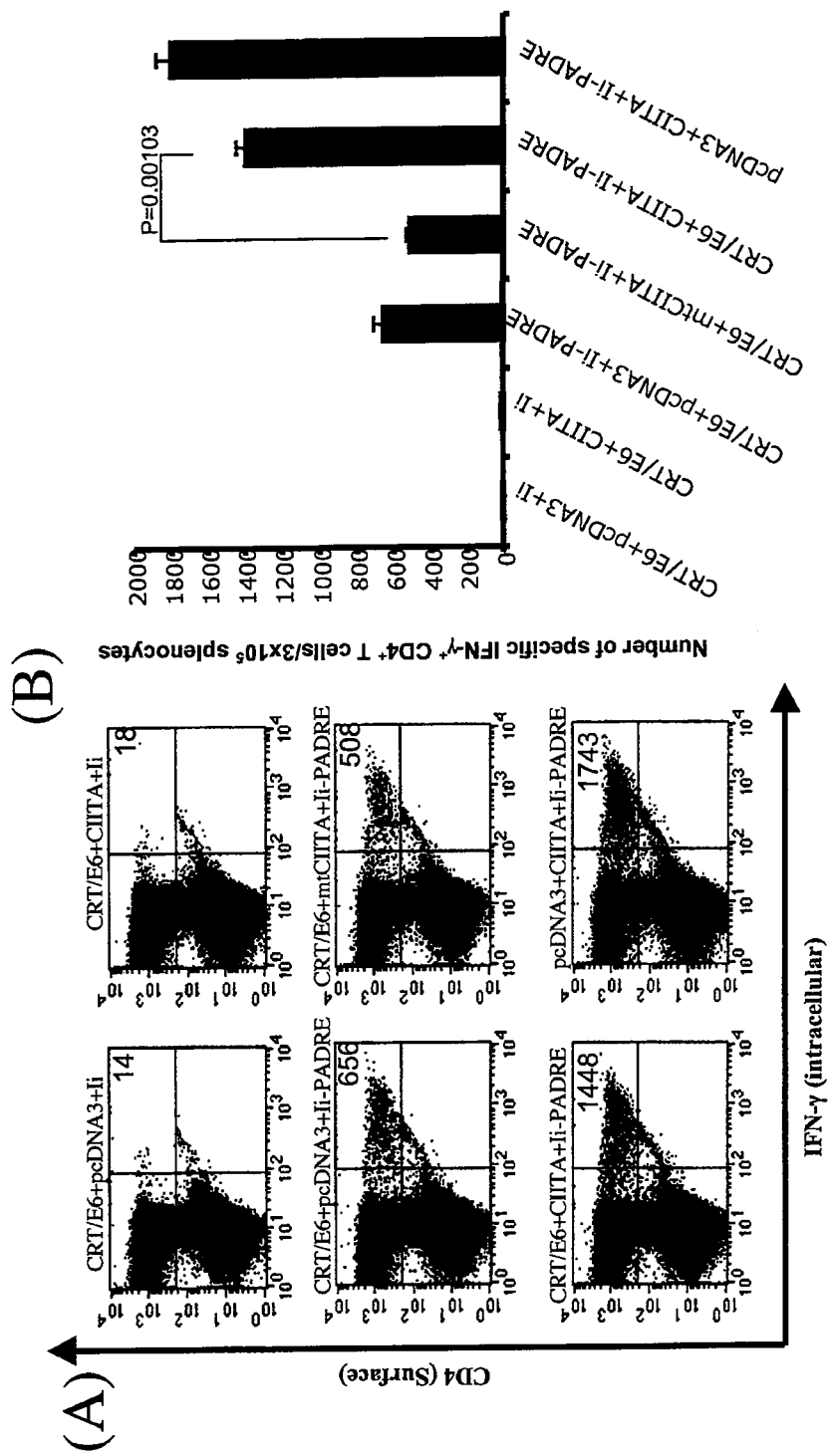
FIG. 33: Characterization of the PADRE-specific CD4+ T cell immune responses in mice vaccinated with CRT6/E6, CIITA DNA and Ii-PADRE DNA vaccines. C57BL/6 mice (5 per group) were immunized with 2 µg/mouse twice with a 1-week interval of the DNA combinations listed in Table 1. Splenocytes from vaccinated mice were harvested 1 week after the last vaccination and were characterized for PADRE-specific CD4+ T cells using intracellular IFN-γ staining followed by flow cytometry analysis. A. Representative flow cytometry data. The numbers in the upper right-hand corner represent the number of PADRE-specific CD4+ T cells per $5 \times 10^6$ pooled splenocytes. B. Bar graphs depicting the numbers of PADRE-specific CD4+ T cells per $5 \times 10^6$ pooled splenocytes (means+/−s.d.). The data presented in this figure are from one representative experiment of two performed.
Figure 34:
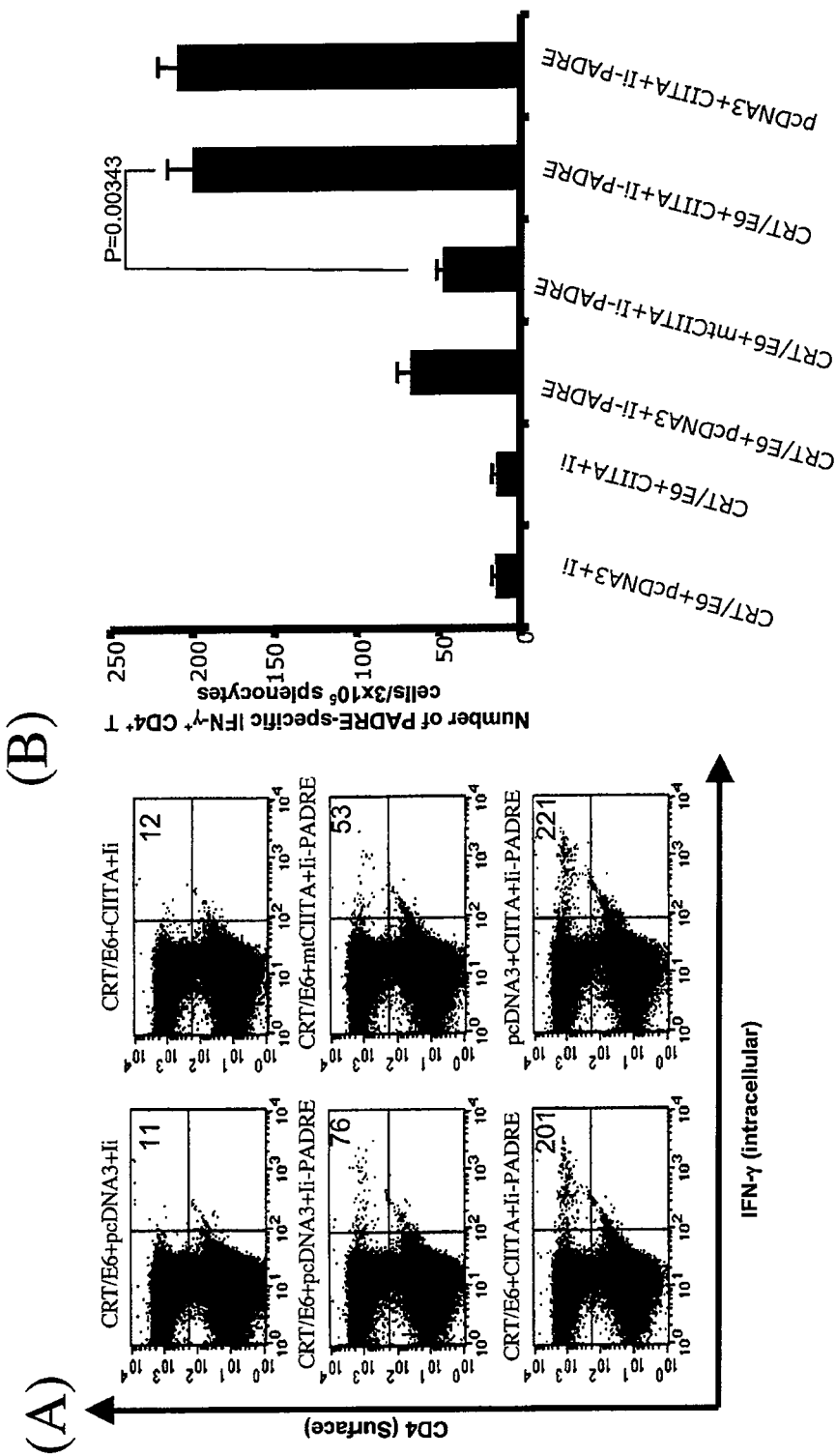
FIG. 34: Characterization of the long-term PADRE-specific CD4+ T cell immune response in mice vaccinated with CRT6/E6, CIITA DNA and Ii-PADRE DNA vaccines. C57BL/6 mice (5 per group) were immunized with 2 µg/mouse twice with a 1-week interval of the DNA combinations listed in Table 1. Splenocytes from vaccinated mice were harvested 60 days after the last vaccination and were characterized for PADRE-specific CD4+ T cells using intracellular IFN-γ staining followed by flow cytometry analysis. A. Representative flow cytometry data. The numbers in the upper right-hand corner represent the number of memory PADRE-specific CD4+ T cells per $5 \times 10^6$ pooled splenocytes. B. Bar graphs depicting the numbers of memory PADRE-specific CD4+ T cells per $5 \times 10^6$ pooled splenocytes (means+/−s.d.). The data presented in this figure are from one representative experiment of two performed.

We recently demonstrated that DNA vaccines encoding HPV-16 E6 and/or E7 antigens co-administered with Ii-PA- DRE could improve the HPV antigen-specific CD8+ T cell immune responses in vaccinated mice (12). Since the strategy to enhance CD4+ T cell help represents a different strategy to enhance DNA vaccine potency, we explored if this strategy (Ii-PADRE) can be combined with the strategies to enhance MHC class I/II presentation (CIITA) to further enhance the antigen-specific T cell immune responses in vaccinated mice. Thus, we vaccinated C57BL/6 mice with the combinations of DNA constructs illustrated in Table 1. One week after the last vaccination, we measured the E6-specific CD8+ cell immune responses in vaccinated mice using intracellular IFN-γ staining followed by flow cytometry analysis. As shown in FIG. 28, mice vaccinated with CRT/E6, Ii-PADRE and CIITA DNA generated significantly higher numbers of E6-specific CD8+ T cells compared to mice vaccinated with CRT/E6, Ii-PADRE and with pcDNA3 DNA (p=0.00343) or with mutant CIITA DNA (p=0.00201). We also characterized the PADRE-specific CD4+ T cell immune responses in vaccinated mice. We found that mice vaccinated with CRT/E6, Ii-PADRE and CIITA DNA generated significantly higher number of PADRE-specific CD4+ T cells compared to vaccination with CRT/E6, Ii-PADRE and mtCIITA DNA (FIG. 33). Thus, our results suggest that co-administration of CRT/E6 DNA with CIITA DNA and Ii-PADRE DNA further enhances E6-specific CD8+ T cell immune responses in vaccinated mice.

TABLE 1

Vaccinations of Mice with various DNA combination with pcDNA3-CIITA**

| Mouse Group # | Names of the DNA Constructs used in the Mixtures* | | | Notes |
|---|---|---|---|---|
| 1 | pcDNA3-CRT/E6 | pcDNA3 | pcDNA3-Ii | |
| 2 | pcDNA3-CRT/E6 | pcDNA3-CIITA | pcDNA3-Ii | |
| 3 | pcDNA3-CRT/E6 | pcDNA3 | pcDNA3-Ii-PADRE | |
| 4 | pcDNA3-CRT/E6 | pcDNA3-mtCIITA | pcDNA3-Ii-PADRE | |
| 5 | pcDNA3-CRT/E6 | pcDNA3-CIITA | pcDNA3-Ii-PADRE | |
| 6 | pcDNA3 | pcDNA3-CIITA | pcDNA3-Ii-PADRE | |
| Amount of DNA in one bullet | 0.33 µg | 0.33 µg | 0.33 µg | Total DNA = 1.0 µg/bullet |

**C57BL/6 mice (5 per group) were administered 2 bullets of the DNA mixtures twice with a 1-wk interval.
*pcDNA3 Vector backbone for all plasmids; CRT calreticulin E6 HPV type-16 E6 protein; CIITA MHC class II transactivator; Ii Invariant chain; PADRE Pan HLA DR-binding epitope Treatment with a Combination of CIITA DNA, CRT/E6 and Ii-PADRE DNA Leads to Enhanced Antitumor Effects and Prolonged Survival in TC-1 Tumor-Bearing Mice.

Figure 29:
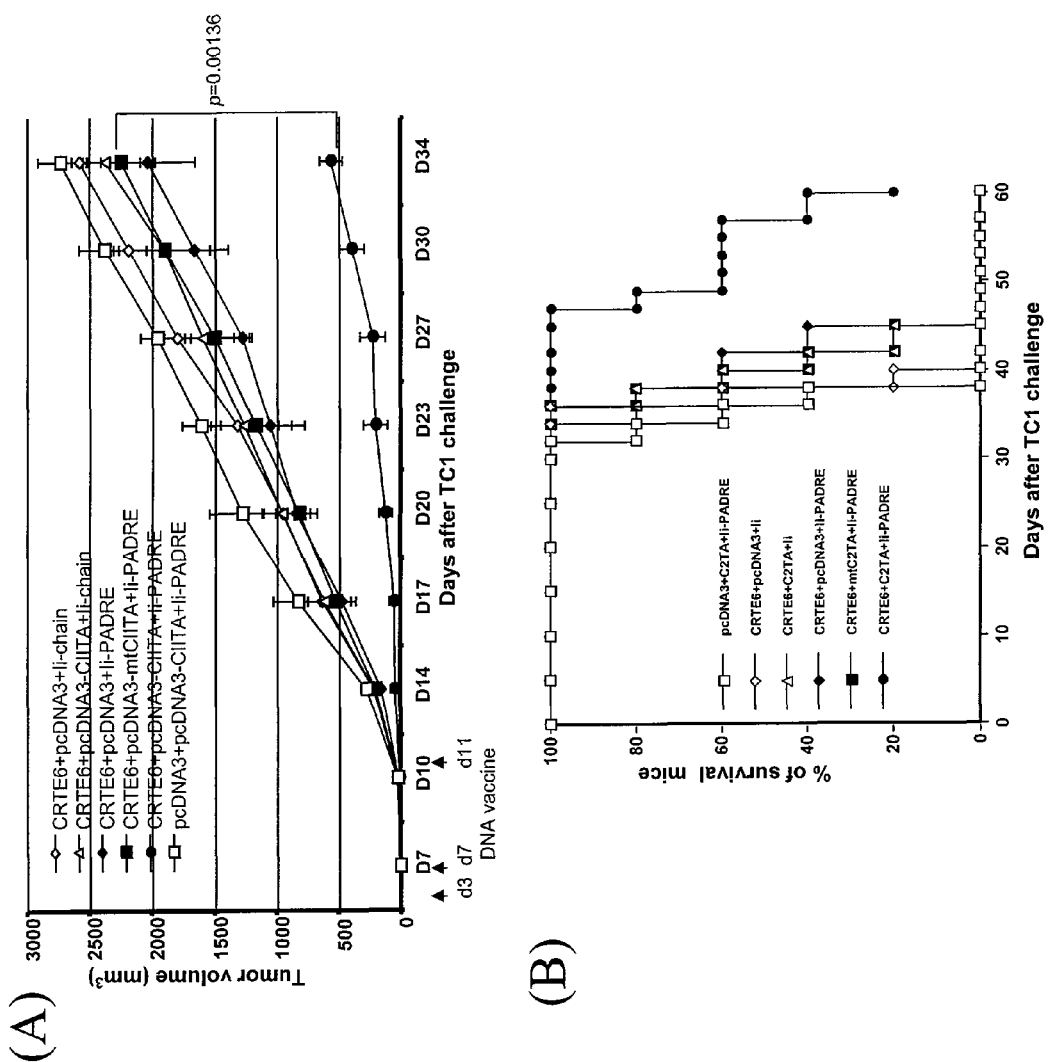
FIG. 29: In vivo tumor treatment experiments. C57BL/6 mice (5 per group) were first challenged with $5 \times 10^4$/mouse of TC-1 tumor cells by subcutaneous injection. Three days after tumor challenge, the mice were administered 2 µg DNA/mouse 3 times with 4-day intervals of the various DNA vaccine mixtures listed in Table 1. The mice were monitored for evidence of tumor growth by inspection and palpation twice a week. Tumor volumes were measured starting from day 7 after tumor challenge. (A) Line graph depicting the tumor volumes in mice of different tumor treatments (means±s.d.). (B) Kaplan & Meier survival analysis in mice of the tumor treatment experiments. The data shown here are from one representative experiment of two performed.

In order to determine if the enhanced E6-specific T cell response generated by co-administration of the combination of CIITA, CRT/E6 and Ii-PADRE DNA translates into therapeutic antitumor effects, we performed in vivo tumor treatment experiments using an HPV-16 E6/E7-expressing tumor model, TC-1. C57BL/6 mice were first challenged subcutaneously with TC-1 tumor cells and then, three days later, treated with the combinations of DNA constructs illustrated in Table 1. The treated mice were monitored for tumor growth. As shown in FIG. 29A, tumor-bearing mice treated with the combination of CRT/E6, CIITA DNA and Ii-PADRE DNA exhibited significantly decreased tumor growth compared to the tumor-bearing mice treated with CRT/E6, Ii-PADRE DNA and the mutant CIITA DNA (p=0.00136). We also performed Kaplan-Meier survival analysis of the treated mice. As shown in FIG. 29B, tumor-challenged mice treated with the combination of CRT/E6, CIITA DNA and Ii-PADRE DNA also exhibited significantly prolonged survival compared to the other treatment groups. Thus, our data indicates that treatment with a combination of CIITA DNA, CRT/E6 and Ii-PADRE DNA leads to enhanced antitumor effects and prolonged survival in TC-1 tumor-bearing mice.

Co-Administration of CRT/E6 DNA with CIITA DNA and Ii-PADRE Leads to Enhanced E6-Specific CD8+ Memory T Cells in Vaccinated Mice.

Figure 30:
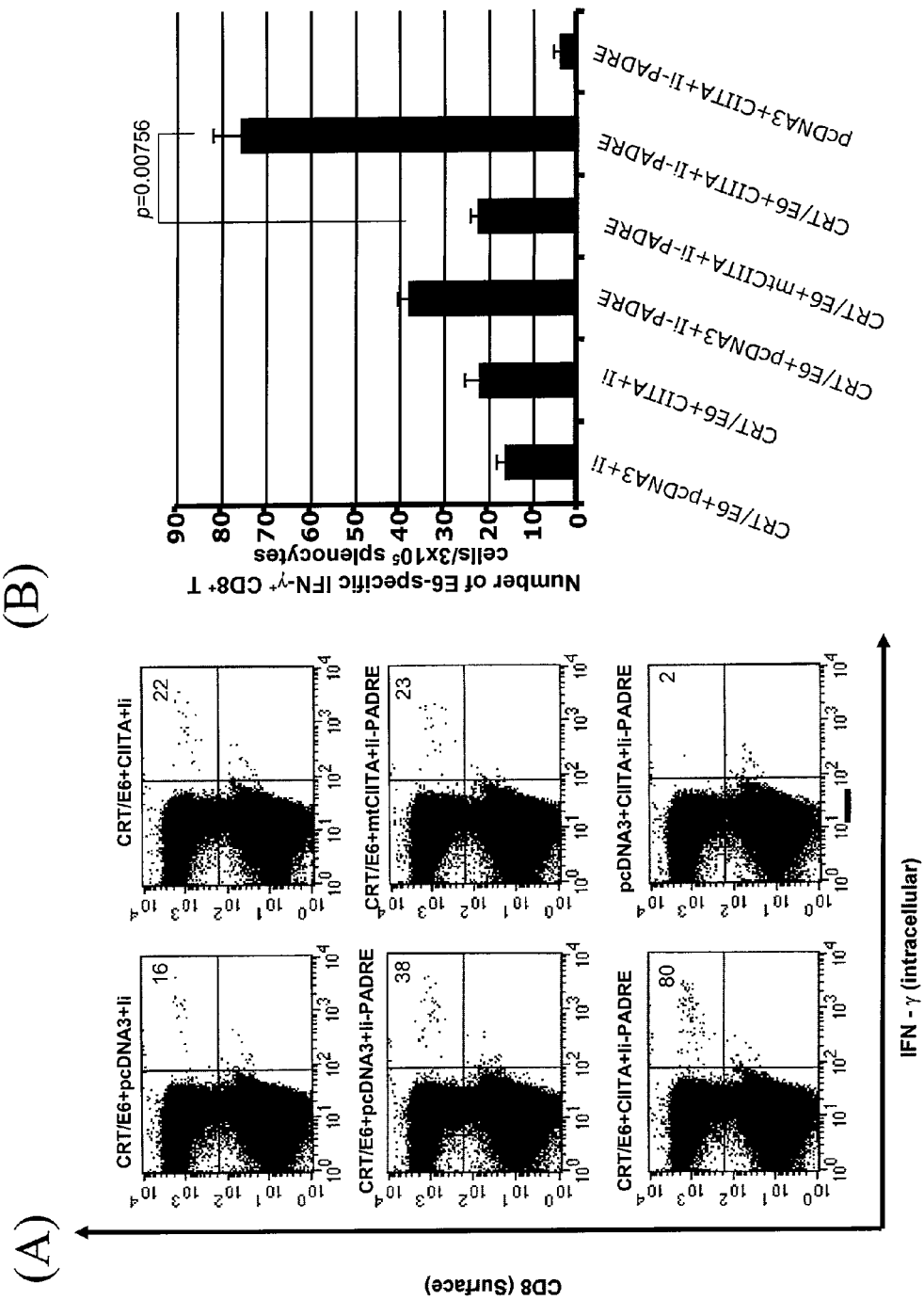
FIG. 30: Characterization of the long-term E6-specific CD8+ T cell immune response in mice vaccinated with CRT/E6, CIITA DNA and Ii-PADRE DNA vaccines. C57BL/6 mice (5 per group) were immunized with 2 µg/mouse twice with a 1-wk interval of the DNA combinations listed in Table 1. Splenocytes from vaccinated mice were harvested 60 days after the last vaccination and characterized for E6-specific CD8+ T cells using intracellular IFN-γ staining followed by flow cytometry analysis. A. Representative flow cytometry data. The numbers in the upper right-hand corner represent the number of memory E6-specific IFN-γ-secreting CD8+ T per $5 \times 10^6$ pooled splenocytes. B. Bar graphs depicting the numbers of memory E6-specific IFN-γ-secreting CD8+ T cells per $5 \times 10^6$ pooled splenocytes (means±s.d.). The data presented in this figure are from one representative experiment of two performed.

We also characterized the long-term antigen specific immune responses to vaccination with the combination of CIITA, CRT/E6 and Ii-PADRE DNA. C57BL/6 mice were vaccinated with the combinations of DNA constructs illustrated in Table 1. Sixty days later, we measured the E6-specific CD8+ cell immune responses in vaccinated mice using intracellular IFN-γ staining followed by flow cytometry analysis. As shown in FIG. 30, vaccination with CRT/E6, Ii-PADRE and CIITA DNA generated higher numbers of E6-specific CD8+ memory T cells compared to vaccination with CRT/E6 and Ii-PADRE with mutant CIITA DNA (p=0.00756). We also determined the PADRE-specific CD4+ T cell long-term immune responses in mice vaccinated with CRT/E6, Ii-PADRE and CIITA DNA compared to the other DNA construct combinations. Mice vaccinated with CRT/E6, Ii-PADRE and CIITA DNA generated significantly higher number of PADRE-specific CD4+ T memory cells compared to vaccination with CRT/E6, Ii-PADRE and mtCIITA DNA (data not shown). Thus, our data indicate that co-administration of CRT/E6 DNA with CIITA DNA and Ii-PADRE leads to enhanced E6-specific CD8+ memory T cells in vaccinated mice.

Co-Administration of CRT/E6 DNA with CIITA DNA and Ii-PADRE Leads to Long-Term Protection Against TC-1 Tumors and Prolonged Survival in Vaccinated Mice.

Figure 31:
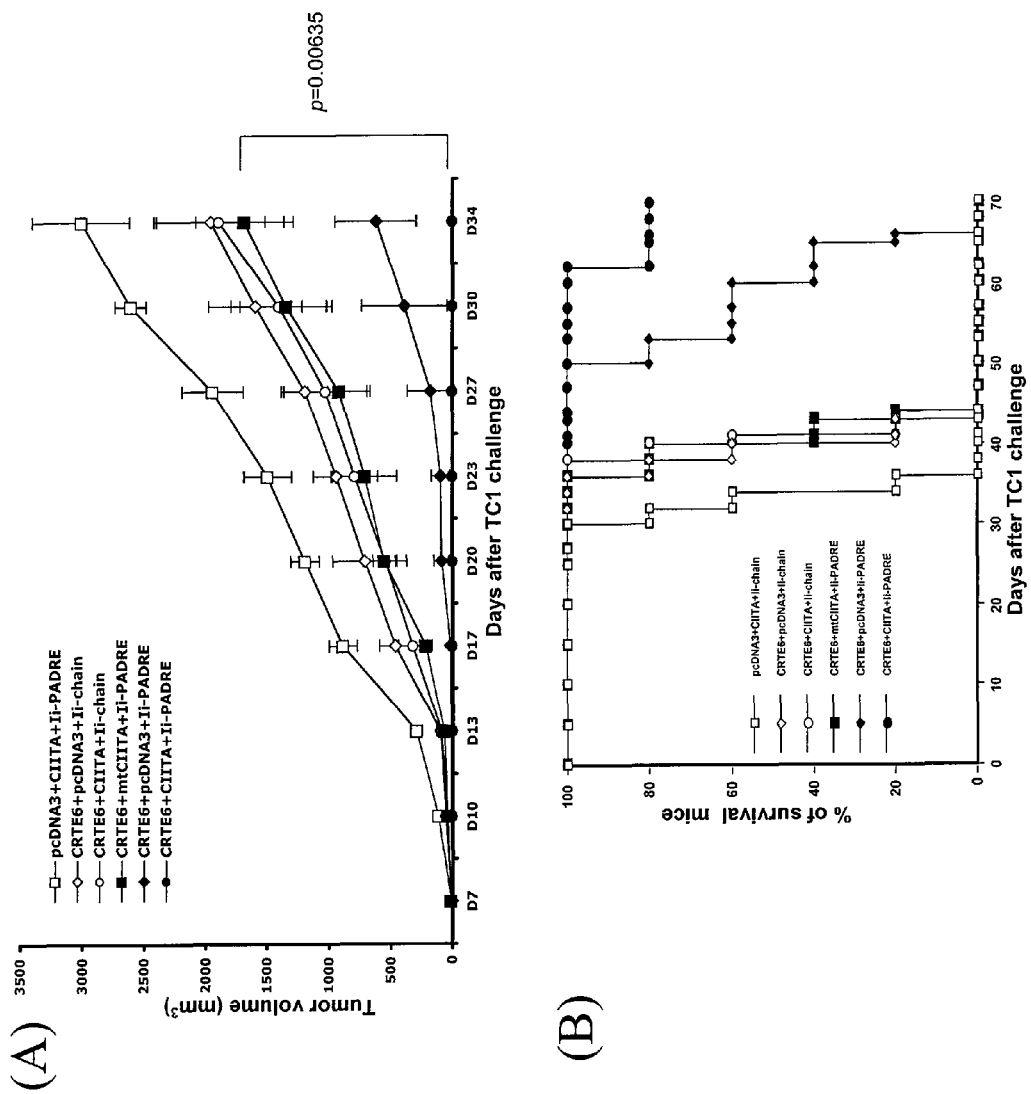
FIG. 31: Long-term in vivo tumor protection experiments. C57BL/6 mice (5 per group) were immunized with 2 µg DNA/mouse twice with a 1-week interval of the various DNA vaccine mixtures listed in Table 1. Two months after the last vaccination, the mice were challenged by subcutaneous injection of $1 \times 10^5$/mouse of TC-1 cells. The mice were monitored for evidence of tumor growth by inspection and palpation twice a week. Tumor volumes were measured starting from day 7 after tumor challenge. (A) Line graph depicting tumor volume in mice challenged with TC-1 cells (means±s.d.). (B) Kaplan & Meier survival analysis in mice challenged with TC-1 cells. The data shown here are from one representative experiment of two performed.

To determine whether the observed increase in E6-specific CD8+ memory T cells generated by the combination of CIITA DNA, CRT/E6 and Ii-PADRE DNA could be translated into long-term protective anti-tumor effects, we performed long-term in vivo tumor protection experiments. C57BL/6 mice were vaccinated with the various DNA constructs illustrated in Table 1. Two months after the last vaccination, immunized mice were subcutaneously challenged with TC-1 tumor cells and then monitored for tumor growth. As shown in FIG. 31A, mice vaccinated with CIITA DNA, CRT/E6 DNA and Ii-PADRE DNA demonstrated almost complete inhibition of tumor growth compared to mice vaccinated with CRT/E6 DNA, Ii-PADRE DNA and the mutant CIITA DNA. We also performed Kaplan Meier survival analysis. As shown in FIG. 31, we observed significantly prolonged survival in these mice. These data suggest that the co-administration of the combination of CIITA DNA and Ii-PADRE DNA can further enhance the ability of CRT/E6 DNA to generate long-term protective antitumor effects against TC-1 tumors in vaccinated mice.

Discussion

In the current study, we employed a combination of DNA vaccines encoding CRT/E6, Ii-PADRE DNA and CIITA DNA to further improve DNA vaccine potency. We showed that DC-1 cells transfected with CIITA DNA exhibited enhanced MHC I/II expression leading to improved antigen presentation through the MHC class I/II pathways. Co-administration of the combination of CRT/E6 DNA with CIITA DNA and Ii-PADRE further enhanced E6-specific CD8+ T cell immune responses and the antitumor effects in TC-1 tumor-bearing mice. Vaccination with the combination vaccine also led to enhanced E6-specific CD8+ memory T cell response, long-term protection against TC-1 tumors and prolonged survival in vaccinated mice. Thus, the combination of CIITA DNA with CRT/E6 and Ii-PADRE DNA vaccines represents a promising approach to further enhance the potency of DNA vaccines.

The employment of gene gun administration is important for the success of the current strategy. All these strategies most likely require the direct delivery of DNA into the DCs in order to effectively influence the priming of the T cells. For example, intracellular targeting strategies using CRT require the linked antigen to be directly targeted to the endoplasmic reticulum in order enhance the antigen processing. Furthermore, the Ii-PADRE DNA strategy requires the induction of CD4+ T helper cells in the vicinity of antigen-specific CD8+ T cells in order to enhance T cell activation. Finally, the strategy employing CIITA DNA is required to be delivered directly to the DCs so that it can increased expression of MHC class I/II molecules on its surface, leading to enhanced MHC class I/II antigen processing and presentation. Thus, all the strategies employed in the current study rely heavily on the intradermal delivery of antigen via gene gun.

In our study, we have successfully employed DNA vaccines encoding the CIITA DNA to enhance DNA vaccine potency. Previously, the CIITA has been used in other vaccine systems, particularly tumor-cell based vaccines to successfully improve vaccine potency (23-26). Furthermore, tumor cells transfected with CIITA and/or CD80 has been shown to activate tumor-specific CD4+ T cells (25, 26). Thus, the employment CIITA has been shown to be promising in the enhancement of cancer vaccine potency.

It is important to identify the best vaccine for future clinical translation. DNA vaccines employing different strategies to improve vaccine potency modify the properties of DCs through different, complementary mechanisms. In our study, we showed that the intradermal administration of the combination of CRT/E6, Ii-PADRE and CIITA DNA vaccines generated the best E6-specific CD8+ T cell immune responses and antitumor effects against TC-1 tumors. Each of the DNA constructs employs strategies to modify the properties of DCs through different mechanisms. It is likely that the potency of this combination of DNA vaccines can be further enhanced by the addition of a DNA vaccine employing a strategy that operates through another mechanism. For example, one potential strategy is to modify the properties of DCs using co-administration of DNA encoding antiapoptotic proteins. We have previously shown that co-administration of DNA vaccines with DNA encoding antiapoptotic proteins such Bcl-xL has led to the prolonged life of DCs, resulting in significant enhancement of antigen-specific CD8+ T cell immune responses (27). It would be of interest to see if this antiapoptotic strategy can be combined with the aforementioned DNA vaccine strategies to further enhance DNA vaccine potency for eventual clinical translation.

In summary, we have identified an innovative strategy to increase the expression of MHC class I/II molecules on DCs to enhance DNA vaccine potency. This strategy can potentially be used in other antigenic systems for the control of infectious diseases and cancer.

REFERENCES

1. Porgador, A., K. R. Irvine, A. Iwasaki, B. H. Barber, N. P. Restifo, and R. N. Germain. 1998. Predominant role for directly transfected dendritic cells in antigen presentation to CD8+ T cells after gene gun immunization. *J Exp Med* 188:1075-1082.
2. Condon, C., S. C. Watkins, C. M. Celluzzi, K. Thompson, and L. D. Falo, Jr. 1996. DNA-based immunization by in vivo transfection of dendritic cells. *Nat Med* 2:1122-1128.
3. Hung, C. F., M. Yang, and T. C. Wu. 2006. Modifying professional antigen-presenting cells to enhance DNA vaccine potency. *Methods Mol Med* 127:199-220.
4. Tsen, S. W., A. H. Paik, C. F. Hung, and T. C. Wu. 2007. Enhancing DNA vaccine potency by modifying the properties of antigen-presenting cells. *Expert Rev Vaccines* 6:227-239.
5. Cheng, W. F., C. F. Hung, C. Y. Chai, K. F. Hsu, L. He, M. Ling, and T. C. Wu. 2001. Tumor-specific immunity and antiangiogenesis generated by a DNA vaccine encoding calreticulin linked to a tumor antigen. *J Clin Invest* 108:669-678.
6. Nash, P. D., M. Opas, and M. Michalak. 1994. Calreticulin: not just another calcium-binding protein. *Mol Cell Biochem* 135:71-78.
7. Spee, P., and J. Neefjes. 1997. TAP-translocated peptides specifically bind proteins in the endoplasmic reticulum, including gp96, protein disulfide isomerase and calreticulin. *Eur J Immunol* 27:2441-2449.
8. Sadasivan, B., P. J. Lehner, B. Ortmann, T. Spies, and P. Cresswell. 1996. Roles for calreticulin and a novel glycoprotein, tapasin, in the interaction of MHC class 1 molecules with TAP. *Immunity* 5:103-114.
9. Peng, S., H. Ji, C. Trimble, L. He, Y. C. Tsai, J. Yeatermeyer, D. A. Boyd, C. F. Hung, and T. C. Wu. 2004. Development of a DNA vaccine targeting human papillomavirus type 16 oncoprotein E6. *J Virol* 78:8468-8476.
10. Castellino, F., and R. N. Germain. 2006. Cooperation between CD4+ and CD8+ T cells: when, where, and how. *Ann Rev Immunol* 24:519-540.
11. Alexander, J., J. Sidney, S. Southwood, J. Ruppert, C. Oseroff, A. Maewal, K. Snoke, H. M. Serra, R. T. Kubo, A. Sette, and et al. 1994. Development of high potency universal DR-restricted helper epitopes by modification of high affinity DR-blocking peptides. *Immunity* 1:751-761.
12. Hung, C. F., Y. C. Tsai, L. He, and T. C. Wu. 2007. DNA vaccines encoding Ii-PADRE generates potent PADRE-specific CD4+ T-cell immune responses and enhances vaccine potency. *Mol Ther* 15:1211-1219.
13. Kim, D., T. Hoory, T. C. Wu, and C. F. Hung. 2007. Enhancing DNA vaccine potency by combining a strategy to prolong dendritic cell life and intracellular targeting strategies with a strategy to boost CD4+ T cell. *Human gene therapy* 18:1129-1139.
14. Ting, J. P., and J. Trowsdale. 2002. Genetic control of MHC class II expression. *Cell* 109 Suppl:S21-33.
15. Reith, W., S. LeibundGut-Landmann, and J. M. Waldburger. 2005. Regulation of MHC class II gene expression by the class II transactivator. *Nat Rev Immunol* 5:793-806.
16. Martin, B. K., K. C. Chin, J. C. Olsen, C. A. Skinner, A. Dey, K. Ozato, and J. P. Ting. 1997. Induction of MHC class I expression by the MHC class II transactivator CIITA. *Immunity* 6:591-600.
17. Gobin, S. J., A. Peijnenburg, V. Keijsers, and P. J. van den Elsen. 1997. Site alpha is crucial for two routes of IFN gamma-induced MHC class I transactivation: the ISRE-mediated route and a novel pathway involving CIITA. *Immunity* 6:601-611.
18. Shen, Z., G. Reznikoff, G. Dranoff, and K. L. Rock. 1997. Cloned dendritic cells can present exogenous antigens on both MHC class I and class II molecules. *J Immunol* 158:2723-2730.
19. Kim, T. W., C. F. Hung, D. A. Boyd, L. He, C. T. Lin, D. Kaiserman, P. I. Bird, and T. C. Wu. 2004. Enhancement of DNA vaccine potency by coadministration of a tumor antigen gene and DNA encoding serine protease inhibitor-6. *Cancer Res* 64:400-405.
20. Lin, K. Y., F. G. Guarnieri, K. F. Staveley-O'Carroll, H. I. Levitsky, J. T. August, D. M. Pardoll, and T. C. Wu. 1996. Treatment of established tumors with a novel vaccine that enhances major histocompatibility class II presentation of tumor antigen. *Cancer Res* 56:21-26.
21. Greer, S. F., J. A. Harton, M. W. Linhoff, C. A. Janczak, J. P. Ting, and D. E. Cressman. 2004. Serine residues 286, 288, and 293 within the CIITA: a mechanism for down-regulating CIITA activity through phosphorylation. *J Immunol* 173:376-383.
22. Chen, C. H., T. L. Wang, C. F. Hung, Y. Yang, R. A. Young, D. M. Pardoll, and T. C. Wu. 2000. Enhancement of DNA vaccine potency by linkage of antigen gene to an HSP70 gene. *Cancer Res* 60:1035-1042.
23. Armstrong, T. D., V. K. Clements, B. K. Martin, J. P. Ting, and S. Ostrand-Rosenberg. 1997. Major histocompatibility complex class I-transfected tumor cells present endogenous antigen and are potent inducers of tumor-specific immunity. *Proceedings of the National Academy of Sciences of the United States of America* 94:6886-6891.
24. Dissanayake, S. K., J. A. Thompson, J. J. Bosch, V. K. Clements, P. W. Chen, B. R. Ksander, and S. Ostrand-Rosenberg. 2004. Activation of tumor-specific CD4(+) T lymphocytes by major histocompatibility complex class II tumor cell vaccines: a novel cell-based immunotherapy. *Cancer Res* 64:1867-1874.
25. Thompson, J. A., S. K. Dissanayake, B. R. Ksander, K. L. Knutson, M. L. Disis, and S. Ostrand-Rosenberg. 2006. Tumor cells transduced with the MHC class II Transactivator and CD80 activate tumor-specific CD4+ T cells whether or not they are silenced for invariant chain. *Cancer Res* 66:1147-1154.
26. Thompson, J. A., M. K. Srivastava, J. J. Bosch, V. K. Clements, B. R. Ksander, and S. Ostrand-Rosenberg. 2008. The absence of invariant chain in MHC II cancer vaccines enhances the activation of tumor-reactive type 1 CD4(+) T lymphocytes. *Cancer Immunol Immunother* 57:389-398.
27. Kim, T. W., C. F. Hung, M. Ling, J. Juang, L. He, J. M. Hardwick, S. Kumar, and T. C. Wu. 2003. Enhancing DNA vaccine potency by coadministration of DNA encoding antiapoptotic proteins. *J Clin Invest* 112:109-117.

All references cited above are all incorporated by reference herein, in their entirety, whether specifically incorporated or not. All publications, patents, patent applications, GenBank sequences and ATCC deposits, cited herein are hereby expressly incorporated by reference for all purposes. In particular, all nucleotide sequences, amino acid sequences, nucleic construes, DNA vaccines, methods of administration, particular orders of administration of DNA vaccines and agents that are described in the patents, patent applications and other publications referred to herein or authored by one or more of the inventors of this application are specifically incorporated by reference herein. In case of conflict, the definitions within the instant application govern.

Having now fully described this invention, it will be appreciated by those skilled in the art that the same can be performed within a wide range of equivalent parameters, concentrations, and conditions without departing from the spirit and scope of the invention and without undue experimentation.

The invention claimed is:

1. A composition comprising a first nucleic acid encoding the amino acid sequence of a fusion protein as set forth in SEQ ID NO: 91, wherein the fusion protein stimulates a CD4+ immune response; and a second nucleic acid encoding an antigen, wherein the first nucleic acid enhances a CD8+ T cell immune response generated from the second nucleic acid.

2. The composition of claim 1, wherein the antigen is linked to an immunogenicity potentiating peptide (IPP).

3. The composition of claim 2, wherein the IPP is selected from the group consisting of a cytoplasmic chaperone protein, an endoplasmic reticulum chaperone protein, a viral intercellular spreading protein, a cytoplasmic translocation polypeptide domain of a pathogenic toxin, and a polypeptide that targets the centrosome compartment of a cell, a protein involved in sorting of the lysosome-associated membrane protein type 1.

4. The composition of claim 3, wherein the IPP is calreticulin (CRT), N-CRT, P-CRT, C-CRT, *Mycobacterium tuberculosis* HSP70, a protein consisting of amino acids 517-625 of *M. tuberculosis* HSP70, a protein consisting of amino acids 161-370 and 517-625 of *M. tuberculosis* HSP70, 7-tubulin, Sig/LAMP-1 or VP22.

5. A composition comprising a first nucleic acid encoding the amino acid sequence of a fusion protein as set forth in SEQ ID NO: 91, wherein the fusion protein stimulates a CD4+ immune response; a second nucleic acid encoding protein comprising the amino acid sequence as set forth in SEQ ID NO: 95, wherein the composition stimulates a CD8+ T cell immune response; and a third nucleic acid encoding an antigen, wherein the first and second nucleic acids enhance a CD8+ T cell immune response generated from the third nucleic acid.

6. The composition of claim 1, further comprising a chemotherapeutic drug.

7. The composition of claim 6, wherein the chemotherapeutic drug is selected from the group consisting of epigallocatechin-3-gallate (EGCG), 5,6 di-methylxanthenone-4-acetic acid (DMXAA), cisplatin, apigenin, doxorubicin, an anti-death receptor 5 antibody, a proteasome inhibitor, an inhibitor of DNA methylation, genistein, celecoxib and biologically active analogs thereof.

8. A kit comprising a first nucleic acid encoding the amino acid sequence of a fusion protein as set forth in SEQ ID NO: 91, wherein the fusion protein stimulates a CD4+ immune response; and a second a nucleic acid encoding protein comprising the amino acid sequence set forth in SEQ ID NO: 95 or a second nucleic acid encoding an antigen, wherein the first nucleic acid enhances a CD8+ T cell immune response generated from the second nucleic acid.

9. The composition of any one of claims 1 and 5, wherein the antigen is selected from the group consisting of HPV-16 E6, HPV-16 E7, and HPV-16 E6 and E7, optionally wherein the HPV-16 E6 and/or HPV-16 E7 are detoxified.

* * * * *

SEQUENCE LISTING

```
<160> NUMBER OF SEQ ID NOS: 138

<210> SEQ ID NO 1
<211> LENGTH: 5431
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gacggatcgg gagatctccc gatccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca tgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
```

```
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaacgg gccctctaga ctcgagcggc cgccactgtg ctggatatct gcagaattcc      960
accacactgg actagtggat ccgagctcgg taccaagctt aagtttaaac cgctgatcag     1020
cctcgactgt gccttctagt tgccagccat ctgttgtttg cccctccccc gtgccttcct     1080
tgaccctgga aggtgccact cccactgtcc tttcctaata aaatgaggaa attgcatcgc     1140
attgtctgag taggtgtcat tctattctgg ggggtggggt ggggcaggac agcaagggggg    1200 aggattggga agacaatagc aggcatgctg gggatgcggt gggctctatg cttctgagg      1260 cggaaagaac cagctggggc tctagggggt atccccacgc gccctgtagc ggcgcattaa     1320
gcgcggcggg tgtggtggtt acgcgcagcg tgaccgctac acttgccagc gccctagcgc     1380
ccgctccttt cgctttcttc ccttcctttc tcgccacgtt cgccggcttt ccccgtcaag     1440
ctctaaatcg gggcatccct ttagggttcc gatttagtgc tttacggcac ctcgacccca     1500
aaaaacttga ttagggtgat ggttcacgta gtgggccatc gccctgatag acggtttttc     1560
gccctttgac gttggagtcc acgttcttta atagtggact cttgttccaa actggaacaa     1620
cactcaaccc tatctcggtc tattcttttg atttataagg gattttgggg atttcggcct     1680
attggttaaa aaatgagctg atttaacaaa aatttaacgc gaattaattc tgtgaatgt      1740 gtgtcagtta gggtgtggaa agtccccagg ctccccaggc aggcagaagt atgcaaagca     1800
tgcatctcaa ttagtcagca accaggtgtg gaaagtcccc aggctcccca gcaggcagaa     1860
gtatgcaaag catgcatctc aattagtcag caaccatagt cccgccccta actccgccca     1920
tcccgcccct aactccgccc agttccgccc attctccgcc ccatggctga ctaattttttt    1980 ttatttatgc agaggccgag gccgcctctg cctctgagct attccagaag tagtgaggag     2040
gcttttttgg aggcctaggc ttttgcaaaa agctcccggg agcttgtata tccattttcg     2100
gatctgatca agagacagga tgaggatcgt ttcgcatgat tgaacaagat ggattgcacg     2160
caggttctcc ggccgcttgg gtggagaggc tattcggcta tgactgggca acagacaa      2220 tcggctgctc tgatgccgcc gtgttccggc tgtcagcgca ggggcgcccg gttcttttttg    2280 tcaagaccga cctgtccggt gccctgaatg aactgcagga cgaggcagcg cggctatcgt     2340
ggctggccac gacgggcgtt ccttgcgcag ctgtgctcga cgttgtcact gaagcgggaa     2400
gggactggct gctattgggc gaagtgccgg ggcaggatct cctgtcatct caccttgctc     2460
ctgccgagaa agtatccatc atggctgatg caatgcggcg gctgcatacg cttgatccgg     2520
ctacctgccc attcgaccac caagcgaaac atcgcatcga gcgagcacgt actcggatgg     2580
aagccggtct tgtcgatcag gatgatctgg acgaagagca tcaggggctc gcgccagccg     2640
aactgttcgc caggctcaag gcgcgcatgc ccgacggcga ggatctcgtc gtgacccatg     2700
gcgatgcctg cttgccgaat atcatggtgg aaaatggccg cttttctgga ttcatcgact     2760
gtggccggct gggtgtggcg gaccgctatc aggacatagc gttggctacc cgtgatattg     2820
ctgaagagct tggcggcgaa tgggctgacc gcttcctcgt gctttacggt atcgccgctc     2880
ccgattcgca gcgcatcgcc ttctatcgcc ttcttgacga gttcttctga gcgggactct     2940
ggggttcgaa atgaccgacc aagcgacgcc caacctgcca tcacgagatt tcgattccac     3000
cgccgccttc tatgaaaggt tgggcttcgg aatcgttttc cgggacgccg gctggatgat     3060
cctccagcgc ggggatctca tgctggagtt cttcgcccac cccaacttgt ttattgcagc     3120
```

```
ttataatggt tacaaataaa gcaatagcat cacaaatttc acaaataaag cattttttc      3180
actgcattct agttgtggtt tgtccaaact catcaatgta tcttatcatg tctgtatacc      3240
gtcgacctct agctagagct tggcgtaatc atggtcatag ctgtttcctg tgtgaaattg      3300
ttatccgctc acaattccac acaacatacg agccggaagc ataaagtgta aagcctgggg      3360
tgcctaatga gtgagctaac tcacattaat tgcgttgcgc tcactgcccg ctttccagtc      3420
gggaaacctg tcgtgccagc tgcattaatg aatcggccaa cgcgcgggga gaggcggttt      3480
gcgtattggg cgctcttccg cttcctcgct cactgactcg ctgcgctcgg tcgttcggct      3540
gcggcgagcg gtatcagctc actcaaaggc ggtaatacgg ttatccacag aatcaggggga     3600
taacgcagga aagaacatgt gagcaaaagg ccagcaaaag gccaggaacc gtaaaaaggc      3660
cgcgttgctg gcgttttcc ataggctccg ccccctgac gagcatcaca aaatcgacg       3720
ctcaagtcag aggtggcgaa acccgacagg actataaaga taccaggcgt ttcccctgg      3780
aagctccctc gtgcgctctc ctgttccgac cctgccgctt accggatacc tgtccgcctt     3840
tctcccttcg ggaagcgtgg cgctttctca atgctcacgc tgtaggtatc tcagttcggt     3900
gtaggtcgtt cgctccaagc tgggctgtgt gcacgaaccc cccgttcagc ccgaccgctg     3960
cgccttatcc ggtaactatc gtcttgagtc caacccggta agacacgact tatcgccact     4020
ggcagcagcc actggtaaca ggattagcag agcgaggtat gtaggcggtg ctacagagtt     4080
cttgaagtgg tggcctaact acggctacac tagaaggaca gtatttggta tctgcgctct     4140
gctgaagcca gttaccttcg gaaaaagagt tggtagctct tgatccggca acaaaccac      4200
cgctggtagc ggtggttttt ttgtttgcaa gcagcagatt acgcgcagaa aaaaggatc      4260
tcaagaagat cctttgatct tttctacggg gtctgacgct cagtggaacg aaaactcacg     4320
ttaagggatt ttggtcatga gattatcaaa aaggatcttc acctagatcc ttttaaatta     4380
aaaatgaagt tttaaatcaa tctaaagtat atatgagtaa acttggtctg acagttacca     4440
atgcttaatc agtgaggcac ctatctcagc gatctgtcta tttcgttcat ccatagttgc     4500
ctgactcccc gtcgtgtaga taactacgat acgggagggc ttaccatctg gccccagtgc     4560
tgcaatgata ccgcgagacc cacgctcacc ggctccagat ttatcagcaa taaaccagcc     4620
agccggaagg gccgagcgca gaagtggtcc tgcaacttta tccgcctcca tccagtctat     4680
taattgttgc cgggaagcta gagtaagtag ttcgccagtt aatagtttgc gcaacgttgt     4740
tgccattgct acaggcatcg tggtgtcacg ctcgtcgttt ggtatggctt cattcagctc     4800
cggttcccaa cgatcaaggc gagttacatg atccccatg ttgtgcaaaa aagcggttag      4860
ctccttcggt cctccgatcg ttgtcagaag taagttggcc gcagtgttat cactcatggt     4920
tatggcagca ctgcataatt ctcttactgt catgccatcc gtaagatgct tttctgtgac     4980
tggtgagtac tcaaccaagt cattctgaga atagtgtatg cggcgaccga gttgctcttg     5040
cccggcgtca atacgggata ataccgcgcc acatagcaga actttaaaag tgctcatcat     5100
tggaaaacgt tcttcggggc gaaaactctc aaggatctta ccgctgttga tccagttc      5160
gatgtaaccc actcgtgcac ccaactgatc ttcagcatct tttactttca ccagcgtttc     5220
tgggtgagca aaaacaggaa ggcaaaatgc cgcaaaaaag gaataagggc gacacggaa      5280
atgttgaata ctcatactct tcctttttca atattattga agcatttatc agggttattg     5340
tctcatgagc ggatacatat ttgaatgtat ttagaaaaat aaacaaatag gggttccgcg     5400
cacatttccc cgaaaagtgc cacctgacgt c                                    5431
```

<210> SEQ ID NO 2
<211> LENGTH: 4479
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

| | | | | | |
|---|---|---|---|---|---|
| tggccattgc | atacgttgta | tccatatcat | aatatgtaca | tttatattgg | ctcatgtcca | 60 |
| acattaccgc | catgttgaca | ttgattattg | actagttatt | aatagtaatc | aattacgggg | 120 |
| tcattagttc | atagcccata | tatggagttc | cgcgttacat | aacttacggt | aaatggcccg | 180 |
| cctggctgac | cgcccaacga | cccccgccca | ttgacgtcaa | taatgacgta | tgttcccata | 240 |
| gtaacgccaa | tagggacttt | ccattgacgt | caatgggtgg | agtatttacg | gtaaactgcc | 300 |
| cacttggcag | tacatcaagt | gtatcatatg | ccaagtacgc | cccctattga | cgtcaatgac | 360 |
| ggtaaatggc | ccgcctggca | ttatgcccag | tacatgacct | tatgggactt | tcctacttgg | 420 |
| cagtacatct | acgtattagt | catcgctatt | accatggtga | tgcggttttg | gcagtacatc | 480 |
| aatgggcgtg | gatagcggtt | tgactcacgg | ggatttccaa | gtctccaccc | cattgacgtc | 540 |
| aatgggagtt | tgttttggca | ccaaaatcaa | cgggactttc | caaaatgtcg | taacaactcc | 600 |
| gccccattga | cgcaaatggg | cggtaggcgt | gtacggtggg | aggtctatat | aagcagagct | 660 |
| cgtttagtga | accgtcagat | cgcctggaga | cgccatccac | gctgttttga | cctccataga | 720 |
| agacaccggg | accgatccag | cctccgcggc | cgggaacggt | gcattggaac | gcggattccc | 780 |
| cgtgccaaga | gtgacgtaag | taccgcctat | agagtctata | ggcccacccc | cttggcttct | 840 |
| tatgcatgct | atactgtttt | tggcttgggg | tctatacacc | cccgcttcct | catgttatag | 900 |
| gtgatggtat | agcttagcct | ataggtgtgg | gttattgacc | attattgacc | actccaacgg | 960 |
| tggagggcag | tgtagtctga | gcagtactcg | ttgctgccgc | gcgcgccacc | agacataata | 1020 |
| gctgacagac | taacagactg | ttcctttcca | tgggtctttt | ctgcagtcac | cgtcgtcgac | 1080 |
| ggtatcgata | agcttgatat | cgaattcacg | tgggcccggt | accgtatact | ctagagcggc | 1140 |
| cgcggatcca | gatctttttc | cctcgccaaa | aattatgggg | acatcatgaa | gccccttgag | 1200 |
| catctgactt | ctggctaata | aaggaaattt | atttcattgc | aatagtgtgt | tggaattttt | 1260 |
| tgtgtctctc | actcggaagg | acatatggga | gggcaaatca | tttaaaacat | cagaatcagt | 1320 |
| atttggttta | gagtttggca | acatatgcca | ttcttccgct | tcctcgctca | ctgactcgct | 1380 |
| gcgctcggtc | gttcggctgc | ggcgagcggt | atcagctcac | tcaaaggcgg | taatacggtt | 1440 |
| atccacagaa | tcaggggata | acgcaggaaa | gaacatgtga | gcaaaaggcc | agcaaaaggc | 1500 |
| caggaaccgt | aaaaaggccg | cgttgctggc | gtttttccat | aggctccgcc | ccctgacga | 1560 |
| gcatcacaaa | aatcgacgct | caagtcagag | gtggcgaaac | ccgacaggac | tataaagata | 1620 |
| ccaggcgttt | cccctggaa | gctccctcgt | gcgctctcct | gttccgaccc | tgccgcttac | 1680 |
| cggatacctg | tccgcctttc | tcccttcggg | aagcgtggcg | ctttctcaat | gctcacgctg | 1740 |
| taggtatctc | agttcggtgt | aggtcgttcg | ctccaagctg | ggctgtgtgc | acgaaccccc | 1800 |
| cgttcagccc | gaccgctgcg | ccttatccgg | taactatcgt | cttgagtcca | acccggtaag | 1860 |
| acacgactta | tcgccactgg | cagcagccac | tggtaacagg | attagcagag | cgaggtatgt | 1920 |
| aggcggtgct | acagagttct | tgaagtggtg | gcctaactac | ggctacacta | gaaggacagt | 1980 |
| atttggtatc | tgcgctctgc | tgaagccagt | taccttcgga | aaaagagttg | gtagctcttg | 2040 |
| atccggcaaa | caaaccaccg | ctggtagcgg | tggttttttt | gtttgcaagc | agcagattac | 2100 |

```
gcgcagaaaa aaaggatctc aagaagatcc tttgatcttt tctacggggt ctgacgctca    2160
gtggaacgaa aactcacgtt aagggatttt ggtcatgaga ttatcaaaaa ggatcttcac    2220
ctagatcctt ttaaattaaa aatgaagttt taaatcaatc taaagtatat atgagtaaac    2280
ttggtctgac agttaccaat gcttaatcag tgaggcacct atctcagcga tctgtctatt    2340
tcgttcatcc atagttgcct gactccgggg ggggggggcg ctgaggtctg cctcgtgaag    2400
aaggtgttgc tgactcatac cagggcaacg ttgttgccat tgctacaggc atcgtggtgt    2460
cacgctcgtc gtttggtatg gcttcattca gctccggttc ccaacgatca aggcgagtta    2520
catgatcccc catgttgtgc aaaaaagcgg ttagctcctt cggtcctccg atcgttgtca    2580
gaagtaagtt ggccgcagtg ttatcactca tggttatggc agcactgcat aattctctta    2640
ctgtcatgcc atccgtaaga tgcttttctg tgactggtga gtactcaacc aagtcattct    2700
gagaatagtg tatgcggcga ccgagttgct cttgcccggc gtcaatacgg gataataccg    2760
cgccacatag cagaacttta aaagtgctca tcattggaaa acgttcttcg gggcgaaaac    2820
tctcaaggat cttaccgctg ttgagatcca gttcgatgta acccactcgt gcacctgaat    2880
cgccccatca tccagccaga aagtgaggga gccacggttg atgagagctt tgttgtaggt    2940
ggaccagttg gtgattttga acttttgctt tgccacggaa cggtctgcgt tgtcgggaag    3000
atgcgtgatc tgatccttca actcagcaaa agttcgattt attcaacaaa gccgccgtcc    3060
cgtcaagtca gcgtaatgct ctgccagtgt tacaaccaat taaccaattc tgattagaaa    3120
aactcatcga gcatcaaatg aaactgcaat ttattcatat caggattatc ataccatat    3180 ttttgaaaaa gccgtttctg taatgaagga gaaaactcac cgaggcagtt ccataggatg    3240
gcaagatcct ggtatcggtc tgcgattccg actcgtccaa catcaataca acctattaat    3300
ttcccctcgt caaaaataag gttatcaagt gagaaatcac catgagtgac gactgaatcc    3360
ggtgagaatg gcaaaagctt atgcatttct ttccagactt gttcaacagg ccagccatta    3420
cgctcgtcat caaaatcact cgcatcaacc aaaccgttat tcattcgtga ttgcgcctga    3480
gcgagacgaa atacgcgatc gctgttaaaa ggacaattac aaacaggaat cgaatgcaac    3540
cggcgcagga acactgccag cgcatcaaca atattttcac ctgaatcagg atattcttct    3600
aatacctgga atgctgtttt cccggggatc gcagtggtga gtaaccatgc atcatcagga    3660
gtacggataa aatgcttgat ggtcggaaga ggcataaatt ccgtcagcca gtttagtctg    3720
accatctcat ctgtaacatc attggcaacg ctacctttgc catgtttcag aaacaactct    3780
ggcgcatcgg gcttcccata caatcgatag attgtcgcac ctgattgccc gacattatcg    3840
cgagcccatt tatacccata taaatcagca tccatgttgg aatttaatcg cggcctcgag    3900
caagacgttt cccgttgaat atggctcata acaccccttg tattactgtt tatgtaagca    3960
gacagtttta ttgttcatga tgatatattt ttatcttgtg caatgtaaca tcagagattt    4020
tgagacacaa cgtggctttc ccccccccc cattattgaa gcatttatca gggttattgt    4080
ctcatgagcg gatacatatt tgaatgtatt tagaaaaata acaaataggg gttccgcgc    4140 acatttcccc gaaaagtgcc acctgacgtc taagaaacca ttattatcat gacattaacc    4200
tataaaaata ggcgtatcac gaggcccttt cgtcctcgcg cgtttcggtg atgacggtga    4260
aaacctctga cacatgcagc tcccggagac ggtcacagct tgtctgtaag cggatgccgg    4320
gagcagacaa gcccgtcagg gcgcgtcagc gggtgttggc gggtgtcggg gctggcttaa    4380
ctatgcggca tcagagcaga ttgtactgag agtgcaccat atgcggtgtg aaataccgca    4440
```
cagatgcgta aggagaaaat accgcatcag attggctat                                4479

<210> SEQ ID NO 3
<211> LENGTH: 7648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | |
|---|---|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaacgg gccctctaga ctcgagcggc cgccactgtg ctggatatct gcagaattcc | 960 |
| accacactgg actagtggat ccatgcatgg agatacacct acattgcatg aatatatgtt | 1020 |
| agatttgcaa ccagagacaa ctgatctcta ctgttatgag caattaaatg acagctcaga | 1080 |
| ggaggaggat gaaatagatg gtccagctgg acaagcagaa ccggacagag cccattacaa | 1140 |
| tattgtaacc ttttgttgca agtgtgactc tacgcttcgg ttgtgcgtac aaagcacaca | 1200 |
| cgtagacatt cgtactttgg aagacctgtt aatgggcaca ctaggaattg tgtgccccat | 1260 |
| ctgttctcaa ggatccatgg ctcgtgcggt cgggatcgac ctcgggacca ccaactccgt | 1320 |
| cgtctcggtt ctggaaggtg gcgacccggt cgtcgtcgcc aactccgagg gctccaggac | 1380 |
| caccccgtca attgtcgcgt tcgccgcaa cggtgaggtg ctggtcggcc agcccgccaa | 1440 |
| gaaccaggca gtgaccaacg tcgatcgcac cgtgcgctcg gtcaagcgac acatgggcag | 1500 |
| cgactggtcc atagagattg acggcaagaa ataccaccgc ccggagatca gcgcccgcat | 1560 |
| tctgatgaag ctgaagcgcg acgccgaggc ctacctcggt gaggacatta ccgacgcggt | 1620 |
| tatcacgacg cccgcctact tcaatgacgc ccagcgtcag gccaccaagg acgccggcca | 1680 |
| gatcgccggc ctcaacgtgc tgcggatcgt caacgagccg accgcggccg cgctggccta | 1740 |
| cggcctcgac aagggcgaga aggagcagcg aatcctggtc ttcgacttgg gtggtggcac | 1800 |
| tttcgacgtt tccctgctgg agatcggcga gggtgtggtt gaggtccgtg ccacttcggg | 1860 |
| tgacaaccac ctcggcggcg acgactggga ccagcgggtc gtcgattggc tggtggacaa | 1920 |
| gttcaagggc accagcggca tcgatctgac caaggacaag atggcgatgc agcggctgcg | 1980 |

```
ggaagccgcc gagaaggcaa agatcgagct gagttcgagt cagtccacct cgatcaacct    2040
gccctacatc accgtcgacg ccgacaagaa cccgttgttc ttagacgagc agctgacccg    2100
cgcggagttc aacggatca ctcaggacct gctggaccgc actcgcaagc cgttccagtc     2160
ggtgatcgct gacaccggca tttcggtgtc ggagatcgat cacgttgtgc tcgtgggtgg    2220
ttcgacccgg atgcccgcgg tgaccgatct ggtcaaggaa ctcaccggcg gcaaggaacc    2280
caacaagggc gtcaaccccg atgaggttgt cgcggtggga gccgctctgc aggcggcgt     2340 cctcaagggc gaggtgaaag acgttctgct gcttgatgtt accccgctga gcctgggtat    2400
cgagaccaag ggcggggtga tgaccaggct catcgagcgc aacaccacga tccccaccaa    2460
gcggtcggag actttcacca ccgccgacga caaccaaccg tcggtgcaga tccaggtcta    2520 tcaggggag cgtgagatcg ccgcgcacaa caagttgctc gggtccttcg agctgaccgg     2580
catcccgccg gcgccgcggg ggattccgca gatcgaggtc actttcgaca tcgacgccaa    2640
cggcattgtg cacgtcaccg ccaaggacaa gggcaccggc aaggagaaca cgatccgaat    2700
ccaggaaggc tcgggcctgt ccaaggaaga cattgaccgc atgatcaagg acgccgaagc    2760
gcacgccgag gaggatcgca agcgtcgcga ggaggccgat gttcgtaatc aagccgagac    2820
attggtctac cagacggaga agttcgtcaa agaacagcgt gaggccgagg gtggttcgaa    2880
gttcgtaatc aagccgagac attggtctac cagacggaga agttcgtcaa agaacagcgt    2940
gaggccgagg gtggttcgaa ggtacctgaa gacacgctga acaaggttga tgccgcggtg    3000
gcggaagcga aggcggcact tggcggatcg gatatttcgg ccatcaagtc ggcgatggag    3060
aagctgggcc aggagtcgca ggctctgggg caagcgatct acgaagcagc tcaggctgcg    3120
tcacaggcca ctggcgctgc ccaccccggc tcggctgatg aaagcttaag tttaaaccgc    3180
tgatcagcct cgactgtgcc ttctagttgc cagccatctg ttgtttgccc ctccccgtg     3240 ccttccttga ccctggaagg tgccactccc actgtccttt cctaataaaa tgaggaaatt    3300
gcatcgcatt gtctgagtag gtgtcattct attctggggg gtggggtggg caggacagc     3360 aagggggagg attgggaaga caatagcagg catgctgggg atgcggtggg ctctatggct    3420
tctgaggcgg aaagaaccag ctggggctct aggggtatc cccacgcgcc ctgtagcggc     3480
gcattaagcg cggcgggtgt ggtggttacg cgcagcgtga ccgctacact tgccagcgcc    3540
ctagcgcccg ctcctttcgc tttcttccct tcctttctcg ccacgttcgc cggctttccc    3600
cgtcaagctc taaatcgggg catccctta gggttccgat ttagtgcttt acggcacctc     3660
gaccccaaaa aacttgatta gggtgatggt tcacgtagtg gccatcgcc ctgatagacg     3720 gttttttcgcc ctttgacgtt ggagtccacg ttctttaata gtggactctt gttccaaact    3780
ggaacaacac tcaaccctat ctcggtctat tcttttgatt tataagggat tttgggattt    3840
tcggcctatt ggttaaaaa tgagctgatt taacaaaaat ttaacgcgaa ttaattctgt      3900
ggaatgtgtg tcagttaggg tgtggaaagt ccccaggctc cccaggcagg cagaagtatg    3960
caaagcatgc atctcaatta gtcagcaacc aggtgtggaa agtccccagg ctccccagca    4020
ggcagaagta tgcaaagcat gcatctcaat tagtcagcaa ccatagtccc gcccctaact    4080
ccgcccatcc cgcccctaac tccgcccagt tccgcccatt ctccgcccca tggctgacta    4140 attttttta tttatgcaga ggccgaggcc gcctctgcct ctgagctatt ccagaagtag     4200
tgaggaggct ttttggagg cctaggcttt tgcaaaaagc tcccgggagc ttgtatatcc     4260
attttcggat ctgatcaaga dacaggatga ggatcgtttc gcatgattga acaagatgga    4320
ttgcacgcag gttctccggc cgcttgggtg gagaggctat tcggctatga ctgggcacaa    4380
```

```
cagacaatcg gctgctctga tgccgccgtg ttccggctgt cagcgcaggg gcgcccggtt    4440 cttttgtca agaccgacct gtccggtgcc ctgaatgaac tgcaggacga ggcagcgcgg      4500
ctatcgtggc tggccacgac gggcgttcct tgcgcagctg tgctcgacgt tgtcactgaa    4560
tgcaggacga ggcagcgcgg ctatcgtggc tggccacgac gggcgttcct tgcgcagctg    4620
tgctcgacgt tgtcactgaa gcgggaaggg actggctgct attgggcgaa gtgccggggc    4680
aggatctcct gtcatctcac cttgctcctg ccgagaaagt atccatcatg gctgatgcaa    4740
tgcggcggct gcatacgctt gatccggcta cctgcccatt cgaccaccaa gcgaaacatc    4800
gcatcgagcg agcacgtact cggatggaag ccggtcttgt cgatcaggat gatctggacg    4860
aagagcatca ggggctcgcg ccagccgaac tgttcgccag gctcaaggcg cgcatgcccg    4920
acggcgagga tctcgtcgtg acccatggcg atggctgctt gccgaatatc atggtggaaa    4980
atggccgctt ttctggattc atcgactgtg gccggctggg tgtggcggac cgctatcagg    5040
acatagcgtt ggctacccgt gatattgctg aagagcttgg cggcgaatgg gctgaccgct    5100
tcctcgtgct ttacggtatc gccgctcccg attcgcagcg catcgccttc tatcgccttc    5160
ttgacgagtt cttctgagcg ggactctggg gttcgaaatg accgaccaag cgacgcccaa    5220
cctgccatca cgagatttcg attccaccgc cgccttctat gaaaggttgg gcttcggaat    5280
cgttttccgg gacgccggct ggatgatcct ccagcgcggg gatctcatgc tggagttctt    5340
cgcccacccc aacttgttta ttgcagctta taatggttac aaataaagca atagcatcac    5400
aaatttcaca aataaagcat tttttcact gcattctagt tgtggtttgt ccaaactcat      5460
caatgtatct tatcatgtct gtataccgtc gacctctagc tagagcttgg cgtaatcatg    5520
gtcatagctg tttcctgtgt gaaattgtta tccgctcaca attccacaca acatacgagc    5580
cggaagcata aagtgtaaag cctggggtgc ctaatgagtg agctaactca cattaattgc    5640
gttgcgctca ctgcccgctt tccagtcggg aaacctgtcg tgccagctgc attaatgaat    5700
cggccaacgc gcggggagag gcggtttgcg tattgggcgc tcttccgctt cctcgctcac    5760
tgactcgctg cgctcggtcg ttcggctgcg gcgagcggta tcagctcact caaaggcggt    5820
aatacggtta tccacagaat cagggggataa cgcaggaaag aacatgtgag caaaaggcca    5880
gcaaaaggcc aggaaccgta aaaaggccgc gttgctggcg catcacaaaa atcgacgctc    5940
aagtcagagg tggcgaaacc cgacaggact ataaagatac caggcgtttc ccccctggaag   6000 ctccctcgtg cgctctcctg ttccgaccct gccgcttacc ggatacctgt ccgcctttct    6060
cccttcggga agcgtggcgc tttctcaatg ctcacgctgt aggtatctca gttcggtgta    6120
ggtcgttcgc tccaagctgg gctgtgtgca cgaaccccc gttcagcccg accgctgcgc     6180
cttatccggt aactatcgtc ttgagtccaa cccggtaaga cacgacttat cgccactggc    6240
agcagccact ggtaacagga ttagcagagc gaggtatgta ggcggtgcta cagagttctt    6300
gaagtggtgg cctaactacg gctacactag aaggacagta tttggtatct gcgctctgct    6360
gaagccagtt accttcggaa aaagagttgg tagctcttga tccggcaaac aaaccaccgc    6420
tggtagcggt ggtttttttg tttgcaagca gcagattacg cgcagaaaaa aaggatctca    6480
agaagatcct ttgatctttt ctacgggtc tgacgctcag tggaacgaaa actcacgtta     6540
agggattttg gtcatgagat tatcaaaaag gatcttcacc tagatccttt taaattaaaa    6600
atgaagtttt aaatcaatct aaagtatata tgagtaaact tggtctgaca gttaccaatg    6660
cttaatcagt gaggcaccta tctcagcgat ctgtctattt cgttcatcca tagttgcctg    6720
```

```
actccccgtc gtgtagataa ctacgatacg ggagggctta ccatctggcc ccagtgctgc   6780
aatgataccg cgagacccac gctcaccggc tccagattta tcagcaataa accagccagc   6840
cggaagggcc gagcgcagaa gtggtcctgc aactttatcc gcctccatcc agtctattaa   6900
ttgttgccgg gaagctagag taagtagttc gccagttaat agtttgcgca acgttgttgc   6960
cattgctaca ggcatcgtgg tgtcacgctc gtcgtttggt atggcttcat tcagctccgg   7020
ttcccaacga tcaaggcgag ttacatgatc ccccatgttg tgcaaaaaag cggttagctc   7080
cttcggtcct ccgatcgttg tcagaagtaa gttggccgca gtgttatcac tcatggttat   7140
ggcagcactg cataattctc ttactgtcat gccatccgta agatgctttt ctgtgactgg   7200
tgagtactca accaagtcat tctgagaata gtgtatgcgg cgaccgagtt gctcttgccc   7260
ggcgtcaata cgggataata ccgcgccaca tagcagaact ttaaaagtgc tcatcattgg   7320
aaaacgttct cggggcgaaa actctcaag gatcttaccg ctgttgagat ccagttcgat   7380
gtaacccact cgtgcaccca actgatcttc agcatctttt actttcacca gcgtttctgg   7440
gtgagcaaaa acaggaaggc aaaatgccgc aaaaaaggga ataagggcga cacggaaatg   7500
ttgaatactc atactcttcc tttttcaata ttattgaagc atttatcagg gttattgtct   7560
catgagcgga tacatatttg aatgtattta gaaaaataaa caaatagggg ttccgcgcac   7620
atttccccga aaagtgccac ctgacgtc                                       7648
```

<210> SEQ ID NO 4
<211> LENGTH: 6221
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
gacggatcgg gagatctccc gatccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagaattca    960
tgcgcctgca ctttcccgag ggcggcagcc tggccgcgct gaccgcgcac caggcttgcc   1020
acctgccgct ggagactttc acccgtcatc gccagccgcg cggctgggaa caactggagc   1080
```

```
agtgcggcta tccggtgcag cggctggtcg ccctctacct ggcggcgcgg ctgtcgtgga    1140
accaggtcga ccaggtgatc cgcaacgccc tggccagccc cggcagcggc ggcgacctgg    1200
gcgaagcgat ccgcgagcag ccggagcagg cccgtctggc cctgaccctg ccgccgccg    1260 agagcgagcg cttcgtccgg cagggcaccg gcaacgacga ggccggcgcg gccaacgccg    1320
acgtggtgag cctgacctgc ccggtcgccg ccggtgaatg cgcgggcccg gcggacagcg    1380
gcgacgccct gctggagcgc aactatccca ctggcgcgga gttcctcggc gacggcggcg    1440
acgtcagctt cagcacccgc ggcacgcaga acgaattcat gcatggagat acacctacat    1500
tgcatgaata tatgttagat ttgcaaccag agacaactga tctctactgt tatgagcaat    1560
taaatgacag ctcagaggag gaggatgaaa tagatggtcc agctggacaa gcagaaccgg    1620
acagagccca ttacaatatt gtaacctttt gttgcaagtg tgactctacg cttcggttgt    1680
gcgtacaaag cacacacgta gacattcgta ctttggaaga cctgttaatg ggcacactag    1740
gaattgtgtg ccccatctgt tctcaaggat ccgagctcgg taccaagctt aagtttaaac    1800
cgctgatcag cctcgactgt gccttctagt tgccagccat ctgttgtttg ccctccccc    1860 gtgccttcct tgaccctgga aggtgccact cccactgtcc tttcctaata aaatgaggaa    1920
attgcatcgc attgtctgag taggtgtcat tctattctgg ggggtggggt ggggcaggac    1980
agcaaggggg aggattggga agacaatagc aggcatgctg gggatgcggt gggctctatg    2040
gcttctgagg cggaaagaac cagctggggc tctagggggt atccccacgc gccctgtagc    2100
ggcgcattaa gcgcggcggg tgtggtggtt acgcgcagcg tgaccgctac acttgccagc    2160
gccctagcgc ccgctccttt cgctttcttc ccttcctttc tcgccacgtt cgccggcttt    2220
ccccgtcaag ctctaaatcg gggcatccct ttagggttcc gatttagtgc tttacggcac    2280
ctcgacccca aaaaacttga ttagggtgat ggttcacgta gtgggccatc gccctgatag    2340 acggttttc gccctttgac gttggagtcc acgttcttta atagtggact cttgttccaa    2400
actggaacaa cactcaaccc tatctcggtc tattcttttg atttataagg gattttgggg    2460
atttcggcct attggttaaa aaatgagctg atttaacaaa aatttaacgc gaattaattc    2520
tgtggaatgt gtgtcagtta gggtgtggaa agtccccagg ctccccaggc aggcagaagt    2580
atgcaaagca tgcatctcaa ttagtcagca accaggtgtg gaaagtcccc aggctcccca    2640
gcaggcagaa gtatgcaaag catgcatctc aattagtcag caaccatagt cccgccccta    2700
actccgccca tcccgcccct aactccgccc agttccgccc attctccgcc ccatggctga    2760
ctaatttttt ttatttatgc agaggccgag gccgcctctg cctctgagct attccagaag    2820
tagtgaggag gcttttttgg aggcctaggc ttttgcaaaa agctcccggg agcttgtata    2880
tccattttcg gatctgatca agagacagga tgaggatcgt ttcgcatgat tgaacaagat    2940
ggattgcacg caggttctcc ggccgcttgg gtggagaggc tattcggcta tgactgggca    3000
caacagacaa tcggctgctc tgatgccgcc gtgttccggc tgtcagcgca ggggcgcccg    3060 gttcttttg tcaagaccga cctgtccggt gccctgaatg aactgcagga cgaggcagcg    3120
cggctatcgt ggctggccac gacgggcgtt ccttgcgcag ctgtgctcga cgttgtcact    3180
gaagcgggaa gggactggct gctattgggc gaagtgccgg ggcaggatct cctgtcatct    3240
caccttgctc ctgccgagaa agtatccatc atggctgatg caatgcggcg gctgcatacg    3300
cttgatccgg ctacctgccc attcgaccac caagcgaaac atcgcatcga gcgagcacgt    3360
actcggatgg aagccggtct tgtcgatcag gatgatctgg acgaagagca tcaggggctc    3420
gcgccagccg aactgttcgc caggctcaag gcgcgcatgc ccgacggcga ggatctcgtc    3480
```

```
gtgacccatg gcgatgcctg cttgccgaat atcatggtgg aaaatggccg cttttctgga    3540
ttcatcgact gtggccggct gggtgtggcg gaccgctatc aggacatagc gttggctacc    3600
cgtgatattg ctgaagagct tggcggcgaa tgggctgacc gcttcctcgt gctttacggt    3660
atcgccgctc ccgattcgca gcgcatcgcc ttctatcgcc ttcttgacga gttcttctga    3720
gcgggactct ggggttcgaa atgaccgacc aagcgacgcc caacctgcca tcacgagatt    3780
tcgattccac cgccgccttc tatgaaaggt tgggcttcgg aatcgttttc cgggacgccg    3840
gctggatgat cctccagcgc ggggatctca tgctggagtt cttcgcccac cccaacttgt    3900
ttattgcagc ttataatggt tacaaataaa gcaatagcat cacaaatttc acaaataaag    3960
catttttttc actgcattct agttgtggtt tgtccaaact catcaatgta tcttatcatg    4020
tctgtatacc gtcgacctct agctagagct tggcgtaatc atggtcatag ctgtttcctg    4080
tgtgaaattg ttatccgctc acaattccac acaacatacg agccgaagc ataaagtgta    4140
aagcctgggg tgcctaatga gtgagctaac tcacattaat tgcgttgcgc tcactgcccg    4200
ctttccagtc gggaaacctg tcgtgccagc tgcattaatg aatcggccaa cgcgcgggga    4260
gaggcggttt gcgtattggg cgctcttccg cttcctcgct cactgactcg ctgcgctcgg    4320
tcgttcggct gcggcgagcg gtatcagctc actcaaaggc ggtaatacgg ttatccacag    4380
aatcagggga taacgcagga aagaacatgt gagcaaaagg ccagcaaaag gccaggaacc    4440
gtaaaaaggc cgcgttgctg gcgttttttcc ataggctccg ccccctgac gagcatcaca    4500
aaaatcgacg ctcaagtcag aggtggcgaa acccgacagg actataaaga taccaggcgt    4560
ttccccctgg aagctccctc gtgcgctctc ctgttccgac cctgccgctt accggatacc    4620
tgtccgcctt tctcccttcg ggaagcgtgg cgctttctca atgctcacgc tgtaggtatc    4680
tcagttcggt gtaggtcgtt cgctccaagc tgggctgtgt gcacgaaccc cccgttcagc    4740
ccgaccgctg cgccttatcc ggtaactatc gtcttgagtc aacccggta agacacgact    4800
tatcgccact ggcagcagcc actggtaaca ggattagcag agcgaggtat gtaggcggtg    4860
ctacagagtt cttgaagtgg tggcctaact acggctacac tagaaggaca gtatttggta    4920
tctgcgctct gctgaagcca gttaccttcg gaaaaagagt tggtagctct tgatccggca    4980
aacaaaccac cgctggtagc ggtggttttt ttgtttgcaa gcagcagatt acgcgcagaa    5040
aaaaaggatc tcaagaagat cctttgatct tttctacggg gtctgacgct cagtggaacg    5100
aaaactcacg ttaagggatt ttggtcatga gattatcaaa aaggatcttc acctagatcc    5160
ttttaaatta aaaatgaagt tttaaatcaa ttgaatgtat atatgagtaa acttggtctg    5220
acagttacca atgcttaatc agtgaggcac ctatctcagc gatctgtcta tttcgttcat    5280
ccatagttgc ctgactcccc gtcgtgtaga taactacgat acgggagggc ttaccatctg    5340
gccccagtgc tgcaatgata ccgcgagacc cacgctcacc ggctccagat ttatcagcaa    5400
taaaccagcc agccggaagg gccgagcgca gaagtggtcc tgcaacttta tccgcctcca    5460
tccagtctat taattgttgc cgggaagcta gagtaagtag ttcgccagtt aatagtttgc    5520
gcaacgttgt tgccattgct acaggcatcg tggtgtcacg ctcgtcgttt ggtatggctt    5580
cattcagctc cggttcccaa cgatcaaggc gagttacatg atccccatg ttgtgcaaaa    5640
aagcggttag ctccttcggt cctccgatcg ttgtcagaag taagttggcc gcagtgttat    5700
cactcatggt tatggcagca ctgcataatt ctcttactgt catgccatcc gtaagatgct    5760
tttctgtgac tggtgagtac tcaaccaagt cattctgaga atagtgtatg cggcgaccga    5820
```

```
gttgctcttg cccggcgtca atacgggata ataccgcgcc acatagcaga actttaaaag    5880
tgctcatcat tggaaaacgt tcttcggggc gaaaactctc aaggatctta ccgctgttga    5940
gatccagttc gatgtaaccc actcgtgcac ccaactgatc ttcagcatct tttactttca    6000
ccagcgtttc tgggtgagca aaaacaggaa ggcaaaatgc cgcaaaaaag gaataagggg    6060
cgacacggaa atgttgaata ctcatactct tccttttca  atattattga agcatttatc    6120
agggttattg tctcatgagc ggatacatat ttgaatgtat ttagaaaaat aaacaaatag    6180
gggttccgcg cacatttccc cgaaaagtgc cacctgacgt c                       6221

<210> SEQ ID NO 5
<211> LENGTH: 5970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gctccgcccc cctgacgagc atcacaaaaa tcgacgctca agtcagaggt ggcgaaaccc      60
gacaggacta taaagatacc aggcgtttcc ccctggaagc tccctcgtgc gctctcctgt     120
tccgaccctg ccgcttaccg gatacctgtc cgcctttctc ccttcgggaa gcgtggcgct     180
ttctcatagc tcacgctgta ggtatctcag ttcggtgtag gtcgttcgct ccaagctggg     240
ctgtgtgcac gaaccccccg ttcagcccga ccgctgcgcc ttatccggta actatcgtct     300
tgagtccaac ccggtaagac acgacttatc gccactggca gcagccactg gtaacaggat     360
tagcagagcg aggtatgtag gcggtgctac agagttcttg aagtggtggc ctaactacgg     420
ctacactaga agaacagtat ttggtatctg cgctctgctg aagccagtta ccttcggaaa     480
aagagttggt agctcttgat ccggcaaaca aaccaccgct ggtagcggtg gtttttttgt     540
ttgcaagcag cagattacgc gcagaaaaaa aggatctcaa gaagatcctt tgatcttttc     600
tacggggtct gacgctcagt ggaacgaaaa ctcacgttaa gggattttgg tcatgagatt     660
atcaaaaagg atcttcacct agatcctttt aaattaaaaa tgaagtttta atcaatcta     720 aagtatatat gagtaaactt ggtctgacag ttaccaatgc ttaatcagtg aggcacctat     780
ctcagcgatc tgtctatttc gttcatccat agttgcctga ctcgggggg  ggggcgctg    840 aggtctgcct cgtgaagaag gtgttgctga ctcataccag gcaacgttg  ttgccattgc    900 tacaggcatc gtggtgtcac gctcgtcgtt tggtatggct tcattcagct ccggttccca    960
acgatcaagg cgagttacat gatcccccat gttgtgcaaa aaagcggtta gctccttcgg   1020
tcctccgatc gttgtcagaa gtaagttggc cgcagtgtta tcactcatgg ttatggcagc   1080
actgcataat tctcttactg tcatgccatc cgtaagatgc ttttctgtga ctggtgagta   1140
ctcaaccaag tcattctgag aatagtgtat gcggcgaccg agttgctctt gcccggcgtc   1200
aatacgggat aataccgcgc cacatagcag aactttaaaa gtgctcatca ttggaaaacg   1260
ttcttcgggg cgaaaactct caaggatctt accgctgttg agatccagtt cgatgtaacc   1320
cactcgtgca cctgaatcgc cccatcatcc agccagaaag tgagggagcc acggttgatg   1380
agagctttgt tgtaggtgga ccagttggtg attttgaact tttgctttgc cacggaacgg   1440
tctgcgttgt cgggaagatg cgtgatctga tccttcaact cagcaaaagt tcgatttatt   1500
caacaaagcc gccgtcccgt caagtcagcg taatgctctg ccagtgttac aaccaattaa   1560
ccaattctga ttagaaaaac tcatcgagca tcaaatgaaa ctgcaattta ttattaatag   1620
```

```
gattatcaat accatatttt tgaaaaagcc gtttctgtaa tgaaggagaa aactcaccga    1680
ggcagttcca taggatggca agatcctggt atcggtctgc gattccgact cgtccaacat    1740
caatacaacc tattaatttc ccctcgtcaa aaataaggtt atcaagtgag aaatcaccat    1800
gagtgacgac tgaatccggt gagaatggca aaagcttatg catttctttc cagacttgtt    1860
caacaggcca gccattacgc tcgtcatcaa aatcactcgc atcaaccaaa ccgttattca    1920
ttcgtgattg cgcctgagcg agacgaaata cgcgatcgct gttaaaagga caattacaaa    1980
caggaatcga atgcaaccgg cgcaggaaca ctgccagcgc atcaacaata ttttcacctg    2040
aatcaggata ttcttctaat acctggaatg ctgttttccc ggggatcgca gtggtgagta    2100
accatgcatc atcaggagta cggataaaat gcttgatggt cggaagaggc ataaattccg    2160
tcagccagtt tagtctgacc atctcatctg taacatcatt ggcaacgcta cctttgccat    2220
gtttcagaaa caactctggc gcatcgggct tcccatacaa tcgatagatt gtcgcacctg    2280
attgcccgac attatcgcga gcccatttat acccatataa atcagcatcc atgttggaat    2340
ttaatcgcgg cctcgagcaa gacgtttccc gttgaatatg gctcataaca ccccttgtat    2400
tactgtttat gtaagcagac agttttattg ttcatgatga tatatttta tcttgtgcaa    2460 tgtaacatca gagattttga gacacaacgt ggctttcccc cccccccat tattgaagca    2520 tttatcaggg ttattgtctc atgagcggat acatatttga atgtatttag aaaaataaac    2580 aaatagggt tccgcgcaca tttccccgaa agtgccacc tgacgtctaa gaaaccatta    2640
ttatcatgac attaacctat aaaaataggc gtatcacgag gccctttcgt ctcgcgcgtt    2700
tcggtgatga cggtgaaaac ctctgacaca tgcagctccc ggagacggtc acagcttgtc    2760
tgtaagcgga tgccgggagc agacaagccc gtcagggcgc gtcagcgggt gttggcgggt    2820 gtcgggctg gcttaactat gcggcatcag agcagattgt actgagagtg caccatatgc    2880
ggtgtgaaat accgcacaga tgcgtaagga gaaaataccg catcagattg gctattggcc    2940
attgcatacg ttgtatccat atcataatat gtacatttat attggctcat gtccaacatt    3000
accgccatgt tgacattgat tattgactag ttattaatag taatcaatta cggggtcatt    3060
agttcatagc ccatatatgg agttccgcgt tacataactt acggtaaatg gcccgcctgg    3120
ctgaccgccc aacgaccccc gcccattgac gtcaataatg acgtatgttc ccatagtaac    3180
gccaataggg actttccatt gacgtcaatg ggtggagtat ttacggtaaa ctgcccactt    3240
ggcagtacat caagtgtatc atatgccaag tacgccccct attgacgtca atgacggtaa    3300
atggcccgcc tggcattatg cccagtacat gaccttatgg gactttccta cttggcagta    3360
catctacgta ttagtcatcg ctattaccat ggtgatgcgg ttttggcagt acatcaatgg    3420
gcgtggatag cggtttgact cacgggatt ccaagtctc cacccattg acgtcaatgg    3480 gagtttgttt tggcaccaaa atcaacggga ctttccaaaa tgtcgtaaca actccgcccc    3540
attgacgcaa atgggcggta ggcgtgtacg gtgggaggtc tatataagca gagctcgttt    3600
agtgaaccgt cagatcgcct ggagacgcca tccacgctgt tttgacctcc atagaagaca    3660
ccgggaccga tccagcctcc gcggccggga acggtgcatt ggaacgcgga ttccccgtgc    3720
caagagtgac gtaagtaccg cctatagact ctataggcac ccccttggg ctcttatgca    3780 tgctatactg ttttttggctt ggggcctata cacccccgct tccttatgct ataggtgatg    3840
gtatagctta gcctataggt gtgggttatt gaccattatt gaccactcca acggtggagg    3900
gcagtgtagt ctgagcagta ctcgttgctg ccgcgcgcgc caccagacat aatagctgac    3960
agactaacag actgttcctt tccatgggtc ttttctgcag tcaccgtcgt cgacatgctg    4020
```

```
ctatccgtgc cgctgctgct cggcctcctc ggcctggccg tcgccgagcc tgccgtctac    4080
ttcaaggagc agtttctgga cggggacggg tggacttccc gctggatcga atccaaacac    4140 aagtcgatatt ttggcaaatt cgttctcagt tccggcaagt tctacggtga cgaggagaaa    4200
```

```
ctatccgtgc cgctgctgct cggcctcctc ggcctggccg tcgccgagcc tgccgtctac    4080
ttcaaggagc agtttctgga cggggacggg tggacttccc gctggatcga atccaaacac    4140
aagtcgatt ttggcaaatt cgttctcagt tccggcaagt tctacggtga cgaggagaaa     4200
gataaaggtt tgcagacaag ccaggatgca cgcttttatg ctctgtcggc cagtttcgag    4260
cctttcagca caaaggcca gacgctggtg gtgcagttca cggtgaaaca tgagcagaac     4320
atcgactgtg ggggcggcta tgtgaagctg tttcctaata gtttggacca gacagacatg    4380
cacggagact cagaatacaa catcatgttt ggtcccgaca tctgtggccc tggcaccaag    4440
aaggttcatg tcatcttcaa ctacaagggc aagaacgtgc tgatcaacaa ggacatccgt    4500
tgcaaggatg atgagtttac acacctgtac acactgattg tgcggccaga caacacctat    4560
gaggtgaaga ttgacaacag ccaggtggag tccggctcct tggaagacga ttgggacttc    4620
ctgccaccca agaagataaa ggatcctgat gcttcaaaac cggaagactg ggatgagcgg    4680
gccaagatcg atgatcccac agactccaag cctgaggact gggacaagcc cgagcatatc    4740
cctgaccctg atgctaagaa gcccgaggac tgggatgaag agatggacgg agagtgggaa    4800
cccccagtga ttcagaaccc tgagtacaag ggtgagtgga gccccggca gatcgacaac     4860
ccagattaca agggcacttg gatccacccca gaaattgaca ccccgagta ttctcccgat    4920
cccagtatct atgcctatga taactttggc gtgctgggcc tggacctctg gcaggtcaag    4980
tctggcacca tctttgacaa cttcctcatc accaacgatg aggcatacgc tgaggagttt    5040
ggcaacgaga cgtggggcgt aacaaaggca gcagagaaac aaatgaagga caaacaggac    5100
gaggagcaga ggcttaagga ggaggaagaa gacaagaaac gcaaagagga ggaggaggca    5160
gaggacaagg aggatgatga ggacaaagat gaggatgagg aggatgagga ggacaaggag    5220
gaagatgagg aggaagatgt ccccggccag gccaaggacg agctggaatt catgcatgga    5280
gatacaccta cattgcatga atatatgtta gatttgcaac cagagacaac tgatctctac    5340
ggttatgggc aattaaatga cagctcagag gaggaggatg aaatagatgg tccagctgga    5400
caagcagaac cggacagagc ccattacaat attgtaacct tttgttgcaa gtgtgactct    5460
acgcttcggt tgtgcgtaca aagcacacac gtagacattc gtactttgga agacctgtta    5520
atgggcacac taggaattgt gtgccccatc tgttctcaga aaccataagg atccagatct    5580
ttttccctct gccaaaaatt atgggacat catgaagccc cttgagcatc tgacttctgg    5640
ctaataaagg aaatttattt tcattgcaat agtgtgttgg aatttttgt gtctctcact     5700
cggaaggaca tatgggaggg caaatcattt aaaacatcag aatgagtatt tggtttagag   5760
tttggcaaca tatgcccatt cttccgcttc ctcgctcact gactcgctgc gctcggtcgt    5820
tcggctgcgg cgagcggtat cagctcactc aaaggcggta atacggttat ccacagaatc    5880
agggggataac gcaggaaaga acatgtgagc aaaaggccag caaaaggcca ggaaccgtaa    5940
aaaggccgcg ttgctggcgt ttttccatag                                     5970
```

<210> SEQ ID NO 6
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1257)

-continued

<400> SEQUENCE: 6

| | | | | | | | | | | | | | | | | |
|---|---|---|---|---|---|---|---|---|---|---|---|---|---|---|---|---|
| atg | acc | tct | cgc | cgc | tcc | gtg | aag | tcg | ggt | ccg | cgg | gag | gtt | ccg | cgc | 48 |
| Met | Thr | Ser | Arg | Arg | Ser | Val | Lys | Ser | Gly | Pro | Arg | Glu | Val | Pro | Arg | |
| 1 | | | | 5 | | | | | 10 | | | | | 15 | | |
| gat | gag | tac | gag | gat | ctg | tac | tac | acc | ccg | tct | tca | ggt | atg | gcg | agt | 96 |
| Asp | Glu | Tyr | Glu | Asp | Leu | Tyr | Tyr | Thr | Pro | Ser | Ser | Gly | Met | Ala | Ser | |
| | | | 20 | | | | | 25 | | | | | 30 | | | |
| ccc | gat | agt | ccg | cct | gac | acc | tcc | cgc | cgt | ggc | gcc | cta | cag | aca | cgc | 144 |
| Pro | Asp | Ser | Pro | Pro | Asp | Thr | Ser | Arg | Arg | Gly | Ala | Leu | Gln | Thr | Arg | |
| | | 35 | | | | | 40 | | | | | 45 | | | | |
| tcg | cgc | cag | agg | ggc | gag | gtc | cgt | ttc | gtc | cag | tac | gac | gag | tcg | gat | 192 |
| Ser | Arg | Gln | Arg | Gly | Glu | Val | Arg | Phe | Val | Gln | Tyr | Asp | Glu | Ser | Asp | |
| | 50 | | | | | 55 | | | | | 60 | | | | | |
| tat | gcc | ctc | tac | ggg | ggc | tcg | tct | tcc | gaa | gac | gac | gaa | cac | ccg | gag | 240 |
| Tyr | Ala | Leu | Tyr | Gly | Gly | Ser | Ser | Ser | Glu | Asp | Asp | Glu | His | Pro | Glu | |
| 65 | | | | | 70 | | | | | 75 | | | | | 80 | |
| gtc | ccc | cgg | acg | cgg | cgt | ccc | gtt | tcc | ggg | gcg | gtt | ttg | tcc | ggc | ccg | 288 |
| Val | Pro | Arg | Thr | Arg | Arg | Pro | Val | Ser | Gly | Ala | Val | Leu | Ser | Gly | Pro | |
| | | | | 85 | | | | | 90 | | | | | 95 | | |
| ggg | cct | gcg | cgg | gcg | cct | ccg | cca | ccc | gct | ggg | tcc | gga | ggg | gcc | gga | 336 |
| Gly | Pro | Ala | Arg | Ala | Pro | Pro | Pro | Pro | Ala | Gly | Ser | Gly | Gly | Ala | Gly | |
| | | | 100 | | | | | 105 | | | | | 110 | | | |
| cgc | aca | ccc | acc | acc | gcc | ccc | cgg | gcc | ccc | cga | acc | cag | cgg | gtg | gcg | 384 |
| Arg | Thr | Pro | Thr | Thr | Ala | Pro | Arg | Ala | Pro | Arg | Thr | Gln | Arg | Val | Ala | |
| | | 115 | | | | | 120 | | | | | 125 | | | | |
| tct | aag | gcc | ccc | gcg | gcc | ccg | gcg | gcg | gag | acc | acc | cgc | ggc | agg | aaa | 432 |
| Ser | Lys | Ala | Pro | Ala | Ala | Pro | Ala | Ala | Glu | Thr | Thr | Arg | Gly | Arg | Lys | |
| | 130 | | | | | 135 | | | | | 140 | | | | | |
| tcg | gcc | cag | cca | gaa | tcc | gcc | gca | ctc | cca | gac | gcc | ccc | gcg | tcg | acg | 480 |
| Ser | Ala | Gln | Pro | Glu | Ser | Ala | Ala | Leu | Pro | Asp | Ala | Pro | Ala | Ser | Thr | |
| 145 | | | | | 150 | | | | | 155 | | | | | 160 | |
| gcg | cca | acc | cga | tcc | aag | aca | ccc | gcg | cag | ggg | ctg | gcc | aga | aag | ctg | 528 |
| Ala | Pro | Thr | Arg | Ser | Lys | Thr | Pro | Ala | Gln | Gly | Leu | Ala | Arg | Lys | Leu | |
| | | | | 165 | | | | | 170 | | | | | 175 | | |
| cac | ttt | agc | acc | gcc | ccc | cca | aac | ccc | gac | gcg | cca | tgg | acc | ccc | cgg | 576 |
| His | Phe | Ser | Thr | Ala | Pro | Pro | Asn | Pro | Asp | Ala | Pro | Trp | Thr | Pro | Arg | |
| | | | 180 | | | | | 185 | | | | | 190 | | | |
| gtg | gcc | ggc | ttt | aac | aag | cgc | gtc | ttc | tgc | gcc | gcg | gtc | ggg | cgc | ctg | 624 |
| Val | Ala | Gly | Phe | Asn | Lys | Arg | Val | Phe | Cys | Ala | Ala | Val | Gly | Arg | Leu | |
| | | 195 | | | | | 200 | | | | | 205 | | | | |
| gcg | gcc | atg | cat | gcc | cgg | atg | gcg | gct | gtc | cag | ctc | tgg | gac | atg | tcg | 672 |
| Ala | Ala | Met | His | Ala | Arg | Met | Ala | Ala | Val | Gln | Leu | Trp | Asp | Met | Ser | |
| | 210 | | | | | 215 | | | | | 220 | | | | | |
| cgt | ccg | cgc | aca | gac | gaa | gac | ctc | aac | gaa | ctc | ctt | ggc | atc | acc | acc | 720 |
| Arg | Pro | Arg | Thr | Asp | Glu | Asp | Leu | Asn | Glu | Leu | Leu | Gly | Ile | Thr | Thr | |
| 225 | | | | | 230 | | | | | 235 | | | | | 240 | |
| atc | cgc | gtg | acg | gtc | tgc | gag | ggc | aaa | aac | ctg | ctt | cag | cgc | gcc | aac | 768 |
| Ile | Arg | Val | Thr | Val | Cys | Glu | Gly | Lys | Asn | Leu | Leu | Gln | Arg | Ala | Asn | |
| | | | | 245 | | | | | 250 | | | | | 255 | | |
| gag | ttg | gtg | aat | cca | gac | gtg | gtg | cag | gac | gtc | gac | gcg | gcc | acg | gcg | 816 |
| Glu | Leu | Val | Asn | Pro | Asp | Val | Val | Gln | Asp | Val | Asp | Ala | Ala | Thr | Ala | |
| | | | 260 | | | | | 265 | | | | | 270 | | | |
| act | cga | ggg | cgt | tct | gcg | gcg | tcg | cgc | ccc | acc | gag | cga | cct | cga | gcc | 864 |
| Thr | Arg | Gly | Arg | Ser | Ala | Ala | Ser | Arg | Pro | Thr | Glu | Arg | Pro | Arg | Ala | |
| | | 275 | | | | | 280 | | | | | 285 | | | | |
| cca | gcc | cgc | tcc | gct | tct | cgc | ccc | aga | cgg | ccc | gtc | gag | ggt | acc | gag | 912 |
| Pro | Ala | Arg | Ser | Ala | Ser | Arg | Pro | Arg | Arg | Pro | Val | Glu | Gly | Thr | Glu | |
| | 290 | | | | | 295 | | | | | 300 | | | | | |
| ctc | gga | tcc | atg | cat | gga | gat | aca | cct | aca | ttg | cat | gaa | tat | atg | tta | 960 |

```
Leu Gly Ser Met His Gly Asp Thr Pro Thr Leu His Glu Tyr Met Leu
305                 310                 315                 320 gat ttg caa cca gag aca act gat ctc tac tgt tat gag caa tta aat    1008
Asp Leu Gln Pro Glu Thr Thr Asp Leu Tyr Cys Tyr Glu Gln Leu Asn
                325                 330                 335 gac agc tca gag gag gag gat gaa ata gat ggt cca gct gga caa gca    1056
Asp Ser Ser Glu Glu Glu Asp Glu Ile Asp Gly Pro Ala Gly Gln Ala
            340                 345                 350 gaa ccg gac aga gcc cat tac aat att gta acc ttt tgt tgc aag tgt    1104
Glu Pro Asp Arg Ala His Tyr Asn Ile Val Thr Phe Cys Cys Lys Cys
        355                 360                 365 gac tct acg ctt cgg ttg tgc gta caa agc aca cac gta gac att cgt    1152
Asp Ser Thr Leu Arg Leu Cys Val Gln Ser Thr His Val Asp Ile Arg
    370                 375                 380 act ttg gaa gac ctg tta atg ggc aca cta gga att gtg tgc ccc atc    1200
Thr Leu Glu Asp Leu Leu Met Gly Thr Leu Gly Ile Val Cys Pro Ile
385                 390                 395                 400 tgt tct cag gat aag ctt aag ttt aaa ccg ctg atc agc ctc gac tgt    1248
Cys Ser Gln Asp Lys Leu Lys Phe Lys Pro Leu Ile Ser Leu Asp Cys
                405                 410                 415 gcc ttc tag                                                         1257
Ala Phe <210> SEQ ID NO 7
<211> LENGTH: 903
<212> TYPE: DNA
<213> ORGANISM: Human herpesvirus
<220> FEATURE:
<221> NAME/KEY: CDS
<222> LOCATION: (1)..(903)

<400> SEQUENCE: 7 atg acc tct cgc cgc tcc gtg aag tcg ggt ccg cgg gag gtt ccg cgc    48
Met Thr Ser Arg Arg Ser Val Lys Ser Gly Pro Arg Glu Val Pro Arg
1               5                   10                  15 gat gag tac gag gat ctg tac tac acc ccg tct tca ggt atg gcg agt    96
Asp Glu Tyr Glu Asp Leu Tyr Tyr Thr Pro Ser Ser Gly Met Ala Ser
                20                  25                  30 ccc gat agt ccg cct gac acc tcc cgc cgt ggc gcc cta cag aca cgc    144
Pro Asp Ser Pro Pro Asp Thr Ser Arg Arg Gly Ala Leu Gln Thr Arg
            35                  40                  45 tcg cgc cag agg ggc gag gtc cgt ttc gtc cag tac gac gag tcg gat    192
Ser Arg Gln Arg Gly Glu Val Arg Phe Val Gln Tyr Asp Glu Ser Asp
        50                  55                  60 tat gcc ctc tac ggg ggc tcg tct tcc gaa gac gac gaa cac ccg gag    240
Tyr Ala Leu Tyr Gly Gly Ser Ser Ser Glu Asp Asp Glu His Pro Glu
65                  70                  75                  80 gtc ccc cgg acg cgg cgt ccc gtt tcc ggg gcg gtt ttg tcc ggc ccg    288
Val Pro Arg Thr Arg Arg Pro Val Ser Gly Ala Val Leu Ser Gly Pro
                85                  90                  95 ggg cct gcg cgg gcg cct ccg cca ccc gct ggg tcc gga ggg gcc gga    336
Gly Pro Ala Arg Ala Pro Pro Pro Ala Gly Ser Gly Gly Ala Gly
            100                 105                 110 cgc aca ccc acc acc gcc ccc cgg gcc ccc cga acc cag cgg gtg gcg    384
Arg Thr Pro Thr Thr Ala Pro Arg Ala Pro Arg Thr Gln Arg Val Ala
        115                 120                 125 tct aag gcc ccc gcg gcc ccg gcg gcg gag acc acc cgc ggc agg aaa    432
Ser Lys Ala Pro Ala Ala Pro Ala Ala Glu Thr Thr Arg Gly Arg Lys
    130                 135                 140 tcg gcc cag cca gaa tcc gcc gca ctc cca gac gcc ccc gcg tcg acg    480
Ser Ala Gln Pro Glu Ser Ala Ala Leu Pro Asp Ala Pro Ala Ser Thr
```

```
gcg cca acc cga tcc aag aca ccc gcg cag ggg ctg gcc aga aag ctg    528
Ala Pro Thr Arg Ser Lys Thr Pro Ala Gln Gly Leu Ala Arg Lys Leu
            165                 170                 175 cac ttt agc acc gcc ccc cca aac ccc gac gcg cca tgg acc ccc cgg    576
His Phe Ser Thr Ala Pro Pro Asn Pro Asp Ala Pro Trp Thr Pro Arg
            180                 185                 190 gtg gcc ggc ttt aac aag cgc gtc ttc tgc gcc gcg gtc ggg cgc ctg    624
Val Ala Gly Phe Asn Lys Arg Val Phe Cys Ala Ala Val Gly Arg Leu
            195                 200                 205 gcg gcc atg cat gcc cgg atg gcg gct gtc cag ctc tgg gac atg tcg    672
Ala Ala Met His Ala Arg Met Ala Ala Val Gln Leu Trp Asp Met Ser
        210                 215                 220 cgt ccg cgc aca gac gaa gac ctc aac gaa ctc ctt ggc atc acc acc    720
Arg Pro Arg Thr Asp Glu Asp Leu Asn Glu Leu Leu Gly Ile Thr Thr
225                 230                 235                 240 atc cgc gtg acg gtc tgc gag ggc aaa aac ctg ctt cag cgc gcc aac    768
Ile Arg Val Thr Val Cys Glu Gly Lys Asn Leu Leu Gln Arg Ala Asn
                245                 250                 255 gag ttg gtg aat cca gac gtg gtg cag gac gtc gac gcg gcc acg gcg    816
Glu Leu Val Asn Pro Asp Val Val Gln Asp Val Asp Ala Ala Thr Ala
            260                 265                 270 act cga ggg cgt tct gcg gcg tcg cgc ccc acc gag cga cct cga gcc    864
Thr Arg Gly Arg Ser Ala Ala Ser Arg Pro Thr Glu Arg Pro Arg Ala
        275                 280                 285 cca gcc cgc tcc gct tct cgc ccc aga cgg ccc gtc gag                903
Pro Ala Arg Ser Ala Ser Arg Pro Arg Arg Pro Val Glu
        290                 295                 300

<210> SEQ ID NO 8
<211> LENGTH: 297
<212> TYPE: DNA
<213> ORGANISM: Human papillomavirus
<220> FEATURE:
<221> NAME/KEY: CDS
<222> LOCATION: (1)..(297)

<400> SEQUENCE: 8 atg cat gga gat aca cct aca ttg cat gaa tat atg tta gat ttg caa     48
Met His Gly Asp Thr Pro Thr Leu His Glu Tyr Met Leu Asp Leu Gln
1               5                   10                  15 cca gag aca act gat ctc tac tgt tat gag caa tta aat gac agc tca     96
Pro Glu Thr Thr Asp Leu Tyr Cys Tyr Glu Gln Leu Asn Asp Ser Ser
            20                  25                  30 gag gag gag gat gaa ata gat ggt cca gct gga caa gca gaa ccg gac    144
Glu Glu Glu Asp Glu Ile Asp Gly Pro Ala Gly Gln Ala Glu Pro Asp
        35                  40                  45 aga gcc cat tac aat att gta acc ttt tgt tgc aag tgt gac tct acg    192
Arg Ala His Tyr Asn Ile Val Thr Phe Cys Cys Lys Cys Asp Ser Thr
    50                  55                  60 ctt cgg ttg tgc gta caa agc aca cac gta gac att cgt act ttg gaa    240
Leu Arg Leu Cys Val Gln Ser Thr His Val Asp Ile Arg Thr Leu Glu
65                  70                  75                  80 gac ctg tta atg ggc aca cta gga att gtg tgc ccc atc tgt tct cag    288
Asp Leu Leu Met Gly Thr Leu Gly Ile Val Cys Pro Ile Cys Ser Gln
                85                  90                  95 gat aag ctt                                                         297
Asp Lys Leu

<210> SEQ ID NO 9
<211> LENGTH: 99
```

<212> TYPE: PRT
<213> ORGANISM: Human papillomavirus

<400> SEQUENCE: 9

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Asp Lys Leu

<210> SEQ ID NO 10
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met His Gly Asp Thr Pro Thr Leu His Glu Tyr Met Leu Asp Leu Gln
1               5                   10                  15

Pro Glu Thr Thr Asp Leu Tyr Gly Tyr Glu Gln Asp Ser Ser Glu Glu
            20                  25                  30

Glu Asp Glu Ile Asp Gly Pro Ala Gly Gln Ala Glu Pro Asp Arg Ala
        35                  40                  45

His Tyr Asn Ile Val Thr Phe Cys Cys Lys Cys Asp Ser Thr Leu Arg
50                  55                  60

Leu Cys Val Gln Ser Thr His Val Asp Ile Arg Thr Leu Glu Asp Leu
65                  70                  75                  80

Leu Met Gly Thr Leu Gly Ile Val Cys Pro Ile Cys Ser Gln Lys Pro
                85                  90                  95

<210> SEQ ID NO 11
<211> LENGTH: 477
<212> TYPE: DNA
<213> ORGANISM: Human papillomavirus
<220> FEATURE:
<221> NAME/KEY: CDS
<222> LOCATION: (1)..(477)

<400> SEQUENCE: 11 atg cac caa aag aga act gca atg ttt cag gac cca cag gag cga ccc    48
Met His Gln Lys Arg Thr Ala Met Phe Gln Asp Pro Gln Glu Arg Pro
1               5                   10                  15 aga aag tta cca cag tta tgc aca gag ctg caa aca act ata cat gat    96
Arg Lys Leu Pro Gln Leu Cys Thr Glu Leu Gln Thr Thr Ile His Asp
            20                  25                  30 ata ata tta gaa tgt gtg tac tgc aag caa cag tta ctg cga cgt gag   144
Ile Ile Leu Glu Cys Val Tyr Cys Lys Gln Gln Leu Leu Arg Arg Glu
        35                  40                  45 gta tat gac ttt gct ttt cgg gat tta tgc ata gta tat aga gat ggg   192
Val Tyr Asp Phe Ala Phe Arg Asp Leu Cys Ile Val Tyr Arg Asp Gly

```
                    50                  55                  60
aat cca tat gct gta tgt gat aaa tgt tta aag ttt tat tct aaa att    240
Asn Pro Tyr Ala Val Cys Asp Lys Cys Leu Lys Phe Tyr Ser Lys Ile
65                  70                  75                  80 agt gag tat aga cat tat tgt tat agt ttg tat gga aca aca tta gaa    288
Ser Glu Tyr Arg His Tyr Cys Tyr Ser Leu Tyr Gly Thr Thr Leu Glu
                    85                  90                  95 cag caa tac aac aaa ccg ttg tgt gat ttg tta att agg tgt att aac    336
Gln Gln Tyr Asn Lys Pro Leu Cys Asp Leu Leu Ile Arg Cys Ile Asn
                100                 105                 110 tgt caa aag cca ctg tgt cct gaa gaa aag caa aga cat ctg gac aaa    384
Cys Gln Lys Pro Leu Cys Pro Glu Glu Lys Gln Arg His Leu Asp Lys
            115                 120                 125 aag caa aga ttc cat aat ata agg ggt cgg tgg acc ggt cga tgt atg    432
Lys Gln Arg Phe His Asn Ile Arg Gly Arg Trp Thr Gly Arg Cys Met
        130                 135                 140 tct tgt tgc aga tca tca aga aca cgt aga gaa acc cag ctg taa        477
Ser Cys Cys Arg Ser Ser Arg Thr Arg Arg Glu Thr Gln Leu
145                 150                 155
```

<210> SEQ ID NO 12
<211> LENGTH: 158
<212> TYPE: PRT
<213> ORGANISM: Human papillomavirus

<400> SEQUENCE: 12

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155
```

<210> SEQ ID NO 13
<211> LENGTH: 149
<212> TYPE: PRT
<213> ORGANISM: Human papillomavirus

<400> SEQUENCE: 13

```
Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Cys Val Tyr Cys Lys
            20                  25                  30

Gln Gln Leu Leu Arg Arg Glu Val Tyr Asp Phe Ala Phe Arg Asp Leu
```

-continued

```
        35                  40                  45

Cys Ile Val Tyr Arg Asp Gly Asn Pro Tyr Ala Val Cys Asp Lys Cys
    50                  55                  60

Leu Lys Phe Tyr Ser Lys Ile Ser Glu Tyr Arg His Tyr Cys Tyr Ser
65                  70                  75                  80

Leu Tyr Gly Thr Thr Leu Glu Gln Gln Tyr Asn Lys Pro Leu Cys Asp
                85                  90                  95

Leu Leu Ile Arg Cys Ile Asn Cys Gln Lys Pro Leu Cys Pro Glu Glu
            100                 105                 110

Lys Gln Arg His Leu Asp Lys Lys Gln Arg Phe His Asn Ile Arg Gly
        115                 120                 125

Arg Trp Thr Gly Arg Cys Met Ser Cys Cys Arg Ser Ser Arg Thr Arg
    130                 135                 140

Arg Glu Thr Gln Leu
145

<210> SEQ ID NO 14
<211> LENGTH: 1698
<212> TYPE: DNA
<213> ORGANISM: Influenza A virus

<400> SEQUENCE: 14
atgaaggcaa acctactggt cctgttaagt gcacttgcag ctgcagatgc agacacaata      60
tgtataggct accatgcgaa caattcaacc gacactgttg acacagtact cgagaagaat     120
gtgacagtga cacactctgt taacctgctc gaagacagcc acaacggaaa actatgtaga     180
ttaaaaggaa tagccccact acaattgggg aaatgtaaca tcgccggatg gctcttggga     240
aacccagaat gcgacccact gcttccagtg agatcatggt cctacattgt agaaacacca     300
aactctgaga atggaatatg ttatccagga gatttcatcg actatgagga gctgagggag     360
caattgagct cagtgtcatc attcgaaaga ttcgaaatat ttcccaaaga aagctcatgg     420
cccaaccaca acacaaacgg agtaacggca gcatgctccc atgaggggaa aagcagtttt     480
tacagaaatt tgctatggct gacggagaag gagggctcat acccaaagct gaaaaattct     540
tatgtgaaca aaaaagggaa agaagtcctt gtactgtggg gtattcatca cccgcctaac     600
agtaaggaac aacagaatat ctatcagaat gaaaatgctt atgtctctgt agtgacttca     660
aattataaca ggagatttac cccggaaata gcagaaagac ccaaagtaag agatcaagct     720
gggaggatga actattactg gaccttgcta aaacccggag acacaataat atttgaggca     780
aatggaaatc taatagcacc aatgtatgct ttcgcactga gtagaggctt tgggtccggc     840
atcatcacct caaacgcatc aatgcatgag tgtaacacga agtgtcaaac acccctggga     900
gctataaaca gcagtctccc ttaccagaat atacacccag tcacaatagg agagtgccca     960
aaatacgtca ggagtgccaa attgaggatg gttacaggac taaggaacac tccgtccatt    1020
caatccagag gtctatttgg agccattgcc ggttttattg aagggggatg gactggaatg    1080
atagatggat ggtatggtta tcatcatcag aatgaacagg gatcaggcta tgcagcggat    1140
caaaaaagca cacaaaatgc cattaacggg attacaaaca aggtgaacac tgttatcgag    1200
aaaatgaaca ttcaattcac agctgtgggt aaagaattca acaaattaga aaaaaggatg    1260
gaaaatttaa ataaaaaagt tgatgatgga tttctggaca tttggacata taatgcagaa    1320
ttgttagttc tactggaaaa tgaaaggact ctggatttcc atgactcaaa tgtgaagaat    1380
ctgtatgaga aagtaaaaag ccaattaaag aataatgcca aagaaatcgg aaatggatgt    1440
```

-continued

```
tttgagttct accacaagtg tgacaatgaa tgcatggaaa gtgtaagaaa tgggacttat    1500
gattatccca aatattcaga agagtcaaag ttgaacaggg aaaaggtaga tggagtgaaa    1560
ttggaatcaa tggggatcta tcagattctg gcgatctact caactgtcgc cagttcactg    1620
gtgcttttgg tctccctggg ggcaatcagt ttctggatgt gttctaatgg atctttgcag    1680
tgcagaatat gcatctga                                                   1698
```

<210> SEQ ID NO 15
<211> LENGTH: 563
<212> TYPE: PRT
<213> ORGANISM: Influenza A virus

<400> SEQUENCE: 15

```
Met Lys Ala Asn Leu Leu Val Leu Ser Ala Ala Asp Ala Asp
1               5                   10                  15

Thr Ile Cys Ile Gly Tyr His Ala Asn Asn Ser Thr Asp Thr Val Asp
                20                  25                  30

Thr Val Leu Glu Lys Asn Val Thr Val Thr His Ser Val Asn Leu Leu
            35                  40                  45

Glu Asp Ser His Asn Gly Lys Leu Cys Arg Leu Lys Gly Ile Ala Pro
        50                  55                  60

Leu Gln Leu Gly Lys Cys Asn Ile Ala Gly Trp Leu Leu Gly Asn Pro
65                  70                  75                  80

Glu Cys Asp Pro Leu Leu Pro Val Arg Ser Trp Ser Tyr Ile Val Glu
                85                  90                  95

Thr Pro Asn Ser Glu Asn Gly Ile Cys Tyr Pro Gly Asp Phe Ile Asp
            100                 105                 110

Tyr Glu Glu Leu Arg Glu Gln Leu Ser Ser Val Ser Ser Phe Glu Arg
        115                 120                 125

Phe Glu Ile Phe Pro Lys Glu Ser Ser Trp Pro Asn His Asn Thr Asn
    130                 135                 140

Gly Val Thr Ala Ala Cys Ser His Glu Gly Lys Ser Ser Phe Tyr Arg
145                 150                 155                 160

Asn Leu Leu Trp Leu Thr Glu Lys Glu Gly Ser Tyr Pro Lys Leu Lys
                165                 170                 175

Asn Ser Tyr Val Asn Lys Lys Gly Lys Glu Val Leu Val Leu Trp Gly
            180                 185                 190

Ile His His Pro Pro Asn Ser Lys Glu Gln Gln Asn Ile Tyr Gln Asn
        195                 200                 205

Glu Asn Ala Tyr Val Ser Val Val Thr Ser Asn Tyr Asn Arg Arg Phe
    210                 215                 220

Thr Pro Glu Ile Ala Glu Arg Pro Lys Val Arg Asp Gln Ala Gly Arg
225                 230                 235                 240

Met Asn Tyr Tyr Trp Thr Leu Leu Lys Pro Gly Asp Thr Ile Ile Phe
                245                 250                 255

Glu Ala Asn Gly Asn Leu Ile Ala Pro Met Tyr Ala Phe Ala Leu Ser
            260                 265                 270

Arg Gly Phe Gly Ser Gly Ile Ile Thr Ser Asn Ala Ser Met His Glu
        275                 280                 285

Cys Asn Thr Lys Cys Gln Thr Pro Leu Gly Ala Ile Asn Ser Ser Leu
    290                 295                 300

Pro Tyr Gln Asn Ile His Pro Val Thr Ile Gly Glu Cys Pro Lys Tyr
305                 310                 315                 320

Val Arg Ser Ala Lys Leu Arg Met Val Thr Gly Leu Arg Asn Thr Pro
```

```
                325                 330                 335
Ser Ile Gln Ser Arg Gly Leu Phe Gly Ala Ile Ala Gly Phe Ile Glu
            340                 345                 350
Gly Gly Trp Thr Gly Met Ile Asp Gly Trp Tyr Gly Tyr His His Gln
        355                 360                 365
Asn Glu Gln Gly Ser Gly Tyr Ala Ala Asp Gln Lys Ser Thr Gln Asn
    370                 375                 380
Ala Ile Asn Gly Ile Thr Asn Lys Val Asn Thr Val Ile Glu Lys Met
385                 390                 395                 400
Asn Ile Gln Phe Thr Ala Val Gly Lys Glu Phe Asn Lys Leu Glu Lys
                405                 410                 415
Arg Met Glu Asn Leu Asn Lys Lys Val Asp Asp Gly Phe Leu Asp Ile
            420                 425                 430
Trp Thr Tyr Asn Ala Glu Leu Leu Val Leu Leu Glu Asn Glu Arg Thr
        435                 440                 445
Leu Asp Phe His Asp Ser Asn Val Lys Asn Leu Tyr Glu Lys Val Lys
    450                 455                 460
Ser Gln Leu Lys Asn Asn Ala Lys Glu Ile Gly Asn Gly Cys Phe Glu
465                 470                 475                 480
Phe Tyr His Lys Cys Asp Asn Glu Cys Met Glu Ser Val Arg Asn Gly
                485                 490                 495
Thr Tyr Asp Tyr Pro Lys Tyr Ser Glu Glu Ser Lys Leu Asn Arg Glu
            500                 505                 510
Lys Val Asp Gly Val Lys Leu Glu Ser Met Gly Ile Tyr Gln Ile Leu
        515                 520                 525
Ala Ile Tyr Ser Thr Val Ala Ser Ser Leu Val Leu Leu Val Ser Leu
    530                 535                 540
Gly Ala Ile Ser Phe Trp Met Cys Ser Asn Gly Ser Leu Gln Cys Arg
545                 550                 555                 560
Ile Cys Ile

<210> SEQ ID NO 16
<211> LENGTH: 501
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atggcggccc ccggcgcccg gcggccgctg ctcctgctgc tgctggcagg ccttgcacat      60
ggcgcctcag cactctttga ggatctaatc atgcatggag atacacctac attgcatgaa     120
tatatgttag atttgcaacc agagacaact gatctctact gttatgagca attaaatgac     180
agctcagagg aggaggatga aatagatggt ccagctggac aagcagaacc ggacagagcc     240
cattacaata ttgttacctt tgttgcaagt gtgactctac gcttcggtt gtgcgtacaa      300 agcacacacg tagacattcg tactttggaa gacctgttaa tgggcacact aggaattgtg     360
tgccccatct gttctcagga tcttaacaac atgttgatcc ccattgctgt gggcggtgcc     420
ctggcagggc tggtcctcat cgtcctcatt gcctacctca ttggcaggaa gaggagtcac     480
gccggctatc agaccatcta g                                              501

<210> SEQ ID NO 17
<211> LENGTH: 166
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 17

```
Met Ala Ala Pro Gly Ala Arg Arg Pro Leu Leu Leu Leu Leu Leu Ala
1               5                   10                  15

Gly Leu Ala His Gly Ala Ser Ala Leu Phe Glu Asp Leu Ile Met His
            20                  25                  30

Gly Asp Thr Pro Thr Leu His Glu Tyr Met Leu Asp Leu Gln Pro Glu
        35                  40                  45

Thr Thr Asp Leu Tyr Cys Tyr Glu Gln Leu Asn Asp Ser Ser Glu Glu
    50                  55                  60

Glu Asp Glu Ile Asp Gly Pro Ala Gly Gln Ala Glu Pro Asp Arg Ala
65                  70                  75                  80

His Tyr Asn Ile Val Thr Phe Cys Cys Lys Cys Asp Ser Thr Leu Arg
                85                  90                  95

Leu Cys Val Gln Ser Thr His Val Asp Ile Arg Thr Leu Glu Asp Leu
            100                 105                 110

Leu Met Gly Thr Leu Gly Ile Val Cys Pro Ile Cys Ser Gln Asp Leu
        115                 120                 125

Asn Asn Met Leu Ile Pro Ile Ala Val Gly Gly Ala Leu Ala Gly Leu
130                 135                 140

Val Leu Ile Val Leu Ile Ala Tyr Leu Ile Gly Arg Lys Arg Ser His
145                 150                 155                 160

Ala Gly Tyr Gln Thr Ile
                165
```

<210> SEQ ID NO 18
<211> LENGTH: 5915
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caactccgcc ccattgacgc aaatgggcg      780 gtaggcgtgt acggtgggag gtctatataa gcagagctct ctggctaact agagaaccca     840
```

```
ctgcttactg gcttatcgaa attaatacga ctcactatag ggagacccaa gctggctagc    900
gtttaaacgg gccctctaga ctcgagcggc cgccactgtg ctggatatct gcagaattca    960
tggcggcccc cggcgccggg cggccgctgc tcctgctgct gctggcaggc cttgcacatg   1020
gcgcctcagc actctttgag gatctaatca tgcatggaga tacacctaca ttgcatgaat   1080
atatgttaga tttgcaacca gagacaactg atctctactg ttatgagcaa ttaaatgaca   1140
gctcagagga ggaggatgaa atagatggtc cagctggaca agcagaaccg gacagagccc   1200
attacaatat tgttaccttt tgttgcaagt gtgactctac gcttcggttg tgcgtacaaa   1260
gcacacacgt agacattcgt actttggaag acctgttaat gggcacacta ggaattgtgt   1320
gccccatctg ttctcaggat cttaacaaca tgttgatccc cattgctgtg gcggtgcccc   1380
tggcagggct ggtcctcatc gtcctcattg cctacctcat ggcaggaag aggagtcacg   1440
ccggctatca gaccatctag ggatccgagc tcggtaccaa gcttaagttt aaaccgctga   1500
tcagcctcga ctgtgccttc tagttgccag ccatctgttg tttgcccctc cccgtgcct    1560
tccttgaccc tggaaggtgc cactcccact gtcctttcct aataaaatga ggaaattgca   1620
tcgcattgtc tgagtaggtg tcattctatt ctggggggtg gggtggggca ggacagcaag   1680
ggggaggatt gggaagacaa tagcaggcat gctgggatg cggtgggctc tatggcttct   1740
gaggcggaaa gaaccagctg gggctctagg gggtatcccc acgcgccctg tagcggcgca   1800
ttaagcgcgg cgggtgtggt ggttacgcgc agcgtgaccg ctacacttgc cagcgcccta   1860
gcgcccgctc ctttcgcttt cttcccttcc tttctcgcca cgttcgccgg ctttccccgt   1920
caagctctaa atcggggcat ccctttaggg ttccgattta gtgctttacg gcacctcgac   1980
cccaaaaaac ttgattaggg tgatggttca cgtagtgggc catcgccctg atagacggtt   2040
tttcgccctt tgacgttgga gtccacgttc tttaatagtg gactcttgtt ccaaactgga   2100
acaacactca accctatctc ggtctattct tttgatttat aagggatttt ggggatttcg   2160
gcctattggt taaaaaatga gctgatttaa caaaaattta cgcgaatta attctgtgga   2220
atgtgtgtca gttagggtgt ggaaagtccc caggctcccc aggcaggcag aagtatgcaa   2280
agcatgcatc tcaattagtc agcaaccagg tgtggaaagt ccccaggctc ccagcaggc    2340
agaagtatgc aaagcatgca tctcaattag tcagcaacca tagtcccgcc cctaactccg   2400
cccatcccgc ccctaactcc gcccagttcc gcccattctc cgccccatgg ctgactaatt   2460
ttttttattt atgcagaggc cgaggccgcc tctgcctctg agctattcca gaagtagtga   2520
ggaggctttt ttggaggcct aggcttttgc aaaaagctcc cgggagcttg tatatccatt   2580
ttcggatctg atcaagagac aggatgagga tcgtttcgca tgattgaaca agatggattg   2640
cacgcaggtt ctccggccgc ttgggtggag aggctattcg gctatgactg gcacaacag    2700
acaatcggct gctctgatgc cgccgtgttc cggctgtcag cgcaggggcg cccggttctt   2760
tttgtcaaga ccgacctgtc cggtgccctg aatgaactgc aggacgaggc agcgcggcta   2820
tcgtggctgg ccacgacggg cgttccttgc gcagctgtgc tcgacgttgt cactgaagcg   2880
ggaagggact ggctgctatt gggcgaagtg ccggggcagg atctcctgtc atctcacctt   2940
gctcctgccg agaaagtatc catcatggct gatgcaatgc ggcggctgca tacgcttgat   3000
ccggctacct gcccattcga ccaccaagcg aaacatcgca tcgagcgagc acgtactcgg   3060
atggaagccg gtcttgtcga tcaggatgat ctggacgaag agcatcaggg gctcgcgcca   3120
gccgaactgt tcgccaggct caaggcgcgc atgcccgacg cgaggatct cgtcgtgacc   3180
catggcgatg cctgcttgcc gaatatcatg gtggaaaatg gccgcttttc tggattcatc   3240
```

```
gactgtggcc ggctgggtgt ggcggaccgc tatcaggaca tagcgttggc tacccgtgat   3300
attgctgaag agcttggcgg cgaatgggct gaccgcttcc tcgtgcttta cggtatcgcc   3360
gctcccgatt cgcagcgcat cgccttctat cgccttcttg acgagttctt ctgagcggga   3420
ctctggggtt cgaaatgacc gaccaagcga cgcccaacct gccatcacga gatttcgatt   3480
ccaccgccgc cttctatgaa aggttgggct tcggaatcgt tttccgggac gccggctgga   3540
tgatcctcca gcgcggggat ctcatgctgg agttcttcgc ccaccccaac ttgtttattg   3600
cagcttataa tggttacaaa taaagcaata gcatcacaaa tttcacaaat aaagcatttt   3660
tttcactgca ttctagttgt ggtttgtcca aactcatcaa tgtatcttat catgtctgta   3720
taccgtcgac ctctagctag agcttggcgt aatcatggtc atagctgttt cctgtgtgaa   3780
attgttatcc gctcacaatt ccacacaaca tacgagccgg aagcataaag tgtaaagcct   3840
ggggtgccta atgagtgagc taactcacat taattgcgtt gcgctcactg cccgctttcc   3900
agtcgggaaa cctgtcgtgc cagctgcatt aatgaatcgg ccaacgcgcg gggagaggcg   3960
gtttgcgtat tgggcgctct tccgcttcct cgctcactga ctcgctgcgc tcggtcgttc   4020
ggctgcggcg agcggtatca gctcactcaa aggcggtaat acggttatcc acagaatcag   4080
gggataacgc aggaaagaac atgtgagcaa aaggccagca aaaggccagg aaccgtaaaa   4140
aggccgcgtt gctggcgttt ttccataggc tccgccccccc tgacgagcat cacaaaaatc   4200
gacgctcaag tcagaggtgg cgaaacccga caggactata agataccag gcgtttcccc   4260 ctggaagctc cctcgtgcgc tctcctgttc cgaccctgcc gcttaccgga tacctgtccg   4320
cctttctccc ttcgggaagc gtggcgcttt ctcaatgctc acgctgtagg tatctcagtt   4380
cggtgtaggt cgttcgctcc aagctgggct gtgtgcacga accccccgtt cagcccgacc   4440
gctgcgcctt atccggtaac tatcgtcttg agtccaaccc ggtaagacac gacttatcgc   4500
cactggcagc agccactggt aacaggatta gcagagcgag gtatgtaggc ggtgctacag   4560
agttcttgaa gtggtggcct aactacggct acactagaag gacagtattt ggtatctgcg   4620
ctctgctgaa gccagttacc ttcggaaaaa gagttggtag ctcttgatcc ggcaaacaaa   4680
ccaccgctgg tagcggtggt ttttttgttt gcaagcagca gattacgcgc agaaaaaaag   4740
gatctcaaga agatccttg atcttttcta cggggtctga cgctcagtgg aacgaaaact   4800
cacgttaagg gattttggtc atgagattat caaaaaggat cttcacctag atccttttaa   4860
attaaaaatg aagttttaaa tcaatctaaa gtatatatga gtaaacttgg tctgacagtt   4920
accaatgctt aatcagtgag gcacctatct cagcgatctg tctatttcgt tcatccatag   4980
ttgcctgact ccccgtcgtg tagataacta cgatacggga gggcttacca tctggcccca   5040
gtgctgcaat gataccgcga gacccacgct caccggctcc agatttatca gcaataaacc   5100
agccagccgg aagggccgag cgcagaagtg gtcctgcaac tttatccgcc tccatccagt   5160
ctattaattg ttgccgggaa gctagagtaa gtagttcgcc agttaatagt ttgcgcaacg   5220
ttgttgccat tgctacaggc atcgtggtgt cacgctcgtc gtttggtatg gcttcattca   5280
gctccggttc ccaacgatca aggcgagtta catgatcccc catgttgtgc aaaaaagcgg   5340
ttagctcctt cggtcctccg atcgttgtca gaagtaagtt ggccgcagtg ttatcactca   5400
tggttatggc agcactgcat aattctctta ctgtcatgcc atccgtaaga tgcttttctg   5460
tgactggtga gtactcaacc aagtcattct gagaatagtg tatgcggcga ccgagttgct   5520
cttgcccggc gtcaatacgg gataataccg cgccacatag cagaacttta aaagtgctca   5580
```

| | |
|---|---|
| tcattggaaa acgttcttcg gggcgaaaac tctcaaggat cttaccgctg ttgagatcca | 5640 |
| gttcgatgta acccactcgt gcacccaact gatcttcagc atctttact ttcaccagcg | 5700 |
| tttctgggtg agcaaaaaca ggaaggcaaa atgccgcaaa aagggaata agggcgacac | 5760 |
| ggaaatgttg aatactcata ctcttccttt ttcaatatta ttgaagcatt tatcagggtt | 5820 |
| attgtctcat gagcggatac atatttgaat gtatttagaa aaataaacaa ataggggttc | 5880 |
| cgcgcacatt tccccgaaaa gtgccacctg acgtc | 5915 |

<210> SEQ ID NO 19
<211> LENGTH: 1878
<212> TYPE: DNA
<213> ORGANISM: Mycobacterium tuberculosis

<400> SEQUENCE: 19

| | |
|---|---|
| atggctcgtg cggtcgggat cgacctcggg accaccaact ccgtcgtctc ggttctggaa | 60 |
| ggtggcgacc cggtcgtcgt cgccaactcc gagggctcca ggaccacccc gtcaattgtc | 120 |
| gcgttcgccc gcaacggtga ggtgctggtc ggccagcccg ccaagaacca ggcagtgacc | 180 |
| aacgtcgatc gcaccgtgcg ctcggtcaag cgacacatgg gcagcgactg gtccatagag | 240 |
| attgacggca agaaatacac cgcgccggag atcagcgccc gcattctgat gaagctgaag | 300 |
| cgcgacgccg aggcctacct cggtgaggac attaccgacg cggttatcac gacgcccgcc | 360 |
| tacttcaatg acgcccagcg tcaggccacc aaggacgccg ccagatcgc cggcctcaac | 420 |
| gtgctgcgga tcgtcaacga gccgaccgcg gccgcgctgg cctacggcct cgacaagggc | 480 |
| gagaaggagc agcgaatcct ggtcttcgac ttgggtggtg gcactttcga cgtttccctg | 540 |
| ctggagatcg gcgagggtgt ggttgaggtc cgtgccactt cgggtgacaa ccacctcggc | 600 |
| ggcgacgact gggaccagcg ggtcgtcgat tggctggtgg acaagttcaa gggcaccagc | 660 |
| ggcatcgatc tgaccaagga caagatggcg atgcagcggc tgcgggaagc cgccgagaag | 720 |
| gcaaagatcg agctgagttc gagtcagtcc acctcgatca acctgcccta catcaccgtc | 780 |
| gacgccgaca agaacccgtt gttcttagac gagcagctga cccgcgcgga gttccaacgg | 840 |
| atcactcagg acctgctgga ccgcactcgc aagccgttcc agtcggtgat cgctgacacc | 900 |
| ggcatttcgg tgtcggagat cgatcacgtt gtgctcgtgg gtggttcgac ccggatgccc | 960 |
| gcggtgaccg atctggtcaa ggaactcacc ggcggcaagg aacccaacaa gggcgtcaac | 1020 |
| cccgatgagg ttgtcgcggt gggagccgct ctgcaggccg gcgtcctcaa gggcgaggtg | 1080 |
| aaagacgttc tgctgcttga tgttacccg ctgagcctgg gtatcgagac caagggcggg | 1140 |
| gtgatgacca ggctcatcga gcgcaacacc acgatcccca ccaagcggtc ggagactttc | 1200 |
| accaccgccg acgacaacca accgtcggtg cagatccagg tctatcaggg ggagcgtgag | 1260 |
| atcgccgcgc acaacaagtt gctcgggtcc ttcgagctga ccggcatccc gccggcgccg | 1320 |
| cggggattc gcagatcga ggtcactttc gacatcgacg ccaacggcat tgtgcacgtc | 1380 |
| accgccaagg acaagggcac cggcaaggag aacacgatcc gaatccagga aggctcgggc | 1440 |
| ctgtccaagg aagacattga ccgcatgatc aaggacgccg aagcgcacgc cgaggaggat | 1500 |
| cgcaagcgtc gcgaggaggc cgatgttcgt aatcaagccg agacattggt ctaccagacg | 1560 |
| gagaagttcg tcaaagaaca gcgtgaggcc gagggtggtt cgaaggtacc tgaagacacg | 1620 |
| ctgaacaagg ttgatgccgc ggtggcggaa gcgaaggcgg cacttggcgg atcggatatt | 1680 |
| tcggccatca gtcggcgat ggagaagctg gccaggagt cgcaggctct ggggcaagcg | 1740 |
| atctacgaag cagctcaggc tgcgtcacag gccactggcg ctgcccaccc cggcggcgag | 1800 |

```
ccgggcggtg cccaccccgg ctcggctgat gacgttgtgg acgcggaggt ggtcgacgac 1860
ggccgggagg ccaagtga 1878

<210> SEQ ID NO 20
<211> LENGTH: 621
<212> TYPE: PRT
<213> ORGANISM: Mycobacterium tuberculosis

<400> SEQUENCE: 20
```

Met Ala Arg Ala Val Gly Ile Asp Leu Gly Thr Thr Asn Ser Val Val
1 5 10 15

Ser Val Leu Glu Gly Gly Asp Pro Val Val Val Ala Asn Ser Glu Gly
20 25 30

Ser Arg Thr Thr Pro Ser Ile Val Ala Phe Ala Arg Asn Gly Glu Val
35 40 45

Leu Val Gly Gln Pro Ala Lys Asn Gln Ala Val Thr Asn Val Asp Arg
50 55 60

Thr Val Arg Ser Val Lys Arg His Met Gly Ser Asp Trp Ser Ile Glu
65 70 75 80

Ile Asp Gly Lys Lys Tyr Thr Ala Pro Glu Ile Ser Ala Arg Ile Leu
85 90 95

Met Lys Leu Lys Arg Asp Ala Glu Ala Tyr Leu Gly Glu Asp Ile Thr
100 105 110

Asp Ala Val Ile Thr Thr Pro Ala Tyr Phe Asn Asp Ala Gln Arg Gln
115 120 125

Ala Thr Lys Asp Ala Gly Gln Ile Ala Gln Val Leu Arg Ile Val Asn
130 135 140

Glu Pro Thr Ala Ala Ala Tyr Gly Leu Asp Lys Gly Glu Lys Glu Gln
145 150 155 160

Arg Ile Leu Val Phe Asp Leu Gly Gly Gly Thr Phe Asp Val Ser Leu
165 170 175

Leu Glu Ile Gly Glu Gly Val Val Glu Val Arg Ala Thr Ser Gly Asp
180 185 190

Asn His Leu Gly Gly Asp Asp Trp Asp Gln Arg Val Val Asp Trp Leu
195 200 205

Val Asp Lys Phe Lys Gly Thr Ser Gly Ile Asp Leu Thr Lys Asp Lys
210 215 220

Met Ala Met Gln Arg Leu Arg Glu Ala Ala Glu Lys Ala Lys Ile Glu
225 230 235 240

Leu Ser Ser Ser Gln Ser Thr Ser Ile Asn Leu Pro Tyr Ile Thr Val
245 250 255

Asp Ala Asp Lys Asn Pro Leu Phe Leu Asp Glu Gln Leu Thr Arg Ala
260 265 270

Glu Phe Gln Arg Ile Thr Gln Asp Leu Leu Asp Arg Thr Arg Lys Pro
275 280 285

Phe Gln Ser Val Ile Ala Asp Thr Gly Ile Ser Val Ser Glu Ile Asp
290 295 300

His Val Val Leu Val Gly Gly Ser Thr Arg Met Pro Ala Val Thr Asp
305 310 315 320

Leu Val Lys Glu Leu Thr Gly Gly Lys Glu Pro Asn Lys Gly Val Asn
325 330 335

Pro Asp Glu Val Val Ala Val Gly Ala Ala Leu Gln Ala Gly Val Leu
340 345 350

```
Lys Gly Glu Val Lys Asp Val Leu Leu Asp Val Thr Pro Leu Ser
            355                 360                 365
Leu Gly Ile Glu Thr Lys Gly Val Met Thr Arg Leu Ile Glu Arg
    370                 375                 380
Asn Thr Thr Ile Pro Thr Lys Arg Ser Glu Thr Phe Thr Ala Asp
385                 390                 395                 400
Asp Asn Gln Pro Ser Val Gln Ile Gln Val Tyr Gln Gly Glu Arg Glu
                405                 410                 415
Ile Ala Ala His Asn Lys Leu Leu Gly Ser Phe Glu Leu Thr Gly Ile
            420                 425                 430
Pro Pro Ala Pro Arg Gly Ile Pro Gln Ile Glu Val Thr Phe Asp Ile
        435                 440                 445
Asp Ala Asn Gly Ile Val His Val Thr Ala Lys Asp Lys Gly Thr Gly
    450                 455                 460
Lys Glu Asn Thr Ile Arg Ile Gln Glu Gly Ser Gly Leu Ser Lys Glu
465                 470                 475                 480
Asp Ile Asp Arg Met Ile Lys Asp Ala Glu Ala His Ala Glu Glu Asp
                485                 490                 495
Arg Lys Arg Arg Glu Glu Ala Asp Val Arg Asn Gln Ala Glu Thr Leu
            500                 505                 510
Val Tyr Gln Thr Glu Lys Phe Val Lys Glu Gln Arg Glu Ala Glu Gly
        515                 520                 525
Gly Ser Lys Val Pro Glu Asp Thr Leu Asn Lys Val Asp Ala Ala Val
    530                 535                 540
Ala Glu Ala Lys Ala Ala Leu Gly Gly Ser Asp Ile Ser Ala Ile Lys
545                 550                 555                 560
Ser Ala Met Glu Lys Leu Gly Gln Glu Ser Gln Ala Leu Gly Gln Ala
                565                 570                 575
Ile Tyr Glu Ala Ala Gln Ala Ala Ser Gln Ala Thr Gly Ala Ala His
            580                 585                 590
Pro Gly Gly Glu Pro Gly Gly Ala His Pro Gly Ser Ala Asp Asp Val
        595                 600                 605
Val Asp Ala Glu Val Val Asp Asp Gly Arg Glu Ala Lys
    610                 615                 620

<210> SEQ ID NO 21
<211> LENGTH: 2104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(2103)

<400> SEQUENCE: 21 atg cat gga gat aca cct aca ttg cat gaa tat atg tta gat ttg caa        48
Met His Gly Asp Thr Pro Thr Leu His Glu Tyr Met Leu Asp Leu Gln
1               5                   10                  15 cca gag aca act gat ctc tac tgt tat gag caa tta aat gac agc tca        96
Pro Glu Thr Thr Asp Leu Tyr Cys Tyr Glu Gln Leu Asn Asp Ser Ser
                20                  25                  30 gag gag gag gat gaa ata gat ggt cca gct gga caa gca gaa ccg gac       144
Glu Glu Glu Asp Glu Ile Asp Gly Pro Ala Gly Gln Ala Glu Pro Asp
            35                  40                  45 aga gcc cat tac aat att gta acc ttt tgt tgc aag tgt gac tct acg       192
Arg Ala His Tyr Asn Ile Val Thr Phe Cys Cys Lys Cys Asp Ser Thr
```

-continued

|  |  |  |  |  |
|---|---|---|---|---|
| | 50 | 55 | 60 | |
| ctt cgg ttg tgc gta caa agc aca cac gta gac att cgt act ttg gaa<br>Leu Arg Leu Cys Val Gln Ser Thr His Val Asp Ile Arg Thr Leu Glu<br>65                        70                        75                        80 | | | | 240 |
| gac ctg tta atg ggc aca cta gga att gtg tgc ccc atc tgt tct caa<br>Asp Leu Leu Met Gly Thr Leu Gly Ile Val Cys Pro Ile Cys Ser Gln<br>                    85                        90                        95 | | | | 288 |
| gga tcc atg gct cgt gcg gtc ggg atc gac ctc ggg acc acc aac tcc<br>Gly Ser Met Ala Arg Ala Val Gly Ile Asp Leu Gly Thr Thr Asn Ser<br>              100                       105                       110 | | | | 336 |
| gtc gtc tcg gtt ctg gaa ggt ggc gac ccg gtc gtc gtc gcc aac tcc<br>Val Val Ser Val Leu Glu Gly Gly Asp Pro Val Val Val Ala Asn Ser<br>              115                       120                       125 | | | | 384 |
| gag ggc tcc agg acc acc ccg tca att gtc gcg ttc gcc cgc aac ggt<br>Glu Gly Ser Arg Thr Thr Pro Ser Ile Val Ala Phe Ala Arg Asn Gly<br>130                        135                       140 | | | | 432 |
| gag gtg ctg gtc ggc cag ccc gcc aag aac cag gca gtg acc aac gtc<br>Glu Val Leu Val Gly Gln Pro Ala Lys Asn Gln Ala Val Thr Asn Val<br>145                        150                       155                       160 | | | | 480 |
| gat cgc acc gtg cgc tcg gtc aag cga cac atg ggc agc gac tgg tcc<br>Asp Arg Thr Val Arg Ser Val Lys Arg His Met Gly Ser Asp Trp Ser<br>              165                       170                       175 | | | | 528 |
| ata gag att gac ggc aag aaa tac acc gcg ccg gag atc agc gcc cgc<br>Ile Glu Ile Asp Gly Lys Lys Tyr Thr Ala Pro Glu Ile Ser Ala Arg<br>                    180                       185                       190 | | | | 576 |
| att ctg atg aag ctg aag cgc gac gcc gag gcc tac ctc ggt gag gac<br>Ile Leu Met Lys Leu Lys Arg Asp Ala Glu Ala Tyr Leu Gly Glu Asp<br>              195                       200                       205 | | | | 624 |
| att acc gac gcg gtt atc acg acg ccc gcc tac ttc aat gac gcc cag<br>Ile Thr Asp Ala Val Ile Thr Thr Pro Ala Tyr Phe Asn Asp Ala Gln<br>          210                       215                       220 | | | | 672 |
| cgt cag gcc acc aag gac gcc ggc cag atc gcc ggc ctc aac gtg ctg<br>Arg Gln Ala Thr Lys Asp Ala Gly Gln Ile Ala Gly Leu Asn Val Leu<br>225                        230                       235                       240 | | | | 720 |
| cgg atc gtc aac gag ccg acc gcg gcc gcg ctg gcc tac ggc ctc gac<br>Arg Ile Val Asn Glu Pro Thr Ala Ala Ala Leu Ala Tyr Gly Leu Asp<br>                    245                       250                       255 | | | | 768 |
| aag ggc gag aag gag cag cga atc ctg gtc ttc gac ttg ggt ggt ggc<br>Lys Gly Glu Lys Glu Gln Arg Ile Leu Val Phe Asp Leu Gly Gly Gly<br>              260                       265                       270 | | | | 816 |
| act ttc gac gtt tcc ctg ctg gag atc ggc gag ggt gtg gtt gag gtc<br>Thr Phe Asp Val Ser Leu Leu Glu Ile Gly Glu Gly Val Val Glu Val<br>          275                       280                       285 | | | | 864 |
| cgt gcc act tcg ggt gac aac cac ctc ggc ggc gac gac tgg gac cag<br>Arg Ala Thr Ser Gly Asp Asn His Leu Gly Gly Asp Asp Trp Asp Gln<br>290                        295                       300 | | | | 912 |
| cgg gtc gtc gat tgg ctg gtg gac aag ttc aag ggc acc agc ggc atc<br>Arg Val Val Asp Trp Leu Val Asp Lys Phe Lys Gly Thr Ser Gly Ile<br>305                        310                       315                       320 | | | | 960 |
| gat ctg acc aag gac aag atg gcg atg cag cgg ctg cgg gaa gcc gcc<br>Asp Leu Thr Lys Asp Lys Met Ala Met Gln Arg Leu Arg Glu Ala Ala<br>                    325                       330                       335 | | | | 1008 |
| gag aag gca aag atc gag ctg agt tcg agt cag tcc acc tcg atc aac<br>Glu Lys Ala Lys Ile Glu Leu Ser Ser Ser Gln Ser Thr Ser Ile Asn<br>              340                       345                       350 | | | | 1056 |
| ctg ccc tac atc acc gtc gac gcc gac aag aac ccg ttg ttc tta gac<br>Leu Pro Tyr Ile Thr Val Asp Ala Asp Lys Asn Pro Leu Phe Leu Asp<br>          355                       360                       365 | | | | 1104 |
| gag cag ctg acc cgc gcg gag ttc caa cgg atc act cag gac ctg ctg | | | | 1152 |

```
Glu Gln Leu Thr Arg Ala Glu Phe Gln Arg Ile Thr Gln Asp Leu Leu
    370             375             380 gac cgc act cgc aag ccg ttc cag tcg gtg atc gct gac acc ggc att      1200
Asp Arg Thr Arg Lys Pro Phe Gln Ser Val Ile Ala Asp Thr Gly Ile
385             390             395             400 tcg gtg tcg gag atc gat cac gtt gtg ctc gtg ggt ggt tcg acc cgg      1248
Ser Val Ser Glu Ile Asp His Val Val Leu Val Gly Gly Ser Thr Arg
            405             410             415 atg ccc gcg gtg acc gat ctg gtc aag gaa ctc acc ggc ggc aag gaa      1296
Met Pro Ala Val Thr Asp Leu Val Lys Glu Leu Thr Gly Gly Lys Glu
        420             425             430 ccc aac aag ggc gtc aac ccc gat gag gtt gtc gcg gtg gga gcc gct      1344
Pro Asn Lys Gly Val Asn Pro Asp Glu Val Val Ala Val Gly Ala Ala
    435             440             445 ctg cag gcc ggc gtc ctc aag ggc gag gtg aaa gac gtt ctg ctg ctt      1392
Leu Gln Ala Gly Val Leu Lys Gly Glu Val Lys Asp Val Leu Leu Leu
450             455             460 gat gtt acc ccg ctg agc ctg ggt atc gag acc aag ggc ggg gtg atg      1440
Asp Val Thr Pro Leu Ser Leu Gly Ile Glu Thr Lys Gly Gly Val Met
465             470             475             480 acc agg ctc atc gag cgc aac acg atc ccc acc aag cgg tcg gag          1488
Thr Arg Leu Ile Glu Arg Asn Thr Thr Ile Pro Thr Lys Arg Ser Glu
            485             490             495 act ttc acc acc gcc gac gac aac caa ccg tcg gtg cag atc cag gtc      1536
Thr Phe Thr Thr Ala Asp Asp Asn Gln Pro Ser Val Gln Ile Gln Val
        500             505             510 tat cag ggg gag cgt gag atc gcc gcg cac aac aag ttg ctc ggg tcc      1584
Tyr Gln Gly Glu Arg Glu Ile Ala Ala His Asn Lys Leu Leu Gly Ser
    515             520             525 ttc gag ctg acc ggc atc ccg ccg gcg ccg cgg ggg att ccg cag atc      1632
Phe Glu Leu Thr Gly Ile Pro Pro Ala Pro Arg Gly Ile Pro Gln Ile
530             535             540 gag gtc act ttc gac atc gac gcc aac ggc att gtg cac gtc acc gcc      1680
Glu Val Thr Phe Asp Ile Asp Ala Asn Gly Ile Val His Val Thr Ala
545             550             555             560 aag gac aag ggc acc ggc aag gag aac acg atc cga atc cag gaa ggc      1728
Lys Asp Lys Gly Thr Gly Lys Glu Asn Thr Ile Arg Ile Gln Glu Gly
            565             570             575 tcg ggc ctg tcc aag gaa gac att gac cgc atg atc aag gac gcc gaa      1776
Ser Gly Leu Ser Lys Glu Asp Ile Asp Arg Met Ile Lys Asp Ala Glu
        580             585             590 gcg cac gcc gag gag gat cgc aag cgt cgc gag gag gcc gat gtt cgt      1824
Ala His Ala Glu Glu Asp Arg Lys Arg Arg Glu Glu Ala Asp Val Arg
    595             600             605 aat caa gcc gag aca ttg gtc tac cag acg gag aag ttc gtc aaa gaa      1872
Asn Gln Ala Glu Thr Leu Val Tyr Gln Thr Glu Lys Phe Val Lys Glu
610             615             620 cag cgt gag gcc gag ggt ggt tcg aag gta cct gaa gac acg ctg aac      1920
Gln Arg Glu Ala Glu Gly Gly Ser Lys Val Pro Glu Asp Thr Leu Asn
625             630             635             640 aag gtt gat gcc gcg gtg gcg gaa gcg aag gcg gca ctt ggc gga tcg      1968
Lys Val Asp Ala Ala Val Ala Glu Ala Lys Ala Ala Leu Gly Gly Ser
            645             650             655 gat att tcg gcc atc aag tcg gcg atg gag aag ctg ggc cag gag tcg      2016
Asp Ile Ser Ala Ile Lys Ser Ala Met Glu Lys Leu Gly Gln Glu Ser
        660             665             670 cag gct ctg ggg caa gcg atc tac gaa gca gct cag gct gcg tca cag      2064
Gln Ala Leu Gly Gln Ala Ile Tyr Glu Ala Ala Gln Ala Ala Ser Gln
    675             680             685
```

```
gcc act ggc gct gcc cac ccc ggc tcg gct gat gaa agc a              2104
Ala Thr Gly Ala Ala His Pro Gly Ser Ala Asp Glu Ser
690                 695                 700
```

<210> SEQ ID NO 22
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Gly Ser Met Ala Arg Ala Val Gly Ile Asp Leu Gly Thr Thr Asn Ser
            100                 105                 110

Val Val Ser Val Leu Glu Gly Gly Asp Pro Val Val Ala Asn Ser
        115                 120                 125

Glu Gly Ser Arg Thr Thr Pro Ser Ile Val Ala Phe Ala Arg Asn Gly
    130                 135                 140

Glu Val Leu Val Gly Gln Pro Ala Lys Asn Gln Ala Val Thr Asn Val
145                 150                 155                 160

Asp Arg Thr Val Arg Ser Val Lys Arg His Met Gly Ser Asp Trp Ser
                165                 170                 175

Ile Glu Ile Asp Gly Lys Lys Tyr Thr Ala Pro Glu Ile Ser Ala Arg
            180                 185                 190

Ile Leu Met Lys Leu Lys Arg Asp Ala Glu Ala Tyr Leu Gly Glu Asp
        195                 200                 205

Ile Thr Asp Ala Val Ile Thr Thr Pro Ala Tyr Phe Asn Asp Ala Gln
    210                 215                 220

Arg Gln Ala Thr Lys Asp Ala Gly Gln Ile Ala Gly Leu Asn Val Leu
225                 230                 235                 240

Arg Ile Val Asn Glu Pro Thr Ala Ala Ala Leu Ala Tyr Gly Leu Asp
                245                 250                 255

Lys Gly Glu Lys Glu Gln Arg Ile Leu Val Phe Asp Leu Gly Gly Gly
            260                 265                 270

Thr Phe Asp Val Ser Leu Leu Glu Ile Gly Glu Gly Val Val Glu Val
        275                 280                 285

Arg Ala Thr Ser Gly Asp Asn His Leu Gly Gly Asp Asp Trp Asp Gln
    290                 295                 300

Arg Val Val Asp Trp Leu Val Asp Lys Phe Lys Gly Thr Ser Gly Ile
305                 310                 315                 320

Asp Leu Thr Lys Asp Lys Met Ala Met Gln Arg Leu Arg Glu Ala Ala
                325                 330                 335

Glu Lys Ala Lys Ile Glu Leu Ser Ser Ser Gln Ser Thr Ser Ile Asn
```

```
                    340                 345                 350
Leu Pro Tyr Ile Thr Val Asp Ala Asp Lys Asn Pro Leu Phe Leu Asp
            355                 360                 365

Glu Gln Leu Thr Arg Ala Glu Phe Gln Arg Ile Thr Gln Asp Leu Leu
        370                 375                 380

Asp Arg Thr Arg Lys Pro Phe Gln Ser Val Ile Ala Asp Thr Gly Ile
385                 390                 395                 400

Ser Val Ser Glu Ile Asp His Val Val Leu Val Gly Gly Ser Thr Arg
                405                 410                 415

Met Pro Ala Val Thr Asp Leu Val Lys Glu Leu Thr Gly Gly Lys Glu
            420                 425                 430

Pro Asn Lys Gly Val Asn Pro Asp Glu Val Val Ala Val Gly Ala Ala
        435                 440                 445

Leu Gln Ala Gly Val Leu Lys Gly Glu Val Lys Asp Val Leu Leu Leu
    450                 455                 460

Asp Val Thr Pro Leu Ser Leu Gly Ile Glu Thr Lys Gly Gly Val Met
465                 470                 475                 480

Thr Arg Leu Ile Glu Arg Asn Thr Thr Ile Pro Thr Lys Arg Ser Glu
                485                 490                 495

Thr Phe Thr Thr Ala Asp Asp Asn Gln Pro Ser Val Gln Ile Gln Val
            500                 505                 510

Tyr Gln Gly Glu Arg Glu Ile Ala Ala His Asn Lys Leu Leu Gly Ser
        515                 520                 525

Phe Glu Leu Thr Gly Ile Pro Pro Ala Pro Arg Gly Ile Pro Gln Ile
    530                 535                 540

Glu Val Thr Phe Asp Ile Asp Ala Asn Gly Ile Val His Val Thr Ala
545                 550                 555                 560

Lys Asp Lys Gly Thr Gly Lys Glu Asn Thr Ile Arg Ile Gln Glu Gly
                565                 570                 575

Ser Gly Leu Ser Lys Glu Asp Ile Asp Arg Met Ile Lys Asp Ala Glu
            580                 585                 590

Ala His Ala Glu Glu Asp Arg Lys Arg Arg Glu Glu Ala Asp Val Arg
        595                 600                 605

Asn Gln Ala Glu Thr Leu Val Tyr Gln Thr Glu Lys Phe Val Lys Glu
    610                 615                 620

Gln Arg Glu Ala Glu Gly Gly Ser Lys Val Pro Glu Asp Thr Leu Asn
625                 630                 635                 640

Lys Val Asp Ala Ala Val Ala Glu Ala Lys Ala Leu Gly Gly Ser
                645                 650                 655

Asp Ile Ser Ala Ile Lys Ser Ala Met Glu Lys Leu Gly Gln Glu Ser
            660                 665                 670

Gln Ala Leu Gly Gln Ala Ile Tyr Glu Ala Ala Gln Ala Ala Ser Gln
        675                 680                 685

Ala Thr Gly Ala Ala His Pro Gly Ser Ala Asp Glu Ser
    690                 695                 700

<210> SEQ ID NO 23
<211> LENGTH: 2760
<212> TYPE: DNA
<213> ORGANISM: Pseudomonas aeruginosa

<400> SEQUENCE: 23
ctgcagctgg tcaggccgtt tccgcaacgc ttgaagtcct ggccgatata ccggcagggc      60
cagccatcgt tcgacgaata aagccacctc agccatgatg cccttttccat ccccagcgga   120
```

| | |
|---|---|
| acccccgacat ggacgccaaa gccctgctcc tcggcagcct ctgcctggcc gccccattcg | 180 |
| ccgacgcggc gacgctcgac aatgctctct ccgcctgcct cgccgcccgg ctcggtgcac | 240 |
| cgcacacggc ggagggccag ttgcacctgc cactcaccct tgaggcccgg cgctccaccg | 300 |
| gcgaatgcgg ctgtacctcg gcgctggtgc gatatcggct gctggccagg ggcgccagcg | 360 |
| ccgacagcct cgtgcttcaa gagggctgct cgatagtcgc caggacacgc gcgcacgct | 420 |
| gaccctggcg gcggacgccg gcttggcgag cggccgcgaa ctggtcgtca ccctgggttg | 480 |
| tcaggcgcct gactgacagg ccgggctgcc accaccaggc cgagatggac gccctgcatg | 540 |
| tatcctccga tcggcaagcc tcccgttcgc acattcacca ctctgcaatc cagttcataa | 600 |
| atcccataaa agccctcttc cgctccccgc cagcctcccc gcatcccgca ccctagacgc | 660 |
| cccgccgctc tccgccggct cgcccgacaa gaaaaaccaa ccgctcgatc agcctcatcc | 720 |
| ttcacccatc acaggagcca tcgcgatgca cctgatacccc cattggatcc ccctggtcgc | 780 |
| cagcctcggc ctgctcgccg gcggctcgtc cgcgtccgcc gccgaggaag ccttcgacct | 840 |
| ctggaacgaa tgcgccaaag cctgcgtgct cgacctcaag gacggcgtgc gttccagccg | 900 |
| catgagcgtc gacccggcca tcgccgacac caacggccag ggcgtgctgc actactccat | 960 |
| ggtcctggag ggcggcaacg acgcgctcaa gctggccatc gacaacgccc tcagcatcac | 1020 |
| cagcgacggc ctgaccatcc gcctcgaagg cggcgtcgag ccgaacaagc cggtgcgcta | 1080 |
| cagctacacg cgccaggcgc gcggcagttg gtcgctgaac tggctggtac cgatcggcca | 1140 |
| cgagaagccc tcgaacatca aggtgttcat ccacgaactg aacgccggca accagctcag | 1200 |
| ccacatgtcg ccgatctaca ccatcgagat gggcgacgag ttgctggcga agctggcgcg | 1260 |
| cgatgccacc ttcttcgtca gggcgcacga gagcaacgag atgcagccga cgctcgccat | 1320 |
| cagccatgcc ggggtcagcg tggtcatggc ccagacccag ccgcgccggg aaaagcgctg | 1380 |
| gagcgaatgg gccagcggca aggtgttgtg cctgctcgac ccgctggacg gggtctacaa | 1440 |
| ctacctcgcc cagcaacgct gcaacctcga cgatacctgg gaaggcaaga tctaccgggt | 1500 |
| gctcgccggc aacccggcga agcatgacct ggacatcaaa cccacggtca tcagtcatcg | 1560 |
| cctgcacttt cccgagggcg gcagcctggc cgcgctgacc gcgcaccagg cttgccacct | 1620 |
| gccgctggag actttcaccc gtcatcgcca gccgcgcggc tgggaacaac tggagcagtg | 1680 |
| cggctatccg gtgcagcggc tggtcgccct ctacctggcg gcgcggctgt cgtggaacca | 1740 |
| ggtcgaccag gtgatccgca acgccctggc cagccccggc agcggcggcg acctgggcga | 1800 |
| agcgatccgc gagcagccgg agcaggcccg tctggccctg accctggccg ccgccgagag | 1860 |
| cgagcgcttc gtccggcagg gcaccggcaa cgacgaggcc ggcgcggcca acgccgacgt | 1920 |
| ggtgagcctg acctgcccgg tcgccgccgg tgaatgcgcg ggcccggcgg acagcggcga | 1980 |
| cgccctgctg gagcgcaact atcccactgg cgcggagttc ctcggcgacg gcggcgacgt | 2040 |
| cagcttcagc acccgcggca cgcagaactg gacggtggag cggctgctcc aggcgcaccg | 2100 |
| ccaactggag gagcgcggct atgtgttcgt cggctaccac ggcaccttcc tcgaagcggc | 2160 |
| gcaaagcatc gtcttcggcg gggtgcgcgc gcgcagccag gacctcgacg cgatctggcg | 2220 |
| cggtttctat atcgccggcg atccggcgct ggcctacggc tacgcccagg accaggaacc | 2280 |
| cgacgcacgc ggccggatcc gcaacggtgc cctgctgcgg gtctatgtgc cgcgctcgag | 2340 |
| cctgccgggc ttctaccgca ccagcctgac cctggccgcg ccggaggcgg cgggcgaggt | 2400 |
| cgaacggctg atcggccatc cgctgccgct gcgcctggac gccatcaccg gccccgagga | 2460 |

-continued

```
ggaaggcggg cgcctggaga ccattctcgg ctggccgctg gccgagcgca ccgtggtgat    2520
tccctcggcg atccccaccg acccgcgcaa cgtcggcggc gacctcgacc cgtccagcat    2580
ccccgacaag gaacaggcga tcagcgccct gccggactac gccagccagc ccggcaaacc    2640
gccgcgcgag gacctgaagt aactgccgcg accggccggc tcccttcgca ggagccggcc    2700
ttctcggggc ctggccatac atcaggtttt cctgatgcca gcccaatcga atatgaattc    2760
```

<210> SEQ ID NO 24
<211> LENGTH: 628
<212> TYPE: PRT
<213> ORGANISM: Pseudomonas aeruginosa

<400> SEQUENCE: 24

```
Met His Leu Ile Pro His Trp Ile Pro Leu Val Ala Ser Leu Gly Leu
1               5                   10                  15

Leu Ala Gly Gly Ser Ser Ala Ser Ala Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Glu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Arg Ser Trp Ser Leu Asn Trp Leu Val Pro Ile
        115                 120                 125

Gly His Glu Lys Pro Ser Asn Ile Lys Val Phe Ile His Glu Leu Asn
    130                 135                 140

Ala Gly Asn Gln Leu Ser His Met Ser Pro Ile Tyr Thr Ile Glu Met
145                 150                 155                 160

Gly Asp Glu Leu Leu Ala Lys Leu Ala Arg Asp Ala Thr Phe Phe Val
                165                 170                 175

Arg Ala His Glu Ser Asn Glu Met Gln Pro Thr Leu Ala Ile Ser His
            180                 185                 190

Ala Gly Val Ser Val Val Met Ala Gln Thr Gln Pro Arg Arg Glu Lys
        195                 200                 205

Arg Trp Ser Glu Trp Ala Ser Gly Lys Val Leu Cys Leu Leu Asp Pro
    210                 215                 220

Leu Asp Gly Val Tyr Asn Tyr Leu Ala Gln Gln Arg Cys Asn Leu Asp
225                 230                 235                 240

Asp Thr Trp Glu Gly Lys Ile Tyr Arg Val Leu Ala Gly Asn Pro Ala
                245                 250                 255

Lys His Asp Leu Asp Ile Lys Pro Thr Val Ile Ser His Arg Leu His
            260                 265                 270

Phe Pro Glu Gly Gly Ser Leu Ala Ala Leu Thr Ala His Gln Ala Cys
        275                 280                 285

His Leu Pro Leu Glu Thr Phe Thr Arg His Arg Gln Pro Arg Gly Trp
    290                 295                 300

Glu Gln Leu Glu Gln Cys Gly Tyr Pro Val Gln Arg Leu Val Ala Leu
305                 310                 315                 320

Tyr Leu Ala Ala Arg Leu Ser Trp Asn Gln Val Asp Gln Val Ile Arg
```

```
                325                 330                 335
Asn Ala Leu Asp Gly Ser Gly Gly Asp Leu Gly Glu Ala Ile Arg Glu
            340                 345                 350
Gln Pro Glu Gln Ala Arg Leu Ala Leu Thr Leu Ala Ala Glu Ser
        355                 360                 365
Phe Val Arg Gln Gly Thr Gly Asn Asp Glu Ala Gly Ala Ala Asn Ala
370                 375                 380
Asp Val Val Ser Leu Thr Cys Pro Val Ala Gly Glu Cys Ala Gly
385                 390                 395                 400
Pro Ala Asp Ser Gly Asp Ala Leu Leu Glu Arg Asn Tyr Pro Thr Gly
                405                 410                 415
Ala Glu Phe Leu Gly Asp Gly Asp Val Ser Phe Ser Thr Arg Gly
            420                 425                 430
Thr Gln Asn Trp Thr Val Glu Arg Leu Leu Gln Ala His Arg Gln Leu
        435                 440                 445
Glu Glu Arg Gly Tyr Val Phe Val Gly Tyr His Gly Thr Phe Leu Glu
450                 455                 460
Ala Ala Gln Ser Ile Val Phe Gly Gly Val Arg Ala Arg Ser Gln Asp
465                 470                 475                 480
Leu Asp Ala Ile Trp Arg Gly Phe Tyr Ile Ala Gly Asp Pro Ala Tyr
                485                 490                 495
Gly Tyr Ala Gln Asp Gln Glu Pro Asp Arg Arg Ile Arg Asn Gly Ala
            500                 505                 510
Leu Leu Arg Val Tyr Val Pro Arg Ser Ser Leu Pro Gly Phe Tyr Arg
        515                 520                 525
Thr Ser Leu Thr Leu Ala Ala Pro Glu Ala Gly Glu Val Glu Arg
530                 535                 540
Leu Ile Gly His Pro Leu Pro Leu Arg Leu Asp Ala Ile Thr Gly Pro
545                 550                 555                 560
Glu Glu Glu Gly Gly Arg Leu Glu Thr Ile Leu Gly Trp Pro Leu Ala
                565                 570                 575
Glu Arg Thr Val Val Ile Pro Ser Ala Ile Pro Thr Asp Pro Arg Asn
            580                 585                 590
Val Gly Gly Asp Leu Asp Pro Ser Ile Pro Asp Lys Glu Gln Ala
        595                 600                 605
Ile Ser Ala Leu Pro Asp Tyr Ala Ser Gln Pro Gly Lys Pro Pro Arg
    610                 615                 620
Glu Asp Leu Lys
625

<210> SEQ ID NO 25
<211> LENGTH: 167
<212> TYPE: PRT
<213> ORGANISM: Pseudomonas aeruginosa

<400> SEQUENCE: 25

Arg Leu His Phe Pro Glu Gly Gly Ser Leu Ala Ala Leu Thr Ala His
1               5                   10                  15
Gln Ala Cys His Leu Pro Leu Glu Thr Phe Thr Arg His Arg Gln Pro
            20                  25                  30
Arg Gly Trp Glu Gln Leu Glu Gln Cys Gly Tyr Pro Val Gln Arg Leu
        35                  40                  45
Val Ala Leu Tyr Leu Ala Ala Arg Leu Ser Trp Asn Gln Val Asp Gln
    50                  55                  60
```

```
Val Ile Arg Asn Ala Leu Asp Gly Ser Gly Gly Asp Leu Gly Glu Ala
 65                  70                  75                  80

Ile Arg Glu Gln Pro Glu Gln Ala Arg Leu Ala Leu Thr Leu Ala Ala
                 85                  90                  95

Ala Glu Ser Phe Val Arg Gln Gly Thr Gly Asn Asp Glu Ala Gly Ala
            100                 105                 110

Ala Asn Ala Asp Val Val Ser Leu Thr Cys Pro Val Ala Ala Gly Glu
        115                 120                 125

Cys Ala Gly Pro Ala Asp Ser Gly Asp Ala Leu Leu Glu Arg Asn Tyr
    130                 135                 140

Pro Thr Gly Ala Glu Phe Leu Gly Asp Gly Gly Asp Val Ser Phe Ser
145                 150                 155                 160

Thr Arg Gly Thr Gln Asn Trp
                165

<210> SEQ ID NO 26
<211> LENGTH: 870
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(867)

<400> SEQUENCE: 26 atg cgc ctg cac ttt ccc gag ggc ggc agc ctg gcc gcg ctg acc gcg     48
Met Arg Leu His Phe Pro Glu Gly Gly Ser Leu Ala Ala Leu Thr Ala
1               5                  10                  15 cac cag gct tgc cac ctg ccg ctg gag act ttc acc cgt cat cgc cag     96
His Gln Ala Cys His Leu Pro Leu Glu Thr Phe Thr Arg His Arg Gln
            20                  25                  30 ccg cgc ggc tgg gaa caa ctg gag cag tgc ggc tat ccg gtg cag cgg    144
Pro Arg Gly Trp Glu Gln Leu Glu Gln Cys Gly Tyr Pro Val Gln Arg
        35                  40                  45 ctg gtc gcc ctc tac ctg gcg gcg cgg ctg tcg tgg aac cag gtc gac    192
Leu Val Ala Leu Tyr Leu Ala Ala Arg Leu Ser Trp Asn Gln Val Asp
    50                  55                  60 cag gtg atc cgc aac gcc ctg gcc agc ccc ggc agc ggc ggc gac ctg    240
Gln Val Ile Arg Asn Ala Leu Ala Ser Pro Gly Ser Gly Gly Asp Leu
65                  70                  75                  80 ggc gaa gcg atc cgc gag cag ccg gag cag gcc cgt ctg gcc ctg acc    288
Gly Glu Ala Ile Arg Glu Gln Pro Glu Gln Ala Arg Leu Ala Leu Thr
                85                  90                  95 ctg gcc gcc gcc gag agc gag cgc ttc gtc cgg cag ggc acc ggc aac    336
Leu Ala Ala Ala Glu Ser Glu Arg Phe Val Arg Gln Gly Thr Gly Asn
            100                 105                 110 gac gag gcc ggc gcg gcc aac gcc gac gtg gtg agc ctg acc tgc ccg    384
Asp Glu Ala Gly Ala Ala Asn Ala Asp Val Val Ser Leu Thr Cys Pro
        115                 120                 125 gtc gcc gcc ggt gaa tgc gcg ggc ccg gcg gac agc ggc gac gcc ctg    432
Val Ala Ala Gly Glu Cys Ala Gly Pro Ala Asp Ser Gly Asp Ala Leu
    130                 135                 140 ctg gag cgc aac tat ccc act ggc gcg gag ttc ctc ggc gac ggc ggc    480
Leu Glu Arg Asn Tyr Pro Thr Gly Ala Glu Phe Leu Gly Asp Gly Gly
145                 150                 155                 160 gac gtc agc ttc agc acc cgc ggc acg cag aac gaa ttc atg cat gga    528
Asp Val Ser Phe Ser Thr Arg Gly Thr Gln Asn Glu Phe Met His Gly
                165                 170                 175
```

```
gat aca cct aca ttg cat gaa tat atg tta gat ttg caa cca gag aca    576
Asp Thr Pro Thr Leu His Glu Tyr Met Leu Asp Leu Gln Pro Glu Thr
            180                 185                 190 act gat ctc tac tgt tat gag caa tta aat gac agc tca gag gag gag    624
Thr Asp Leu Tyr Cys Tyr Glu Gln Leu Asn Asp Ser Ser Glu Glu Glu
        195                 200                 205 gat gaa ata gat ggt cca gct gga caa gca gaa ccg gac aga gcc cat    672
Asp Glu Ile Asp Gly Pro Ala Gly Gln Ala Glu Pro Asp Arg Ala His
    210                 215                 220 tac aat att gta acc ttt tgt tgc aag tgt gac tct acg ctt cgg ttg    720
Tyr Asn Ile Val Thr Phe Cys Cys Lys Cys Asp Ser Thr Leu Arg Leu
225                 230                 235                 240 tgc gta caa agc aca cac gta gac att cgt act ttg gaa gac ctg tta    768
Cys Val Gln Ser Thr His Val Asp Ile Arg Thr Leu Glu Asp Leu Leu
                245                 250                 255 atg ggc aca cta gga att gtg tgc ccc atc tgt tct caa gga tcc gag    816
Met Gly Thr Leu Gly Ile Val Cys Pro Ile Cys Ser Gln Gly Ser Glu
            260                 265                 270 ctc ggt acc aag ctt aag ttt aaa ccg ctg atc agc ctc gac tgt gcc    864
Leu Gly Thr Lys Leu Lys Phe Lys Pro Leu Ile Ser Leu Asp Cys Ala
        275                 280                 285 ttc tag                                                            870
Phe

<210> SEQ ID NO 27
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Arg Leu His Phe Pro Glu Gly Gly Ser Leu Ala Ala Leu Thr Ala
1               5                   10                  15

His Gln Ala Cys His Leu Pro Leu Glu Thr Phe Thr Arg His Arg Gln
            20                  25                  30

Pro Arg Gly Trp Glu Gln Leu Glu Gln Cys Gly Tyr Pro Val Gln Arg
        35                  40                  45

Leu Val Ala Leu Tyr Leu Ala Ala Arg Leu Ser Trp Asn Gln Val Asp
    50                  55                  60

Gln Val Ile Arg Asn Ala Leu Ala Ser Pro Gly Ser Gly Gly Asp Leu
65                  70                  75                  80

Gly Glu Ala Ile Arg Glu Gln Pro Glu Gln Ala Arg Leu Ala Leu Thr
                85                  90                  95

Leu Ala Ala Ala Glu Ser Glu Arg Phe Val Arg Gln Gly Thr Gly Asn
            100                 105                 110

Asp Glu Ala Gly Ala Ala Asn Ala Asp Val Val Ser Leu Thr Cys Pro
        115                 120                 125

Val Ala Ala Gly Glu Cys Ala Gly Pro Ala Asp Ser Gly Asp Ala Leu
    130                 135                 140

Leu Glu Arg Asn Tyr Pro Thr Gly Ala Glu Phe Leu Gly Asp Gly Gly
145                 150                 155                 160

Asp Val Ser Phe Ser Thr Arg Gly Thr Gln Asn Glu Phe Met His Gly
                165                 170                 175

Asp Thr Pro Thr Leu His Glu Tyr Met Leu Asp Leu Gln Pro Glu Thr
            180                 185                 190

Thr Asp Leu Tyr Cys Tyr Glu Gln Leu Asn Asp Ser Ser Glu Glu Glu
```

```
                    195                 200                 205
Asp Glu Ile Asp Gly Pro Ala Gly Gln Ala Glu Pro Asp Arg Ala His
    210                 215                 220

Tyr Asn Ile Val Thr Phe Cys Cys Lys Cys Asp Ser Thr Leu Arg Leu
225                 230                 235                 240

Cys Val Gln Ser Thr His Val Asp Ile Arg Thr Leu Glu Asp Leu Leu
                245                 250                 255

Met Gly Thr Leu Gly Ile Val Cys Pro Ile Cys Ser Gln Gly Ser Glu
            260                 265                 270

Leu Gly Thr Lys Leu Lys Phe Lys Pro Leu Ile Ser Leu Asp Cys Ala
        275                 280                 285

Phe

<210> SEQ ID NO 28
<211> LENGTH: 1254
<212> TYPE: DNA
<213> ORGANISM: Homo sapiens

<400> SEQUENCE: 28
atgctgctat ccgtgccgct gctgctcggc ctcctcggcc tggccgtcgc cgagcccgcc      60
gtctacttca aggagcagtt tctggacgga cgggtggac cttcccgctg gatcgaatcc      120
aaacacaagt cagattttgg caaattcgtt ctcagttccg gcaagttcta cggtgacgag      180
gagaaagata aggtttgca gacaagccag gatgcacgct tttatgctct gtcggccagt      240
ttcgagcctt tcagcaacaa aggccagacg ctggtggtgc agttcacggt gaaacatgag      300
cagaacatcg actgtggggg cggctatgtg aagctgtttc taatagtttt ggaccagaca      360
gacatgcacg gagactcaga atacaacatc atgtttggtc ccgacatctg tggccctggc      420
accaagaagg ttcatgtcat cttcaactac aagggcaaga acgtgctgat caacaaggac      480
atccgttgca aggatgatga gtttacacac ctgtacacac tgattgtgcg gccagacaac      540
acctatgagg tgaagattga caacagccag gtggagtccg gctccttgga agacgattgg      600
gacttcctgc cacccaagaa gataaaggat cctgatgctt caaaaccgga agactgggat      660
gagcgggcca agatcgatga tcccacagac tccaagcctg aggactggga caagcccgag      720
catatccctg accctgatgc taagaagccc gaggactggg atgaagagat ggacggagag      780
tgggaacccc cagtgattca gaaccctgag tacaaggggt agtggaagcc ccggcagatc      840
gacaacccag attacaaggg cacttggatc cacccagaaa ttgacaaccc cgagtattct      900
cccgatccca gtatctatgc ctatgataac tttggcgtgc tgggcctgga cctctggcag      960
gtcaagtctg gcaccatctt tgacaacttc ctcatcacca acgatgaggc atacgctgag      1020
gagtttggca cgagacgtg gggcgtaaca aaggcagcag agaaacaaat gaaggacaaa      1080
caggacgagg agcagaggct taaggaggag gaagaagaca gaaacgcaa agaggaggag      1140 gaggcagagg acaaggagga tgatgaggac aaagatgagg atgaggagga tgaggaggac      1200
aaggaggaag atgaggagga agatgtcccc ggccaggcca aggacgagct gtag           1254

<210> SEQ ID NO 29
<211> LENGTH: 417
<212> TYPE: PRT
<213> ORGANISM: Homo sapiens

<400> SEQUENCE: 29

Met Leu Leu Ser Val Pro Leu Leu Leu Gly Leu Leu Gly Leu Ala Val
1               5                   10                  15
```

```
Ala Glu Pro Ala Val Tyr Phe Lys Glu Gln Phe Leu Asp Gly Asp Gly
             20                  25                  30

Trp Thr Ser Arg Trp Ile Glu Ser Lys His Lys Ser Asp Phe Gly Lys
         35                  40                  45

Phe Val Leu Ser Ser Gly Lys Phe Tyr Gly Asp Glu Glu Lys Asp Lys
     50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                 85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
    290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Glu Ala Glu Asp
    370                 375                 380

Lys Glu Asp Asp Glu Asp Lys Asp Glu Asp Glu Glu Asp Glu Glu Asp
385                 390                 395                 400

Lys Glu Glu Asp Glu Glu Asp Val Pro Gly Gln Ala Lys Asp Glu
                405                 410                 415

Leu
```

-continued

<210> SEQ ID NO 30
<211> LENGTH: 170
<212> TYPE: PRT
<213> ORGANISM: Homo sapiens

<400> SEQUENCE: 30

Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
                20                  25                  30

Trp Thr Ser Arg Trp Ile Glu Ser Lys His Lys Ser Asp Phe Gly Lys
                35                  40                  45

Phe Val Leu Ser Ser Gly Lys Phe Tyr Gly Asp Glu Glu Lys Asp Lys
    50                      55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
                100                 105                 110

Phe Pro Asn Ser Leu Asp Gln Thr Asp Met His Gly Asp Ser Glu Tyr
                115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His
                165                 170

<210> SEQ ID NO 31
<211> LENGTH: 109
<212> TYPE: PRT
<213> ORGANISM: Homo sapiens

<400> SEQUENCE: 31

Leu Tyr Thr Leu Ile Val Arg Pro Asp Asn Thr Tyr Glu Val Lys Ile
1               5                   10                  15

Asp Asn Ser Gln Val Glu Ser Gly Ser Leu Glu Asp Asp Trp Asp Phe
                20                  25                  30

Leu Pro Pro Lys Lys Ile Lys Asp Pro Asp Ala Ser Lys Pro Glu Asp
                35                  40                  45

Trp Asp Glu Arg Ala Lys Ile Asp Asp Pro Thr Asp Ser Lys Pro Glu
    50                      55                  60

Asp Trp Asp Lys Pro Glu His Ile Pro Asp Pro Asp Ala Lys Lys Pro
65                  70                  75                  80

Glu Asp Trp Asp Glu Glu Met Asp Gly Glu Trp Glu Pro Pro Val Ile
                85                  90                  95

Gln Asn Pro Glu Tyr Lys Gly Glu Trp Lys Pro Arg Gln
                100                 105

<210> SEQ ID NO 32
<211> LENGTH: 138
<212> TYPE: PRT
<213> ORGANISM: Homo sapiens

<400> SEQUENCE: 32

Ile Asp Asn Pro Asp Tyr Lys Gly Thr Trp Ile His Pro Glu Ile Asp
1               5                   10                  15

Asn Pro Glu Tyr Ser Pro Asp Pro Ser Ile Tyr Ala Tyr Asp Asn Phe
            20                  25                  30

Gly Val Leu Gly Leu Asp Leu Trp Gln Val Lys Ser Gly Thr Ile Phe
        35                  40                  45

Asp Asn Phe Leu Ile Thr Asn Asp Glu Ala Tyr Ala Glu Glu Phe Gly
    50                  55                  60

Asn Glu Thr Trp Gly Val Thr Lys Ala Ala Glu Lys Gln Met Lys Asp
65                  70                  75                  80

Lys Gln Asp Glu Glu Gln Arg Leu Lys Glu Glu Glu Asp Lys Lys
                85                  90                  95

Arg Lys Glu Glu Glu Ala Glu Asp Lys Glu Asp Asp Glu Asp Lys
                100                 105                 110

Asp Glu Asp Glu Glu Asp Glu Glu Asp Lys Glu Glu Asp Glu Glu
        115                 120                 125

Asp Val Pro Gly Gln Ala Lys Asp Glu Leu
        130                 135

<210> SEQ ID NO 33
<211> LENGTH: 540
<212> TYPE: DNA
<213> ORGANISM: Homo sapiens

<400> SEQUENCE: 33
atgctgctat ccgtgccgct gctgctcggc ctcctcggcc tggccgtcgc cgagcccgcc      60
gtctacttca aggagcagtt tctggacgga cgggtggga cttcccgctg atcgaatcc      120 aaacacaagt cagattttgg caaattcgtt ctcagttccg gcaagttcta cggtgacgag    180
gagaaagata aggtttgca gacaagccag gatgcacgct tttatgctct gtcggccagt    240
ttcgagcctt tcagcaacaa aggccagacg ctggtggtgc agttcacggt gaaacatgag    300
cagaacatcg actgtggggg cggctatgtg aagctgtttc ctaatagttt ggaccagaca    360
gacatgcacg gagactcaga atacaacatc atgtttggtc ccgacatctg tggccctggc    420
accaagaagg ttcatgtcat cttcaactac aagggcaaga acgtgctgat caacaaggac    480
atccgttgca aggatgatga gtttacacac ctgtacacac tgattgtgcg gccagacaac    540

<210> SEQ ID NO 34
<211> LENGTH: 267
<212> TYPE: DNA
<213> ORGANISM: Homo sapiens

<400> SEQUENCE: 34
acctatgagg tgaagattga acacagccag gtggagtccg gctccttgga agacgattgg      60
gacttcctgc cacccaagaa gataaaggat cctgatgctt caaaaccgga agactgggat    120
gagcgggcca agatcgatga tcccacagac tccaagcctg aggactggga caagcccgag    180
catatccctg accctgatgc taagaagccc gaggactggg atgaagagat ggacggagag    240
tgggaacccc cagtgattca gaaccct                                        267

<210> SEQ ID NO 35
<211> LENGTH: 444
<212> TYPE: DNA
<213> ORGANISM: Homo sapiens

<400> SEQUENCE: 35
gagtacaagg gtgagtggaa gccccggcag atcgacaacc cagattacaa gggcacttgg      60

```
atccacccag aaattgacaa ccccgagtat tctcccgatc ccagtatcta tgcctatgat      120
aactttggcg tgctgggcct ggacctctgg caggtcaagt ctggcaccat ctttgacaac      180
ttcctcatca ccaacgatga ggcatacgct gaggagtttg gcaacgagac gtgggggcgta     240 acaaaggcag cagagaaaca aatgaaggac aaacaggacg aggagcagag gcttaaggag      300
gaggaagaag acaagaaacg caaagaggag gaggaggcag aggacaagga ggatgatgag      360
gacaaagatg aggatgagga ggatgaggag gacaaggagg aagatgagga ggaagatgtc      420
cccggccagg ccaaggacga gctg                                             444
```

<210> SEQ ID NO 36
<211> LENGTH: 5970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
gctccgcccc cctgacgagc atcacaaaaa tcgacgctca agtcagaggt ggcgaaaccc       60
gacaggacta taaagatacc aggcgtttcc ccctggaagc tccctcgtgc gctctcctgt      120
tccgaccctg ccgcttaccg gatacctgtc cgcctttctc ccttcgggaa gcgtggcgct      180
ttctcatagc tcacgctgta ggtatctcag ttcggtgtag tcgttcgct  ccaagctggg      240 ctgtgtgcac gaaccccccg ttcagcccga ccgctgcgcc ttatccggta actatcgtct      300
tgagtccaac ccggtaagac acgacttatc gccactggca gcagccactg gtaacaggat      360
tagcagagcg aggtatgtag gcggtgctac agagttcttg aagtggtggc ctaactacgg      420
ctacactaga agaacagtat ttggtatctg cgctctgctg aagccagtta ccttcggaaa      480
aagagttggt agctcttgat ccggcaaaca aaccaccgct ggtagcggtg gtttttttgt      540
ttgcaagcag cagattacgc gcagaaaaaa aggatctcaa gaagatcctt tgatcttttc      600 tacgggtct  gacgctcagt ggaacgaaaa ctcacgttaa gggattttgg tcatgagatt      660
atcaaaaagg atcttcacct agatcctttt aaattaaaaa tgaagtttta atcaatctaa     720
aagtatatat gagtaaactt ggtctgacag ttaccaatgc ttaatcagtg aggcaccta t     780 ctcagcgatc tgtctatttc gttcatccat agttgcctga ctcggggggg ggggcgctg      840 aggtctgcct cgtgaagaag gtgttgctga ctcataccag gcaacgttg  ttgccattgc      900 tacaggcatc gtggtgtcac gctcgtcgtt tggtatggct tcattcagct ccggttccca      960
acgatcaagg cgagttacat gatccccat  gttgtgcaaa aaagcggtta gctccttcgg     1020
tcctccgatc gttgtcagaa gtaagttggc cgcagtgtta tcactcatgg ttatggcagc     1080
actgcataat tctcttactg tcatgccatc cgtaagatgc ttttctgtga ctggtgagta     1140
ctcaaccaag tcattctgag aatagtgtat gcggcgaccg agttgctctt gcccggcgtc     1200
aatacgggat aataccgcgc cacatagcag aactttaaaa gtgctcatca ttggaaaacg     1260
ttcttcgggg cgaaaactct caaggatctt accgctgttg agatccagtt cgatgtaacc     1320
cactcgtgca cctgaatcgc ccatcatcc  agccagaaag tgagggagcc acggttgatg     1380
agagctttgt tgtaggtgga ccagttggtg attttgaact tttgctttgc cacggaacgg     1440
tctgcgttgt cgggaagatg cgtgatctga tccttcaact cagcaaaagt tcgatttatt     1500
caacaaagcc gccgtcccgt caagtcagcg taatgctctg ccagtgttac aaccaattaa     1560
ccaattctga ttagaaaaac tcatcgagca tcaaatgaaa ctgcaattta ttcatatcag     1620
```

```
gattatcaat accatatttt tgaaaaagcc gtttctgtaa tgaaggagaa aactcaccga    1680
ggcagttcca taggatggca agatcctggt atcggtctgc gattccgact cgtccaacat    1740
caatacaacc tattaatttc ccctcgtcaa aaataaggtt atcaagtgag aaatcaccat    1800
gagtgacgac tgaatccggt gagaatggca aaagcttatg catttctttc cagacttgtt    1860
caacaggcca gccattacgc tcgtcatcaa aatcactcgc atcaaccaaa ccgttattca    1920
ttcgtgattg cgcctgagcg agacgaaata cgcgatcgct gttaaaagga caattacaaa    1980
caggaatcga atgcaaccgg cgcaggaaca ctgccagcgc atcaacaata ttttcacctg    2040
aatcaggata ttcttctaat acctggaatg ctgttttccc ggggatcgca gtggtgagta    2100
accatgcatc atcaggagta cggataaaat gcttgatggt cggaagaggc ataaattccg    2160
tcagccagtt tagtctgacc atctcatctg taacatcatt ggcaacgcta cctttgccat    2220
gtttcagaaa caactctggc gcatcgggct tcccatacaa tcgatagatt gtcgcacctg    2280
attgcccgac attatcgcga gcccatttat acccatataa atcagcatcc atgttggaat    2340
ttaatcgcgg cctcgagcaa gacgtttccc gttgaatatg gctcataaca ccccttgtat    2400
tactgtttat gtaagcagac agttttattg ttcatgatga tatattttta tcttgtgcaa    2460
tgtaacatca gagattttga gacacaacgt ggctttcccc ccccccccat tattgaagca    2520
tttatcaggg ttattgtctc atgagcggat acatatttga atgtatttag aaaaataaac    2580 aaatagggt tccgcgcaca tttccccgaa aagtgccacc tgacgtctaa gaaaccatta    2640
ttatcatgac attaacctat aaaaataggc gtatcacgag gccctttcgt ctcgcgcgtt    2700
tcggtgatga cggtgaaaac ctctgacaca tgcagctccc ggagacggtc acagcttgtc    2760
tgtaagcgga tgccgggagc agacaagccc gtcagggcgc gtcagcgggt gttggcgggt    2820 gtcgggctg gcttaactat gcggcatcag agcagattgt actgagagtg caccatatgc    2880
ggtgtgaaat accgcacaga tgcgtaagga gaaaataccg catcagattg gctattggcc    2940
attgcatacg ttgtatccat atcataatat gtacatttat attggctcat gtccaacatt    3000
accgccatgt tgacattgat tattgactag ttattaatag taatcaatta cggggtcatt    3060
agttcatagc ccatatatgg agttccgcgt tacataactt acggtaaatg gcccgcctgg    3120
ctgaccgccc aacgaccccc gcccattgac gtcaataatg acgtatgttc ccatagtaac    3180
gccaataggg actttccatt gacgtcaatg ggtggagtat ttacggtaaa ctgcccactt    3240
ggcagtacat caagtgtatc atatgccaag tacgccccct attgacgtca atgacggtaa    3300
atggcccgcc tggcattatg cccagtacat gaccttatgg gactttccta cttggcagta    3360
catctacgta ttagtcatcg ctattaccat ggtgatgcgg ttttggcagt acatcaatgg    3420
gcgtggatag cggtttgact cacggggatt tccaagtctc cacccattg acgtcaatgg    3480 gagtttgttt tggcaccaaa atcaacggga ctttccaaaa tgtcgtaaca actccgcccc    3540
attgacgcaa atgggcggta ggcgtgtacg gtgggaggtc tatataagca gagctcgttt    3600
agtgaaccgt cagatcgcct ggagacgcca tccacgctgt tttgacctcc atagaagaca    3660
ccgggaccga tccagcctcc gcggccggga acggtgcatt ggaacgcgga ttccccgtgc    3720
caagagtgac gtaagtaccg cctatagact ctataggcac acccctttgg ctcttatgca    3780
tgctatactg ttttttggctt ggggcctata cacccccgct tccttatgct ataggtgatg    3840
gtatagctta gcctataggt gtgggttatt gaccattatt gaccactcca acggtggagg    3900
gcagtgtagt ctgagcagta ctcgttgctg ccgcgcgcgc caccagacat aatagctgac    3960
agactaacag actgttcctt tccatgggtc ttttctgcag tcaccgtcgt cgacatgctg    4020
```

```
ctatccgtgc cgctgctgct cggcctcctc ggcctggccg tcgccgagcc tgccgtctac    4080
ttcaaggagc agtttctgga cggggacggg tggacttccc gctggatcga atccaaacac    4140 aagtcgagatt ttggcaaatt cgttctcagt tccggcaagt tctacggtga cgaggagaaa    4200
gataaaggtt tgcagacaag ccaggatgca cgcttttatg ctctgtcggc cagtttcgag    4260
cctttcagca acaaaggcca gacgctggtg gtgcagttca cggtgaaaca tgagcagaac    4320
atcgactgtg ggggcggcta tgtgaagctg tttcctaata gtttggacca gacagacatg    4380
cacggagact cagaatacaa catcatgttt ggtcccgaca tctgtggccc tggcaccaag    4440
aaggttcatg tcatcttcaa ctacaagggc aagaacgtgc tgatcaacaa ggacatccgt    4500
tgcaaggatg atgagtttac acacctgtac acactgattg tgcggccaga caacacctat    4560
gaggtgaaga ttgacaacag ccaggtggag tccggctcct tggaagacga ttgggacttc    4620
ctgccaccca agaagataaa ggatcctgat gcttcaaaac cggaagactg ggatgagcgg    4680
gccaagatcg atgatcccac agactccaag cctgaggact gggacaagcc cgagcatatc    4740
cctgaccctg atgctaagaa gcccgaggac tgggatgaag agatggacgg agagtgggaa    4800 ccccagtga ttcagaaccc tgagtacaag ggtgagtgga gccccggca gatcgacaac    4860 ccagattaca agggcacttg gatccacca gaaattgaca ccccgagta ttctcccgat    4920 cccagtatct atgcctatga taactttggc gtgctgggcc tggacctctg gcaggtcaag    4980
tctggcacca tctttgacaa cttcctcatc accaacgatg aggcatacgc tgaggagttt    5040
ggcaacgaga cgtggggcgt aacaaaggca gcagagaaac aaatgaagga caaacaggac    5100
gaggagcaga ggcttaagga ggaggaagaa gacaagaaac gcaaagagga ggaggaggca    5160
gaggacaagg aggatgatga ggacaaagat gaggatgagg aggatgagga ggacaaggag    5220
gaagatgagg aggaagatgt ccccggccag gccaaggacg agctggaatt catgcatgga    5280
gatacaccta cattgcatga atatatgtta gatttgcaac cagagacaac tgatctctac    5340
ggttatgggc aattaaatga cagctcagag gaggaggatg aaatagatgg tccagctgga    5400
caagcagaac cggacagagc ccattacaat attgtaacct tttgttgcaa gtgtgactct    5460
acgcttcggt tgtgcgtaca aagcacacac gtagacattc gtactttgga agacctgtta    5520
atgggcacac taggaattgt gtgccccatc tgttctcaga aaccataagg atccagatct    5580
ttttccctct gccaaaaatt atggggacat catgaagccc cttgagcatc tgacttctgg    5640
ctaataaagg aaatttattt tcattgcaat agtgtgttgg aatttttttgt gtctctcact    5700 cggaaggaca tatgggaggg caaatcattt aaaacatcag aatgagtatt tggtttagag    5760
tttggcaaca tatgcccatt cttccgcttc ctcgctcact gactcgctgc gctcggtcgt    5820
tcggctgcgg cgagcggtat cagctcactc aaaggcggta atacggttat ccacagaatc    5880 agggggataac gcaggaaaga acatgtgagc aaaaggccag caaaaggcca ggaaccgtaa    5940
aaaggccgcg ttgctggcgt ttttccatag                                    5970
```

<210> SEQ ID NO 37
<211> LENGTH: 750
<212> TYPE: DNA
<213> ORGANISM: Marek's disease virus

<400> SEQUENCE: 37

```
atgggggatt ctgaaaggcg g

```
caggatgatt tgtcaaaaca tggaccattt accgaccatc aacacaaaa acataaatcg    180 gcgaaagccg tatcggaaga cgtttcgtct accacccggg gtggctttac aaacaaaccc    240
cgtaccaagc ccggggtcag agctgtacaa agtaataaat tcgctttcag tacggctcct    300
tcatcagcat ctagcacttg gagatcaaat acagtggcat ttaatcagcg tatgttttgc    360
ggagcggttg caactgtggc tcaatatcac gcataccaag gcgcgctcgc cctttggcgt    420
caagatcctc gcgaacaaa tgaagaatta gatgcatttc tttccagagc tgtcattaaa    480
attaccattc aagagggtcc aaatttgatg ggggaagccg aaacctgtgc ccgcaaacta    540
ttggaagagt ctggattatc caggggaac gagaacgtaa agtccaaatc tgaacgtaca    600
accaaatctg aacgtacaag acgcggcggt gaaattgaaa tcaaatcgcc agatccggga    660
tctcatcgta cacataaccc tcgcactccc gcaacttcgc gtcgccatca ttcatccgcc    720
cgcggatatc gtagcagtga tagcgaataa                                    750
```

```
<210> SEQ ID NO 38
<211> LENGTH: 301
<212> TYPE: PRT
<213> ORGANISM: Human herpesvirus

<400> SEQUENCE: 38
```

```
Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
                20                  25                  30

Pro Asp Ser Pro Pro Asp Thr Ser Arg Arg Gly Ala Leu Gln Thr Arg
            35                  40                  45

Ser Arg Gln Arg Gly Glu Val Arg Phe Val Gln Tyr Asp Glu Ser Asp
        50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gln Arg Val Ala
        115                 120                 125

Ser Lys Ala Pro Ala Ala Pro Ala Ala Glu Thr Thr Arg Gly Arg Lys
130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
        195                 200                 205

Ala Ala Met His Ala Arg Met Ala Ala Val Gln Leu Trp Asp Met Ser
    210                 215                 220

Arg Pro Arg Thr Asp Glu Asp Leu Asn Glu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
```

```
                260                 265                 270
Thr Arg Gly Arg Ser Ala Ala Ser Arg Pro Thr Glu Arg Pro Arg Ala
            275                 280                 285

Pro Ala Arg Ser Ala Ser Arg Pro Arg Pro Val Glu
            290                 295                 300

<210> SEQ ID NO 39
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gln Arg Val Ala
        115                 120                 125

Ser Lys Ala Pro Ala Ala Pro Ala Ala Glu Thr Thr Arg Gly Arg Lys
    130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
        195                 200                 205

Ala Ala Met His Ala Arg Met Ala Ala Val Gln Leu Trp Asp Met Ser
    210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
            260                 265                 270

Thr Arg Gly Arg Ser Ala Ala Ser Arg Pro Thr Glu Arg Pro Arg Ala
        275                 280                 285

Pro Ala Arg Ser Ala Ser Arg Pro Arg Pro Val Glu Gly Thr Glu
    290                 295                 300

Leu Gly Ser Met His Gly Asp Thr Pro Thr Leu His Glu Tyr Met Leu
305                 310                 315                 320
```

-continued

Asp Leu Gln Pro Glu Thr Thr Asp Leu Tyr Cys Tyr Glu Gln Leu Asn
            325                 330                 335

Asp Ser Ser Glu Glu Glu Asp Glu Ile Asp Gly Pro Ala Gly Gln Ala
        340                 345                 350

Glu Pro Asp Arg Ala His Tyr Asn Ile Val Thr Phe Cys Cys Lys Cys
        355                 360                 365

Asp Ser Thr Leu Arg Leu Cys Val Gln Ser Thr His Val Asp Ile Arg
370                 375                 380

Thr Leu Glu Asp Leu Leu Met Gly Thr Leu Gly Ile Val Cys Pro Ile
385                 390                 395                 400

Cys Ser Gln Asp Lys Leu Lys Phe Lys Pro Leu Ile Ser Leu Asp Cys
            405                 410                 415

Ala Phe

<210> SEQ ID NO 40
<211> LENGTH: 249
<212> TYPE: PRT
<213> ORGANISM: Marek's disease virus

<400> SEQUENCE: 40

Met Gly Asp Ser Glu Arg Arg Lys Ser Glu Arg Arg Ser Leu Gly
1               5                   10                  15

Tyr Pro Ser Ala Tyr Asp Asp Val Ser Ile Pro Ala Arg Arg Pro Ser
            20                  25                  30

Thr Arg Thr Gln Arg Asn Leu Asn Gln Asp Asp Leu Ser Lys His Gly
        35                  40                  45

Pro Phe Thr Asp His Pro Thr Gln Lys His Lys Ser Ala Lys Ala Val
    50                  55                  60

Ser Glu Asp Val Ser Ser Thr Thr Arg Gly Gly Phe Thr Asn Lys Pro
65                  70                  75                  80

Arg Thr Lys Pro Gly Val Arg Ala Val Gln Ser Asn Lys Phe Ala Phe
            85                  90                  95

Ser Thr Ala Pro Ser Ser Ala Ser Ser Thr Trp Arg Ser Asn Thr Val
            100                 105                 110

Ala Phe Asn Gln Arg Met Phe Cys Gly Ala Val Ala Thr Val Ala Gln
        115                 120                 125

Tyr His Ala Tyr Gln Gly Ala Leu Ala Leu Trp Arg Gln Asp Pro Pro
    130                 135                 140

Arg Thr Asn Glu Glu Leu Asp Ala Phe Leu Ser Arg Ala Val Ile Lys
145                 150                 155                 160

Ile Thr Ile Gln Glu Gly Pro Asn Leu Met Gly Glu Ala Glu Thr Cys
            165                 170                 175

Ala Arg Lys Leu Leu Glu Glu Ser Gly Leu Ser Gln Gly Asn Glu Asn
        180                 185                 190

Val Lys Ser Lys Ser Glu Arg Thr Thr Lys Ser Glu Arg Thr Arg Arg
    195                 200                 205

Gly Gly Glu Ile Glu Ile Lys Ser Pro Asp Pro Gly Ser His Arg Thr
210                 215                 220

His Asn Pro Arg Thr Pro Ala Thr Ser Arg Arg His His Ser Ser Ala
225                 230                 235                 240

Arg Gly Tyr Arg Ser Ser Asp Ser Glu
            245

<210> SEQ ID NO 41
<211> LENGTH: 96

<212> TYPE: PRT
<213> ORGANISM: Human papillomavirus

<400> SEQUENCE: 41

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95
```

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 42
ugccuacgaa cucuucaccu t                                        21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 43
ggugaagagu ucguaggcau t                                        21

<210> SEQ ID NO 44
<211> LENGTH: 627
<212> TYPE: DNA
<213> ORGANISM: Mus musculus

<400> SEQUENCE: 44
atggcatctg gacaaggacc aggtccccccg aaggtgggct gcgatgagtc cccgtccccct    60
tctgaacagc aggttgccca ggacacagag gaggtctttc gaagctacgt tttttacctc   120
caccagcagg aacaggagac ccaggggcgg ccgcctgcca accccgagat ggacaacttg   180
cccctggaac ccaacagcat cttgggtcag gtgggtcggc agcttgctct catcggagat   240
gatattaacc ggcgctacga cacagagttc cagaatttac tagaacagct tcagcccaca   300
gccgggaatg cctacgaact cttcaccaag atcgcctcca gcctatttaa gagtggcatc   360
agctggggcc gcgtggtggc tctcctgggc tttggctacc gtctggccct gtacgtctac   420
cagcgtggtt tgaccggctt cctgggccag gtgacctgct ttttggctga tatcatactg   480
```

```
catcattaca tcgccagatg gatcgcacag agaggcggtt gggtggcagc cctgaatttg    540
cgtagagacc ccatcctgac cgtaatggtg attttggtg tggttctgtt gggccaattc    600
gtggtacaca gattcttcag atcatga                                        627
```

```
<210> SEQ ID NO 45
<211> LENGTH: 19
<212> TYPE: DNA
<213> ORGANISM: Mus musculus

<400> SEQUENCE: 45
tgcctacgaa ctcttcacc                                                 19

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
uauggagcug cagaggaugt t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
cauccucugc agcuccauat t                                              21

<210> SEQ ID NO 48
<211> LENGTH: 579
<212> TYPE: DNA
<213> ORGANISM: Mus musculus

<400> SEQUENCE: 48
atggacgggt ccggggagca gcttgggagc ggcgggccca ccagctctga acagatcatg    60
aagacagggg cctttttgct acagggtttc atccaggatc gagcagggag gatggctggg   120
gagacacctg agctgacctt ggagcagccg ccccaggatg cgtccaccaa gaagctgagc   180
gagtgtctcc ggcgaattgg agatgaactg gatagcaata tggagctgca gaggatgatt   240
gctgacgtgg acacggactc cccccgagag gtcttcttcc gggtggcagc tgacatgttt   300
gctgatggca acttcaactg gggccgcgtg gttgccctct tctactttgc tagcaaactg   360
gtgctcaagg ccctgtgcac taaagtgccc gagctgatca gaaccatcat gggctggaca   420
ctggacttcc tccgtgagcg gctgcttgtc tggatccaag accagggtgg ctgggaaggc   480
ctcctctcct acttcgggac ccccacatgg cagacagtga ccatctttgt ggctggagtc   540
ctcaccgcct cgctcaccat ctggaagaag atgggctga                          579

<210> SEQ ID NO 49
<211> LENGTH: 19
```

```
<212> TYPE: DNA
<213> ORGANISM: Mus musculus

<400> SEQUENCE: 49
tatggagctg cagaggatg                                                    19

<210> SEQ ID NO 50
<211> LENGTH: 1491
<212> TYPE: DNA
<213> ORGANISM: Homo sapiens

<400> SEQUENCE: 50
atggacttca gcagaaatct ttatgatatt ggggaacaac tggacagtga agatctggcc        60
tccctcaagt tcctgagcct ggactacatt ccgcaaagga agcaagaacc catcaaggat       120
gccttgatgt tattccagag actccaggaa aagagaatgt tggaggaaag caatctgtcc       180
ttcctgaagg agctgctctt ccgaattaat agactggatt tgctgattac ctacctaaac       240
actagaaagg aggagatgga aagggaactt cagacaccag gcagggctca aatttctgcc       300
tacaggttcc acttctgccg catgagctgg gctgaagcaa acagccagtg ccagacacag       360
tctgtacctt tctggcggag ggtcgatcat ctattaataa gggtcatgct ctatcagatt       420
tcagaagaag tgagcagatc agaattgagg tcttttaagt ttcttttgca agaggaaatc       480
tccaaatgca aactggatga tgacatgaac ctgctggata ttttcataga gatggagaag       540
agggtcatcc tgggagaagg aaagttggac atcctgaaaa gagtctgtgc ccaaatcaac       600
aagagcctgc tgaagataat caacgactat gaagaattca gcaaagggga ggagttgtgt       660
ggggtaatga caatctcgga ctctccaaga gaacaggata gtgaatcaca gactttggac       720
aaagtttacc aaatgaaaag caaacctcgg ggatactgtc tgatcatcaa caatcacaat       780
tttgcaaaag cacgggagaa agtgcccaaa cttcacagca ttagggacag gaatggaaca       840
cacttggatg cagggcttt gaccacgacc tttgaagagc ttcattttga gatcaagccc       900
cacgatgact gcacagtaga gcaaatctat gagattttga aaatctacca actcatggac       960
cacagtaaca tggactgctt catctgctgt atcctctccc atggagacaa gggcatcatc      1020
tatggcactg atgacagga ggccccatc tatgagctga catctcagtt cactggtttg       1080
aagtgccctt cccttgctgg aaaacccaaa gtgttttta ttcaggcttg tcagggggat       1140
aactaccaga aaggtatacc tgttgagact gattcagagg agcaaccta tttagaaatg       1200 gatttatcat cacctcaaac gagatatatc ccggatgagg ctgactttct gctggggatg       1260
gccactgtga taactgtgt ttcctaccga aaccctgcag agggaacctg gtacatccag       1320
tcactttgcc agagcctgag agagcgatgt cctcgaggcg atgatattct caccatcctg       1380
actgaagtga actatgaagt aagcaacaag gatgacaaga aaacatggg gaaacagatg      1440 cctcagccta ctttcacact aagaaaaaaa cttgtcttcc cttctgattg a                1491

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
```
aaccucgggg auacugucug att    23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 52
ucagacagua uccccgaggu utt    23

<210> SEQ ID NO 53
<211> LENGTH: 1251
<212> TYPE: DNA
<213> ORGANISM: Homo sapiens

<400> SEQUENCE: 53
atggacgaag cggatcggcg gctcctgcgg cggtgccggc tgcggctggt ggaagagctg    60
caggtggacc agctctggga cgccctgctg agccgcgagc tgttcaggcc ccatatgatc    120
gaggacatcc agcgggcagg ctctggatct cggcgggatc aggccaggca gctgatcata    180
gatctggaga ctcgagggag tcaggctctt cctttgttca tctcctgctt agaggacaca    240
ggccaggaca tgctggcttc gtttctgcga actaacaggc aagcagcaaa gttgtcgaag    300
ccaaccctag aaaaccttac cccagtggtg ctcagaccag agattcgcaa accagaggtt    360
ctcagaccgg aaacacccag accagtggac attggttctg gaggatttgg tgatgtcggt    420
gctcttgaga gtttgagggg aaatgcagat ttggcttaca tcctgagcat ggagccctgt    480
ggccactgcc tcattatcaa caatgtgaac ttctgccgtg agtccgggct ccgcacccgc    540
actggctcca acatcgactg tgagaagttg cggcgtcgct tctcctcgct gcatttcatg    600
gtggaggtga agggcgacct gactgccaag aaaatggtgc tggctttgct ggagctggcg    660
cagcaggacc acggtgctct ggactgctgc gtggtggtca ttctctctca cggctgtcag    720
gccagccacc tgcagttccc aggggctgtc tacggcacag atggatgccc tgtgtcggtc    780
gagaagattg tgaacatctt caatgggacc agctgcccca gcctgggagg gaagcccaag    840
ctcttttca tccaggcctg tggtggggag cagaaagacc atgggtttga ggtggcctcc    900
acttcccctg aagacgagtc ccctggcagt aaccccgagc agatgccac cccgttccag    960
gaaggtttga ggaccttcga ccagctggac gccatatcta gtttgccac acccagtgac    1020
atctttgtgt cctactctac tttcccaggt tttgtttcct ggagggaccc caagagtggc    1080
tcctggtacg ttgagaccct ggacgacatc tttgagcagt gggctcactc tgaagacctg    1140
cagtccctcc tgcttagggt cgctaatgct gtttcggtga aagggattta taaacagatg    1200
cctggttgct taatttcct ccggaaaaaa cttttcttta aacatcata a    1251

<210> SEQ ID NO 54
<211> LENGTH: 834
<212> TYPE: DNA
<213> ORGANISM: Homo sapiens

<400> SEQUENCE: 54
atggagaaca ctgaaaactc agtggattca aaatccatta aaatttggga accaaagatc    60
atacatggaa gcgaatcaat ggactctgga atatccctgg acaacagtta taaatggat    120

| | | |
|---|---|---|
| tatcctgaga tgggtttatg tataataatt aataataaga attttcataa aagcactgga | 180 | |
| atgacatctc ggtctggtac agatgtcgat gcagcaaacc tcagggaaac attcagaaac | 240 | |
| ttgaaatatg aagtcaggaa taaaaatgat cttacacgtg aagaaattgt ggaattgatg | 300 | |
| cgtgatgttt ctaagaaga tcacagcaaa aggagcagtt ttgttgtgt gcttctgagc | 360 | |
| catggtgaag aaggaataat ttttggaaca atggacctg ttgacctgaa aaaataaca | 420 | |
| aacttttca gagggatcg ttgtagaagt ctaactggaa acccaaact tttcattatt | 480 | |
| caggcctgcc gtggtacaga actggactgt ggcattgaga cagacagtgg tgttgatgat | 540 | |
| gacatggcgt gtcataaaat accagtggag gccgacttct tgtatgcata ctccacagca | 600 | |
| cctggttatt attcttggcg aaattcaaag gatggctcct ggttcatcca gtcgctttgt | 660 | |
| gccatgctga acagtatgc cgacaagctt gaatttatgc acattcttac ccgggttaac | 720 | |
| cgaaaggtgg caacagaatt tgagtccttt tcctttgacg ctactttca tgcaaagaaa | 780 | |
| cagattccat gtattgtttc catgctcaca aagaactct attttatca ctaa | 834 | |

<210> SEQ ID NO 55
<211> LENGTH: 750
<212> TYPE: DNA
<213> ORGANISM: Homo sapiens

<400> SEQUENCE: 55

| | | |
|---|---|---|
| atggcgtacc catacgatgt tccagattac gctagcttga gatctaccat gtctcagagc | 60 | |
| aaccgggagc tggtggttga ctttctctcc tacaagcttt cccagaaagg atacagctgg | 120 | |
| agtcagttta gtgatgtgga agagaacagg actgaggccc cagaagggac tgaatcggag | 180 | |
| atggagaccc ccagtgccat caatggcaac ccatcctggc acctggcaga cagccccgcg | 240 | |
| gtgaatggag ccactgcgca cagcagcagt ttggatgccc gggaggtgat ccccatggca | 300 | |
| gcagtaaagc aagcgctgag ggaggcaggc gacgagtttg aactgcggta ccggcgggca | 360 | |
| ttcagtgacc tgacatccca gctccacatc accccaggga cagcatatca gagctttgaa | 420 | |
| caggtagtga atgaactctt ccgggatggg gtaaactggg gtcgcattgt ggccttttc | 480 | |
| tccttcggcg gggcactgtg cgtggaaagc gtagacaagg atgcaggt attggtgagt | 540 | |
| cggatcgcag cttggatggc cacttacctg aatgaccacc tagagccttg gatccaggag | 600 | |
| aacggcggct gggatacttt tgtggaactc tatgggaaca tgcagcagc cgagagccga | 660 | |
| aagggccagg aacgcttcaa ccgctggttc ctgacgggca tgactgtggc cggcgtggtt | 720 | |
| ctgctgggct cactcttcag tcggaaatga | 750 | |

<210> SEQ ID NO 56
<211> LENGTH: 249
<212> TYPE: PRT
<213> ORGANISM: Homo sapiens

<400> SEQUENCE: 56

Met Ala Tyr Pro Tyr Asp Val Pro Asp Tyr Ala Ser Leu Arg Ser Thr
1               5                   10                  15

Met Ser Gln Ser Asn Arg Glu Leu Val Val Asp Phe Leu Ser Tyr Lys
            20                  25                  30

Leu Ser Gln Lys Gly Tyr Ser Trp Ser Gln Phe Ser Asp Val Glu Glu
        35                  40                  45

Asn Arg Thr Glu Ala Pro Glu Gly Thr Glu Ser Glu Met Glu Thr Pro
    50                  55                  60

Ser Ala Ile Asn Gly Asn Pro Ser Trp His Leu Ala Asp Ser Pro Ala
 65                  70                  75                  80

Val Asn Gly Ala Thr Ala His Ser Ser Leu Asp Ala Arg Glu Val
             85                  90                  95

Ile Pro Met Ala Ala Val Lys Gln Ala Leu Arg Glu Ala Gly Asp Glu
            100                 105                 110

Phe Glu Leu Arg Tyr Arg Arg Ala Phe Ser Asp Leu Thr Ser Gln Leu
        115                 120                 125

His Ile Thr Pro Gly Thr Ala Tyr Gln Ser Phe Glu Gln Val Val Asn
    130                 135                 140

Glu Leu Phe Arg Asp Gly Val Asn Trp Gly Arg Ile Val Ala Phe Phe
145                 150                 155                 160

Ser Phe Gly Gly Ala Leu Cys Val Glu Ser Val Asp Lys Glu Met Gln
                165                 170                 175

Val Leu Val Ser Arg Ile Ala Ala Trp Met Ala Thr Tyr Leu Asn Asp
            180                 185                 190

His Leu Glu Pro Trp Ile Gln Glu Asn Gly Gly Trp Asp Thr Phe Val
        195                 200                 205

Glu Leu Tyr Gly Asn Asn Ala Ala Ala Glu Ser Arg Lys Gly Gln Glu
    210                 215                 220

Arg Phe Asn Arg Trp Phe Leu Thr Gly Met Thr Val Ala Gly Val Val
225                 230                 235                 240

Leu Leu Gly Ser Leu Phe Ser Arg Lys
                245

<210> SEQ ID NO 57
<211> LENGTH: 6187
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagaattcc    960

```
accacactgg actagtggat ctatggcgta cccatacgat gttccagatt acgctagctt    1020
gagatctacc atgtctcaga gcaaccggga gctggtggtt gactttctct cctacaagct    1080
ttcccagaaa ggatacagct ggagtcagtt tagtgatgtg aagagaaca ggactgaggc     1140 cccagaaggg actgaatcgg agatggagac ccccagtgcc atcaatggca acccatcctg    1200
gcacctggca gacagccccg cggtgaatgg agccactgcg cacagcagca gtttggatgc    1260
ccgggaggtg atccccatgg cagcagtaaa gcaagcgctg agggaggcag gcgacgagtt    1320
tgaactgcgg taccggcggg cattcagtga cctgacatcc cagctccaca tcaccccagg    1380
gacagcatat cagagctttg aacaggtagt gaatgaactc ttccgggatg ggtaaactg     1440 gggtcgcatt gtggccttt tctccttcgg cggggcactg tgcgtggaaa gcgtagacaa     1500
ggagatgcag gtattggtga gtcggatcgc agcttggatg gccacttacc tgaatgacca    1560
cctagagcct tggatccagg agaacggcgg ctgggatact tttgtggaac tctatgggaa    1620
caatgcagca gccgagagcc gaaagggcca ggaacgcttc aaccgctggt tcctgacggg    1680
catgactgtg gccggcgtgg ttctgctggg ctcactcttc agtcggaaat gaagatccga    1740
gctcggtacc aagcttaagt ttaaaccgct gatcagcctc gactgtgcct tctagttgcc    1800
agccatctgt tgtttgcccc tccccgtgc cttccttgac cctggaaggt gccactccca     1860
ctgtcctttc ctaataaaat gaggaaaatg catcgcattg tctgagtagg tgtcattcta    1920
ttctgggggg tggggtgggg caggacagca aggggggagga ttgggaagac aatagcaggc   1980
atgctgggga tgcggtgggc tctatggctt ctgaggcgga aagaaccagc tggggctcta    2040
gggggtatcc ccacgcgccc tgtagcgcg cattaagcgc ggcgggtgtg gtggttacgc     2100
gcagcgtgac cgctacactt gccagcgccc tagcgcccgc tcctttcgct ttcttccctt    2160
cctttctcgc cacgttcgcc ggctttcccc gtcaagctct aaatcggggc atccctttag    2220
ggttccgatt tagtgcttta cggcacctcg accccaaaaa acttgattag ggtgatggtt    2280
cacgtagtgg gccatcgccc tgatagacgg ttttttcgcc tttgacgttg gagtccacgt    2340
tctttaatag tggactcttg ttccaaactg gaacaacact caaccctatc tcggtctatt    2400
cttttgattt ataagggatt tgggggattt cggcctattg gttaaaaaat gagctgattt    2460
aacaaaaatt taacgcgaat taattctgtg gaatgtgtgt cagttagggt gtggaaagtc    2520
cccaggctcc ccaggcaggc agaagtatgc aaagcatgca tctcaattag tcagcaacca    2580
ggtgtggaaa gtccccaggc tccccagcag gcagaagtat gcaaagcatg catctcaatt    2640
agtcagcaac catagtcccg cccctaactc cgcccatccc gcccctaact ccgcccagtt    2700
ccgcccattc tccgccccat ggctgactaa ttttttttat ttatgcagag gccgaggccg    2760
cctctgcctc tgagctattc cagaagtagt gaggaggctt ttttggaggc ctaggctttt    2820
gcaaaaagct cccgggagct tgtatatcca ttttcggatc tgatcaagag acaggatgag    2880
gatcgtttcg catgattgaa caagatggat tgcacgcagg ttctccggcc gcttgggtgg    2940
agaggctatt cggctatgac tgggcacaac agacaatcgg ctgctctgat gccgccgtgt    3000
tccggctgtc agcgcagggg cgcccggttc tttttgtcaa gaccgacctg tccggtgccc    3060
tgaatgaact gcaggacgag gcagcgcggc tatcgtggct ggccacgacg ggcgttcctt    3120
gcgcagctgt gctcgacgtt gtcactgaag cgggaaggga ctggctgcta ttgggcgaag    3180
tgccggggca ggatctcctg tcatctcacc ttgctcctgc cgagaaagta tccatcatgg    3240
ctgatgcaat gcggcggctg catacgcttg atccggctac ctgcccattc gaccaccaag    3300
cgaaacatcg catcgagcga gcacgtactc ggatggaagc cggtcttgtc gatcaggatg    3360
```

```
atctggacga agagcatcag gggctcgcgc cagccgaact gttcgccagg ctcaaggcgc    3420
gcatgcccga cggcgaggat ctcgtcgtga cccatggcga tgcctgcttg ccaatatca     3480
tggtggaaaa tggccgcttt tctggattca tcgactgtgg ccggctgggt gtggcggacc    3540
gctatcagga catagcgttg gctacccgtg atattgctga agagcttggc ggcgaatggg    3600
ctgaccgctt cctcgtgctt tacggtatcg ccgctcccga ttcgcagcgc atcgccttct    3660
atcgccttct tgacgagttc ttctgagcgg gactctgggg ttcgaaatga ccgaccaagc    3720
gacgcccaac ctgccatcac gagatttcga ttccaccgcc gccttctatg aaaggtttggg   3780
cttcggaatc gttttccggg acgccggctg gatgatcctc cagcgcgggg atctcatgct    3840
ggagttcttc gcccacccca acttgtttat tgcagcttat aatggttaca aataaagcaa    3900
tagcatcaca aatttcacaa ataaagcatt tttttcactg cattctagtt gtggttttgtc   3960
caaactcatc aatgtatctt atcatgtctg tataccgtcg acctctagct agagcttggc    4020
gtaatcatgg tcatagctgt ttcctgtgtg aaattgttat ccgctcacaa ttccacacaa    4080
catacgagcc ggaagcataa agtgtaaagc ctggggtgcc taatgagtga gctaactcac    4140
attaattgcg ttgcgctcac tgcccgcttt ccagtcggga aacctgtcgt gccagctgca    4200
ttaatgaatc ggccaacgcg cggggagagg cggtttgcgt attgggcgct cttccgcttc    4260
ctcgctcact gactcgctgc gctcggtcgt tcggctgcgg cgagcggtat cagctcactc    4320
aaaggcggta atacggttat ccacagaatc aggggataac gcaggaaaga acatgtgagc    4380
aaaaggccag caaaaggcca ggaaccgtaa aaaggccgcg ttgctggcgt ttttccatag    4440
gctccgcccc cctgacgagc atcacaaaaa tcgacgctca agtcagaggt ggcgaaaccc    4500
gacaggacta taaagatacc aggcgtttcc ccctggaagc tccctcgtgc gctctcctgt    4560
tccgaccctg ccgcttaccg gatacctgtc cgcctttctc ccttcgggaa gcgtggcgct    4620
ttctcaatgc tcacgctgta ggtatctcag ttcggtgtag gtcgttcgct ccaagctggg    4680
ctgtgtgcac gaaccccccg ttcagcccga ccgctgcgcc ttatccggta actatcgtct    4740
tgagtccaac ccggtaagac acgacttatc gccactggca gcagccactg gtaacaggat    4800
tagcagagcg aggtatgtag cggtgctac agagttcttg aagtggtggc ctaactacgg    4860
ctacactaga aggacagtat ttggtatctg cgctctgctg aagccagtta ccttcggaaa    4920
aagagttggt agctcttgat ccggcaaaca aaccaccgct ggtagcggtg ttttttttgt    4980
ttgcaagcag cagattacgc gcagaaaaaa aggatctcaa gaagatcctt tgatctttc    5040
tacgggtct gacgctcagt ggaacgaaaa ctcacgttaa gggattttgg tcatgagatt     5100
atcaaaaagg atcttcacct agatcctttt aaattaaaaa tgaagttta aatcaatcta     5160
aagtatatat gagtaaactt ggtctgacag ttaccaatgc ttaatcagtg aggcacctat    5220
ctcagcgatc tgtctatttc gttcatccat agttgcctga ctccccgtcg tgtagataac    5280
tacgatacgg gagggcttac catctggccc cagtgctgca atgataccgc gagacccacg    5340
ctcaccggct ccagatttat cagcaataaa ccagccagcc ggaagggccg agcgcagaag    5400
tggtcctgca actttatccg cctccatcca gtctattaat tgttgccggg aagctagagt    5460
aagtagttcg ccagttaata gtttgcgcaa cgttgttgcc attgctacag gcatcgtggt    5520
gtcacgctcg tcgtttggta tggcttcatt cagctccggt tcccaacgat caaggcgagt    5580
tacatgatcc cccatgttgt gcaaaaaagc ggttagctcc ttcggtcctc cgatcgttgt    5640
cagaagtaag ttggccgcag tgttatcact catggttatg gcagcactgc ataattctct    5700
```

```
tactgtcatg ccatccgtaa gatgcttttc tgtgactggt gagtactcaa ccaagtcatt    5760
ctgagaatag tgtatgcggc gaccgagttg ctcttgcccg gcgtcaatac gggataatac    5820
cgcgccacat agcagaactt taaaagtgct catcattgga aaacgttctt cggggcgaaa    5880
actctcaagg atcttaccgc tgttgagatc cagttcgatg taacccactc gtgcacccaa    5940
ctgatcttca gcatctttta ctttcaccag cgtttctggg tgagcaaaaa caggaaggca    6000
aaatgccgca aaaagggaa taagggcgac acggaaatgt tgaatactca tactcttcct    6060
ttttcaatat tattgaagca tttatcaggg ttattgtctc atgagcggat acatatttga    6120
atgtatttag aaaaataaac aaatagggt tccgcgcaca tttccccgaa aagtgccacc    6180
tgacgtc                                                             6187

<210> SEQ ID NO 58
<211> LENGTH: 6452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gacggatcgg gagatctccc gatccctat ggtcgactct cagtacaatc tgctctgatg    60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagaattca    960
tgcatggaga tacacctaca ttgcatgaat atatgttaga tttgcaacca gagacaactg    1020
atctctactg ttatgagcaa ttaaatgaca gctcagagga ggaggatgaa atagatggtc    1080
cagctggaca agcagaaccg gacagagccc attacaatat tgtaacccttt tgttgcaagt    1140 gtgactctac gcttcggttg tgcgtacaaa gcacacacgt agacattcgt actttggaag    1200
acctgttaat gggcacacta ggaattgtgt gccccatctg ttctcagaaa ccaggatcta    1260
tggcgtaccc atacgatgtt ccagattacg ctagcttgag atctaccatg tctcagagca    1320
accgggagct ggtggttgac tttctctcct acaagctttc ccagaaagga tacagctgga    1380
gtcagtttag tgatgtggaa gagaacagga ctgaggcccc agaagggact gaatcggaga    1440
tggagacccc cagtgccatc aatggcaacc catcctggca cctggcagac agccccgcgg    1500
```

```
tgaatggagc cactgcgcac agcagcagtt tggatgcccg ggaggtgatc cccatggcag    1560
cagtaaagca agcgctgagg gaggcaggcg acgagtttga actgcggtac cggcgggcat    1620
tcagtgacct gacatcccag ctccacatca ccccagggac agcatatcag agctttgaac    1680
aggtagtgaa tgaactcttc cgggatgggg taaactgggg tcgcattgtg cctttttct     1740 ccttcggcgg ggcactgtgc gtggaaagcg tagacaagga gatgcaggta ttggtgagtc    1800
ggatcgcagc ttgatggcc acttacctga atgaccacct agagccttgg atccaggaga     1860
acggcggctg ggatactttt gtggaactct atgggaacaa tgcagcagcc gagagccgaa    1920
agggccagga acgcttcaac cgctggttcc tgacgggcat gactgtggcc ggcgtggttc    1980
tactgggctc actcttcagt cggaaatgaa gatccaagct taagtttaaa ccgctgatca    2040
gcctcgactg tgccttctag ttgccagcca tctgttgttt gccctccc cgtgccttcc      2100 ttgaccctgg aaggtgccac tcccactgtc ctttcctaat aaaatgagga aattgcatcg    2160
cattgtctga gtaggtgtca ttctattctg ggggtgggg tggggcagga cagcaagggg     2220
gaggattggg aagacaatag caggcatgct ggggatgcgg tgggctctat ggcttctgag    2280
gcggaaagaa ccagctgggg ctctaggggg tatcccacg cgccctgtag cggcgcatta     2340
agcgcggcgg gtgtggtggt tacgcgcagc gtgaccgcta cacttgccag cgccctagcg    2400
cccgctcctt tcgctttctt cccttccttt ctcgccacgt tcgccggctt tccccgtcaa    2460
gctctaaatc gggggcatccc tttagggttc gatttagtg ctttacggca cctcgacccc    2520
aaaaaacttg attagggtga tggttcacgt agtgggccat cgccctgata cggttttt     2580 cgcccttga cgttggagtc cacgttcttt aatagtggac tcttgttcca aactggaaca    2640
acactcaacc ctatctcggt ctattctttt gatttataag ggattttggg gatttcggcc    2700
tattggttaa aaaatgagct gatttaacaa aaatttaacg cgaattaatt ctgtggaatg    2760
tgtgtcagtt agggtgtgga aagtccccag gctccccagg caggcagaag tatgcaaagc    2820
atgcatctca attagtcagc aaccaggtgt ggaaagtccc caggctcccc agcaggcaga    2880
agtatgcaaa gcatgcatct caattagtca gcaaccatag tcccgcccct aactccgccc    2940
atcccgcccc taactccgcc cagttccgcc cattctccgc cccatggctg actaattttt    3000
tttatttatg cagaggccga ggccgcctct gcctctgagc tattccagaa gtagtgagga    3060
ggcttttttg gaggcctagg cttttgcaaa aagctcccgg gagcttgtat atccatttc     3120 ggatctgatc aagagacagg atgaggatcg tttcgcatga ttgaacaaga tggattgcac    3180
gcaggttctc cggccgcttg ggtggagagg ctattcggct atgactgggc acaacagaca    3240
atcggctgct ctgatgccgc cgtgttccgg ctgtcagcgc aggggcgccc ggttcttttt    3300
gtcaagaccg acctgtccgg tgccctgaat gaactgcagg acgaggcagc gcggctatcg    3360
tggctggcca cgacgggcgt tccttgcgca gctgtgctcg acgttgtcac tgaagcggga    3420
agggactggc tgctattggg cgaagtgccg gggcaggatc tcctgtcatc tcaccttgct    3480
cctgccgaga aagtatccat catggctgat gcaatgcggc ggctgcatac gcttgatccg    3540
gctacctgcc cattcgacca ccaagcgaaa catcgcatcg agcgagcacg tactcggatg    3600
gaagccggtc ttgtcgatca ggatgatctg gacgaagagc atcaggggct cgcgccagcc    3660
gaactgttcg ccaggctcaa ggcgcgcatg cccgacggcg aggatctcgt cgtgacccat    3720
ggcgatgcct gcttgccgaa tatcatggtg gaaaatggcc gcttttctgg attcatcgac    3780
tgtggccggc tgggtgtggc ggaccgctat caggacatag cgttggctac ccgtgatatt    3840
gctgaagagc ttggcggcga atgggctgac cgcttcctcg tgctttacgg tatcgccgct    3900
```

```
cccgattcgc agcgcatcgc cttctatcgc cttcttgacg agttcttctg agcgggactc    3960
tggggttcga aatgaccgac caagcgacgc ccaacctgcc atcacgagat ttcgattcca    4020
ccgccgcctt ctatgaaagg ttgggcttcg gaatcgtttt ccgggacgcc ggctggatga    4080
tcctccagcg cggggatctc atgctggagt tcttcgccca ccccaacttg tttattgcag    4140
cttataatgg ttacaaataa agcaatagca tcacaaattt cacaaataaa gcattttttt    4200
cactgcattc tagttgtggt ttgtccaaac tcatcaatgt atcttatcat gtctgtatac    4260
cgtcgacctc tagctagagc ttggcgtaat catggtcata gctgtttcct gtgtgaaatt    4320
gttatccgct cacaattcca cacaacatac gagccggaag cataaagtgt aaagcctggg    4380
gtgcctaatg agtgagctaa ctcacattaa ttgcgttgcg ctcactgccc gctttccagt    4440
cgggaaacct gtcgtgccag ctgcattaat gaatcggcca acgcgcgggg agaggcggtt    4500
tgcgtattgg gcgctcttcc gcttcctcgc tcactgactc gctgcgctcg tcgttcggc    4560 tgcggcgagc ggtatcagct cactcaaagg cggtaatacg ttatccaca gaatcagggg    4620 ataacgcagg aaagaacatg tgagcaaaag gccagcaaaa ggccaggaac cgtaaaaagg    4680
ccgcgttgct ggcgtttttc cataggctcc gcccccctga cgagcatcac aaaaatcgac    4740
gctcaagtca gaggtggcga aacccgacag gactataaag ataccaggcg tttccccctg    4800
gaagctccct cgtgcgctct cctgttccga cctgccgct taccggatac ctgtccgcct    4860
ttctcccttc gggaagcgtg gcgctttctc aatgctcacg ctgtaggtat ctcagttcgg    4920
tgtaggtcgt tcgctccaag ctgggctgtg tgcacgaacc ccccgttcag cccgaccgct    4980
gcgccttatc cggtaactat cgtcttgagt ccaacccggt aagacacgac ttatcgccac    5040
tggcagcagc cactggtaac aggattagca gagcgaggta tgtaggcggt gctacagagt    5100
tcttgaagtg gtggcctaac tacggctaca ctagaaggac agtatttggt atctgcgctc    5160
tgctgaagcc agttaccttc ggaaaaagag ttggtagctc ttgatccggc aaacaaacca    5220
ccgctggtag cggtggtttt tttgtttgca agcagcagat tacgcgcaga aaaaaggat    5280 ctcaagaaga tccttggatc ttttctacgg ggtctgacgc tcagtggaac gaaaactcac    5340
gttaagggat tttggtcatg agattatcaa aaaggatctt cacctagatc cttttaaatt    5400
aaaaatgaag ttttaaatca atctaaagta tatatgagta aacttggtct gacagttacc    5460
aatgcttaat cagtgaggca cctatctcag cgatctgtct atttcgttca tccatagttg    5520
cctgactccc cgtcgtgtag ataactacga tacgggaggg cttaccatct ggccccagtg    5580
ctgcaatgat accgcgagac ccacgctcac cggctccaga tttatcagca ataaaccagc    5640
cagccggaag ggccgagcgc agaagtggtc ctgcaacttt atccgcctcc atccagtcta    5700
ttaattgttg ccgggaagct agagtaagta gttcgccagt taatagtttg cgcaacgttg    5760
ttgccattgc tacaggcatc gtggtgtcac gctcgtcgtt tggtatggct tcattcagct    5820
ccggttccca acgatcaagg cgagttacat gatccccat gttgtgcaaa aaagcggtta    5880
gctccttcgg tcctccgatc gttgtcagaa gtaagttggc cgcagtgtta tcactcatgg    5940
ttatggcagc actgcataat tctcttactg tcatgccatc cgtaagatgc ttttctgtga    6000
ctggtgagta ctcaaccaag tcattctgag aatagtgtat gcggcgaccg agttgctctt    6060
gcccggcgtc aatacgggat aataccgcgc cacatagcag aactttaaaa gtgctcatca    6120
ttggaaaacg ttcttcgggg cgaaaactct caaggatctt accgctgttg agatccagtt    6180
cgatgtaacc cactcgtgca cccaactgat cttcagcatc ttttactttc accagcgttt    6240
```

```
ctgggtgagc aaaaacagga aggcaaaatg ccgcaaaaaa gggaataagg gcgacacgga      6300
aatgttgaat actctatactc ttccttttc aatattattg aagcatttat cagggttatt      6360
gtctcatgag cggatacata tttgaatgta tttagaaaaa taaacaaata ggggttccgc      6420
gcacatttcc ccgaaaagtg ccacctgacg tc                                    6452
```

<210> SEQ ID NO 59
<211> LENGTH: 349
<212> TYPE: PRT
<213> ORGANISM: Homo sapiens

<400> SEQUENCE: 59

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Gly Ser Met Ala Tyr Pro Tyr Asp Val Pro Asp Tyr Ala Ser
            100                 105                 110

Leu Arg Ser Thr Met Ser Gln Ser Asn Arg Glu Leu Val Val Asp Phe
        115                 120                 125

Leu Ser Tyr Lys Leu Ser Gln Lys Gly Tyr Ser Trp Ser Gln Phe Ser
130                 135                 140

Asp Val Glu Glu Asn Arg Thr Glu Ala Pro Glu Gly Thr Glu Ser Glu
145                 150                 155                 160

Met Glu Thr Pro Ser Ala Ile Asn Gly Asn Pro Ser Trp His Leu Ala
                165                 170                 175

Asp Ser Pro Ala Val Asn Gly Ala Thr Ala His Ser Ser Ser Leu Asp
            180                 185                 190

Ala Arg Glu Val Ile Pro Met Ala Ala Val Lys Gln Ala Leu Arg Glu
        195                 200                 205

Ala Gly Asp Glu Phe Glu Leu Arg Tyr Arg Arg Ala Phe Ser Asp Leu
210                 215                 220

Thr Ser Gln Leu His Ile Thr Pro Gly Thr Ala Tyr Gln Ser Phe Glu
225                 230                 235                 240

Gln Val Val Asn Glu Leu Phe Arg Asp Gly Val Asn Trp Gly Arg Ile
                245                 250                 255

Val Ala Phe Phe Ser Phe Gly Gly Ala Leu Cys Val Glu Ser Val Asp
            260                 265                 270

Lys Glu Met Gln Val Leu Val Ser Arg Ile Ala Ala Trp Met Ala Thr
        275                 280                 285

Tyr Leu Asn Asp His Leu Glu Pro Trp Ile Gln Glu Asn Gly Gly Trp
290                 295                 300

Asp Thr Phe Val Glu Leu Tyr Gly Asn Asn Ala Ala Ala Glu Ser Arg
305                 310                 315                 320

Lys Gly Gln Glu Arg Phe Asn Arg Trp Phe Leu Thr Gly Met Thr Val
                325                 330                 335
```

Ala Gly Val Val Leu Leu Gly Ser Leu Phe Ser Arg Lys
        340                 345

<210> SEQ ID NO 60
<211> LENGTH: 750
<212> TYPE: DNA
<213> ORGANISM: Homo sapiens

<400> SEQUENCE: 60
atggcgtacc catacgatgt tccagattac gctagcttga gatctaccat gtctcagagc    60
aaccgggagc tggtggttga ctttctctcc tacaagcttt cccagaaagg atacagctgg   120
agtcagttta gtgatgtgga agagaacagg actgaggccc cagaagggac tgaatcggag   180
atggagaccc ccagtgccat caatggcaac ccatcctggc acctggcaga cagccccgcg   240
gtgaatggag ccactgcgca cagcagcagt ttggatgccc gggaggtgat ccccatggca   300
gcagtaaagc aagcgctgag ggaggcaggc gacgagtttg aactgcggta ccggcgggca   360
ttcagtgacc tgcatatccca gctccacatc accccaggga cagcatatca gagctttgaa   420
caggtagtga atgaactctt ccgggatggg gtagccattc ttcgcattgt ggccttttc   480 tccttcggcg gggcactgtg cgtggaaagc gtagacaagg agatgcaggt attggtgagt   540
cggatcgcag cttggatggc cacttacctg aatgaccacc tagagccttg gatccaggag   600
aacggcggct gggatacttt tgtggaactc tatgggaaca atgcagcagc cgagagccga   660
aagggccagg aacgcttcaa ccgctggttc ctgacgggca tgactgtggc cggcgtggtt   720
ctgctgggct cactcttcag tcggaaatga                                    750

<210> SEQ ID NO 61
<211> LENGTH: 249
<212> TYPE: PRT
<213> ORGANISM: Homo sapiens

<400> SEQUENCE: 61

Met Ala Tyr Pro Tyr Asp Val Pro Asp Tyr Ala Ser Leu Arg Ser Thr
1               5                   10                  15

Met Ser Gln Ser Asn Arg Glu Leu Val Val Asp Phe Leu Ser Tyr Lys
            20                  25                  30

Leu Ser Gln Lys Gly Tyr Ser Trp Ser Gln Phe Ser Asp Val Glu Glu
        35                  40                  45

Asn Arg Thr Glu Ala Pro Glu Gly Thr Glu Ser Glu Met Glu Thr Pro
    50                  55                  60

Ser Ala Ile Asn Gly Asn Pro Ser Trp His Leu Ala Asp Ser Pro Ala
65                  70                  75                  80

Val Asn Gly Ala Thr Ala His Ser Ser Ser Leu Asp Ala Arg Glu Val
                85                  90                  95

Ile Pro Met Ala Ala Val Lys Gln Ala Leu Arg Glu Ala Gly Asp Glu
            100                 105                 110

Phe Glu Leu Arg Tyr Arg Arg Ala Phe Ser Asp Leu Thr Ser Gln Leu
        115                 120                 125

His Ile Thr Pro Gly Thr Ala Tyr Gln Ser Phe Glu Gln Val Val Asn
    130                 135                 140

Glu Leu Phe Arg Asp Gly Val Ala Ile Leu Arg Ile Val Ala Phe Phe
145                 150                 155                 160

Ser Phe Gly Gly Ala Leu Cys Val Glu Ser Val Asp Lys Glu Met Gln
                165                 170                 175

Val Leu Val Ser Arg Ile Ala Ala Trp Met Ala Thr Tyr Leu Asn Asp

```
                180                 185                 190
His Leu Glu Pro Trp Ile Gln Glu Asn Gly Gly Trp Asp Thr Phe Val
            195                 200                 205

Glu Leu Tyr Gly Asn Asn Ala Ala Glu Ser Arg Lys Gly Gln Glu
            210                 215                 220

Arg Phe Asn Arg Trp Phe Leu Thr Gly Met Thr Val Ala Gly Val Val
225                 230                 235                 240

Leu Leu Gly Ser Leu Phe Ser Arg Lys
            245

<210> SEQ ID NO 62
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Gly Ser Met Ala Tyr Pro Tyr Asp Val Pro Asp Tyr Ala Ser
            100                 105                 110

Leu Arg Ser Thr Met Ser Gln Ser Asn Arg Glu Leu Val Val Asp Phe
        115                 120                 125

Leu Ser Tyr Lys Leu Ser Gln Lys Gly Tyr Ser Trp Ser Gln Phe Ser
    130                 135                 140

Asp Val Glu Glu Asn Arg Thr Glu Ala Pro Glu Gly Thr Glu Ser Glu
145                 150                 155                 160

Met Glu Thr Pro Ser Ala Ile Asn Gly Asn Pro Ser Trp His Leu Ala
                165                 170                 175

Asp Ser Pro Ala Val Asn Gly Ala Thr Ala His Ser Ser Ser Leu Asp
            180                 185                 190

Ala Arg Glu Val Ile Pro Met Ala Ala Val Lys Gln Ala Leu Arg Glu
        195                 200                 205

Ala Gly Asp Glu Phe Glu Leu Arg Tyr Arg Arg Ala Phe Ser Asp Leu
    210                 215                 220

Thr Ser Gln Leu His Ile Thr Pro Gly Thr Ala Tyr Gln Ser Phe Glu
225                 230                 235                 240

Gln Val Val Asn Glu Leu Phe Arg Asp Gly Val Ala Ile Leu Arg Ile
                245                 250                 255

Val Ala Phe Phe Ser Phe Gly Gly Ala Leu Cys Val Glu Ser Val Asp
            260                 265                 270

Lys Glu Met Gln Val Leu Val Ser Arg Ile Ala Ala Trp Met Ala Thr
        275                 280                 285
```

| | | | | | | | | | | | | |
|---|---|---|---|---|---|---|---|---|---|---|---|---|
|Tyr|Leu|Asn|Asp|His|Leu|Glu|Pro|Trp|Ile|Gln|Glu|Asn|Gly|Gly|Trp|
| |290| | | |295| | | |300| | | | | | |

| | | | | | | | | | | | | |
|---|---|---|---|---|---|---|---|---|---|---|---|---|
|Asp|Thr|Phe|Val|Glu|Leu|Tyr|Gly|Asn|Asn|Ala|Ala|Glu|Ser|Arg|
|305| | | | |310| | | | |315| | | | |320|

| | | | | | | | | | | | | |
|---|---|---|---|---|---|---|---|---|---|---|---|---|
|Lys|Gly|Gln|Glu|Arg|Phe|Asn|Arg|Trp|Phe|Leu|Thr|Gly|Met|Thr|Val|
| | | | |325| | | | |330| | | | |335| |

| | | | | | | | | | |
|---|---|---|---|---|---|---|---|---|---|
|Ala|Gly|Val|Val|Leu|Leu|Gly|Ser|Leu|Phe|Ser|Arg|Lys|
| | | |340| | | |345| | | | | |

<210> SEQ ID NO 63
<211> LENGTH: 6187
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

| | | | | | |
|---|---|---|---|---|---|
|gacggatcgg|gagatctccc|gatcccctat|ggtcgactct|cagtacaatc|tgctctgatg|60|
|ccgcatagtt|aagccagtat|ctgctccctg|cttgtgtgtt|ggaggtcgct|gagtagtgcg|120|
|cgagcaaaat|ttaagctaca|acaaggcaag|gcttgaccga|caattgcatg|aagaatctgc|180|
|ttagggttag|gcgttttgcg|ctgcttcgcg|atgtacgggc|cagatatacg|cgttgacatt|240|
|gattattgac|tagttattaa|tagtaatcaa|ttacggggtc|attagttcat|agcccatata|300|
|tggagttccg|cgttacataa|cttacggtaa|atggcccgcc|tggctgaccg|cccaacgacc|360|
|cccgcccatt|gacgtcaata|atgacgtatg|ttcccatagt|aacgccaata|gggactttcc|420|
|attgacgtca|atgggtggac|tatttacggt|aaactgccca|cttggcagta|catcaagtgt|480|
|atcatatgcc|aagtacgccc|cctattgacg|tcaatgacgg|taaatggccc|gcctggcatt|540|
|atgcccagta|catgacctta|tgggactttc|ctacttggca|gtacatctac|gtattagtca|600|
|tcgctattac|catggtgatg|cggttttggc|agtacatcaa|tgggcgtgga|tagcggtttg|660|
|actcacgggg|atttccaagt|ctccacccca|ttgacgtcaa|tgggagtttg|ttttggcacc|720|
|aaaatcaacg|ggactttcca|aaatgtcgta|acaactccgc|cccattgacg|caaatgggcg|780|
|gtaggcgtgt|acggtgggag|gtctatataa|gcagagctct|ctggctaact|agagaaccca|840|
|ctgcttactg|gcttatcgaa|attaatacga|ctcactatag|ggagacccaa|gctggctagc|900|
|gtttaaacgg|gccctctaga|ctcgagcggc|cgccactgtg|ctggatatct|gcagaattcc|960|
|accacactgg|actagtggat|ctatggcgta|cccatacgat|gttccagatt|acgctagctt|1020|
|gagatctacc|atgtctcaga|gcaaccggga|gctggtggtt|gactttctct|cctacaagct|1080|
|ttcccagaaa|ggatacagct|ggagtcagtt|tagtgatgtg|gaagagaaca|ggactgaggc|1140|
|cccagaaggg|actgaatcgg|agatggagac|cccagtgcc|atcaatggca|acccatcctg|1200|
|gcacctggca|gacagccccg|cggtgaatgg|agccactgcg|cacagcagca|gtttggatgc|1260|
|ccgggaggtg|atccccatgg|cagcagtaaa|gcaagcgctg|agggaggcag|gcgacgagtt|1320|
|tgaactgcgg|taccggcggg|cattcagtga|cctgacatcc|cagctccaca|tcaccccagg|1380|
|gacagcatat|cagagctttg|aacaggtagt|gaatgaactc|ttccgggatg|ggtagccat|1440|
|tcttcgcatt|gtggccttt|tctccttcgg|cggggcactg|tgcgtggaaa|gcgtagacaa|1500|
|ggagatgcag|gtattggtga|gtcggatcgc|agcttggatg|ccacttaccc|tgaatgacca|1560|
|cctagagcct|tggatccagg|agaacggcgg|ctgggatact|tttgtggaac|tctatgggaa|1620|
|caatgcagca|gccgagagcc|gaaagggcca|ggaacgcttc|aaccgctggt|tcctgacggg|1680|

-continued

```
catgactgtg gccggcgtgg ttctgctggg ctcactcttc agtcggaaat gaagatccga    1740
gctcggtacc aagcttaagt ttaaaccgct gatcagcctc gactgtgcct tctagttgcc    1800
agccatctgt tgtttgcccc tcccccgtgc cttccttgac cctggaaggt gccactccca    1860
ctgtcctttc ctaataaaat gaggaaaatg catcgcattg tctgagtagg tgtcattcta    1920
ttctgggggg tggggtgggg caggacagca aggggagga ttgggaagac aatagcaggc     1980
atgctgggga tgcggtgggc tctatggctt ctgaggcgga aagaaccagc tggggctcta    2040
gggggtatcc ccacgcgccc tgtagcggcg cattaagcgc ggcgggtgtg gtggttacgc    2100
gcagcgtgac cgctacactt gccagcgccc tagcgcccgc tcctttcgct ttcttccctt    2160
cctttctcgc cacgttcgcc ggctttcccc gtcaagctct aaatcggggc atccctttag    2220
ggttccgatt tagtgcttta cggcacctcg accccaaaaa acttgattag ggtgatggtt    2280
cacgtagtgg gccatcgccc tgatagacgg ttttcgccc tttgacgttg gagtccacgt     2340
tctttaatag tggactcttg ttccaaactg gaacaacact caaccctatc tcggtctatt    2400
cttttgattt ataagggatt tgggggattt cggcctattg gttaaaaaat gagctgattt    2460
aacaaaaatt taacgcgaat taattctgtg gaatgtgtgt cagttagggt gtggaaagtc    2520
cccaggctcc ccaggcaggc agaagtatgc aaagcatgca tctcaattag tcagcaacca    2580
ggtgtggaaa gtccccaggc tccccagcag gcagaagtat gcaaagcatg catctcaatt    2640
agtcagcaac catagtcccg cccctaactc cgcccatccc gcccctaact ccgcccagtt    2700
ccgcccattc tccgccccat ggctgactaa ttttttttat ttatgcagag gccgaggccg    2760
cctctgcctc tgagctattc cagaagtagt gaggaggctt ttttggaggc ctaggctttt    2820
gcaaaaagct cccgggagct tgtatatcca ttttcggatc tgatcaagag acaggatgag    2880
gatcgtttcg catgattgaa caagatggat tgcacgcagg ttctccggcc gcttgggtgg    2940
agaggctatt cggctatgac tgggcacaac agacaatcgg ctgctctgat gccgccgtgt    3000
tccggctgtc agcgcagggg cgcccggttc ttttgtcaa gaccgacctg tccggtgccc    3060
tgaatgaact gcaggacgag gcagcgcggc tatcgtggct ggccacgacg gcgttccttt    3120
gcgcagctgt gctcgacgtt gtcactgaag cgggaaggga ctggctgcta ttgggcgaag    3180
tgccggggca ggatctcctg tcatctcacc ttgctcctgc cgagaaagta ccatcatgg     3240 ctgatgcaat gcggcggctg catacgcttg atccggctac ctgcccattc gaccaccaag    3300
cgaaacatcg catcgagcga gcacgtactc ggatggaagc cggtcttgtc gatcaggatg    3360
atctggacga agagcatcag gggctcgcgc cagccgaact gttcgccagg ctcaaggcgc    3420
gcatgcccga cggcgaggat ctcgtcgtga cccatggcga tgcctgcttg ccgaatatca    3480
tggtggaaaa tggccgcttt tctggattca tcgactgtgg ccggctgggt gtggcggacc    3540
gctatcagga catagcgttg gctacccgtg atattgctga agagcttggc ggcgaatggg    3600
ctgaccgctt cctcgtgctt tacggtatcg ccgctcccga ttcgcagcgc atcgccttct    3660
atcgccttct tgacgagttc ttctgagcgg actctgggg ttcgaaatga ccgaccaagc     3720
gacgcccaac ctgccatcac gagatttcga ttccaccgcc gccttctatg aaaggttggg    3780
cttcggaatc gttttccggg acgccggctg atgatcctc cagcgcgggg atctcatgct     3840
ggagttcttc gcccacccca acttgtttat tgcagcttat aatggttaca aataaagcaa    3900
tagcatcaca aatttcacaa ataaagcatt ttttcactg cattctagtt gtggtttgtc     3960
caaactcatc aatgtatctt atcatgtctg tataccgtcg acctctagct agagcttggc    4020
gtaatcatgg tcatagctgt ttcctgtgtg aaattgttat ccgctcacaa ttccacacaa    4080
```

```
catacgagcc ggaagcataa agtgtaaagc ctggggtgcc taatgagtga gctaactcac    4140
attaattgcg ttgcgctcac tgcccgcttt ccagtcggga aacctgtcgt gccagctgca    4200
ttaatgaatc ggccaacgcg cggggagagg cggtttgcgt attgggcgct cttccgcttc    4260
ctcgctcact gactcgctgc gctcggtcgt tcggctgcgg cgagcggtat cagctcactc    4320
aaaggcggta atacggttat ccacagaatc aggggataac gcaggaaaga acatgtgagc    4380
aaaaggccag caaaaggcca ggaaccgtaa aaaggccgcg ttgctggcgt ttttccatag    4440
gctccgcccc cctgacgagc atcacaaaaa tcgacgctca agtcagaggt ggcgaaaccc    4500
gacaggacta taaagatacc aggcgtttcc ccctggaagc tccctcgtgc gctctcctgt    4560
tccgaccctg ccgcttaccg gatacctgtc cgcctttctc ccttcgggaa gcgtggcgct    4620
ttctcaatgc tcacgctgta ggtatctcag ttcggtgtag tcgttcgct ccaagctggg    4680 ctgtgtgcac gaaccccccg ttcagcccga ccgctgcgcc ttatccggta actatcgtct    4740
tgagtccaac ccggtaagac acgacttatc gccactggca gcagccactg gtaacaggat    4800
tagcagagcg aggtatgtag gcggtgctac agagttcttg aagtggtggc ctaactacgg    4860
ctacactaga aggacagtat ttggtatctg cgctctgctg aagccagtta ccttcggaaa    4920
aagagttggt agctcttgat ccggcaaaca aaccaccgct ggtagcggtg gtttttttgt    4980
ttgcaagcag cagattacgc gcagaaaaaa aggatctcaa gaagatcctt tgatcttttc    5040
tacggggtct gacgctcagt ggaacgaaaa ctcacgttaa gggattttgg tcatgagatt    5100
atcaaaaagg atcttcacct agatcctttt aaattaaaaa tgaagtttta atcaatcta    5160 aagtatatat gagtaaactt ggtctgacag ttaccaatgc ttaatcagtg aggcacctat    5220
ctcagcgatc tgtctatttc gttcatccat agttgcctga ctccccgtcg tgtagataac    5280
tacgatacgg gagggcttac catctggccc cagtgctgca atgataccgc gagacccacg    5340
ctcaccggct ccagatttat cagcaataaa ccagccagcc ggaagggccg agcgcagaag    5400
tggtcctgca actttatccg cctccatcca gtctattaat tgttgccggg aagctagagt    5460
aagtagttcg ccagttaata gtttgcgcaa cgttgttgcc attgctacag gcatcgtggt    5520
gtcacgctcg tcgtttggta tggcttcatt cagctccggt tcccaacgat caaggcgagt    5580
tacatgatcc cccatgttgt gcaaaaaagc ggttagctcc ttcggtcctc cgatcgttgt    5640
cagaagtaag ttggccgcag tgttatcact catggttatg gcagcactgc ataattctct    5700
tactgtcatg ccatccgtaa gatgcttttc tgtgactggt gagtactcaa ccaagtcatt    5760
ctgagaatag tgtatgcggc gaccgagttg ctcttgcccg gcgtcaatac gggataatac    5820
cgcgccacat agcagaactt taaaagtgct catcattgga aaacgttctt cggggcgaaa    5880
actctcaagg atcttaccgc tgttgagatc cagttcgatg taacccactc gtgcacccaa    5940
ctgatcttca gcatctttta ctttcaccag cgtttctggg tgagcaaaaa caggaaggca    6000
aaatgccgca aaaaagggaa taagggcgac acggaaatgt tgaatactca tactcttcct    6060
ttttcaatat tattgaagca tttatcaggg ttattgtctc atgagcggat acatatttga    6120
atgtatttag aaaaataaac aaataggggt tccgcgcaca tttccccgaa aagtgccacc    6180
tgacgtc                                                               6187

<210> SEQ ID NO 64
<211> LENGTH: 6452
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 64

```
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacgggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagaattca    960
tgcatggaga tacacctaca ttgcatgaat atatgttaga tttgcaacca gagacaactg   1020
atctctactg ttatgagcaa ttaaatgaca gctcagagga ggaggatgaa atagatggtc   1080
cagctggaca agcagaaccg gacagagccc attacaatat tgtaaccttt tgttgcaagt   1140
gtgactctac gcttcggttg tgcgtacaaa gcacacacgt agacattcgt actttggaag   1200
acctgttaat gggcacacta ggaattgtgt gcccccatctg ttctcagaaa ccaggatcta   1260
tggcgtaccc atacgatgtt ccagattacg ctagcttgag atctaccatg tctcagagca   1320
accgggagct ggtggttgac tttctctcct acaagctttc ccagaaagga tacagctgga   1380
gtcagtttag tgatgtggaa gagaacagga ctgaggcccc agaagggact gaatcggaga   1440
tggagacccc cagtgccatc aatggcaacc catcctggca cctggcagac agccccgcgg   1500
tgaatggagc cactgcgcac agcagcagtt tggatgcccg ggaggtgatc cccatggcag   1560
cagtaaagca agcgctgagg gaggcaggcg acgagtttga actgcggtac cggcgggcat   1620
tcagtgacct gacatcccag ctccacatca ccccagggac agcatatcag agctttgaac   1680
aggtagtgaa tgaactcttc cgggatgggt agccattct tcgcattgtg gcctttttct   1740
ccttcggcgg ggcactgtgc gtggaaagcg tagacaagga gatgcaggta ttggtgagtc   1800
ggatcgcagc ttggatggcc acttacctga atgaccacct agagccttgg atccaggaga   1860
acggcggctg ggatactttt gtggaactct atgggaacaa tgcagcagcc gagagccgaa   1920
agggccagga acgcttcaac cgctggttcc tgacgggcat gactgtggcc ggcgtggttc   1980
tgctgggctc actcttcagt cggaaatgaa gatccaagct taagtttaaa ccgctgatca   2040
gcctcgactg tgccttctag ttgccagcca tctgttgttt gcccctcccc cgtgccttcc   2100
ttgaccctgg aaggtgccac tcccactgtc ctttcctaat aaaatgagga aattgcatcg   2160
cattgtctga gtaggtgtca ttctattctg gggggtgggg tggggcagga cagcaagggg   2220
```

```
gaggattggg aagacaatag caggcatgct ggggatgcgg tgggctctat ggcttctgag    2280
gcggaaagaa ccagctgggg ctctaggggg tatccccacg cgccctgtag cggcgcatta    2340
agcgcggcgg gtgtggtggt tacgcgcagc gtgaccgcta cacttgccag cgccctagcg    2400
cccgctcctt tcgctttctt cccttccttt ctcgccacgt tcgccggctt tccccgtcaa    2460
gctctaaatc ggggcatccc tttagggttc cgatttagtg ctttacggca cctcgacccc    2520
aaaaaacttg attagggtga tggttcacgt agtgggccat cgccctgata gacggttttt    2580
cgcccttgta cgttggagtc cacgttcttt aatagtggac tcttgttcca aactggaaca    2640
acactcaacc ctatctcggt ctattctttt gatttataag gattttggg gatttcggcc      2700 tattggttaa aaatgagct gatttaacaa aaatttaacg cgaattaatt ctgtggaatg      2760
tgtgtcagtt agggtgtgga aagtccccag gctccccagg caggcagaag tatgcaaagc    2820
atgcatctca attagtcagc aaccaggtgt ggaaagtccc caggctcccc agcaggcaga    2880
agtatgcaaa gcatgcatct caattagtca gcaaccatag tcccgcccct aactccgccc    2940
atcccgcccc taactccgcc cagttccgcc cattctccgc cccatggctg actaattttt    3000
tttatttatg cagaggccga ggccgcctct gcctctgagc tattccagaa gtagtgagga    3060
ggcttttttg gaggcctagg cttttgcaaa aagctcccgg gagcttgtat atccatttc     3120 ggatctgatc aagagacagg atgaggatcg tttcgcatga ttgaacaaga tggattgcac    3180
gcaggttctc cggccgcttg ggtggagagg ctattcggct atgactgggc acaacagaca    3240
atcggctgct ctgatgccgc cgtgttccgg ctgtcagcgc aggggcgccc ggttcttttt    3300
gtcaagaccg acctgtccgg tgccctgaat gaactgcagg acgaggcagc gcggctatcg    3360
tggctggcca cgacgggcgt tccttgcgca gctgtgctcg acgttgtcac tgaagcggga    3420
agggactggc tgctattggg cgaagtgccg gggcaggatc tcctgtcatc tcaccttgct    3480
cctgccgaga aagtatccat catggctgat gcaatgcggc ggctgcatac gcttgatccg    3540
gctacctgcc cattcgacca ccaagcgaaa catcgcatcg agcgagcacg tactcggatg    3600
gaagccggtc ttgtcgatca ggatgatctg gacgaagagc atcaggggct cgcgccagcc    3660
gaactgttcg ccaggctcaa ggcgcgcatg cccgacggcg aggatctcgt cgtgacccat    3720
ggcgatgcct gcttgccgaa tatcatggtg gaaaatggcc gcttttctgg attcatcgac    3780
tgtggccggc tgggtgtggc ggaccgctat caggacatag cgttggctac ccgtgatatt    3840
gctgaagagc ttggcggcga atgggctgac cgcttcctcg tgctttacgg tatcgccgct    3900
cccgattcgc agcgcatcgc cttctatcgc cttcttgacg agttcttctg agcgggactc    3960
tggggttcga aatgaccgac caagcgacgc ccaacctgcc atcacgagat ttcgattcca    4020
ccgccgcctt ctatgaaagg ttgggcttcg aatcgttttt ccgggacgcc ggctggatga    4080
tcctccagcg cggggatctc atgctggagt tcttcgccca ccccaacttg tttattgcag    4140
cttataatgg ttacaaataa agcaatagca tcacaaattt cacaaataaa gcatttttt    4200 cactgcattc tagttgtggt ttgtccaaac tcatcaatgt atcttatcat gtctgtatac    4260
cgtcgacctc tagctagagc ttggcgtaat catggtcata gctgtttcct gtgtgaaatt    4320
gttatccgct cacaattcca cacaacatac gagccgaaag cataaagtgt aaagcctggg    4380
gtgcctaatg agtgagctaa ctcacattaa ttgcgttgcg ctcactgccc gctttccagt    4440
cgggaaacct gtcgtgccag ctgcattaat gaatcggcca acgcgcgggg agaggcggtt    4500
tgcgtattgg gcgctcttcc gcttcctcgc tcactgactc gctgcgctcg gtcgttcggc    4560
tgcggcgagc ggtatcagct cactcaaagg cggtaatacg ttatccaca gaatcagggg    4620
```

-continued

```
ataacgcagg aaagaacatg tgagcaaaag gccagcaaaa ggccaggaac cgtaaaaagg    4680
ccgcgttgct ggcgttttc cataggctcc gccccctga cgagcatcac aaaaatcgac    4740
gctcaagtca gaggtggcga aacccgacag gactataaag ataccaggcg tttccccctg    4800
gaagctccct cgtgcgctct cctgttccga ccctgccgct taccggatac ctgtccgcct    4860
ttctcccttc gggaagcgtg gcgctttctc aatgctcacg ctgtaggtat ctcagttcgg    4920
tgtaggtcgt tcgctccaag ctgggctgtg tgcacgaacc cccgttcag cccgaccgct    4980 gcgccttatc cggtaactat cgtcttgagt ccaacccggt aagacacgac ttatcgccac    5040
tggcagcagc cactggtaac aggattagca gagcgaggta tgtaggcggt gctacagagt    5100
tcttgaagtg gtggcctaac tacggctaca ctagaaggac agtatttggt atctgcgctc    5160
tgctgaagcc agttaccttc ggaaaaagag ttggtagctc ttgatccggc aaacaaacca    5220
ccgctggtag cggtggtttt tttgtttgca agcagcagat tacgcgcaga aaaaaggat    5280 ctcaagaaga tccttttgatc ttttctacgg ggtctgacgc tcagtggaac gaaaactcac    5340
gttaagggat tttggtcatg agattatcaa aaaggatctt cacctagatc cttttaaatt    5400
aaaaatgaag ttttaaatca atctaaagta tatatgagta aacttggtct gacagttacc    5460
aatgcttaat cagtgaggca cctatctcag cgatctgtct atttcgttca tccatagttg    5520
cctgactccc cgtcgtgtag ataactacga tacgggaggg cttaccatct ggccccagtg    5580
ctgcaatgat accgcgagac ccacgctcac cggctccaga tttatcagca ataaaccagc    5640
cagccggaag ggccgagcgc agaagtggtc ctgcaacttt atccgcctcc atccagtcta    5700
ttaattgttg ccgggaagct agagtaagta gttcgccagt taatagtttg cgcaacgttg    5760
ttgccattgc tacaggcatc gtggtgtcac gctcgtcgtt tggtatggct tcattcagct    5820
ccggttccca acgatcaagg cgagttacat gatccccat gttgtgcaaa aaagcggtta    5880
gctccttcgg tcctccgatc gttgtcagaa gtaagttggc cgcagtgtta tcactcatgg    5940
ttatggcagc actgcataat tctcttactg tcatgccatc cgtaagatgc ttttctgtga    6000
ctggtgagta ctcaaccaag tcattctgag aatagtgtat gcggcgaccg agttgctctt    6060
gcccggcgtc aatacgggat aataccgcgc cacatagcag aactttaaaa gtgctcatca    6120
ttggaaaacg ttcttcgggg cgaaaactct caaggatctt accgctgttg agatccagtt    6180
cgatgtaacc cactcgtgca cccaactgat cttcagcatc ttttactttc accagcgttt    6240
ctgggtgagc aaaaacagga aggcaaaatg ccgcaaaaaa gggaataagg gcgacacgga    6300
aatgttgaat actcatactc ttcctttttc aatattattg aagcatttat cagggttatt    6360
gtctcatgag cggatacata tttgaatgta tttagaaaaa taaacaaata ggggttccgc    6420
gcacatttcc ccgaaaagtg ccacctgacg tc                                  6452
```

<210> SEQ ID NO 65
<211> LENGTH: 12347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
atggcggatg tgtgacatac acgacgccaa aagattttgt tccagctcct gccacctccg     60
ctacgcgaga gattaaccac ccacgatggc cgccaaagtg catgttgata ttgaggctga    120
cagcccattc atcaagtctt tgcagaaggc atttccgtcg ttcgaggtgg agtcattgca    180
```

-continued

```
ggtcacacca aatgaccatg caaatgccag agcattttcg cacctggcta ccaaattgat      240
cgagcaggag actgacaaag acacactcat cttggatatc ggcagtgcgc cttccaggag      300
aatgatgtct acgcacaaat accactgcgt atgccctatg cgcagcgcag aagaccccga      360
aaggctcgat agctacgcaa agaaactggc agcggcctcc gggaaggtgc tggatagaga      420
gatcgcagga aaaatcaccg acctgcagac cgtcatggct acgccagacg ctgaatctcc      480 tacctttgc ctgcatacag acgtcacgtg tcgtacggca gccgaagtgg ccgtatacca       540
ggacgtgtat gctgtacatg caccaacatc gctgtaccat caggcgatga aggtgtcag      600 aacgcgtat tggattgggt ttgacaccac cccgtttatg tttgacgcgc tagcaggcgc       660
gtatccaacc tacgccacaa actgggccga cgagcaggtg ttacaggcca ggaacatagg      720
actgtgtgca gcatccttga ctgagggaag actcggcaaa ctgtccattc tccgcaagaa      780
gcaattgaaa ccttgcgaca cagtcatgtt ctcggtagga tctacattgt acactgagag      840
cagaaagcta ctgaggagct ggcacttacc ctccgtattc cacctgaaag gtaaacaatc      900
ctttacctgt aggtgcgata ccatcgtatc atgtgaaggg tacgtagtta agaaaatcac      960
tatgtgcccc ggcctgtacg gtaaaacggt agggtacgcc gtgacgtatc acgcggaggg     1020
attcctagtg tgcaagacca cagacactgt caaaggagaa agagtctcat tccctgtatg     1080
cacctacgtc ccctcaacca tctgtgatca aatgactggc atactagcga ccgacgtcac     1140
accggaggac gcacagaagt tgttagtggg attgaatcag aggatagttg tgaacggaag     1200
aacacagcga aacactaaca cgatgaagaa ctatctgctt ccgattgtgg ccgtcgcatt     1260
tagcaagtgg gcgagggaat acaaggcaga ccttgatgat gaaaaacctc tgggtgtccg     1320
agagaggtca cttacttgct gctgcttgtg ggcatttaaa acgaggaaga tgcacaccat     1380
gtacaagaaa ccagacaccc agacaatagt gaaggtgcct tcagagttta actcgttcgt     1440
catcccgagc ctatggtcta caggcctcgc aatcccagtc agatcacgca ttaagatgct     1500
tttggccaag aagaccaagc gagagttaat acctgttctc gacgcgtcgt cagccaggga     1560
tgctgaacaa gaggagaagg agaggttgga ggccgagctg actagagaag ccttaccacc     1620
cctcgtcccc atcgcgccgg cggagacggg agtcgtcgac gtcgacgttg aagaactaga     1680
gtatcacgca ggtgcagggg tcgtggaaac acctcgcagc gcgttgaaag tcaccgcaca     1740
gccgaacgac gtactactag gaaattacgt agttctgtcc ccgcagaccg tgctcaagag     1800
ctccaagttg gcccccgtgc accctctagc agagcaggtg aaaataataa cacataacgg     1860
gagggccggc ggttaccagg tcgacggata tgacggcagg gtcctactac catgtggatc     1920
ggccattccg gtccctgagt ttcaagcttt gagcgagagc gccactatgg tgtacaacga     1980
aagggagttc gtcaacagga actatacca tattgccgtt cacggaccgt cgctgaacac     2040
cgacgaggag aactacgaga agtcagagc tgaaagaact gacgccgagt acgtgttcga     2100
cgtagataaa aaatgctgcg tcaagagaga ggaagcgtcg gtttggtgt tggtgggaga      2160 gctaaccaac cccccgttcc atgaattcgc ctacgaaggg ctgaagatca ggccgtcggc     2220
accatataag actacagtag taggagtctt tggggttccg ggatcaggca agtctgctat     2280
tattaagagc ctcgtgacca aacacgatct ggtcaccagc ggcaagaagg agaactgcca     2340
ggaaatagtt aacgacgtga agaagcaccg cgggaagggg acaagtaggg aaaacagtga     2400
ctccatcctg ctaaacgggt gtcgtcgtgc cgtggacatc ctatatgtgg acgaggcttt     2460
cgctagccat tccggtactc tgctggccct aattgctctt gttaaacctc ggagcaaagt     2520
```

-continued

```
ggtgttatgc ggagacccca agcaatgcgg attcttcaat atgatgcagc ttaaggtgaa    2580
cttcaaccac aacatctgca ctgaagtatg tcataaaagt atatccagac gttgcacgcg    2640
tccagtcacg gccatcgtgt ctacgttgca ctacggaggc aagatgcgca cgaccaaccc    2700
gtgcaacaaa cccataatca tagacaccac aggacagacc aagcccaagc caggagacat    2760
cgtgttaaca tgcttccgag gctgggcaaa gcagctgcag ttggactacc gtggacacga    2820
agtcatgaca gcagcagcat ctcagggcct cacccgcaaa ggggtatacg ccgtaaggca    2880
gaaggtgaat gaaaatccct tgtatgcccc tgcgtcggag cacgtgaatg tactgctgac    2940
gcgcactgag gataggctgg tgtggaaaac gctggccggc gatccctgga ttaaggtcct    3000
atcaaacatt ccacagggta actttacggc cacattggaa gaatggcaag aagaacacga    3060
caaaataatg aaggtgattg aaggaccggc tgcgcctgtg gacgcgttcc agaacaaagc    3120
gaacgtgtgt tgggcgaaaa gcctggtgcc tgtcctggac actgccggaa tcagattgac    3180
agcagaggag tggagcacca taattacagc atttaaggag gacagagctt actctccagt    3240
ggtggccttg aatgaaattt gcaccaagta ctatggagtt gacctggaca gtggcctgtt    3300
ttctgccccg aaggtgtccc tgtattacga gaacaaccac tgggataaca gacctggtgg    3360
aaggatgtat ggattcaatg ccgcaacagc tgccaggctg gaagctagac ataccttcct    3420
gaaggggcag tggcatacgg gcaagcaggc agttatcgca gaaagaaaaa tccaaccgct    3480
ttctgtgctg acaatgtaa ttcctatcaa ccgcaggctg ccgcacgccc tggtggctga    3540
gtacaagacg gttaaaggca gtagggttga gtggctggtc aataaagtaa gagggtacca    3600
cgtcctgctg gtgagtgagt acaacctggc tttgcctcga cgcagggtca cttggttgtc    3660
accgctgaat gtcacaggcg ccgataggtg ctacgaccta agtttaggac tgccggctga    3720
cgccggcagg ttcgacttgg tctttgtgaa cattcacacg gaattcagaa tccaccacta    3780
ccagcagtgt gtcgaccacg ccatgaagct gcagatgctt gggggagatg cgctacgact    3840
gctaaaaccc ggcggcatct tgatgagagc ttacggatac gccgataaaa tcagcgaagc    3900
cgttgtttcc tccttaagca gaaagttctc gtctgcaaga gtgttgcgcc cggattgtgt    3960
caccagcaat acagaagtgt tcttgctgtt ctccaacttt gacaacggaa agagaccctc    4020
tacgctacac cagatgaata ccaagctgag tgccgtgtat gccggagaag ccatgcacac    4080
ggccgggtgt gcaccatcct acagagttaa gagagcagac atagccacgt gcacagaagc    4140
ggctgtggtt aacgcagcta cgcccgtgg aactgtaggg gatggcgtat gcagggccgt    4200
ggcgaagaaa tggccgtcag cctttaaggg agcagcaaca ccagtgggca caattaaaac    4260
agtcatgtgc ggctcgtacc ccgtcatcca cgctgtagcg cctaatttct ctgccacgac    4320
tgaagcggaa ggggaccgcg aattggccgc tgtctaccgg gcagtggccg ccgaagtaaa    4380
cagactgtca ctgagcagcg tagccatccc gctgctgtcc acaggagtgt tcagcggcgg    4440
aagagatagg ctgcagcaat ccctcaacca tctattcaca gcaatggacg ccacggacgc    4500
tgacgtgacc atctactgca gagacaaaag ttggagaaag aaaatccagg aagccattga    4560
catgaggacg gctgtggagt tgctcaatga tgacgtggag ctgaccacag acttggtgag    4620
agtgcacccg gacagcagcc tggtgggtcg taagggctac agtaccactg acgggtcgct    4680
gtactcgtac tttgaaggta cgaaattcaa ccaggctgct attgatatgg cagagatact    4740
gacgttgtgg cccagactgc aagaggcaaa cgaacagata tgcctatacg cgctgggcga    4800
aacaatggac aacatcagat ccaaatgtcc ggtgaacgat tccgattcat caacacctcc    4860
caggacagtg ccctgcctgt gccgctacgc aatgacagca gaacggatcg cccgccttag    4920
```

```
gtcacaccaa gttaaaagca tggtggtttg ctcatctttt cccctcccga ataccatgt     4980 agatggggtg cagaaggtaa agtgcgagaa ggttctcctg ttcgacccga cggtaccttc    5040
agtggttagt ccgcggaagt atgccgcatc tacgacggac cactcagatc ggtcgttacg    5100
agggtttgac ttggactgga ccaccgactc gtcttccact gccagcgata ccatgtcgct    5160
acccagtttg cagtcgtgtg acatcgactc gatctacgag ccaatggctc ccatagtagt    5220
gacggctgac gtacaccctg aacccgcagg catcgcggac ctggcggcag atgtgcaccc    5280
tgaacccgca gaccatgtgg acctcgagaa cccgattcct ccaccgcgcc cgaagagagc    5340
tgcatacctt gcctcccgcg cggcggagcg accggtgccg gcgccgagaa agccgacgcc    5400
tgccccaagg actgcgttta ggaacaagct gcctttgacg ttcggcgact ttgacgagca    5460
cgaggtcgat gcgttggcct ccgggattac tttcggagac ttcgacgacg tcctgcgact    5520
aggccgcgcg ggtgcatata ttttctcctc ggacactggc agcggacatt tacaacaaaa    5580
atccgttagg cagcacaatc tccagtgcgc acaactggat gcggtccagg aggagaaaat    5640
gtacccgcca aaattggata ctgagaggga aagctgttg ctgctgaaaa tgcagatgca     5700
cccatcggag gctaataaga gtcgatacca gtctcgcaaa gtggagaaca tgaaagccac    5760
ggtggtggac aggctcacat cgggggccag attgtacacg ggagcggacg taggccgcat    5820
accaacatac gcggttcggt accccgcccc cgtgtactcc cctaccgtga tcgaaagatt    5880
ctcaagcccc gatgtagcaa tcgcagcgtg caacgaatac ctatccagaa attacccaac    5940
agtggcgtcg taccagataa cagatgaata cgacgcatac ttggacatgg ttgacgggtc    6000
ggatagttgc ttggacagag cgacattctg cccggcgaag ctccggtgct acccgaaaca    6060
tcatgcgtac caccagccga ctgtacgcag tgccgtcccg tcacccttc agaacacact     6120 acagaacgtg ctagcggccg ccaccaagag aaactgcaac gtcacgcaaa tgcgagaact    6180
acccaccatg gactcggcag tgttcaacgt ggagtgcttc aagcgctatg cctgctccgg    6240
agaatattgg gaagaatatg ctaaacaacc tatccggata accactgaga acatcactac    6300
ctatgtgacc aaattgaaag ccccgaaagc tgctgccttg ttcgctaaga cccacaactt    6360
ggttccgctg caggaggttc ccatggacag attcacggtc gacatgaaac gagatgtcaa    6420
agtcactcca gggacgaaac acacagagga aagacccaaa gtccaggtaa ttcaagcagc    6480
ggagccattg gcgaccgctt acctgtgcgg catccacagg gaattagtaa ggagactaaa    6540
tgctgtgtta cgccctaacg tgcacacatt gtttgatatg tcggccgaag actttgacgc    6600
gatcatcgcc tctcacttcc acccaggaga cccggttcta gagacggaca ttgcatcatt    6660
cgacaaaagc caggacgact ccttggctct tacaggttta atgatcctcg aagatctagg    6720
ggtggatcag tacctgctgg acttgatcga ggcagccttt ggggaaatat ccagctgtca    6780
cctaccaact ggcacgcgct tcaagttcgg agctatgatg aaatcgggca tgtttctgac    6840
tttgtttatt aacactgttt tgaacatcac catagcaagc agggtactgg agcagagact    6900
cactgactcc gcctgtgcgg ccttcatcgg cgacgacaac atcgttcacg gagtgatctc    6960
cgacaagctg atggcggaga ggtgcgcgtc gtgggtcaac atggaggtga agatcattga    7020
cgctgtcatg ggcgaaaaac ccccatattt tgtgggggga ttcatagttt ttgacagcgt    7080
cacacagacc gcctgccgtg tttcagaccc acttaagcgc ctgttcaagt tgggtaagcc    7140
gctaacagct gaagacaagc aggacgaaga caggcgacga gcactgagtg acagaggttag  7200 caagtggttc cggacaggct tggggccga actggaggtg gcactaacat ctaggtatga    7260
```

```
ggtagagggc tgcaaaagta tcctcatagc catggccacc ttggcgaggg acattaaggc    7320
gtttaagaaa ttgagaggac ctgttataca cctctacggc ggtcctagat tggtgcgtta    7380
atacacagaa ttctgattgg atcccaaacg ggccctctag actcgagcgg ccgccactgt    7440
gctggatatc tgcagaattc caccacactg gactagtgga tctatggcgt acccatacga    7500
tgttccagat tacgctagct tgagatctac catgtctcag agcaaccggg agctggtggt    7560
tgactttctc tcctacaagc tttcccagaa aggatacagc tggagtcagt ttagtgatgt    7620
ggaagagaac aggactgagg ccccagaagg gactgaatcg gagatggaga ccccagtgc    7680
catcaatggc aacccatcct ggcacctggc agacagcccc gcggtgaatg gagccactgc    7740
gcacagcagc agtttggatg cccgggaggt gatccccatg gcagcagtaa agcaagcgct    7800
gagggaggca ggcgacgagt ttgaactgcg gtaccggcgg gcattcagtg acctgacatc    7860
ccagctccac atcaccccag ggacagcata tcagagcttt gaacaggtag tgaatgaact    7920
cttccgggat ggggtaaact ggggtcgcat tgtggccttt ttctccttcg gcggggcact    7980
gtgcgtggaa agcgtagaca aggagatgca ggtattggtg agtcggatcg cagcttggat    8040
ggccacttac ctgaatgacc acctagagcc ttggatccag gagaacggcg gctgggatac    8100
ttttgtggaa ctctatggga caatgcagc agccgagagc cgaaagggcc aggaacgctt    8160
caaccgctgg ttcctgacgg gcatgactgt ggccggcatg gttctactgg gctcactctt    8220
cagtcggaaa tgaagatccg agctcggtac caagcttaag tttgggtaat taattgaatt    8280
acatccctac gcaaacgttt tacggccgcc ggtggcgccc gcgcccggcg gccgtccttt    8340
ggccgttgca ggccactccg gtggctcccg tcgtccccga cttccaggcc cagcagatgc    8400
agcaactcat cagcgccgta atgcgctga caatgagaca gaacgcaatt gctcctgcta    8460
ggcctcccaa accaaagaag aagaagacaa ccaaaccaaa gccgaaaacg cagcccaaga    8520
agatcaacgg aaaaacgcag cagcaaaaga agaaagacaa gcaagccgac aagaagaaga    8580
agaaacccgg aaaaagagaa agaatgtgca tgaagattga aaatgactgt atcttcgtat    8640
gcggctagcc acagtaacgt agtgtttcca gacatgtcgg gcaccgcact atcatgggtg    8700
cagaaaatct cggtggtct ggggccttc gcaatcggcg ctatcctggt gctggttgtg    8760
gtcacttgca ttgggctccg cagataagtt agggtaggca atggcattga tatagcaaga    8820
aaattgaaaa cagaaaaagt tagggtaagc aatggcatat aaccataact gtataacttg    8880
taacaaagcg caacaagacc tgcgcaattg gccccgtggt ccgcctcacg gaaactcggg    8940
gcaactcata ttgacacatt aattggcaat aattggaagc ttacataagc ttaattcgac    9000
gaataattgg attttatttt tattttgcaa ttggttttta atatttccaa aaaaaaaaa    9060
aaaaaaaaa aaaaaaaaa aaaaaaaaa aaaaaaaaa aaaaaaaaa aaaaaaact    9120
agtgatcata atcagccata ccacatttgt agaggtttta cttgctttaa aaaacctccc    9180
acacctcccc ctgaacctga aacataaaat gaatgcaatt gttgttgtta acttgtttat    9240
tgcagcttat aatggttaca aataaagcaa tagcatcaca aatttcacaa ataaagcatt    9300
tttttcactg cattctagtt gtggtttgtc caaactcatc aatgtatctt atcatgtctg    9360
gatctagtct gcattaatga atcggccaac gcgcggggag aggcggtttg cgtattgggc    9420
gctcttccgc ttcctcgctc actgactcgc tgcgctcggt cgttcggctg cggcgagcgg    9480
tatcagctca ctcaaaggcg gtaatacggt tatccacaga atcaggggat aacgcaggaa    9540
agaacatgtg agcaaaaggc cagcaaaagg ccaggaaccg taaaaaggcc gcgttgctgg    9600
cgttttttcca taggctccgc cccctgacg agcatcacaa aaatcgacgc tcaagtcaga    9660
```

```
ggtggcgaaa cccgacagga ctataaagat accaggcgtt tcccctggga agctccctcg    9720
tgcgctctcc tgttccgacc ctgccgctta ccggatacct gtccgccttt ctcccttcgg    9780
gaagcgtggc gctttctcaa tgctcgcgct gtaggtatct cagttcggtg taggtcgttc    9840
gctccaagct gggctgtgtg cacgaacccc cgttcagcc cgaccgctgc gccttatccg     9900
gtaactatcg tcttgagtcc aacccggtaa gacacgactt atcgccactg gcagcagcca    9960
ctggtaacag gattagcaga gcgaggtatg taggcggtgc tacagagttc ttgaagtggt   10020
ggcctaacta cggctacact agaaggacag tatttggtat ctgcgctctg ctgaagccag   10080
ttaccttcgg aaaaagagtt ggtagctctt gatccggcaa acaaaccacc gctggtagcg   10140
gtggtttttt tgtttgcaag cagcagatta cgcgcagaaa aaaggatctc aagaagatc    10200
ctttgatctt ttctacgggg cattctgacg ctcagtggaa cgaaaactca cgttaaggga   10260
ttttggtcat gagattatca aaaggatctt cacctagat ccttttaaat taaaaatgaa    10320
gttttaaatc aatctaaagt atatatgagt aaacttggtc tgacagttac caatgcttaa   10380
tcagtgaggc acctatctca gcgatctgtc tatttcgttc atccatagtt gcctgactcc   10440
ccgtcgtgta gataactacg atacgggagg gcttaccatc tggccccagt gctgcaatga   10500
taccgcgaga cccacgctca ccggctccag atttatcagc aataaaccag ccagccggaa   10560
gggccgagcg cagaagtggt cctgcaactt tatccgcctc catccagtct attaattgtt   10620
gccgggaagc tagagtaagt agttcgccag ttaatagttt gcgcaacgtt gttgccattg   10680
ctacaggcat cgtggtgtca cgctcgtcgt ttggtatggc ttcattcagc tccggttccc   10740
aacgatcaag gcgagttaca tgatccccca tgttgtgcaa aaaagcggtt agctccttcg   10800
gtcctccgat cgttgtcaga agtaagttgg ccgcagtgtt atcactcatg gttatggcag   10860
cactgcataa ttctcttact gtcatgccat ccgtaagatg ctttctgtg actggtgagt    10920
actcaaccaa gtcattctga gaatagtgta tgcggcgacc gagttgctct tgcccggcgt   10980
caatacggga taataccgcg ccacatagca gaactttaaa agtgctcatc attggaaaac   11040
gttcttcggg gcgaaaactc tcaaggatct taccgctgtt gagatccagt tcgatgtaac   11100
ccactcgtgc acccaactga tcttcagcat cttttacttt caccagcgtt tctgggtgag   11160
caaaaacagg aaggcaaaat gccgcaaaaa agggaataag ggcgacacgg aaatgttgaa   11220
tactcatact cttccttttt caatattatt gaagcattta tcagggttat tgtctcatga   11280
gcggatacat atttgaatgt atttagaaaa ataaacaaat aggggttccg cgcacatttc   11340
cccgaaaagt gccacctgac gtctaagaaa ccattattat catgacatta acctataaaa   11400
ataggcgtat cacgaggccc tttcgtctcg cgcgtttcgg tgatgacggt gaaaacctct   11460
gacacatgca gctcccggag acggtcacag cttctgtcta gcggatgcc gggagcagac    11520
aagcccgtca gggcgcgtca gcgggtgttg gcgggtgtcg ggctggctt aactatgcgg    11580
catcagagca gattgtactg agagtgcacc atatcgacgc tctcccttat gcgactcctg   11640
cattaggaag cagcccagta ctaggttgag gccgttgagc accgccgccg caaggaatgg   11700
tgcatgcgta atcaattacg ggtcattag ttcatagccc atatatggag ttccgcgtta    11760
cataacttac ggtaaatggc ccgcctggct gaccgcccaa cgacccccgc ccattgacgt   11820
caataatgac gtatgttccc atagtaacgc caatagggac tttccattga cgtcaatggg   11880
tggagtattt acggtaaact gcccacttgg cagtacatca agtgtatcat atgccaagta   11940
cgccccctat tgacgtcaat gacggtaaat ggcccgcctg gcattatgcc cagtacatga   12000
```

-continued

| | | |
|---|---|---|
| ccttatggga ctttcctact tggcagtaca tctacgtatt agtcatcgct attaccatgg | 12060 | |
| tgatgcggtt ttggcagtac atcaatgggc gtggatagcg gtttgactca cggggatttc | 12120 | |
| caagtctcca ccccattgac gtcaatggga gtttgttttg gcaccaaaat caacgggact | 12180 | |
| ttccaaaatg tcgtaacaac tccgccccat tgacgcaaat gggcggtagg cgtgtacggt | 12240 | |
| gggaggtcta tataagcaga gctctctggc taactagaga acccactgct taactggctt | 12300 | |
| atcgaaatta atacgactca ctatagggag accggaagct tgaattc | 12347 | |

<210> SEQ ID NO 66
<211> LENGTH: 12612
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

| | | |
|---|---|---|
| atggcggatg tgtgacatac acgacgccaa aagattttgt tccagctcct gccacctccg | 60 | |
| ctacgcgaga gattaaccac ccacgatggc cgccaaagtg catgttgata ttgaggctga | 120 | |
| cagcccattc atcaagtctt tgcagaaggc atttccgtcg ttcgaggtgg agtcattgca | 180 | |
| ggtcacacca aatgaccatg caaatgccag agcattttcg cacctggcta ccaaattgat | 240 | |
| cgagcaggag actgacaaag acacactcat cttggatatc ggcagtgcgc cttccaggag | 300 | |
| aatgatgtct acgcacaaat accactgcgt atgcccctatg cgcagcgcag aagaccccga | 360 | |
| aaggctcgat agctacgcaa agaaactggc agcggcctcc gggaaggtgc tggatagaga | 420 | |
| gatcgcagga aaaatcaccg acctgcagac cgtcatggct acgccagacg ctgaatctcc | 480 | |
| tacctttgc ctgcatacag acgtcacgtg tcgtacggca gccgaagtgg ccgtatacca | 540 | |
| ggacgtgtat gctgtacatg caccaacatc gctgtaccat caggcgatga aggtgtcag | 600 | |
| aacggcgtat tggattgggt ttgacaccac cccgtttatg tttgacgcgc tagcaggcgc | 660 | |
| gtatccaacc tacgccacaa actgggccga cgagcaggtg ttacaggcca ggaacatagg | 720 | |
| actgtgtgca gcatccttga ctgagggaag actcggcaaa ctgtccattc tccgcaagaa | 780 | |
| gcaattgaaa ccttgcgaca cagtcatgtt ctcggtagga tctacattgt acactgagag | 840 | |
| cagaaagcta ctgaggagct ggcacttacc ctccgtattc cacctgaaag gtaaacaatc | 900 | |
| ctttacctgt aggtgcgata ccatcgtatc atgtgaaggg tacgtagtta agaaaatcac | 960 | |
| tatgtgcccc ggcctgtacg gtaaaacggt agggtacgcc gtgacgtatc acgcggaggg | 1020 | |
| attcctagtg tgcaagacca cagacactgt caaaggagaa agagtctcat tccctgtatg | 1080 | |
| cacctacgtc ccctcaacca tctgtgatca aatgactggc atactagcga ccgacgtcac | 1140 | |
| accgaggac gcacagaagt tgttagtggg attgaatcag aggatagttg tgaacggaag | 1200 | |
| aacacagcga aacactaaca cgatgaagaa ctatctgctt ccgattgtgg ccgtcgcatt | 1260 | |
| tagcaagtgg gcgagggaat acaaggcaga ccttgatgat gaaaaacctc tgggtgtccg | 1320 | |
| agagaggtca cttacttgct gctgcttgtg ggcatttaaa acgaggaaga tgcacaccat | 1380 | |
| gtacaagaaa ccagacaccc agacaatagt gaaggtgcct tcagagttta actcgttcgt | 1440 | |
| catcccgagc ctatggtcta caggcctcgc aatcccagtc agatcacgca ttaagatgct | 1500 | |
| tttggccaag aagaccaagc gagagttaat acctgttctc gacgcgtcgt cagccaggga | 1560 | |
| tgctgaacaa gaggagaagg agaggttgga ggccgagctg actagagaag ccttaccacc | 1620 | |
| cctcgtcccc atcgcgccgg cggagacggg agtcgtcgac gtcgacgttg aagaactaga | 1680 | |

```
gtatcacgca ggtgcagggg tcgtggaaac acctcgcagc gcgttgaaag tcaccgcaca    1740
gccgaacgac gtactactag gaaattacgt agttctgtcc ccgcagaccg tgctcaagag    1800
ctccaagttg gcccccgtgc accctctagc agagcaggtg aaaataataa cacataacgg    1860
gagggccggc ggttaccagg tcgacggata tgacggcagg gtcctactac catgtggatc    1920
ggccattccg gtccctgagt ttcaagcttt gagcgagagc gccactatgg tgtacaacga    1980
aagggagttc gtcaacagga aactatacca tattgccgtt cacggaccgt cgctgaacac    2040
cgacgaggag aactacgaga agtcagagc tgaaagaact gacgccgagt acgtgttcga    2100
cgtagataaa aaatgctgcg tcaagagaga ggaagcgtcg ggtttggtgt tggtgggaga    2160
gctaaccaac cccccgttcc atgaattcgc ctacgaaggg ctgaagatca ggccgtcggc    2220
accatataag actacagtag taggagtctt tggggttccg ggatcaggca agtctgctat    2280
tattaagagc ctcgtgacca aacacgatct ggtcaccagc ggcaagaagg agaactgcca    2340
ggaaatagtt aacgacgtga agaagcaccg cgggaagggg acaagtaggg aaaacagtga    2400
ctccatcctg ctaaacgggt gtcgtcgtgc cgtggacatc ctatatgtgg acgaggcttt    2460
cgctagccat tccggtactc tgctggccct aattgctctt gttaaacctc ggagcaaagt    2520
ggtgttatgc ggagacccca agcaatgcgg attcttcaat atgatgcagc ttaaggtgaa    2580
cttcaaccac aacatctgca ctgaagtatg tcataaaagt atatccagac gttgcacgcg    2640
tccagtcacg gccatcgtgt ctacgttgca ctacggaggc aagatgcgca cgaccaaccc    2700
gtgcaacaaa cccataatca tagacaccac aggacagacc aagcccaagc caggagacat    2760
cgtgttaaca tgcttccgag gctgggcaaa gcagctgcag ttggactacc gtggacacga    2820
agtcatgaca gcagcagcat ctcagggcct cacccgcaaa ggggtatacg ccgtaaggca    2880
gaaggtgaat gaaaatccct tgtatgcccc tgcgtcggag cacgtgaatg tactgctgac    2940
gcgcactgag gataggctgg tgtggaaaac gctggccggc gatccctgga ttaaggtcct    3000
atcaaacatt ccacagggta actttacggc cacattggaa gaatggcaag aagaacacga    3060
caaaataatg aaggtgattg aaggaccggc tgcgcctgtg gacgcgttcc agaacaaagc    3120
gaacgtgtgt tgggcgaaaa gcctggtgcc tgtcctggac actgccggaa tcagattgac    3180
agcagaggag tggagcacca taattacagc atttaaggag gacagagctt actctccagt    3240
ggtggccttg aatgaaattt gcaccaagta ctatggagtt gacctggaca gtggcctgtt    3300
ttctgccccg aaggtgtccc tgtattacga gaacaaccac tgggataaca gacctggtgg    3360
aaggatgtat ggattcaatg ccgcaacagc tgccaggctg gaagctagac ataccttcct    3420
gaaggggcag tggcatacgg gcaagcaggc agttatcgca gaaagaaaaa tccaaccgct    3480
ttctgtgctg gacaatgtaa ttcctatcaa ccgcaggctg ccgcacgccc tggtggctga    3540
gtacaagacg gttaaaggca gtagggttga gtggctggtc aataaagtaa gagggtacca    3600
cgtcctgctg gtgagtgagt acaacctggc tttgcctcga cgcagggtca cttggttgtc    3660
accgctgaat gtcacaggcg ccgataggtg ctacgaccta agtttaggac tgccggctga    3720
cgccggcagg ttcgacttgg tctttgtgaa cattcacacg gaattcagaa tccaccacta    3780
ccagcagtgt gtcgaccacg ccatgaagct gcagatgctt ggggagatg cgctacgact    3840
gctaaaaccc ggcggcatct tgatgagagc ttacggatac gccgataaaa tcagcgaagc    3900
cgttgtttcc tccttaagca gaaagttctc gtctgcaaga gtgttgcgcc cggattgtgt    3960
caccagcaat acagaagtgt tcttgctgtt ctccaacttt gacaacggaa agagaccctc    4020
tacgctacac cagatgaata ccaagctgag tgccgtgtat gccggagaag ccatgcacac    4080
```

```
ggccgggtgt gcaccatcct acagagttaa gagagcagac atagccacgt gcacagaagc   4140
ggctgtggtt aacgcagcta acgcccgtgg aactgtaggg gatggcgtat gcagggccgt   4200
ggcgaagaaa tggccgtcag cctttaaggg agcagcaaca ccagtgggca caattaaaac   4260
agtcatgtgc ggctcgtacc ccgtcatcca cgctgtagcg cctaatttct ctgccacgac   4320
tgaagcggaa ggggaccgcg aattggccgc tgtctaccgg gcagtggccg ccgaagtaaa   4380
cagactgtca ctgagcagcg tagccatccc gctgctgtcc acaggagtgt tcagcggcgg   4440
aagagatagg ctgcagcaat ccctcaacca tctattcaca gcaatggacg ccacggacgc   4500
tgacgtgacc atctactgca gagacaaaag ttgggagaag aaaatccagg aagccattga   4560
catgaggacg gctgtggagt tgctcaatga tgacgtggag ctgaccacag acttggtgag   4620
agtgcacccg gacagcagcc tggtgggtcg taagggctac agtaccactg acgggtcgct   4680
gtactcgtac tttgaaggta cgaaattcaa ccaggctgct attgatatgg cagagatact   4740
gacgttgtgg cccagactgc aagaggcaaa cgaacagata tgcctatacg cgctgggcga   4800
aacaatggac aacatcagat ccaaatgtcc ggtgaacgat tccgattcat caacacctcc   4860
caggacagtg ccctgcctgt gccgctacgc aatgacagca gaacggatcg cccgccttag   4920
gtcacaccaa gttaaaagca tggtggtttg ctcatctttt cccctcccga ataccatgt    4980
agatggggtg cagaaggtaa agtgcgagaa ggttctcctg ttcgacccga cggtaccttc   5040
agtggttagt ccgcggaagt atgccgcatc tacgacggac cactcagatc ggtcgttacg   5100
agggtttgac ttggactgga ccaccgactc gtcttccact gccagcgata ccatgtcgct   5160
acccagtttg cagtcgtgtg acatcgactc gatctacgag ccaatggctc ccatagtagt   5220
gacggctgac gtacaccctg aacccgcagg catcgcggac ctggcggcag atgtgcaccc   5280
tgaacccgca gaccatgtgg acctcgagaa cccgattcct ccaccgcgcc cgaagagagc   5340
tgcataccct gcctcccgcg cggcggagcg accggtgccg gcgccgagaa agccgacgcc   5400
tgccccaagg actgcgttta ggaacaagct gcctttgacg ttcggcgact ttgacgagca   5460
cgaggtcgat gcgttggcct ccgggattac tttcggagac ttcgacgacg tcctgcgact   5520
aggccgcgcg ggtgcatata ttttctcctc ggacactggc agcggacatt tacaacaaaa   5580
atccgttagg cagcacaatc tccagtgcgc acaactggat gcggtccagg aggagaaaat   5640
gtacccgcca aaattggata ctgagaggga gaagctgttg ctgctgaaaa tgcagatgca   5700
cccatcggag gctaataaga gtcgatacca gtctcgcaaa gtggagaaca tgaaagccac   5760
ggtggtggac aggctcacat cggggggccag attgtacacg ggagcggacg taggccgcat   5820
accaacatac gcggttcggt acccccgccc cgtgtactcc cctaccgtga tcgaaagatt   5880
ctcaagcccc gatgtagcaa tcgcagcgtg caacgaatac ctatccagaa attacccaac   5940
agtggcgtcg taccagataa cagatgaata cgacgcatac ttggacatgg ttgacgggtc   6000
ggatagttgc ttgacagag cgacattctg cccggcgaag ctccggtgct acccgaaaca   6060
tcatgcgtac caccagccga ctgtacgcag tgccgtcccg tcacccttc agaacacact    6120
acagaacgtg ctagcggccg ccaccaagag aaactgcaac gtcacgcaaa tgcgagaact   6180
acccaccatg gactcggcag tgttcaacgt ggagtgcttc aagcgctatg cctgctccgg   6240
agaatattgg gaagaatatg ctaaacaacc tatccggata accactgaga acatcactac   6300
ctatgtgacc aaaattgaaag gcccgaaagc tgctgccttg ttcgctaaga cccacaactt   6360
ggttccgctg caggaggttc ccatggacag attcacggtc gacatgaaac gagatgtcaa   6420
```

```
agtcactcca gggacgaaac acacagagga aagacccaaa gtccaggtaa ttcaagcagc    6480
ggagccattg cgaccgcttt acctgtgcgg catccacagg gaattagtaa ggagactaaa    6540
tgctgtgtta cgccctaacg tgcacacatt gtttgatatg tcggccgaag actttgacgc    6600
gatcatcgcc tctcacttcc acccaggaga cccggttcta gagacggaca ttgcatcatt    6660
cgacaaaagc caggacgact ccttggctct tacaggttta atgatcctcg aagatctagg    6720
ggtggatcag tacctgctgg acttgatcga ggcagccttt ggggaaatat ccagctgtca    6780
cctaccaact ggcacgcgct tcaagttcgg agctatgatg aaatcgggca tgtttctgac    6840
tttgtttatt aacactgttt tgaacatcac catagcaagc agggtactgg agcagagact    6900
cactgactcc gcctgtgcgg ccttcatcgg cgacgacaac atcgttcacg gagtgatctc    6960
cgacaagctg atggcggaga ggtgcgcgtc gtgggtcaac atggaggtga agatcattga    7020
cgctgtcatg ggcgaaaaac ccccatattt ttgtggggga ttcatagttt ttgacagcgt    7080
cacacagacc gcctgccgtg tttcagaccc acttaagcgc ctgttcaagt tgggtaagcc    7140
gctaacagct gaagacaagc aggacgaaga caggcgacga gcactgagtg acgaggttag    7200
caagtggttc cggacaggct tgggggccga actggaggtg gcactaacat ctaggtatga    7260
ggtagagggc tgcaaaagta tcctcatagc catggccacc ttggcgaggg acattaaggc    7320
gtttaagaaa ttgagaggac ctgttataca cctctacggc ggtcctagat tggtgcgtta    7380
atacacagaa ttctgattgg atcccaaacg ggccctctag actcgagcgg ccgccactgt    7440
gctggatatc tgcagaattc atgcatggag atacacctac attgcatgaa tatatgttag    7500
atttgcaacc agagacaact gatctctact gttatgagca attaaatgac agctcagagg    7560
aggaggatga aatagatggt ccagctggac aagcagaacc ggacagagcc cattacaata    7620 ttgtaaccit ttgttgcaag tgtgactcta cgcttcggtt gtgcgtacaa agcacacacg    7680
tagacattcg tactttggaa gacctgttaa tgggcacact aggaattgtg tgccccatct    7740
gttctcagaa accaggatct atggcgtacc catacgatgt tccagattac gctagcttga    7800
gatctaccat gtctcagagc aaccgggagc tggtggttga cttttctctcc tacaagcttt    7860 cccagaaagg atacactggg agtcagttta gtgatgtgga agagaacagg actgaggccc    7920
cagaagggac tgaatcggag atggagaccc ccagtgccat caatggcaac ccatcctggc    7980
acctggcaga cagccccgcg gtgaatggag ccactgcgca cagcagcagt ttggatgccc    8040
gggaggtgat ccccatggca gcagtaaagc aagcgctgag ggaggcaggc gacgagtttg    8100
aactgcggta ccggcgggca ttcagtgacc tgacatccca gctccacatc accccaggga    8160
cagcatatca gagctttgaa caggtagtga atgaactctt ccgggatggg gtaaactggg    8220
gtcgcattgt ggccttttc tccttcggcg gggcactgtg cgtggaaagc gtagacaagg    8280
agatgcaggt attggtgagt cggatcgcag cttggatggc cacttacctg aatgaccacc    8340
tagagccttg gatccaggag aacggcggct gggatacttt tgtggaactc tatgggaaca    8400
atgcagcagc cgagagccga aagggccagg aacgcttcaa ccgctggttc ctgacgggca    8460
tgactgtggc cggcgtggtt ctgctgggct cactcttcag tcggaaatga agatccaagc    8520
ttaagtttgg gtaattaatt gaattacatc cctacgcaaa cgttttacgg ccgccggtgg    8580
cgcccgcgcc cggcggcccg tccttggccg ttgcaggcca ctccggtggc tcccgtcgtc    8640
cccgacttcc aggcccagca gatgcagcaa ctcatcagcg ccgtaaatgc gctgacaatg    8700
agacagaacg caattgctcc tgctaggcct cccaaaccaa agaagaagaa gacaaccaaa    8760
ccaaagccga aaacgcagcc caagaagatc aacgaaaaaa cgcagcagca aagaagaaaa    8820
```

```
gacaagcaag ccgacaagaa gaagaagaaa cccggaaaaa gagaaagaat gtgcatgaag    8880
attgaaaatg actgtatctt cgtatgcggc tagccacagt aacgtagtgt ttccagacat    8940
gtcgggcacc gcactatcat gggtgcagaa atctcgggt ggtctggggg ccttcgcaat     9000
cggcgctatc ctggtgctgg ttgtggtcac ttgcattggg ctccgcagat aagttagggt    9060
aggcaatggc attgatatag caagaaaatt gaaacagaa aaagttaggg taagcaatgg     9120
catataacca taactgtata acttgtaaca aagcgcaaca agacctgcgc aattggcccc    9180
gtggtccgcc tcacggaaac tcggggcaac tcatattgac acattaattg gcaataattg    9240
gaagcttaca taagcttaat tcgacgaata attggatttt tattttattt tgcaattggt    9300
ttttaatatt tccaaaaaaa aaaaaaaaa aaaaaaaaa aaaaaaaaa aaaaaaaaa        9360 aaaaaaaaa aaaaaaaaa aaactagtga tcataatcag ccataccaca tttgtagagg     9420
ttttacttgc tttaaaaaac ctcccacacc tccccctgaa cctgaaacat aaaatgaatg    9480
caattgttgt tgttaacttg tttattgcag cttataatgg ttacaaataa agcaatagca    9540
tcacaaattt cacaaataaa gcatttttt cactgcattc tagttgtggt ttgtccaaac    9600
tcatcaatgt atcttatcat gtctggatct agtctgcatt aatgaatcgg ccaacgcgcg    9660
gggagaggcg gtttgcgtat tgggcgctct tccgcttcct cgctcactga ctcgctgcgc    9720
tcggtcgttc ggctgcggcg agcggtatca gctcactcaa aggcggtaat acggttatcc    9780
acagaatcag gggataacgc aggaaagaac atgtgagcaa aaggccagca aaaggccagg    9840
aaccgtaaaa aggccgcgtt gctggcgttt ttccataggc tccgcccccc tgacgagcat    9900
cacaaaaatc gacgctcaag tcagaggtgg cgaaacccga caggactata agataccag    9960 gcgtttcccc ctggaagctc cctcgtgcgc tctcctgttc cgaccctgcc gcttaccgga   10020
tacctgtccg cctttctccc ttcgggaagc gtggcgcttt ctcaatgctc gcgctgtagg   10080
tatctcagtt cggtgtaggt cgttcgctcc aagctgggct gtgtgcacga accccccgtt   10140
cagcccgacc gctgcgcctt atccggtaac tatcgtcttg agtccaaccc ggtaagacac   10200
gacttatcgc cactggcagc agccactggt aacaggatta gcagagcgag gtatgtaggc   10260
ggtgctacag agttcttgaa gtggtggcct aactacggct acactagaag gacagtattt   10320
ggtatctgcg ctctgctgaa gccagttacc ttcggaaaaa gagttggtag ctcttgatcc   10380
ggcaaacaaa ccaccgctgg tagcggtggt ttttttgttt gcaagcagca gattacgcgc   10440
agaaaaaaag gatctcaaga agatcctttg atcttttcta cggggcattc tgacgctcag   10500
tggaacgaaa actcacgtta agggattttg gtcatgagat tatcaaaaag gatcttcacc   10560
tagatccttt taaattaaaa atgaagtttt aaatcaatct aaagtatata tgagtaaact   10620
tggtctgaca gttaccaatg cttaatcagt gaggcaccta tctcagcgat ctgtctattt   10680
cgttcatcca tagttgcctg actccccgtc gtgtagataa ctacgatacg ggagggctta   10740
ccatctggcc ccagtgctgc aatgatacc gagacccac gctcaccggc tccagattta   10800
tcagcaataa accagccagc cggaagggcc gagcgcagaa gtggtcctgc aactttatcc   10860
gcctccatcc agtctattaa ttgttgccgg gaagctagag taagtagttc gccagttaat   10920
agtttgcgca acgttgttgc cattgctaca ggcatcgtgg tgtcacgctc gtcgtttggt   10980
atggcttcat tcagctccgg ttcccaacga tcaaggcgag ttacatgatc ccccatgttg   11040
tgcaaaaaag cggttagctc cttcggtcct ccgatcgttg tcagaagtaa gttggccgca   11100
gtgttatcac tcatggttat ggcagcactg cataattctc ttactgtcat gccatccgta   11160
```

```
agatgctttt ctgtgactgg tgagtactca accaagtcat tctgagaata gtgtatgcgg    11220
cgaccgagtt gctcttgccc ggcgtcaata cgggataata ccgcgccaca tagcagaact    11280
ttaaaagtgc tcatcattgg aaaacgttct tcggggcgaa aactctcaag gatcttaccg    11340
ctgttgagat ccagttcgat gtaacccact cgtgcaccca actgatcttc agcatctttt    11400
actttcacca gcgtttctgg gtgagcaaaa acaggaaggc aaaatgccgc aaaaaaggga    11460
ataagggcga cacggaaatg ttgaatactc atactcttcc ttttttcaata ttattgaagc    11520 atttatcagg gttattgtct catgagcgga tacatatttg aatgtattta gaaaaataaa    11580
caaatagggg ttccgcgcac atttccccga aaagtgccac ctgacgtcta agaaaccatt    11640
attatcatga cattaaccta taaaaatagg cgtatcacga ggccctttcg tctcgcgcgt    11700
ttcggtgatg acggtgaaaa cctctgacac atgcagctcc cggagacggt cacagcttct    11760
gtctaagcgg atgccgggag cagacaagcc cgtcagggcg cgtcagcggg tgttggcggg    11820
tgtcggggct ggcttaacta tgcggcatca gagcagattg tactgagagt gcaccatatc    11880
gacgctctcc cttatgcgac tcctgcatta ggaagcagcc cagtactagg ttgaggccgt    11940
tgagcaccgc cgccgcaagg aatggtgcat gcgtaatcaa ttacgggtc attagttcat    12000 agcccatata tggagttccg cgttacataa cttacggtaa atggcccgcc tggctgaccg    12060
cccaacgacc cccgcccatt gacgtcaata atgacgtatg ttcccatagt aacgccaata    12120
gggactttcc attgacgtca atgggtggag tatttacggt aaactgccca cttggcagta    12180
catcaagtgt atcatatgcc aagtacgccc cctattgacg tcaatgacgg taaatggccc    12240
gcctggcatt atgcccagta catgacctta tgggactttc ctacttggca gtacatctac    12300
gtattagtca tcgctattac catggtgatg cggttttggc agtacatcaa tgggcgtgga    12360
tagcggtttg actcacgggg atttccaagt ctccacccca ttgacgtcaa tgggagtttg    12420
ttttggcacc aaaatcaacg ggactttcca aaatgtcgta caactccgc cccattgacg    12480 caaatgggcg gtaggcgtgt acggtgggag gtctatataa gcagagctct ctggctaact    12540
agagaaccca ctgcttaact ggcttatcga aattaatacg actcactata gggagaccgg    12600
aagcttgaat tc                                                       12612
```

<210> SEQ ID NO 67
<211> LENGTH: 12347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
atggcggatg tgtgacatac acgacgccaa aagattttgt tccagctcct gccacctccg      60
ctacgcgaga gattaaccac ccacgatggc cgccaaagtg catgttgata ttgaggctga     120
cagcccattc atcaagtctt tgcagaaggc atttccgtcg ttcgaggtgg agtcattgca     180
ggtcacacca aatgaccatg caaatgccag agcattttcg cacctggcta ccaaattgat     240
cgagcaggag actgacaaag acacactcat cttggatatc ggcagtgcgc cttccaggag     300
aatgatgtct acgcacaaat accactgcgt atgcccctatg cgcagcgcag aagacccga     360 aaggctcgat agctacgcaa agaaactggc agcggcctcc gggaaggtgc tggatagaga     420
gatcgcagga aaaatcaccg acctgcagac cgtcatggct acgccagacg ctgaatctcc     480
taccttttgc ctgcatacag acgtcacgtg tcgtacggca gccgaagtgg ccgtatacca     540
```

-continued

```
ggacgtgtat gctgtacatg caccaacatc gctgtaccat caggcgatga aaggtgtcag    600
aacggcgtat tggattgggt ttgacaccac cccgtttatg tttgacgcgc tagcaggcgc    660
gtatccaacc tacgccacaa actgggccga cgagcaggtg ttacaggcca ggaacatagg    720
actgtgtgca gcatccttga ctgagggaag actcggcaaa ctgtccattc tccgcaagaa    780
gcaattgaaa ccttgcgaca cagtcatgtt ctcggtagga tctacattgt acactgagag    840
cagaaagcta ctgaggagct ggcacttacc ctccgtattc cacctgaaag gtaaacaatc    900
ctttacctgt aggtgcgata ccatcgtatc atgtgaaggg tacgtagtta agaaaatcac    960
tatgtgcccc ggcctgtacg gtaaaacggt agggtacgcc gtgacgtatc acgcggaggg   1020
attcctagtg tgcaagacca cagacactgt caaaggagaa agagtctcat tccctgtatg   1080
cacctacgtc ccctcaacca tctgtgatca aatgactggc atactagcga ccgacgtcac   1140
accggaggac gcacagaagt tgttagtggg attgaatcag aggatagttg tgaacggaag   1200
aacacacgcg aacactaaca cgatgaagaa ctatctgctt ccgattgtgg ccgtcgcatt   1260
tagcaagtgg gcgagggaat acaaggcaga ccttgatgat gaaaaacctc tgggtgtccg   1320
agagaggtca cttacttgct gctgcttgtg ggcatttaaa acgaggaaga tgcacaccat   1380
gtacaagaaa ccagacaccc agacaatagt gaaggtgcct tcagagttta actcgttcgt   1440
catcccgagc ctatggtcta caggcctcgc aatcccagtc agatcacgca ttaagatgct   1500
tttggccaag aagaccaagc gagagttaat acctgttctc gacgcgtcgt cagccaggga   1560
tgctgaacaa gaggagaagg agaggttgga ggccgagctg actagagaag ccttaccacc   1620
cctcgtcccc atcgcgccgg cggagacggg agtcgtcgac gtcgacgttg aagaactaga   1680
gtatcacgca ggtgcagggg tcgtggaaac acctcgcagc gcgttgaaag tcaccgcaca   1740
gccgaacgac gtactactag gaaattacgt agttctgtcc ccgcagaccg tgctcaagag   1800
ctccaagttg gcccccgtgc accctctagc agagcaggtg aaaataataa cacataacgg   1860
gagggccggc ggttaccagg tcgacggata tgacggcagg gtcctactac catgtggatc   1920
ggccattccg gtccctgagt ttcaagcttt gagcgagagc gccactatgg tgtacaacga   1980
aagggagttc gtcaacagga aactatacca tattgccgtt cacggaccgt cgctgaacac   2040
cgacgaggag aactacgaga agtcagagc tgaaagaact gacgccgagt acgtgttcga   2100
cgtagataaa aaatgctgcg tcaagagaga ggaagcgtcg ggtttggtgt tggtgggaga   2160
gctaaccaac ccccgttcc atgaattcgc ctacgaaggg ctgaagatca ggccgtcggc   2220
accatataag actacagtag taggagtctt tggggttccg ggatcaggca agtctgctat   2280
tattaagagc ctcgtgacca aacacgatct ggtcaccagc ggcaagaagg agaactgcca   2340
ggaaatagtt aacgacgtga agaagcaccg cgggaagggg acaagtaggg aaaacagtga   2400
ctccatcctg ctaaacgggt gtcgtcgtgc cgtggacatc ctatatgtgg acgaggcttt   2460
cgctagccat tccggtactc tgctggccct aattgctctt gttaaacctc ggagcaaagt   2520
ggtgttatgc ggagacccca gcaatgcgg attcttcaat atgatgcagc ttaaggtgaa   2580
cttcaaccac aacatctgca ctgaagtatg tcataaaagt atatccagac gttgcacgcg   2640
tccagtcacg gccatcgtgt ctacgttgca ctacggaggc aagatgcgca cgaccaaccc   2700
gtgcaacaaa cccataatca tagacaccac aggacagacc aagcccaagc caggagacat   2760
cgtgttaaca tgcttccgag gctgggcaaa gcagctgcag ttggactacc gtggacacga   2820
agtcatgaca gcagcagcat ctcagggcct caccgcaaa gggtatacg ccgtaaggca   2880 gaaggtgaat gaaaatccct tgtatgcccc tgcgtcggag cacgtgaatg tactgctgac   2940
```

```
gcgcactgag gataggctgg tgtggaaaac gctggccggc gatccctgga ttaaggtcct    3000
atcaaacatt ccacagggta actttacggc cacattggaa gaatggcaag aagaacacga    3060
caaaataatg aaggtgattg aaggaccggc tgcgcctgtg gacgcgttcc agaacaaagc    3120
gaacgtgtgt tgggcgaaaa gcctggtgcc tgtcctggac actgccggaa tcagattgac    3180
agcagaggag tggagcacca taattacagc atttaaggag gacagagctt actctccagt    3240
ggtggccttg aatgaaattt gcaccaagta ctatggagtt gacctggaca gtggcctgtt    3300
ttctgccccg aaggtgtccc tgtattacga gaacaaccac tgggataaca gacctggtgg    3360
aaggatgtat ggattcaatg ccgcaacagc tgccaggctg gaagctagac ataccttcct    3420 gaagggcag tggcatacgg gcaagcaggc agttatcgca gaaagaaaaa tccaaccgct    3480
ttctgtgctg gacaatgtaa ttcctatcaa ccgcaggctg ccgcacgccc tggtggctga    3540
gtacaagacg gttaaaggca gtagggttga gtggctggtc aataaagtaa gagggtacca    3600
cgtcctgctg gtgagtgagt acaacctggc tttgcctcga cgcagggtca cttggttgtc    3660
accgctgaat gtcacaggcg ccgataggtg ctacgaccta agtttaggac tgccggctga    3720
cgccggcagg ttcgacttgg tctttgtgaa cattcacacg gaattcagaa tccaccacta    3780
ccagcagtgt gtcgaccacg ccatgaagct gcagatgctt gggggagatg cgctacgact    3840
gctaaaaccc ggcggcatct tgatgagagc ttacggatac gccgataaaa tcagcgaagc    3900
cgttgtttcc tccttaagca gaaagttctc gtctgcaaga gtgttgcgcc cggattgtgt    3960
caccagcaat acagaagtgt tcttgctgtt ctccaacttt gacaacggaa agagaccctc    4020
tacgctacac cagatgaata ccaagctgag tgccgtgtat gccggagaag ccatgcacac    4080
ggccgggtgt gcaccatcct acagagttaa gagagcagac atagccacgt gcacagaagc    4140
ggctgtggtt aacgcagcta cgcccgtgg aactgtaggg gatggcgtat gcagggccgt    4200
ggcgaagaaa tggccgtcag cctttaaggg agcagcaaca ccagtgggca caattaaaac    4260
agtcatgtgc ggctcgtacc ccgtcatcca cgctgtagcg cctaatttct ctgccacgac    4320
tgaagcggaa ggggaccgcg aattggccgc tgtctaccgg gcagtggccg ccgaagtaaa    4380
cagactgtca ctgagcagcg tagccatccc gctgctgtcc acaggagtgt tcagcggcgg    4440
aagagatagg ctgcagcaat ccctcaacca tctattcaca gcaatggacg ccacggacgc    4500
tgacgtgacc atctactgca gagacaaaag ttgggagaag aaaatccagg aagccattga    4560
catgaggacg gctgtggagt tgctcaatga tgacgtggag ctgaccacag acttggtgag    4620
agtgcacccg gacagcagcc tggtgggtcg taagggctac agtaccactg acgggtcgct    4680
gtactcgtac tttgaaggta cgaaattcaa ccaggctgct attgatatgg cagagatact    4740
gacgttgtgg cccagactgc aagaggcaaa cgaacagata tgcctatacg cgctgggcga    4800
aacaatggac aacatcagat ccaaatgtcc ggtgaacgat tccgattcat caacacctcc    4860
caggacagtg ccctgcctgt gccgctacgc aatgacagca gaacggatcg cccgccttag    4920
gtcacaccaa gttaaaagca tggtggtttg ctcatctttt ccctcccga aataccatgt    4980 agatggggtg cagaaggtaa agtgcgagaa ggttctcctg ttcgacccga cggtaccttc    5040
agtggttagt ccgcggaagt atgccgcatc tacgacggca cactcagatc ggtcgttacg    5100
agggtttgac ttggactgga ccaccgactc gtcttccact gccagcgata ccatgtcgct    5160
acccagtttg cagtcgtgtg acatcgactc gatctacgag ccaatggctc ccatagtagt    5220
gacggctgac gtacaccctg aacccgcagg catcgcggac ctggcggcag atgtgcaccc    5280
```

```
tgaacccgca gaccatgtgg acctcgagaa cccgattcct ccaccgcgcc cgaagagagc    5340
tgcataccct gcctcccgcg cggcggagcg accggtgccg gcgccgagaa agccgacgcc    5400
tgccccaagg actgcgttta ggaacaagct gcctttgacg ttcggcgact ttgacgagca    5460
cgaggtcgat gcgttggcct ccgggattac tttcggagac ttcgacgacg tcctgcgact    5520
aggccgcgcg ggtgcatata ttttctcctc ggacactggc agcggacatt tacaacaaaa    5580
atccgttagg cagcacaatc tccagtgcgc acaactggat gcggtccagg aggagaaaat    5640
gtacccgcca aaattggata ctgagaggga gaagctgttg ctgctgaaaa tgcagatgca    5700
cccatcggag gctaataaga gtcgatacca gtctcgcaaa gtggagaaca tgaaagccac    5760
ggtggtggac aggctcacat cgggggccag attgtacacg ggagcggacg taggccgcat    5820
accaacatac gcggttcggt accccgcccc cgtgtactcc cctaccgtga tcgaaagatt    5880
ctcaagcccc gatgtagcaa tcgcagcgtg caacgaatac ctatccagaa attacccaac    5940
agtggcgtcg taccagataa cagatgaata cgacgcatac ttggacatgg ttgacgggtc    6000
ggatagttgc ttggacagag cgacattctg cccggcgaag ctccggtgct acccgaaaca    6060
tcatgcgtac caccagccga ctgtacgcag tgccgtcccg tcaccctttc agaacacact    6120
acagaacgtg ctagcggccg ccaccaagag aaactgcaac gtcacgcaaa tgcgagaact    6180
acccaccatg gactcggcag tgttcaacgt ggagtgcttc aagcgctatg cctgctccgg    6240
agaatattgg gaagaatatg ctaaacaacc tatccggata accactgaga acatcactac    6300
ctatgtgacc aaattgaaag gcccgaaagc tgctgccttg ttcgctaaga cccacaactt    6360
ggttccgctg caggaggttc ccatggacag attcaccgtc gacatgaaac gagatgtcaa    6420
agtcactcca gggacgaaac acacagagga agacccaaa gtccaggtaa ttcaagcagc    6480
ggagccattg gcgaccgctt acctgtgcgg catccacagg gaattagtaa ggagactaaa    6540
tgctgtgtta cgccctaacg tgcacacatt gtttgatatg tcggccgaag actttgacgc    6600
gatcatcgcc tctcacttcc acccaggaga cccggttcta gagacggaca ttgcatcatt    6660
cgacaaaagc caggacgact ccttggctct acaggtttta atgatcctcg aagatctagg    6720
ggtggatcag tacctgctgg acttgatcga ggcagccttt ggggaaatat ccagctgtca    6780
cctaccaact ggcacgcgct tcaagttcgg agctatgatg aaatcgggca tgtttctgac    6840
tttgtttatt aacactgttt tgaacatcac catagcaagc agggtactgg agcagagact    6900
cactgactcc gcctgtgcgg ccttcatcgg cgacgacaac atcgttcacg gagtgatctc    6960
cgacaagctg atggcggaga ggtgcgcgtc gtgggtcaac atggaggtga agatcattga    7020
cgctgtcatg ggcgaaaaac cccatatttt tgtgggggga ttcatagttt ttgacagcgt    7080
cacacagacc gcctgccgtg tttcagaccc acttaagcgc ctgttcaagt tgggtaagcc    7140
gctaacagct gaagacaagc aggacgaaga caggcgacga gcactgagtg acgaggttag    7200
caagtggttc cggacaggct ggggggccga actggaggtg gcactaacat ctaggtatga    7260
ggtagagggc tgcaaaagta tcctcatagc catggccacc ttggcgaggg acattaaggc    7320
gtttaagaaa ttgagaggac ctgttataca cctctacggc ggtcctagat ggtgcgttaa    7380
atacacagaa ttctgattgg atcccaaacg ggccctctag actcgagcgg ccgccactgt    7440
gctggatatc tgcagaattc caccacactg gactagtgga tctatggcgt acccatacga    7500
tgttccagat tacgctagct tgagatctac catgtctcag agcaaccggg agctggtggt    7560
tgactttctc tcctacaagc tttcccgaa aggatacagc tggagtcagt ttagtgatgt    7620
ggaagagaac aggactgagg ccccagaagg gactgaatcg gagatggaga cccccagtgc    7680
```

```
catcaatggc aacccatcct ggcacctggc agacagcccc gcggtgaatg gagccactgc   7740
gcacagcagc agtttggatg cccgggaggt gatccccatg gcagcagtaa agcaagcgct   7800
gagggaggca ggcgacgagt ttgaactgcg gtaccggcgg gcattcagtg acctgacatc   7860
ccagctccac atcaccccag ggacagcata tcagagcttt gaacaggtag tgaatgaact   7920
cttccgggat ggggtagcca ttcttcgcat tgtggccttt ttctccttcg gcggggcact   7980
gtgcgtggaa agcgtagaca aggagatgca ggtattggtg agtcggatcg cagcttggat   8040
ggccacttac ctgaatgacc acctagagcc ttggatccag gagaacggcg gctgggatac   8100
ttttgtggaa ctctatggga acaatgcagc agccgagagc cgaaagggcc aggaacgctt   8160
caaccgctgg ttcctgacgg gcatgactgt ggccggcgtg gttctgctgg gctcactctt   8220
cagtcggaaa tgaagatccg agctcggtac caagcttaag tttgggtaat taattgaatt   8280
acatccctac gcaaacgttt tacggccgcc ggtggcgccc gcgccggcg gcccgtcctt    8340
ggccgttgca ggccactccg gtggctcccg tcgtccccga cttccaggcc cagcagatgc   8400
agcaactcat cagcgccgta atgcgctga caatgagaca gaacgcaatt gctcctgcta    8460
ggcctcccaa accaaagaag aagaagacaa ccaaaccaaa gccgaaaacg cagcccaaga   8520
agatcaacgg aaaaacgcag cagcaaaaga agaaagacaa gcaagccgac aagaagaaga   8580
agaaacccgg aaaaagagaa agaatgtgca tgaagattga aaatgactgt atcttcgtat   8640
gcggctagcc acagtaacgt agtgtttcca gacatgtcgg gcaccgcact atcatgggtg   8700
cagaaaatct cgggtggtct gggggccttc gcaatcggcg ctatcctggt gctggttgtg   8760
gtcacttgca ttgggctccg cagataagtt agggtaggca atggcattga tatagcaaga   8820
aaattgaaaa cagaaaaagt tagggtaagc aatggcatat aaccataact gtataacttg   8880
taacaaagcg caacaagacc tgcgcaattg gccccgtggt ccgcctcacg gaaactcggg   8940
gcaactcata ttgacacatt aattggcaat aattggaagc ttacataagc ttaattcgac   9000
gaataattgg attttattt tattttgcaa ttggttttta atatttccaa aaaaaaaaaa   9060
aaaaaaaaaa aaaaaaaaaa aaaaaaaaaa aaaaaaaaaa aaaaaaaaaa aaaaaaaact   9120
agtgatcata atcagccata ccacatttgt agaggtttta cttgctttaa aaaacctccc   9180
acacctcccc ctgaacctga acataaaat gaatgcaatt gttgttgtta acttgtttat    9240
tgcagcttat aatggttaca aataaagcaa tagcatcaca aatttcacaa ataaagcatt   9300
tttttcactg cattctagtt gtggtttgtc caaactcatc aatgtatctt atcatgtctg   9360
gatctagtct gcattaatga atcggccaac gcgcggggag aggcggtttg cgtattgggc   9420
gctcttccgc ttcctcgctc actgactcgc tgcgctcggt cgttcggctg cggcgagcgg   9480
tatcagctca ctcaaaggcg gtaatacggt tatccacaga atcaggggat aacgcaggaa   9540
agaacatgtg agcaaaaggc cagcaaaagg ccaggaaccg taaaaaggcc gcgttgctgg   9600
cgttttccca taggctccgc cccccctgac gagcatcaca aaaatcgacg ctcaagtcaga  9660
ggtggcgaaa cccgacagga ctataaagat accaggcgtt tccccctgga agctccctcg   9720
tgcgctctcc tgttccgacc ctgccgctta ccggatacct gtccgccttt ctcccttcgg   9780
gaagcgtggc gctttctcaa tgctcgcgct gtaggtatct cagttcggtg taggtcgttc   9840
gctccaagct gggctgtgtg cacgaacccc ccgttcagcc cgaccgctgc gccttatccg   9900
gtaactatcg tcttgagtcc aacccggtaa gacacgactt atcgccactg gcagcagcca   9960
ctggtaacag gattagcaga gcgaggtatg taggcggtgc tacagagttc ttgaagtggt  10020
```

```
ggcctaacta cggctacact agaaggacag tatttggtat ctgcgctctg ctgaagccag   10080
ttaccttcgg aaaaagagtt ggtagctctt gatccggcaa acaaaccacc gctggtagcg   10140
gtggtttttt tgtttgcaag cagcagatta cgcgcagaaa aaaggatctc aagaagatc    10200 ctttgatctt ttctacgggg cattctgacg ctcagtggaa cgaaaactca cgttaaggga   10260
ttttggtcat gagattatca aaaggatctt cacctagat cctttttaaat taaaaatgaa   10320 gttttaaatc aatctaaagt atatatgagt aaacttggtc tgacagttac caatgcttaa   10380
tcagtgaggc acctatctca gcgatctgtc tatttcgttc atccatagtt gcctgactcc   10440
ccgtcgtgta gataactacg atacgggagg gcttaccatc tggccccagt gctgcaatga   10500
taccgcgaga cccacgctca ccggctccag atttatcagc aataaaccag ccagccggaa   10560
gggccgagcg cagaagtggt cctgcaactt tatccgcctc catccagtct attaattgtt   10620
gccgggaagc tagagtaagt agttcgccag ttaatagttt gcgcaacgtt gttgccattg   10680
ctacaggcat cgtggtgtca cgctcgtcgt ttggtatggc ttcattcagc tccggttccc   10740
aacgatcaag gcgagttaca tgatccccca tgttgtgcaa aaaagcggtt agctccttcg   10800
gtcctccgat cgttgtcaga agtaagttgg ccgcagtgtt atcactcatg gttatggcag   10860
cactgcataa ttctcttact gtcatgccat ccgtaagatg cttttctgtg actggtgagt   10920
actcaaccaa gtcattctga gaatagtgta tgcggcgacc gagttgctct tgcccggcgt   10980
caatacggga taataccgcg ccacatagca gaactttaaa agtgctcatc attggaaaac   11040
gttcttcggg gcgaaaactc tcaaggatct taccgctgtt gagatccagt tcgatgtaac   11100
ccactcgtgc acccaactga tcttcagcat cttttacttt caccagcgtt tctgggtgag   11160
caaaaacagg aaggcaaaat gccgcaaaaa agggaataag ggcgacacgg aaatgttgaa   11220
tactcatact cttccttttt caatattatt gaagcattta tcagggttat tgtctcatga   11280
gcggatacat atttgaatgt atttagaaaa ataaacaaat aggggttccg cgcacatttc   11340
cccgaaaagt gccacctgac gtctaagaaa ccattattat catgacatta acctataaaa   11400
ataggcgtat cacgaggccc tttcgtctcg cgcgtttcgg tgatgacggt gaaaacctct   11460
gacacatgca gctcccggag acggtcacag cttctgtcta gcggatgcc gggagcagac   11520 aagcccgtca gggcgcgtca gcgggtgttg gcgggtgtcg ggctggctt aactatgcgg   11580 catcagagca gattgtactg agagtgcacc atatcgacgc tctcccttat gcgactcctg   11640
cattaggaag cagcccagta ctaggttgag gccgttgagc accgccgccg caaggaatgg   11700
tgcatgcgta atcaattacg gggtcattag ttcatagccc atatatggag ttccgcgtta   11760
cataacttac ggtaaatggc ccgcctggct gaccgcccaa cgacccccgc ccattgacgt   11820
caataatgac gtatgttccc atagtaacgc caatagggac tttccattga cgtcaatggg   11880
tggagtattt acggtaaact gcccacttgg cagtacatca agtgtatcat atgccaagta   11940
cgccccctat tgacgtcaat gacggtaaat ggcccgcctg gcattatgcc cagtacatga   12000
ccttatggga ctttcctact tggcagtaca tctacgtatt agtcatcgct attaccatgg   12060
tgatgcggtt ttggcagtac atcaatgggc gtggatagcg gtttgactca cggggatttc   12120
caagtctcca ccccattgac gtcaatggga gtttgttttg gcaccaaaat caacgggact   12180
ttccaaaatg tcgtaacaac tccgccccat tgacgcaaat gggcggtagg cgtgtacggt   12240
gggaggtcta tataagcaga gctctctggc taactagaga acccactgct taactggctt   12300
atcgaaatta atacgactca ctatagggag accggaagct tgaattc                 12347
```

-continued

<210> SEQ ID NO 68
<211> LENGTH: 12612
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

| | | | | | |
|---|---|---|---|---|---|
| atggcggatg | tgtgacatac | acgacgccaa | aagattttgt | tccagctcct | gccacctccg | 60 |
| ctacgcgaga | gattaaccac | ccacgatggc | cgccaaagtg | catgttgata | ttgaggctga | 120 |
| cagcccattc | atcaagtctt | tgcagaaggc | atttccgtcg | ttcgaggtgg | agtcattgca | 180 |
| ggtcacacca | aatgaccatg | caaatgccag | agcattttcg | cacctggcta | ccaaattgat | 240 |
| cgagcaggag | actgacaaag | acacactcat | cttggatatc | ggcagtgcgc | cttccaggag | 300 |
| aatgatgtct | acgcacaaat | accactgcgt | atgccctatg | cgcagcgcag | aagaccccga | 360 |
| aaggctcgat | agctacgcaa | agaaactggc | agcggcctcc | gggaaggtgc | tggatagaga | 420 |
| gatcgcagga | aaaatcaccg | acctgcagac | cgtcatggct | acgccagacg | ctgaatctcc | 480 |
| tacctttgc | ctgcatacag | acgtcacgtg | tcgtacggca | gccgaagtgg | ccgtatacca | 540 |
| ggacgtgtat | gctgtacatg | caccaacatc | gctgtaccat | caggcgatga | aaggtgtcag | 600 |
| aacggcgtat | tggattgggt | ttgacaccac | cccgtttatg | tttgacgcgc | tagcaggcgc | 660 |
| gtatccaacc | tacgccacaa | actgggccga | cgagcaggtg | ttacaggcca | ggaacatagg | 720 |
| actgtgtgca | gcatccttga | ctgagggaag | actcggcaaa | ctgtccattc | tccgcaagaa | 780 |
| gcaattgaaa | ccttgcgaca | cagtcatgtt | ctcggtagga | tctacattgt | acactgagag | 840 |
| cagaaagcta | ctgaggagct | ggcacttacc | ctccgtattc | cacctgaaag | gtaaacaatc | 900 |
| ctttacctgt | aggtgcgata | ccatcgtatc | atgtgaaggg | tacgtagtta | agaaaatcac | 960 |
| tatgtgcccc | ggcctgtacg | gtaaaacggt | agggtacgcc | gtgacgtatc | acgcggaggg | 1020 |
| attcctagtg | tgcaagacca | cagacactgt | caaaggagaa | agagtctcat | tccctgtatg | 1080 |
| cacctacgtc | ccctcaacca | tctgtgatca | aatgactggc | atactagcga | ccgacgtcac | 1140 |
| accggaggac | gcacagaagt | tgttagtggg | attgaatcag | aggatagttg | tgaacggaag | 1200 |
| aacacagcga | aacactaaca | cgatgaagaa | ctatctgctt | ccgattgtgg | ccgtcgcatt | 1260 |
| tagcaagtgg | gcgagggaat | acaaggcaga | ccttgatgat | gaaaaacctc | tgggtgtccg | 1320 |
| agagaggtca | cttacttgct | gctgcttgtg | ggcattaaa | acgaggaaga | tgcacaccat | 1380 |
| gtacaagaaa | ccagacaccc | agacaatagt | gaaggtgcct | tcagagttta | actcgttcgt | 1440 |
| catcccgagc | ctatggtcta | caggcctcgc | aatcccagtc | agatcacgca | ttaagatgct | 1500 |
| tttggccaag | aagaccaagc | gagagttaat | acctgttctc | gacgcgtcgt | cagccaggga | 1560 |
| tgctgaacaa | gaggagaagg | agaggttgga | ggccgagctg | actagagaag | ccttaccacc | 1620 |
| cctcgtcccc | atcgcgccgg | cggagacggg | agtcgtcgac | gtcgacgttg | aagaactaga | 1680 |
| gtatcacgca | ggtgcagggg | tcgtggaaac | acctcgcagc | gcgttgaaag | tcaccgcaca | 1740 |
| gccgaacgac | gtactactag | gaaattacgt | agttctgtcc | ccgcagaccg | tgctcaagag | 1800 |
| ctccaagttg | gccccgtgc | accctctagc | agagcaggtg | aaaataataa | cataacgg | 1860 |
| gagggccggc | ggttaccagg | tcgacggata | tgacggcagg | gtcctactac | catgtggatc | 1920 |
| ggccattccg | gtccctgagt | ttcaagcttt | gagcgagagc | gccactatgg | tgtacaacga | 1980 |
| aagggagttc | gtcaacagga | aactatacca | tattgccgtt | cacggaccgt | cgctgaacac | 2040 |
| cgacgaggag | aactacgaga | agtcagagc | tgaaagaact | gacgccgagt | acgtgttcga | 2100 |

```
cgtagataaa aaatgctgcg tcaagagaga ggaagcgtcg ggtttggtgt tggtgggaga    2160
gctaaccaac cccccgttcc atgaattcgc ctacgaaggg ctgaagatca ggccgtcggc    2220
accatataag actacagtag taggagtctt tggggttccg ggatcaggca agtctgctat    2280
tattaagagc ctcgtgacca aacacgatct ggtcaccagc ggcaagaagg agaactgcca    2340
ggaaatagtt aacgacgtga agaagcaccg cgggaagggg acaagtaggg aaaacagtga    2400
ctccatcctg ctaaacgggt gtcgtcgtgc cgtggacatc ctatatgtgg acgaggcttt    2460
cgctagccat tccggtactc tgctggccct aattgctctt gttaaacctc ggagcaaagt    2520
ggtgttatgc ggagacccca agcaatgcgg attcttcaat atgatgcagc ttaaggtgaa    2580
cttcaaccac aacatctgca ctgaagtatg tcataaaagt atatccagac gttgcacgcg    2640
tccagtcacg gccatcgtgt ctacgttgca ctacggaggc aagatgcgca cgaccaaccc    2700
gtgcaacaaa cccataatca tagacaccac aggacagacc aagcccaagc caggagacat    2760
cgtgttaaca tgcttccgag ctgggcaaa gcagctgcag ttggactacc gtggacacga    2820
agtcatgaca gcagcagcat ctcagggcct cacccgcaaa ggggtatacg ccgtaaggca    2880
gaaggtgaat gaaaatccct tgtatgcccc tgcgtcggag cacgtgaatg tactgctgac    2940
gcgcactgag gataggctgg tgtggaaaac gctggccggc gatccctgga ttaaggtcct    3000
atcaaacatt ccacagggta actttacggc cacattggaa gaatggcaag aagaacacga    3060
caaaataatg aaggtgattg aaggaccggc tgcgcctgtg gacgcgttcc agaacaaagc    3120
gaacgtgtgt tgggcgaaaa gcctggtgcc tgtcctggac actgccggaa tcagattgac    3180
agcagaggag tggagcacca taattacagc atttaaggag gacagagctt actctccagt    3240
ggtggccttg aatgaaattt gcaccaagta ctatggagtt gacctggaca gtggcctgtt    3300
ttctgccccg aaggtgtccc tgtattacga gaacaaccac tgggataaca gacctggtgg    3360
aaggatgtat ggattcaatg ccgcaacagc tgccaggctg gaagctagac ataccttcct    3420
gaaggggcag tggcatacgg gcaagcaggc agttatcgca gaaagaaaaa tccaaccgct    3480
ttctgtgctg gacaatgtaa ttcctatcaa ccgcaggctg ccgcacgccc tggtggctga    3540
gtacaagacg gttaaaggca gtaggggttga gtggctggtc aataaagtaa gagggtacca    3600
cgtcctgctg gtgagtgagt acaacctggc tttgcctcga cgcagggtca cttggttgtc    3660
accgctgaat gtcacaggcg ccgataggtg ctacgaccta agtttaggac tgccggctga    3720
cgccggcagg ttcgacttgg tctttgtgaa cattcacacg gaattcagaa tccaccacta    3780
ccagcagtgt gtcgaccacg ccatgaagct gcagatgctt ggggagatg cgctacgact    3840 gctaaaaccc ggcggcatct tgatgagagc ttacggatac gccgataaaa tcagcgaagc    3900 cgttgttttcc tccttaagca gaaagttctc gtctgcaaga gtgttgcgcc cggattgtgt    3960
caccagcaat acagaagtgt tcttgctgtt ctccaacttt gacaacggaa agagaccctc    4020
tacgctacac cagatgaata ccaagctgag tgccgtgtat gccggagaag ccatgcacac    4080
ggccgggtgt gcaccatcct acagagttaa gagagcagac atagccacgt gcacagaagc    4140
ggctgtggtt aacgcagcta acgcccgtgg aactgtaggg gatggcgtat gcagggccgt    4200
ggcgaagaaa tggccgtcag cctttaaggg agcagcaaca ccagtgggca caattaaaac    4260
agtcatgtgc ggctcgtacc ccgtcatcca cgctgtagcg cctaatttct ctgccacgac    4320
tgaagcggaa ggggaccgcg aattggccgc tgtctaccgg gcagtggccg ccgaagtaaa    4380
cagactgtca ctgagcagcg tagccatccc gctgctgtcc acaggagtgt tcagcggcgg    4440
```

```
aagagatagg ctgcagcaat ccctcaacca tctattcaca gcaatggacg ccacggacgc   4500
tgacgtgacc atctactgca gagacaaaag ttgggagaag aaaatccagg aagccattga   4560
catgaggacg gctgtggagt tgctcaatga tgacgtggag ctgaccacag acttggtgag   4620
agtgcacccg gacagcagcc tggtgggtcg taagggctac agtaccactg acgggtcgct   4680
gtactcgtac tttgaaggta cgaaattcaa ccaggctgct attgatatgg cagagatact   4740
gacgttgtgg cccagactgc aagaggcaaa cgaacagata tgcctatacg cgctgggcga   4800
aacaatggac aacatcagat ccaaatgtcc ggtgaacgat tccgattcat caacacctcc   4860
caggacagtg ccctgcctgt gccgctacgc aatgacagca gaacggatcg cccgccttag   4920
gtcacaccaa gttaaaagca tggtggtttg ctcatctttt cccctcccga ataccatgt    4980
agatggggtg cagaaggtaa agtgcgagaa ggttctcctg ttcgacccga cggtaccttc   5040
agtggttagt ccgcggaagt atgccgcatc tacgacggac cactcagatc ggtcgttacg   5100
agggtttgac ttggactgga ccaccgactc gtcttccact gccagcgata ccatgtcgct   5160
acccagtttg cagtcgtgtg acatcgactc gatctacgag ccaatggctc ccatagtagt   5220
gacggctgac gtacaccctg aacccgcagg catcgcggac ctggcggcag atgtgcaccc   5280
tgaacccgca gaccatgtgg acctcgagaa cccgattcct ccaccgcgcc cgaagagagc   5340
tgcataccct gcctcccgcg cggcggagcg accggtgccg gcgccgagaa agccgacgcc   5400
tgccccaagg actgcgttta ggaacaagct gcctttgacg ttcggcgact ttgacgagca   5460
cgaggtcgat gcgttggcct ccgggattac tttcggagac ttcgacgacg tcctgcgact   5520
aggccgcgcg ggtgcatata ttttctcctc ggacactggc agcggacatt tacaacaaaa   5580
atccgttagg cagcacaatc tccagtgcgc acaactggat gcggtccagg aggagaaaat   5640
gtacccgcca aaattggata ctgagaggga gaagctgttg ctgctgaaaa tgcagatgca   5700
cccatcggag gctaataaga gtcgatacca gtctcgcaaa gtggagaaca tgaaagccac   5760
ggtggtggac aggctcacat cgggggccag attgtacacg ggagcggacg taggccgcat   5820
accaacatac gcggttcggt accccgccc cgtgtactcc cctaccgtga tcgaaagatt   5880
ctcaagcccc gatgtagcaa tcgcagcgtg caacgaatac ctatccagaa attacccaac   5940
agtggcgtcg taccagataa cagatgaata cgacgcatac ttggacatgg ttgacgggtc   6000
ggatagttgc ttggacagag cgacattctg cccggcgaag ctccggtgct acccgaaaca   6060
tcatgcgtac caccagccga ctgtacgcag tgccgtcccg tcacccttc agaacacact    6120
acagaacgtg ctagcggccg ccaccaagag aaactgcaac gtcacgcaaa tgcgagaact   6180
acccaccatg gactcggcag tgttcaacgt ggagtgcttc aagcgctatg cctgctccgg   6240
agaatattgg gaagaatatg ctaaacaacc tatccggata accactgaga acatcactac   6300
ctatgtgacc aaattgaaag gcccgaaagc tgctgccttg ttcgctaaga cccacaactt   6360
ggttccgctg caggaggttc ccatggacag attcacggtc gacatgaaac gagatgtcaa   6420
agtcactcca gggacgaaac acacagagga aagacccaaa gtccaggtaa ttcaagcagc   6480
ggagccattg gcgaccgctt acctgtgcgg catccacagg gaattagtaa ggagactaaa   6540
tgctgtgtta cgccctaacg tgcacacatt gtttgatatg tcggccgaag actttgacgc   6600
gatcatcgcc tctcacttcc acccaggaga cccggttcta gagacggaca ttgcatcatt   6660
cgacaaaagc caggacgact ccttggctct acaggtttta atgatcctcg aagatctagg   6720
ggtggatcag tacctgctgg acttgatcga ggcagccttt ggggaaatat ccagctgtca   6780
cctaccaact ggcacgcgct tcaagttcgg agctatgatg aaatcgggca tgtttctgac   6840
```

```
tttgtttatt aacactgttt tgaacatcac catagcaagc agggtactgg agcagagact    6900
cactgactcc gcctgtgcgg ccttcatcgg cgacgacaac atcgttcacg gagtgatctc    6960
cgacaagctg atggcggaga ggtgcgcgtc gtgggtcaac atggaggtga agatcattga    7020
cgctgtcatg ggcgaaaaac ccccatattt ttgtggggga ttcatagttt ttgacagcgt    7080
cacacagacc gcctgccgtg tttcagaccc acttaagcgc ctgttcaagt tgggtaagcc    7140
gctaacagct gaagacaagc aggacgaaga caggcgacga gcactgagtg acgaggttag    7200
caagtggttc cggacaggct tgggggccga actggaggtg gcactaacat ctaggtatga    7260
ggtagagggc tgcaaaagta tcctcatagc catggccacc ttggcgaggg acattaaggc    7320
gtttaagaaa ttgagaggac ctgttataca cctctacggc ggtcctagat tggtgcgtta    7380
atacacagaa ttctgattgg atcccaaacg ggccctctag actcgagcgg ccgccactgt    7440
gctggatatc tgcagaattc atgcatggag atacacctac attgcatgaa tatatgttag    7500
atttgcaacc agagacaact gatctctact gttatgagca attaaatgac agctcagagg    7560
aggaggatga aatagatggt ccagctggac aagcagaacc ggacagagcc cattacaata    7620
ttgtaacctt ttgttgcaag tgtgactcta cgcttcggtt gtgcgtacaa agcacacacg    7680
tagacattcg tactttggaa gacctgttaa tgggcacact aggaattgtg tgccccatct    7740
gttctcagaa accaggatct atggcgtacc catacgatgt tccagattac gctagcttga    7800
gatctaccat gtctcagagc aaccgggagc tggtggttga ctttctctcc tacaagcttt    7860
cccagaaagg atacgctgg agtcagttta gtgatgtgga agagaacagg actgaggccc    7920
cagaagggac tgaatcggag atggagaccc ccagtgccat caatggcaac ccatcctggc    7980
acctggcaga cagccccgcg gtgaatggag ccactgcgca cagcagcagt ttggatgccc    8040
gggaggtgat ccccatggca gcagtaaagc aagcgctgag ggaggcaggc gacgagtttg    8100
aactgcggta ccggcgggca ttcagtgacc tgacatccca gctccacatc accccaggga    8160
cagcatatca gagctttgaa caggtagtga atgaactctt ccgggatggg gtagccattc    8220
ttcgcattgt ggccttttttc tccttcggcg gggcactgtg cgtggaaagc gtagacaagg    8280
agatgcaggt attggtgagt cggatcgcag cttggatggc cacttacctg aatgaccacc    8340
tagagccttg gatccaggag aacggcggct gggatacttt tgtggaactc tatgggaaca    8400
atgcagcagc cgagagccga aagggccagg aacgcttcaa ccgctggttc ctgacgggca    8460
tgactgtggc cggcgtggtt ctgctgggct cactcttcag tcggaaatga agatccaagc    8520
ttaagtttgg gtaattaatt gaattacatc cctacgcaaa cgttttacgg ccgccggtgg    8580
cgcccgcgcc cggcggcccg tccttggccg ttgcaggcca ctccggtggc tcccgtcgtc    8640
cccgacttcc aggcccagca gatgcagcaa ctcatcagcg ccgtaaatgc gctgacaatg    8700
agacagaacg caattgctcc tgctaggcct cccaaaccaa agaagaagaa gacaaccaaa    8760
ccaaagccga aaacgcagcc caagaagatc aacggaaaaa cgcagcagca aaagaagaaa    8820
gacaagcaag ccgacaagaa gaagaagaaa cccggaaaaa gagaaagaat gtgcatgaag    8880
attgaaaatg actgtatctt cgtatgcggc tagccacagt aacgtagtgt ttccagacat    8940
gtcgggcacc gcactatcat gggtgcagaa aatctcgggt ggtctggggg ccttcgcaat    9000
cggcgctatc ctggtgctgg ttgtggtcac ttgcattggg ctccgcagat aagttagggt    9060
aggcaatggc attgatatag caagaaaatt gaaaacagaa aaagttaggg taagcaatgg    9120
catataacca taactgtata acttgtaaca aagcgcaaca agacctgcgc aattggcccc    9180
```

```
gtggtccgcc tcacggaaac tcggggcaac tcatattgac acattaattg gcaataattg   9240
gaagcttaca taagcttaat tcgacgaata attggatttt tattttattt tgcaattggt   9300
ttttaatatt tccaaaaaaa aaaaaaaaaa aaaaaaaaaa aaaaaaaaaa aaaaaaaaaa   9360
aaaaaaaaaa aaaaaaaaaa aaactagtga tcataatcag ccataccaca tttgtagagg   9420
ttttacttgc tttaaaaaac ctcccacacc tccccctgaa cctgaaacat aaaatgaatg   9480
caattgttgt tgttaacttg tttattgcag cttataatgg ttacaaataa agcaatagca   9540
tcacaaattt cacaaataaa gcattttttt cactgcattc tagttgtggt ttgtccaaac   9600
tcatcaatgt atcttatcat gtctggatct agtctgcatt aatgaatcgg ccaacgcgcg   9660
gggagaggcg gtttgcgtat tgggcgctct tccgcttcct cgctcactga ctcgctgcgc   9720
tcggtcgttc ggctgcggcg agcggtatca gctcactcaa aggcggtaat acggttatcc   9780
acagaatcag gggataacgc aggaaagaac atgtgagcaa aaggccagca aaaggccagg   9840
aaccgtaaaa aggccgcgtt gctggcgttt ttccataggc tccgcccccc tgacgagcat   9900
cacaaaaatc gacgctcaag tcagaggtgg cgaaacccga caggactata agataccag    9960 gcgtttcccc ctggaagctc cctcgtgcgc tctcctgttc cgaccctgcc gcttaccgga  10020
tacctgtccg cctttctccc ttcgggaagc gtggcgcttt ctcaatgctc gcgctgtagg  10080
tatctcagtt cggtgtaggt cgttcgctcc aagctgggct gtgtgcacga accccccgtt  10140
cagcccgacc gctgcgcctt atccggtaac tatcgtcttg agtccaaccc ggtaagacac  10200
gacttatcgc cactggcagc agccactggt aacaggatta gcagagcgag gtatgtaggc  10260
ggtgctacag agttcttgaa gtggtggcct aactacggct acactagaag gacagtattt  10320
ggtatctgcg ctctgctgaa gccagttacc ttcggaaaaa gagttggtag ctcttgatcc  10380
ggcaaacaaa ccaccgctgg tagcggtggt ttttttgttt gcaagcagca gattacgcgc  10440
agaaaaaaag gatctcaaga agatcctttg atcttttcta cggggcattc tgacgctcag  10500
tggaacgaaa actcacgtta agggattttg gtcatgagat tatcaaaaag gatcttcacc  10560
tagatccttt taaattaaaa atgaagtttt aaatcaatct aaagtatata tgagtaaact  10620
tggtctgaca gttaccaatg cttaatcagt gaggcaccta tctcagcgat ctgtctattt  10680
cgttcatcca tagttgcctg actccccgtc gtgtagataa ctacgatacg ggagggctta  10740
ccatctggcc ccagtgctgc aatgataccg cgagacccac gctcaccggc tccagattta  10800
tcagcaataa accagccagc cggaagggcc gagcgcagaa gtggtcctgc aactttatcc  10860
gcctccatcc agtctattaa ttgttgccgg gaagctagag taagtagttc gccagttaat  10920
agtttgcgca acgttgttgc cattgctaca ggcatcgtgg tgtcacgctc gtcgtttggt  10980
atggcttcat tcagctccgg ttcccaacga tcaaggcgag ttacatgatc ccccatgttg  11040
tgcaaaaaag cggttagctc cttcggtcct ccgatcgttg tcagaagtaa gttggccgca  11100
gtgttatcac tcatggttat ggcagcactg cataattctc ttactgtcat gccatccgta  11160
agatgctttt ctgtgactgg tgagtactca accaagtcat tctgagaata gtgtatgcgg  11220
cgaccgagtt gctcttgccc ggcgtcaata cgggataata ccgcgccaca tagcagaact  11280
ttaaaagtgc tcatcattgg aaaacgttct cggggcgaaa actctcaag gatcttaccg  11340 ctgttgagat ccagttcgat gtaacccact cgtgcaccca actgatcttc agcatctttt  11400
actttcacca gcgtttctgg gtgagcaaaa acaggaaggc aaaatgccgc aaaaagggga  11460
ataagggcga cacggaaatg ttgaatactc atactcttcc ttttccaata ttattgaagc  11520
atttatcagg gttattgtct catgagcgga tacatatttg aatgtattta gaaaaataaa  11580
```

```
caaataggggg ttccgcgcac atttccccga aaagtgccac ctgacgtcta agaaaccatt    11640
attatcatga cattaaccta taaaaatagg cgtatcacga ggccctttcg tctcgcgcgt    11700
ttcggtgatg acggtgaaaa cctctgacac atgcagctcc cggagacggt cacagcttct    11760
gtctaagcga tgccgggag cagacaagcc cgtcagggcg cgtcagcggg tgttggcggg    11820
tgtcggggct ggcttaacta tgcggcatca gagcagattg tactgagagt gcaccatatc    11880
gacgctctcc cttatgcgac tcctgcatta ggaagcagcc cagtactagg ttgaggccgt    11940
tgagcaccgc cgccgcaagg aatggtgcat gcgtaatcaa ttacgggtc attagttcat     12000
agcccatata tggagttccg cgttacataa cttacggtaa atggcccgcc tggctgaccg    12060
cccaacgacc cccgcccatt gacgtcaata atgacgtatg ttcccatagt aacgccaata    12120
gggactttcc attgacgtca atgggtggag tatttacggt aaactgccca cttggcagta    12180
catcaagtgt atcatatgcc aagtacgccc cctattgacg tcaatgacgg taaatggccc    12240
gcctggcatt atgcccagta catgacctta tgggactttc ctacttggca gtacatctac    12300
gtattagtca tcgctattac catggtgatg cggttttggc agtacatcaa tgggcgtgga    12360
tagcggtttg actcacgggg atttccaagt ctccacccca ttgacgtcaa tgggagtttg    12420
ttttggcacc aaaatcaacg ggactttcca aaatgtcgta caactccgc cccattgacg     12480
caaatgggcg gtaggcgtgt acggtgggag gtctatataa gcagagctct ctggctaact    12540
agagaaccca ctgcttaact ggcttatcga aattaatacg actcactata gggagaccgg    12600
aagcttgaat tc                                                        12612

<210> SEQ ID NO 69
<211> LENGTH: 4832
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
gtcgacttct gaggcggaaa gaaccagctg tggaatgtgt gtcagttagg gtgtggaaag      60
tccccaggct ccccagcagg cagaagtatg caaagcatgc atctcaatta gtcagcaacc     120
aggtgtggaa agtccccagg ctccccagca ggcagaagta tgcaaagcat gcatctcaat     180
tagtcagcaa ccatagtccc gcccctaact ccgcccatcc cgcccctaac tccgcccagt     240
tccgcccatt ctccgcccca tggctgacta attttttta tttatgcaga ggccgaggcc      300
gcctcggcct ctgagctatt ccagaagtag tgaggaggct ttttggagg cctaggcttt      360
tgcaaaaagc tggatcgatc ctgagaactt cagggtgagt ttggggaccc ttgattgttc     420
tttctttttc gctattgtaa aattcatgtt atatggaggg gcaaagtttt cagggtgtt      480
gtttagaatg ggaagatgtc ccttgtatca ccatggaccc tcatgataat tttgtttctt     540
tcactttcta ctctgttgac aaccattgtc tcctcttatt ttcttttcat tttctgtaac     600
tttttcgtta aactttagct tgcatttgta acgaattttt aaattcactt tgtttatt     660
gtcagattgt aagtactttc tctaatcact tttttttcaa ggcaatcagg gtatattata     720
ttgtacttca gcacagtttt agagaacaat tgttataatt aaatgataag gtagaatatt     780
tctgcatata aattctggct ggcgtggaaa tattcttatt ggtagaaaca actacatcct     840
ggtcatcatc ctgcctttct ctttatggtt acaatgatat acactgtttg agatgaggat     900
aaaatactct gagtccaaac cgggcccctc tgctaaccat gttcatgcct tcttcttttt     960
```

```
cctacagctc ctgggcaacg tgctggttat tgtgctgtct catcattttg gcaaagaatt    1020
gtaatacgac tcactatagg gcgaattcgg atccagatct atggcgtacc catacgatgt    1080
tccagattac gctagcttga gatctaccat gtctcagagc aaccgggagc tggtggttga    1140 cttttctctcc tacaagcttt cccagaaagg atacagctgg agtcagttta gtgatgtgga    1200
agagaacagg actgaggccc cagaagggac tgaatcggag atggagaccc ccagtgccat    1260
caatggcaac ccatcctggc acctggcaga cagccccgcg gtgaatggag ccactgcgca    1320
cagcagcagt ttggatgccc gggaggtgat ccccatggca gcagtaaagc aagcgctgag    1380
ggaggcaggc gacgagtttg aactgcggta ccggcgggca ttcagtgacc tgacatccca    1440
gctccacatc accccaggga cagcatatca gagctttgaa caggtagtga atgaactctt    1500
ccgggatggg gtaaactggg gtcgcattgt ggccttttc tccttcggcg ggcactgtg    1560 cgtggaaagc gtagacaagg agatgcaggt attggtgagt cggatcgcag cttggatggc    1620
cacttacctg aatgaccacc tagagccttg gatccaggag aacggcggct gggatacttt    1680
tgtggaactc tatgggaaca atgcagcagc cgagagccga aagggccagg aacgcttcaa    1740
ccgctggttc ctgacgggca tgactgtggc cggcgtggtt ctgctgggct cactcttcag    1800
tcggaaatga agatcttatt aaagcagaac ttgtttattg cagcttataa tggttacaaa    1860
taaagcaata gcatcacaaa tttcacaaat aaagcatttt tttcactgca ttctagttgt    1920
ggtttgtcca aactcatcaa tgtatcttat catgtctggt cgactctaga ctcttccgct    1980
tcctcgctca ctgactcgct gcgctcggtc gttcggctgc ggcgagcggt atcagctcac    2040
tcaaaggcgg taatacggtt atccacagaa tcaggggata acgcaggaaa gaacatgtga    2100
gcaaaggcca gcaaaaggcc aggaaccgta aaaaggccgc gttgctggcg ttttttccat    2160
aggctccgcc cccctgacga gcatcacaaa aatcgacgct caagtcagag gtggcgaaac    2220
ccgacaggac tataaagata ccaggcgttt ccccctggaa gctccctcgt gcgctctcct    2280
gttccgaccc tgccgcttac cggatacctg tccgcctttc tcccttcggg aagcgtggcg    2340
ctttctcaat gctcacgctg taggtatctc agttcggtgt aggtcgttcg ctccaagctg    2400
ggctgtgtgc acgaaccccc cgttcagccc gaccgctgcg ccttatccgg taactatcgt    2460
cttgagtcca acccggtaag acacgactta tcgccactgg cagcagccac tggtaacagg    2520
attagcagag cgaggtatgt aggcggtgct acagagttct tgaagtggtg cctaactac    2580 ggctacacta aaggacagt atttggtatc tgcgctctgc tgaagccagt taccttcgga    2640
aaaagagttg gtagctcttg atccggcaaa caaaccaccg ctggtagcgg tggttttttt    2700
gtttgcaagc agcagattac gcgcagaaaa aaaggatctc aagaagatcc tttgatcttt    2760
tctacggggt ctgacgctca gtggaacgaa aactcacgtt aagggatttt ggtcatgaga    2820
ttatcaaaaa ggatcttcac ctagatcctt ttaaattaaa aatgaagttt taaatcaatc    2880
taaagtatat atgagtaaac ttggtctgac agttaccaat gcttaatcag tgaggcacct    2940
atctcagcga tctgtctatt tcgttcatcc atagttgcct gactccccgt cgtgtagata    3000
actacgatac gggagggctt accatctggc cccagtgctg caatgatacc gcgagaccca    3060
cgctcaccgg ctccagattt atcagcaata accagccag ccggaagggc cgagcgcaga    3120
agtggtcctg caactttatc cgcctccatc cagtctatta attgttgccg ggaagctaga    3180
gtaagtagtt cgccagttaa tagtttgcgc aacgttgttg ccattgctac aggcatcgtg    3240
gtgtcacgct cgtcgtttgg tatggcttca ttcagctccg gttcccaacg atcaaggcga    3300
```

```
gttacatgat cccccatgtt gtgcaaaaaa gcggttagct ccttcggtcc tccgatcgtt    3360
gtcagaagta agttggccgc agtgttatca ctcatggtta tggcagcact gcataattct    3420
cttactgtca tgccatccgt aagatgcttt tctgtgactg gtgagtactc aaccaagtca    3480
ttctgagaat agtgtatgcg gcgaccgagt tgctcttgcc cggcgtcaat acgggataat    3540
accgcgccac atagcagaac tttaaaagtg ctcatcattg gaaaacgttc ttcggggcga    3600
aaactctcaa ggatcttacc gctgttgaga tccagttcga tgtaacccac tcgtgcaccc    3660
aactgatctt cagcatcttt tactttcacc agcgtttctg ggtgagcaaa aacaggaagg    3720
caaaatgccg caaaaaaggg aataagggcg acacggaaat gttgaatact catactcttc    3780
ttttttcaat attattgaag catttatcag ggttattgtc tcatgagcgg atacatattt    3840
gaatgtattt agaaaaataa acaaataggg gttccgcgca catttccccg aaaagtgcca    3900
cctgacgtct aagaaaccat tattatcatg acattaacct ataaaaatag gcgtatcacg    3960 aggcccctt cgtctcgcgc gtttcggtga tgacggtgaa aacctctgac acatgcagct    4020
cccggagacg gtcacagctt gtctgtaagc ggatgccggg agcagacaag cccgtcaggg    4080
cgcgtcagcg ggtgttggcg ggtgtcgggg ctggcttaac tatgcggcat cagagcagat    4140
tgtactgaga gtgcaccata tgcggtgtga ataccgcac agatgcgtaa ggagaaaata    4200
ccgcatcagg aaattgtaaa cgttaatatt ttgttaaaat tcgcgttaaa ttttgttaa    4260 atcagctcat ttttaacca ataggccgaa atcggcaaaa tcccttataa atcaaaagaa    4320
tagaccgaga tagggttgag tgttgttcca gtttggaaca agagtccact attaaagaac    4380
gtggactcca acgtcaaagg gcgaaaaacc gtctatcagg gcgatggccc actacgtgaa    4440
ccatcaccct aatcaagttt ttggggtcg aggtgccgta aagcactaaa tcggaaccct    4500
aaagggagcc cccgatttag agcttgacgg ggaaagccgg cgaacgtggc gagaaaggaa    4560
gggaagaaag cgaaaggagc gggcgctagg gcgctggcaa gtgtagcggt cacgctgcgc    4620
gtaaccacca caccgccgc gcttaatgcg ccgctacagg gcgcgtcgcg ccattcgcca    4680
ttcaggctac gcaactgttg ggaagggcga tcggtgcggg cctcttcgct attacgccag    4740
ctggcgaagg ggggatgtgc tgcaaggcga ttaagttggg taacgccagg gttttcccag    4800
tcacgacgtt gtaaaacgac ggccagtgaa tt                                 4832
```

<210> SEQ ID NO 70
<211> LENGTH: 4832
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
gtcgacttct gaggcggaaa gaaccagctg tggaatgtgt gtcagttagg gtgtggaaag      60
tccccaggct ccccagcagg cagaagtatg caaagcatgc atctcaatta gtcagcaacc     120
aggtgtggaa agtccccagg ctccccagca ggcagaagta tgcaaagcat gcatctcaat     180
tagtcagcaa ccatagtccc gcccctaact ccgcccatcc cgcccctaac tccgcccagt     240
tccgcccatt ctccgcccca tggctgacta attttttta tttatgcaga ggccgaggcc     300
gcctcggcct ctgagctatt ccagaagtag tgaggaggct ttttggagg cctaggcttt     360 tgcaaaaagc tggatcgatc ctgagaactt cagggtgagt ttggggaccc ttgattgttc     420
tttctttttc gctattgtaa aattcatgtt atatggaggg ggcaaagttt tcagggtgtt     480
```

```
gtttagaatg ggaagatgtc ccttgtatca ccatggaccc tcatgataat tttgtttctt      540
tcactttcta ctctgttgac aaccattgtc tcctcttatt ttcttttcat tttctgtaac      600
tttttcgtta aactttagct tgcatttgta acgaattttt aaattcactt ttgtttattt      660
gtcagattgt aagtactttc tctaatcact ttttttcaa ggcaatcagg gtatattata       720
ttgtacttca gcacagtttt agagaacaat tgttataatt aaatgataag gtagaatatt      780
tctgcatata aattctggct ggcgtggaaa tattcttatt ggtagaaaca actacatcct      840
ggtcatcatc ctgcctttct ctttatggtt acaatgatat acactgtttg agatgaggat      900
aaaatactct gagtccaaac cgggcccctc tgctaaccat gttcatgcct tcttcttttt      960
cctacagctc ctgggcaacg tgctggttat tgtgctgtct catcattttg gcaaagaatt     1020
gtaatacgac tcactatagg gcgaattcgg atccagatct atggcgtacc catacgatgt     1080
tccagattac gctagcttga gatctaccat gtctcagagc aaccgggagc tggtggttga     1140
ctttctctcc tacaagcttt cccagaaagg atacagctgg agtcagttta gtgatgtgga     1200
agagaacagg actgaggccc cagaaggac tgaatcggag atggagaccc ccagtgccat      1260
caatggcaac ccatcctggc acctggcaga cagccccgcg gtgaatggag ccactgcgca     1320
cagcagcagt ttggatgccc gggaggtgat ccccatggca gcagtaaagc aagcgctgag     1380
ggaggcaggc gacgagtttg aactgcggta ccggcgggca ttcagtgacc tgacatccca     1440
gctccacatc accccaggga cagcatatca gagctttgaa caggtagtga atgaactctt     1500
ccgggatggg gtagccattc ttcgcattgt ggccttttc tccttcggcg gggcactgtg      1560
cgtggaaagc gtagacaagg agatgcaggt attggtgagt cggatcgcag cttggatggc     1620
cacttacctg aatgaccacc tagagccttg gatccaggag aacggcggct gggatacttt     1680 tgtgaactc tatgggaaca atgcagcagc cgagagccga aagggccagg aacgcttcaa      1740
ccgctggttc ctgacgggca tgactgtggc cggcgtggtt ctgctgggct cactcttcag     1800
tcggaaatga agatcttatt aaagcagaac ttgtttattg cagcttataa tggttacaaa     1860
taaagcaata gcatcacaaa tttcacaaat aaagcatttt tttcactgca ttctagttgt     1920
ggtttgtcca aactcatcaa tgtatcttat catgtctggt cgactctaga ctcttccgct     1980
tcctcgctca ctgactcgct gcgctcggtc gttcggctgc ggcgagcggt atcagctcac     2040
tcaaaggcgg taatacggtt atccacagaa tcaggggata acgcaggaaa gaacatgtga     2100
gcaaaggcca gcaaaaggcc aggaaccgta aaaaggccgc gttgctggcg ttttttccat     2160
aggctccgcc cccctgacga gcatcacaaa aatcgacgct caagtcagag gtggcgaaac     2220
ccgacaggac tataaagata ccaggcgttt ccccctggaa gctccctcgt gcgctctcct     2280
gttccgaccc tgccgcttac cggatacctg tccgcctttc tcccttcggg aagcgtggcg     2340
ctttctcaat gctcacgctg taggtatctc agttcggtgt aggtcgttcg ctccaagctg     2400
ggctgtgtgc acgaaccccc cgttcagccc gaccgctgcg ccttatccgg taactatcgt     2460
cttgagtcca acccggtaag acacgactta tcgccactgg cagcagccac tggtaacagg     2520
attagcagag cgaggtatgt aggcggtgct acagagttct tgaagtggtg gcctaactac     2580
ggctacacta aaggacagt atttggtatc tgcgctctgc tgaagccagt taccttcgga     2640
aaaagagttg gtagctcttg atccggcaaa caaaccaccg ctggtagcgg tggtttttt       2700 gtttgcaagc agcagattac gcgcagaaaa aaggatctc aagaagatcc tttgatcttt       2760
tctacggggt ctgacgctca gtggaacgaa aactcacgtt aagggatttt ggtcatgaga     2820
ttatcaaaaa ggatcttcac ctagatcctt ttaaattaaa aatgaagttt taaatcaatc     2880
```

```
taaagtatat atgagtaaac ttggtctgac agttaccaat gcttaatcag tgaggcacct   2940
atctcagcga tctgtctatt tcgttcatcc atagttgcct gactccccgt cgtgtagata   3000
actacgatac gggagggctt accatctggc cccagtgctg caatgatacc gcgagaccca   3060
cgctcaccgg ctccagattt atcagcaata aaccagccag ccggaagggc cgagcgcaga   3120
agtggtcctg caactttatc cgcctccatc cagtctatta attgttgccg ggaagctaga   3180
gtaagtagtt cgccagttaa tagtttgcgc aacgttgttg ccattgctac aggcatcgtg   3240
gtgtcacgct cgtcgtttgg tatggcttca ttcagctccg gttcccaacg atcaaggcga   3300
gttacatgat cccccatgtt gtgcaaaaaa gcggttagct ccttcggtcc tcgatcgtt   3360
gtcagaagta agttggccgc agtgttatca ctcatggtta tggcagcact gcataattct   3420
cttactgtca tgccatccgt aagatgcttt tctgtgactg gtgagtactc aaccaagtca   3480
ttctgagaat agtgtatgcg cgaccgagt tgctcttgcc cggcgtcaat acgggataat   3540
accgcgccac atagcagaac tttaaaagtg ctcatcattg gaaaacgttc ttcggggcga   3600
aaactctcaa ggatcttacc gctgttgaga tccagttcga tgtaacccac tcgtgcaccc   3660
aactgatctt cagcatcttt tactttcacc agcgtttctg ggtgagcaaa aacaggaagg   3720
caaaatgccg caaaaaaggg aataagggcg acacggaaat gttgaatact catactcttc   3780
ttttttcaat attattgaag catttatcag ggttattgtc tcatgagcgg atacatattt   3840
gaatgtattt agaaaaataa acaaataggg gttccgcgca catttccccg aaaagtgcca   3900
cctgacgtct aagaaaccat tattatcatg acattaacct ataaaaatag gcgtatcacg   3960
aggccccttt cgtctcgcgc gtttcggtga tgacggtgaa aacctctgac acatgcagct   4020
cccggagacg gtcacagctt gtctgtaagc ggatgccggg agcagacaag cccgtcaggg   4080
cgcgtcagcg ggtgttggcg ggtgtcgggg ctggcttaac tatgcggcat cagagcagat   4140
tgtactgaga gtgcaccata tgcggtgtga aataccgcac agatgcgtaa ggagaaaata   4200
ccgcatcagg aaattgtaaa cgttaatatt ttgttaaaat tcgcgttaaa ttttttgttaa   4260
atcagctcat tttttaacca ataggccgaa atcggcaaaa tcccttataa atcaaaagaa   4320
tagaccgaga tagggttgag tgttgttcca gtttggaaca agagtccact attaaagaac   4380
gtggactcca acgtcaaagg gcgaaaaacc gtctatcagg gcgatggccc actacgtgaa   4440
ccatcaccct aatcaagttt tttggggtcg aggtgccgta agcactaaa tcggaaccct   4500
aaagggagcc cccgatttag agcttgacgg ggaaagccgg cgaacgtggc gagaaaggaa   4560
gggaagaaag cgaaaggagc gggcgctagg gcgctggcaa gtgtagcggt cacgctgcgc   4620
gtaaccacca cacccgccgc gcttaatgcg ccgctacagg gcgcgtcgcg ccattcgcca   4680
ttcaggctac gcaactgttg ggaagggcga tcggtgcggg cctcttcgct attacgccag   4740
ctggcgaagg ggggatgtgc tgcaaggcga ttaagttggg taacgccagg gttttcccag   4800
tcacgacgtt gtaaaacgac ggccagtgaa tt                                 4832
```

<210> SEQ ID NO 71
<211> LENGTH: 1499
<212> TYPE: DNA
<213> ORGANISM: Homo sapiens

<400> SEQUENCE: 71

```
atgactttta acagttttga aggatctaaa acttgtgtac ctgcagacat caataaggaa     60
gaagaatttg tagaagagtt taatagatta aaaactttg ctaattttcc aagtggtagt     120
```

```
cctgtttcag catcaacact ggcacgagca gggtttcttt atactggtga aggagatacc      180
gtgcggtgct ttagttgtca tgcagctgta gatagatggc aatatggaga ctcagcagtt      240
ggaagacaca ggaaagtatc cccaaattgc agatttatca acggctttta tcttgaaaat      300
agtgccacgc agtctacaaa ttctggtatc cagaatggtc agtacaaagt tgaaaactat      360
ctgggaagca gagatcattt tgccttagac aggccatctg agacacatgc agactatctt      420
ttgagaactg gcaggttgt agatatatca gacaccatat acccgaggaa ccctgccatg       480
tattgtgaag aagctagatt aaagtccttt cagaactggc agactatgc tcacctaacc       540
ccaagagagt tagcaagtgc tggactctac tacacaggta ttggtgacca agtgcagtgc      600
ttttgttgtg gtggaaaact gaaaaattgg gaaccttgtg atcgtgcctg gtcagaacac      660
aggcgacact ttcctaattg cttctttgtt ttgggccgga atcttaatat tcgaagtgaa      720
tctgatgctg tgagttctga taggaatttc ccaaattcaa caaatcttcc aagaaatcca      780
tccatggcag attatgaagc acggatcttt acttttggga catggatata ctcagttaac      840
aaggagcagc ttcaagagc tggattttat gctttaggtg aaggtgataa agtaaagtgc      900
tttcactgtg gaggagggct aactgattgg aagcccagtg aagacccttg gaacaacat      960
gctaaatggt atccagggtg caaatatctg ttagaacaga agggacaaga atatataaac     1020
aatattcatt taactcattc acttgaggag tgtctggtaa gaactactga gaaaacacca     1080
tcactaacta aagaattga tgataccatc ttccaaaatc ctatggtaca agaagctata     1140
cgaatggggt tcagtttcaa ggacattaag aaaataatgg aggaaaaaat tcagatatct     1200
gggagcaact ataaatcact tgaggttctg gttgcagatc tagtgaatgc tcagaaagac     1260
agtatgcaag atgagtcaag tcagacttca ttacagaaag agattagtac tgaagagcag     1320
ctaaggcgcc tgcaagagga gaagcttgc aaaatctgta tggatagaaa tattgctatc     1380
gttttgttc cttgtggaca tctagtcact tgtaaacaat gtgctgaagc agttgacaag     1440
tgtcccatgt gctacacagt cattactttc aagcaaaaaa tttttatgtc ttaatctaa      1499
```

<210> SEQ ID NO 72
<211> LENGTH: 497
<212> TYPE: PRT
<213> ORGANISM: Homo sapiens

<400> SEQUENCE: 72

```
Met Thr Phe Asn Ser Phe Glu Gly Ser Lys Thr Cys Val Pro Ala Asp
1               5                   10                  15

Ile Asn Lys Glu Glu Glu Phe Val Glu Phe Asn Arg Leu Lys Thr
        20                  25                  30

Phe Ala Asn Phe Pro Ser Gly Ser Pro Val Ser Ala Ser Thr Leu Ala
            35                  40                  45

Arg Ala Gly Phe Leu Tyr Thr Gly Glu Gly Asp Thr Val Arg Cys Phe
        50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
                100                 105                 110

Gly Gln Tyr Lys Val Glu Asn Tyr Leu Gly Ser Arg Asp His Phe Ala
            115                 120                 125

Leu Asp Arg Pro Ser Glu Thr His Ala Asp Tyr Leu Leu Arg Thr Gly
```

```
            130                 135                 140
Gln Val Val Asp Ile Ser Asp Thr Ile Tyr Pro Arg Asn Pro Ala Met
145                 150                 155                 160

Tyr Cys Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
                180                 185                 190

Gly Ile Gly Asp Gln Val Gln Cys Phe Cys Gly Gly Lys Leu Lys
            195                 200                 205

Asn Trp Glu Pro Cys Asp Arg Ala Trp Ser Glu His Arg Arg His Phe
        210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
                260                 265                 270

Gly Thr Trp Ile Tyr Ser Val Asn Lys Glu Gln Leu Ala Arg Ala Gly
            275                 280                 285

Phe Tyr Ala Leu Gly Glu Gly Asp Lys Val Lys Cys Phe His Cys Gly
        290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335

Glu Tyr Ile Asn Asn Ile His Leu Thr His Ser Leu Glu Glu Cys Leu
            340                 345                 350

Val Arg Thr Thr Glu Lys Thr Pro Ser Leu Thr Arg Arg Ile Asp Asp
        355                 360                 365

Thr Ile Phe Gln Asn Pro Met Val Gln Glu Ala Ile Arg Met Gly Phe
                375                 380
370

Ser Phe Lys Asp Ile Lys Lys Ile Met Glu Glu Lys Ile Gln Ile Ser
385                 390                 395                 400

Gly Ser Asn Tyr Lys Ser Leu Glu Val Leu Val Ala Asp Leu Val Asn
                405                 410                 415

Ala Gln Lys Asp Ser Met Gln Asp Glu Ser Ser Gln Thr Ser Leu Gln
            420                 425                 430

Lys Glu Ile Ser Thr Glu Glu Gln Leu Arg Arg Leu Gln Glu Glu Lys
        435                 440                 445

Leu Cys Lys Ile Cys Met Asp Arg Asn Ile Ala Ile Val Phe Val Pro
450                 455                 460

Cys Gly His Leu Val Thr Cys Lys Gln Cys Ala Glu Ala Val Asp Lys
465                 470                 475                 480

Cys Pro Met Cys Tyr Thr Val Ile Thr Phe Lys Gln Lys Ile Phe Met
                485                 490                 495

Ser

<210> SEQ ID NO 73
<211> LENGTH: 5575
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 73

```
gtcgacttct gaggcggaaa gaaccagctg tggaatgtgt gtcagttagg gtgtggaaag      60
tccccaggct ccccagcagg cagaagtatg caaagcatgc atctcaatta gtcagcaacc     120
aggtgtggaa agtccccagg ctccccagca ggcagaagta tgcaaagcat gcatctcaat     180
tagtcagcaa ccatagtccc gcccctaact ccgcccatcc cgcccctaac tccgcccagt     240
tccgcccatt ctccgcccca tggctgacta attttttta tttatgcaga ggccgaggcc     300
gcctcggcct ctgagctatt ccagaagtag tgaggaggct ttttggagg cctaggcttt      360
tgcaaaaagc tggatcgatc ctgagaactt cagggtgagt ttggggaccc ttgattgttc     420
tttcttttc gctattgtaa aattcatgtt atatggaggg ggcaaagttt tcagggtgtt      480
gtttagaatg ggaagatgtc ccttgtatca ccatggaccc tcatgataat tttgtttctt     540
tcactttcta ctctgttgac aaccattgtc tcctcttatt ttcttttcat tttctgtaac     600
tttttcgtta aactttagct tgcatttgta acgaattttt aaattcactt ttgtttattt     660
gtcagattgt aagtactttc tctaatcact tttttttcaa ggcaatcagg gtatattata    720
ttgtacttca gcacagtttt agagaacaat tgttataatt aaatgataag gtagaatatt     780
tctgcatata aattctggct ggcgtggaaa taatcttatt ggtagaaaca actacatcct     840
ggtcatcatc ctgcctttct ctttatggtt acaatgatat acactgtttg agatgaggat     900
aaaatactct gagtccaaac cgggcccctc tgctaaccat gttcatgcct tcttcttttt     960
cctacagctc ctgggcaacg tgctggttat tgtgctgtct catcattttg gcaaagaatt    1020
gtaatacgac tcactatagg gcgaattcgg atccatgact tttaacagtt ttgaaggatc    1080
taaaacttgt gtacctgcag acatcaataa ggaagaagaa tttgtagaag agtttaatag    1140
attaaaaact tttgctaatt ttccaagtgg tagtcctgtt tcagcatcaa cactggcacg    1200
agcagggttt ctttatactg gtgaaggaga taccgtgcgg tgctttagtt gtcatgcagc    1260
tgtagataga tggcaatatg gagactcagc agttggaaga cacaggaaag tatccccaaa    1320
ttgcagattt atcaacggct tttatcttga aaatagtgcc acgcagtcta caaattctgg    1380
tatccagaat ggtcagtaca agttgaaaac tatctgggga agcagagatc attttgcctt    1440
agacaggcca tctgagacac atgcagacta tcttttgaga actgggcagg ttgtagatat    1500
atcagacacc atatacccga ggaaccctgc catgtattgt gaagaagcta gattaaagtc    1560
ctttcagaac tggccagact atgctcacct aaccccaaga gagttagcaa gtgctggact    1620
ctactacaca ggtattggtg accaagtgca gtgcttttgt tgtggtggaa aactgaaaaa    1680
ttgggaacct tgtgatcgtg cctggtcaga acacaggcga cactttccta attgcttctt    1740
tgttttgggc cggaatctta atattcgaag tgaatctgat gctgtgagtt ctgataggaa    1800
tttcccaaat tcaacaaatc ttccaagaaa tccatccatg gcagattatg aagcacggat    1860
ctttacttt gggacatgga tatactcagt taacaaggag cagcttgcaa gagctggatt     1920
ttatgcttta ggtgaaggtg ataaagtaaa gtgctttcac tgtggaggag gctaactga    1980
ttggaagccc agtgaagacc cttgggaaca acatgctaaa tggtatccag ggtgcaaata    2040
tctgttagaa cagaagggac aagaatatat aaacaatatt catttaactc attcacttga    2100
ggagtgtctg gtaagaacta ctgagaaaac accatcacta actagaagaa ttgatgatac    2160
catcttccaa aatcctatgg tacaagaagc tatacgaatg gggttcagtt tcaaggacat    2220
taagaaaata atggaggaaa aaattcagat atctgggagc aactataaat cacttgaggt    2280
tctggttgca gatctagtga atgctcagaa agacagtatg caagatgagt caagtcagac    2340
```

```
ttcattacag aaagagatta gtactgaaga gcagctaagg cgcctgcaag aggagaagct    2400
ttgcaaaatc tgtatggata gaaatattgc tatcgttttt gttccttgtg acatctagt    2460
cacttgtaaa caatgtgctg aagcagttga caagtgtccc atgtgctaca cagtcattac    2520
tttcaagcaa aaattttta tgtcttaatc taaagatctt attaaagcag aacttgttta    2580
ttgcagctta taatggttac aaataaagca atagcatcac aaatttcaca ataaagcat    2640
ttttttcact gcattctagt tgtggtttgt ccaaactcat caatgtatct tatcatgtct    2700
ggtcgactct agactcttcc gcttcctcgc tcactgactc gctgcgctcg gtcgttcggc    2760
tgcggcgagc ggtatcagct cactcaaagg cggtaatacg gttatccaca gaatcagggg    2820
ataacgcagg aaagaacatg tgagcaaaag gccagcaaaa ggccaggaac cgtaaaaagg    2880
ccgcgttgct ggcgtttttc cataggctcc gcccccctga cgagcatcac aaaaatcgac    2940
gctcaagtca gaggtggcga aacccgacag gactataaag ataccaggcg tttccccctg    3000
gaagctccct cgtgcgctct cctgttccga cctgccgct taccggatac ctgtccgcct    3060
ttctcccttc gggaagcgtg gcgctttctc aatgctcacg ctgtaggtat ctcagttcgg    3120
tgtaggtcgt tcgctccaag ctgggctgtg tgcacgaacc ccccgttcag cccgaccgct    3180
gcgccttatc cggtaactat cgtcttgagt ccaacccggt aagacacgac ttatcgccac    3240
tggcagcagc cactggtaac aggattagca gagcgaggta tgtaggcggt gctacagagt    3300
tcttgaagtg gtggcctaac tacggctaca ctagaaggac agtatttggt atctgcgctc    3360
tgctgaagcc agttaccttc ggaaaaagag ttggtagctc ttgatccggc aaacaaacca    3420
ccgctggtag cggtggtttt tttgtttgca agcagcagat tacgcgcaga aaaaaggat    3480
ctcaagaaga tcctttgatc ttttctacgg ggtctgacgc tcagtggaac gaaaactcac    3540
gttaagggat tttggtcatg agattatcaa aaaggatctt cacctagatc cttttaaatt    3600
aaaaatgaag ttttaaatca atctaaagta tatatgagta aacttggtct gacagttacc    3660
aatgcttaat cagtgaggca cctatctcag cgatctgtct atttcgttca tccatagttg    3720
cctgactccc cgtcgtgtag ataactacga tacgggaggg cttaccatct ggccccagtg    3780
ctgcaatgat accgcgagac ccacgctcac cggctccaga tttatcagca ataaaccagc    3840
cagccggaag ggccgagcgc agaagtggtc ctgcaacttt atccgcctcc atccagtcta    3900
ttaattgttg ccgggaagct agagtaagta gttcgccagt taatagtttg cgcaacgttg    3960
ttgccattgc tacaggcatc gtggtgtcac gctcgtcgtt tggtatggct tcattcagct    4020
ccggttccca acgatcaagg cgagttacat gatccccat gttgtgcaaa aaagcggtta    4080
gctccttcgg tcctccgatc gttgtcagaa gtaagttggc cgcagtgtta tcactcatgg    4140
ttatggcagc actgcataat tctcttactg tcatgccatc cgtaagatgc ttttctgtga    4200
ctggtgagta ctcaaccaag tcattctgag aatagtgtat gcggcgaccg agttgctctt    4260
gcccggcgtc aatacgggat aataccgcgc cacatagcag aactttaaaa gtgctcatca    4320
ttggaaaacg ttcttcgggg cgaaaactct caaggatctt accgctgttg agatccagtt    4380
cgatgtaacc cactcgtgca cccaactgat cttcagcatc ttttactttc accagcgttt    4440
ctgggtgagc aaaaacagga aggcaaaatg ccgcaaaaaa gggaataagg gcgacacgga    4500
aatgttgaat actcatactc ttcctttttc aatattattg aagcatttat cagggttatt    4560
gtctcatgag cggatacata tttgaatgta tttagaaaaa taaacaaata ggggttccgc    4620
gcacatttcc ccgaaaagtg ccacctgacg tctaagaaac cattattatc atgacattaa    4680
```

| | |
|---|---|
| cctataaaaa taggcgtatc acgaggcccc tttcgtctcg cgcgtttcgg tgatgacggt | 4740 |
| gaaaacctct gacacatgca gctcccggag acggtcacag cttgtctgta agcggatgcc | 4800 |
| gggagcagac aagcccgtca gggcgcgtca gcgggtgttg gcgggtgtcg gggctggctt | 4860 |
| aactatgcgg catcagagca gattgtactg agagtgcacc atatgcggtg tgaaataccg | 4920 |
| cacagatgcg taaggagaaa ataccgcatc aggaaattgt aaacgttaat attttgttaa | 4980 |
| aattcgcgtt aaattttgt taaatcagct cattttttaa ccataggcc gaaatcggca | 5040 |
| aaatcccta taaatcaaaa gaatagaccg agatagggtt gagtgttgtt ccagtttgga | 5100 |
| acaagagtcc actattaaag aacgtggact ccaacgtcaa agggcgaaaa accgtctatc | 5160 |
| agggcgatgg cccactacgt gaaccatcac cctaatcaag ttttttgggg tcgaggtgcc | 5220 |
| gtaaagcact aaatcggaac cctaaaggga gccccgatt tagagcttga cggggaaagc | 5280 |
| cggcgaacgt ggcgagaaag gaagggaaga agcgaaagg agcgggcgct agggcgctgg | 5340 |
| caagtgtagc ggtcacgctg cgcgtaacca ccacacccgc cgcgcttaat gcgccgctac | 5400 |
| agggcgcgtc gcgccattcg ccattcaggc tacgcaactg ttgggaaggg cgatcggtgc | 5460 |
| gggcctcttc gctattacgc cagctggcga gggggggatg tgctgcaagg cgattaagtt | 5520 |
| gggtaacgcc agggttttcc cagtcacgac gttgtaaaac gacggccagt gaatt | 5575 |

<210> SEQ ID NO 74
<211> LENGTH: 1395
<212> TYPE: DNA
<213> ORGANISM: Homo sapiens

<400> SEQUENCE: 74

| | |
|---|---|
| atggacttca gcagaaatct ttatgatatt ggggaacaac tggacagtga agatctggcc | 60 |
| tccctcaagt tcctgagcct ggactacatt ccgcaaagga agcaagaacc catcaaggat | 120 |
| gccttgatgt tattccagag actccaggaa aagagaatgt tggaggaaag caatctgtcc | 180 |
| ttcctgaagg agctgctctt ccgaattaat agactggatt tgctgattac ctacctaaac | 240 |
| actagaaagg aggagatgga agggaactt cagacaccag gcagggctca aatttctgcc | 300 |
| tacagggtca tgctctatca gatttcagaa gaagtgagca gatcagaatt gaggtctttt | 360 |
| aagtttcttt tgcaagagga aatctccaaa tgcaaactgg atgatgacat gaacctgctg | 420 |
| gatatttca tagagatgga aagagggtc atcctgggag aaggaaagtt ggacatcctg | 480 |
| aaaagagtct gtgcccaaat caacaagagc ctgctgaaga taatcaacga ctatgaagaa | 540 |
| ttcagcaaag gggaggagtt gtgtggggta atgacaatct cggactctcc aagagaacag | 600 |
| gatagtgaat cacagacttt ggacaaagtt taccaaatga aaagcaaacc tcggggatac | 660 |
| tgtctgatca tcaacaatca cattttgca aaagcacggg agaaagtgcc caaacttcac | 720 |
| agcattaggg acaggaatgg aacacacttg gatgcagggg cttttgaccac gacctttgaa | 780 |
| gagcttcatt ttgagatcaa gccccacgat gactgcacag tagagcaaat ctatgagatt | 840 |
| ttgaaaatct accaactcat ggaccacagt aacatggact gcttcatctg ctgtatcctc | 900 |
| tcccatggag acaagggcat catctatggc actgatggac aggaggcccc catctatgag | 960 |
| ctgacatctc agttcactgg tttgaagtgc cctttccttg ctggaaaacc caaagtgttt | 1020 |
| tttattcagg cttgtcaggg ggataactac cagaaaggta tacctgttga gactgattca | 1080 |
| gaggagcaac cctatttaga aatggattta tcatcacctc aaacgagata tatcccggat | 1140 |
| gaggctgact ttctgctggg gatggccact gtgaataact gtgttcctac cgaaaccct | 1200 |
| gcagagggaa cctggtacat ccagtcactt tgccagagcc tgagagagcg atgtcctcga | 1260 |

```
ggcgatgata ttctcaccat cctgactgaa gtgaactatg aagtaagcaa caaggatgac    1320
aagaaaaaca tggggaaaca gatgcctcag cctactttca cactaagaaa aaaacttgtc    1380
ttcccttctg attga                                                     1395
```

<210> SEQ ID NO 75
<211> LENGTH: 464
<212> TYPE: PRT
<213> ORGANISM: Homo sapiens

<400> SEQUENCE: 75

```
Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Gly Glu Glu Leu Cys Gly Val Met Thr
            180                 185                 190

Ile Ser Asp Ser Pro Arg Glu Gln Asp Ser Glu Ser Gln Thr Leu Asp
        195                 200                 205

Lys Val Tyr Gln Met Lys Ser Lys Pro Arg Gly Tyr Cys Leu Ile Ile
    210                 215                 220

Asn Asn His Asn Phe Ala Lys Ala Arg Glu Lys Val Pro Lys Leu His
225                 230                 235                 240

Ser Ile Arg Asp Arg Asn Gly Thr His Leu Asp Ala Gly Ala Leu Thr
                245                 250                 255

Thr Thr Phe Glu Glu Leu His Phe Glu Ile Lys Pro His Asp Asp Cys
            260                 265                 270

Thr Val Glu Gln Ile Tyr Glu Ile Leu Lys Ile Tyr Gln Leu Met Asp
        275                 280                 285

His Ser Asn Met Asp Cys Phe Ile Cys Cys Ile Leu Ser His Gly Asp
    290                 295                 300

Lys Gly Ile Ile Tyr Gly Thr Asp Gly Gln Glu Ala Pro Ile Tyr Glu
305                 310                 315                 320

Leu Thr Ser Gln Phe Thr Gly Leu Lys Cys Pro Ser Leu Ala Gly Lys
                325                 330                 335

Pro Lys Val Phe Phe Ile Gln Ala Cys Gln Gly Asp Asn Tyr Gln Lys
```

```
                  340                 345                 350
Gly Ile Pro Val Glu Thr Asp Ser Glu Glu Gln Pro Tyr Leu Glu Met
            355                 360                 365

Asp Leu Ser Ser Pro Gln Thr Arg Tyr Ile Pro Asp Glu Ala Asp Phe
        370                 375                 380

Leu Leu Gly Met Ala Thr Val Asn Asn Cys Val Ser Tyr Arg Asn Pro
385                 390                 395                 400

Ala Glu Gly Thr Trp Tyr Ile Gln Ser Leu Cys Gln Ser Leu Arg Glu
                405                 410                 415

Arg Cys Pro Arg Gly Asp Asp Ile Leu Thr Ile Leu Thr Glu Val Asn
            420                 425                 430

Tyr Glu Val Ser Asn Lys Asp Lys Lys Asn Met Gly Lys Gln Met
        435                 440                 445

Pro Gln Pro Thr Phe Thr Leu Arg Lys Lys Leu Val Phe Pro Ser Asp
    450                 455                 460
```

<210> SEQ ID NO 76
<211> LENGTH: 5471
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76

```
gtcgacttct gaggcggaaa gaaccagctg tggaatgtgt gtcagttagg gtgtggaaag    60
tccccaggct ccccagcagg cagaagtatg caaagcatgc atctcaatta gtcagcaacc   120
aggtgtggaa agtccccagg ctccccagca ggcagaagta tgcaaagcat gcatctcaat   180
tagtcagcaa ccatagtccc gcccctaact ccgcccatcc cgcccctaac tccgcccagt   240
tccgcccatt ctccgcccca tggctgacta atttttttta tttatgcaga ggccgaggcc   300
gcctcggcct ctgagctatt ccagaagtag tgaggaggct tttttggagg cctaggcttt   360
tgcaaaaagc tggatcgatc ctgagaactt cagggtgagt ttggggaccc ttgattgttc   420
tttcttttc gctattgtaa aattcatgtt atatggaggg gcaaagtttt cagggtgtt    480
gtttagaatg ggaagatgtc ccttgtatca ccatggaccc tcatgataat tttgtttctt   540
tcactttcta ctctgttgac aaccattgtc tcctcttatt ttcttttcat tttctgtaac   600
ttttcgtta acttttagct tgcatttgta acgaattttt aaattcactt tgtttatt    660
gtcagattgt aagtactttc tctaatcact ttttttcaa gcaatcagg gtatattata    720
ttgtacttca gcacagtttt agagaacaat tgttataatt aaatgataag gtagaatatt   780
tctgcatata aattctggct ggcgtggaaa tattcttatt ggtagaaaca actacatcct   840
ggtcatcatc ctgcctttct ctttatggtt acaatgatat acactgtttg agatgaggat   900
aaaatactct gagtccaaac cgggcccctc tgctaaccat gttcatgcct tcttctttt    960
cctacagctc ctgggcaacg tgctggttat tgtgctgtct catcattttg gcaagaatt   1020
gtaatacgac tcactatagg gcgaattcat ggacttcagc agaaatcttt atgatattgg   1080
ggaacaactg gacagtgaag atctggcctc cctcaagttc ctgagcctgg actacattcc   1140
gcaaaggaag caagaaccca tcaaggatgc cttgatgtta ttccagagac tccaggaaaa   1200
gagaatgttg gaggaaagca atcgtcctt cctgaaggag ctgctcttcc gaattaatag   1260
actggatttg ctgattaccct acctaaacac tagaaaggag gagatggaaa gggaacttca   1320
gacaccaggc agggctcaaa tttctgccta cagggtcatg ctctatcaga tttcagaaga   1380
```

```
agtgagcaga tcagaattga ggtcttttaa gtttcttttg caagaggaaa tctccaaatg   1440
caaactggat gatgacatga acctgctgga tattttcata gagatggaga agagggtcat   1500
cctgggagaa ggaaagttgg acatcctgaa aagagtctgt gcccaaatca acaagagcct   1560
gctgaagata atcaacgact atgaagaatt cagcaaaggg gaggagttgt gtggggtaat   1620
gacaatctcg gactctccaa gagaacagga tagtgaatca cagactttgg acaaagttta   1680
ccaaatgaaa agcaaacctc gggatactgt ctgatcatca acaatcacaa ttttgcaaaa   1740
gcacgggaga aagtgcccca aacttcacag cattagggac aggaatggaa cacacttgga   1800
tgcaggggct ttgaccacga cctttgaaga gcttcatttt gagatcaagc ccacgatga   1860 ctgcacagta gagcaaatct atgagatttt gaaaatctac caactcatgg accacagtaa   1920
catggactgc ttcatctgct gtatcctctc ccatggagac aagggcatca tctatggcac   1980
tgatggacag gaggccccca tctatgagct gacatctcag ttcactggtt gaagtgccc   2040 ttcccttgct ggaaaaccca aagtgttttt tattcaggct tgtcagggg ataactacca   2100 gaaaggtata cctgttgaga ctgattcaga ggagcaaccc tatttagaaa tggatttatc   2160
atcacctcaa acgagatata tcccggatga ggctgacttt ctgctgggga tggccactgt   2220
gaataactgt gtttcctacc gaaaccctgc agagggaacc tggtacatcc agtcactttg   2280
ccagagcctg agagagcgat gtcctcgagg cgatgatatt ctcaccatcc tgactgaagt   2340
gaactatgaa gtaagcaaca aggatgacaa gaaaaacatg gggaaacaga tgcctcagcc   2400
tactttcaca ctaagaaaaa aacttgtctt cccttctgat tgaggatcca gatcttatta   2460
aagcagaact tgtttattgc agcttataat ggttacaaat aaagcaatag catcacaaat   2520
ttcacaaata aagcattttt ttcactgcat tctagttgtg gtttgtccaa actcatcaat   2580
gtatcttatc atgtctggtc gactctagac tcttccgctt cctcgctcac tgactcgctg   2640
cgctcggtcg ttcggctgcg gcgagcggta tcagctcact caaaggcggt aatacggtta   2700
tccacagaat caggggataa cgcaggaaag aacatgtgag caaaaggcca gcaaaaggcc   2760
aggaaccgta aaaaggccgc gttgctggcg ttttttccata ggctccgccc ccctgacgag   2820
catcacaaaa atcgacgctc aagtcagagg tggcgaaacc cgacaggact ataaagatac   2880
caggcgtttc cccctggaag ctccctcgtg cgctctcctg ttccgaccct gccgcttacc   2940
ggatacctgt ccgcctttct cccttcggga agcgtggcgc tttctcaatg ctcacgctgt   3000
aggtatctca gttcggtgta ggtcgttcgc tccaagctgg gctgtgtgca cgaaccccc   3060 gttcagcccg accgctgcgc cttatccggt aactatcgtc ttgagtccaa cccggtaaga   3120
cacgacttat cgccactggc agcagccact ggtaacagga ttagcagagc gaggtatgta   3180
ggcggtgcta cagagttctt gaagtggtgg cctaactacg gctacactag aaggacagta   3240
tttggtatct gcgctctgct gaagccagtt accttcggaa aaagagttgg tagctcttga   3300
tccggcaaac aaaccaccgc tggtagcggt ggttttttg tttgcaagca gcagattacg   3360
cgcagaaaaa aaggatctca agaagatcct ttgatctttt ctacggggtc tgacgctcag   3420
tggaacgaaa actcacgtta agggattttg gtcatgagat tatcaaaaag gatcttcacc   3480
tagatccttt taaattaaaa atgaagtttt aaatcaatct aaagtatata tgagtaaact   3540
tggtctgaca gttaccaatg cttaatcagt gaggcaccta tctcagcgat ctgtctattt   3600
cgttcatcca tagttgcctg actccccgtc gtgtagataa ctacgatacg ggagggctta   3660
ccatctggcc ccagtgctgc aatgataccg cgagacccac gctcaccggc tccagattta   3720
```

```
tcagcaataa accagccagc cggaagggcc gagcgcagaa gtggtcctgc aactttatcc    3780
gcctccatcc agtctattaa ttgttgccgg gaagctagag taagtagttc gccagttaat    3840
agtttgcgca acgttgttgc cattgctaca ggcatcgtgg tgtcacgctc gtcgtttggt    3900
atggcttcat tcagctccgg ttcccaacga tcaaggcgag ttacatgatc ccccatgttg    3960
tgcaaaaaag cggttagctc cttcggtcct ccgatcgttg tcagaagtaa gttggccgca    4020
gtgttatcac tcatggttat ggcagcactg cataattctc ttactgtcat gccatccgta    4080
agatgctttt ctgtgactgg tgagtactca accaagtcat tctgagaata gtgtatgcgg    4140
cgaccgagtt gctcttgccc ggcgtcaata cgggataata ccgcgccaca tagcagaact    4200
ttaaaagtgc tcatcattgg aaaacgttct cggggcgaaa actctcaag  gatcttaccg    4260
ctgttgagat ccagttcgat gtaacccact cgtgcaccca actgatcttc agcatctttt    4320
actttcacca gcgtttctgg gtgagcaaaa acaggaaggc aaaatgccgc aaaaaaggga    4380
ataagggcga cacggaaatg ttgaatactc atactcttct ttttcaata ttattgaagc     4440
atttatcagg gttattgtct catgagcgga tacatatttg aatgtattta gaaaaataaa    4500
caaatagggg ttccgcgcac atttccccga aaagtgccac ctgacgtcta gaaaccatt     4560
attatcatga cattaaccta aaaaatagg cgtatcacga ggcccctttc gtctcgcgcg     4620
tttcggtgat gacggtgaaa acctctgaca catgcagctc ccggagacgg tcacagcttg    4680
tctgtaagcg gatgccggga gcagacaagc ccgtcagggc gcgtcagcgg gtgttggcgg    4740
gtgtcggggc tggcttaact atgcggcatc agagcagatt gtactgagag tgcaccatat    4800
gcggtgtgaa ataccgcaca gatgcgtaag gagaaaatac cgcatcagga aattgtaaac    4860
gttaatattt tgttaaaatt cgcgttaaat ttttgttaaa tcagctcatt ttttaaccaa    4920
taggccgaaa tcggcaaaat cccttataaa tcaaagaat agaccgagat agggttgagt     4980
gttgttccag tttggaacaa gagtccacta ttaaagaacg tggactccaa cgtcaaaggg    5040
cgaaaaaccg tctatcaggg cgatggccca ctacgtgaac catcacccta atcaagtttt    5100
ttggggtcga ggtgccgtaa agcactaaat cggaaccta aagggagccc ccgatttaga     5160
gcttgacggg gaaagccggc gaacgtggcg agaaaggaag ggaagaaagc gaaggagcg     5220
ggcgctaggg cgctggcaag tgtagcggtc acgctgcgcg taaccaccac acccgccgcg    5280
cttaatgcgc cgctacaggg cgcgtcgcgc cattcgccat tcaggctacg caactgttgg    5340
gaagggcgat cggtgcgggc ctcttcgcta ttacgccagc tggcgaaggg gggatgtgct    5400
gcaaggcgat taagttgggt aacgccaggg ttttcccagt cacgacgttg taaaacgacg    5460
gccagtgaat t                                                         5471
```

<210> SEQ ID NO 77
<211> LENGTH: 618
<212> TYPE: DNA
<213> ORGANISM: Homo sapiens

<400> SEQUENCE: 77

```
atggcgcacg ctgggagaac agggtacgat aaccgggaga tagtgatgaa gtacatccat      60
tataagctgt cgcagagggg ctacgagtgg gatgcgggca atgtgggcgc cgcgcccccg     120
ggggccgccc ccgcaccggg catcttctcc tcccagcccg ggcacacgcc ccatccagcc     180
gcatcccggg acccggtcgc caggacctcg ccgctgcaga cccggctgc ccccggcgcc     240
gccgcggggc ctgcgctcag cccggtgcca cctgtggtcc acctgaccct ccgccaggcc     300
ggcgacgact tctcccgccg ctaccgccgc gacttcgccg agatgtccag ccagctgcac    360
```

```
ctgacgccct tcaccgcgcg gggacgcttt gccacggtgg tggaggagct cttcagggac      420
ggggtgaact gggggaggat tgtggccttc tttgagttcg gtggggtcat gtgtgtggag      480
agcgtcaacc gggagatgtc gccctggtg dacaacatcg ccctgtggat gactgagtac      540
ctgaaccggc acctgcacac ctggatccag gataacggag ctgggtagg tgcacttggt      600 gatgtgagtc tgggctga                                                    618
```

<210> SEQ ID NO 78
<211> LENGTH: 205
<212> TYPE: PRT
<213> ORGANISM: Homo sapiens

<400> SEQUENCE: 78

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Val Gly Ala Leu Gly Asp Val Ser Leu Gly
        195                 200                 205
```

<210> SEQ ID NO 79
<211> LENGTH: 4699
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
gtcgacttct gaggcggaaa gaaccagctg tggaatgtgt gtcagttagg gtgtggaaag      60
tccccaggct cccagcagg cagaagtatg caaagcatgc atctcaatta gtcagcaacc       120
aggtgtggaa agtccccagg ctccccagca ggcagaagta tgcaaagcat gcatctcaat      180
tagtcagcaa ccatagtccc gcccctaact ccgcccatcc cgcccctaac tccgccagt      240 tccgcccatt ctccgcccca tggctgacta attttttta tttatgcaga ggccgaggcc      300
```

```
gcctcggcct ctgagctatt ccagaagtag tgaggaggct ttttggagg cctaggcttt      360 tgcaaaaagc tggatcgatc ctgagaactt cagggtgagt ttggggaccc ttgattgttc      420 tttcttttc gctattgtaa aattcatgtt atatggaggg ggcaaagttt tcagggtgtt      480
gtttagaatg ggaagatgtc ccttgtatca ccatggaccc tcatgataat tttgtttctt      540
tcactttcta ctctgttgac aaccattgtc tcctcttatt ttcttttcat tttctgtaac      600
tttttcgtta aactttagct tgcatttgta acgaattttt aaattcactt ttgtttattt      660
gtcagattgt aagtactttc tctaatcact ttttttcaa ggcaatcagg gtatattata      720
ttgtacttca gcacagtttt agagaacaat tgttataatt aaatgataag gtagaatatt      780
tctgcatata aattctggct ggcgtggaaa tattcttatt ggtagaaaca actacatcct      840
ggtcatcatc ctgcctttct ctttatggtt acaatgatat acactgtttg agatgaggat      900
aaaatactct gagtccaaac cgggcccctc tgctaaccat gttcatgcct tcttcttttt      960
cctacagctc ctgggcaacg tgctggttat tgtgctgtct catcattttg gcaaagaatt     1020
gtaatacgac tcactatagg gcgaattcgg atccagatct atggcgcacg ctgggagaac     1080
agggtacgat aaccgggaga tagtgatgaa gtacatccat tataagctgt cgcagagggg     1140
ctacgagtgg gatgcgggag atgtgggcgc gcgcccccg ggggccgccc ccgcaccggg     1200
catcttctcc tcccagcccg ggcacacgcc ccatccagcc gcatcccggg acccggtcgc     1260
caggacctcg ccgctgcaga ccccggctgc ccccggcgcc gccgcgggc ctgcgctcag     1320 cccggtgcca cctgtggtcc acctgaccct ccgccaggcc ggcgacgact tctcccgccg     1380
ctaccgccgc gacttcgccg agatgtccag ccagctgcac ctgacgccct tcaccgcgcg     1440
gggacgcttt gccacggtgg tggaggagct cttcagggac ggggtgaact ggggaggat     1500 tgtggccttc tttgagttcg gtggggtcat gtgtgtggag agcgtcaacc gggagatgtc     1560 gccctggtg gacaacatcg ccctgtggat gactgagtac ctgaaccggc acctgcacac     1620
ctggatccag gataacggag gctgggtagg tgcacttggt gatgtgagtc tgggctgaag     1680
atcttattaa agcagaactt gtttattgca gcttataatg gttacaaata aagcaatagc     1740
atcacaaatt tcacaaataa agcatttttt tcactgcatt ctagttgtgg tttgtccaaa     1800
ctcatcaatg tatcttatca tgtctggtcg actctagact cttccgcttc ctcgctcact     1860
gactcgctgc gctcggtcgt tcggctgcgg cgagcggtat cagctcactc aaaggcggta     1920
atacggttat ccacagaatc aggggataac gcaggaaaga acatgtgagc aaaaggccag     1980
caaaaggcca ggaaccgtaaa aaggccgcgt tgctggcgtt tttccatagg ctccgccccc     2040
ctgacgagca tcacaaaaat cgacgctcaa gtcagaggtg gcgaaacccg acaggactat     2100
aaagatacca ggcgtttccc cctggaagct ccctcgtgcg ctctcctgtt ccgaccctgc     2160
cgcttaccgg atacctgtcc gcctttctcc cttcgggaag cgtggcgctt tctcaatgct     2220
cacgctgtag gtatctcagt tcggtgtagg tcgttcgctc caagctgggc tgtgtgcacg     2280
aaccccccgt tcagcccgac cgctgcgcct tatccggtaa ctatcgtctt gagtccaacc     2340
cggtaagaca cgacttatcg ccactggcag cagccactgg taacaggatt agcagagcga     2400
ggtatgtagg cggtgctaca gagttcttga agtggtggcc taactacggc tacactagaa     2460
ggacagtatt tggtatctgc gctctgctga agccagttac cttcggaaaa agagttggta     2520
gctcttgatc cggcaaacaa accaccgctg gtagcggtgg ttttttgtt tgcaagcagc     2580 agattacgcg cagaaaaaaa ggatctcaag aagatccttt gatctttct acggggtctg     2640 acgctcagtg gaacgaaaac tcacgttaag ggattttggt catgagatta tcaaaaagga     2700
```

```
tcttcaccta gatcctttta aattaaaaat gaagttttaa atcaatctaa agtatatatg    2760
agtaaacttg gtctgacagt taccaatgct taatcagtga ggcacctatc tcagcgatct    2820
gtctatttcg ttcatccata gttgcctgac tccccgtcgt gtagataact acgatacggg    2880
agggcttacc atctggcccc agtgctgcaa tgataccgcg agaccacgc tcaccggctc     2940 cagatttatc agcaataaac cagccagccg gaagggccga gcgcagaagt ggtcctgcaa    3000
ctttatccgc ctccatccag tctattaatt gttgccggga agctagagta agtagttcgc    3060
cagttaatag tttgcgcaac gttgttgcca ttgctacagg catcgtggtg tcacgctcgt    3120
cgtttggtat ggcttcattc agctccggtt cccaacgatc aaggcgagtt acatgatccc    3180
ccatgttgtg caaaaaagcg gttagctcct tcggtcctcc gatcgttgtc agaagtaagt    3240
tggccgcagt gttatcactc atggttatgg cagcactgca taattctctt actgtcatgc    3300
catccgtaag atgcttttct gtgactggtg agtactcaac caagtcattc tgagaatagt    3360
gtatgcggcg accgagttgc tcttgcccgg cgtcaatacg ggataatacc gcgccacata    3420
gcagaacttt aaaagtgctc atcattggaa aacgttcttc ggggcgaaaa ctctcaagga    3480
tcttaccgct gttgagatcc agttcgatgt aacccactcg tgcacccaac tgatcttcag    3540
catcttttac tttcaccagc gtttctgggt gagcaaaaac aggaaggcaa aatgccgcaa    3600
aaaagggaat aagggcgaca cggaaatgtt gaatactcat actcttcttt tttcaatatt    3660
attgaagcat ttatcagggt tattgtctca tgagcggata catatttgaa tgtatttaga    3720
aaaataaaca aataggggtt ccgcgcacat ttccccgaaa agtgccacct gacgtctaag    3780
aaaccattat tatcatgaca ttaacctata aaaataggcg tatcacgagg ccctttcgt    3840 ctcgcgcgtt tcggtgatga cggtgaaaac ctctgacaca tgcagctccc ggagacggtc    3900
acagcttgtc tgtaagcgga tgccgggagc agacaagccc gtcagggcgc gtcagcgggt    3960
gttggcgggt gtcggggctg gcttaactat gcggcatcag agcagattgt actgagagtg    4020
caccatatgc ggtgtgaaat accgcacaga tgcgtaagga gaaaataccg catcaggaaa    4080
ttgtaaacgt taatattttg ttaaaattcg cgttaaattt ttgttaaatc agctcatttt    4140
ttaaccaata ggccgaaatc ggcaaaatcc cttataaatc aaaagaatag accgagatag    4200
ggttgagtgt tgttccagtt tggaacaaga gtccactatt aaagaacgtg gactccaacg    4260 tcaagggcg aaaaccgtc tatcagggcg atggcccact acgtgaacca tcaccctaat    4320
caagtttttt ggggtcgagg tgccgtaaag cactaaatcg gaaccctaaa gggagccccc    4380
gatttagagc ttgacgggga agccggcga acgtggcgag aaaggaaggg aagaaagcga    4440
aaggagcggg cgctagggcg ctggcaagtg tagcggtcac gctgcgcgta accaccacac    4500
ccgccgcgct taatgcgccg ctacaggcg cgtcgcgcca ttcgccattc aggctacgca    4560
actgttggga agggcgatcg gtgcgggcct cttcgctatt acgccagctg gcgaaggggg    4620
gatgtgctgc aaggcgatta agttgggtaa cgccagggtt ttcccagtca cgacgttgta    4680
aaacgacggc cagtgaatt                                                 4699
```

<210> SEQ ID NO 80
<211> LENGTH: 5471
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80

```
gtcgacttct gaggcggaaa gaaccagctg tggaatgtgt gtcagttagg gtgtggaaag      60
tccccaggct ccccagcagg cagaagtatg caaagcatgc atctcaatta gtcagcaacc     120
aggtgtggaa agtccccagg ctccccagca ggcagaagta tgcaaagcat gcatctcaat     180
tagtcagcaa ccatagtccc gcccctaact ccgcccatcc cgcccctaac tccgcccagt     240
tccgcccatt ctccgcccca tggctgacta atttttttta tttatgcaga ggccgaggcc     300
gcctcggcct ctgagctatt ccagaagtag tgaggaggct tttttggagg cctaggcttt     360
tgcaaaaagc tggatcgatc ctgagaactt cagggtgagt ttggggaccc ttgattgttc     420 tttcttttc gctattgtaa aattcatgtt atatggaggg ggcaaagttt cagggtgtt      480 gtttagaatg ggaagatgtc ccttgtatca ccatggaccc tcatgataat tttgtttctt     540
tcactttcta ctctgttgac aaccattgtc tcctcttatt ttcttttcat tttctgtaac     600
tttttcgtta aactttagct tgcatttgta acgaattttt aaattcactt ttgtttattt     660
gtcagattgt aagtactttc tctaatcact ttttttcaa ggcaatcagg gtatattata      720
ttgtacttca gcacagtttt agagaacaat tgttataatt aaatgataag gtagaatatt     780
tctgcatata aattctggct ggcgtggaaa tattcttatt ggtagaaaca actacatcct     840
ggtcatcatc ctgcctttct ctttatggtt acaatgatat acactgtttg agatgaggat     900
aaaatactct gagtccaaac cgggcccctc tgctaaccat gttcatgcct tcttcttttt     960
cctacagctc ctgggcaacg tgctggttat tgtgctgtct catcattttg gcaagaatt    1020 gtaatacgac tcactatagg gcgaattcgg atccatggac ttcagcagaa atctttatga    1080
tattggggaa caactggaca gtgaagatct ggcctccctc aagttcctga gcctggacta    1140
cattccgcaa aggaagcaag aacccatcaa ggatgccttg atgttattcc agagactcca    1200
ggaaaagaga atgttggagg aaagcaatct gtccttcctg aaggagctgc tcttccgaat    1260
taatagactg gatttgctga ttacctacct aaacactaga aaggaggaga tggaaaggga    1320
acttcagaca ccaggcaggg ctcaaatttc tgcctacagg gtcatgctct atcagatttc    1380
agaagaagtg agcagatcag aattgaggtc ttttaagttt cttttgcaag aggaaatctc    1440
caaatgcaaa ctggatgatg acatgaacct gctggatatt ttcatagaga tggagaagag    1500
ggtcatcctg ggagaaggaa agttggacat cctgaaaaga gtctgtgccc aaatcaacaa    1560
gagcctgctg aagataatca cgactatga agaattcagc aaaggggagg agttgtgtgg    1620
ggtaatgaca atctcggact ctccaagaga acaggatagt gaatcacaga ctttggacaa    1680
agtttaccaa atgaaaagca aacctcgggg atactgtctg atcatcaaca atcacaattt    1740
tgcaaaagca cgggagaaag tgcccaaact tcacagcatt agggacagga atggaacaca    1800
cttggatgca ggggctttga ccacgacctt tgaagagctt cattttgaga tcaagccccca    1860 cgatgactgc acagtagagc aaatctatga gatttttgaaa atctaccaac tcatggacca    1920
cagtaacatg gactgcttca tctgctgtat cctctcccat ggagacaagg gcatcatcta    1980
tggcactgat ggacaggagg cccccatcta tgagctgaca tctcagttca ctggtttgaa    2040
gtgcccttcc cttgctggaa acccaaaagt gttttttatt caggcttctc aggggggataa    2100 ctaccagaaa ggtatacctg ttgagactga ttcagaggag caaccctatt tagaaatgga    2160
tttatcatca cctcaaacga gatatatccc ggatgaggct gactttctgc tggggatggc    2220
cactgtgaat aactgtgttt cctaccgaaa ccctgcagag ggaacctggt acatccagtc    2280
actttgccag agcctgagag agcgatgtcc tcgaggcgat gatattctca ccatcctgac    2340
```

```
tgaagtgaac tatgaagtaa gcaacaagga tgacaagaaa acatggggga aacagatgcc    2400
tcagcctact ttcacactaa gaaaaaaact tgtcttccct tctgattgaa gatcttatta    2460
aagcagaact tgtttattgc agcttataat ggttacaaat aaagcaatag catcacaaat    2520
ttcacaaata aagcattttt ttcactgcat tctagttgtg gtttgtccaa actcatcaat    2580
gtatcttatc atgtctggtc gactctagac tcttccgctt cctcgctcac tgactcgctg    2640
cgctcggtcg ttcggctgcg gcgagcggta tcagctcact caaaggcggt aatacggtta    2700
tccacagaat caggggataa cgcaggaaag aacatgtgag caaaaggcca gcaaaaggcc    2760
aggaaccgta aaaaggccgc gttgctggcg ttttttccata ggctccgccc ccctgacgag    2820
catcacaaaa atcgacgctc aagtcagagg tggcgaaacc cgacaggact ataaagatac    2880
caggcgtttc cccctggaag ctccctcgtg cgctctcctg ttccgaccct gccgcttacc    2940
ggatacctgt ccgcctttct cccttcggga agcgtggcgc tttctcaatg ctcacgctgt    3000
aggtatctca gttcggtgta ggtcgttcgc tccaagctgg gctgtgtgca cgaaccccc    3060 gttcagcccg accgctgcgc cttatccggt aactatcgtc ttgagtccaa cccggtaaga    3120
cacgacttat cgccactggc agcagccact ggtaacagga ttagcagagc gaggtatgta    3180
ggcggtgcta cagagttctt gaagtggtgg cctaactacg gctacactag aaggacagta    3240
tttggtatct gcgctctgct gaagccagtt accttcggaa aaagagttgg tagctcttga    3300
tccggcaaac aaaccaccgc tggtagcggt ggttttttg tttgcaagca gcagattacg    3360
cgcagaaaaa aaggatctca agaagatcct ttgatctttt ctacggggtc tgacgctcag    3420
tggaacgaaa actcacgtta agggattttg gtcatgagat tatcaaaaag gatcttcacc    3480
tagatccttt taaattaaaa atgaagtttt aaatcaatct aaagtatata tgagtaaact    3540
tggtctgaca gttaccaatg cttaatcagt gaggcaccta tctcagcgat ctgtctattt    3600
cgttcatcca tagttgcctg actccccgtc gtgtagataa ctacgatacg ggagggctta    3660
ccatctggcc ccagtgctgc aatgatacCg cgagacccac gctcaccggc tccagattta    3720
tcagcaataa accagccagc cggaagggcc gagcgcagaa gtggtcctgc aactttatcc    3780
gcctccatcc agtctattaa ttgttgccgg gaagctagag taagtagttc gccagttaat    3840
agtttgcgca acgttgttgc cattgctaca ggcatcgtgg tgtcacgctc gtcgtttggt    3900
atggcttcat tcagctccgg ttcccaacga tcaaggcgag ttacatgatc ccccatgttg    3960
tgcaaaaaag cggttagctc cttcggtcct ccgatcgttg tcagaagtaa gttggccgca    4020
gtgttatcac tcatggttat ggcagcactg cataattctc ttactgtcat gccatccgta    4080
agatgctttt ctgtgactgg tgagtactca accaagtcat tctgagaata gtgtatgcgg    4140
cgaccgagtt gctcttgccc ggcgtcaata cgggataata ccgcgccaca tagcagaact    4200
ttaaaagtgc tcatcattgg aaaacgttct cggggcgaa aactctcaag gatcttaccg    4260
ctgttgagat ccagttcgat gtaacccact cgtgcaccca actgatcttc agcatctttt    4320
actttcacca gcgtttctgg gtgagcaaaa acaggaaggc aaaatgccgc aaaaaaggga    4380
ataagggcga cacggaaatg ttgaatactc atactcttct tttttcaata ttattgaagc    4440
atttatcagg gttattgtct catgagcgga tacatatttg aatgtattta gaaaaataaa    4500
caaatagggg ttccgcgcac atttccccga aaagtgccac ctgacgtcta agaaaccatt    4560
attatcatga cattaaccta taaaaatagg cgtatcacga ggccccttc gtctcgcgcg    4620 tttcggtgat gacggtgaaa acctctgaca catgcagctc ccgagacgg tcacagcttg    4680 tctgtaagcg gatgccggga gcagacaagc ccgtcagggc gcgtcagcgg gtgttggcgg    4740
```

-continued

```
gtgtcggggc tggcttaact atgcggcatc agagcagatt gtactgagag tgcaccatat   4800
gcggtgtgaa ataccgcaca gatgcgtaag gagaaaatac cgcatcagga aattgtaaac   4860
gttaatattt tgttaaaatt cgcgttaaat ttttgttaaa tcagctcatt ttttaaccaa   4920
taggccgaaa tcggcaaaat cccttataaa tcaaaagaat agaccgagat agggttgagt   4980
gttgttccag tttggaacaa gagtccacta ttaagaacg tggactccaa cgtcaaggg    5040 cgaaaaaccg tctatcaggg cgatggccca ctacgtgaac catcacccta atcaagtttt   5100
ttggggtcga ggtgccgtaa agcactaaat cggaacccta agggagcccc cgatttaga    5160 gcttgacggg gaaagccggc gaacgtggcg agaaaggaag gaagaaagc gaaggagcg     5220 ggcgctaggg cgctggcaag tgtagcggtc acgctgcgcg taaccaccac acccgccgcg   5280
cttaatgcgc cgctacaggg cgcgtcgcgc cattcgccat tcaggctacg caactgttgg   5340
gaagggcgat cggtgcgggc ctcttcgcta ttacgccagc tggcgaaggg gggatgtgct   5400
gcaaggcgat taagttgggt aacgccaggg ttttcccagt cacgacgttg taaaacgacg   5460
gccagtgaat t                                                        5471
```

<210> SEQ ID NO 81
<211> LENGTH: 464
<212> TYPE: PRT
<213> ORGANISM: Homo sapiens

<400> SEQUENCE: 81

```
Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Gly Glu Glu Leu Cys Gly Val Met Thr
            180                 185                 190

Ile Ser Asp Ser Pro Arg Glu Gln Asp Ser Glu Ser Gln Thr Leu Asp
        195                 200                 205

Lys Val Tyr Gln Met Lys Ser Lys Pro Arg Gly Tyr Cys Leu Ile Ile
    210                 215                 220

Asn Asn His Asn Phe Ala Lys Ala Arg Glu Lys Val Pro Lys Leu His
225                 230                 235                 240
```

Ser Ile Arg Asp Arg Asn Gly Thr His Leu Asp Ala Gly Ala Leu Thr
            245                 250                 255

Thr Thr Phe Glu Glu Leu His Phe Glu Ile Lys Pro His Asp Asp Cys
        260                 265                 270

Thr Val Glu Gln Ile Tyr Glu Ile Leu Lys Ile Tyr Gln Leu Met Asp
    275                 280                 285

His Ser Asn Met Asp Cys Phe Ile Cys Cys Ile Leu Ser His Gly Asp
290                 295                 300

Lys Gly Ile Ile Tyr Gly Thr Asp Gly Gln Glu Ala Pro Ile Tyr Glu
305                 310                 315                 320

Leu Thr Ser Gln Phe Thr Gly Leu Lys Cys Pro Ser Leu Ala Gly Lys
            325                 330                 335

Pro Lys Val Phe Phe Ile Gln Ala Ser Gln Gly Asp Asn Tyr Gln Lys
        340                 345                 350

Gly Ile Pro Val Glu Thr Asp Ser Glu Glu Gln Pro Tyr Leu Glu Met
    355                 360                 365

Asp Leu Ser Ser Pro Gln Thr Arg Tyr Ile Pro Asp Glu Ala Asp Phe
370                 375                 380

Leu Leu Gly Met Ala Thr Val Asn Asn Cys Val Ser Tyr Arg Asn Pro
385                 390                 395                 400

Ala Glu Gly Thr Trp Tyr Ile Gln Ser Leu Cys Gln Ser Leu Arg Glu
            405                 410                 415

Arg Cys Pro Arg Gly Asp Asp Ile Leu Thr Ile Leu Thr Glu Val Asn
        420                 425                 430

Tyr Glu Val Ser Asn Lys Asp Asp Lys Lys Asn Met Gly Lys Gln Met
    435                 440                 445

Pro Gln Pro Thr Phe Thr Leu Arg Lys Lys Leu Val Phe Pro Ser Asp
450                 455                 460

<210> SEQ ID NO 82
<211> LENGTH: 5327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
gtcgacttct gaggcggaaa gaaccagctg tggaatgtgt gtcagttagg gtgtggaaag      60
tccccaggct ccccagcagg cagaagtatg caaagcatgc atctcaatta gtcagcaacc     120
aggtgtggaa agtccccagg ctccccagca ggcagaagta tgcaaagcat gcatctcaat     180
tagtcagcaa ccatagtccc gcccctaact ccgcccatcc cgcccctaac tccgcccagt     240
tccgcccatt ctccgcccca tggctgacta attttttttta tttatgcaga ggccgaggcc     300
gcctcggcct ctgagctatt ccagaagtag tgaggaggct ttttttggagg cctaggcttt     360 tgcaaaaagc tggatcgatc ctgagaactt cagggtgagt ttggggaccc ttgattgttc     420 tttcttttc gctattgtaa aattcatgtt atatggaggg ggcaaagttt tcagggtgtt     480
gtttagaatg ggaagatgtc ccttgtatca ccatggaccc tcatgataat tttgtttctt     540
tcactttcta ctctgttgac aaccattgtc tcctcttatt ttcttttcat ttctgtaac     600 tttttcgtta aacttagct tgcatttgta acgaattttt aaattcactt tgtttattt     660 gtcagattgt aagtactttc tctaatcact tttttttcaa ggcaatcagg gtatattata     720
ttgtacttca gcacagtttt agagaacaat tgttataatt aaatgataag gtagaatatt     780

-continued

```
tctgcatata aattctggct ggcgtggaaa tattcttatt ggtagaaaca actacatcct      840
ggtcatcatc ctgcctttct ctttatggtt acaatgatat acactgtttg agatgaggat      900
aaaatactct gagtccaaac cgggcccctc tgctaaccat gttcatgcct tcttcttttt      960
cctacagctc ctgggcaacg tgctggttat tgtgctgtct catcattttg caaagaatt      1020
gtaatacgac tcactatagg gcgaattcgg atccatggac gaagcggatc ggcggctcct     1080
gcggcggtgc cggctgcggc tggtggaaga gctgcaggtg gaccagctct gggacgccct     1140
gctgagccgc gagctgttca ggccccatat gatcgaggac atccagcggg caggctctgg     1200
atctcggcgg gatcaggcca ggcagctgat catagatctg gagactcgag ggagtcaggc     1260
tcttcctttg ttcatctcct gcttagagga cacaggccag gacatgctgg cttcgtttct     1320
gcgaactaac aggcaagcag caaagttgtc gaagccaacc ctagaaaacc ttaccccagt     1380
ggtgctcaga ccagagattc gcaaaccaga ggttctcaga ccggaaacac ccagaccagt     1440
ggacattggt tctggaggat ttggtgatgt cggtgctctt gagagtttga ggggaaatgc     1500
agatttggct tacatcctga gcatggagcc ctgtggccac tgcctcatta tcaacaatgt     1560
gaacttctgc cgtgagtccg ggctccgcac ccgcactggc tccaacatcg actgtgagaa     1620
gttgcggcgt cgcttctcct cgctgcattt catggtggag gtgaagggcg acctgactgc     1680
caagaaaatg gtgctggctt tgctggagct ggcgcagcag gaccacggtg ctctggactg     1740
ctgcgtggtg gtcattctct ctcacggctg tcaggccagc cacctgcagt tcccaggggc     1800
tgtctacggc acagatggat gccctgtgtc ggtcgagaag attgtgaaca tcttcaatgg     1860
gaccagctgc cccagcctgg gagggaagcc caagctcttt ttcatccagg cctctggtgg     1920
ggagcagaaa gaccatgggt ttgaggtggc ctccacttcc cctgaagacg agtcccctgg     1980
cagtaacccc gagccagatg ccaccccgtt ccaggaaggt tgaggacct tcgaccagct     2040
ggacgccata tctagtttgc ccacacccag tgacatcttt gtgtcctact ctactttccc     2100
aggttttgtt tcctggaggg accccaagag tggctcctgg tacgttgaga ccctggacga     2160
catctttgag cagtgggctc actctgaaga cctgcagtcc ctcctgctta gggtcgctaa     2220
tgctgtttcg gtgaaaggga tttataaaca gatgcctggt tgctttaatt tcctccggaa     2280
aaaacttttc tttaaaacat cataaagatc ttattaaagc agaacttgtt tattgcagct     2340
tataatggtt acaaataaag caatagcatc acaaatttca caaataaagc atttttttca     2400
ctgcattcta gttgtggttt gtccaaactc atcaatgtat cttatcatgt ctggtcgact     2460
ctagactctt ccgcttcctc gctcactgac tcgctgcgct cggtcgttcg gctgcggcga     2520
gcggtatcag ctcactcaaa ggcggtaata cggttatcca cagaatcagg ggataacgca     2580
ggaaagaaca tgtgagcaaa aggccagcaa aaggccagga accgtaaaaa ggccgcgttg     2640
ctggcgtttt tccataggct ccgcccccct gacgagcatc acaaaaatcg acgctcaagt     2700
cagaggtggc gaaacccgac aggactataa agataccagg cgtttccccc tggaagctcc     2760
ctcgtgcgct ctcctgttcc gaccctgccg cttaccggat acctgtccgc ctttctccct     2820
tcgggaagcg tggcgctttc tcaatgctca cgctgtaggt atctcagttc ggtgtaggtc     2880
gttcgctcca agctgggctg tgtgcacgaa ccccccgttc agcccgaccg ctgcgcctta     2940
tccggtaact atcgtcttga gtccaacccg gtaagacacg acttatcgcc actggcagca     3000
gccactggta acaggattag cagagcgagg tatgtaggcg gtgctacaga gttcttgaag     3060
tggtggccta actacggcta cactagaagg acagtatttg gtatctgcgc tctgctgaag     3120
```

```
ccagttacct tcggaaaaag agttggtagc tcttgatccg gcaaacaaac caccgctggt    3180
agcggtggtt tttttgtttg caagcagcag attacgcgca gaaaaaaagg atctcaagaa    3240
gatcctttga tcttttctac ggggtctgac gctcagtgga acgaaaactc acgttaaggg    3300
attttggtca tgagattatc aaaaaggatc ttcacctaga tccttttaaa ttaaaaatga    3360
agttttaaat caatctaaag tatatatgag taaacttggt ctgacagtta ccaatgctta    3420
atcagtgagg cacctatctc agcgatctgt ctatttcgtt catccatagt tgcctgactc    3480
cccgtcgtgt agataactac gatacgggag ggcttaccat ctggccccag tgctgcaatg    3540
ataccgcgag acccacgctc accggctcca gatttatcag caataaacca gccagccgga    3600
agggccgagc gcagaagtgg tcctgcaact ttatccgcct ccatccagtc tattaattgt    3660
tgccgggaag ctagagtaag tagttcgcca gttaatagtt tgcgcaacgt tgttgccatt    3720
gctacaggca tcgtggtgtc acgctcgtcg tttggtatgg cttcattcag ctccggttcc    3780
caacgatcaa ggcgagttac atgatccccc atgttgtgca aaaaagcggt tagctccttc    3840
ggtcctccga tcgttgtcag aagtaagttg gccgcagtgt tatcactcat ggttatggca    3900
gcactgcata attctcttac tgtcatgcca tccgtaagat gcttttctgt gactggtgag    3960
tactcaacca agtcattctg agaatagtgt atgcggcgac cgagttgctc ttgcccggcg    4020
tcaatacggg ataataccgc gccacatagc agaactttaa aagtgctcat cattggaaaa    4080
cgttcttcgg ggcgaaaact ctcaaggatc ttaccgctgt tgagatccag ttcgatgtaa    4140
cccactcgtg cacccaactg atcttcagca tcttttactt tcaccagcgt ttctgggtga    4200
gcaaaaacag gaaggcaaaa tgccgcaaaa aagggaataa gggcgacacg gaaatgttga    4260
atactcatac tcttcttttt tcaatattat tgaagcattt atcagggtta ttgtctcatg    4320
agcggataca tatttgaatg tatttagaaa aataaacaaa tagggggttcc gcgcacattt    4380 ccccgaaaag tgccacctga cgtctaagaa accattatta tcatgacatt aacctataaa    4440
aataggcgta tcacgaggcc ctttcgtct cgcgcgtttc ggtgatgacg gtgaaaacct    4500
ctgacacatg cagctcccgg agacggtcac agcttgtctg taagcggatg ccgggagcag    4560
acaagcccgt cagggcgcgt cagcgggtgt tggcgggtgt cggggctggc ttaactatgc    4620
ggcatcagag cagattgtac tgagagtgca ccatatgcgg tgtgaaatac cgcacagatg    4680
cgtaaggaga aaataccgca tcaggaaatt gtaaacgtta atattttgtt aaaattcgcg    4740
ttaaattttt gttaaatcag ctcattttt aaccaatagg ccgaaatcgg caaaatccct    4800
tataaatcaa aagaatagac cgagataggg ttgagtgttg ttccagtttg gaacaagagt    4860
ccactattaa agaacgtgga ctccaacgtc aaagggcgaa aaaccgtcta tcagggcgat    4920
ggcccactac gtgaaccatc acctaatca agtttttgg ggtcgaggtg ccgtaaagca    4980
ctaaatcgga accctaaagg gagcccccga tttagagctt gacggggaaa gccggcgaac    5040
gtggcgagaa aggaagggaa gaaagcgaaa ggagcgggcg ctagggcgct ggcaagtgta    5100
gcggtcacgc tgcgcgtaac caccacaccc gccgcgctta atgcgccgct acagggcgcg    5160
tcgcgccatt cgccattcag gctacgcaac tgttgggaag ggcgatcggt gcgggcctct    5220
tcgctattac gccagctggc gaagggggga tgtgctgcaa ggcgattaag ttgggtaacg    5280
ccagggtttt cccagtcacg acgttgtaaa acgacggcca gtgaatt              5327
```

<210> SEQ ID NO 83
<211> LENGTH: 416
<212> TYPE: PRT
<213> ORGANISM: Homo sapiens

<400> SEQUENCE: 83

```
Met Asp Glu Ala Asp Arg Arg Leu Leu Arg Cys Arg Leu Arg Leu
1               5                   10                  15

Val Glu Glu Leu Gln Val Asp Gln Leu Trp Asp Ala Leu Leu Ser Arg
            20                  25                  30

Glu Leu Phe Arg Pro His Met Ile Glu Asp Ile Gln Arg Ala Gly Ser
        35                  40                  45

Gly Ser Arg Arg Asp Gln Ala Arg Gln Leu Ile Ile Asp Leu Glu Thr
    50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
        115                 120                 125

Val Asp Ile Gly Ser Gly Gly Phe Gly Asp Val Gly Ala Leu Glu Ser
130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Leu His Phe Met Val Glu Val Lys Gly Asp Leu Thr
        195                 200                 205

Ala Lys Lys Met Val Leu Ala Leu Leu Glu Leu Ala Gln Gln Asp His
    210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Ser Gly
        275                 280                 285

Gly Glu Gln Lys Asp His Gly Phe Glu Val Ala Ser Thr Ser Pro Glu
    290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
        355                 360                 365

Asp Ile Phe Glu Gln Trp Ala His Ser Glu Asp Leu Gln Ser Leu Leu
    370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
```

<210> SEQ ID NO 84
<211> LENGTH: 1819
<212> TYPE: DNA
<213> ORGANISM: Mus sp.

<400> SEQUENCE: 84

```
gaattccggg ctggattgag aagccgcaac tgtgactctg catcatgaat actctgtctg    60
aaggaaatgg cacctttgcc atccatcttt tgaagatgct atgtcaaagc aacccttcca   120
aaaatgtatg ttattctcct gcgagcatct cctctgctct agctatggtt ctcttgggtg   180
caaagggaca gacggcagtc cagatatctc aggcacttgg tttgaataaa gaggaaggca   240
tccatcaggg tttccagttg cttctcagga agctgaacaa gccagacaga aagtactctc   300
ttagagtggc caacaggctc tttgcagaca aaacttgtga agtcctccaa acctttaagg   360
agtcctctct tcacttctat gactcagaga tggagcagct ctcctttgct gaagaagcag   420
aggtgtccag gcaacacata aacacatggg tctccaaaca aactgaaggt aaaattccag   480
agttgttgtc aggtggctcc gtcgattcag aaaccaggct ggttctcatc aatgccttat   540
attttaaagg aaagtggcat caaccattta acaaagagta cacaatggac atgcccttta   600
aaataaacaa ggatgagaaa aggccagtgc agatgatgtg tcgtgaagac acatataacc   660
tcgcctatgt gaaggaggtg caggcgcaag tgctggtgat gccatatgaa ggaatggagc   720
tgagcttggt ggttctgctc ccagatgagg gtgtggacct cagcaaggtg gaaaacaatc   780
tcacttttga gaagttaaca gcctggatgg aagcagattt tatgaagagc actgatgttg   840
aggttttcct tccaaaattt aaactccaag aggattatga catggagtct ctgtttcagc   900
gcttgggagt ggtggatgtc ttccaagagg acaaggctga cttatcagga atgtctccag   960
agagaaacct gtgtgtgtcc aagtttgttc accagagtgt agtggagatc aatgaggaag  1020
gcacagaggc tgcagcagcc tctgccatca tagaattttg ctgtgcctct tctgtcccaa  1080
cattctgtgc tgaccacccc ttccttttct tcatcaggca caacaaagca acagcatcc   1140
tgttctgtgg caggttctca tctccataaa gacacatata ctacagggg agagttctct   1200
cttcagtatc cctaccactc ctacagctct gtcaagatgg gcaagtaggg ggaagtcatg  1260
ttctaagatg aagacacttt ccttctctgt cagcctgatc ttataatgcc tgcattcaac  1320
tctccctgtc ttgaatgcat ctatgccctt taccaggtta tgtctaatga tgccaaatac  1380
cttctgctat gctattgatt gatagccctag ccagtaattt atagccagtt agaactgact  1440
tgactgtgca agaatgctat aatggagcta gagagaaggc acaaacacta ggaaaggttg  1500
ctgttttgc agaggacaca gggacatttc ccaccactca catggctgct tacaacctct   1560
ggaaattcca gtttctgtcc atgacttgat tcctttcttt ggcttctact ggctccagca  1620
tcctgcacat acatgtatcg tcattcagtt acacacaaac aagtaaaatt ttaaaaataa  1680
ataaaaattt aaagagagag tctaaaattt tagtaatggt tagataatag ctgctattgt  1740
gccttttttca ggttttaatg tcattattct tgtgtataaa gtcaataatt tataggaaaa  1800
catcagtgcc ccggaattc                                                1819
```

<210> SEQ ID NO 85
<211> LENGTH: 374
<212> TYPE: PRT
<213> ORGANISM: Mus sp.

<400> SEQUENCE: 85

```
Met Asn Thr Leu Ser Glu Gly Asn Gly Thr Phe Ala Ile His Leu Leu
 1               5                  10                  15

Lys Met Leu Cys Gln Ser Asn Pro Lys Asn Val Cys Tyr Ser Pro
                20                  25                  30

Ala Ser Ile Ser Ser Ala Leu Ala Met Val Leu Leu Gly Ala Lys Gly
             35                  40                  45

Gln Thr Ala Val Gln Ile Ser Gln Ala Leu Gly Leu Asn Lys Glu Glu
 50                  55                  60

Gly Ile His Gln Gly Phe Gln Leu Leu Leu Arg Lys Leu Asn Lys Pro
 65                  70                  75                  80

Asp Arg Lys Tyr Ser Leu Arg Val Ala Asn Arg Leu Phe Ala Asp Lys
                 85                  90                  95

Thr Cys Glu Val Leu Gln Thr Phe Lys Glu Ser Ser Leu His Phe Tyr
                100                 105                 110

Asp Ser Glu Met Glu Gln Leu Ser Phe Ala Glu Glu Ala Glu Val Ser
                115                 120                 125

Arg Gln His Ile Asn Thr Trp Val Ser Lys Gln Thr Glu Gly Lys Ile
130                 135                 140

Pro Glu Leu Leu Ser Gly Gly Ser Val Asp Ser Glu Thr Arg Leu Val
145                 150                 155                 160

Leu Ile Asn Ala Leu Tyr Phe Lys Gly Lys Trp His Gln Pro Phe Met
                165                 170                 175

Lys Glu Tyr Thr Met Asp Met Pro Phe Lys Ile Asn Lys Asp Glu Lys
                180                 185                 190

Arg Pro Val Gln Met Met Cys Arg Glu Asp Thr Tyr Asn Leu Ala Tyr
                195                 200                 205

Val Lys Glu Val Gln Ala Gln Val Leu Val Met Pro Tyr Glu Gly Met
210                 215                 220

Glu Leu Ser Leu Val Val Leu Pro Asp Glu Gly Val Asp Leu Ser
225                 230                 235                 240

Lys Val Glu Asn Asn Leu Thr Phe Glu Lys Leu Thr Ala Trp Met Glu
                245                 250                 255

Ala Asp Phe Met Lys Ser Thr Asp Val Glu Val Phe Leu Pro Lys Phe
                260                 265                 270

Lys Leu Gln Glu Asp Tyr Asp Met Glu Ser Leu Phe Gln Arg Leu Gly
                275                 280                 285

Val Val Asp Val Phe Gln Glu Asp Lys Ala Asp Leu Ser Gly Met Ser
                290                 295                 300

Pro Glu Arg Asn Leu Cys Val Ser Lys Phe Val His Gln Ser Val Val
305                 310                 315                 320

Glu Ile Asn Glu Glu Gly Thr Glu Ala Ala Ala Ser Ala Ile Ile
                325                 330                 335

Glu Phe Cys Cys Ala Ser Ser Val Pro Thr Phe Cys Ala Asp His Pro
                340                 345                 350

Phe Leu Phe Phe Ile Arg His Asn Lys Ala Asn Ser Ile Leu Phe Cys
                355                 360                 365

Gly Arg Phe Ser Ser Pro
            370
```

<210> SEQ ID NO 86
<211> LENGTH: 1125
<212> TYPE: DNA
<213> ORGANISM: Mus sp.

<400> SEQUENCE: 86

```
atgaatactc tgtctgaagg aaatggcacc tttgccatcc atcttttgaa gatgctatgt      60
caaagcaacc cttccaaaaa tgtatgttat tctcctgcga gcatctcctc tgctctagct     120
atggttctct gggtgcaaa gggacagacg gcagtccaga tatctcaggc acttggtttg      180
aataaagagg aaggcatcca tcagggtttc cagttgcttc tcaggaagct gaacaagcca     240
gacagaaagt actctcttag agtggccaac aggctctttg cagacaaaac ttgtgaagtc     300
ctccaaacct ttaaggagtc ctctcttcac ttctatgact cagagatgga gcagctctcc     360
tttgctgaag aagcagaggt gtccaggcaa cacataaaca catgggtctc caaacaaact     420
gaaggtaaaa ttccagagtt gttgtcaggt ggctccgtcg attcagaaac caggctggtt     480
ctcatcaatg ccttatattt taaggaaag tggcatcaac catttaacaa agagtacaca      540
atggacatgc cctttaaaat aaacaaggat gagaaaaggc cagtgcagat gatgtgtcgt     600
gaagacacat ataacctcgc ctatgtgaag gaggtgcagg cgcaagtgct ggtgatgcca     660
tatgaaggaa tggagctgag cttggtggtt ctgctcccag atgagggtgt ggacctcagc     720
aaggtggaaa acaatctcac ttttgagaag ttaacagcct ggatggaagc agattttatg     780
aagagcactg atgttgaggt tttccttcca aaatttaaac tccaagagga ttatgacatg     840
gagtctctgt ttcagcgctt gggagtggtg gatgtcttcc aagaggacaa ggctgactta     900
tcaggaatgt ctccagagag aaacctgtgt gtgtccaagt tgttcacca gagtgtagtg      960
gagatcaatg aggaaggcag agaggctgca gcagcctctg ccatcataga attttgctgt    1020
gcctcttctg tcccaacatt ctgtgctgac caccccttcc ttttcttcat caggcacaac    1080
aaagcaaaca gcatcctgtt ctgtggcagg ttctcatctc cataa                    1125
```

<210> SEQ ID NO 87
<211> LENGTH: 374
<212> TYPE: PRT
<213> ORGANISM: Mus sp.

<400> SEQUENCE: 87

```
Met Asn Thr Leu Ser Glu Gly Asn Gly Thr Phe Ala Ile His Leu Leu
1               5                   10                  15

Lys Met Leu Cys Gln Ser Asn Pro Ser Lys Asn Val Cys Tyr Ser Pro
            20                  25                  30

Ala Ser Ile Ser Ser Ala Leu Ala Met Val Leu Leu Gly Ala Lys Gly
        35                  40                  45

Gln Thr Ala Val Gln Ile Ser Gln Ala Leu Gly Leu Asn Lys Glu Glu
    50                  55                  60

Gly Ile His Gln Gly Phe Gln Leu Leu Leu Arg Lys Leu Asn Lys Pro
65                  70                  75                  80

Asp Arg Lys Tyr Ser Leu Arg Val Ala Asn Arg Leu Phe Ala Asp Lys
                85                  90                  95

Thr Cys Glu Val Leu Gln Thr Phe Lys Glu Ser Ser Leu His Phe Tyr
            100                 105                 110

Asp Ser Glu Met Glu Gln Leu Ser Phe Ala Glu Glu Ala Glu Val Ser
        115                 120                 125

Arg Gln His Ile Asn Thr Trp Val Ser Lys Gln Thr Glu Gly Lys Ile
    130                 135                 140

Pro Glu Leu Leu Ser Gly Gly Ser Val Asp Ser Glu Thr Arg Leu Val
145                 150                 155                 160

Leu Ile Asn Ala Leu Tyr Phe Lys Gly Lys Trp His Gln Pro Phe Asn
```

```
                     165                 170                 175
Lys Glu Tyr Thr Met Asp Met Pro Phe Lys Ile Asn Lys Asp Glu Lys
                 180                 185                 190

Arg Pro Val Gln Met Met Cys Arg Glu Asp Thr Tyr Asn Leu Ala Tyr
             195                 200                 205

Val Lys Glu Val Gln Ala Gln Val Leu Val Met Pro Tyr Glu Gly Met
         210                 215                 220

Glu Leu Ser Leu Val Val Leu Leu Pro Asp Glu Gly Val Asp Leu Ser
225                 230                 235                 240

Lys Val Glu Asn Asn Leu Thr Phe Glu Lys Leu Thr Ala Trp Met Glu
                245                 250                 255

Ala Asp Phe Met Lys Ser Thr Asp Val Glu Val Phe Leu Pro Lys Phe
            260                 265                 270

Lys Leu Gln Glu Asp Tyr Asp Met Glu Ser Leu Phe Gln Arg Leu Gly
        275                 280                 285

Val Val Asp Val Phe Gln Glu Asp Lys Ala Asp Leu Ser Gly Met Ser
    290                 295                 300

Pro Glu Arg Asn Leu Cys Val Ser Lys Phe Val His Gln Ser Val Val
305                 310                 315                 320

Glu Ile Asn Glu Glu Gly Arg Glu Ala Ala Ala Ser Ala Ile Ile
                325                 330                 335

Glu Phe Cys Cys Ala Ser Ser Val Pro Thr Phe Cys Ala Asp His Pro
            340                 345                 350

Phe Leu Phe Phe Ile Arg His Asn Lys Ala Asn Ser Ile Leu Phe Cys
        355                 360                 365

Gly Arg Phe Ser Ser Pro
370

<210> SEQ ID NO 88
<211> LENGTH: 6539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
```

-continued

```
ctgcttactg gcttatcgaa attaatacga ctcactatag ggagacccaa gctggctagc      900
gtttaaacgg gccctctaga ctcgagcggc cgccactgtg ctggatatct gcagaattca      960
tgaatactct gtctgaagga aatggcacct tgccatcca tcttttgaag atgctatgtc     1020
aaagcaaccc ttccaaaaat gtatgttatt ctcctgcgag catctcctct gctctagcta     1080
tggttctctt gggtgcaaag ggacagacgg cagtccagat atctcaggca cttggtttga     1140
ataaagagga aggcatccat cagggtttcc agttgcttct caggaagctg aacaagccag     1200
acagaaagta ctctcttaga gtggccaaca ggctctttgc agacaaaact tgtgaagtcc     1260
tccaaacctt taaggagtcc tctcttcact tctatgactc agagatggag cagctctcct     1320
ttgctgaaga agcagaggtg tccaggcaac acataaacac atgggtctcc aaacaaactg     1380
aaggtaaaat tccagagttg ttgtcaggtg gctccgtcga ttcagaaacc aggctggttc     1440
tcatcaatgc cttatatttt aaaggaaagt ggcatcaacc atttaacaaa gagtacacaa     1500
tggacatgcc ctttaaaata aacaaggatg agaaaaggcc agtgcagatg atgtgtcgtg     1560
aagacacata taacctcgcc tatgtgaagg aggtgcaggc gcaagtgctg gtgatgccat     1620
atgaaggaat ggagctgagc ttggtggttc tgctcccaga tgagggtgtg acctcagca     1680
aggtggaaaa caatctcact tttgagaagt taacagcctg gatggaagca gattttatga     1740
agagcactga tgttgaggtt ttccttccaa aatttaaact ccaagaggat tatgacatgg     1800
agtctctgtt tcagcgcttg ggagtggtgg atgtcttcca agaggacaag gctgacttat     1860
caggaatgtc tccagagaga aacctgtgtg tgtccaagtt tgttcaccag agtgtagtgg     1920
agatcaatga ggaaggcaca gaggctgcag cagcctctgc catcatagaa ttttgctgtg     1980
cctcttctgt cccaacattc tgtgctgacc accccttcct tttcttcatc aggcacaaca     2040
aagcaaacag catcctgttc tgtggcaggt tctcatctcc ataaggatcc gagctcggta     2100
ccaagcttaa gtttaaaccg ctgatcagcc tcgactgtgc cttctagttg ccagccatct     2160
gttgtttgcc cctcccccgt gccttccttg accctggaag gtgccactcc cactgtcctt     2220
tcctaataaa atgaggaaat tgcatcgcat tgtctgagta ggtgtcattc tattctgggg     2280
ggtggggtgg ggcaggacag caaggggag gattgggaag acaatagcag gcatgctggg     2340
gatgcggtgg gctctatggc ttctgaggcg gaaagaacca gctggggctc taggggtat     2400
ccccacgcgc cctgtagcgg cgcattaagc gcggcgggtg tggtggttac gcgcagcgtg     2460
accgctacac ttgccagcgc cctagcgccc gctcctttcg ctttcttccc ttcctttctc     2520
gccacgttcg ccggctttcc ccgtcaagct ctaaatcggg gcatcccttt agggttccga     2580
tttagtgctt tacggcacct cgaccccaaa aaacttgatt agggtgatgg ttcacgtagt     2640
gggccatcgc cctgatagac ggtttttcgc cctttgacgt tggagtccac gttctttaat     2700
agtggactct tgttccaaac tggaacaaca ctcaaccta tctcggtcta ttcttttgat     2760
ttataaggga ttttggggat ttcggcctat tggttaaaaa atgagctgat ttaacaaaaa     2820
tttaacgcga attaattctg tggaatgtgt gtcagttagg gtgtggaaag tccccaggct     2880
ccccaggcag gcagaagtat gcaaagcatg catctcaatt agtcagcaac caggtgtgga     2940
aagtccccag gctccccagc aggcagaagt atgcaaagca tgcatctcaa ttagtcagca     3000
accatagtcc cgcccctaac tccgcccatc ccgcccctaa ctccgcccag ttccgcccat     3060
tctccgcccc atggctgact aatttttttt atttatgcag aggccgaggc cgcctctgcc     3120
tctgagctat tccagaagta gtgaggaggc ttttttggag gcctaggctt ttgcaaaaag     3180
```

```
ctcccgggag cttgtatatc cattttcgga tctgatcaag agacaggatg aggatcgttt    3240
cgcatgattg aacaagatgg attgcacgca ggttctccgg ccgcttgggt ggagaggcta    3300
ttcggctatg actgggcaca acagacaatc ggctgctctg atgccgccgt gttccggctg    3360
tcagcgcagg ggcgcccggt tcttttttgtc aagaccgacc tgtccggtgc cctgaatgaa   3420
ctgcaggacg aggcagcgcg gctatcgtgg ctggccacga cgggcgttcc ttgcgcagct    3480
gtgctcgacg ttgtcactga agcgggaagg gactggctgc tattgggcga agtgccgggg    3540
caggatctcc tgtcatctca ccttgctcct gccgagaaag tatccatcat ggctgatgca    3600
atgcggcggc tgcatacgct tgatccggct acctgcccat tcgaccacca agcgaaacat    3660
cgcatcgagc gagcacgtac tcggatggaa gccggtcttg tcgatcagga tgatctggac    3720
gaagagcatc aggggctcgc gccagccgaa ctgttcgcca ggctcaaggc gcgcatgccc    3780
gacggcgagg atctcgtcgt gacccatggc gatgcctgct tgccgaatat catggtggaa    3840
aatggccgct tttctggatt catcgactgt ggccggctgg gtgtggcgga ccgctatcag    3900
gacatagcgt tggctacccg tgatattgct gaagagcttg gcggcgaatg ggctgaccgc    3960
ttcctcgtgc tttacggtat cgccgctccc gattcgcagc gcatcgcctt ctatcgcctt    4020
cttgacgagt tcttctgagc gggactctgg ggttcgaaat gaccgaccaa gcgacgccca    4080
acctgccatc acgagatttc gattccaccg ccgccttcta tgaaaggttg gcttcggaa    4140 tcgtttttccg ggacgccggc tggatgatcc tccagcgcgg ggatctcatg ctggagttct    4200
tcgcccaccc caacttgttt attgcagctt ataatggtta caaataaagc aatagcatca    4260
caaatttcac aaataaagca ttttttttcac tgcattctag ttgtggtttg tccaaactca    4320
tcaatgtatc ttatcatgtc tgtataccgt cgacctctag ctagagcttg gcgtaatcat    4380
ggtcatagct gtttcctgtg tgaaattgtt atccgctcac aattccacac aacatacgag    4440
ccggaagcat aaagtgtaaa gcctggggtg cctaatgagt gagctaactc acattaattg    4500
cgttgcgctc actgcccgct ttccagtcgg gaaacctgtc gtgccagctg cattaatgaa    4560
tcggccaacg cgcggggaga ggcggtttgc gtattgggcg ctcttccgct tcctcgctca    4620
ctgactcgct gcgctcggtc gttcggctgc ggcgagcgg atcagctcac tcaaaggcgg    4680
taatacggtt atccacagaa tcaggggata acgcaggaaa gaacatgtga gcaaaaggcc    4740
agcaaaaggc caggaaccgt aaaaaggccg cgttgctggc gttttttccat aggctccgcc    4800 ccccctgacga gcatcacaaa aatcgacgct caagtcagag gtggcgaaac ccgacaggac    4860
tataaagata ccaggcgttt ccccctggaa gctccctcgt gcgctctcct gttccgaccc    4920
tgccgcttac cggatacctg tccgcctttc tcccttcggg aagcgtggcg ctttctcaat    4980
gctcacgctg taggtatctc agttcggtgt aggtcgttcg ctccaagctg ggctgtgtgc    5040
acgaaccccc cgttcagccc gaccgctgcg ccttatccgg taactatcgt cttgagtcca    5100
acccggtaag acacgactta tcgccactgg cagcagccac tggtaacagg attagcagag    5160
cgaggtatgt aggcggtgct acagagttct tgaagtggtg cctaactac ggctacacta    5220 gaaggacagt atttggtatc tgcgctctgc tgaagccagt taccttcgga aaaagagttg    5280
gtagctcttg atccggcaaa caaaccaccg ctggtagcgg tggttttttt gtttgcaagc    5340
agcagattac gcgcagaaaa aaaggatctc aagaagatcc tttgatcttt tctacggggt    5400
ctgacgctca gtggaacgaa aactcacgtt aagggatttt ggtcatgaga ttatcaaaaa    5460
ggatcttcac ctagatcctt ttaaattaaa aatgaagttt taaatcaatc taaagtatat    5520
atgagtaaac ttggtctgac agttaccaat gcttaatcag tgaggcacct atctcagcga    5580
```

```
tctgtctatt tcgttcatcc atagttgcct gactccccgt cgtgtagata actacgatac    5640
gggagggctt accatctggc cccagtgctg caatgatacc gcgagaccca cgctcaccgg    5700
ctccagattt atcagcaata aaccagccag ccggaagggc cgagcgcaga agtggtcctg    5760
caactttatc cgcctccatc cagtctatta attgttgccg ggaagctaga gtaagtagtt    5820
cgccagttaa tagtttgcgc aacgttgttg ccattgctac aggcatcgtg gtgtcacgct    5880
cgtcgtttgg tatggcttca ttcagctccg gttcccaacg atcaaggcga gttacatgat    5940
cccccatgtt gtgcaaaaaa gcggttagct ccttcggtcc tccgatcgtt gtcagaagta    6000
agttggccgc agtgttatca ctcatggtta tggcagcact gcataattct cttactgtca    6060
tgccatccgt aagatgcttt tctgtgactg gtgagtactc aaccaagtca ttctgagaat    6120
agtgtatgcg gcgaccgagt tgctcttgcc cggcgtcaat acgggataat accgcgccac    6180
atagcagaac tttaaaagtg ctcatcattg gaaaacgttc ttcggggcga aaactctcaa    6240
ggatcttacc gctgttgaga tccagttcga tgtaacccac tcgtgcaccc aactgatctt    6300
cagcatcttt tactttcacc agcgtttctg ggtgagcaaa acaggaagg caaaatgccg    6360 caaaaaaggg aataagggcg acacggaaat gttgaatact catactcttc ctttttcaat    6420
attattgaag catttatcag ggttattgtc tcatgagcgg atacatattt gaatgtattt    6480
agaaaaataa acaaataggg gttccgcgca catttccccg aaaagtgcca cctgacgtc     6539
```

<210> SEQ ID NO 89
<211> LENGTH: 6539
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 89

```
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagaattca    960
tgaatactct gtctgaagga atggcacct ttgccatcca tcttttgaag atgctatgtc    1020
aaagcaaccc ttccaaaaat gtatgttatt ctcctgcgag catctcctct gctctagcta    1080
```

```
tggttctctt gggtgcaaag ggacagacgg cagtccagat atctcaggca cttggtttga    1140
ataaagagga aggcatccat cagggtttcc agttgcttct caggaagctg aacaagccag    1200
acagaaagta ctctcttaga gtggccaaca ggctctttgc agacaaaact tgtgaagtcc    1260
tccaaacctt taaggagtcc tctcttcact tctatgactc agagatggag cagctctcct    1320
ttgctgaaga agcagaggtg tccaggcaac acataaacac atgggtctcc aaacaaactg    1380
aaggtaaaat tccagagttg ttgtcaggtg gctccgtcga ttcagaaacc aggctggttc    1440
tcatcaatgc cttatatttt aaaggaaagt ggcatcaacc atttaacaaa gagtacacaa    1500
tggacatgcc ctttaaaata aacaaggatg agaaaaggcc agtgcagatg atgtgtcgtg    1560
aagacacata taacctcgcc tatgtgaagg aggtgcaggc gcaagtgctg gtgatgccat    1620
atgaaggaat ggagctgagc ttggtggttc tgctcccaga tgagggtgtg gacctcagca    1680
aggtggaaaa caatctcact tttgagaagt taacagcctg gatggaagca gattttatga    1740
agagcactga tgttgaggtt ttccttccaa aatttaaact ccaagaggat tatgacatgg    1800
agtctctgtt tcagcgcttg ggagtggtgg atgtcttcca agaggacaag gctgacttat    1860
caggaatgtc tccagagaga aacctgtgtg tgtccaagtt tgttcaccag agtgtagtgg    1920
agatcaatga ggaaggcaga gaggctgcag cagcctctgc catcatagaa ttttgctgtg    1980
cctcttctgt cccaacattc tgtgctgacc accccttcct tttcttcatc aggcacaaca    2040
aagcaaacag catcctgttc tgtggcaggt tctcatctcc ataaggatcc gagctcggta    2100
ccaagcttaa gtttaaaccg ctgatcagcc tcgactgtgc cttctagttg ccagccatct    2160
gttgtttgcc cctcccccgt gccttccttg accctggaag gtgccactcc cactgtcctt    2220
tcctaataaa atgaggaaat tgcatcgcat tgtctgagta ggtgtcattc tattctgggg    2280
ggtggggtgg ggcaggacag caaggggag gattgggaag acaatagcag gcatgctggg    2340
gatgcggtgg gctctatggc ttctgaggcg gaaagaacca gctggggctc tagggggtat    2400
ccccacgcgc cctgtagcgg cgcattaagc gcggcgggtg tggtggttac gcgcagcgtg    2460
accgctacac ttgccagcgc cctagcgccc gctcctttcg ctttcttccc ttcctttctc    2520
gccacgttcg ccggctttcc ccgtcaagct ctaaatcggg gcatcccttt agggttccga    2580
tttagtgctt tacggcacct cgaccccaaa aaacttgatt agggtgatgg ttcacgtagt    2640
gggccatcgc cctgatagac ggttttcgc cctttgacgt tggagtccac gttctttaat    2700
agtggactct tgttccaaac tggaacaaca ctcaaccctca tctcggtcta ttcttttgat    2760
ttataaggga ttttgggat tcggcctat tggttaaaaa atgagctgat ttaacaaaaa    2820
tttaacgcga attaattctg tggaatgtgt gtcagttagg gtgtggaaag tccccaggct    2880
ccccaggcag gcagaagtat gcaaagcatg catctcaatt agtcagcaac caggtgtgga    2940
aagtccccag gctccccagc aggcagaagt atgcaaagca tgcatctcaa ttagtcagca    3000
accatagtcc cgcccctaac tccgcccatc ccgcccctaa ctccgcccag ttccgcccat    3060
tctccgcccc atggctgact aatttttttt atttatgcag aggccgaggc cgcctctgcc    3120
tctgagctat tccagaagta gtgaggaggc ttttttggag gcctaggctt ttgcaaaaag    3180
ctcccgggag cttgtatatc cattttcgga tctgatcaag agacaggatg aggatcgttt    3240
cgcatgattg aacaagatgg attgcacgca ggttctccgg ccgcttgggt ggagaggcta    3300
ttcggctatg actgggcaca acagacaatc ggctgctctg atgccgccgt gttccggctg    3360
tcagcgcagg ggcgcccggt tctttttgtc aagaccgacc tgtccggtgc cctgaatgaa    3420
```

-continued

```
ctgcaggacg aggcagcgcg gctatcgtgg ctggccacga cgggcgttcc ttgcgcagct    3480
gtgctcgacg ttgtcactga agcgggaagg gactggctgc tattgggcga agtgccgggg    3540
caggatctcc tgtcatctca ccttgctcct gccgagaaag tatccatcat ggctgatgca    3600
atgcggcggc tgcatacgct tgatccggct acctgcccat cgaccacca agcgaaacat    3660
cgcatcgagc gagcacgtac tcggatggaa gccggtcttg tcgatcagga tgatctggac    3720
gaagagcatc aggggctcgc gccagccgaa ctgttcgcca ggctcaaggc gcgcatgccc    3780
gacggcgagg atctcgtcgt gacccatggc gatgcctgct tgccgaatat catggtggaa    3840
aatggccgct tttctggatt catcgactgt ggccggctgg gtgtggcgga ccgctatcag    3900
gacatagcgt tggctacccg tgatattgct gaagagcttg gcggcgaatg ggctgaccgc    3960
ttcctcgtgc tttacggtat cgccgctccc gattcgcagc gcatcgcctt ctatcgcctt    4020
cttgacgagt tcttctgagc gggactctgg ggttcgaaat gaccgaccaa gcgacgccca    4080
acctgccatc acgagatttc gattccaccg ccgccttcta tgaaaggttg gcttcggaa    4140
tcgtttccg ggacgccggc tggatgatcc tccagcgcgg ggatctcatg ctggagttct    4200
tcgcccaccc caacttgttt attgcagctt ataatggtta caaataaagc aatagcatca    4260
caaatttcac aaataaagca ttttttttcac tgcattctag ttgtggtttg tccaaactca    4320
tcaatgtatc ttatcatgtc tgtataccgt cgacctctag ctagagcttg gcgtaatcat    4380
ggtcatagct gtttcctgtg tgaaattgtt atccgctcac aattccacac aacatacgag    4440
ccggaagcat aaagtgtaaa gcctggggtg cctaatgagt gagctaactc acattaattg    4500
cgttgcgctc actgcccgct ttccagtcgg gaaacctgtc gtgccagctg cattaatgaa    4560
tcggccaacg cgcggggaga ggcggtttgc gtattgggcg ctcttccgct tcctcgctca    4620
ctgactcgct gcgctcggtc gttcggctgc ggcgagcgg atcagctcac tcaaaggcgg    4680
taatacggtt atccacagaa tcaggggata acgcaggaaa gaacatgtga gcaaaaggcc    4740
agcaaaaggc caggaaccgt aaaaaggccg cgttgctggc gtttttccat aggctccgcc    4800
cccctgacga gcatcacaaa aatcgacgct caagtcagag gtggcgaaac ccgacaggac    4860
tataaagata ccaggcgttt ccccctggaa gctccctcgt gcgctctcct gttccgaccc    4920
tgccgcttac cggatacctg tccgcctttc tcccttcggg aagcgtggcg ctttctcaat    4980
gctcacgctg taggtatctc agttcggtgt aggtcgttcg ctccaagctg ggctgtgtgc    5040
acgaaccccc cgttcagccc gaccgctgcg ccttatccgg taactatcgt cttgagtcca    5100
acccggtaag acacgactta tcgccactgg cagcagccac tggtaacagg attagcagag    5160
cgaggtatgt aggcggtgct acagagttct tgaagtggtg gcctaactac ggctacacta    5220
gaaggacagt atttggtatc tgcgctctgc tgaagccagt taccttcgga aaaagagttg    5280
gtagctcttg atccggcaaa caaaccaccg ctggtagcgg tggttttttt gtttgcaagc    5340
agcagattac gcgcagaaaa aaaggatctc aagaagatcc tttgatcttt tctacggggt    5400
ctgacgctca gtggaacgaa aactcacgtt aagggatttt ggtcatgaga ttatcaaaaa    5460
ggatcttcac ctagatcctt ttaaattaaa aatgaagttt taaatcaatc taaagtatat    5520
atgagtaaac ttggtctgac agttaccaat gcttaatcag tgaggcacct atctcagcga    5580
tctgtctatt tcgttcatcc atagttgcct gactccccgt cgtgtagata actacgatac    5640
gggagggctt accatctggc cccagtgctg caatgatacc gcgagaccca cgctcaccgg    5700
ctccagattt atcagcaata aaccagccag ccggaagggc cgagcgcaga agtggtcctg    5760
caactttatc cgcctccatc cagtctatta attgttgccg ggaagctaga gtaagtagtt    5820
```

-continued

```
cgccagttaa tagtttgcgc aacgttgttg ccattgctac aggcatcgtg gtgtcacgct    5880
cgtcgtttgg tatggcttca ttcagctccg gttcccaacg atcaaggcga gttacatgat    5940
cccccatgtt gtgcaaaaaa gcggttagct ccttcggtcc tccgatcgtt gtcagaagta    6000
agttggccgc agtgttatca ctcatggtta tggcagcact gcataattct cttactgtca    6060
tgccatccgt aagatgcttt tctgtgactg gtgagtactc aaccaagtca ttctgagaat    6120
agtgtatgcg gcgaccgagt tgctcttgcc cggcgtcaat acgggataat accgcgccac    6180
atagcagaac tttaaaagtg ctcatcattg gaaaacgttc ttcggggcga aaactctcaa    6240
ggatcttacc gctgttgaga tccagttcga tgtaacccac tcgtgcaccc aactgatctt    6300
cagcatcttt tactttcacc agcgtttctg ggtgagcaaa acaggaagg caaaatgccg    6360 caaaaaggg aataagggcg acacggaaat gttgaatact catactcttc cttttcaat     6420 attattgaag catttatcag ggttattgtc tcatgagcgg atacatattt gaatgtattt    6480
agaaaaataa acaaataggg gttccgcgca catttccccg aaaagtgcca cctgacgtc    6539
```

<210> SEQ ID NO 90
<211> LENGTH: 810
<212> TYPE: DNA
<213> ORGANISM: Homo sapiens

<400> SEQUENCE: 90

```
atggatgacc agcgcgacct tatctccaac aatgagcaac tgcccatgct gggccggcgc     60
cctggggccc cggagagcaa gtgcagccgc ggagccctgt acacaggctt ttccatcctg    120
gtgactctgc tcctcgctgg ccaggccacc accgccttact tcctgtacca gcagcagggc    180
cggctggaca aactgacagt cacctcccag aacctgcagc tggagaacct gcgcatgaag    240
cttgccaagt tcgtggctgc ctggaccctg aaggctgccg ctgccctgcc ccaggggccc    300
atgcagaatg ccaccaagta tggcaacatg acagaggacc atgtgatgca cctgctccag    360
aatgctgacc ccctgaaggt gtacccgcca ctgaaggga gcttcccgga gaacctgaga    420
caccttaaga acaccatgga gaccatagac tggaaggtct ttgagagctg gatgcaccat    480
tggctcctgt ttgaaatgag caggcactcc ttggagcaaa agcccactga cgctccaccg    540
aaagtactga ccaagtgcca ggaagaggtc agccacatcc ctgctgtcca cccgggttca    600
ttcaggccca gtgcgacga gaacggcaac tatctgccac tccagtgcta tgggagcatc    660
ggctactgct ggtgtgtctt ccccaacggc acggaggtcc ccaacaccag aagccgcggg    720
caccataact gcagtgagtc actggaactg gaggaccgt cttctgggct gggtgtgacc    780
aagcaggatc tgggcccagt cccccatgtga                                    810
```

<210> SEQ ID NO 91
<211> LENGTH: 269
<212> TYPE: PRT
<213> ORGANISM: Homo sapiens

<400> SEQUENCE: 91

```
Met Asp Asp Gln Arg Asp Leu Ile Ser Asn Asn Glu Gln Leu Pro Met
1               5                  10                  15

Leu Gly Arg Arg Pro Gly Ala Pro Glu Ser Lys Cys Ser Arg Gly Ala
            20                  25                  30

Leu Tyr Thr Gly Phe Ser Ile Leu Val Thr Leu Leu Leu Ala Gly Gln
        35                  40                  45

Ala Thr Thr Ala Tyr Phe Leu Tyr Gln Gln Gln Gly Arg Leu Asp Lys
```

```
                50                  55                  60
Leu Thr Val Thr Ser Gln Asn Leu Gln Leu Glu Asn Leu Arg Met Lys
 65                  70                  75                  80

Leu Ala Lys Phe Val Ala Ala Trp Thr Leu Lys Ala Ala Ala Ala Leu
                 85                  90                  95

Pro Gln Gly Pro Met Gln Asn Ala Thr Lys Tyr Gly Asn Met Thr Glu
                100                 105                 110

Asp His Val Met His Leu Leu Gln Asn Ala Asp Pro Leu Lys Val Tyr
                115                 120                 125

Pro Pro Leu Lys Gly Ser Phe Pro Glu Asn Leu Arg His Leu Lys Asn
                130                 135                 140

Thr Met Glu Thr Ile Asp Trp Lys Val Phe Glu Ser Trp Met His His
145                 150                 155                 160

Trp Leu Leu Phe Glu Met Ser Arg His Ser Leu Glu Gln Lys Pro Thr
                165                 170                 175

Asp Ala Pro Pro Lys Val Leu Thr Lys Cys Gln Glu Glu Val Ser His
                180                 185                 190

Ile Pro Ala Val His Pro Gly Ser Phe Arg Pro Lys Cys Asp Glu Asn
                195                 200                 205

Gly Asn Tyr Leu Pro Leu Gln Cys Tyr Gly Ser Ile Gly Tyr Cys Trp
                210                 215                 220

Cys Val Phe Pro Asn Gly Thr Glu Val Pro Asn Thr Arg Ser Arg Gly
225                 230                 235                 240

His His Asn Cys Ser Glu Ser Leu Glu Leu Glu Asp Pro Ser Ser Gly
                245                 250                 255

Leu Gly Val Thr Lys Gln Asp Leu Gly Pro Val Pro Met
                260                 265

<210> SEQ ID NO 92
<211> LENGTH: 17
<212> TYPE: PRT
<213> ORGANISM: Mus sp.

<400> SEQUENCE: 92

Lys Pro Val Ser Gln Met Arg Met Ala Thr Pro Leu Leu Met Arg Pro
 1               5                  10                  15

Met

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Lys Phe Val Ala Ala Trp Thr Leu Lys Ala Ala Ala
 1               5                  10

<210> SEQ ID NO 94
<211> LENGTH: 3392
<212> TYPE: DNA
<213> ORGANISM: Homo sapiens

<400> SEQUENCE: 94
atgcgttgcc tggctccacg ccctgctggg tcctacctgt cagagcccca aggcagctca      60
cagtgtgcca ccatggagtt ggggccccta gaaggtggct acctggagct tcttaacagc     120
```

```
gatgctgacc cctgtgcctc taccacttct atgaccagat ggacctggct ggagaagaag    180
agattgagct ctactcagaa cccgacacag acaccatcaa ctgcgaccag ttcagcaggc    240
tgttgtgtga catggaaggt gatgaagaga ccagggaggc ttatgccaat atcgcggaac    300
tggaccagta tgtcttccag gactcccagc tggagggcct gagcaaggac atttcaagc     360 acataggacc agatgaagtg atcggtgaga gtatggagat gccagcagaa gttgggcaga    420
aaagtcagaa aagacccttc ccagaggagc ttccggcaga cctgaagcac tggaagccag    480
ctgagccccc cactgtggtg actggcagtc cctagtggga ccagtgagc gactgctcca     540 ccctgccctg cctgccactg cctgcgctgt caaccagga gccagcctcc ggccagatgc     600
gcctggagaa aaccgaccag attcccatgc ctttctccag ttcctcgttg agctgcctga    660
atctccctga gggacccatc cagttgtcc ccaccatctc cactctgccc catgggctct     720
ggcaaatctc tgaggctgga cagggtgtct ccagtatatt catctaccat ggtgaggtgc    780
cccaggccag ccaagtaccc cctcccagtg gattcactgt ccacggcctc ccaacatctc    840
cagaccggcc aggctccacc agccccttcg ctccatcagc cactgacctg cccagcatgc    900
ctgaacctgc cctgacctcc cgagcaaaca tgacagagca aagacgtcc cccacccaat      960 gcccggcagc tggagaggtc tccaacaagc ttccaaatg gcctgagccg gtggagcagt    1020
tctaccgctc actgcaggac acgtatggtg ccgagcccgc aggcccggat ggcatcctag    1080
tggaggtgga tctggtgcag gccaggctgg agaggagcag cagcaagagc ctggagcggg    1140
aactggccac cccggactgg gcagaacggc agctggccca aggaggcctg gctgaggtgc    1200
tgttggctgc caaggagcac cggcggccgc gtgagacacg agtgattgct gtgctgggca    1260
aagctggtca gggcaagagc tattgggctg gggcagtgag ccgggcctgg gcttgtggcc    1320
ggcttcccca gtacgacttt gtcttctctg tccctgcca ttgcttgaac cgtccgggg     1380 atgcctatgg cctgcaggat ctgctcttct ccctgggccc acagccactc gtggcggccg    1440
atgaggtttt cagccacatc ttgaagagac ctgaccgcgt tctgctcatc ctagacggct    1500
tcgaggagct ggaagcgcaa gatggcttcc tgcacagcac gtgcggaccg gcaccggcgg    1560
agccctgctc cctccggggg ctgctggccg gcctttcca aagaagctg ctccgaggtt     1620 gcaccctcct cctcacagcc cggccccggg gccgctggt ccagagcctg agcaaggccg     1680 acgcctatt tgagctgtcc ggcttctcca tggagcaggc ccaggcatac gtgatgcgct    1740
actttgagag ctcagggatg acagagcacc aagacagagc cctgacgctc ctccgggacc    1800
ggccacttct tctcagtcac agccacagcc tactttgtg ccgggcagtg tgccagctct     1860
cagaggccct gctggagctt ggggaggacg ccaagctgcc ctccacgctc acgggactct    1920
atgtcggcct gctgggccgt gcagccctcg acagccccc cggggccctg cagagctgg     1980 ccaagctggc ctgggagctg gccgcagac atcaaagtac cctacaggag gaccagttcc    2040
catccgcaga cgtgaggacc tgggcgatgg ccaaaggctt agtccaacac ccaccgcggg    2100
ccgcagagtc cgagctggcc ttccccagct tcctcctgca atgcttcctg ggggccctgt    2160
ggctggctct gagtggcgaa atcaaggaca aggagctccc gcagtaccta gcattgaccc    2220
caaggaagaa gaggccctat gacaactggc tggagggcgt gccacgcttt ctggctgggc    2280
tgatcttcca gcctcccgcc cgctgcctgg gagccatact cgggccatcg gcggctgcct    2340
cggtggacag gaagcagaag gtgcttgcga ggtacctgaa gcggctgcag ccggggacac    2400
tgcgggcgcg gcagctgctg gagctgctgc actgcgccca cgaggccgag gaggctggaa    2460
```

```
tttggcagca cgtggtacag gagctccccg gccgcctctc ttttctgggc acccgcctca    2520
cgcctcctga tgcacatgta ctgggcaagg ccttggaggc ggcgggccaa gacttctccc    2580
tggacctccg cagcactggc atttgccccc ctggattggg gagcctcgtg ggactcagct    2640
gtgtcacccg tttcagggct gccttgagcg acacggtggc gctgtgggag tccctgcagc    2700
agcatgggga gaccaagcta cttcaggcag cagaggagaa gttcaccatc gagcctttca    2760
aagccaagtc cctgaaggat gtggaagacc tgggaaagct tgtgcagact cagaggacga    2820
gaagttcctc ggaagacaca gctggggagc tccctgctgt tcgggaccta agaaactgg     2880 agtttgcgct gggccctgtc tcaggccccc aggctttccc caaactggtg cggatcctca    2940
cggccttttc ctccctgcag catctggacc tggatgcgct gagtgagaac aagatcgggg    3000
acgagggtgt ctcgcagctc tcagccacct tcccccagct gaagtccttg gaaaccctca    3060
atctgtccca gaacaacatc actgacctgg gtgcctacaa actcgccgag gccctgcctt    3120
cgctcgctgc atccctgctc aggctaagct tgtacaataa ctgcatctgc gacgtgggag    3180
ccgagagctt ggctcgtgtg cttccggaca tggtgtccct ccggggtgatg gacgtccagt    3240 acaacaagtt cacggctgcc ggggcccagc agctcgctgc cagccttcgg aggtgtcctc    3300
atgtggagac gctggcgatg tggacgccca ccatcccatt cagtgtccag gaacacctgc    3360
aacaacagga ttcacggatc agcctgagat ga                                  3392
```

```
<210> SEQ ID NO 95
<211> LENGTH: 1130
<212> TYPE: PRT
<213> ORGANISM: Homo sapiens

<400> SEQUENCE: 95

Met Arg Cys Leu Ala Pro Arg Pro Ala Gly Ser Tyr Leu Ser Glu Pro
1               5                   10                  15

Gln Gly Ser Ser Gln Cys Ala Thr Met Glu Leu Gly Pro Leu Glu Gly
            20                  25                  30

Gly Tyr Leu Glu Leu Leu Asn Ser Asp Ala Asp Pro Leu Cys Leu Tyr
        35                  40                  45

His Phe Tyr Asp Gln Met Asp Leu Ala Gly Glu Glu Ile Glu Leu
    50                  55                  60

Tyr Ser Glu Pro Asp Thr Asp Thr Ile Asn Cys Asp Gln Phe Ser Arg
65                  70                  75                  80

Leu Leu Cys Asp Met Glu Gly Asp Glu Glu Thr Arg Glu Ala Tyr Ala
                85                  90                  95

Asn Ile Ala Glu Leu Asp Gln Tyr Val Phe Gln Asp Ser Gln Leu Glu
            100                 105                 110

Gly Leu Ser Lys Asp Ile Phe Lys His Ile Gly Pro Asp Glu Val Ile
        115                 120                 125

Gly Glu Ser Met Glu Met Pro Ala Glu Val Gly Gln Lys Ser Gln Lys
    130                 135                 140

Arg Pro Phe Pro Glu Glu Leu Pro Ala Asp Leu Lys His Trp Lys Pro
145                 150                 155                 160

Ala Glu Pro Pro Thr Val Val Thr Gly Ser Leu Leu Val Gly Pro Val
                165                 170                 175

Ser Asp Cys Ser Thr Leu Pro Cys Leu Pro Leu Pro Ala Leu Phe Asn
            180                 185                 190

Gln Glu Pro Ala Ser Gly Gln Met Arg Leu Glu Lys Thr Asp Gln Ile
        195                 200                 205
```

```
Pro Met Pro Phe Ser Ser Ser Ser Leu Ser Cys Leu Asn Leu Pro Glu
210                 215                 220

Gly Pro Ile Gln Phe Val Pro Thr Ile Ser Thr Leu Pro His Gly Leu
225                 230                 235                 240

Trp Gln Ile Ser Glu Ala Gly Thr Gly Val Ser Ser Ile Phe Ile Tyr
                245                 250                 255

His Gly Glu Val Pro Gln Ala Ser Gln Val Pro Pro Ser Gly Phe
                260                 265                 270

Thr Val His Gly Leu Pro Thr Ser Pro Asp Arg Pro Gly Ser Thr Ser
                275                 280                 285

Pro Phe Ala Pro Ser Ala Thr Asp Leu Pro Ser Met Pro Glu Pro Ala
290                 295                 300

Leu Thr Ser Arg Ala Asn Met Thr Glu His Lys Thr Ser Pro Thr Gln
305                 310                 315                 320

Cys Pro Ala Ala Gly Glu Val Ser Asn Lys Leu Pro Lys Trp Pro Glu
                325                 330                 335

Pro Val Glu Gln Phe Tyr Arg Ser Leu Gln Asp Thr Tyr Gly Ala Glu
                340                 345                 350

Pro Ala Gly Pro Asp Gly Ile Leu Val Glu Val Asp Leu Val Gln Ala
                355                 360                 365

Arg Leu Glu Arg Ser Ser Lys Ser Leu Glu Arg Glu Leu Ala Thr
370                 375                 380

Pro Asp Trp Ala Glu Arg Gln Leu Ala Gln Gly Gly Leu Ala Glu Val
385                 390                 395                 400

Leu Leu Ala Ala Lys Glu His Arg Arg Pro Arg Glu Thr Arg Val Ile
                405                 410                 415

Ala Val Leu Gly Lys Ala Gly Gln Gly Lys Ser Tyr Trp Ala Gly Ala
                420                 425                 430

Val Ser Arg Ala Trp Ala Cys Gly Arg Leu Pro Gln Tyr Asp Phe Val
                435                 440                 445

Phe Ser Val Pro Cys His Cys Leu Asn Arg Pro Gly Asp Ala Tyr Gly
450                 455                 460

Leu Gln Asp Leu Leu Phe Ser Leu Gly Pro Gln Pro Leu Val Ala Ala
465                 470                 475                 480

Asp Glu Val Phe Ser His Ile Leu Lys Arg Pro Asp Arg Val Leu Leu
                485                 490                 495

Ile Leu Asp Gly Phe Glu Glu Leu Glu Ala Gln Asp Gly Phe Leu His
                500                 505                 510

Ser Thr Cys Gly Pro Ala Pro Ala Glu Pro Cys Ser Leu Arg Gly Leu
                515                 520                 525

Leu Ala Gly Leu Phe Gln Lys Lys Leu Leu Arg Gly Cys Thr Leu Leu
530                 535                 540

Leu Thr Ala Arg Pro Arg Gly Arg Leu Val Gln Ser Leu Ser Lys Ala
545                 550                 555                 560

Asp Ala Leu Phe Glu Leu Ser Gly Phe Ser Met Glu Gln Ala Gln Ala
                565                 570                 575

Tyr Val Met Arg Tyr Phe Glu Ser Ser Gly Met Thr Glu His Gln Asp
                580                 585                 590

Arg Ala Leu Thr Leu Leu Arg Asp Arg Pro Leu Leu Leu Ser His Ser
                595                 600                 605

His Ser Pro Thr Leu Cys Arg Ala Val Cys Gln Leu Ser Glu Ala Leu
            610                 615                 620

Leu Glu Leu Gly Glu Asp Ala Lys Leu Pro Ser Thr Leu Thr Gly Leu
```

```
                625                 630                 635                 640
        Tyr Val Gly Leu Leu Gly Arg Ala Ala Leu Asp Ser Pro Pro Gly Ala
                        645                 650                 655

Leu Ala Glu Leu Ala Lys Leu Ala Trp Glu Leu Gly Arg Arg His Gln
                        660                 665                 670

Ser Thr Leu Gln Glu Asp Gln Phe Pro Ser Ala Asp Val Arg Thr Trp
                        675                 680                 685

Ala Met Ala Lys Gly Leu Val Gln His Pro Pro Arg Ala Ala Glu Ser
                        690                 695                 700

Glu Leu Ala Phe Pro Ser Phe Leu Leu Gln Cys Phe Leu Gly Ala Leu
        705                 710                 715                 720

Trp Leu Ala Leu Ser Gly Glu Ile Lys Asp Lys Glu Leu Pro Gln Tyr
                        725                 730                 735

Leu Ala Leu Thr Pro Arg Lys Lys Arg Pro Tyr Asp Asn Trp Leu Glu
                        740                 745                 750

Gly Val Pro Arg Phe Leu Ala Gly Leu Ile Phe Gln Pro Pro Ala Arg
                        755                 760                 765

Cys Leu Gly Ala Leu Leu Gly Pro Ser Ala Ala Ser Val Asp Arg
                        770                 775                 780

Lys Gln Lys Val Leu Ala Arg Tyr Leu Lys Arg Leu Gln Pro Gly Thr
        785                 790                 795                 800

Leu Arg Ala Arg Gln Leu Leu Glu Leu His Cys Ala His Glu Ala
                        805                 810                 815

Glu Glu Ala Gly Ile Trp Gln His Val Val Gln Glu Leu Pro Gly Arg
                        820                 825                 830

Leu Ser Phe Leu Gly Thr Arg Leu Thr Pro Pro Asp Ala His Val Leu
                        835                 840                 845

Gly Lys Ala Leu Glu Ala Ala Gly Gln Asp Phe Ser Leu Asp Leu Arg
                        850                 855                 860

Ser Thr Gly Ile Cys Pro Ser Gly Leu Gly Ser Leu Val Gly Leu Ser
        865                 870                 875                 880

Cys Val Thr Arg Phe Arg Ala Ala Leu Ser Asp Thr Val Ala Leu Trp
                        885                 890                 895

Glu Ser Leu Gln Gln His Gly Glu Thr Lys Leu Leu Gln Ala Ala Glu
                        900                 905                 910

Glu Lys Phe Thr Ile Glu Pro Phe Lys Ala Lys Ser Leu Lys Asp Val
                        915                 920                 925

Glu Asp Leu Gly Lys Leu Val Gln Thr Gln Arg Thr Arg Ser Ser Ser
                        930                 935                 940

Glu Asp Thr Ala Gly Glu Leu Pro Ala Val Arg Asp Leu Lys Lys Leu
        945                 950                 955                 960

Glu Phe Ala Leu Gly Pro Val Ser Gly Pro Gln Ala Phe Pro Lys Leu
                        965                 970                 975

Val Arg Ile Leu Thr Ala Phe Ser Ser Leu Gln His Leu Asp Leu Asp
                        980                 985                 990

Ala Leu Ser Glu Asn Lys Ile Gly Asp Glu Gly Val Ser Gln Leu Ser
                        995                 1000                1005

Ala Thr Phe Pro Gln Leu Lys Ser Leu Glu Thr Leu Asn Leu Ser
                        1010                1015                1020

Gln Asn Asn Ile Thr Asp Leu Gly Ala Tyr Lys Leu Ala Glu Ala
                        1025                1030                1035

Leu Pro Ser Leu Ala Ala Ser Leu Leu Arg Leu Ser Leu Tyr Asn
                        1040                1045                1050
```

```
Asn Cys Ile Cys Asp Val Gly Ala Glu Ser Leu Ala Arg Val Leu
    1055            1060                1065

Pro Asp Met Val Ser Leu Arg Val Met Asp Val Gln Tyr Asn Lys
    1070            1075                1080

Phe Thr Ala Ala Gly Ala Gln Gln Leu Ala Ala Ser Leu Arg Arg
    1085            1090                1095

Cys Pro His Val Glu Thr Leu Ala Met Trp Thr Pro Thr Ile Pro
    1100            1105                1110

Phe Ser Val Gln Glu His Leu Gln Gln Gln Asp Ser Arg Ile Ser
    1115            1120                1125

Leu Arg
    1130

<210> SEQ ID NO 96
<211> LENGTH: 17
<212> TYPE: PRT
<213> ORGANISM: Human herpesvirus

<400> SEQUENCE: 96

Tyr Leu Gln Gln Asn Trp Trp Thr Leu Leu Val Asp Leu Leu Trp Leu
1               5                   10                  15

Leu

<210> SEQ ID NO 97
<211> LENGTH: 16
<212> TYPE: PRT
<213> ORGANISM: Homo sapiens

<400> SEQUENCE: 97

Ile Gly His Val Tyr Ile Phe Ala Thr Cys Leu Gly Leu Ser Tyr Asp
1               5                   10                  15

<210> SEQ ID NO 98
<211> LENGTH: 8
<212> TYPE: PRT
<213> ORGANISM: Mycoplasma penetrans

<400> SEQUENCE: 98

Ile Tyr Ile Phe Ala Ala Cys Leu
1               5

<210> SEQ ID NO 99
<211> LENGTH: 15
<212> TYPE: PRT
<213> ORGANISM: Unknown
<220> FEATURE:
<223> OTHER INFORMATION: Description of Unknown: Six-transmembrane
      epithelial antigen of prostate peptide

<400> SEQUENCE: 99

His Gln Gln Tyr Phe Tyr Lys Ile Pro Ile Leu Val Ile Asn Lys
1               5                   10                  15

<210> SEQ ID NO 100
<211> LENGTH: 15
<212> TYPE: PRT
<213> ORGANISM: Unknown
<220> FEATURE:
<223> OTHER INFORMATION: Description of Unknown: Six-transmembrane
      epithelial antigen of prostate peptide

<400> SEQUENCE: 100
```

```
Leu Leu Asn Trp Ala Tyr Gln Gln Val Gln Gln Asn Lys Glu Asp
1               5                   10                  15

<210> SEQ ID NO 101
<211> LENGTH: 14
<212> TYPE: PRT
<213> ORGANISM: Homo sapiens

<400> SEQUENCE: 101

Glu Phe His Ala Cys Trp Pro Ala Phe Thr Val Leu Gly Glu
1               5                   10

<210> SEQ ID NO 102
<211> LENGTH: 15
<212> TYPE: PRT
<213> ORGANISM: Homo sapiens

<400> SEQUENCE: 102

Trp Gln Pro Phe Leu Lys Asp His Arg Ile Ser Thr Phe Lys Asn
1               5                   10                  15

<210> SEQ ID NO 103
<211> LENGTH: 15
<212> TYPE: PRT
<213> ORGANISM: Human papillomavirus

<400> SEQUENCE: 103

Leu Phe Val Val Tyr Arg Asp Ser Ile Pro His Ala Ala Cys His
1               5                   10                  15

<210> SEQ ID NO 104
<211> LENGTH: 15
<212> TYPE: PRT
<213> ORGANISM: Human papillomavirus

<400> SEQUENCE: 104

Gly Leu Tyr Asn Leu Leu Ile Arg Cys Leu Arg Cys Gln Lys Pro
1               5                   10                  15

<210> SEQ ID NO 105
<211> LENGTH: 13
<212> TYPE: PRT
<213> ORGANISM: Homo sapiens

<400> SEQUENCE: 105

Leu Trp Trp Val Asn Asn Gln Ser Leu Pro Val Ser Pro
1               5                   10

<210> SEQ ID NO 106
<211> LENGTH: 25
<212> TYPE: PRT
<213> ORGANISM: Mycobacterium tuberculosis

<400> SEQUENCE: 106

Phe Ser Lys Leu Pro Ala Ser Thr Ile Asp Glu Leu Lys Thr Asn Ser
1               5                   10                  15

Ser Leu Leu Thr Ser Ile Leu Thr Tyr
            20                  25

<210> SEQ ID NO 107
<211> LENGTH: 28
<212> TYPE: PRT
<213> ORGANISM: Mycobacterium tuberculosis

<400> SEQUENCE: 107
```

```
Gly Asn Ala Asp Val Val Cys Gly Gly Val Ser Thr Ala Asn Ala Thr
1               5                   10                  15

Val Tyr Met Ile Asp Ser Val Leu Met Pro Pro Ala
            20                  25

<210> SEQ ID NO 108
<211> LENGTH: 13
<212> TYPE: PRT
<213> ORGANISM: Homo sapiens

<400> SEQUENCE: 108

Gly Ser Pro Tyr Val Ser Arg Leu Leu Gly Ile Cys Leu
1               5                   10

<210> SEQ ID NO 109
<211> LENGTH: 17
<212> TYPE: PRT
<213> ORGANISM: Homo sapiens

<400> SEQUENCE: 109

Lys Val Pro Ile Lys Trp Met Ala Leu Glu Ser Ile Leu Arg Arg Arg
1               5                   10                  15

Phe

<210> SEQ ID NO 110
<211> LENGTH: 25
<212> TYPE: PRT
<213> ORGANISM: Homo sapiens

<400> SEQUENCE: 110

Pro Gly Val Leu Leu Lys Glu Phe Thr Val Ser Gly Asn Ile Leu Thr
1               5                   10                  15

Ile Arg Leu Thr Ala Ala Asp His Arg
            20                  25

<210> SEQ ID NO 111
<211> LENGTH: 15
<212> TYPE: PRT
<213> ORGANISM: Clostridium tetani

<400> SEQUENCE: 111

Val Ser Ile Asp Lys Phe Arg Ile Phe Cys Lys Ala Asn Pro Lys
1               5                   10                  15

<210> SEQ ID NO 112
<211> LENGTH: 16
<212> TYPE: PRT
<213> ORGANISM: Clostridium tetani

<400> SEQUENCE: 112

Leu Lys Phe Ile Ile Lys Arg Tyr Thr Pro Asn Asn Glu Ile Asp Ser
1               5                   10                  15

<210> SEQ ID NO 113
<211> LENGTH: 15
<212> TYPE: PRT
<213> ORGANISM: Clostridium tetani

<400> SEQUENCE: 113

Ile Arg Glu Asp Asn Asn Ile Thr Leu Lys Leu Asp Arg Cys Asn
1               5                   10                  15
```

<210> SEQ ID NO 114
<211> LENGTH: 21
<212> TYPE: PRT
<213> ORGANISM: Clostridium tetani

<400> SEQUENCE: 114

```
Phe Asn Asn Phe Thr Val Ser Phe Trp Leu Arg Val Pro Lys Val Ser
1               5                   10                  15

Ala Ser His Leu Glu
            20
```

<210> SEQ ID NO 115
<211> LENGTH: 14
<212> TYPE: PRT
<213> ORGANISM: Clostridium tetani

<400> SEQUENCE: 115

```
Gln Tyr Ile Lys Ala Asn Ser Lys Phe Ile Gly Ile Thr Glu
1               5                   10
```

<210> SEQ ID NO 116
<211> LENGTH: 20
<212> TYPE: PRT
<213> ORGANISM: Hepatitis B virus

<400> SEQUENCE: 116

```
Pro His His Thr Ala Leu Arg Gln Ala Ile Leu Cys Trp Gly Glu Leu
1               5                   10                  15

Met Thr Leu Ala
            20
```

<210> SEQ ID NO 117
<211> LENGTH: 13
<212> TYPE: PRT
<213> ORGANISM: Influenza A virus

<400> SEQUENCE: 117

```
Pro Lys Tyr Val Lys Gln Asn Thr Leu Lys Leu Ala Thr
1               5                   10
```

<210> SEQ ID NO 118
<211> LENGTH: 15
<212> TYPE: PRT
<213> ORGANISM: Hepatitis B virus

<400> SEQUENCE: 118

```
Phe Phe Leu Leu Thr Arg Ile Leu Thr Ile Pro Gln Ser Leu Asp
1               5                   10                  15
```

<210> SEQ ID NO 119
<211> LENGTH: 16
<212> TYPE: PRT
<213> ORGANISM: Influenza A virus

<400> SEQUENCE: 119

```
Tyr Ser Gly Pro Leu Lys Ala Glu Ile Ala Gln Arg Leu Glu Asp Val
1               5                   10                  15
```

<210> SEQ ID NO 120
<211> LENGTH: 18
<212> TYPE: PRT
<213> ORGANISM: Plasmodium falciparum

<400> SEQUENCE: 120

```
Glu Lys Lys Ile Ala Lys Met Glu Lys Ala Ser Ser Val Phe Asn Val
1               5                   10                  15

Val Asn

<210> SEQ ID NO 121
<211> LENGTH: 4
<212> TYPE: PRT
<213> ORGANISM: Human papillomavirus

<400> SEQUENCE: 121

Gln Asp Lys Leu
1

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Val Tyr Asp Phe Phe Val Trp Leu
1               5

<210> SEQ ID NO 123
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ccggtttgta tgctgtgtat gacttttttg tgtggctcgg aggaggtg                  48

<210> SEQ ID NO 124
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ctagcacctc ctccgagcca cacaaaaaag tcatacacag catacaaa                  48

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
aaagaattca tggatgacca acgcgacctc                                      30

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
```

```
aaaggatcct cacagggtga cttgacccag                                          30
```

<210> SEQ ID NO 127
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127

```
tccaggcagc cacgaacttg gcaagcttca tgcgaaggct ct                            42
```

<210> SEQ ID NO 128
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128

```
ctggaccctg aaggctgccg ctatggataa catgctcctt gg                            42
```

<210> SEQ ID NO 129
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129

```
gccaagttcg tggctgcctg gaccctgaag gctgccgct                                39
```

<210> SEQ ID NO 130
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130

```
aaatctagaa tggcggcccc cggcgcccg                                           29
```

<210> SEQ ID NO 131
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131

```
ggggaattct agatcctcaa agagtgctg                                           29
```

<210> SEQ ID NO 132
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132

```
aattcgccaa gttcgtggct gcctggaccc tgaaggctgc cgcttgaa                 48
```

<210> SEQ ID NO 133
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133

```
agctttcaag cggcagcctt cagggtccag gcagccacga acttggcg                 48
```

<210> SEQ ID NO 134
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134

```
aaagaattcg ccaagttcgt ggctgcctgg accctgaagg ctgccgctct taacaacatg    60
ttgatcccc                                                             69
```

<210> SEQ ID NO 135
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135

```
tttggatccc tagatggtct gatagccgg                                       29
```

<210> SEQ ID NO 136
<211> LENGTH: 9
<212> TYPE: PRT
<213> ORGANISM: Human papillomavirus

<400> SEQUENCE: 136

Arg Ala His Tyr Asn Ile Val Thr Phe
1               5

<210> SEQ ID NO 137
<211> LENGTH: 17
<212> TYPE: PRT
<213> ORGANISM: Gallus gallus

<400> SEQUENCE: 137

Ile Ser Gln Ala Val His Ala Ala His Ala Glu Ile Asn Glu Ala Gly
1               5                   10                  15

Arg

<210> SEQ ID NO 138
<211> LENGTH: 8
<212> TYPE: PRT
<213> ORGANISM: Human papillomavirus

<400> SEQUENCE: 138

Tyr Asp Phe Ala Phe Arg Asp Leu
1               5